United States Patent
Wells et al.

(10) Patent No.: US 11,085,054 B2
(45) Date of Patent: Aug. 10, 2021

(54) UNGULATES WITH GENETICALLY MODIFIED IMMUNE SYSTEMS

(71) Applicant: Revivicor, Inc., Blacksburg, VA (US)

(72) Inventors: Kevin Wells, Christianburg, VA (US); David Ayares, Blacksburg, VA (US)

(73) Assignee: Revivicor, Inc., Blacksburg, VA (US)

( * ) Notice: Subject to any disclaimer, the term of this patent is extended or adjusted under 35 U.S.C. 154(b) by 0 days.

(21) Appl. No.: 16/291,583

(22) Filed: Mar. 4, 2019

(65) Prior Publication Data

US 2020/0109415 A1   Apr. 9, 2020

Related U.S. Application Data

(63) Continuation of application No. 15/430,583, filed on Feb. 13, 2017, now abandoned, which is a continuation of application No. 12/433,477, filed on Apr. 30, 2009, now Pat. No. 9,585,374, which is a continuation of application No. 11/789,961, filed on Apr. 26, 2007, now abandoned, which is a continuation-in-part of application No. 11/257,817, filed on Oct. 24, 2005, now abandoned.

(60) Provisional application No. 60/794,963, filed on Apr. 26, 2006, provisional application No. 60/621,433, filed on Oct. 22, 2004.

(51) Int. Cl.
*C12N 15/85* (2006.01)
*A01K 67/027* (2006.01)
*C12N 15/873* (2010.01)

(52) U.S. Cl.
CPC ...... *C12N 15/8509* (2013.01); *A01K 67/0275* (2013.01); *A01K 67/0276* (2013.01); *C12N 15/873* (2013.01); *A01K 2207/15* (2013.01); *A01K 2217/00* (2013.01); *A01K 2217/075* (2013.01); *A01K 2227/101* (2013.01); *A01K 2227/102* (2013.01); *A01K 2227/103* (2013.01); *A01K 2227/108* (2013.01); *A01K 2267/01* (2013.01); *A01K 2267/02* (2013.01); *A01K 2267/025* (2013.01); *A01K 2267/0387* (2013.01); *C12N 2015/8536* (2013.01); *C12N 2800/204* (2013.01); *C12N 2800/206* (2013.01); *C12N 2800/30* (2013.01)

(58) Field of Classification Search
CPC .............. C12N 15/8509; C12N 15/873; C12N 2800/30; C12N 2800/206; C12N 2015/8536; C12N 2800/204; A01K 67/0276; A01K 67/0275; A01K 2267/01; A01K 2227/102; A01K 2227/101; A01K 2217/00; A01K 2267/0387; A01K 2207/15; A01K 2217/075; A01K 2227/103; A01K 2227/108; A01K 2267/02; A01K 2267/025

See application file for complete search history.

(56) References Cited

U.S. PATENT DOCUMENTS

| | | |
|---|---|---|
| 5,545,806 A | 8/1996 | Lonberg et al. |
| 5,545,807 A | 8/1996 | Surani et al. |
| 5,569,825 A | 10/1996 | Lonberg et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,625,825 A | 4/1997 | Rostoker et al. |
| 5,633,425 A | 5/1997 | Lonberg et al. |
| 5,643,763 A | 7/1997 | Dunn et al. |
| 5,661,016 A | 8/1997 | Lonberg et al. |
| 5,721,367 A | 2/1998 | Kay et al. |
| 5,770,429 A | 6/1998 | Lonberg et al. |
| 5,789,215 A | 8/1998 | Berns et al. |
| 5,789,650 A | 8/1998 | Lonberg et al. |
| 5,814,318 A | 9/1998 | Lonberg et al. |
| 7,074,983 B2 | 7/2006 | Robl et al. |
| 7,414,170 B2 | 8/2008 | Robl et al. |
| 2003/0037347 A1 | 2/2003 | Robl et al. |
| 2003/0056237 A1 | 3/2003 | Goldsby et al. |
| 2004/0068760 A1 | 4/2004 | Robl et al. |
| 2005/0155095 A1 | 7/2005 | Koike |
| 2005/0223418 A1 | 10/2005 | Koike |

(Continued)

FOREIGN PATENT DOCUMENTS

| | | |
|---|---|---|
| EP | 0 843 961 | 5/1998 |
| WO | WO 91/10741 | 7/1991 |

(Continued)

OTHER PUBLICATIONS

Rohrer, Gary; Beever, Jonathan E.; Rothschild, Max F.; Schook, Lawrence; Gibbs, Richard; and Weinstock, George, "Porcine Genomic Sequencing Initiative" (2002).*

(Continued)

*Primary Examiner* — Thaian N. Ton

(74) *Attorney, Agent, or Firm* — Foley & Lardner LLP

(57) ABSTRACT

The present invention provides ungulate animals, tissue and organs as well as cells and cell lines derived from such animals, tissue and organs, which lack expression of functional endogenous immunoglobulin loci. The present invention also provides ungulate animals, tissue and organs as well as cells and cell lines derived from such animals, tissue and organs, which express xenogenous, such as human, immunoglobulin loci. The present invention further provides ungulate, such as porcine genomic DNA sequence of porcine heavy and light chain immunogobulins. Such animals, tissues, organs and cells can be used in research and medical therapy. In addition, methods are provided to prepare such animals, organs, tissues, and cells.

15 Claims, 7 Drawing Sheets

Specification includes a Sequence Listing.

(56) References Cited

U.S. PATENT DOCUMENTS

| | | |
|---|---|---|
| 2006/0068479 A1 | 3/2006 | Koike |
| 2006/0117394 A1 | 6/2006 | Robl et al. |
| 2006/0130157 A1 | 6/2006 | Wells et al. |

FOREIGN PATENT DOCUMENTS

| | | |
|---|---|---|
| WO | WO 92/03918 | 3/1992 |
| WO | WO 92/22645 | 12/1992 |
| WO | WO 92/22647 | 12/1992 |
| WO | WO 92/22670 | 12/1992 |
| WO | WO 93/12227 | 6/1993 |
| WO | WO 94/00569 | 1/1994 |
| WO | WO 94/02602 | 2/1994 |
| WO | WO 94/25585 | 11/1994 |
| WO | WO 96/14436 | 5/1996 |
| WO | WO 96/34096 | 10/1996 |
| WO | WO 97/13852 | 4/1997 |
| WO | WO 98/24884 | 6/1998 |
| WO | WO 98/24893 | 6/1998 |
| WO | WO 00/51424 | 9/2000 |
| WO | WO 01/35735 | 5/2001 |
| WO | WO 02/07648 | 1/2002 |
| WO | WO 02/070648 | 9/2002 |
| WO | WO 03/047336 | 6/2003 |
| WO | WO 04/028243 | 4/2004 |
| WO | WO 06/047603 | 5/2006 |

OTHER PUBLICATIONS

Altschul, S.F. et al. Nucleic Acids Res vol. 25, pp. 3389-3402; Jun./Jul. 1997.
Bodey, B., "Human cancer detection and immunotherapy with conjugated and non-conjugated mono-clonal antibodies," *Anticancer Res.*, 16(2):661-674 (Mar.-Apr. 1996).
Bonnefoy-Berard, N., and Revillard, J.P., "Mechanisms of immunosuppression induced by antithymocyte globulins and OKT3," *J. Heart Lung Transplant*, 15(5):435-442 (May 1996).
Brown, W.R., and Butler, J.E. "Characterization of a C alpha gene of swine," *Mol. Immunol.*, 31(8):633-642 (Jun. 1994).
Brüggemann, M., et al. "A repertoire of monoclonal antibodies with human heavy chains from transgenic mice," *Proc. Nat'l. Acad. Sci. USA*, 86(17):6709-6713 (Sep. 1989).
Brüggemann, M., et al., "The immunogenicity of chimeric antibodies," *J. Exp. Med.*, 170(6):2153-2157 (Dec. 1, 1989).
Burnett, R. C, et al., "The IgA heavy-chain gene family in rabbit: cloning and sequence analysis of 13 C alpha genes," *EMBO J.*, 8(13):4041-4047 (Dec. 20, 1989).
Butler et al., Frontiers in Immunology, 3: 1-14, Jun. 2012.
Butler, J.E., and Brown, W.R., et al , "The immunoglobulins and immunoglobulin genes of swine," *Vet. Immunol. Immunopathol.*, 43(1-3):5-12 (Oct. 1994).
Butler, J.E., et al, "Swine have a single $J_H$, <20 $V_H$ genes and no IgD," Chapter 27 in *Advances in Swine in Biomedical Research*, Tumbleson and Schook, eds. (Plenum Press, New York, 1996), pp. 291-305.
Butler, J.E., et al., "The swine Ig heavy chain locus has a single JH and no identifiable IgD," *Intl. Immunol.*, 8(12):1897-1904 (Dec. 1996).
Cai et al. Genomics vol. 29, 1995, pp. 413-425.
Casadevall, A., and Scharff, M.D., "Return to the past: the case for antibody-based therapies in infectious diseases," *Clinical Infectious Diseases*, 21(1):150-161 (Jul. 1995).
Casadevall, Arturo, "Passive Antibody Administration (Immediate Immunity) as a Specific Defense Against Biological Weapons" *Emerging Infectious Diseases* (Centers for Disease Control and Prevention (CDC)), 8(8):833-841 (Aug. 2002).
Cendrowski, W., "Antilymphocyte globulin and adrenal steroids in the treatment of multiple sclerosis: short report based on seven cases," *Boll. Ist. Sieroter. Milan*, 58(4):339-343 (Sep. 30, 1979).

Chen, J., et al., "Immunoglobulin gene rearrangement in B cell deficient mice generated by targeted deletion of the JH locus," *International Immunology*, 5(6):647-656 (Jun. 1993).
Choi, T.K., et al., "Transgenic mice containing a human heavy chain immunoglobulin gene fragment cloned in a yeast artificial chromosome," *Nature Genetics*, 4(2):117-123 (Jun. 1993).
Cibelli, J.B., et al., "Cloned transgenic calves produced from nonquiescent fetal fibroblasts," *Science*, 280(5367):1256-1258 (May 22, 1998).
Colby, C., et al., "Antithymocyte immunoglobulin in severe aplastic anemia and bone marrow transplantation," *Ann. Pharmacother.*, 30(10):1164-1174 (Oct. 1996).
Couronne et al.; Strategies and Tools for Whole-Genome Alignments; *Genome Research*; vol. 13:73-80; Sep. 4, 2002.
Dai, Y., et al., "Targeted disruption of the α1,3-galactosyltransferase gene in cloned pigs," *Nature Biotechnology*, 20:251-255 (Mar. 2002).
Doetschman et al. Nature vol. 330, 1987, pp. 576-578.
Dufour, V, et al., "The sheep Ig variable region repertoire consists of a single VH family," *J. Immunol,.* 156(6):2163-2170 (Mar. 15, 1996).
Dugan, M.J., et al, "ATG plus corticosteroid therapy for acute graft-versus-host disease: predictors of response and survival," *Ann. Hematol.*, 75(1-2):41-46 (Jul.-Aug. 1997).
Extended European Search Report for EP 09824080.7 dated Feb. 27, 2012.
Fishwild, D.M., et al., "High-avidity human IgG kappa monoclonal antibodies from a novel strain of minilocus transgenic mice," *Nature Biotech.*, 14(7):845-851 (Jul. 1996).
Green, L.L., and Jakobovits, A., "Regulation of B cell development by variable gene complexity in mice reconstituted with human immunoglobulin yeast artificial chromosomes," *J. Exp. Med.*, 188(3):483-495 (Aug. 3, 1998).
Green, L.L., et al., "Antigen-specific human monoclonal antibodies from mice engineered with human Ig heavy and light chain YACs," *Nature Genetics*, 7(1):13-21 (May 1994).
Hao-Chin, Tai et al., Progress in xenotransplantation following the introduction of gene-knockout technology, *Transplant International*, vol. 20, No. 2, Feb. 1, 2007, pp. 107-117.
Honjo, T., et al., "Constant-region genes of the immunoglobulin heavy chain and the molecular mechanism of class switching," Chapter 7 in Honjo, T, Alt. F. W. T. H. eds, *Immunoglobulin Genes* (Academic Press, New York, 1989) pp. 123-149.
International Search Report, for PCT/US09/62265 dated Dec. 9, 2009.
Jeon et al.; *Mol. Cells*; vol. 16, No. 1, pp. 113-116; Apr. 10, 2003.
Jones, P.T.,, et al., "Replacing the complementarity-determining regions in a human antibody with those from a mouse," *Nature*, 321(6069):522-525 (May 29-Jun. 4, 1986).
Joyner et al. Nature vol. 338, 1989, pp. 153-156.
Kacskovics, I, et al., "Five putative subclasses of swine IgG identified from the cDNA sequences of a single animal," *J. Immunol.*, 153(8):3565-3573 (Oct. 15, 1994).
Karlin et al. Proc. Natl. Acad. Sci. USA vol. 87, pp. 2264-2268.
Kaster et al.; Nucleic Acids Research vol. 11, 1983, pp. 6895-6911.
Kastrukoff, L. K.,, et al., "Multiple sclerosis treated with antithymocyte globulin—a five year follow-up," *Can. J. Neurol. Sci.*, 5(2):175-178 (May 1978).
Kaushik et al., Veterinary Immunology and Immunopathology, 87: 347-350, 2000.
Kim; Smithies Nucleic Acids Res. vol. 16, 1988, pp. 8887-8903.
Kitamura et al., (1991) Nature 350, 423-426.
Kolber-Simonds, D., et al., "Production of alpha-1,3-galactosyltransferase null pigs by means of nuclear transfer with fibroblasts bearing loss of heterozygosity mutations," *Proc. Natl. Acad. Sci. USA*, 101(19):7335-7340 (May 11, 2004) (Electronic publication May 3, 2004).
Kubota, C., et al., "Six cloned calves produced from adult fibroblast cells after long-term culture," *Proc. Nat'l. Acad. Sci. USA*, 97(3):990-995 (Feb. 1, 2000).
Kucherlapati et al. Mol. Cell. Bio. vol. 5, 1985, pp. 714-720.
Kucherlapati et al. Proc. Natl. Acad. Sci. USA vol. 81, 1984, pp. 3153-3157.

(56) References Cited

OTHER PUBLICATIONS

Kuriowa et al., Sequential Targeting of the Genes Encoding Immunoglobulin-μ and Prion Protein in Cattle; (2004) Nat Genet. 36, 775-780.

Kuroiwa, Y., et al., "Cloned transchromosomic calves producing human immunoglobulin," *Nature Biotechnology*, 20(9):889-894 (Sep. 2002) (Electronic publication Aug. 12, 2002).

Kuroiwa, Y., et al., "Sequential targeting of the genes encoding immunoglobulin-mu and prion protein in cattle," *Nat. Genet.*, 36(7):775-780 (Jul. 2004) (Electronic publication Jun. 6, 2004).

Kuroiwa, Yoshimi et al.; Nature Biotechnology. vol. 27, No. 2. Feb. 2009.

Lai, L., et al., "Production of α-1,3-galactosyltransferase knockout pigs by nuclear transfer cloning," *Science* 295:1089-1092 (Feb. 8, 2002) and supplementary data, *Science Express*, Jan. 3, 2002.

Lonberg, N., et al., "Antigen-specific human antibodies from mice comprising four distinct genetic modifications," *Nature*, 368(6474):856-859 (Apr. 28, 1994).

Mansour et al. Nature vol. 336, 1988, pp. 348-352.

Matsushita, Hiroaki, et al.; Plos One. vol. 9, Issue 3. Mar. 2014.

Mendez., M.J., et al., "Functional transplant of megabase human immunoglobulin loci recapitulates human antibody response in mice," *Nature Genetics*, 15(2):146-156 (Feb. 1997).

Mendicino, M. et al., "Generation of antibody- and B cell-deficient pigs by targeted disruption of the J-region gene segment of the heavy chain locus," Transgenic Research, Kluwer Academic Publishers, vol. 20, No. 3, Sep. 26, 2010, pp. 625-641.

Morrison, S.L., et al., "Chimeric human antibody molecules: mouse antigen-binding domains with human constant region domains," *Proc. Natl. Acad. Sci. USA*, 81(21):6851-6855 (Nov. 1984).

Nandi et al. Proc. Natl. Acad. Sci. USA vol. 85, 1988, pp. 3845-3849.

Parng., et al., Immunology, 157: 5478-5486, 1996.

Patel et al., Animal Pharming for the Production of Pharmaceutical Proteins, Drug Delivery Technology, Apr. 2007, vol. 7, No. 4, pp. 47-53.

Phelps, C.J., et al., "Production of α1,3-galactosyltransferase-deficient pigs," *Science*, 299:411-414 (Jan. 17, 2003).

Polejaeva, I.A., et al., "Cloned pigs produced by nuclear transfer from adult somatic cells," *Nature*, 407:86-90 (Sep. 7, 2000).

Ramsoondar J. et al., "Targeted disruption of the porcine immunoglobin kappa light chain locus," *Transgenic Research*, Kluwer Academic Publishers, vol. 20, No. 3, Sep. 26, 2010 pp. 643-653.

Ramsoondar, J.J., et al., "Production of α1,3-galactosyltransferase-knockout cloned pigs expressing human α1,2-fucosyltransferase," *Biol. of Reproduction*, 69:437-445 (online before print Apr. 2, 2003).

Rathbun, G., "Organization and expression of the mammalian heavy-chain variable-region locus," Chapter 4 in *Immunoglobulin Genes*, Honjo, T. Alt. F. W. and Rabbitts, T. H., eds, (Academic Press, New York, 1989), pp. 63-90.

Renner, C.,, et al, "Monoclonal antibodies in the treatment of non-Hodgkin's lymphoma: recent results and future prospects," *Leukemia*, 11( Suppl 2):S55-S59 (1997). miscite as Botti, C., et al., & w/o title.

Reynaud, C.A., et al., "Formation of the chicken B-cell repertoire: ontogenesis, regulation of Ig gene rearrangement, and diversification by gene conversion," *Adv. Immunol.*, 57:353-378 (1994).

Robl., et al., Theriogenology, 59: 107-113, 2003.

Schwartz, et al., Immunogenetics, (64): 399-407, 2012.

Sendal Y., et al., "Heterozygous disruption of the alpha1,3-galactosyltransferase gene in cattle," *Transplantation*, (2003) 76(6):900-902 (Sep. 27, 2003).

Sinclair, M.C., et al, "Bovine IgG repertoire is dominated by a single diversified VH gene family," *J. Immunol.*, 159(8): 3883-3889, (Oct. 15, 1997).

Song, K-Y. et al. Proc. Nat'l Acad. Sci. U.S.A. vol. 84, 1987, pp. 6820-6824.

Sun, J., et al., "Expressed swine VH genes belong to a small VH gene family homologous to human VHIII," *J. Immunol.*, 153(12): 5618-5627, (Dec. 15, 1994).

Sutherland et al; *Transplantation*, 2000, vol. 69, pp. 1806-1812.

Taylor, L.D., et al., "A transgenic mouse that expresses a diversity of human sequence heavy and light chain immunoglobulins," *Nucleic Acids Research*, 20(23):6287-6295 (Dec. 11, 1992).

Taylor, L.D., et al., "Human immunoglobulin transgenes undergo rearrangement, somatic mutation and class switching in mice that lack endogenous IgM," *Intl. Immunol.*, 6(4):579-591 (Apr. 1994).

Thomas; Capecchi Cell vol. 51, 1987, pp. 503-512.

Tsai, H.F., et al., "Gene conversion-like sequence transfers in a mouse antibody transgene: antigen selection allows sensitive detection of V region interactions based on homology," *International Immunology*, vol. 14(1):55-64 (Jan. 2002).

Tuaillon, N., et al., "Analysis of direct and inverted DJH rearrangements in a human Ig heavy chain transgenic minilocus," *J. Immunol.*, 154(12):6453-6465 (Jun. 15, 1995).

Uenishi et al.; *Nucleic Acids Research*, Aug. 16, 2003; vol. 32; pp. 2-6.

Wake et al. Mol. Cell. Bio. vol. 8, 1985, pp. 2080-2089.

Walker, J. E.,, et al., "A trial of antilymphocyte globulin in the treatment of chronic progressive multiple sclerosis," *J. Neurol. Sci.*, 29(2-4):303-309 (Oct. 1976).

Wilmut, I.,, et al., "Viable offspring derived from fetal and adult mammalian cells," *Nature*, 385(6619):810-813 (Feb. 27, 1997).

Yates et al.; *Blood*, 2002, vol. 100, pp. 3942-3949.

Zhao, Y., et al., "Physical mapping of the bovine immunoglobulin heavy chain constant region gene locus," *J. Biol. Chem.*, 278(37):35024-35032 (Sep. 12, 2003) (Electronic publication Jun. 26, 2003).

Zhao, Y., et al., "The porcine Ig delta gene: unique chimeric splicing of the first constant region domain in its heavy chain transcripts.," *J. Immunol.*, 171(3):1312-8 (Aug. 1, 2003).

Zou et al., J. Immunol., 170(3):1354-1361 (Feb. 2003).

Fahrenkrug et al., *Mammalian Genome*, 2002, 13:475-478.

Capecchi et al., *Scientific American*, 1994, 2703(3):34-41.

\* cited by examiner

Figure 4
Graphic view of Human sequence AC002060 and NG_000002 with Porcine lambda contigs that flank the JC cluster.
Aproximate scale: one block is about 1 kb
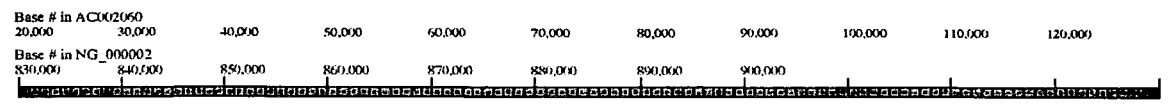
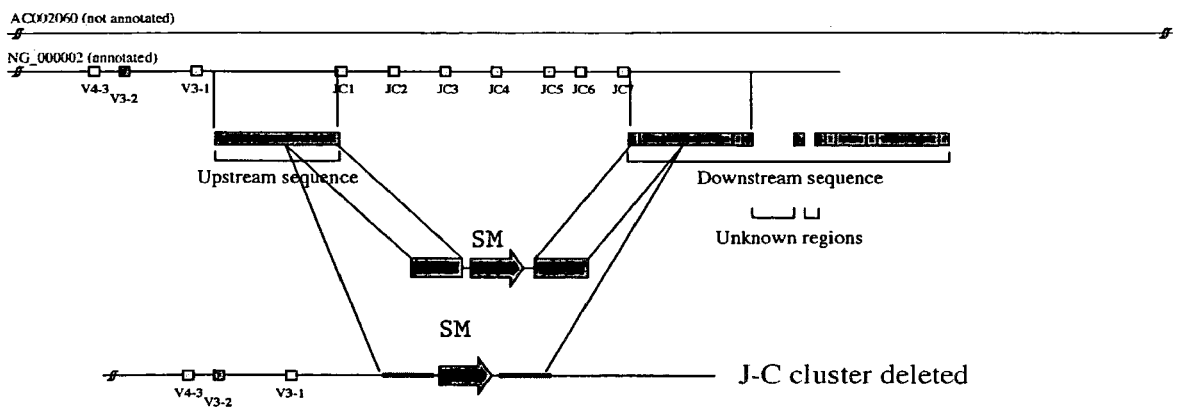

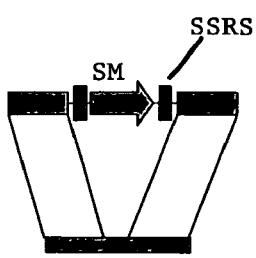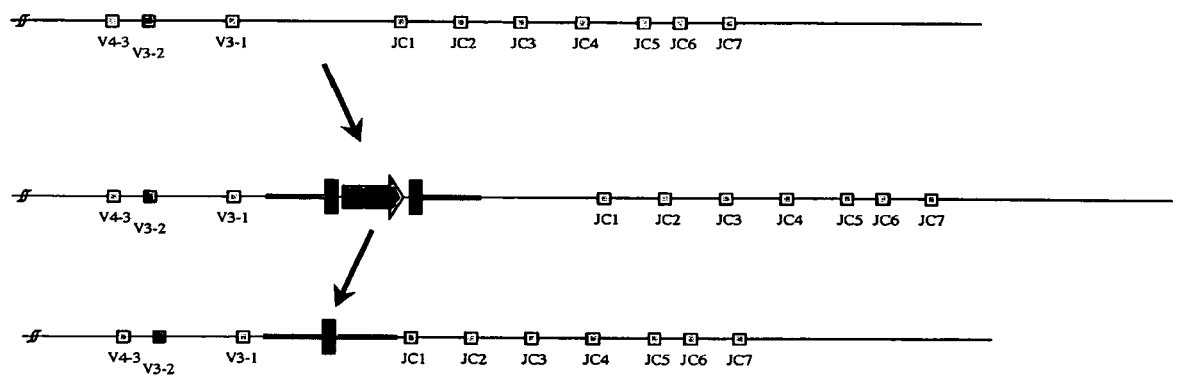
Figure 5

Figure 7
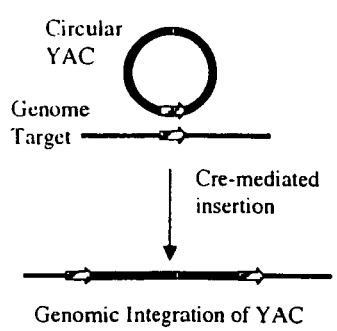
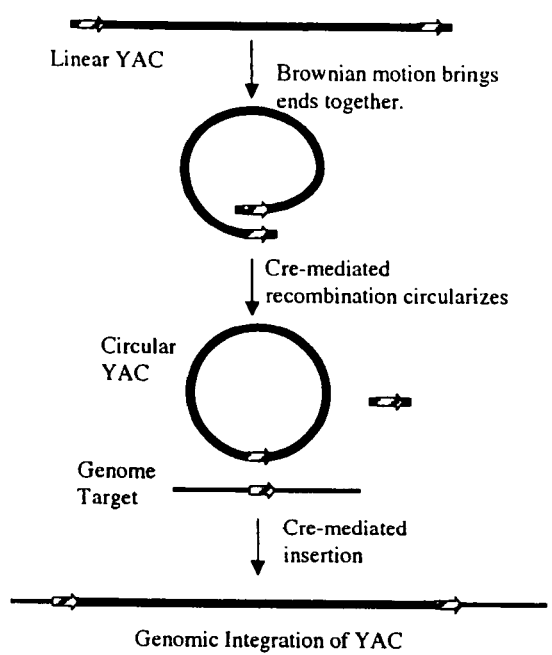

SEQUENCE LISTING

<160> NUMBER OF SEQ ID NOS: 50

<210> SEQ ID NO 1
<211> LENGTH: 666
<212> TYPE: DNA

<213> ORGANISM: Sus sp.

<400> SEQUENCE: 1

| | | |
|---|---|---|
| tctagaagac gctggagaga ggccagactt cctcggaaca gctcaaagag ctctgtcaaa | 60 | |
| gccagatccc atcacacgtg ggcaccaata ggccatgcca gcctccaagg gccgaactgg | 120 | |
| gttctccacg gcgcacatga agcctgcagc ctggcttatc ctcttccgtg gtgaagaggc | 180 | |
| aggcccggga ctggacgagg ggctagcagg gtgtggtagg cacctttgcgc cccccacccc | 240 | |
| ggcaggaacc agagaccctg gggctgagag tgagcctcca aacaggatgc cccacccttc | 300 | |
| aggccacctt tcaatccagc tacactccac ctgccattct cctctgggca cagggcccag | 360 | |
| cccctggatc ttggccttgg ctcgacttgc acccacgcgc acacacacac ttcctaacgt | 420 | |
| gctgtccgct cacccctccc cagcgtggtc catgggcagc acggcagtgc gcgtccggcg | 480 | |
| gtagtgagtg cagaggtccc ttcccctccc ccaggagccc caggggtgtg tgcagatctg | 540 | |
| ggggctcctg tcccttacac cttcatgccc ctcccctcat acccaccctc caggcgggag | 600 | |
| gcagcgagac ctttgcccag ggactcagcc aacgggcaca cggaggcca gccctcagca | 660 | |
| gctggg | 666 | |

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2

| | | |
|---|---|---|
| ggccagactt cctcggaaca gctca | 25 | |

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3

| | | |
|---|---|---|
| ttccaggaga aggtgacgga gct | 23 | |

<210> SEQ ID NO 4
<211> LENGTH: 9175
<212> TYPE: DNA
<213> ORGANISM: Sus sp.

<400> SEQUENCE: 4

| | | |
|---|---|---|
| ggccagactt cctcggaaca gctcaaagag ctctgtcaaa gccagatccc atcacacgtg | 60 | |
| ggcaccaata ggccatgcca gcctccaagg gccgaactgg gttctccacg gcgcacatga | 120 | |
| agcctgcagc ctggcttatc ctcttccgtg gtgaagaggc aggcccggga ctggacgagg | 180 | |
| ggctagcagg gtgtggtagg cacctttgcgc cccccacccc ggcaggaacc agagaccctg | 240 | |
| gggctgagag tgagcctcca aacaggatgc cccacccttc aggccacctt tcaatccagc | 300 | |
| tacactccac ctgccattct cctctgggca cagggcccag cccctggatc ttggccttgg | 360 | |
| ctcgacttgc acccacgcgc acacacacac ttcctaacgt gctgtccgct cacccctccc | 420 | |
| cagcgtggtc catgggcagc acggcagtgc gcgtccggcg gtagtgagtg cagaggtccc | 480 | |
| ttcccctccc ccaggagccc caggggtgtg tgcagatctg ggggctcctg tcccttacac | 540 | |
| cttcatgccc ctcccctcat acccaccctc caggcgggag gcagcgagac ctttgcccag | 600 | |

```
ggactcagcc aacgggcaca cgggaggcca gccctcagca gctggctccc aaagaggagg    660
tgggaggtag gtccacagct gccacagaga gaaaccctga cggaccccac aggggccacg    720
ccagccggaa ccagctccct cgtgggtgag caatggccag gccccgccg gccaccacgg     780 ctggccttgc gccagctgag aactcacgtc cagtgcaggg agactcaaga cagcctgtgc    840
acacagcctc ggatctgctc ccatttcaag cagaaaaagg aaaccgtgca ggcagccctc    900
agcatttcaa ggattgtagc agcggccaac tattcgtcgg cagtggccga ttagaatgac    960
cgtggagaag ggcggaaggg tctctcgtgg gctctgcggc caacaggccc tggctccacc   1020
tgcccgctgc cagcccgagg ggcttgggcc gagccaggaa ccacagtgct caccgggacc   1080
acagtgactg accaaactcc cggccagagc agccccaggc cagccgggct ctcgccctgg   1140
aggactcacc atcagatgca caaggggcg agtgtggaag agacgtgtcg cccgggccat    1200
ttgggaaggc gaagggacct tccaggtgga caggaggtgg gacgcactcc aggcaaggga   1260
ctgggtcccc aaggcctggg gaaggggtac tggcttgggg gttagcctgg ccagggaacg   1320
gggagcgggg cggggggctg agcagggagg acctgacctc gtgggagcga ggcaagtcag   1380
gcttcaggca gcagccgcac atcccagacc aggaggctga ggcaggaggg gcttgcagcg   1440 gggcggggc ctgcctggct ccgggggctc ctgggggacg ctggctcttg tttccgtgtc    1500
ccgcagcaca gggccagctc gctgggccta tgcttacctt gatgtctggg gccgggggcgt  1560 cagggtcgtc gtctcctcag gggagagtcc cctgaggcta cgctgggggg ggactatggc   1620
agctccacca ggggcctggg gaccaggggc ctggaccagg ctgcagcccg gaggacgggc   1680
agggctctgg ctctccagca tctggccctc ggaaatggca gaaccctgg cgggtgagcg     1740 agctgagagc gggtcagaca gacagggccc ggccggaaag gagaagttgg gggcagagcc   1800
cgccaggggc caggcccaag gttctgtgtg ccagggcctg ggtgggcaca ttggtgtggc   1860
catggctact tagattcgtg gggccagggc atcctggtca ccgtctcctc aggtgagcct   1920
ggtgtctgat gtccagctag gcgctggtgg gccgcgggtg ggcctgtctc aggctagggc   1980
aggggctggg atgtgtattt gtcaaggagg ggcaacaggg tgcagactgt gcccctggaa   2040
acttgaccac tggggcaggg gcgtcctggt cacgtctcct caggtaagac ggccctgtgc   2100
ccctctctcg cgggactgga aaaggaattt tccaagattc cttggtctgt gtggggccct   2160
ctggggcccc cggggtggc tcccctcctg cccagatggg gcctcggcct gtggagcacg    2220
ggctgggcac acagctcgag tctagggcca cagaggcccg ggctcagggc tctgtgtggc   2280
ccggcgactg gcagggggct cgggtttttg gacaccccct aatgggggcc acagcactgt   2340
gaccatcttc acagctgggg ccgaggagtc gaggtcaccg tctcctcagg tgagtcctcg   2400
tcagccctct ctcactctct gggggttttt gctgcatttt gtggggaaa gaggatgcct    2460 gggtctcagg tctaaaggtc tagggccagc gccgggccc aggaaggggc cgagggccca    2520
ggctcggctc ggccaggagc agagcttcca gacatctcgc ctcctggcgg ctgcagtcag   2580
gcctttggcc gggggggtct cagcaccacc aggcctcttg gctcccgagg tccccggccc   2640
cggctgcctc accaggcacc gtgcgcggtg ggcccgggct cttggtcggc cacccttcct   2700
taactgggat ccgggcttag ttgtcgcaat gtgacaacgg gctcgaaagc tggggccagg   2760
ggaccctagt tacgacgcct cgggtggtg tcccgcaccc ctccccactt tcacggcact    2820
cggcgagacc tggggagtca ggtgttgggg acactttgga ggtcaggaac gggagctggg   2880
gagagggctc tgtcagcggg gtccagagat gggccgccct ccaaggacgc cctgcgcggg   2940
```

```
gacaagggct tcttggcctg gcctggccgc ttcacttggg cgtcaggggg ggcttcccgg    3000
ggcaggcggg cagtcgaggc gggttggaat tctgagtctg ggttcgggt tcggggttcg    3060 gccttcatga acagacagcc caggcgggcc gttgtttggc ccctgggggc ctggttggaa    3120
tgcgaggtct cggaagtca ggagggagcc tggccagcag agggttccca gccctgcggc     3180
cgagggacct ggagacgggc agggcattgg ccgtcgcagg gccaggccac acccccagg    3240 tttttgtggg gcgagcctgg agattgcacc actgtgatta ctatgctatg gatctctggg    3300
gcccaggcgt tgaagtcgtc gtgtcctcag gtaagaacgg ccctccaggg cctttaattt    3360
ctgctctcgt ctgtgggctt ttctgactct gatcctcggg aggcgtctgt gccccccccg    3420
gggatgaggc cggcttgcca ggaggggtca ggaccagga gcctgtggga agttctgacg     3480
ggggctgcag gcgggaaggg ccccaccggg gggcgagccc caggccgctg gcggcagga    3540 gacccgtgag agtgcgcctt gaggagggtg tctgcggaac cacgaacgcc cgccgggaag    3600
ggcttgctgc aatgcggtct tcagacggga ggcgtcttct gccctcaccg tctttcaagc    3660
ccttgtgggt ctgaaagagc catgtcgag agagaaggga caggcctgtc ccgacctggc     3720
cgagagcggg cagccccggg ggagagcggg gcgatcggcc tgggctctgt gaggccaggt    3780
ccaagggagg acgtgtggtc ctcgtgacag gtgcacttgc gaaaccttag aagacggggg    3840
atgttggaag cggctcctga tgtttaagaa aagggagact gtaaagtgag cagagtcctc    3900
aagtgtgtta aggttttaaa ggtcaaagtg ttttaaacct ttgtgactgc agttagcaag    3960
cgtgcgggga gtgaatgggg tgccagggtg gccgagaggc agtacgaggg ccgtgccgtc    4020
ctctaattca gggcttagtt ttgcagaata aagtcggcct gttttctaaa agcattggtg    4080
gtgctgagct ggtggaggag gccgcgggca gccctggcca cctgcagcag gtggcaggaa    4140
gcaggtcggc caagaggcta ttttaggaag ccagaaaaca cggtcgatga atttatagct    4200 tctggttttcc aggaggtggt tgggcatggc tttgcgcagc gccacagaac cgaaagtgcc    4260
cactgagaaa aaacaactcc tgcttaattt gcattttct aaaagaagaa acagaggctg     4320
acggaaactg gaaagttcct gtttttaacta ctcgaattga gttttcggtc ttagcttatc    4380
aactgctcac ttagattcat tttcaaagta aacgtttaag agccgaggca ttcctatcct    4440
cttctaaggc gttattcctg gaggctcatt caccgccagc acctccgctg cctgcaggca    4500
ttgctgtcac cgtcaccgtg acggcgcgca cgattttcag ttggcccgct tcccctcgtg    4560
attaggacag acgcgggcac tctggcccag ccgtcttggc tcagtatctg caggcgtccg    4620
tctcgggacg gagctcaggg gaagagcgtg actccagttg aacgtgatag tcggtgcgtt    4680
gagaggagac ccagtcgggt gtcgagtcag aaggggcccg ggcccgagg ccctgggcag     4740 gacgcccgt gccctgcatc acgggcccag cgtcctagag gcaggactct ggtgagagt     4800 gtgagggtgc ctggggcccc tccggagctg gggccgtgcg gtgcaggttg ggctctcggc    4860
gcggtgttgg ctgtttctgc gggatttgga ggaattcttc cagtgatggg agtcgccagt    4920
gaccgggcac caggctggta agaggaggc cgccgtcgtg gccagagcag ctgggagggt     4980
tcggtaaaag gctcgcccgt ttccttaat gaggactttt cctggagggc atttagtcta     5040
gtcgggaccg ttttcgactc gggaagaggg atgcggagga gggcatgtgc ccaggagccg    5100
aaggcgccgc ggggagaagc ccagggctct cctgtcccca cagaggcgac gccactgccg    5160
cagacagaca gggcctttcc ctctgatgac ggcaaaggcg cctcggctct tgcggggtgc    5220
tgggggggag tcgccccgaa gccgctcacc cagaggcctg aggggtgaga ctgaccgatg    5280
cctcttggcc gggcctgggg ccggaccgag ggggactccg tggaggcagg gcgatggtgg    5340
```

```
ctgcgggagg gaaccgaccc tgggccgagc ccggcttggc gattcccggg cgagggccct    5400
cagccgaggc gagtgggtcc ggcggaacca cccttctgg ccagcgccac agggctctcg    5460
ggactgtccg gggcgacgct gggctgcccg tggcaggcct gggctgacct ggacttcacc    5520
agacagaaca gggcttcag ggctgagctg agccaggttt agcgaggcca agtgggctg     5580 aaccaggctc aactggcctg agctgggttg agctgggctg acctgggctg agctgagctg    5640
ggctgggctg ggctgggctg ggctgggctg ggctggactg gctgagctga gctgggttga    5700
gctgagctga gctggcctgg gttgagctgg gctgggttga gctgagctgg gttgagctgg    5760
gttgagctgg gttgatctga gctgagctgg gctgagctga gctaggctgg ggtgagctgg    5820
gctgagctgg tttgagttgg gttgagctga gctgagctgg gctgtgctgg ctgagctagg    5880
ctgagctagg ctaggttgag ctgggctggg ctgagctgag ctaggctggg ctgatttggg    5940
ctgagctgag ctgagctagg ctgcgttgag ctggctgggc tggattgagc tggctgagct    6000
ggctgagctg ggctgagctg gcctgggttg agctgagctg gactggtttg agctgggtcg    6060 atctggttg agctgtcctg ggttgagctg ggctgggttg agctgagctg ggttgagctg    6120
ggctcagcag agctgggttg ggctgagctg ggttgagctg agctgggctg agctggcctg    6180
ggttgagctg ggctgagctg agctgggctg agctggcctg tgttgagctg ggctgggttg    6240
agctgggctg agctggattg agctgggttg agctgagctg ggctgggctg tgctgactga    6300
gctgggctga gctaggctgg ggtgagctgg gctgagctga tccgagctag gctgggctgg    6360
tttgggctga gctgagctga gctaggctgg attgatctgg ctgagctggg ttgagctgag    6420
ctgggctgag ctggtctgag ctggcctggg tcgagctgag ctggactggt ttgagctggg    6480
tcgatctggg ctgagctggc ctgggttgag ctgggctggg ttgagctgag ctgggttgag    6540
ctgggctgag ctgagggctg gggtgagctg ggctgaacta gcctagctag gttgggctga    6600
gctgggctgg tttgggctga gctgagctga gctaggctgc attgagcagg ctgagctggg    6660
ctgagcaggc ctggggtgag ctgggctagg tggagctgag ctgggtcgag ctgagttggg    6720
ctgagctggc ctgggttgag gtaggctgag ctgagctgag ctaggctggg ttgagctggc    6780
tgggctggtt tgcgctgggt caagctgggc cgagctggcc tgggttgagc tgggctcggt    6840
tgagctgggc tgagctgagc cgacctaggc tgggatgagc tgggctgatt tgggctgagc    6900
tgagctgagc taggctgcat tgagcaggct gagctgggcc tggagcctgg cctggggtga    6960
gctgggctga gctgcgctga gctaggctgg gttgagctgg ctgggctggt ttgcgctggg    7020
tcaagctggg ccgagctggc ctgggatgag ctgggccggt ttgggctgag ctgagctgag    7080
ctaggctgca ttgagcaggc tgagctgggc tgagctggcc tggggtgagc tgggctgagc    7140
taagctgagc tgggctggtt tgggctgagc tggctgagct gggtcctgct gagctgggct    7200
gagctgacca ggggtgagct gggctgagtt aggctgggct cagctaggct gggttgatct    7260
ggcagggctg gtttgcgctg gtcaagctc ccggagatg gcctgggatg agctgggctg    7320
gtttgggctg agctgagctg agctgagcta ggctgcattg agcaggctga gctgggctga    7380
gctggcctgg ggtgagctgg gctgggtgga gctgagctgg gctgaactgg gctaagctgg    7440
ctgagctgga tcgagctgag ctgggctgag ctggcctggg gttagctggg ctgagctgag    7500
ctgagctagg ctgggttgag ctggctgggc tggtttgcgc tgggtcaagc tgggccgagc    7560
tggcctgggt tgagctgggc tgggctgagc tgagctaggc tgggttgagc tgggctgggc    7620
tgagctgagc taggctgcat tgagctggct gggatggatt gagctggctg agctggctga    7680
```

```
gctggctgag ctgggctgag ctggcctggg ttgagctggg ctgggttgag ctgagctggg    7740
ctgagctggg ctcagcagag ctgggttgag ctgagctggg ttgagctggg gtgagctggg    7800
ctgagcagag ctgggttgag ctgagctggg ttgagctggg ctcgagcaga gctgggttga    7860
gctgagctgg gttgagctgg gctcagcaga gctgggttga gctgagctgg gttgagctgg    7920
gctgagctag ctgggctcag ctaggctggg ttgagctgag ctgggctgaa ctgggctgag    7980
ctgggctgaa ctgggctgag ctgggctgag ctgggctgag cagagctggg ctgagcagag    8040
ctgggttggt ctgagctggg ttgagctggg ctgagctggg ctgagcagag ttgggttgag    8100
ctgagctggg ttcagctggg ctgagctagg ctgggttgag ctgggttgag ttgggctgag    8160
ctgggctggg ttgagcggag ctgggctgaa ctgggctgag ctgggctgag cggaactggg    8220
ttgatctgaa ttgagctggg ctgagccggg ctgagccggg ctgagctggg ctaggttgag    8280
cttgggtgag cttgcctcag ctggtctgag ctaggttggg tggagctagg ctggattgag    8340
ctgggctgag ctgagctgat ctggcctcag ctgggctgag gtaggctgaa ctgggctgtg    8400
ctgggctgag ctgagctgag ccagtttgag ctgggttgag ctgggctgag ctgggctgtg    8460
ttgatctttc ctgaactggg ctgagctggg ctgagctggc ctagctggat tgaacggggg    8520
taagctgggc caggctggac tgggctgagc tgagctaggc tgagctgagt tgaattgggt    8580
taagctgggc tgagatgggc tgagctgggc tgagctgggt tgagccaggt cggactgggt    8640
taccctgggc cacactgggc tgagctgggc ggagctcgat taacctggtc aggctgagtc    8700
gggtccagca gacatgcgct ggccaggctg gcttgacctg gacacgttcg atgagctgcc    8760
ttgggatggt tcacctcagc tgagccaggt ggctccagct gggctgagct ggtgaccctg    8820
ggtgacctcg gtgaccaggt tgtcctgagt ccgggccaag ccgaggctgc atcagactcg    8880
ccagacccaa ggcctgggcc ccggctgcaa gccaggggc ggtgaaggct gggctggcag    8940
gactgtcccg gaaggaggtg cacgtggagc cgcccggacc ccgaccggca ggacctggaa    9000
agacgcctct cactcccctt tctcttctgt ccctctcgg gtcctcagag agccagtctg     9060
ccccgaatct ctaccccctc gtctcctgcg tcagccccc gtccgatgag agcctggtgg      9120
ccctgggctg cctggcccgg gacttcctgc ccagctccgt caccttctcc tggaa         9175
```

<210> SEQ ID NO 5
<211> LENGTH: 9200
<212> TYPE: DNA
<213> ORGANISM: Artificial Sequence
<220> FEATURE:
<223> OTHER INFORMATION: Synthetic

<400> SEQUENCE: 5

```
ggccagactt cctcggaaca gctcaaagag ctctgtcaaa gccagatccc atcacacgtg      60
ggcaccaata ggccatgcca gcctccaagg gccgaactgg gttctccacg gcgcacatga    120
agcctgcagc ctggcttatc ctcttccgtg gtgaagaggc aggcccggga ctggacgagg    180
ggctagcagg gtgtggtagg caccttgcgc ccccaccccc gcaggaacc agagaccctg     240 gggctgagag tgagcctcca aacaggatgc cccacccttc aggccacctt tcaatccagc    300
tacactccac ctgccattct cctctgggca caggcccag ccctggatc ttggcctggg      360 ctcgacttgc acccacgcgc acacacacac ttcctaacgt gctgtccgct caccctccc     420 cagcgtggtc catgggcagc acggcagtgc gcgtccggcg gtagtgagtg cagaggtccc    480
ttcccctccc ccaggagccc cagggtgtgt tgcagatctg ggggctcctg tcccttacac    540
cttcatgccc ctcccctcat acccaccctc caggcgggag gcagcgagac ctttgcccag    600
```

```
ggactcagcc aacgggcaca cgggaggcca gccctcagca gctggctccc aaagaggagg    660
tgggaggtag gtccacagct gccacagaga gaaaccctga cggaccccac aggggccacg    720
ccagccggaa ccagctccct cgtgggtgag caatggccag ggccccgccg gccaccacgg    780
ctggccttgc gccagctgag aactcacgtc cagtgcaggg agactcaaga cagcctgtgc    840
acacagcctc ggatctgctc ccatttcaag cagaaaaagg aaaccgtgca ggcagccctc    900
agcatttcaa ggattgtagc agcggccaac tattcgtcgg cagtggccga ttagaatgac    960
cgtggagaag ggcggaaggg tctctcgtgg gctctgcggc caacaggccc tggctccacc   1020
tgcccgctgc cagcccgagg ggcttgggcc gagccaggaa ccacagtgct caccgggacc   1080
acagtgactg accaaactcc cggccagagc agccccaggc cagccgggct ctcgccctgg   1140
aggactcacc atcagatgca caaggggcg agtgtggaag agacgtgtcg cccgggccat    1200
ttgggaaggc gaagggacct tccaggtgga caggaggtgg gacgcactcc aggcaaggga   1260
ctgggtcccc aaggcctggg aaggggtac tggcttgggg gttagcctgg ccagggaacg    1320
gggagcgggg cggggggctg agcagggagg acctgacctc gtgggagcga ggcaagtcag   1380
gcttcaggca gcagccgcac atcccagacc aggaggctga ggcaggaggg gcttgcagcg   1440 gggcggggc ctgcctggct ccgggggctc ctggggacg ctggctcttg tttccgtgtc     1500
ccgcagcaca gggccagctc gctgggccta tgcttacctt gatgtctggg gccggggcgt   1560
cagggtcgtc gtctcctcag gggagagtcc cctgaggcta cgctgggggg gactatggc    1620 agctccacca ggggcctggg gaccaggggc ctggaccagg ctgcagcccg gaggacgggc   1680
agggctctgg ctctccagca tctggccctc ggaaatggca gaaccctgg cgggtgagcg    1740 agctgagagc gggtcagaca gacagggcc ggccggaaag gagaagttgg gggcagagcc    1800 cgccagggc caggcccaag gttctgtgtg ccagggcctg ggtgggcaca ttggtgtggc    1860
catggctact tagacgcgtg atcaaggcg aattccagca cactggcggc cgttactagt    1920
ggatcccggc gcgccctacc gggtagggga ggcgcttttc ccaaggcagt ctggagcatg   1980
cgctttagca gccccgctgg gcacttggcg ctacacaagt ggcctctggc ctcgcacaca   2040
ttccacatcc accggtaggc gccaaccggc tccgttcttt ggtggcccct tcgcgccacc   2100
ttctactcct cccctagtca ggaagttccc ccccgccccg cagctcgcgt cgtgcaggac   2160
gtgacaaatg gaagtagcac gtctcactag tctcgtgcag atggacagca ccgctgagca   2220
atggaagcgg gtaggccttt ggggcagcgg ccaatagcag cttttggctcc ttcgctttct   2280 gggctcagag gctgggaagg ggtgggtccg ggggcgggct caggggcggg ctcaggggcg   2340
gggcgggcgc ccgaaggtcc tccggaagcc cggcattctg cacgcttcaa aagcgcacgt   2400
ctgccgcgct gttctcctct tcctcatctc cgggcctttc gacctgcagc caatatggga   2460
tcggccattg aacaagatgg attgcacgca ggttctccgg ccgcttgggt ggagaggcta   2520
ttcggctatg actgggcaca acagacaatc ggctgctctg atgccgccgt gttccggctg   2580
tcagcgcagg ggcgcccggt tctttttgtc aagaccgacc tgtccggtgc cctgaatgaa   2640
ctgcaggacg aggcagcgcg gctatcgtgg ctggccacga cgggcgttcc ttgcgcagct   2700
gtgctcgacg ttgtcactga agcgggaagg gactggctgc tattgggcga agtgccgggg   2760
caggatctcc tgtcatctca ccttgctcct gccgagaaag tatccatcat ggctgatgca   2820
atgcggcggc tgcatacgct tgatccggct acctgcccat tcgaccacca agcgaaacat   2880
cgcatcgagc gagcacgtac tcggatggaa gccggtcttg tcaatcagga tgatctggac   2940
```

```
gaagagcatc agggctcgc gccagccgaa ctgttcgcca ggctcaaggc gcgcatgccc   3000
gacggcgagg atctcgtcgt gacccatggc gatgcctgct tgccgaatat catggtggaa   3060
aatggccgct tttctggatt catcgactgt ggccggctgg gtgtggcgga tcgctatcag   3120
gacatagcgt tggctacccg tgatattgct gaagagcttg gcggcgaatg ggctgaccgc   3180
ttcctcgtgc tttacggtat cgccgctccc gattcgcagc gcatcgcctt ctatcgcctt   3240
cttgacgagt tcttctgagg ggatcaattc tctagatgca tgctcgagcg gccgccagtg   3300
tgatggatat ctgcagaatt cgcccttcca ggcgttgaag tcgtcgtgtc ctcaggtaag   3360
aacggccctc cagggccttt aatttctgct ctcgtctgtg ggcttttctg actctgatcc   3420
tcgggaggcg tctgtgcccc ccccggggat gaggccggct gccaggagg ggtcagggac   3480
caggagcctg tgggaagttc tgacggggc tgcaggcggg aagggcccca ccgggggcg   3540
agccccaggc cgctgggcgg caggagaccc gtgagagtgc gccttgagga gggtgtctgc   3600
ggaaccacga acgcccgccg ggaagggctt gctgcaatgc ggtcttcaga cgggaggcgt   3660
cttctgccct caccgtcttt caagcccttg tgggtctgaa agagcatgt cggagagaga   3720
agggacaggc ctgtcccgac ctggccgaga gcgggcagcc ccgggggaga gcggggcgat   3780
cggcctgggc tctgtgaggc caggtccaag ggaggacgtg tggtcctcgt gacaggtgca   3840
cttgcgaaac cttagaagac ggggtatgtt ggaagcggct cctgatgttt aagaaaaggg   3900
agactgtaaa gtgagcagag tcctcaagtg tgttaaggtt ttaaaggtca aagtgttta   3960
aacctttgtg actgcagtta gcaagcgtgc ggggagtgaa tgggggtgcca gggtggccga   4020
gaggcagtac gagggccgtg ccgtcctcta attcagggct tagttttgca gaataaagtc   4080
ggcctgtttt ctaaaagcat tggtggtgct gagctggtgg aggaggccgc gggcagccct   4140
ggccacctgc agcaggtggc aggaagcagg tcggccaaga ggctatttta ggaagccaga   4200
aaacacggtc gatgaattta tagcttctgg tttccaggag gtggttgggc atggctttgc   4260
gcagcgccac agaaccgaaa gtgcccactg agaaaaaaca actcctgctt aatttgcatt   4320
tttctaaaag aagaaacaga ggctgacgga aactggaaag ttcctgtttt aactactcga   4380
attgagtttt cggtcttagc ttatcaactg ctcacttaga ttcattttca aagtaaacgt   4440
ttaagagccg aggcattcct atcctcttct aaggcgttat tcctggaggc tcattcaccg   4500
ccagcacctc cgctgcctgc aggcattgct gtcaccgtca ccgtgacggc gcgcacgatt   4560
ttcagttggc ccgcttcccc tcgtgattag acagacgcg ggcactctgg cccagccgtc   4620
ttggctcagt atctgcaggc gtccgtctcg ggacggagct caggggaaga gcgtgactcc   4680
agttgaacgt gatagtcggt gcgttgagag agacccagt cgggtgtcga gtcagaaggg   4740
gcccggggcc cgaggccctg gcaggacgg cccgtgccct gcatcacggg ccagcgtcc   4800
tagaggcagg actctggtgg agagtgtgag ggtgcctggg gcccctccgg agctgggcc   4860
gtgcggtgca ggttgggctc tcggcgcggt gttggctgtt tctgcgggat ttggaggaat   4920
tcttccagtg atgggagtcg ccagtgaccg ggcaccagc tggtaagagg gaggccgccg   4980
tcgtggccag agcagctggg agggttcggt aaaaggctcg cccgtttcct ttaatgagga   5040
cttttcctgg agggcattta gtctagtcgg gaccgtttc gactcgggaa gagggatgcg   5100
gaggagggca tgtgcccagg agccgaaggc gccgcgggga aagcccagg gctctcctgt   5160
ccccacagag gcgacgccac tgccgcagac agacagggcc tttccctctg atgacggcaa   5220
aggcgcctcg gctcttgcgg ggtgctgggg gggagtcgcc ccgaagccgc tcacccagag   5280
gcctgagggg tgagactgac cgatgcctct tggccgggcc tggggccgga ccgaggggga   5340
```

```
ctccgtggag gcagggcgat ggtggctgcg ggagggaacc gaccctgggc cgagcccggc    5400
ttggcgattc ccgggcgagg gccctcagcc gaggcgagtg ggtccggcgg aaccacccTT    5460
tctggccagc gccacagggc tctcgggact gtccggggcg acgctgggct gcccgtggca    5520
ggcctgggct gacctggact tcaccagaca gaacagggct tcagggctg agctgagcca     5580 ggtttagcga ggccaagtgg ggctgaacca ggctcaactg gcctgagctg ggttgagctg    5640
ggctgacctg ggctgagctg agctgggctg ggctgggctg ggctgggctg ggctgggctg    5700
gactggctga gctgagctgg gttgagctga gctgagctgg cctgggttga gctgggctgg    5760
gttgagctga gctgggttga gctgggttga gctgggttga tctgagctga gctgggctga    5820
gctgagctag gctggggtga gctgggctga gctggtttga gttgggttga gctgagctga    5880
gctgggctgt gctggctgag ctaggctgag ctaggctagg ttgagctggg ctgggctgag    5940
ctgagctagg ctgggctgat ttgggctgag ctgagctgag ctaggctgcg ttgagctggc    6000
tgggctggat tgagctggct gagctggctg agctgggctg agctgcctg ggttgagctg     6060 agctggactg gtttgagctg ggtcgatctg ggttgagctg tcctgggttg agctgggctg    6120
ggttgagctg agctgggttg agctgggctc agcagagctg ggttgggctg agctgggttg    6180
agctgagctg ggctgagctg gcctgggttg agctgggctg agctgagctg ggctgagctg    6240
gcctgtgttg agctgggctg ggttgagctg ggctgagctg gattgagctg ggttgagctg    6300
agctgggctg ggctgtgctg actgagctgg gctgagctag gctggggtga gctgggctga    6360
gctgatccga gctaggctgg gctggttttgg gctgagctga gctgagctag gctggattga    6420
tctggctgag ctgggttgag ctgagctggg ctgagctggt ctgagctggc ctgggtcgag    6480
ctgagctgga ctggtttgag ctgggtcgat ctgggctgag ctggcctggg ttgagctggg    6540
ctgggttgag ctgagctggg ttgagctggg ctgagctgag gctggggtg agctgggctg     6600 aactagccta gctaggttgg gctgagctgg gctggtttgg gctgagctga gctgagctag    6660
gctgcattga gcaggctgag ctgggctgag caggcctggg gtgagctggg ctaggtggag    6720
ctgagctggg tcgagctgag ttgggctgag ctggcctggg ttgaggtagg ctgagctgag    6780
ctgagctagg ctgggttgag ctggctgggc tggtttgcgc tgggtcaagc tgggccgagc    6840
tggcctgggt tgagctgggc tcggttgagc tgggctgagc tgagccgacc taggctggga    6900
tgagctgggc tgatttgggc tgagctgagc tgagctaggc tgcattgagc aggctgagct    6960
gggcctggag cctggcctgg ggtgagctgg gctgagctgc gctgagctag gctgggttga    7020
gctggctggg ctggtttgcg ctgggtcaag ctgggccgag ctggcctggg atgagctggg    7080
ccggtttggg ctgagctgag ctgagctagg ctgcattgag caggctgagc tgggctgagc    7140
tggcctgggg tgagctgggc tgagctaagc tgagctgggc tggtttgggc tgagctggct    7200
gagctgggtc ctgctgagct gggctgagct gaccaggggt gagctgggct gagttaggct    7260
gggctcagct aggctgggtt gatctggcag ggctggtttg cgctgggtca agctcccggg    7320
agatggcctg ggatgagctg ggctggtttg ggctgagctg agctgagctg agctaggctg    7380
cattgagcag gctgagctgg gctgagctgg cctggggtga gctgggctgg gtggagctga    7440
gctgggctga actgggctaa gctggctgag ctggatcgag ctgagctggg ctgagctggc    7500
ctggggttag ctgggctgag ctgggctgag ctaggctggg ttgagctggc tgggctggtt    7560
tgcgctgggc caagctgggc cgagctgcc tgggttgagc tgggctgggc tgagctgagc     7620
taggctgggt tgagctgggc tgggctgagc tgagctaggc tgcattgagc tggctgggat    7680
```

-continued

```
ggattgagct ggctgagctg gctgagctgg ctgagctggg ctgagctggg ctgggttgag     7740
ctgggctggg ttgagctgag ctgggctgag ctgggctcag cagagctggg ttgagctgag     7800
ctgggttgag ctggggtgag ctgggctgag cagagctggg ttgagctgag ctgggttgag     7860
ctgggctcga gcagagctgg gttgagctga gctgggttga gctgggctca gcagagctgg     7920
gttgagctga gctgggttga gctgggctga gctagctggg ctcagctagg ctgggttgag     7980
ctgagctggg ctgaactggg ctgagctggg ctgaactggg ctgagctggg ctgagctggg     8040
ctgagcagag ctgggctgag cagagctggg ttggtctgag ctgggttgag ctgggctgag     8100
ctgggctgag cagagttggg ttgagctgag ctgggttcag ctgggctgag ctaggctggg     8160
ttgagctggg ttgagttggg ctgagctggg ctgggttgag cggagctggg ctgaactggg     8220
ctgagctggg ctgagcggaa ctgggttgat ctgaattgag ctgggctgag ccgggctgag     8280
ccgggctgag ctgggctagg ttgagcttgg gtgagcttgc ctcagctggt ctgagctagg     8340
ttgggtggag ctaggctgga ttgagctggg ctgagctgag ctgatctggc ctcagctggg     8400
ctgaggtagg ctgaactggg ctgtgctggg ctgagctgag ctgagccagt ttgagctggg     8460
ttgagctggg ctgagctggg ctgtgttgat cttccctgaa ctgggctgag ctgggctgag     8520
ctggcctagc tggattgaac gggggtaagc tgggccaggc tggactgggc tgagctgagc     8580
taggctgagc tgagttgaat tgggttaagc tgggctgaga tgggctgagc tgggctgagc     8640
tgggttgagc caggtcggac tgggttaccc tgggccacac tgggctgagc tgggcggagc     8700
tcgattaacc tggtcaggct gagtcgggtc cagcagacat gcgctggcca ggctggcttg     8760
acctggacac gttcgatgag ctgccttggg atggttcacc tcagctgagc caggtggctc     8820
cagctgggct gagctggtga ccctgggtga cctcggtgac caggttgtcc tgagtccggg     8880
ccaagccgag gctgcatcag actcgccaga cccaaggcct gggccccggc tggcaagcca     8940
ggggcggtga aggctgggct ggcaggactg tcccggaagg aggtgcacgt ggagccgccc     9000
ggaccccgac cggcaggacc tggaaagacg cctctcactc cccttctct tctgtccct      9060 ctcgggtcct cagagagcca gtctgccccg aatctctacc ccctcgtctc ctgcgtcagc     9120
cccccgtccg atgagagcct ggtggccctg ggctgcctgg cccgggactt cctgcccagc     9180
tccgtcacct tctcctggaa                                                 9200
```

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
tctagaagac gctggagaga ggccag                                          26

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
taaagcgcat gctccagact gcctt                                           25

<210> SEQ ID NO 8
<211> LENGTH: 22

```
<212> TYPE: DNA
<213> ORGANISM: Artificial Sequence
<220> FEATURE:
<223> OTHER INFORMATION: Synthetic

<400> SEQUENCE: 8
catcgccttc tatcgccttc tt                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
aagtacttgc cgcctctcag ga                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
caaggagacc aagctggaac tc                                              22

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
tgatcaagca caccacagag acag                                            24

<210> SEQ ID NO 12
<211> LENGTH: 4277
<212> TYPE: DNA
<213> ORGANISM: Sus sp.

<400> SEQUENCE: 12
caaggaacca agctggaact caaacgtaag tcaatccaaa cgttccttcc ttggctgtct      60
gtgtcttacg gtctctgtgg ctctgaaatg attcatgtgc tgactctctg aaaccagact     120
gacattctcc agggcaaaac taaagcctgt catcaaactg gaaaactgag ggcacatttt     180
ctgggcagaa ctaagagtca ggcactgggt gaggaaaaac ttgttagaat gatagtttca     240
gaaacttact gggaagcaaa gcccatgttc tgaacagagc tctgctcaag ggtcaggagg     300
ggaaccagtt tttgtacagg agggaagttg agacgaaccc ctgtgtatat ggtttcggcg     360
cggggaccaa gctggagctc aaacgtaagt ggcttttttcc gactgattct ttgctgtttc    420
taattgttgg ttggcttttt gtccattttt cagtgttttc atcgaattag ttgtcaggga     480
ccaaacaaat tgccttccca gattaggtac caggagggg acattgctgc atgggagacc      540
agagggtggc taatttttaa cgtttccaag ccaaataaac tggggaaggg ggcttgctgt     600
cctgtgaggg taggttttta tagaagtgga agttaagggg aaatcgctat ggttcacttt     660
tggctcgggg accaaagtgg agcccaaaat tgagtacatt ttccatcaat tatttgtgag     720 attttttgtcc tgttgtgtca tttgtgcaag ttttttgacat tttggttgaa tgagccattc    780
```

```
ccagggaccc aaaaggatga gaccgaaaag tagaaaagag ccaactttta agctgagcag   840
acagaccgaa ttgttgagtt tgtgaggaga gtagggtttg tagggagaaa ggggaacaga   900
tcgctggctt tttctctgaa ttagcctttc tcatgggact ggcttcagag ggggttttg    960 atgagggaag tgttctagag ccttaactgt gggttgtgtt cggtagcggg accaagctgg  1020
aaatcaaacg taagtgcact tttctactcc tttttctttc ttatacgggt gtgaaattgg  1080
ggacttttca tgtttggagt atgagttgag gtcagttctg aagagagtgg gactcatcca  1140
aaaatctgag gagtaagggt cagaacagag ttgtctcatg gaagaacaaa gacctagtta  1200
gttgatgagg cagctaaatg agtcagttga cttgggatcc aaatggccag acttcgtctg  1260
taaccaacaa tctaatgaga tgtagcagca aaaagagatt tccattgagg ggaaagtaaa  1320
attgttaata ttgtggatca cctttggtga agggacatcc gtggagattg aacgtaagta  1380
ttttttctct actaccttct gaaatttgtc taaatgccag tgttgacttt tagaggctta  1440
agtgtcagtt ttgtgaaaaa tgggtaaaca agagcatttc atatttatta tcagtttcaa  1500
aagttaaact cagctccaaa aatgaatttg tagacaaaaa gattaattta agccaaattg  1560
aatgattcaa aggaaaaaaa aattagtgta gatgaaaaag gaattcttac agctccaaag  1620
agcaaaagcg aattaatttt ctttgaactt tgccaaatct tgtaaatgat ttttgttctt  1680
tacaatttaa aaaggttaga gaaatgtatt tcttagtctg ttttctctct tctgtctgat  1740
aaattattat atgagataaa aatgaaaatt aataggatgt gctaaaaaat cagtaagaag  1800
ttagaaaaat atatgtttat gttaaagttg ccacttaatt gagaatcaga agcaatgtta  1860
tttttaaagt ctaaaatgag agataaactg tcaatactta aattctgcag agattctata  1920
tcttgacaga tatctccttt ttcaaaaatc caatttctat ggtagactaa atttgaaatg  1980
atcttcctca taatggaggg aaaagatgga ctgaccccaa aagctcagat ttaagaaaac  2040
ctgtttaagg aaagaaaata aaagaactgc atttttaaaa ggcccatgaa tttgtagaaa  2100
aataggaaat attttaataa gtgtattctt ttattttcct gttattactt gatggtgttt  2160
ttataccgcc aaggaggccg tggcaccgtc agtgtgatct gtagacccca tggcggcctt  2220
ttttcgcgat tgaatgacct tggcggtggg tccccagggc tctggtggca gcgcaccagc  2280
cgctaaaagc cgctaaaaac tgccgctaaa ggccacagca accccgcgac cgcccgttca  2340
actgtgctga cacagtgata cagataatgt cgctaacaga ggagaataga aatatgacgg  2400
gcacacgcta atgtggggaa aagagggaga agcctgattt ttattttta gagattctag  2460 agataaaatt cccagtatta tatccttta ataaaaaatt tctattagga gattataaag  2520
aatttaaagc tatttttta agtggggtgt aattctttca gtagtctctt gtcaaatgga  2580
tttaagtaat agaggcttaa tccaaatgag agaaatagac gcataaccct tcaaggcaa   2640 aagctacaag agcaaaaatt gaacacagca gccagccatc tagccactca gattttgatc  2700
agttttactg agtttgaagt aaatatcatg aaggtataat tgctgataaa aaataagat   2760 acaggtgtga cacatcttta agtttcagaa atttaatggc ttcagtagga ttatatttca  2820
cgtatacaaa gtatctaagc agataaaaat gccattaatg gaaacttaat agaaatatat  2880
ttttaaattc cttcattctg tgacagaaat tttctaatct gggtctttta atcacctacc  2940
ctttgaaaga gtttagtaat ttgctatttg ccatcgctgt ttactccagc taatttcaaa  3000
agtgatactt gagaaagatt ttttttggtt tgcaaccacc tggcaggact attttagggc  3060
cattttaaaa ctcttttcaa actaagtatt ttaaactgtt ctaaaccatt tagggccttt  3120
taaaaatctt ttcatgaatt tcaaacttcg ttaaaagtta ttaaggtgtc tggcaagaac  3180
```

| | | | | |
|---|---|---|---|---|
| ttccttatca | aatatgctaa | tagtttaatc | tgttaatgca | ggatataaaa | ttaaagtgat | 3240 |
| caaggcttga | cccaaacagg | agtatcttca | tagcatattt | cccctccttt | tttttctagaa | 3300 |
| ttcatatgat | tttgctgcca | aggctatttt | atataatctc | tggaaaaaaa | atagtaatga | 3360 |
| aggttaaaag | agaagaaaat | atcagaacat | taagaattcg | gtattttact | aactgcttgg | 3420 |
| ttaacatgaa | ggtttttatt | ttattaaggt | ttctatcttt | ataaaaatct | gttccctttt | 3480 |
| ctgctgattt | ctccaagcaa | aagattcttg | atttgttttt | taactcttac | tctcccaccc | 3540 |
| aagggcctga | atgcccacaa | aggggacttc | caggaggcca | tctggcagct | gctcaccgtc | 3600 |
| agaagtgaag | ccagccagtt | cctcctgggc | aggtggccaa | aattacagtt | gacccctcct | 3660 |
| ggtctggctg | aaccttgccc | catatggtga | cagccatctg | gccagggccc | aggtctccct | 3720 |
| ctgaagcctt | tgggaggaga | gggagagtgg | ctggcccgat | cacagatgcg | aaggggctg | 3780 |
| actcctcaac | cggggtgcag | actctgcagg | gtgggtctgg | gcccaacaca | cccaaagcac | 3840 |
| gcccaggaag | gaaaggcagc | ttggtatcac | tgcccagagc | taggagaggc | accgggaaaa | 3900 |
| tgatctgtcc | aagacccgtt | cttgcttcta | aactccgagg | gggtcagatg | aagtggtttt | 3960 |
| gtttcttggc | ctgaagcatc | gtgttccctg | caagaagcgg | ggaacacaga | ggaaggagag | 4020 |
| aaaagatgaa | ctgaacaaag | catgcaaggc | aaaaaaggcc | ttaggatggc | tgcaggaagt | 4080 |
| tagttcttct | gcattggctc | cttactggct | cgtcgatcgc | ccacaaacaa | cgcacccagt | 4140 |
| ggagaacttc | cctgttactt | aaacaccatt | ctctgtgctt | gcttcctcag | gggctgatgc | 4200 |
| caagccatcc | gtcttcatct | tcccgccatc | gaaggagcag | ttagcgaccc | caactgtctc | 4260 |
| tgtggtgtgc | ttgatca | | | | | 4277 |

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
gatgccaagc catccgtctt catc                                       24

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
tgaccaaagc agtgtgacgg ttgc                                       24

<210> SEQ ID NO 15
<211> LENGTH: 2027
<212> TYPE: DNA
<213> ORGANISM: Sus sp.

<400> SEQUENCE: 15

| | | | | | |
|---|---|---|---|---|---|---|
| gatgccaagc | catccgtctt | catcttcccg | ccatcgaagg | agcagttagc | gaccccaact | 60 |
| gtctctgtgg | tgtgcttgat | caataacttc | ttccccagag | aaatcagtgt | caagtggaaa | 120 |
| gtggatgggg | tggtccaaag | cagtggtcat | ccggatagtg | tcacagagca | ggacagcaag | 180 |
| gacagcacct | acagcctcag | cagcaccctc | tcgctgccca | cgtcacagta | cctaagtcat | 240 |

| | |
|---|---|
| aatttatatt cctgtgaggt cacccacaag accctggcct cccctctggt cacaagcttc | 300 |
| aacaggaacg agtgtgaggc ttagaggccc acaggcccct ggcctgcccc cagccccagc | 360 |
| ccccctcccc acctcaagcc tcaggccctt gcccagagg atccttggca atcccccagc | 420 |
| ccctcttccc tcctcatccc ctcccctct ttggctttaa ccgtgttaat actggggggt | 480 |
| gggggaatga ataaataaag tgaacctttg cacctgtgat ttctctctcc tgtctgattt | 540 |
| taaggttgtt aaatgttgtt ttccccatta tagttaatct tttaaggaac tacatactga | 600 |
| gttgctaaaa actacaccat cacttataaa attcacgcct tctcagttct cccctcccct | 660 |
| cctgtcctcc gtaagacagg cctccgtgaa acccataagc acttctcttt cacccctctc | 720 |
| ctgggccggg gtaggagact ttttgatgtc ccctcttcag caagcctcag aaccattttg | 780 |
| aggggacag ttcttacagt cacattcctg tgatcaatg actttagtta ccgaaaagcc | 840 |
| agtctctcaa aagaaggga acggctagaa accaagtcat agaaatatat atgtataaaa | 900 |
| tatatatata tccatatatg taaaataaca aataatgat aacagcatag gtcaacaggc | 960 |
| aacagggaat gttgaagtcc attctggcac ttcaattaa gggaatagga tgccttcatt | 1020 |
| acattttaaa tacaatacac atggagagct tcctatctgc caaagaccat cctgaatgcc | 1080 |
| ttccacactc actacaaggt taaaagcatt cattacaatg ttgatcgagg agttcccgtt | 1140 |
| gtggctcagc aggttaagaa cgtgactggt atccaggagg atgcgggttt ggtccccagc | 1200 |
| ctcgctcagt ggattaagga tccagtgttg ctgcaagatc acgggctcag atcccgtgtt | 1260 |
| ctatggctat ggtgtaggct ggtagctgca tgcagcccta atttgacccc tagcctggga | 1320 |
| actgccatat gccacatgtg aggcccttaa aacctaaaag aaaaaaaag aaaagaaata | 1380 |
| tcttacaccc aatttataga taagagagaa gctaaggtgg caggcccagg atcaaagccc | 1440 |
| tacctgccta tcttgacacc tgatacaaat tctgtcttct agggtttcca acactgcata | 1500 |
| gaacagaggg tcaaacatgc taccctccca gggactcctc ccttcaaatg acataaattt | 1560 |
| tgttgcccat ctctggggc aaaactcaac aatcaatggc atctctagta ccaagcaagg | 1620 |
| ctcttctcat gaagcaaaac tctgaagcca gatccatcat gacccaagga agtaaagaca | 1680 |
| ggtgttactg gttgaactgt atccttcaat tcaatatgct caatttccaa ctcccagtcc | 1740 |
| ccgtaaatac aaccccc ttt gggaagagag tccttgcaga tgtagccacg ttaaaaagag | 1800 |
| attatacaga aaggctagtg aggatgcagt gaaacgggac cttcataca ttgctggtgg | 1860 |
| aaatgtaaaa tgctgcaggc actctagaaa ataatttgcc agtttttga aaagctaaac | 1920 |
| aaaatagttt agttgcattc tgggttattt atccccaga aattaaaaat tatgtccgca | 1980 |
| caaaaacgtg tacataatca ttcataacag ccttgtacga aaagctt | 2027 |

<210> SEQ ID NO 16
<211> LENGTH: 3918
<212> TYPE: DNA
<213> ORGANISM: Sus sp.

<400> SEQUENCE: 16

| | |
|---|---|
| ggatccttaa cccactaatc gaggatcaaa cacgcatcct catggacaat atgttgggtt | 60 |
| cttagcctgc tgagacacaa caggaactcc cctggcacca ctttagaggc cagagaaaca | 120 |
| gcacagataa aattccctgc cctcatgaag cttatagtct agctggggag atatcatagg | 180 |
| caagataaac acatacaaat acatcatctt aggtaataat atatactaag gagaaaatta | 240 |
| caggggagaa agaggacagg aattgctagg gtaggattat aagttcagat agttcatcag | 300 |
| gaacactgtt gctgagaaga taacatttag gtaaagaccg aagtagtaag gaaatggacc | 360 |

```
gtgtgcctaa gtgggtaaga ccattctagg cagcaggaac agcgatgaaa gcactgaggt    420
gggtgttcac tgcacagagt tgttcactgc acagagttgt gtggggaggg gtaggtcttg    480
caggctctta tggtcacagg aagaattgtt ttactcccac cgagatgaag gttggtggat    540
tttgagcaga agaataattc tgcctggttt atatataaca ggatttccct gggtgctctg    600
atgagaataa tctgtcaggg gtgggatagg gagagatatg gcaataggag ccttggctag    660
gagcccacga caataattcc aagtgagagg tggtgctgca ttgaaagcag gactaacaag    720
acctgctgac agtgtggatg tagaaaaaga tagaggagac gaaggtgcat ctagggtttt    780
ctgcctgagg aattagaaag ataaagctaa agcttataga agatgcagcg ctctggggag    840
aaagaccagc agctcagttt tgatccatct ggaattaatt ttggcataaa gtatgaggta    900
tgtgggttaa cattatttgt ttttttttt tccatgtagc tatccaactg tcccagcatc    960
atttatttta aaagactttc ctttccccta ttggattgtt ttggcacctt cactgaagat   1020
caactgagca taaattggg tctatttcta agctcttgat tccattccat gacctatttg   1080
ttcatcttta ccccagtaga cactgccttg atgattaaag cccctgttac catgtctgtt   1140
ttggacatgg taaatctgag atgcctatta gccaaccaag caagcacggc ccttagagag   1200
ctagatatga gagcctggaa ttcagacgag aaaggtcagt cctagagaca tacatgtagt   1260
gccatcacca tgcggatggt gttaaaagcc atcagactgc aacagactgt gagagggtac   1320
caagctagag agcatggata gagaaaccca agcactgagc tgggaggtgc tcctacatta   1380
agagattagt gagatgaagg actgagaaga ttgatcagag aagaaggaaa atcaggaaaa   1440
tggtgctgtc ctgaaaatcc aagggaagag atgttccaaa gaggagaaaa ctgatcagtt   1500
gtcagctagc gtcaattggg atgaaaatgg accattggac agagggatgt agtgggtcat   1560
gggtgaatag ataagagcag cttctataga atggcagggg caaaattctc atctgatcgg   1620
catgggttct aaagaaaacg ggaagaaaaa attgagtgca tgaccagtcc cttcaagtag   1680
agaggtggaa aagggaagga ggaaaatgag gccacgacaa catgagagaa atgacagcat   1740
ttttaaaaat ttttttatttt attttattta tttattttg cttttaggg ctgcccctgc   1800 aacatatgga ggttcccagg ttaggggtct aatcagagct atagctgcca gcctacacca   1860
cagccatagc aatgccagat ctacatgacc tacaccacag ctcacagcaa cgccggatcc   1920
ttaacccact gagtgaggcc agagatcaaa cccatatcct tatggatact agtcaggttc   1980
attaccactg agccaaaatg ggaaatcctg agtaatgaca gcatttttta atgtgccagg   2040
aagcaaaact tgccaccccg aaatgtctct caggcatgtg gattattttg agctgaaaac   2100
gattaaggcc caaaaaacac aagaagaaat gtggaccttc ccccaacagc ctaaaaaatt   2160
tagattgagg gcctgttccc agaatagagc tattgccaga cttgtctaca gaggctaagg   2220
gctaggtgtg gtggggaaac cctcagagat cagagggacg tttatgtacc aagcattgac   2280
atttccatct ccatgcgaat ggccttcttc ccctctgtag ccccaaacca ccaccccaa   2340 aatcttcttc tgtctttagc tgaagatggt gttgaaggtg atagtttcag ccactttggc   2400
gagttcctca gttgttctgg gtctttcctc cggatccaca ttattcgact gtgtttgatt   2460
ttctcctgtt tatctgtctc attggcaccc atttcattct tagaccagcc caaagaacct   2520
agaagagtga aggaaaattt cttccaccct gacaaatgct aaatgagaat caccgcagta   2580
gaggaaaatg atctggtgct gcgggagata aagagaaaa tcgctggaga gatgtcactg   2640
agtaggtgag atgggaaagg gggggcacag gtggaggtgt tgccctcagc taggaagaca   2700
```

```
gacagttcac agaagagaag cgggtgtccg tggacatctt gcctcatgga tgaggaaacc    2760
gaggctaaga aagactgcaa aagaaaggta aggattgcag agaggtcgat ccatgactaa    2820
aatcacagta accaacccca aaccaccatg ttttctccta gtctggcacg tggcaggtac    2880
tgtgtaggtt ttcaatatta ttggtttgta acagtaccta ttaggcctcc atcccctcct    2940
ctaatactaa caaaagtgtg agactggtca gtgaaaaatg gtcttctttc tctatgcaat    3000
ctttctcaag aagatacata acttttattt ttatcatagg cttgaagagc aaatgagaaa    3060
cagcctccaa cctatgacac cgtaacaaag tgtttatgat cagtgaaggg caagaaacaa    3120
aacatacaca gtaaagaccc tccataatat tgtgggctgg cccaacacag gccaggttgt    3180
aaaagctttt tattctttga tagaggaatg gatagtaatg tttcaacctg gacagagatc    3240
atgttcactg aatccttcca aaaattcatg ggtagtttga attataagga aaataagact    3300
taggataaat actttgtcca gatcccagag ttaatgccaa aatcagtttt cagactccag    3360
gcagcctgat caagagccta aactttaaag acacagtccc ttaataacta ctattcacag    3420
ttgcactttc agggcgcaaa gactcattga atcctacaat agaatgagtt tagatatcaa    3480
atctctcagt aatagatgag gagactaaat agcgggcatg acctggtcac ttaaagacag    3540
aattgagatt caaggctagt gttctttcta cctgttttgt ttctacaaga tgtagcaatg    3600
cgctaattac agacctctca gggaaggaat tcacaaccct cagcaaaaac caaagacaaa    3660
tctaagacaa ctaagagtgt tggtttaatt tggaaaaata actcactaac caaacgcccc    3720
tcttagcacc ccaatgtctt ccaccatcac agtgctcagg cctcaaccat gccccaatca    3780
ccccagcccc agactggtta ttaccaagtt tcatgatgac tggcctgaga agatcaaaaa    3840
agcaatgaca tcttacaggg gactaccccg aggaccaaga tagcaactgt catagcaacc    3900
gtcacactgc tttggtca                                                 3918

<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
ggatcaaaca cgcatcctca tggac                                           25

<210> SEQ ID NO 18
<211> LENGTH: 22
<212> TYPE: DNA
<213> ORGANISM: Artificial Sequence
<220> FEATURE:
<223> OTHER INFORMATION: Synthetic

<400> SEQUENCE: 18
ggtgattggg gcatggttga gg                                              22

<210> SEQ ID NO 19
<211> LENGTH: 3759
<212> TYPE: DNA
<213> ORGANISM: Sus sp.

<400> SEQUENCE: 19
ggatcaaaca cgcatcctca tggacaatat gttgggttct tagcctgctg agacacaaca     60
ggaactcccc tggcaccact ttagaggcca gagaaacagc acagataaaa ttccctgccc    120
tcatgaagct tatagtctag ctggggagat atcataggca agataaacac atacaaatac    180
```

```
atcatcttag gtaataatat atactaagga gaaaattaca ggggagaaag aggacaggaa    240
ttgctagggt aggattataa gttcagatag ttcatcagga acactgttgc tgagaagata    300
acatttaggt aaagaccgaa gtagtaagga aatggaccgt gtgcctaagt gggtaagacc    360
attctaggca gcaggaacag cgatgaaagc actgaggtgg gtgttcactg cacagagttg    420
ttcactgcac agagttgtgt ggggaggggt aggtcttgca ggctcttatg gtcacaggaa    480
gaattgtttt actcccaccg agatgaaggt tggtggattt tgagcagaag aataattctg    540
cctggtttat atataacagg atttccctgg gtgctctgat gagaataatc tgtcaggggt    600 gggatagggga gagatatggc aataggagcc ttggctagga gcccacgaca ataattccaa    660
gtgagaggtg gtgctgcatt gaaagcagga ctaacaagac ctgctgacag tgtggatgta    720
gaaaaagata gaggagacga aggtgcatct agggttttct gcctgaggaa ttagaaagat    780
aaagctaaag cttatagaag atgcagcgct ctggggagaa agaccagcag ctcagttttg    840
atccatctgg aattaatttt ggcataaagt atgaggtatg tggttaaca ttatttgttt    900 ttttttttc catgtagcta tccaactgtc ccagcatcat ttattttaaa agactttcct    960
ttcccctatt ggattgtttt ggcaccttca ctgaagatca actgagcata aaattgggtc   1020
tatttctaag ctcttgattc cattccatga cctatttgtt catctttacc ccagtagaca   1080
ctgccttgat gattaaagcc cctgttacca tgtctgtttt ggacatggta atctgagat   1140 gcctattagc caaccaagca agcacggccc ttagagagct agatatgaga gcctggaatt   1200
cagacgagaa aggtcagtcc tagagacata catgtagtgc catcaccatg cggatggtgt   1260
taaaagccat cagactgcaa cagactgtga gagggtacca agctagagag catggataga   1320
gaaacccaag cactgagctg ggaggtgctc ctacattaag agattagtga gatgaaggac   1380
tgagaagatt gatcagagaa gaaggaaaat caggaaaatg gtgctgtcct gaaaatccaa   1440
gggaagagat gttccaaaga ggagaaaact gatcagttgt cagctagcgt caattgggat   1500
gaaaatggac cattggacag agggatgtag tgggtcatgg gtgaatagat aagagcagct   1560
tctatagaat ggcaggggca aaattctcat ctgatcggca tgggttctaa agaaaacggg   1620
aagaaaaaat tgagtgcatg accagtccct tcaagtagag aggtggaaaa gggaaggagg   1680
aaaatgaggc cacgcaaaca tgagagaaat gacagcattt ttaaaaattt tttattttat   1740
tttatttatt tatttttgct ttttagggct gcccctgcaa catatggagg ttcccaggtt   1800
aggggtctaa tcagagctat agctgccagc ctacaccaca gccatagcaa tgccagatct   1860
acatgaccta caccacagct cacagcaacg ccggatcctt aacccactga gtgaggccag   1920
agatcaaacc catatcctta tggatactag tcaggttcat taccactgag ccaaaatggg   1980
aaatcctgag taatgacagc attttttaat gtgccaggaa gcaaaacttg ccaccccgaa   2040
atgtctctca ggcatgtgga ttattttgag ctgaaaacga ttaaggccca aaaaacacaa   2100
gaagaaatgt ggaccttccc ccaacagcct aaaaaattta gattgagggc ctgttcccag   2160
aatagagcta ttgccagact tgtctacaga ggctaagggc taggtgtggt ggggaaaccc   2220
tcagagatca gagggacgtt tatgtaccaa gcattgacat ttccatctcc atgcgaatgg   2280
ccttcttccc ctctgtagcc ccaaaccacc accccccaaaa tcttcttctg tctttagctg   2340
aagatggtgt tgaaggtgat agtttcagcc actttggcga gttcctcagt tgttctgggt   2400 cttttcctcct gatccacatt attcgactgt gtttgatttt ctcctgttta tctgtctcat   2460
tggcacccat ttcattctta gaccagccca aagaacctag aagagtgaag gaaaatttct   2520
```

| | | |
|---|---|---|
| tccaccctga caaatgctaa atgagaatca ccgcagtaga ggaaaatgat ctggtgctgc | 2580 | |
| gggagataga agagaaaatc gctggagaga tgtcactgag taggtgagat gggaaagggg | 2640 | |
| tgacacaggt ggaggtgttg ccctcagcta ggaagacaga cagttcacag aagagaagcg | 2700 | |
| ggtgtccgtg gacatcttgc ctcatggatg aggaaaccga ggctaagaaa gactgcaaaa | 2760 | |
| gaaaggtaag gattgcagag aggtcgatcc atgactaaaa tcacagtaac caaccccaaa | 2820 | |
| ccaccatgtt ttctcctagt ctggcacgtg gcaggtactg tgtaggtttt caatattatt | 2880 | |
| ggtttgtaac agtacctatt aggcctccat cccctcctct aatactaaca aaagtgtgag | 2940 | |
| actggtcagt gaaaaatggt cttctttctc tatgaatctt tctcaagaag atacataact | 3000 | |
| ttttatttta tcataggctt gaagagcaaa tgagaaacag cctccaacct atgacaccgt | 3060 | |
| aacaaaatgt ttatgatcag tgaagggcaa gaaacaaaac atacacagta aagaccctcc | 3120 | |
| ataatattgt gggtggccca acacaggcca ggttgtaaaa gcttttttatt ctttgataga | 3180 | |
| ggaatggata gtaatgtttc aacctggaca gagatcatgt tcactgaatc cttccaaaaa | 3240 | |
| ttcatgggta gtttgaatta taaggaaaat aagacttagg ataaatactt tgtccaagat | 3300 | |
| cccagagtta atgccaaaat cagttttcag actccaggca gcctgatcaa gagcctaaac | 3360 | |
| tttaaagaca cagtccctta ataactacta ttcacagttg cactttcagg gcgcaaagac | 3420 | |
| tcattgaatc ctacaataga atgagtttag atatcaaatc tctcagtaat agatgaggag | 3480 | |
| actaaatagc gggcatgacc tggtcactta agacagaat tgagattcaa ggctagtgtt | 3540 | |
| cttctaccct gttttgtttc tacaagatgt agcaatgcgc taattacaga cctctcaggg | 3600 | |
| aaggaattca caaccctcag caaaaaccaa agacaaatct aagacaacta agagtgttgg | 3660 | |
| tttaatttgg aaaaataact cactaaccaa acgcccctct tagcaccca atgtcttcca | 3720 | |
| ccatcacagt gctcaggcct caaccatgcc ccaatcacc | 3759 | |

<210> SEQ ID NO 20
<211> LENGTH: 9010
<212> TYPE: DNA
<213> ORGANISM: Sus sp.

<400> SEQUENCE: 20

| | | |
|---|---|---|
| ctcaaacgta agtggctttt tccgactgat tctttgctgt ttctaattgt tggttggctt | 60 | |
| tttgtccatt tttcagtgtt ttcatcgaat tagttgtcag ggaccaaaca aattgccttc | 120 | |
| ccagattagg taccagggag gggacattgc tgcatgggag accagagggt ggctaatttt | 180 | |
| taacgttttcc aagccaaaat aactggggaa ggggcttgc tgtcctgtga gggtaggttt | 240 | |
| ttatagaagt ggaagttaag gggaaatcgc tatggttcac ttttggctcg gggaccaaag | 300 | |
| tggagcccaa aattgagtac attttccatc aattatttgt gagattttg tcctgttgtg | 360 | |
| tcatttgtgc aagttttga cattttggtt gaatgagcca ttcccaggga cccaaaagga | 420 | |
| tgagaccgaa aagtagaaaa gagccaactt ttaagctgag cagacagacc gaattgttga | 480 | |
| gtttgtgagg agagtagggt ttgtagggag aaagggaac agatcgctgg ctttttctct | 540 | |
| gaattagcct ttctcatggg actggcttca gaggggggttt ttgatgaggg aagtgttcta | 600 | |
| gagccttaac tgtgggttgt gttcggtagc gggaccaagc tggaaatcaa acgtaagtgc | 660 | |
| actttctac tccttttct ttcttatacg ggtgtgaaat tggggacttt tcatgtttgg | 720 | |
| agtatgagtt gaggtcagtt ctgaagagag tgggactcat ccaaaaatct gaggagtaag | 780 | |
| ggtcagaaca gagttgtctc atggaagaac aaagacctag ttagttgatg aggcagctaa | 840 | |
| atgagtcagt tgacttggga tccaaatggc cagacttcgt ctgtaaccaa caatctaatg | 900 | |

```
agatgtagca gcaaaaagag atttccattg aggggaaagt aaaattgtta atattgtgga     960
tcacctttgg tgaagggaca tccgtggaga ttgaacgtaa gtatttttc tctactacct    1020
tctgaaattt gtctaaatgc cagtgttgac ttttagaggc ttaagtgtca gttttgtgaa    1080
aaatgggtaa acaagagcat ttcatattta ttatcagttt caaaagttaa actcagctcc    1140
aaaaatgaat ttgtagacaa aaagattaat ttaagccaaa ttgaatgatt caaaggaaaa    1200
aaaaattagt gtagatgaaa aaggaattct tacagctcca aagagcaaaa gcgaattaat    1260
tttctttgaa ctttgccaaa tcttgtaaat gattttgtt ctttacaatt taaaaaggtt    1320
agagaaatgt atttcttagt ctgttttctc tcttctgtct gataaattat tatatgagat    1380
aaaaatgaaa attaatagga tgtgctaaaa aatcagtaag aagttagaaa atatatgtt    1440
tatgttaaag ttgccactta attgagaatc agaagcaatg ttatttttaa agtctaaaat    1500
gagagataaa ctgtcaatac ttaaattctg cagagattct atatcttgac agatatctcc    1560
ttttcaaaa atccaatttc tatggtagac taaatttgaa atgatcttcc tcataatgga    1620
gggaaaagat ggactgaccc caaaagctca gatttaagaa aacctgttta aggaaagaaa    1680
ataaaagaac tgcattttt aaaggcccat gaatttgtag aaaaatagga atatttaa     1740
taagtgtatt ctttattt cctgttatta cttgatggtg tttttatacc gccaaggagg    1800
ccgtggcacc gtcagtgtga tctgtagacc ccatggcggc cttttttcgc gattgaatga    1860
ccttggcggt gggtccccag ggctctggtg gcagcgcacc agccgctaaa agccgctaaa    1920
aactgccgct aaaggccaca gcaacccgc gaccgcccgt tcaactgtgc tgacacagtg    1980
atacagataa tgtcgctaac agaggagaat agaaatatga cgggcacacg ctaatgtggg    2040
gaaaagaggg agaagcctga tttttatttt ttagagattc tagagataaa attcccagta    2100
ttatatcctt ttaataaaaa atttctatta ggagattata aagaatttaa agctatttt    2160
ttaagtgggg tgtaattctt tcagtagtct cttgtcaaat ggatttaagt aatagaggct    2220
taatccaaat gagagaaata gacgcataac cctttcaagg caaaagctac aagagcaaaa    2280
attgaacaca gcagccagcc atctagccac tcagattttg atcagtttta ctgagtttga    2340
agtaaatatc atgaaggtat aattgctgat aaaaaaataa gatacaggtg tgacacatct    2400
ttaagtttca gaaatttaat ggcttcagta ggattatatt tcacgtatac aaagtatcta    2460
agcagataaa aatgccatta atggaaactt aatagaaata tatttttaaa ttccttcatt    2520
ctgtgacaga aattttctaa tctgggtctt ttaatcacct acccttgaa agagtttagt    2580
aatttgctat ttgccatcgc tgtttactcc agctaatttc aaaagtgata cttgagaaag    2640
attattttg gtttgcaacc acctggcagg actattttag ggccatttta aaactctttt    2700
caaactaagt attttaaact gttctaaacc atttagggcc ttttaaaaat cttttcatga    2760
atttcaaact tcgttaaaag ttattaaggt gtctggcaag aacttcctta tcaaatatgc    2820
taatagttta atctgttaat gcaggatata aaattaaagt gatcaaggct tgacccaaac    2880
aggagtatct tcatagcata tttcccctcc ttttttcta gaattcatat gattttgctg    2940
ccaaggctat tttatataat ctctggaaaa aaaatagtaa tgaaggttaa aagagaagaa    3000
aatatcagaa cattaagaat tcggtatttt actaactgct tggttaacat gaaggtttt     3060
atttattaa ggtttctatc tttataaaaa tctgttccct tttctgctga tttctccaag    3120
caaaagattc ttgatttgtt ttttaactct tactctccca cccaagggcc tgaatgccca    3180
caagggggac ttccaggagg ccatctggca gctgctcacc gtcagaagtg aagccagcca    3240
```

```
gttcctcctg ggcaggtggc caaaattaca gttgacccct cctggtctgg ctgaaccttg    3300
ccccatatgg tgacagccat ctggccaggg cccaggtctc cctctgaagc ctttgggagg    3360
agagggagag tggctggccc gatcacagat gcggaagggg ctgactcctc aaccggggtg    3420
cagactctgc agggtgggtc tgggcccaac acacccaaag cacgcccagg aaggaaaggc    3480
agcttggtat cactgcccag agctaggaga ggcaccggga aaatgatctg tccaagaccc    3540
gttcttgctt ctaaactccg aggggtcag atgaagtggt tttgtttctt ggcctgaagc     3600
atcgtgttcc ctgcaagaag cggggaacac agaggaagga gagaaagat gaactgaaca     3660 aagcatgcaa ggcaaaaaag ggggtctagc cgcggtctag aagctttct agggtacctc     3720 tagggatccc ggcgcgccct accgggtagg ggaggcgctt tcccaaggc agtctggagc     3780 atgcgcttta gcagccccgc tgggcacttg gcgctacaca agtggcctct ggcctcgcac    3840
acattccaca tccaccggta ggcgccaacc ggctccgttc tttggtggcc ccttcgcgcc    3900
accttctact cctcccctag tcaggaagtt cccccccgcc ccgcagctcg cgtcgtgcag    3960
gacgtgacaa atgaagtag cacgtctcac tagtctcgtg cagatggaca gcaccgctga     4020
gcaatggaag cgggtaggcc tttggggcag cggccaatag cagctttggc tccttcgctt    4080
tctgggctca gaggctggga aggggtgggt ccggggcgg gctcagggc gggctcaggg      4140 gcggggcggg cgcccgaagg tcctccggaa gcccggcatt ctgcacgctt caaaagcgca    4200
cgtctgccgc gctgttctcc tcttcctcat ctccgggcct ttcgacctgc agccaatatg    4260
ggatcggcca ttgaacaaga tggattgcac gcaggttctc cggccgcttg ggtggagagg    4320
ctattcggct atgactgggc acaacagaca atcggctgct ctgatgccgc cgtgttccgg    4380
ctgtcagcgc aggggcgccc ggttcttttt gtcaagaccg acctgtccgg tgccctgaat    4440
gaactgcagg acgaggcagc gcggctatcg tggctggcca cgacgggcgt tccttgcgca    4500
gctgtgctcg acgttgtcac tgaagcggga agggactggc tgctattggg cgaagtgccg    4560
gggcaggatc tcctgtcatc tcaccttgct cctgccgaga agtatccat catggctgat     4620 gcaatgcggc ggctgcatac gcttgatccg gctacctgcc cattcgacca ccaagcgaaa    4680
catcgcatcg agcgagcacg tactcggatg aagccggtc ttgtcaatca ggatgatctg     4740
gacgaagagc atcaggggct cgcgccagcc gaactgttcg ccaggctcaa ggcgcgcatg    4800
cccgacggcg aggatctcgt cgtgacccat ggcgatgcct gcttgccgaa tatcatggtg    4860
gaaaatggcc gcttttctgg attcatcgac tgtggccggc tgggtgtggc ggatcgctat    4920
caggacatag cgttggctac ccgtgatatt gctgaagagc ttggcggcga atgggctgac    4980
cgcttcctcg tgctttacgg tatcgccgct cccgattcgc agcgcatcgc cttctatcgc    5040
cttcttgacg agttcttctg agggatcaa ttctctagag ctcgctgatc agcctcgact     5100
gtgccttcta gttgccagcc atctgttgtt tgcccctccc ccgtgccttc cttgaccctg    5160
gaaggtgcca ctcccactgt cctttcctaa taaaatgagg aaattgcatc gcattgtctg    5220
agtaggtgtc attctattct ggggggtggg gtggggcagg acagcaaggg ggaggattgg    5280
gaagacaata gcaggcatgc tggggatgcg gtgggctcta tggcttctga ggcggaaaga    5340
accagctggg ggcgcgcccc tcgagcgcc gccagtgtga tggatatctg cagaattcgc     5400
ccttggatca aacacgcatc ctcatggaca atatgttggg ttcttagcct gctgagacac    5460
aacaggaact cccctggcac cactttagag gccagagaaa cagcacagat aaaattccct    5520 gccctctga agcttatagt ctagctgggg agatatcata ggcaagataa acacatacaa    5580
atacatcatc ttaggtaata atatatacta aggagaaaat tacaggggag aaagaggaca    5640
```

-continued

```
ggaattgcta gggtaggatt ataagttcag atagttcatc aggaacactg ttgctgagaa      5700
gataacattt aggtaaagac cgaagtagta aggaaatgga ccgtgtgcct aagtgggtaa      5760
gaccattcta ggcagcagga acagcgatga aagcactgag gtgggtgttc actgcacaga      5820
gttgttcact gcacagagtt gtgtgggag gggtaggtct tgcaggctct tatggtcaca      5880
ggaagaattg ttttactccc accgagatga aggttggtgg attttgagca gaagaataat      5940
tctgcctggt ttatatataa caggatttcc ctgggtgctc tgatgagaat aatctgtcag      6000
gggtgggata gggagagata tggcaatagg agccttggct aggagcccac gacaataatt      6060
ccaagtgaga ggtggtgctg cattgaaagc aggactaaca agacctgctg acagtgtgga      6120
tgtagaaaaa gatagaggag acgaaggtgc atctagggtt ttctgcctga ggaattagaa      6180
agataaagct aaagcttata gaagatgcag cgctctgggg agaaagacca gcagctcagt      6240
tttgatccat ctggaattaa ttttggcata agtatgagg tatgtgggtt aacattattt      6300
gttttttttt tttccatgta gctatccaac tgtcccagca tcatttattt taaaagactt      6360
tcctttcccc tattggattg ttttggcacc ttcactgaag atcaactgag cataaaattg      6420
ggtctatttc taagctcttg attccattcc atgacctatt tgttcatctt taccccagta      6480
gacactgcct tgatgattaa agcccctgtt accatgtctg ttttggacat ggtaaatctg      6540
agatgcctat tagccaacca agcaagcacg gcccttagag agctagatat gagagcctgg      6600
aattcagacg agaaaggtca gtcctagaga catacatgta gtgccatcac catgcggatg      6660
gtgttaaaag ccatcagact gcaacagact gtgagagggt accaagctag agagcatgga      6720
tagagaaacc caagcactga gctgggaggt gctcctacat taagagatta gtgagatgaa      6780
ggactgagaa gattgatcag agaagaagga aaatcaggaa aatggtgctg tcctgaaaat      6840
ccaagggaag agatgttcca aagaggagaa aactgatcag ttgtcagcta gcgtcaattg      6900
ggatgaaaat ggaccattgg acagagggat gtagtgggtc atgggtgaat agataagagc      6960
agcttctata gaatggcagg ggcaaaattc tcatctgatc ggcatgggtt ctaaagaaaa      7020
cgggaagaaa aaattgagtg catgaccagt cccttcaagt agagaggtgg aaaagggaag      7080
gaggaaaatg aggccacgac aacatgagag aaatgacagc attttttaaaa atttttatt      7140 ttattttatt tatttatttt tgcttttttag ggctgcccct gcaacatatg gaggttccca      7200
ggttaggggt ctaatcagag ctatagctgc cagcctacac cacagccata gcaatgccag      7260
atctacatga cctacaccac agctcacagc aacgccggat ccttaaccca ctgagtgagg      7320
ccagagatca aacccatatc cttatggata ctagtcaggt tcattaccac tgagccaaaa      7380
tgggaaatcc tgagtaatga cagcattttt taatgtgcca ggaagcaaaa cttgccaccc      7440
cgaaatgtct ctcaggcatg tggattattt tgagctgaaa acgattaagg cccaaaaaac      7500
acaagaagaa atgtggacct tcccccaaca gcctaaaaaa tttagattga gggcctgttc      7560
ccagaataga gctattgcca gacttgtcta cagaggctaa gggctaggtg tggtggggaa      7620
accctcagag atcagaggga cgtttatgta ccaagcattg acatttccat ctccatgcga      7680
atggccttct tcccctctgt agccccaaac caccaccccc aaaatcttct tctgtctttta      7740 gctgaagatg gtgttgaagg tgatagtttc agccactttg gcgagttcct cagttgttct      7800
gggtctttcc tcctgatcca cattattcga ctgtgtttga ttttctcctg tttatctgtc      7860
tcattggcac ccatttcatt cttagaccag cccaaagaac ctagaagagt gaaggaaaat      7920
ttcttccacc ctgacaaatg ctaaatgaga atcaccgcag tagaggaaaa tgatctggtg      7980
```

| | |
|---|---|
| ctgcgggaga tagaagagaa aatcgctgga gagatgtcac tgagtaggtg agatgggaaa | 8040 |
| ggggtgacac aggtggaggt gttgccctca gctaggaaga cagacagttc acagaagaga | 8100 |
| agcgggtgtc cgtggacatc ttgcctcatg gatgaggaaa ccgaggctaa gaaagactgc | 8160 |
| aaaagaaagg taaggattgc agagaggtcg atccatgact aaaatcacag taaccaaccc | 8220 |
| caaaccacca tgttttctcc tagtctggca cgtggcaggt actgtgtagg ttttcaatat | 8280 |
| tattggtttg taacagtacc tattaggcct ccatcccctc ctctaatact aacaaaagtg | 8340 |
| tgagactggt cagtgaaaaa tggtcttctt tctctatgaa tctttctcaa gaagatacat | 8400 |
| aactttttat tttatcatag gcttgaagag caaatgagaa acagcctcca acctatgaca | 8460 |
| ccgtaacaaa atgtttatga tcagtgaagg gcaagaaaca aaacatacac agtaaagacc | 8520 |
| ctccataata ttgtgggtgg cccaacacag gccaggttgt aaaagctttt tattctttga | 8580 |
| tagaggaatg gatagtaatg tttcaacctg gacagagatc atgttcactg aatccttcca | 8640 |
| aaaattcatg ggtagtttga attataagga aaataagact taggataaat actttgtcca | 8700 |
| agatcccaga gttaatgcca aaatcagttt tcagactcca ggcagcctga tcaagagcct | 8760 |
| aaactttaaa gacacagtcc cttaataact actattcaca gttgcacttt cagggcgcaa | 8820 |
| agactcattg aatcctacaa tagaatgagt ttagatatca aatctctcag taatagatga | 8880 |
| ggagactaaa tagcgggcat gacctggtca cttaaagaca gaattgagat tcaaggctag | 8940 |
| tgttctttct acctgttttg tttctacaag atgtagcaat gcgctaatta cagacctctc | 9000 |
| agggaaggaa | 9010 |

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
cgaacccctg tgtatatagt t                                          21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
gagatgagga agaggagaac a                                          21

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23
gcattgtctg agtaggtgtc att                                        23

<210> SEQ ID NO 24
<211> LENGTH: 22
<212> TYPE: DNA
<213> ORGANISM: Artificial Sequence
<220> FEATURE:
<223> OTHER INFORMATION: Synthetic

<400> SEQUENCE: 24
cgcttcttgc agggaacacg at 22

<210> SEQ ID NO 25
<211> LENGTH: 6772
<212> TYPE: DNA
<213> ORGANISM: Sus sp.

<400> SEQUENCE: 25

| | | | | | |
|---|---|---|---|---|---|
| gcacatggta | ggcaaaggac | tttgcttctc | ccagcacatc | tttctgcaga | gatccatgga | 60 |
| aacaagactc | aactccaaag | cagcaaagaa | gcagcaagtt | ctcaagtgat | ctcctctgac | 120 |
| tccctcctcc | caggctaatg | aagccatgtt | gcccctgggg | gattaagggc | aggtgtccat | 180 |
| tgtggcaccc | agcccgaaga | caagcaattt | gatcaggttc | tgagcactcc | tgaatgtgga | 240 |
| ctctggaatt | ttctcctcac | cttgtggcat | atcagcttaa | gtcaagtaca | agtgacaaac | 300 |
| aacataatcc | taagaagaga | ggaatcaagc | tgaagtcaaa | ggatcactgc | cttggattct | 360 |
| actgtgaatg | atgacctgga | aaatatcctg | aacaacagct | tcagggtgat | catcagagac | 420 |
| aaaagttcca | gagccaggta | gggaaaccct | caagccttgc | aaagagcaaa | atcatgccat | 480 |
| tgggttctta | acctgctgag | tgatttacta | tatgttactg | tgggaggcaa | agcgctcaaa | 540 |
| tagcctgggt | aagtatgtca | ataaaaaagc | aaaagtggtg | tttcttgaaa | tgttagacct | 600 |
| gaggaaggaa | tattgataac | ttaccaataa | ttttcagaat | gatttataga | tgtgcactta | 660 |
| gtcagtgtct | ctccaccccg | cacctgacaa | gcagtttaga | atttattcta | agaatctagg | 720 |
| tttgctgggg | gctacatggg | aatcagcttc | agtgaagagt | ttgttggaat | gattcactaa | 780 |
| attttctatt | tccagcataa | atccaagaac | ctctcagact | agtttattga | cactgctttt | 840 |
| cctccataat | ccatctcatc | tccgtccatc | atggacactt | tgtagaatga | caggtcctgg | 900 |
| cagagactca | cagatgcttc | tgaaacatcc | tttgccttca | aagaatgaac | agcacacata | 960 |
| ctaaggatct | cagtgatcca | caaattagtt | tttgccacaa | tggttcttat | gataaaagtc | 1020 |
| tttcattaac | agcaaattgt | tttataatag | ttgttctgct | ttataataat | tgcatgcttc | 1080 |
| actttctttt | cttttctttt | tttttctttt | tttgcttttt | agtgccgcag | gtgcagcata | 1140 |
| tgaaatttcc | caggctaggg | gtcaaatcag | aactacacct | actggcctac | gccacagcca | 1200 |
| cagcaactca | ggatctaagc | catgtcggtg | acctacacta | cagctcatgg | caatgccaga | 1260 |
| tccttaaccc | aatgagcgag | gccagggatc | gaacccatgt | cctcatggat | actagtcagg | 1320 |
| ctcattatcc | gctgagccat | aacaggaact | cccgagtttg | cttttatca | aaattggtac | 1380 |
| agccttattg | tttctgaaaa | ccacaaaatg | aatgtattca | cataatttta | aaaggttaaa | 1440 |
| taatttatga | tatacaagac | aatagaaaga | gaaaacgtca | ttgcctcttt | cttccacgac | 1500 |
| aacacgcctc | cttaattgat | ttgaagaaat | aactactgag | catggtttag | tgtacttctt | 1560 |
| tcagcaatta | gcctgtattc | atagccatac | atattcaatt | aaaatgagat | catgatatca | 1620 |
| cacaatacat | accatacagc | ctatagggat | ttttacaatc | atcttccaca | tgactacata | 1680 |
| aaaacctacc | taaaaaaaaa | aaaacccta | cttcatcctc | ctattggctg | ctttgtgctc | 1740 |
| cattaaaaag | ctctatcata | attaggttat | gatgaggatt | tccattttct | acctttcaag | 1800 |
| caacatttca | atgcacagtc | ttatatacac | atttgagcct | acttttcttt | ttctttcttt | 1860 |
| ttttggtttt | tttttttttt | tttttttttgg | tcttttgtc | tttctaagg | ctgcatatgg | 1920 |
| aggttcccag | gctagctgtc | taatcagaac | tatagctgct | ggcctacgcc | acatccacag | 1980 |

```
caatacaaga tctgagccat gtctgcaact tacaccacag ctcacagcaa cggtggatcc    2040
ttaaaccact gagcaaggcc agggatcaaa cccataactt catggctcct agttggattt    2100
gttaaccact gagccatgat ggcaactcct gagcctactt ttctaatcat ttccaaccct    2160
aggacacttt tttaagtttc attttttctcc ccccacccc tgttttctga agtgtgtttg    2220
cttccactgg gtgacttcac tcccaggatc tcatctgcag gatactgcag ctaagtgtat    2280
gagctctgaa tttgaatccc aactctgcca ctcaaaggga taggagtttc cgatgtggcc    2340
caatgggatc agtggcatct ctgcagtgcc aggacgcagg ttccatccct ggcccagcac    2400
agtgggttaa gaatctggca ttgctgcagc tgaggcatag atttcaattg tgcctcagat    2460
ctgatccttg gcccaaggac tgcatatgcc tcagggcaac caaaaaagag aaaaggggg     2520 tgatagcatt agtttctaga tttgggggat aattaaataa agtgatccat gtacaatgta    2580
tggcattttg taaatgctca acaaatttca actattatgg agttcccatc atggctcagt    2640
ggaagggaat ctgattagca tccatgagga cacaggtcca accccgacct tgctcagtgg    2700
gcattgctgt gagctgtggc atgggttaca gacgaagctc ggatctggca ttgctgtggc    2760
tgtggtgtaa gccagcaact acagctctca ttcagccct agcctgggaa cctccatatg    2820
cctaaaagac aaaaaataaa atttaaatta aaaataaaga aatgttaact attatgattg    2880
gtactgcttg cattactgca aagaaagtca cttttctatac tctttaatat cttagttgac    2940
tgtgtgctca gtgaactatt ttggacactt aatttccact ctcttctatc tccaacttga    3000
caactctctt tcctctcttc tggtgagatc cactgctgac tttgctcttt aaggcaacta    3060
gaaaagtgct cagtgacaaa atcaagaaa gttaccttaa tcttcagaat tacaatctta    3120
agttctcttg taaagcttac tatttcagtg gttagtatta ttccttggtc ccttacaact    3180
tatcagctct gatctattgc tgattttcaa ctatttattg ttggagtttt ttccttttt     3240 ccctgttcat tctgcaaatg tttgctgagc atttgtcaag tgaagatact ggactgggcc    3300
ttccaaatat aagacaatga acatcgggga gttctcatta tggtgcagca gaaacgaatc    3360
caactaggaa atgtgaggtt gcaggttcga tccctgccct tgctcagtgg gttaaggatc    3420
cagcattacc gtgagctgtg gtgtaggttg cagacgtggc tcagatcctg cgttgctgtg    3480
gctgtggcat aggctggcag ctctagctct gattcgaccg ctagcctggg aacctccatg    3540
cgccccgagt gcagccctta aaagcaaaa aaaaagaaa gaaagaaaaa gacaatgaaa      3600
catcaaacag ctaacaatcc agtagggtag aaagaatctg gcaacagata agagcgatta    3660
aatgttctag gtccagtgac cttgcctctg tgctctacac agtcgtgcca cttgctgagg    3720
gagaaggtct ctcttgagtt gagtcctgaa agacattagt tgttcacaaa ctaatgccag    3780
tgagtgaagg tgtttccaag cagagggaga gtttggtaaa aagctggaag tcacagaaag    3840
actctaaaga gtttaggatg gtgggagcaa catacgctga gatgggctg gaaggttaag     3900 agggaaacaa ctatagtaag tgaagctgga ctcacagcaa agtgaggacc tcagcatcct    3960
tgatggggtt accatggaaa caccaaggca caccttgatt tccaaaacag caggcacctg    4020
attcagccca atgtgacatg gtgggtaccc ctctagctct acctgttctg tgacaactga    4080
caaccaacga agtaagtct ggattttcta ctctgctgat ccttgttttt gtttcacacg     4140
tcatctatag cttcatgcca aaatagagtt caaggtaaga cgcgggcctt ggtttgatat    4200
acatgtagtc tatcttgttt gagacaatat ggtggcaagg aagaggttca aacaggaaaa    4260
tactctctaa ttatgattaa ctgagaaaag ctaaagagtc ccataatgac actgaatgaa    4320
gttcatcatt tgcaaaagcc ttccccccc cccaggagac tataaaaaag tgcaattttt     4380
```

-continued

```
taaatgaact tatttacaaa acagaaatag actcacagac ataggaaacg aacagatggt    4440
taccaagggt gaaagggagt aggagggata aataaggagt ctggggttag cagatacacc    4500
ccagtgtaca caaataaac aacagggacc tactatatag cacagggaac tatatgcagt     4560
agcttacaat aacctataat ggaaaagaat gtgaaaaaga atatatgtat gcgtgtgtgt    4620
gtaactgaat cactttgctg taacctgaat ctaacataac attgtaaatc aactacagtt    4680
tttttttttt ttaagtgcag ggttttggtg tttttttttt ttcattttg ttttgttttt     4740
tgttttttgc ttttagggc cacacccaga catatggggg ttcccaggct aggggtctaa     4800
ttagagctac agttgccggc ttgcaccaca gccacagcaa catcagatcc gagccgcact    4860
tgcgacttac accacagctc atggcaatac cagatcctta acccactgag caaggcccag    4920
ggatcgtacc cgcaacctca tggttcctag tcagattcat ttctgctgcg ctacaatggg    4980
aactccaagt gcagtttttt gtaatgtgct tgtctttctt tgtaattcat attcatccta    5040
cttcccaata aataaataaa tacataaata ataaacatac cattgtaaat caactacaat    5100
ttttttaaa tgcagggttt ttgttttttg tttttgttt tgtcttttg ccttttctag       5160
ggccgctccc atggcatatg gaggttccca ggctaggggt cgaatcggag ctgtagccac    5220
cggcctacgc cagagccaca gcaacgcggg atccgagccg cgtctgcaac ctacaccaca    5280
gctcacggca acgccggatc gttaacccac tgagcaaggg cagggatcga acctgcaacc    5340
tcatggttcc tagtcagatt cgttaactac tgagccacaa cggaaactcc taaagtgcag    5400
tttttaaatg tgcttgtctt tctttgtaat ttacactcaa cctacttccc aataaataaa    5460
taaataaaca aataaatcat agacatggtt gaattctaaa ggaagggacc atcaggcctt    5520
agacagaaat acgtcatctt ctagtatttt aaaacacact aaagaagaca acatgctct     5580
gccagagaag cccagggcct ccacagctgc ttgcaaaggg agttaggctt cagtagctga    5640
cccaaggctc tgttcctctt cagggaaaag ggttttgtt cagtgagaca gcagacagct     5700
gtcactgtgg tggacgttcg gccaaggaac caagctggaa ctcaaacgta agtcaatcca    5760
aacgttcctt ccttggctgt ctgtgtctta cggtctctgt ggctctgaaa tgattcatgt    5820
gctgactctc tgaaaccaga ctgacattct ccagggcaaa actaaagcct gtcatcaaac    5880
cggaaaactg agggcacatt ttctgggcag aactaagagt caggcactgg gtgaggaaaa    5940
acttgttaga atgatagttt cagaaactta ctggaagca aagcccatgt tctgaacaga     6000
gctctgctca agggtcagga ggggaaccag ttttttgtaca ggagggaagt tgagacgaac   6060
ccctgtgtat atggtttcgg cgcggggacc aagctggagc tcaaacgtaa gtggcttttt    6120
ccgactgatt ctttgctgtt tctaattgtt ggttggcttt ttgtccattt ttcagtgttt    6180
tcatcgaatt agttgtcagg gaccaaacaa attgccttcc cagattaggt accagggagg    6240
ggacattgct gcatgggaga ccagagggtg gctaatttt aacgtttcca agccaaaata     6300
actggggaag ggggcttgct gtcctgtgag ggtaggtttt tatagaagtg gaagttaagg    6360
ggaaatcgct atggttcact tttggctcgg ggaccaaagt ggagcccaaa attgagtaca    6420
ttttccatca attatttgtg agatttttgt cctgttgtgt catttgtgca agttttttgac   6480
attttggttg aatgagccat tcccagggac ccaaaaggat gagaccgaaa agtagaaaag    6540
agccaacttt taagctgagc agacagaccg aattgttgag tttgtgagga gagtagggtt    6600
tgtagggaga aaggggaaca gatcgctggc ttttctctg aattagcctt tctcatggga     6660
ctggcttcag aggggttttt tgatgaggga agtgttctag agccttaact gtgggttgtg    6720
```

```
-continued ttcggtagcg ggaccaagct ggaaatcaaa cgtaagtgca cttttctact cc        6772

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
ccttcctcct gcacctgtca ac                                          22

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
tagacacacc agggtggcct tg                                          22

<210> SEQ ID NO 28
<211> LENGTH: 5918
<212> TYPE: DNA
<213> ORGANISM: Sus sp.

<400> SEQUENCE: 28
ccttcctcct gcacctgtca actcccaata aaccgtcctc cttgtcattc agaaatcatg    60
ctctccgctc acttgtgtct acccattttc gggcttgcat ggggtcatcc tcgaaggtgg   120
agagagtccc ccttggcctt ggggaagtcg aggggggcgg ggggaggcct gaggcatgtg   180
ccagcgaggg gggtcacctc cacgcccctg aggaccttct agaaccaggg gcgtggggcc   240
accgcctgag tggaaggctg tccactttc ccccgggccc ccaggctccc tcctccgtgt    300
ggaccttgtc cacctctgac tggcccagcc actcatgcat tgtttcccg aaaccccagg    360 acgatagctc agcacgcgac agtgtccccc tctgagggcc tctgtccatt tcaggacgac   420
ccgcatgtac agcgtgacca ctctgctcac gcccactcac cacgtcctag agccccaccc   480
ccagccccat ccttagggc acagccagct ccgaccgccc cggggacacc accctctgcc    540
ccttccccag gccctccctg tcacacgcac acagggccc tccgtcccga ccctgctc      600 cctcatccct cggtcccctc aggtagcctt ccaccgcgt gtgtcccgag gtcccagatg    660
cagcaaggcc cctgggacaa cgccagatct ctgctctccc cgaccctca gaagccagcc    720 cacgcctggc cccaccacca ctgcctaacg tccaagtgtc cataggcctc gggacctcca   780
agtccaggtt ctgcctctgg gattccgcca tgggtctgcc tgggaaatga tgcacttgga   840
ggagctcagc atgggatgcg ggaccttgtc tctaggcgct ccctcaggat ccacagctg    900 ccctgtgaga cacacacaca cacacacaca cacacacaca cacacaaaca               960
cgcatgcacg cacgccggca cacacgctat tgcagagatg ccacggtag ctgtgcctcg   1020 aggccgagtg gagtgtctag aactctcggg ggtcccctct gcagacgaca ctgctccatc   1080
ccccccgtgc cctgaaggc tcctcactct cccatcagga tctctccaag ctgctgacct   1140
ggagaggaag gggcctggga caggcgggga cactcagacc tccctgctgc ccctcctctg   1200
cctgggcttg gacggctccc cccttccac gggtgaaggt gcaggtgggg agagggcacc    1260
cccctcagcc tccagaccc agaccagccc ccgtggcagg ggcagcctgt gagcctccag   1320
ccagatgcag gtggcctggg gtgggggtg gaggggggcgg gaggtttatg tttgaggctg   1380
```

```
tatcactgtg taatattttc ggcggtggga cccatctgac cgtcctcggt gagtctcccc    1440
ttttctctcc tccttgggga tccgagtgaa atctgggtcg atcttctctc cgttctcctc    1500
cgactggggc tgaggtctga acctcggtgg ggtccgaaga ggaggcccct aggccaggct    1560
cctcagcccc tccagcccga ccggccctct tgacacaggg tccagctaag ggcagacatg    1620
gaggctgcta gtccagggcc aggctctgag acccaagggc gctgcccaag gaacccttgc    1680
cccagggacc ctgggagcaa agctcctcac tcagagcctg cagccctggg gtctgaggac    1740
aaggagggac tgaggactgg gcgtggggag ttcaggcggg gacaccaggt ccagggaggt    1800
gacaaaggcg ctgggagggg gcggacggtg ccggggactc ctcctgggcc ctgtgggctc    1860
ggggtccttg tgaggaccct gagggactga ggggcccctg gcctaggga cttgcagtga    1920 gggaggcagg gagtgtccct tgagaacgtg gcctccgcgg gctgggtccc cctcgtgctc    1980
ccagccggga ggacacccca gagcaagcgc cccaggtggg cggggagggt ctcctcacag    2040
gggcagctga cagatagagg cccccgccag gcagatgctt gatcctggca gttatactgg    2100
gttcgcacaa ctttccctga caaggggcc ctccgaacag acacagacgc aacccagtcg    2160
acccaggctc agcacagaaa atgcactgac acccaaaacc ctcatctggg ggcctggccg    2220
gcatcccgcc ccaggaccca aggcccctgc cccctggcag ccctggacac ggtcctctgt    2280
gggcggtggg gtcggggctg tggtgacggt ggcatcgggg agcctgtgcc ccctccctga    2340
aagggcggag aggctcaaga ggggacagaa atgtcctccc ctaggaagac ctcggacggg    2400
ggcggggggg tggtctccga cagacagatg cccgggaccg acagacctgc cgagggaaga    2460
gggcacctcg gtcgggttag gctccaggca gcacgaggga gcgaggctgg gagggtgagg    2520
acatgggagc ctgaggagga gctggagact tcagcaggcc cccagctccg ggcttcgggc    2580
tctgagatgc tcggacgcaa ggtgagtgac cccacctgtg gctgacctga cctcaggggg    2640
acaaggctca gcctgggact ctgtgtcccc atcgcctgca cagggattc ccctgatgga    2700 cactgagcca acgacctccc gtctctcccc gaccccagg tcagcccaag gccactccca    2760
cggtcaacct cttcccgccc tcctctgagg agctcggcac caacaaggcc accctggtgt    2820
gtctaataag tgacttctac ccgggcgccg tgacggtgac ctggaaggca ggcggcacca    2880
ccgtcaccca gggcgtggag accaccaagc cctcgaaaca gagcaacaac aagtacgcgg    2940
ccagcagcta cctggccctg tccgccagtg actggaaatc ttccagcggc ttcacctgcc    3000
aggtcaccca cgagggggacc attgtggaga agacagtgac gccctccgag tgcgcctagg    3060
tccctgggcc cccaccctca ggggcctgga gccacaggac cccgcgagg gtctccccgc    3120 gaccctggtc cagcccagcc cttcctcctg cacctgtcaa ctcccaataa accgtcctcc    3180
ttgtcattca gaaatcatgc tctccgctca cttgtgtcta cccattttcg ggcttgcatg    3240
gggtcatcct cgaaggtgga gagagtcccc cttggccttg ggaaatcga ggggggcggg    3300 gggaggcctg aggcatgtgc cagcgagggg ggtcacctcc acgcccctga ggaccttcta    3360
gaaccagggg cgtggggcca ccgccagagt ggaaggctgt ccacttttcc cccgggcccc    3420
caggctccct cctccgtgtg gaccttgtcc acctctgact ggcccagcca ctcatgcatt    3480
gtttccccga aacccagga cgatagctca gcacgcgaca gtgtcccct ctgagggcct    3540 ctgtccattt caggacgacc cgcatgtaca gcgtgaccac tctgctcacg cccactcacc    3600
acgtcctaga gccccacccc cagccccatc cttaggggca cagccagctc cgaccgcccc    3660
ggggacacca ccctctgccc cttccccagg ccctcccctgt cacacgcacc acagggccct    3720
```

```
ccgtcccgag accctgctcc ctcatccctc ggtcccctca ggtagccttc cacccgcgtg    3780
tgtcccgagg tcccagatgc agcaaggccc ctgggacaac gccagatctc tgctctcccc    3840
gaccctcaga agccagccca cgcctggccc accaccactg cctaacgtcc aagtgtccat    3900
aggctcggga cctccaagtc caggttctgc ctctgggatt ccgccatggg tctgcctgga    3960
atgatgcact tggaggagct cagcatggga tgcggaactt gtctagcgct cctcagatcc    4020
acagctgcct gtgagacaca cacacacaca cacacacacc aaacacgcat gcacgcacgc    4080
cggcacacac gctattacag agatggccac ggtagctgtg cctcgaggcc gagtggagtg    4140
tctagaactc tcggggggtcc cctctgcaga cgacactgct ccatccccccc cgtgccctga    4200 agggctcctc actctcccat caggatctct ccaagctgct gacctggaga ggaaggggcc    4260
tgggacaggc ggggacactc agacctccct gctgccccctc ctctgcctgg gcttggacgg    4320
ctcccccctt cccacgggtg aaggtgcagg tggggagagg gcaccccccct caccctccca    4380 gacccagacc agccccgtg gcaggggcag cctgtgagcc tccagccaga tgcaggtggc    4440
ctggggtggg gggtggaggg ggcgggaggt ttatgtttga ggctgtattc atctgtgtaa    4500
tattttcggc ggtgggaccc atctgaccgt cctcggtgag tctccccttt tctttcctcc    4560
ttggggatcc gagtgaaatc tgggtcgatc ttctctccgt tctcctccga ctggggctga    4620
ggtctgaacc tcggtggggt ccgaagagga ggccctagg ccggctcctc agccctcca    4680 gcccgacccg ccctcttgac acagggtcca gctaagggca gacatggctg ctagtccagg    4740
gccaggctct gagacccaag ggcgctgccc aaggaaccct tgccccaggg accctgggag    4800
caaagctcct cactcagagc ctgcagccct ggggtctgag acaaggagg gactgaggac    4860 tgggcgtggg gagttcaggc ggggacaccg ggtccaggga ggtgacaaag gcgctgggag    4920
ggggcggacg tgccggaga ctcctcctgg gccctgtggg ctcgtggtcc ttgtgaggac    4980
cctgagggct gaggggcccc tgggcctagg gacttgcagt gagggaggca gggagtgtcc    5040
cttgagaacg tggcctccgc gggctgggtc ccctcgtgc tcccagcagg gaggacaccc    5100
cagagcaagc gccccaggtg ggcggggagg gtctcctcac aggggcagct gacagataga    5160 cggccccgc cagacagatg cttgatcctg gtcagtactg ggttcgccac ttccctgaac    5220
aggggccctc cgaacagaca cagacgcaga ccaggctcag cacagaaaat gcactgacac    5280
ccaaaaccct catctgggggg cctggccggc atcccgcccc aggacccaag gcccctgccc    5340
cctggcagcc ctggacacgg tcctctgtgg gcggtggggt cggggctgtg gtgacggtgg    5400
catcggggag cctgtgcccc ctccctgaaa gggcggagag gctcaagagg ggacagaaat    5460
gtcctcccct aggaagacct cggacggggg cggggggtg gtctccgaca gacagatgcc    5520
cgggaccgac agacctgccg agggaagagg gcacctcggt cgggttaggc tccaggcagc    5580
acgagggagc gaggctggga gggtgaggac atgggagcct gaggaggagc tggagacttc    5640
agcaggcccc cagctccggg cttcgggctc tgagatgctc ggacgcaagg tgagtgaccc    5700
cacctgtggc tgacctgacc tgacctcagg gggacaaggc tcagcctggg actctgtgtc    5760
cccatcgcct gcacagggga ttccctgat ggacactgag ccaacgacct cccgtctctc    5820
cccgaccccc aggtcagccc aaggccactc ccacggtcaa cctcttcccg ccctcctctg    5880
aggagctcgg caccaacaag gccacctgg tgtgtcta                              5918
```

<210> SEQ ID NO 29
<211> LENGTH: 11051
<212> TYPE: DNA
<213> ORGANISM: Sus sp.

<400> SEQUENCE: 29

```
tctagaagac gctggagaga ggccagactt cctcggaaca gctcaaagag ctctgtcaaa      60
gccagatccc atcacacgtg ggcaccaata ggccatgcca gcctccaagg gccgaactgg     120
gttctccacg gcgcacatga agcctgcagc ctggcttatc ctcttccgtg gtgaagaggc     180
aggcccggga ctggacgagg ggctagcagg gtgtggtagg caccttgcgc cccccacccc     240
ggcaggaacc agagaccctg gggctgagag tgagcctcca aacaggatgc cccacccttc     300
aggccacctt tcaatccagc tacactccac ctgccattct cctctgggca cagggcccag     360
cccctggatc ttggccttgg ctcgacttgc acccacgcgc acacacacac ttcctaacgt     420
gctgtccgct caccccctcc cagcgtggtc catgggcagc acggcagtgc gcgtccggcg     480
gtagtgagtg cagaggtccc ttcccctccc ccaggagccc caggggtgtg tgcagatctg     540
ggggctcctg tcccttacac cttcatgccc ctcccctcat acccacccctc caggcgggag     600
gcagcgagac ctttgcccag ggactcagcc aacgggcaca cggagggcca gccctcagca     660
gctggctccc aaagaggagg tgggaggtag gtccacagct gccacagaga gaaaccctga     720
cggaccccac aggggccacg ccagccggaa ccagctccct cgtgggtgag caatggccag     780
ggccccgccg gccaccacgg ctggccttgc gccagctgag aactcacgtc cagtgcaggg     840
agactcaaga cagcctgtgc acacagcctc ggatctgctc ccatttcaag cagaaaaagg     900
aaaccgtgca ggcagccctc agcatttcaa ggattgtagc agcggccaac tattcgtcgg     960
cagtggccga ttagaatgac cgtggagaag ggcggaaggg tctctcgtgg gctctgcggc    1020
caacaggccc tggctccacc tgcccgctgc cagcccgagg ggcttgggcc gagccaggaa    1080
ccacagtgct caccgggacc acagtgactg accaaactcc cggccagagc agccccaggc    1140
cagccgggct ctcgccctgg aggactcacc atcagatgca caaggggcg agtgtggaag    1200
agacgtgtcg cccgggccat ttgggaaggc gaagggacct tccaggtgga caggaggtgg    1260
gacgcactcc aggcaaggga ctgggtcccc aaggcctggg gaaggggtac tggcttgggg    1320
gttagcctgg ccagggaacg gggagcgggg cgggggctg agcagggagg acctgacctc    1380
gtgggagcga ggcaagtcag gcttcaggca gcagccgcac atcccagacc aggaggctga    1440
ggcaggaggg gcttgcagcg gggcggggc ctgcctggct ccggggctc ctggggacg    1500
ctggctcttg tttccgtgtc ccgcagcaca gggccagctc gctgggccta tgcttacctt    1560
gatgtctggg gccggggcgt cagggtcgtc gtctcctcag gggagagtcc cctgaggcta    1620
cgctgggggg ggactatggc agctccacca ggggcctggg gaccagggc ctggaccagg    1680
ctgcagcccg gaggacgggc agggctctgg ctctccagca tctggccctc ggaaatggca    1740
gaaccctgg cgggtgagcg agctgagagc gggtcagaca gacaggggcc ggccggaaag    1800
gagaagttgg gggcagagcc cgccagggggc caggcccaag gttctgtgtg ccagggcctg    1860
ggtgggcaca ttggtgtggc catggctact tagattcgtg gggccagggc atcctggtca    1920
ccgtctcctc aggtgagcct ggtgtctgat gtccagctag gcgctggtgg gccgcgggtg    1980
ggcctgtctc aggctagggc aggggctggg atgtgtattt gtcaaggagg ggcaacaggg    2040
tgcagactgt gccctggaa acttgaccac tgggcaggg gcgtcctggt cacgtctcct    2100
caggtaagac ggccctgtgc ccctctctcg cgggactgga aaaggaattt tccaagattc    2160
cttggtctgt gtggggccct ctggggcccc cggggtggc tcccctcctg cccagatggg    2220
gcctcggcct gtggagcacg ggctgggcac acagctcgag tctagggcca cagaggcccg    2280
```

```
ggctcagggc tctgtgtggc ccggcgactg gcaggggggct cgggttttttg gacaccccct    2340
aatgggggcc acagcactgt gaccatcttc acagctgggg ccgaggagtc gaggtcaccg    2400
tctcctcagg tgagtcctcg tcagccctct ctcactctct ggggggtttt gctgcatttt    2460
gtggggaaaa gaggatgcct gggtctcagg tctaaaggtc tagggccagc gccggggccc    2520
aggaagggggc cgagggggcca ggctcggctc ggccaggagc agagcttcca gacatctcgc    2580
ctcctggcgg ctgcagtcag gcctttggcc gggggggtct cagcaccacc aggcctcttg    2640
gctcccgagg tccccggccc cggctgcctc accaggcacc gtgcgcggtg ggcccgggct    2700
cttggtcggc cacccttct  taactgggat ccgggcttag ttgtcgcaat gtgacaacgg    2760
gctcgaaagc tggggccagg ggaccctagt ctacgacgcc tcgggtgggt gtcccgcacc    2820
cctccccact ttcacggcac tcggcgagac ctggggagtc aggtgttggg gacactttgg    2880
aggtcaggaa cgggagctgg ggagagggct ctgtcagcgg ggtccagaga tgggccgccc    2940
tccaaggacg ccctgcgcgg ggacaagggc ttcttggcct ggcctggccg cttcacttgg    3000
gcgtcagggg gggcttcccg gggcaggcgg tcagtcgagg cgggttggaa ttctgagtct    3060
gggttcgggg ttcggggttc ggccttcatg aacagacagc ccaggcgggc cgttgtttgg    3120
cccctggggg cctggttgga atgcgaggtc tcggaagtc aggagggagc ctggccagca    3180
gagggttccc agccctgcgg ccgagggacc tggagacggg cagggcattg gccgtcgcag    3240
ggccaggcca cacccccccag gttttttgtgg ggcgagcctg gagattgcac cactgtgatt    3300
actatgctat ggatctctgg ggcccaggcg ttgaagtcgt cgtgtcctca ggtaagaacg    3360
gccctccagg gcctttaatt tctgctctcg tctgtgggct tttctgactc tgatcctcgg    3420
gaggcgtctg tgccccccccc ggggatgagg ccggcttgcc aggaggggtc agggaccagg    3480
agcctgtggg aagttctgac gggggctgca ggcgggaagg gccccaccgg ggggcgagcc    3540
ccaggccgct gggcggcagg agacccgtga gagtgcgcct tgaggagggt gtctgcggaa    3600
ccacgaacgc ccgccgggaa gggcttgctg caatgcggtc ttcagacggg aggcgtcttc    3660
tgccctcacc gtcttttcaag cccttgtggg tctgaaagag ccatgtcgga gagagaaggg    3720
acaggcctgt cccgacctgg ccgagagcgg gcagccccgg gggagagcgg ggcgatcggc    3780
ctgggctctg tgaggccagg tccaagggag gacgtgtggt cctcgtgaca ggtgcacttg    3840
cgaaacctta gaagacgggg tatgttggaa gcggctcctg atgtttaaga aaagggagac    3900
tgtaaagtga gcagagtcct caagtgtgtt aaggttttaa aggtcaaagt gttttaaacc    3960
tttgtgactg cagttagcaa gcgtgcgggg agtgaatggg gtgccagggt ggccgagagg    4020
cagtacgagg gccgtgccgt cctctaattc agggcttagt tttgcagaat aaagtcggcc    4080
tgtttttctaa aagcattggt ggtgctgagc tggtggagga ggccgcgggc agccctggcc    4140
acctgcagca ggtggcagga agcaggtcgg ccaagaggct atttttaggaa gccagaaaac    4200
acggtcgatg aatttatagc ttctggtttc caggaggtgg ttgggcatgg ctttgcgcag    4260
cgccacagaa ccgaaagtgc ccactgagaa aaaacaactc ctgcttaatt tgcatttttc    4320
taaaagaaga aacagaggct gacggaaact ggaaagttcc tgtttttaact actcgaattg    4380
agttttcggt cttagcttat caactgctca cttagattca ttttcaaagt aaacgtttaa    4440
gagccgaggc attcctatcc tcttctaagg cgttattcct ggaggctcat tcaccgccag    4500
cacctccgct gcctgcaggc attgctgtca ccgtcaccgt gacggcgcgc acgatttttca    4560
gttgcccgc  ttccctcgt  gattaggaca gacgcgggca ctctggccca gccgtcttgg    4620
ctcagtatct gcaggcgtcc gtctcgggac ggagctcagg ggaagagcgt gactccagtt    4680
```

-continued

```
gaacgtgata gtcggtgcgt tgagaggaga cccagtcggg tgtcgagtca aaggggccc      4740 ggggcccgag gccctgggca ggacggcccg tgccctgcat cacgggccca gcgtcctaga    4800
ggcaggactc tggtggagag tgtgagggtg cctgggccc ctccggagct ggggccgtgc     4860
ggtgcaggtt gggctctcgg cgcggtgttg gctgtttctg cgggatttgg aggaattctt   4920
ccagtgatgg gagtcgccag tgaccgggca ccaggctggt aagagggagg ccgccgtcgt   4980
ggccagagca gctgggaggg ttcggtaaaa ggctcgcccg tttcctttaa tgaggacttt   5040
tcctggaggg catttagtct agtcgggacc gttttcgact cgggaagagg gatgcggagg   5100
agggcatgtg cccaggagcc gaaggcgccg cggggagaag cccagggctc tcctgtcccc   5160
acagaggcga cgccactgcc gcagacagac agggcctttc cctctgatga cggcaaaggc   5220
gcctcggctc ttgcggggtg ctgggggga gtcgccccga agccgctcac ccagaggcct    5280 gagggtgag actgaccgat gcctcttggc cgggcctggg gccggaccga ggggactcc     5340 gtggaggcag ggcgatggtg gctgcgggag ggaaccgacc ctgggccgag cccggcttgg   5400
cgattcccgg gcgagggccc tcagccgagg cgagtgggtc cggcggaacc acccttctg    5460 gccagcgcca cagggctctc gggactgtcc ggggcgacgc tgggctgccc gtggcaggcc   5520
tgggctgacc tggacttcac cagacagaac agggctttca gggctgagct gagccaggtt   5580
tagcgaggcc aagtggggct gaaccaggct caactggcct gagctgggtt gagctgggct   5640
gacctgggct gagctgagct gggctgggct gggctgggct gggctgggct gggctggact   5700
ggctgagctg agctgggttg agctgagctg agctggcctg ggttgagctg ggctgggttg   5760
agctgagctg ggttgagctg ggttgagctg ggttgatctg agctgagctg ggctgagctg   5820
agctaggctg gggtgagctg ggctgagctg gtttgagttg ggttgagctg agctgagctg   5880
ggctgtgctg gctgagctag gctgagctag gctaggttga gctgggctgg gctgagctga   5940
gctaggctgg gctgatttgg gctgagctga gctgagctag gctgcgttga gctggctggg   6000
ctggattgag ctggctgagc tggctgagct gggctgagct ggcctgggtt gagctgagct   6060
ggactggttt gagctgggtc gatctgggtt gagctgtcct gggttgagct gggctgggtt   6120
gagctgagct gggttgagct gggctcagca gagctgggtt gggctgagct ggtttgagct   6180
gagctgggct gagctggcct gggttgagct gggctgagct gagctgggct gagctggcct   6240
gtgttgagct gggctgggtt gagctgggct gagctggatt gagctgggtt gagctgagct   6300
gggctgggct gtgctgactg agctgggctg agctaggctg gggtgagctg ggctgagctg   6360
atccgagcta ggctgggctg gtttgggctg agctgagctg agctaggctg gattgatctg   6420
gctgagctgg gttgagctga gctgggctga gctggtctga gctggcctgg gtcgagctga   6480
gctgactgtg tttgagctgg gtcgatctgg gctgagctgg cctgggttga gctgggctgg   6540
gttgagctga gctgggttga gctgggctga gctgagggct ggggtgagct gggctgaact   6600
agcctagcta ggtgggctg agctgggctg gtttgggctg agctgagctg agctaggctg    6660
cattgagcag gctgagctgg gctgagcagg cctggggtga gctgggctag gtggagctga   6720
gctgggtcga gctgagttgg gctgagctgg cctgggttga ggtaggctga gctgagctga   6780
gctaggctgg gttgagctgg ctgggctggt ttgcgctggg tcaagctggg ccgagctggc   6840
ctgggttgag ctgggctcgg ttgagctggg ctgagctgag ccgacctagg ctgggatgag   6900
ctgggctgat ttgggctgag ctgagctgag ctaggctgca ttgagcaggc tgagctgggc   6960
ctggagcctg gcctgggggtg agctgggctg agctgcgctg agctaggctg ggttgagctg   7020
```

```
gctgggctgg tttgcgctgg gtcaagctgg gccgagctgg cctgggatga gctgggccgg    7080
tttgggctga gctgagctga gctaggctgc attgagcagg ctgagctggg ctgagctggc    7140
ctggggtgag ctgggctgag ctaagctgag ctgggctggt ttgggctgag ctggctgagc    7200
tgggtcctgc tgagctgggc tgagctgacc aggggtgagc tgggctgagt taggctgggc    7260
tcagctaggc tgggttgatc tggcagggct ggtttgcgct gggtcaagct cccgggagat    7320
ggcctgggat gagctgggct ggtttgggct gagctgagct gagctgagct aggctgcatt    7380
gagcaggctg agctgggctg agctggcctg gggtgagctg ggctgggtgg agctgagctg    7440
ggctgaactg ggctaagctg gctgagctgg atcgagctga gctgggctga gctggcctgg    7500
ggttagctgg gctgagctga gctgagctag gctgggttga gctggctggg ctggtttgcg    7560
ctgggtcaag ctgggccgag ctggcctggg ttgagctggg ctgggctgag ctgagctagg    7620
ctgggttgag ctgggctggg ctgagctgag ctaggctgca ttgagctggc tgggatggat    7680
tgagctggct gagctggctg agctggctga gctgggctga gctggcctgg gttgagctgg    7740
gctgggttga gctgagctgg gctgagctgg gctcagcaga gctgggttga gctgagctgg    7800
gttgagctgg ggtgagctgg gctgagcaga gctgggttga gctgagctgg gttgagctgg    7860
gctcgagcag agctgggttg agctgagctg ggttgagctg ggctcagcag agctgggttg    7920
agctgagctg ggttgagctg ggctgagcta gctgggctca gctaggctgg gttgagctga    7980
gctgggctga actgggctga ggggctga actgggctga gctgggctga gctgggctga    8040
gcagagctgg gctgagcaga gctgggttgg tctgagctgg gttgagctgg gctgagctgg    8100
gctgagcaga gttgggttga gctgagctgg gttcagctgg gctgagctag gctgggttga    8160
gctgggttga gttgggctga gctgggctgg gttgagcgga gctgggctga actgggctga    8220
gctgggctga gcggaactgg gttgatctga attgagctgg gctgagccgg gctgagccgg    8280
gctgagctgg gctaggttga gcttgggtga gcttgcctca gctggtctga gctaggttgg    8340
gtggagctag gctggattga gctgggctga gctgagctga tctggcctca gctgggctga    8400
ggtaggctga actgggctgt gctgggctga gctgggctga gccagtttga gctgggttga    8460
gctgggctga gctgggctgt gttgatcttt cctgaactgg gctgagctgg gctgagctgg    8520
cctagctgga ttgaacgggg gtaagctggg ccaggctgga ctgggctgag ctgagctagg    8580
ctgagctgag ttgaattggg ttaagctggg ctgagatggg ctgagctggg ctgagctggg    8640
ttgagccagg tcggactggg ttaccctggg ccacactggg ctgagctggg cggagctcga    8700
ttaacctggt caggctgagt cgggtccagc agacatgcgc tggccaggct ggcttgacct    8760
ggacacgttc gatgagctgc cttgggatgg ttcacctcag ctgagccagg tggctccagc    8820
tgggctgagc tggtgaccct gggtgacctc ggtgaccagg ttgtcctgag tccgggccaa    8880
gccgaggctg catcagactc gccagaccca aggcctgggc cccggctggc aagccagggg    8940
cggtgaaggc tgggctggca ggactgtccc ggaaggaggt gcacgtggag ccgcccggac    9000
cccgaccggc aggacctgga aagacgcctc tcactcccct ttctcttctg tccctctcg    9060
ggtcctcaga gagccagtct gccccgaatc tctacccct cgtctcctgc gtcagccccc    9120
cgtccgatga gagcctggtg gccctgggct cctggcccg ggacttcctg cccagctccg    9180
tcaccttctc ctggaactac aagaacagca gcaaggtcag cagccagaac atccaggact    9240
tcccgtccgt cctgagaggc ggcaagtact tggcctcctc ccgggtgctc ctaccctctg    9300
tgagcatccc ccaggaccca gaggccttcc tggtgtgcga ggtccagcac cccagtggca    9360
ccaagtccgt gtccatctct gggccaggtg agctgggctc cccctgtggc tgtggcgggg    9420
```

| | |
|---|---|
| gcggggccgg gtgccgccgg cacagtgacg ccccgttcct gcctgcagtc gtagaggagc | 9480 |
| agccccccgt cttgaacatc ttcgtcccca cccgggagtc cttctccagt actccccagc | 9540 |
| gcacgtccaa gctcatctgc caggcctcag acttcagccc caagcagatc tccatggcct | 9600 |
| ggttccgtga tgggaaacgg gtggtgtctg gcgtcagcac aggccccgtg gagaccctac | 9660 |
| agtccagtcc ggtgacctac aggctccaca gcatgctgac cgtcacggag tccgagtggc | 9720 |
| tcagccagag cgtcttcacc tgccaggtgg agcacaaagg gctgaactac gagaagaacg | 9780 |
| cgtcctctct gtgcacctcc agtgagtgca gccctcgggc cgggcggcg gggcggcggg | 9840 |
| agccacacac acaccagctg ctccctgagc cttggcttcc gggagtggcc aaggcgggga | 9900 |
| ggggctgtgc agggcagctg agggcactg tcagctgggg cccagcaccc cctcaccccg | 9960 |
| gcagggcccg ggctccgagg ggccccgcag tcgcaggccc tgctcttggg ggaagcccta | 10020 |
| cttggccccct tcagggcgct gacgctcccc ccacccaccc ccgcctagat cccaactctc | 10080 |
| ccatcaccgt cttcgccatc gcccctcct tcgctggcat cttcctcacc aagtcggcca | 10140 |
| agctttcctg cctggtcacg ggcctcgtca ccagggagag cctcaacatc tcctggaccc | 10200 |
| gccaggacgg cgaggttctg aagaccagta tcgtcttctc tgagatctac gccaacggca | 10260 |
| ccttcggcgc caggggcgaa gcctccgtct gcgtggagga ctgggagtcg ggcgacaggt | 10320 |
| tcacgtgcac ggtgacccac acggacctgc cctcgccgct gaagcagagc gtctccaagc | 10380 |
| ccagaggtag gccctgccct gcccctgcct ccgcccggcc tgtgccttgg ccgccggggc | 10440 |
| gggagccgag cctggccgag gagcgccctc ggccccccgc ggtcccgacc cacacccctc | 10500 |
| ctgctctcct ccccagggat cgccaggcac atgccgtccg tgtacgtgct gccgccggcc | 10560 |
| ccggaggagc tgagcctgca ggagtgggcc tcggtcacct gcctggtgaa gggcttctcc | 10620 |
| ccggcggacg tgttcgtgca gtggctgcag aagggggagc ccgtgtccgc cgacaagtac | 10680 |
| gtgaccagcg cgccggtgcc cgagcccgag cccaaggccc ccgcctccta cttcgtgcag | 10740 |
| agcgtcctga cggtgagcgc caaggactgg agcgacgggg agacctacac ctgcgtcgtg | 10800 |
| ggccacgagg ccctgcccca cacggtgacc gagaggaccg tggacaagtc caccggtaaa | 10860 |
| cccaccctgt acaacgtctc cctggtcctg tccgacacgg ccagcacctg ctactgaccc | 10920 |
| cctggctgcc cgccgcggcc ggggccagag ccccgggcg accatcgctc tgtgtgggcc | 10980 |
| tgtgtgcaac ccgaccctgt cggggtgagc ggtcgcattt ctgaaaatta gaaataaaag | 11040 |
| atctcgtgcc g | 11051 |

```
<210> SEQ ID NO 30
<211> LENGTH: 12048
<212> TYPE: DNA
<213> ORGANISM: Sus sp.

<400> SEQUENCE: 30
```

| | |
|---|---|
| gcgtccgaag tcaaaaatat ctgcagcctt catgtattca tagaaacaag gaatgtctac | 60 |
| attttccaaa gtgggaccag aatcttgggt catgtctaag gcatgtgcat ttgcacatgg | 120 |
| taggcaaagg actttgcttc tcccagcaca tctttctgca gagatccatg gaaacaagac | 180 |
| tcaactccaa agcagcaaag aagcagcaag ttctcaagtg atctcctctg actccctcct | 240 |
| cccaggctaa tgaagccatg ttgcccctgg gggattaagg gcaggtgtcc attgtggcac | 300 |
| ccagcccgaa gacaagcaat tgatcaggt tctgagcact cctgaatgtg gactctggaa | 360 |
| ttttctcctc accttgtggc atatcagctt aagtcaagta caagtgacaa acaacataat | 420 |

```
cctaagaaga gaggaatcaa gctgaagtca aaggatcact gccttggatt ctactgtgaa    480
tgatgacctg gaaatatcc tgaacaacag cttcagggtg atcatcagag acaaaagttc     540
cagagccagg tagggaaacc ctcaagcctt gcaaagagca aaatcatgcc attgggttct    600
taacctgctg agtgatttac tatatgttac tgtgggaggc aaagcgctca aatagcctgg    660
gtaagtatgt caaataaaaa gcaaagtgg tgtttcttga atgttagac ctgaggaagg      720
aatattgata acttaccaat aattttcaga atgatttata gatgtgcact tagtcagtgt    780
ctctccaccc cgcacctgac aagcagttta gaatttattc taagaatcta ggtttgctgg    840
gggctacatg ggaatcagct tcagtgaaga gtttgttgga atgattcact aaattttcta    900
tttccagcat aaatccaaga acctctcaga ctagtttatt gacactgctt ttcctccata    960
atccatctca tctccgtcca tcatggacac tttgtagaat gacaggtcct ggcagagact   1020
cacagatgct tctgaaacat cctttgcctt caaagaatga acagcacaca tactaaggat   1080
ctcagtgatc cacaaattag ttttttgccac aatggttctt atgataaaag tctttcatta  1140
acagcaaatt gttttataat agttgttctg ctttataata attgcatgct tcactttctt   1200
ttctttctt ttttttcttt ttttttgcttt ttagtgccgc aggtgcagca tatgaaattt   1260
cccaggctag gggtcaaatc agaactacac ctactggcct acgccacagc cacagcaact  1320
caggatctaa gccatgtcgg tgacctacac tacagctcat ggcaatgcca gatccttaac   1380
ccaatgagcg aggccaggga tcgaacccat gtcctcatgg atactagtca ggctcattat   1440
ccgctgagcc ataacaggaa ctcccgagtt tgcttttat caaaattggt acagccttat    1500
tgtttctgaa aaccacaaaa tgaatgtatt cacataattt taaaaggtta aataatttat   1560
gatatacaag acaatagaaa gagaaaacgt cattgcctct ttcttccacg acaacacgcc   1620
tccttaattg atttgaagaa ataactactg agcatggttt agtgtacttc tttcagcaat   1680
tagcctgtat tcatagccat acatattcaa ttaaaatgag atcatgatat cacacaatac   1740
ataccataca gcctataggg attttttacaa tcatcttcca catgactaca taaaaaccta  1800
cctaaaaaaa aaaaaaaccc tacttcatcc tcctattggc tgctttgtgc tccattaaaa   1860
agctctatca taattaggtt atgatgagga tttccatttt ctacctttca agcaacattt   1920
caatgcacag tcttatatac acatttgagc ctactttct ttttcttct ttttttggtt     1980
ttttttttt tttttttttt ggtcttttg tcttttctaa ggctgcatat ggaggttccc     2040
aggctagctg tctaatcaga actatagctg ctggcctacg ccacatccac agcaatacaa   2100
gatctgagcc atgtctgcaa cttacaccac agctcacagc aacggtggat ccttaaacca   2160
ctgagcaagg ccagggatca aacccataac ttcatggctc ctagttggat ttgttaacca   2220
ctgagccatg atggcaactc ctgagcctac ttttctaatc atttccaacc ctaggacact   2280
tttttaagtt tcattttct ccccccaccc cctgttttct gaagtgtgtt tgcttccact    2340
gggtgacttc actcccagga tctcatctgc aggatactgc agctaagtgt atgagctctg   2400
aatttgaatc ccaactctgc cactcaaagg gataggagtt tccgatgtgg cccaatggga   2460
tcagtggcat ctctgcagtg ccaggacgca ggttccatcc ctggcccagc acagtgggtt   2520
aagaatctgg cattgctgca gctgaggcat agatttcaat tgtgcctcag atctgatcct   2580
tggcccaagg actgcatatg cctcagggca accaaaaaag agaaagggg ggtgatagca   2640
ttagtttcta gatttggggg ataattaaat aaagtgatcc atgtacaatg tatggcattt   2700
tgtaaatgct caacaatttt caactattat ggagttccca tcatggctca gtggaaggga   2760
atctgattag catccatgag gacacaggtc caaccccgac cttgctcagt gggcattgct   2820
```

```
gtgagctgtg gcatgggtta cagacgaagc tcggatctgg cattgctgtg gctgtggtgt    2880
aagccagcaa ctacagctct cattcagccc ctagcctggg aacctccata tgcctaaaag    2940
acaaaaaata aaatttaaat taaaaataaa gaaatgttaa ctattatgat tggtactgct    3000
tgcattactg caaagaaagt cactttctat actctttaat atcttagttg actgtgtgct    3060
cagtgaacta ttttggacac ttaatttcca ctctcttcta tctccaactt gacaactctc    3120
tttcctctct tctggtgaga tccactgctg actttgctct ttaaggcaac tagaaaagtg    3180
ctcagtgaca aaatcaaaga aagttacctt aatcttcaga attacaatct taagttctct    3240
tgtaaagctt actatttcag tggttagtat tattccttgg tcccttacaa cttatcagct    3300
ctgatctatt gctgattttc aactatttat tgttggagtt ttttcctttt ttccctgttc    3360
attctgcaaa tgtttgctga gcatttgtca agtgaagata ctggactggg ccttccaaat    3420
ataagacaat gaaacatcgg gagttctcat tatggtgcag cagaaacgaa tccaactagg    3480
aaatgtgagg ttgcaggttc gatccctgcc cttgctcagt gggttaagga tccagcatta    3540
ccgtgagctg tggtgtaggt tgcagacgtg gctcagatcc tgcgttgctg tggctgtggc    3600
ataggctggc agctctagct ctgattcgac cgctagcctg gaacctcca tgcgccccga    3660 gtgcagccct taaaaagcaa aaaaaaaga aagaaagaaa aagacaatga aacatcaaac    3720
agctaacaat ccagtagggt agaaagaatc tggcaacaga taagagcgat taaatgttct    3780
aggtccagtg accttgcctc tgtgctctac acagtcgtgc cacttgctga gggagaaggt    3840
ctctcttgag ttgagtcctg aaagacatta gttgttcaca aactaatgcc agtgagtgaa    3900
ggtgtttcca agcagaggga gagtttggta aaaagctgga agtcacagaa agactctaaa    3960
gagtttagga tggtgggagc aacatacgct gagatgggc tggaaggtta agagggaaac    4020
aactatagta agtgaagctg gactcacagc aaagtgagga cctcagcatc cttgatgggg    4080
ttaccatgga aacaccaagg cacaccttga tttccaaaac agcaggcacc tgattcagcc    4140
caatgtgaca tggtgggtac ccctctagct ctacctgttc tgtgacaact gacaaccaac    4200
gaagttaagt ctggattttc tactctgctg atccttgttt ttgtttcaca cgtcatctat    4260
agcttcatgc caaatagag ttcaaggtaa dacgcgggcc ttggtttgat atacatgtag    4320
tctatcttgt ttgagacaat atggtggcaa ggaagaggtt caaacaggaa aatactctct    4380
aattatgatt aactgagaaa agctaaagag tcccataatg acactgaatg aagttcatca    4440
tttgcaaaag ccttcccccc cccccaggag actataaaaa agtgcaattt tttaaatgaa    4500
cttatttaca aaacagaaat agactcacag acataggaaa cgaacagatg gttaccaagg    4560
gtgaaaggga gtaggaggga taaataagga gtctggggtt agcagataca ccccagtgta    4620
cacaaaataa acaacaggga cctactatat agcacaggga actatatgca gtagcttaca    4680
ataacctata atggaaaaga atgtgaaaaa gaatatatgt atgcgtgtgt gtgtaactga    4740
atcactttgc tgtaacctga atctaacata acattgtaaa tcaactacag ttttttttt    4800 ttttaagtgc agggttttgg tgttttttttt ttttcatttt tgttttgtt tttgttttttt    4860 gcttttttagg gccacaccca gacatatggg ggttcccagg ctaggggtct aattagagct    4920
acagttgccg gcttgcacca cagccacagc aacatcagat ccgagccgca cttgcgactt    4980
acaccacagc tcatggcaat accagatcct taacccactg agcaaggccc agggatcgta    5040
cccgcaacct catggttcct agtcagattc atttctgctg cgctacaatg ggaactccaa    5100
gtgcagtttt ttgtaatgtg cttgtctttc tttgtaattc atattcatcc tacttcccaa    5160
```

| | |
|---|---|
| taaataaata aatacataaa taataaacat accattgtaa atcaactaca atttttttta | 5220 |
| aatgcagggt ttttgttttt tgttttttgt tttgtctttt tgccttttct agggccgctc | 5280 |
| ccatggcata tggaggttcc caggctaggg gtcgaatcgg agctgtagcc accggcctac | 5340 |
| gccagagcca cagcaacgcg ggatccgagc cgcgtctgca acctacacca cagctcacgg | 5400 |
| caacgccgga tcgttaaccc actgagcaag ggcagggatc gaacctgcaa cctcatggtt | 5460 |
| cctagtcaga ttcgttaact actgagccac aacggaaact cctaaagtgc agttttttaaa | 5520 |
| tgtgcttgtc tttctttgta atttacactc aacctacttc ccaataaata aataaataaa | 5580 |
| caaataaatc atagacatgg ttgaattcta aggaaggga ccatcaggcc ttagacagaa | 5640 |
| atacgtcatc ttctagtatt ttaaaacaca ctaaagaaga caaacatgct ctgccagaga | 5700 |
| agcccaggc ctccacagct gcttgcaaag ggagttaggc ttcagtagct gacccaaggc | 5760 |
| tctgttcctc ttcagggaaa agggtttttg ttcagtgaga cagcagacag ctgtcactgt | 5820 |
| ggtggacgtt cggccaagga accaagctgg aactcaaacg taagtcaatc caaacgttcc | 5880 |
| ttccttggct gtctgtgtct tacggtctct gtggctctga atgattcat gtgctgactc | 5940 |
| tctgaaacca gactgacatt ctccagggca aaactaaagc ctgtcatcaa actggaaaac | 6000 |
| tgagggcaca ttttctgggc agaactaaga gtcaggcact gggtgaggaa aaacttgtta | 6060 |
| gaatgatagt ttcagaaact tactgggaag caaagcccat gttctgaaca gagctctgct | 6120 |
| caagggtcag gaggggaacc agttttttgta caggagggaa gttgagacga accctgtgt | 6180 |
| atatggtttc ggcgcgggga ccaagctgga gctcaaacgt aagtggcttt tccgactga | 6240 |
| ttctttgctg tttctaattg ttggttggct ttttgtccat ttttcagtgt tttcatcgaa | 6300 |
| ttagttgtca gggaccaaac aaattgcctt cccagattag gtaccaggga ggggacattg | 6360 |
| ctgcatggga gaccagaggg tggctaattt ttaacgtttc caagccaaaa taactgggga | 6420 |
| agggggcttg ctgtcctgtg agggtaggtt tttatagaag tggaagttaa ggggaaatcg | 6480 |
| ctatggttca cttttggctc ggggaccaaa gtggagccca aaattgagta cattttccat | 6540 |
| caattatttg tgagattttt gtcctgttgt gtcatttgtg caagtttttg acattttggt | 6600 |
| tgaatgagcc attcccaggg acccaaaagg atgagaccga aaagtagaaa agagccaact | 6660 |
| tttaagctga gcagacagac cgaattgttg agtttgtgag gagagtaggg tttgtaggga | 6720 |
| gaaaggggaa cagatcgctg gcttttctc tgaattagcc tttctcatgg gactggcttc | 6780 |
| agagggggtt tttgatgagg gaagtgttct agagccttaa ctgtgggttg tgttcggtag | 6840 |
| cgggaccaag ctgaaatca aacgtaagtg cacttttcta ctccttttc tttcttatac | 6900 |
| gggtgtgaaa ttggggactt ttcatgtttg gagtatgagt tgaggtcagt tctgaagaga | 6960 |
| gtgggactca tccaaaaatc tgaggagtaa gggtcagaac agagttgtct catggaagaa | 7020 |
| caaagaccta gttagttgat gaggcagcta aatgagtcag ttgacttggg atccaaatgg | 7080 |
| ccagacttcg tctgtaacca acaatctaat gagatgtagc agcaaaaaga gatttccatt | 7140 |
| gagggggaaag taaaattgtt aatattgtgg atcacctttg gtgaagggac atccgtggag | 7200 |
| attgaacgta agtattttt ctctactacc ttctgaaatt tgtctaaatg ccagtgttga | 7260 |
| cttttagagg cttaagtgtc agttttgtga aaaatgggta aacaagagca tttcatattt | 7320 |
| attatcagtt tcaaaagtta aactcagctc caaaaatgaa tttgtagaca aaagattaa | 7380 |
| tttaagccaa attgaatgat tcaaggaaaa aaaaattag tgtagatgaa aaggaattc | 7440 |
| ttacagctcc aaagagcaaa agcgaattaa ttttctttga actttgccaa atcttgtaaa | 7500 |
| tgattttttgt tctttacaat ttaaaaaggt tagagaaatg tatttcttag tctgttttct | 7560 |

```
ctcttctgtc tgataaatta ttatatgaga taaaaatgaa aattaatagg atgtgctaaa    7620
aaatcagtaa gaagttagaa aaatatatgt ttatgttaaa gttgccactt aattgagaat    7680
cagaagcaat gttattttta aagtctaaaa tgagagataa actgtcaata cttaaattct    7740
gcagagattc tatatcttga cagatatctc cttttcaaa aatccaattt ctatggtaga     7800
ctaaatttga aatgatcttc ctcataatgg agggaaaaga tggactgacc ccaaaagctc    7860
agatttaaag aaatctgttt aagtgaaaga aaataaaaga actgcatttt ttaaaggccc    7920
atgaatttgt agaaaaatag gaaatatttt aataagtgta ttcttttatt ttcctgttat    7980
tacttgatgg tgttttttata ccgccaagga ggccgtggca ccgtcagtgt gatctgtaga   8040
ccccatggcg gccttttttc gcgattgaat gaccttggcg gtgggtcccc agggctctgg    8100
tggcagcgca ccagccgcta aaagccgcta aaaactgccg ctaaaggcca cagcaacccc    8160
gcgaccgccc gttcaactgt gctgacacag tgatacagat aatgtcgcta acagaggaga   8220
atagaaatat gacgggcaca cgctaatgtg gggaaaagag ggagaagcct gattttatt    8280 ttttagagat tctagagata aaattcccag tattatatcc ttttaataaa aaatttctat   8340
taggagatta taaagaattt aaagctattt ttttaagtgg ggtgtaattc tttcagtagt   8400
ctcttgtcaa atggatttaa gtaatagagg cttaatccaa atgagagaaa tagacgcata   8460 acccttcaa gcaaaagct acaagagcaa aaattgaaca cagcagccag ccatctagcc     8520
actcagattt tgatcagttt tactgagttt gaagtaaata tcatgaaggt ataattgctg   8580 ataaaaaat aagatacagg tgtgacacat ctttaagttt cagaaattta atggcttcag    8640
taggattata tttcacgtat acaaagtatc taagcagata aaaatgccat taatggaaac   8700
ttaatagaaa tatattttta aattccttca ttctgtgaca gaaattttct aatctgggtc   8760
ttttaatcac ctaccctttg aaagagttta gtaatttgct atttgccatc gctgtttact   8820
ccagctaatt tcaaaagtga tacttgagaa agattatttt tggtttgcaa ccacctggca   8880
ggactatttt agggccattt taaaactctt ttcaaactaa gtattttaaa ctgttctaaa   8940
ccatttaggg cctttttaaaa atcttttcat gaatttcaaa cttcgttaaa agttattaag   9000
gtgtctggca agaacttcct tatcaaatat gctaatagtt taatctgtta atgcaggata   9060
taaaattaaa gtgatcaagg cttgacccaa acaggagtat cttcatagca tatttcccct   9120 ccttttttc tagaattcat atgattttgc tgccaaggct attttatata atctctggaa    9180
aaaaaatagt aatgaaggtt aaaagagaag aaaatatcag aacattaaga attcggtatt    9240
ttactaactg cttggttaac atgaaggttt ttatttttatt aaggtttcta tctttataaa   9300
aatctgttcc cttttctgct gatttctcca agcaaaagat tcttgatttg ttttttaact   9360
cttactctcc cacccaaggg cctgaatgcc cacaaagggg acttccagga ggccatctgg   9420
cagctgctca ccgtcagaag tgaagccagc cagttcctcc tgggcaggtg gccaaaatta   9480
cagttgaccc ctcctggtct ggctgaacct tgccccatat ggtgacagcc atctggccag   9540
ggcccaggtc tccctctgaa gcctttggga ggagagggag agtggctggc ccgatcacag   9600
atgcggaagg ggctgactcc tcaaccgggg tgcagactct gcaggtgggg tctgggccca   9660
acacacccaa agcacgccca ggaaggaaag gcagcttggt atcactgccc agagctagga   9720
gaggcaccgg gaaaatgatc tgtccaagac ccgttcttgc ttctaaactc cgagggggtc   9780
agatgaagtg gttttgtttc ttggcctgaa gcatcgtgtt ccctgcaaga agcgggaac    9840 acagaggaag gagagaaaag atgaactgaa caaagcatgc aaggcaaaaa aggccttagg   9900
```

```
atggctgcag gaagttagtt cttctgcatt ggctccttac tggctcgtcg atcgcccaca    9960
aacaacgcac ccagtggaga acttccctgt tacttaaaca ccattctctg tgcttgcttc   10020
ctcaggggct gatgccaagc catccgtctt catcttcccg ccatcgaagg agcagttagc   10080
gaccccaact gtctctgtgg tgtgcttgat caataacttc ttccccagag aaatcagtgt   10140
caagtggaaa gtggatgggg tggtccaaag cagtggtcat ccggatagtg tcacagagca   10200
ggacagcaag gacagcacct acagcctcag cagcaccctc tcgctgccca cgtcacagta   10260
cctaagtcat aatttatatt cctgtgaggt cacccacaag accctggcct cccctctggt   10320
cacaagcttc aacaggaacg agtgtgaggc ttagaggccc acaggcccct ggcctgcccc   10380
cagccccagc cccctcccc acctcaagcc tcaggccctt gccccagagg atccttggca    10440
atccccagc cctcttccc tcctcatccc ctcccctct ttggctttaa ccgtgttaat      10500
actggggggt gggggaatga ataaataaag tgaacctttg cacctgtgat ttctctctcc   10560
tgtctgattt taaggttgtt aaatgttgtt ttccccatta tagttaatct tttaaggaac   10620
tacatactga gttgctaaaa actacaccat cacttataaa attcacgcct tctcagttct   10680
ccctcccct cctgtcctcc gtaagacagg cctccgtgaa acccataagc acttctcttt    10740
acccctctc ctgggccggg gtaggagact ttttgatgtc ccctcttcag caagcctcag   10800
aaccattttg aggggacag ttcttacagt cacattcctg tgatctaatg actttagtta    10860
ccgaaaagcc agtctctcaa aaagaaggga acggctagaa accaagtcat agaaatatat   10920
atgtataaaa tatatatata tccatatatg taaaataaca aaataatgat aacagcatag   10980
gtcaacaggc aacagggaat gttgaagtcc attctggcac ttcaatttaa gggaatagga   11040
tgccttcatt acatttaaaa tacaatacac atggagagct tcctatctgc caaagaccat   11100
cctgaatgcc ttccacactc actacaaggt taaaagcatt cattacaatg ttgatcgagg   11160
agttcccgtt gtggctcagc aggttaagaa cgtgactggt atccaggagg atgcgggttt   11220
ggtccccagc ctcgctcagt ggattaagga tccagtgttg ctgcaagatc acgggctcag   11280
atcccgtgtt ctatggctat ggtgtaggct ggtagctgca tgcagcccta atttgacccc   11340
tagcctggga actgccatat gccacatgtg aggcccttaa aacctaaaag aaaaaaaaag   11400
aaagaaata tcttacaccc aatttataga taagagagaa gctaaggtgg caggcccagg    11460
atcaaagccc tacctgccta tcttgacacc tgatacaaat tctgtcttct agggtttcca   11520
acactgcata gaacagaggg tcaaacatgc taccctccca gggactcctc ccttcaaatg   11580
acataaattt tgttgcccat ctctgggggc aaaactcaac aatcaatggc atctctagta   11640
ccaagcaagg ctcttctcat gaagcaaaac tctgaagcca gatccatcat gacccaagga   11700
agtaaagaca ggtgttactg gttgaactgt atccttcaat tcaatatgct caatttccaa   11760
ctcccagtcc ccgtaaatac aaccccttt gggaagagag tccttgcaga tgtagccacg    11820
ttaaaaagag attatacaga aaggctagtg aggatgcagt gaaacgggat ctttcataca   11880
ttgctggtgg aaatgtaaaa tgctgcaggc actctagaaa ataatttgcc agttttttga   11940
aaagctaaac aaaatagttt agttgcattc tgggttattt atccccagaa aattaaaaat   12000
tatgtccgca caaaacgtg tacataatca ttcataacag ccttgtac                 12048
```

<210> SEQ ID NO 31
<211> LENGTH: 126068
<212> TYPE: DNA
<213> ORGANISM: Bovine sp.
<220> FEATURE:
<221> NAME/KEY: misc_feature

```
<222> LOCATION: (3591)..(3690)
<223> OTHER INFORMATION: n is a, c, g, or t
<220> FEATURE:
<221> NAME/KEY: misc_feature
<222> LOCATION: (6955)..(6955)
<223> OTHER INFORMATION: n is a, c, g, or t
<220> FEATURE:
<221> NAME/KEY: misc_feature
<222> LOCATION: (6967)..(6967)
<223> OTHER INFORMATION: n is a, c, g, or t
<220> FEATURE:
<221> NAME/KEY: misc_feature
<222> LOCATION: (6974)..(6974)
<223> OTHER INFORMATION: n is a, c, g, or t
<220> FEATURE:
<221> NAME/KEY: misc_feature
<222> LOCATION: (6976)..(6978)
<223> OTHER INFORMATION: n is a, c, g, or t
<220> FEATURE:
<221> NAME/KEY: misc_feature
<222> LOCATION: (6980)..(6980)
<223> OTHER INFORMATION: n is a, c, g, or t
<220> FEATURE:
<221> NAME/KEY: misc_feature
<222> LOCATION: (6985)..(6985)
<223> OTHER INFORMATION: n is a, c, g, or t
<220> FEATURE:
<221> NAME/KEY: misc_feature
<222> LOCATION: (6987)..(6988)
<223> OTHER INFORMATION: n is a, c, g, or t
<220> FEATURE:
<221> NAME/KEY: misc_feature
<222> LOCATION: (7000)..(7000)
<223> OTHER INFORMATION: n is a, c, g, or t
<220> FEATURE:
<221> NAME/KEY: misc_feature
<222> LOCATION: (7534)..(7633)
<223> OTHER INFORMATION: n is a, c, g, or t
<220> FEATURE:
<221> NAME/KEY: misc_feature
<222> LOCATION: (7842)..(7842)
<223> OTHER INFORMATION: n is a, c, g, or t
<220> FEATURE:
<221> NAME/KEY: misc_feature
<222> LOCATION: (11197)..(11197)
<223> OTHER INFORMATION: n is a, c, g, or t
<220> FEATURE:
<221> NAME/KEY: misc_feature
<222> LOCATION: (12793)..(12892)
<223> OTHER INFORMATION: n is a, c, g, or t
<220> FEATURE:
<221> NAME/KEY: misc_feature
<222> LOCATION: (18660)..(18759)
<223> OTHER INFORMATION: n is a, c, g, or t
<220> FEATURE:
<221> NAME/KEY: misc_feature
<222> LOCATION: (23231)..(23330)
<223> OTHER INFORMATION: n is a, c, g, or t
<220> FEATURE:
<221> NAME/KEY: misc_feature
<222> LOCATION: (27257)..(27356)
<223> OTHER INFORMATION: n is a, c, g, or t
<220> FEATURE:
<221> NAME/KEY: misc_feature
<222> LOCATION: (27727)..(27727)
<223> OTHER INFORMATION: n is a, c, g, or t
<220> FEATURE:
<221> NAME/KEY: misc_feature
<222> LOCATION: (32250)..(32349)
<223> OTHER INFORMATION: n is a, c, g, or t
<220> FEATURE:
<221> NAME/KEY: misc_feature
<222> LOCATION: (39216)..(39315)
<223> OTHER INFORMATION: n is a, c, g, or t
<220> FEATURE:
<221> NAME/KEY: misc_feature
<222> LOCATION: (41326)..(41425)
<223> OTHER INFORMATION: n is a, c, g, or t
<220> FEATURE:
```

```
<221> NAME/KEY: misc_feature
<222> LOCATION: (48650)..(48749)
<223> OTHER INFORMATION: n is a, c, g, or t
<220> FEATURE:
<221> NAME/KEY: misc_feature
<222> LOCATION: (55204)..(55204)
<223> OTHER INFORMATION: n is a, c, g, or t
<220> FEATURE:
<221> NAME/KEY: misc_feature
<222> LOCATION: (56436)..(56535)
<223> OTHER INFORMATION: n is a, c, g, or t
<220> FEATURE:
<221> NAME/KEY: misc_feature
<222> LOCATION: (61281)..(61281)
<223> OTHER INFORMATION: n is a, c, g, or t
<220> FEATURE:
<221> NAME/KEY: misc_feature
<222> LOCATION: (61394)..(61493)
<223> OTHER INFORMATION: n is a, c, g, or t
<220> FEATURE:
<221> NAME/KEY: misc_feature
<222> LOCATION: (68709)..(68808)
<223> OTHER INFORMATION: n is a, c, g, or t
<220> FEATURE:
<221> NAME/KEY: misc_feature
<222> LOCATION: (73149)..(73248)
<223> OTHER INFORMATION: n is a, c, g, or t
<220> FEATURE:
<221> NAME/KEY: misc_feature
<222> LOCATION: (80571)..(80670)
<223> OTHER INFORMATION: n is a, c, g, or t
<220> FEATURE:
<221> NAME/KEY: misc_feature
<222> LOCATION: (91799)..(91898)
<223> OTHER INFORMATION: n is a, c, g, or t
<220> FEATURE:
<221> NAME/KEY: misc_feature
<222> LOCATION: (106600)..(106699)
<223> OTHER INFORMATION: n is a, c, g, or t
<220> FEATURE:
<221> NAME/KEY: misc_feature
<222> LOCATION: (121987)..(121987)
<223> OTHER INFORMATION: n is a, c, g, or t
<220> FEATURE:
<221> NAME/KEY: misc_feature
<222> LOCATION: (121993)..(121993)
<223> OTHER INFORMATION: n is a, c, g, or t

<400> SEQUENCE: 31
tgggttctat gccacccagc ttggtctctg atggtcactt gaggccccca tctcatggca      60
aagagggaac tggattgcag atgagggacc gtgggcagac atcagaggga cacagaaccc     120
tcaaggctgg ggaccagagt cagagggcca ggaagggctg ggaccttggg gtctagggat     180
ccgggtcagg gactcggcaa aggtggaggg ctccccaagg cctccatggg gcggacctgc     240
agatcctggg ccggccaggg acccagggaa agtgcaaggg gaagacgggg gaggagaagg     300
tgctgaactc agaactgggg aaagagatag gaggtcagga tgcagggac acggactcct      360 gagtctgcag gacacactcc tcagaagcag gagtccctga agaagcagag agacaggtac     420
cagggcagga aacctccaga cccaagaaga ctcagagagg aacctgagct cagatctgcg     480
gatgggggga ccgaggacag gcagacaggc tcccctcga ccagcacaga ggctccaagg     540
gacacagact tggagaccaa cggacgcctt cgggcaaagg ctcgaacaca catgtcagct     600
caaaatatac ctggactgac tcacaggagg ccagggaggc cacatcatcc actcagggga     660
cagactgcca gccccaggca gacccatca accgtcagac gggcaggcaa ggagagtgag      720
ggtcagatgt ctgtgtggga aaccaagaac cagggagtct caggacagcg ctggcagggg     780
tccaggctca ggctttccca ggaagatggg gaggtgcctg agaaaacccc acccaccttc     840
cctggcacag gccctctggc tcacagtggt gcctggactc ggggtcctgc tgggctctca     900
```

```
aaggatcctg tgtcccsctg tgacacagac tcaggggctc ccatgacggg caccagacct    960
ctgattgtgg tcttcttccc ctcgcccact ttgcaggtca gcccaagtcc acaccctcgg   1020
tcaccctgtt cccgccctcc aaggaggagc tcagcaccaa caaggccacc ctggtgtgtc   1080
tcatcagcga cttctacccg ggtagcgtga ccgtggtcta aaggcagac ggcagcacca   1140
tcacccgcaa cgtggagacc acccgggcct ccaaacagag caacagcaag tacgcggcca   1200
gcagctacct gagcctgatg ggcagcgact ggaaatcgaa aggcagttac agctgcgagg   1260
tcacgcacga ggggagcacc gtgacgaaga cagtgaagcc tcagagtgtt cttagggccc   1320
tgggccccca ccccggaaag ttctaccctc ccaccctggt tcccctagc ccttcctcct   1380
gcacacaatc agctcttaat aaaatgtcct cattgtcatt cagaaatgaa tgctctctgc   1440
tcattttgt tgatacattt ggtgccctga gctcagttat cttcaaagga aacaaatcct   1500
cttagccttt gggaatcagg agagagggtg gaagcttggg ggtttgggga gggatgattt   1560
cactgtcatc cagaatcccc cagagaacat tctggaacag gggatggggc cactgcagga   1620
gtggaagtct gtccacccctc ccatcagcc gccatgcttc ctcctctgtg tggaccgtgt   1680
ccagctctga tggtcacggc aacacactct ggttgccacg ggcccagggc agtatctcgg   1740
ctccctccac tgggtgctca gcaatcacat ctggaagctg ctcctgctca agcggccctc   1800
tgtccactta gatgatgacc ccctgaagt catgcgtgtt ttggctgaaa ccccaccctg   1860
gtgattccca gtcgtcacag ccaagactcc ccccgactcg acctttccaa gggcactacc   1920
ctctgccccc cccccagggc tcccctcac agtcttcagg ggaccggcaa gcccccaacc   1980
ctggtcactc atctcacagt tcccccaggt cgccctcctc ccacttgcat ggcaggaggg   2040
tcccagctga cttcgaggtc tctgaccagc ccagctctgc tctgcgaccc cttaaaactc   2100
agcccaccac ggagcccagc accatctcag gtccaagtgg ccgttttggt tgatgggttc   2160
cgtgagctca agcccagaat caggttaggg aggtcgtggc gtggtcatct ctgaccttgg   2220
gtggtttctt aggagctcag aatgggagct gatacacgga taggctgtgc taggcactcc   2280
cacgggacca cacgtgagca ccgttagaca cacacacaca cacacacaca cacacacaca   2340
cacacacgag tcactacaaa cacggccatg ttggttggac gcatctctag gaccagaggc   2400
gcttccagaa tccgccatgg cctcactctg cggagaccac agctccatcc cctccgggct   2460
gaaaaccgtc tcctcaccct cccaccgggg tgacccccaa agctgctcac gaggagcccc   2520
cacctcctcc aggagaagtt ccctgggacc cggtgtgaca cccagccgtc cctcctgccc   2580
ctcccccgcc tggagatggc cggcgcccca tttcccaggg gtgaactcac aggacggag   2640
gggtcgctcc cctcacccgc ccggagggtc aaccagcccc tttgaccagg agggggcgg   2700
acctgggggct ccgagtgcag ctgcaggcgg gccccgggg gtggcgggc tggcggcagg   2760
gtttatgctg gaggctgtgt cactgtgcgt gtttgctcgg tggagggacc cagctggcca   2820
tccggggtga gtctcccctt tccagctttc cggagtcagg agtgacaaat gggtagattc   2880
ttgtgttttt cttacccatc tggggctgag gtctccgtca ccctaggcct gtaaccctcc   2940
ccctttagc ctgttccctc tgggcttctt cacgtttcct tgaggacag tttcactgtc   3000
acccagcaaa gcccagagaa tatccagatg ggcaggcaa tatgggacgg caagctagtc   3060
caccctctta ccttgggctc cccgcggcct ccggataatg tctgagctgc ctccctggat   3120
gcttcacctt ctgagactgt gaggcaagaa acccctccc caaagggag gagacccgac   3180
cccagtgcag atgaacgtgc tgtgagggga ccctgggagt aagtgggtc tggcggggac   3240
```

```
cgtgatcatt gcagactgat gccccaggca gggtgagagg tcatggccgc cgacaccagc    3300
agctgcaggg agcacaggcc gggggcaagt catgcagaca ggacaggacg tgtgaccctg    3360
aagagtcaga gtgacacgcg ggggggggc ccggagctcc cgagattagg gcttgggtcc     3420
taacgggatc caggagggtc cacgggccca ccccagccct ctccctgcac caatcaact    3480 tgcaataaaa cgtcctctat tgtcttacaa aaaccctgct ctctgctcat gttttcctt    3540 gccccgcatt taatcgtcaa cctctccagg attctggaac tggggtgggg nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn agcttatgtg gtgggcaggg gggtagtaag    3720
atcaaaagtg cttaaattaa taaagccggc atgatatacg agtttggata aaaaatagat    3780
ggaaaagtaa gaaaggacag gagggggtg aggcggaaga aaggggaag aaggaaaaaa     3840 aaataagaga gaggaacaaa gaaagggagg ggggccggtg atggggtgg gatagaatat    3900 aataattgga gtaaagagta gcgggtggct gttaattccg ggggggaata gagaaaaaaa    3960
aaaaaaaatg tgcgggtggg cggtaagtat ggagatttta taaatattat gtgtggaata    4020
atgagcgggg gtggacgggc aaggcgagag taaaaagggg cgagagaaaa aaattaggat    4080
ggaatatatg gggtaaattt taaatagagg gtgatatatg ttagattgag caagatataa    4140
atatagatgg tggggaaaa gagacaaggg tgagcgccaa aacgccctcc cgtatcattt     4200
gccttccttc ctttaccacc tcgttcaaac tcttttcga gaaccctgaa gcggtcaggc    4260
ccggggctgg gggtgggata cccggggagg ggctgcgcct cctcctttgc agaggggtc    4320 gaggagtggg agctgaggca ggagactggc aggctggaga gatggctgtt gacttcctgc    4380
ctgtttgaac tcacagtcac agtgccagac ccactgaatt gggctaaata ccatatttt     4440 ctggggagag agtgtagagc gagcgactga ggcgagctca tgtcatctac agggccgcca    4500
gctgcaggga ctttgtgtgt gtcgtgctcg ttgctcagtt gtgtccgact ctttatgact    4560
tcatggactg taacctgcca ggctcctctg tccgtggaat tctccaggca agaatactgg    4620
agtgggtagc cattctcatc tccggggat cttcctgacc caagaatcaa acctgagtct    4680
cccgcattgc aggcagcttc tttcttgtct gagccaccag ggaagcccct taagtggagg    4740
atctaaatag agtgtttagg agtataagag aaaggaagga cgtctataca agatccttcg    4800
gttcctgtaa ctacgactcg agttaacaag ccctgtgtga gtgagttgcc agtaattatt    4860
gctaacctgt ttctttcact cactgagcca ggtatcctgt gagacggcat acttacctcc    4920
tcttctgcat tcctcgggat ggagctgtgc ggtggcctct aggactacca catcgaccag    4980
gtcagaccca gggacagagg attgctgaga tgcactgaga agtttgtcag cctaggtctt    5040
cacccacaca gactgtgctg tcgtctacca cgtaattctt cctgtccaaa gaactggtta    5100
aacgctcctg aagcgtattc tggtctgctt caaaaagtgc ctctttcctt tataagttcc    5160
gccaatcctg gactttgtcc caggccagtc tactttattt gtgggaaagg ttttttggt    5220 cttttttgtt ttaaactctg cagaaattgc ttacactttt ggtgtgcaat ggctcactct    5280
tacggttcta gctgtattca aaggggttgc ttttctttgt ttttaaagct ttttgaacgt    5340
ggaccatttt taaagtcttt attaaacgtc taacatcgtt tctggtttat tttctggtgg    5400
tctggccatg aggcctacgg gtcttagctc ccctaccagg gtccaaccca catcccttgc    5460
actggacggc aaggtcttaa cctttgaacc accagagagc ttctgaaagg ggctgctttt    5520
ctccaatcct ctttgctccc tgcctgctgg tagggattca gcacccctgc aatagccctg    5580
tctgttctta ggggctcagt agcctttctg cctgggtgtg gagctggggt tgtaagagag    5640
```

```
cttcatggat ttggacacga cctacgactc agaggtaaga ctccatctta gcgctgtaat      5700
gacctctttc aacaaccac ccccaccacc ctgaccact gatcaggaga gatgattctc        5760
tctcttatca tcaacgtggt cagtcccaaa cttgcaccg gcctgtcata gatgtagcag      5820
gtaagcaata aatatttgtt gaatgttaag tgaattgaaa taacataagt gaaaagaaa       5880 acacttaaaa acatgtgttt ttataattac acagtaaaca tataatcatt gtagaaaaaa     5940
atcgaaagag tggcgggggc caagtgaaaa ccaccatccc tggtatgtcc acccgcccgg     6000
gtagccccag gtaagaggtg cggacacgga tggccctgta gacacagaga cacacgctca     6060
tatgctgggt cttgtcttgt gacctcttgg ggatgatgtt attttcacga tgccattcaa     6120
accttctacc acaccatttt tagagggtcg ttcatcgtaa atcagttcac tgctttgttt     6180
tctgattttg aaagtgtcac attcttcgag aaatgagaag gaacaggcgc gcataaggaa     6240
gaaagtaaac acgtggcctt gcttccaggg ggcactcagc gtgttggtgt gcacgctggc     6300
agtcttttct ctgtgacagt catggccttt tcccaaaggt gggctcagat aagaccgcct     6360
cccatcccct gtccctgtcc ccgtccccta cggtggaacc cacccacggc acgtctccga     6420
ggccctttgg ggctgtggac gttaggctgt gtggacatgc tgctggtggg gacccagggc     6480
tgggcagcac gttgtccctg ggtcccgggc cagtgaggag ctcccaagga gcagggctgc     6540
tgggccaaag ggcagtgcgt cccgaggcca tggacaaggg gatacatttc ctgctgaagg     6600
gctggactgc gtctccctgg ggcccttgg agtcatgggc agtggggagg cctctgctca      6660
ccccgttgcc cacccatggc tcagtctgca gccaggagcg cctggggctg ggacgccgag     6720
gccggagccc ctccctgctg tgctgacggg ctcggtgacc ctgccgcccc ctccctgggg     6780
ccctgctgac cgcggggggcc accccggcca gttctgagat tccctggg tccagccctc       6840 caggatccca ggacccagga tggcaaggat gttgaggagg cagctagggg gcagcatcag     6900
gcccagaccg gggctgggca ggggctgggc gcaggcgggt ggggggtct gcacnccccc      6960 acctgcnagc tgcncnnncn tttgntnncg tcctccctgn tcctggtctg tcccgcccgg     7020
ggggcccccc ctggtcttgt tgttccccc tcccgtccc ttccccccctt tttccgtcct       7080 cctcccttct tttattcgcc ccttgtggtc gttttttttc cgtccctctt ttgtttttt       7140 gtcttttct ttttcccct cttctccctt gctctctttt tcattcgtcg gttttctgc         7200 tcccttccct ctcccccccg cttttttttcc ctgtctgctt tttgtgttct ccctctctac    7260 ccccctgca gcctattttt tttatatatc catttccccc tagtatttgg cccccgctta     7320
cttctcccta atttttattt tccttttcttt aactaaaatc accgtgtggt tataagtttt    7380 aaccttttt gcaccgccca caatgcaatc ttcacgcacg ccccccccgt cagcctcctt     7440
aaataccttt gcctactgcc cccctcttg tataataacg cgtcacgtgg tcaaccatta      7500
tcacctctcc accacttac cacatttttcc ttcnnnnnnn nnnnnnnnnn nnnnnnnnnn      7560
nnnnnnnnnn nnnnnnnnnn nnnnnnnnnn nnnnnnnnnn nnnnnnnnnn nnnnnnnnnn     7620
nnnnnnnnnn nnntgaaaaa agaaaaggct gggcaggttt taatatgggg gggttggagt     7680
ggaatgaaaa tgcattggag tggttgcaac aaatggaaag gtctcaggag cgctcctccc     7740
ccatcaggag ctgaaagaa gtggaagcaa agcaaggaat tcgtgtgatg gccagaggtc      7800
aggggcaggg agctgcaaag actgccggct gtttgtgact gnccgtctcc gggtgcattt     7860
gttagcaggg aggcattaca ctcatgtctt ggtttgctaa ctaattctta ctattgttta     7920
gttgcaaggt catgtctgac tctttgcaac ccagggactg cagcccgcca ggctcctctg     7980
```

-continued

| | |
|---|---|
| tccatgggat ttcgcaggca agaatactgg aggtggtagc cattttcttc accatgggat | 8040 |
| cttcccgagc cagaaatgga acccgagtcg cctcctgtgc atggggtctg ctgcctaaca | 8100 |
| ggcagatatt tgacgtctga gccaacaggg aggacagacg gtaattatac caaccattga | 8160 |
| aagaggaatt acacactaat ctttatcaaa atctttcaaa cagtagagga gaaaggatac | 8220 |
| tctctagttt attccataaa gttggaatta cgcttatcaa taaagacatt acaagaaaag | 8280 |
| aaagtgaagc cccaaatgcc ttataaatat acaagaaaaa atcttttaag atattagcca | 8340 |
| acttaatcaa caaaaaatgt atcaaaagtc caagtaacat tcaccccagg aatgcaagtg | 8400 |
| tggttcagcc taagacaatc agtcatgagt ataccacgga aacaaattaa agagaaaaga | 8460 |
| cattaaatct cacaaatggt gcagaaaaag atttggcaat atcgaacatc tttcatgac | 8520 |
| caaaggaaaa aaaagaaaca aaacaccaga aaattctgtg tagaaagaat atatctcaac | 8580 |
| ccaatgaagg gcatttatga aaaacccaca gcatacatca cactccatga gaaagactga | 8640 |
| aagctttccc cactgccatt gaactctgtc ctggaaattc tagtcacagc gacagaacaa | 8700 |
| gagaaagaaa taacggccgt ctaaactggt aggaagaaat caaagcgtct ctattctctg | 8760 |
| ggcgcataat acaatataga caaatttcta aagtccacaa aaattcctag agctcataat | 8820 |
| gaatccagaa atgcgtcagg gctcaagatt cagatgcaaa atcgtctggg gttttgatgc | 8880 |
| accaacaaac aattccatta acaataatac caaggaatta atttaactta gaagagaaaa | 8940 |
| gacctgttta cagagagtta taaaacattt ggtgatgaaa ttaaataaga gtaaatcata | 9000 |
| tagaaacacc gttcgtgttt tggagaccta atgtcataaa cgtggcaaca cagagacgcc | 9060 |
| tcacgggaa ccctgagcct ccttctccaa acaggcctgc tcatcatttc acaggtaacc | 9120 |
| tgagaccta aagcttgact ctgaggcact ttgagggcat gaagagagca gtagctcctc | 9180 |
| ccatgggacc gacagtcaag gcccagggaa tgaccacctg gacagatgac ttcccggcct | 9240 |
| catcagcagt cggtgcagag tggccaccag ggggcagcag agagtcgctc aacactgcac | 9300 |
| ctggagatga ggcaacctgg gcatcaggtg cccatgcagg ggctggatac ccacacctca | 9360 |
| cacctgagga caggggccgg cttttctgtgg tgtcgccctc tcaggatgca cagactccac | 9420 |
| cctcttcgct tgcattgaca gcctctgtcc ttcctggagg acaagctcca ccttcccccat | 9480 |
| ctctccccag ggggctgggg ccaacagtgt tctctcttgt ccactccagg aacacagagc | 9540 |
| caagagattt atttgtctta attagaaaaa ctatttgtat tcctgcattt ccccagtaac | 9600 |
| tgaaggcaac tttaaaaaat gtatttcctg gacttccctg gtgggccagt ggctagactc | 9660 |
| tgagctccca gtgcatgggg cctgggttca atccctgctc aggaaactac atcccacagg | 9720 |
| ctgcaaataa gatcctgcat gccacccgat gcaggcaaag aaacaagtgt tcggtatgca | 9780 |
| tgtatttcac gtgaggtgtt tctataattt acagccagta ttctgtctta cacttagtca | 9840 |
| ttcctttgag cacatgatcg gtcgatggcc cagaccacac acaggaatac tgaggcccag | 9900 |
| cacccaccgg ctgcccagaa cctcatggcc aagggtggac acttacagga cctcagggga | 9960 |
| cctttaagaa cgccccgtgc tcttggcagc ggagcagtgt taagcatggc tctgtccctc | 10020 |
| gggagctgtg tctgggctgc gtgcatcacc tgtggtgtgg gcctggtgag ggtcaccgtc | 10080 |
| caggggccct cgagggtcag aagaaccttc ccttaaaagt tctagaggtg gagctagaac | 10140 |
| cagacccaca tgtgaactgc acccaaaaac agtgaaggat gagacacttc aaagtcctgg | 10200 |
| gtgaaattaa gggccttccc ctgaaccagg atggagcaga ggaaggactt ggcttccagg | 10260 |
| aaaccctgac gtctccaccg tgactctggc cggggtcatg gcaggcccca ggatccttg | 10320 |
| gtgcaaagga ctcagggttc ctggaaaata cagtctccac ctctgagccc tcagtgagaa | 10380 |

```
gggcttctct cccaggagtg gggcaaggac ccagattggg gtggagctgt cccccagac    10440 cctgagacca gcaggtgcag gagcagcccc gggctgaggg gagtgtgagg gacgttcccc    10500
ccgctctcaa ccgctgtagc cctgggctga gcctctccga ccacggctgc aggcagcccc    10560 cacccaccc cccgaccctg gctcggactg atttgtatcc ccagcagcaa ggggataaga    10620
caggcctggg aggagccctg cccagcctgg gtttggcgag cagactcagg gcgcctccac    10680
catggcctgg acccctcct cctcggcctc ctggctcact gcacaggtga gccccagggt    10740
ccacccaccc cagcccagaa ctcggggaca ggcctggccc tgactctgag ctcagtggga    10800
tctgcccgtg agggcaggag gctcctgggg ctgctgcagg gtgggcagct ggaggggctg    10860 aaatcccct ctgtgctcac tgctaggtca gccctgaggg ctgtgcctgc agggaaagg    10920 gggtctcct ttactcagag actccatcca ccaggcacat gagccggggg tgctgagact    10980 gacgggagg gtgtccctgg gggccagaga atctttggca cttaatctgc atcaggcagg    11040
gggcttctgt tcctaggttc ttcacgtcca gctacctctc ctttcctctc ctgcaggcgc    11100
tgtgtcctcc tacgagctga ctcagtcacc cccggcatcg atgtcccag acagacggc    11160 caggatcacg tgttggggc ccagcgttgg aggtganaat gttgagtggc accagcagaa    11220
gccaggccag gcctgtgcgc tggtctccta tggtgacgat aaccgaccca cggggtccc    11280 tgaccagttc tctggcgcca actcagggaa catggccacc ctgccatca gcggggcccg    11340 ggccaaggat gaggccgact attactgtca gctgtgggac agcagcagta caatcctca    11400 cagtgacaca gcagacggg aagggagatg caaacccct gcctggcccg cgcggccag    11460 cctcctcgga gcagctgcag gtcccgctga ggcccggtgc cctctgtgct cagggcctct    11520
gttcatcttg ctgagcagcg gcaagtgggc attggttcca agtcctgggg gcatatcagc    11580
acccttgagc cagagggtta gggggttaggg ttagggttag gctgtcctga gtcctaggac    11640
agccgtgtcc cctgtccatg ctcagcttct ctcaggactg gtgggaagat tccagaacca    11700
ggcaggaaac cgtcagtcgc ttgtggccgc tgagtcaggc agccattctg gtcagcctac    11760
cggatcgtcc agcactgaga cccgggggcct ccctggaggg caggaggtgg gactgcagcc    11820
cggcccccac accgtcaccc caaaccctcg gagaaccgcg ctcccagga cgcctgcccc    11880 tttgcaacct gacatccgaa cattttcatc agaacttctg caaaatattc acaccgctcc    11940
tttatgcaca ttcctcagaa gctaaaagtt atcatggctt gctaaccact ctccttaaat    12000
attcttctct aacgtccatc ttccctgctc cttagacgcg ttttcattcc acatgtctta    12060
ctgcctttgg tctgctcgtg tattttcttt tttttttttt ttttattgga atatatttgc    12120
gttacaatgt tgaatttgaa ttggtttctg ttgtacaaca atgtgaatta gttatacatg    12180
tcctgaggag gggcggctgc gtgggtgcag gagggccgag aggagctact ccacgttcaa    12240
ggtcaggagg ggcggccgtg aggagatacc cctcgtccaa ggtaagagaa acccaagtaa    12300
gacggtaggt gttgcgagag ggcatcgag ggcagacaca ctgaaaccat aatcacagaa    12360
actagccaat gtgatcacac ggaccacagc ctggtctaac tcagtgaaac taagccatgc    12420
ccatggggcc aaccaagatg ggcgggtcat gtgcccatgg ggccaaccaa gatgggcggg    12480
tcatggtgaa gaggtctgat ggaatgtggt ccactggaga agggaaaggc aaaccacttc    12540
agtattcttg ccttgagagc cccatgaaca gtatgaaaag gcaaaatgat aggatactga    12600
aagaggaact cccaggtca gtaggtgccc aatatgctac tggagatcag tggagaaata    12660
actccagaaa gaatgaaggg atggagccaa agcaaaaaca atacccagtt gtggatgtga    12720
```

```
ctggtgatag aagcaagggc caatgatgta aagagcaata ttgcatagga acctggaatg   12780
ttaagtccaa gannnnnnnn nnnnnnnnnn nnnnnnnnnn nnnnnnnnnn nnnnnnnnnn   12840
nnnnnnnnnn nnnnnnnnnn nnnnnnnnnn nnnnnnnnnn nnnnnnnnnn nnagaatttt   12900
gagcattact ttactagcgt gtgagacgag tgcaattgtg cggtagtttg agcattcttt   12960
ggcattgcct ttctttggga ttggaatgaa aactgacctg ttccaggcct gtggccactg   13020
ctgagttttc caaatttgct ggcgtattga gtgcatcact ttaacagcat catcttttag   13080
gatttgaaat agctcaactg gaattctatc actttagcta attccattca ttagctttgt   13140
ttgtagtgat gcttcctaag gccccctgg ctttatcttc ctggatgtct ggctctggtg   13200
agtgatcaca ccgctgtgat tatctgggtc atgaaggtct ttttgtatag ttcttcttag   13260
gaacagatat tatgatctcc atccttgcat ctcgttatat ctagagaagc actgactccc   13320
ttcatggtga cgtcagatcc tcatgactaa caaatggcct tttgtaagat gagtgcctca   13380
tggtattgag ctccccgtc accaagacct tatgactgac ctccccact gccccaggtg   13440 cctctcgaag cgtctgagat gccgcctccc aggctgcact cctcattttg cccccaataa   13500
aacttaactt gcagctctcc agctgtgcat ctgtgtttag ttgacagtac aaatataatg   13560
gaaaatttaa attaaatata atctatgggg agaaatccaa acatcttatg agggagagag   13620
agggagagaa aggaaagaag aagaagcagg aggaggagga gagtagagaa acaggggag   13680 ggcggcaggg agacagaggg gaggacaccg aggggaaagg gaggaaggcg agtgcagtga   13740
gagagaggcc agagttcatc agagtctgga ctcgcagccc aatcccacgg gtgtgtcccg   13800
aagcagggga gagcctgagc caggcggaga cagagctgtg tctccagtcc tcgtggccgt   13860
gacctggagc tgtgtggtca gccccctga ccccagcctg gccctgctgg tggtcggagg   13920
cagtgatcct ggacacagtg tctgagcgtc tgtctgaaat ccctgtggag cgccactca   13980 ggacggacct cgcctggccc cacctggatc tgcaggtcca ggcccgagtg gggcttcctg   14040
cctggaactg agcagctgga ggggcgtctg caccccagca gtggagcggc cccaggggcg   14100
ctcagagctg ccgggggac acagagcttg tctgagaccc agggctcgtc tccgagggt   14160 cccctaaggt gtcttctggc cagggtcaga gccgggatga gcacaggtct gagtcagact   14220
ttcagagctg gtggctgcat ccctggggac agagggctgg gtcctaacct ggggtcaga   14280 gggcaggacg ggagcccagc tgaccctgg ggactggcct cctctgtggt ctccctggg   14340 cagtcacagc ttccccggac gtggactctg aggaggacag ctgggcctg gctgtcagga   14400 gggggtcga gaggccacac tcagaggagg agacctggc ctgcttggt tgtgactgag   14460 tttttgggt cctctaggag actctggccc tgcaggccct gcaaggtcat ctctagtgga   14520
gcaggactcc acaagattga tgaactgaat cctctaggag aggtgtggtt gtgaggggc   14580 agcattctag aaccaacagc gtgtgcaggt agctggcacc gggtctagtg gcggcgggca   14640
gggcactcag ggccgactag gggtctgggg gattcaatgg tgcccacagc actgggtctt   14700
ccatcagaat cccagacttc acaaggcagt ttcggggatt aggtcaggac gtgagggcca   14760
cagagaggtg gtgatggcct agacaagtcc ttcacagaga gagctccagg ggccatgata   14820
agatggatgg gtctgtattg tcagtttccc cacatcaaca ccgtggtccc gccagcccat   14880
aatgctctgt ggatgcccct gtgcagagcc tacctggagg cccgggaggc ggggccgcct   14940
gggggctcag ctccggggta accgggccag gcctgtccct gctgtgtcca cagtcctccc   15000
ggggttggag gagagtgtga gcaggacagg aagggtttgtg tctcacttcc ctggctgtct   15060
gtgtcactgg gaacattgta actgccactg gcccacgaca gacagtaata gtcggcttca   15120
```

```
tcctcggcac ggaccccact gatggtcaag atggctgttt tgccggagct ggagccagag   15180
aactggtcag ggatccctga gcgccgctta ctgtctttat aaatgaccag cttaggggcc   15240
tggcccggct tctgctggta ccactgagta tattgttcat ccagcagctc ccccgagcag   15300
gtgatcttgg ccgtctgtcc caaggccact gacactgaag tcaactgtgt cagttcatag   15360
gagaccacgg agcctggaag agaggaggga gagggatga aaggaagga ctccttcccc   15420 aagtgagaag ggcgcctccc ctgaggttgt gtctgggctg agctctgggt ttgaggcagg   15480
ctcagtcctg agtgctgggg gaccagggcc ggggtgcagt gctgggggc cgcacctgtg   15540 cagagagtga ggaggggcag caggagaggg gtccaggcca tggtggacgt gccccgagct   15600
ctgcctctga gccccagca gtgctgggct ctctgagacc ctttattccc tctcagagct   15660
ttgcaggggc cagtgagggt ttgggtttat gcaaattcac cccccggggg ccctcactc   15720 agaggcgggg tcaccacacc atcagccctg tctgtcccca gcttcctcct cggcttctca   15780
cgtctgcaca tcagacttgt cctcaggac tgaggtcact gtcaccttcc ctgtgtctga   15840
ccacatgacc actgtcccaa gccccctgc ctgtggtcct gggctcccca gtgggcggt   15900 cagcttggca gcgtcctggc cgtggactgc ggcatggtgt cctggggttc actgtgtatg   15960
tgaccctcag aggtggtcac tagttctgag gggatggcct gtccagtcct gacttcctgc   16020
caagcgctgc tccctggaca cctgtggacg cacaggctg gttccctga gccccgctt   16080 gggcagccca gcctctgacc tgctgctcct ggccgcgctc tgctgccccc tgctggctac   16140
cccatgtgct gcctctagca gagctgtgat ttctcagcat aactgattac tgtctccagt   16200
actttcatgt ccctgtgacg ggctgagtta gcatttctca cactagagaa ccacagtcct   16260
cctgtgtaaa gtgatcacac tcctctctgt gggacttttg taaaagattc tgcagccagg   16320
agtcatgggt ggtcttagct gagaaatgct ggatcagaga gacctgataa ccgatgtgaa   16380
gaggggaacc tggaagatct tcagttcagt tcatttcagt cattcagttg tgtccgactg   16440
tttgggatcc catggactgc cacacgccag tcctccctgt ccatcaccaa cttctgaagc   16500
ttgttcaaac tcatgtccat caagttggag atgcctttca accatctcat cctctgtcat   16560 cccttctcc tcccgccttc aatcttccct agcattaggg tctttccgt gagtcagttc   16620 ttcgcatcag gtggccaagt tttggagttt cagtttcagc atcagtcctt caatgaata   16680 gtaaggactg atttccttta ggatggactg gtttgatatc cttgcagttc aagggactct   16740
caagagtctt ctccaacact gcagttaaaa gccatcaatt cttcggtgct cagctttctt   16800
tttggtacaa ctctcacatt catacatgac taccgaaaat acattagtcg tgtagaacca   16860
gtttggggct tcccacgtgg ctctagtggt aaagaatatg cctgccaact cagaagatgt   16920
aagagatgcg gttcaatctc tgggtcggga agatcccctg gagaagggca tgacaaccca   16980
ctccagtatt tttgcctgga gaatcccatg gacagagaag cctggtggac tgcagtccat   17040
ggagtctcac agagtcagac acgactgaag caacttagct acttggaaaa gagcatgcac   17100
gaagctgtct aaaaaacagg tcaagaagtc ttgtgttttg aaggtttact gagaaagttg   17160
atgcactgct ccaacacttc ctctcagttg aaaagatcag aagcgttaga tcaaatggtg   17220
gtcaatacct tggatgcgct ccaacaggtt atatctgcag atggaaatga aggcagttta   17280
tggggtaact ggaggacaag atgagatcat acacttggaa cactgtctgg catcaaaggc   17340
gtgtacagta acattagct gttattagca aaataaattc agcttgaatc acccaaatca   17400
gatggcattc ttaaagccac tgagtggtaa aatcaggggt gtgcagccaa aacgtccatt   17460
```

```
ttgactcatt atgatttcca tgtcacaaga ctagaaagtc actttctcct cagcagaaga   17520
gaaggtagaa cattttaacc ttttttttgga gtgtcaaggg aattttgttt acactgtaaa   17580
gtcagtgaaa atattgaagc ttttcatttg tggaaaatat taaatatgta aaattgaaat   17640
tttaaaattt attcctgggt agttttgttt ttccagtagt catgcatgga tgtgagagtt   17700
ggactataaa gaaagctgag cgctgaagaa ttaatgcttt tgaactgtgg cactggagaa   17760
gactcttgag agtcccttgg tctgcaagga gatcaaacca gtccatccta aaggaaatca   17820
gtcctgaata ttcactggaa ggactgatgc tgaagctgaa actccaatac tttggccacc   17880
tgatgtgaag aactgactca tatgaaaaga ctcagatgct gggaaagatt gaaggtggga   17940
ggagaagggg acgacagagg atgagatggc tgaatggcat caccgactcg atggacatga   18000
gtctgaataa gctctgggag ttgttgatgg acagggaggc cctggagtgc tgcagtccat   18060
gggattgcaa agagttggac atgactgagt gactgaactg aactgagttt ggtaacagat   18120
atgagaatta tataatttaa atctaaactc ttggtatttc tttctttggc ggttccaaaa   18180
gagctgtccc ttctgttaac tatataaatc cttttttgaga attactaaat tgataatgtt   18240
cacaagttat ccaatttctc attactctta gttgtcagta taagaaatcc catttgattt   18300
atcatgttat agtatctgca actctaatag ttcagttctg acaatttttt attttattta   18360
aaaatattgg catacagtaa aatttcaaac aatatacaat tctcccttc agtttaaaaa   18420 acaaacaaa acaaaagtaa tattagttaa aaaaatccgg gaagaatcca agcatttaaa   18480
attgcatcac atttctatgc tagacaagct gatataaagt tataattaat aaaggattgg   18540
actattaaac tctttacata tgaggtaaca tggctctcta gcaaaacatt taaaaatatg   18600
ttgtgggtaa attattgttg tccttaaaga aataaaaaga cataagcgta agcaattggn   18660
nnnnnnnnnn nnnnnnnnnn nnnnnnnnnn nnnnnnnnnn nnnnnnnnnn nnnnnnnnnn   18720
nnnnnnnnnn nnnnnnnnnn nnnnnnnnnn nnnnnnnnna aaatggataa ggggggagga   18780
catgggtagg ggagcgcgat ggaggaagta aggtggtcga gggagttggg ggggaataa    18840 gtgggtaaaa gggaagcggg cggaaggagg gggaagcagg agagaggggt gggcgtcaga   18900
tcgggggagg gggtatgagg gagagggaat ggtagacggg gggtgggaag cataaaggaa   18960
aagatagggg ggggaaaagt tagaagaaga atgagggat aggcggaaag ggaagagaaa    19020
tgggagaaga acagaaaaat aggggagggg ggggcgtaaa gagggggggg gagggcaggt   19080
gtggagatga cagatacggg gaatgccccg gtataaaaga gtatatggcg tggggcgaga   19140
aggctgtcat cctgtgggag gggggacgcg gagaacccct cgggctatag ggaggattcg   19200
gggggatcgt tcgggaaggc agtcagcaca gcacccacca agggtgcagg gatggatctg   19260
gggtcccaaa gaagaggccc aatcccgcgt cttggcagca aggagccctg gagactggga   19320
agtgtccagg acactgaccc aggggttcga ggaacccaga agtgtgtctg tgaagatgtg   19380
ttttgtgggg ggacaggtcc agagctttga gcagaaaagc ggccatggcc tgtggagggc   19440
caaccacgct gatctttttt aaaaggtttt tgttttgatg tggaccattt ttaaagtctt   19500
cattgaattt gctacaatat tgttctggt ttatgctctg gtttcttcgg ctgcaaggtt    19560
tgtgtgatcg tatctcctca accaggactg aacccacagc cctgcactg gaaggcgaag    19620 tcttaaccca gatcgccagg aacgtccctc ccctcactga tctaatccaa gaccctcatt   19680
aaggaaaaac cgagattcaa agctccccca ggaggactcg gtgggaggga gagagccaag   19740
cactcagcac tcagtccagc acggcgccct cctgtccag ggcgagggct cggccgaagg    19800
accaccggag accctgtcgg attcaccagt aggattgtga ggaatttcaa cttactttt    19860
```

```
aaatctgtct ctcaaggctg ttacaagcgg actttaccag taacttaaaa gttgaaaggg    19920
acttcccagg cggcacttgc ggtgaagaac ccgccggctg gttttaggag acataagaga    19980
tgtgggttag atccctggtt caggaggatt cccctggaga aggaaatggc aacccactcc    20040
agtattcttg cctggaaagc ctcacggaca gaggaggctg cgggctaca gtccacgggg    20100 tcgcacacga ctgaatcgac ttagcttcaa gttgagacag aagaggcag tgactggtgg    20160 caaaacaccg cacccatgct cccagggac ctgcagcgct ctggttcatg agctgtgcta    20220
acaaaaatca acccaacgag aggcccagac agagggaagc tgagttcatc aaacacgggc    20280
atgatgtgga ggagataatc caggaaggga cctgccaagc ccatgacaga ccggtgtcct    20340
gtctgagggc cgtcctggca gagcagtgca gggccctccg agaccgcccg agctccagac    20400
ccggctgggg gctacagggt ggggctgagc tgcaaggact ctgctgtgag ccccacgtca    20460 ggaggatca ccttgtttgt tttctgagtt tctcttaaaa tagcctttat gggtcctggt    20520
ctttggtttt aaaataacaa ctgttctccg taaacaacgt gaaaaaaaac aaacaggagg    20580
aaaacaacgc agcccgggca tttcacccgg aagagccgcc tctaacactt tgacgggttg    20640
ccttctattt taaccctgtt ttcattgtaa actgtaaaaa ccacatcata aataaattaa    20700
aggtctctgt gaagtttaaa aagtaagcat ggcggtggcg atggctgtgc cacaccgtga    20760
acgctcgttt caaaacggta aattctaggg accccctggt ggtccagtgg gtgagatttt    20820
gcttccattg caggagccgt gggtttgatc cctggttggg gaactaagat cccacatgct    20880
gtatggagtg gccaaaaaga attttttgta aatggtgagt tttaggtgac gtgaatttcc    20940
cattgatgca cttcacaggc tcagatgcag ccaggccctc aggaagcccg agtccaccgg    21000
tcctttactt ttccttagag ttttatggct tctgtttctg cccttaaacc caccatgttt    21060
caacctcatc tgattttgga ctttataata aagttaggct gtgtttcagg aaactttgct    21120
cagtattctg taataatcta aatggaaaga atttgaaaaa agagcagaca cttgtacatg    21180
cataactgaa tcactttggt gtacacctga aactcgagtg cagccgctca gtcgtgtccg    21240
accctgcgac cccacggact gcagcacgcg ggcttccctg cccatcacca actcccggag    21300
ttcactcaaa cacatgtccg tcgactcggt gatgccgtcc aaccgtctca tcctctgtcg    21360
tccccttctc ctcccgcctt caatcttttc cagcatcagg gtcttttcaa atgagtcagt    21420
tcttcacacc aggtggccag agtattggag tttcagcttc agcatcagcc cttccaacga    21480
ccccccatac ctgaagctaa cacagtgcta atccactgtg ctgcaacatg aaagaaaaac    21540
acatttttta agtttaggct gtgtgtgtct tccttctctc aacactgcgt ctgaccccac    21600
ccacactgcc cagcactgca ttccccgtgg acaggaggcc ccctgcccca cagctgcgtg    21660
ccggccggtc actgccgagc agacctgccc gcccagagtg ggcccctgg cactggggac    21720 aaggcagggg cctctccagg gccggtcact gtccactgtt cctactggtt ttgtttttcaa    21780 aagtggaggc agcgtaatat ttccctgatt ataaaaagaa gtacacaggt tctccacaaa    21840
taaaacaggg gaaaagtata aagaatggaa gttcccagca cagcctggag atcacgccgg    21900
gtgcacctgg ggtgtccttc caggctggac ctcacatttc acgcagacat cagaaggctg    21960
cgagatctac ccagaaggct gggtagatgg gggataggtc agtgacaaac agtagacaga    22020
gagatataca gacagatgat ggatagacag acgctaagac accgagcgag gggacagacg    22080
gatggaagac accatccttt gtcactgacc acacacccac atgggtgtgg tgagccggct    22140
gtcatacttg tgaacctgct gctctcacaa caccagctgg gtccctccag cccagcgtc    22200
```

```
ccacacagca gactcccggc tccatcccca ggcaggaatc ccaccaccaa ctggggtgga   22260
ccctccccgc aggaaggtcg tgctgtctaa ggccttgaga gcaagttaca gacctacttc   22320
tgggaagaca gcgcacaacc gcctaccccg cagagcccag gaggacccct gagtcctagg   22380
gaagggacca cgcggcctgg acggggagcg ccccaggac gctgccccca acctgtccca    22440
cctcactcct gctctgctct gaggcggggc gcagagaggg gccctgaggc ctcttcccag   22500
ttcttgggag cacccactgg gcctgaacca ggccagaagc cccctcctca aggtgtcccc   22560
agaccactcc cctccacctc cggttgctct gtctcctggc agcagggagc cccagtgaga   22620
agagacagct ccaggctgtg atcttggccc ctggctgctc tggcagtgtg ggggtgggg    22680 gtcgctggga ggccatgagt gctggggtc ggggctgtga aagcacctcg aggtcagtgg    22740
gctgttggtc gggctctgcg aggtccgcac gggtagagct gtgccaggac acaggaggcc   22800
tggtcagtgg tcccaagagt cagggccaaa ggaaggggtt cgggcccctc tggttcctca   22860
gcttctgagg ccggggaccc cagtctggcc ttggtagggg ggcgattgga gggtacaacg   22920
atccaaaaga aaacacacat ctacgaggga agagtcctga ggaggagaga gctacacaga   22980
gggtctgcac actgcggaca ctgcttggag tctgagagct cgagtgcggg gcacagtgag   23040
cgaagggagg acggaacctc caaggacacc ggacgccgat ggccagagac acgcacgt     23100 cccatgaggg ccggctgctc agacgcaggg gagctcctca ttaaggcctc tcgctgaata   23160
gtgaggagaa ctggccccgt gtgtggggaa acttagccca aagaaacgc tgccctggcc    23220 ccaaggatca nnnnnnnnnn nnnnnnnnnn nnnnnnnnnn nnnnnnnnnn nnnnnnnnn    23280 nnnnnnnnnn nnnnnnnnnn nnnnnnnnnn nnnnnnnnnn nnnnnnnnnn tgccctttgc   23340
ctccagggag ggaggaagcg tggatcttgg gtttgccttg ggtttaaagg atccacccac   23400
tcccttttta gccactccct gtgctggcaa tttcttaaga ctggaggtcg caaagagttg   23460
gacacactga gcgagtgaac tgcactgagc ctaagaaaag tctttgaatt cctccaaaca   23520
aaacacactt gtcttgggta ctttccttgg ttttgttaca aatgtctggt ccctctgttc   23580
tcctggccag ctcctgggtg tcattttgac ctgacgaagt caaagggagc ctggaccctc   23640
aaaatctgta ggacccagca cccctccatt acacctctgt tccccgcga acgggcacgt    23700 gtttcgccgt ctggcgtaat gtgtaagcga cggtgtgata ctcgggagtc ttactctgtt   23760
tcttttcctt ctggggtgac accaccatcc gcacgactct gtctgaatgt gaacatttgg   23820
gtgatttgat gtggcccaga ctcccccaac gaatgtacct tcaggttggt tttcttcttt   23880
tatattttgc ttttgtgaat agacacagga tcccatcagt tgtatgtagt gagaaagtaa   23940
aaacccactc agccttagct ggatggagat ctagtagtaa gatagcacgt tagccggaaa   24000
tggaaatttc agccagaatc tgaaaagcgt gtcctggaag gagaagaggg actcaggccc   24060
gagcacactg ctccacgctg gagcctcagg ctctgacagc tgtacctgcc ggggtcttca   24120
tgggacaggc catgcaggcc acgatcccgt tgagaagttt cttgcctttc catcacattg   24180
gcaattgcac gctttgctct tgcttctaca tggagttta ctttatccc agacagtttg     24240 gtttcttctc tgattttcgc caattgtaca gatcgttaca gtatttctta accacataga   24300
attcggcagg gggggtgggg ggacaggta gggtgggtg agagtgaggg gaggggctg      24360 caccgagcag catctggggt cgtagctccc tgacggggat agacctcgtg ccctgcagt    24420 gacagcacag agtcctcctc tctgaactgc cagggacgct cctgcaattg acttaatgaa   24480
aggcatctaa ttaggaattt tggggtgaca ttttacattt aagtgtgtga gcagtgatta   24540
tagttcatat catttatag tttcgtgatt ttactagctt aaagggtttt tgggggtttct   24600
```

```
ttttgtttta aaagctaaaa tctgtttttt aattccatgg aatacaaaaa aaaaagtct   24660 gtagaatatt ttaaagagtg aaggctttgt tcggaatgtg agcgctttgc tccactgaac   24720
cgaacggtaa taacatttgt agaagagacg cagagtgaaa ggtacctctt tttattgagt   24780
gacatgacag cacccatcgc gtgagttatt ggctggagtt tagagacagg ccatgttggg   24840
ctaaactcct tattgctgtt ctcagccttt gagtaataat cagaagcttt ctctgaagag   24900
agtggggtca gctgtcagac tcctaggtgt ctacctgcag cagggctggg attaaatgca   24960
gcagccagta gatacgggat ggggcaagag gtcaccttgt cccttttgttg ctgctgggag   25020 agaggcttgt cctggtgcca gtggggccaa agctgtgact ttgtgaccac aggatgtctc   25080
tgaccctgcc ttgggttccc tgagggtgga gggacagcag ggtctccccg gttccttggc   25140
cggagaagga ccccccaccc cttgctctct gacatccccc caggacttgc cccggagtag   25200
gttcttcagg atgggcatcc gggccccacc ctgactcctg gagctggccg gctagagctt   25260
gctgcagaat gaggccttgg ccattgcggc cctgaaggag ctgcccgtca agctcttccc   25320
gaggctgttt acggcggcct ttgccaggag gcacacccat gccgtgaagg cgatggtgca   25380
ggcctggccc ttcccctacc tcccgatggg ggccctgatg aaggactacc agcctcatct   25440
ggagaccttc caggctgtac ttgatggcct ggacctcctg cttgctgagg aggtccgccg   25500
taggtaaggt cgacctggca gactggtggg gcctggggtg tgagcaagat gcagccaggc   25560
caggaagatg aggggtcacc tgggaacagg cgttgggtgt acaggactgg ttgaggctca   25620
gaggggacaa aaggcacgtg ggcctccccc ccagtgtccc ttaaagtggg aaccaagggg   25680
gccccggaag ccggaggagc tgtggtgtgt ggagtgcaga gccctcgcgg ggtcctgatg   25740
cccgtcggac tctgcacagc tcagcgtgtg ccccgcggcc cggtaggcgg tggaagctgc   25800
aggtgctgga cttgcgccgg aacgcccacc agggacttct ggaccttgtg gtccggcatc   25860
aaggccagcg tgtgctcact gctggagccc gagtcagccc agccatgca gaagaggagc   25920 agggtagagg gttccagggg tgggggctga agcctgtgcc gggccctttg gaggtgctgg   25980
tcgacctgtg cctcaaggag gacacgctgg acgagaccct ctgctacctg ctgaagaagg   26040
ccaagcagag gaggagcctg ctgcacctgc gctgccagaa gctgaggatc ttcgccatgc   26100
ccatgcagag catcaggagg atcctgaggc tggtgcagct ggactccatc caggacctgg   26160
aggtgaactg cacctggaag ctggctgggc cggatgggca acctgcgcgg ctgctgctgt   26220
cgtgcatgcg cctgttgccg cgcaccgccc ccgaccggga ggagcactgc gttggccagc   26280
tcaccgccca gttcctgagc ctgccccacc tgcaggagct ctacctggac tccatctcct   26340
tcctcaaggg cccgctgcac caggtgctca ggtgaggcgt ggcgccagct ccaaagacca   26400
gagcaggcct ctcttgtttc gtgccgctg ggacattgc cagggtgccc ggccactcgg   26460
aagtcctcac gatgccaccg ctctgaccct gggcatcttg tcaggtcact tccctggtta   26520
gggtcagagg cgtggcctag gttaaatgct gtcaaagggg actcctttct gggagtccgc   26580
atagtggggg cttggtgtga tgcccttggg aattcttttcc gagagagtga tgtcttagct   26640
gagataatga cagataacta agcgagaagg acggtccatc aggtgtgagg tttgaagtcc   26700
aaagctctgt ctctccctcc cacctgcccc ttctgtcctg agctgtttta ggctccaggt   26760
gagctgtggg aagtgggtga ttctggagat gacaagaagg gatcaggagg ggaaaattgt   26820
ggctcctaag cagtccagag aagagaaaaa gtcaaataag cattattgtt aaagtggctc   26880
cagtctcttt aagtccaaat tataattata atttttcctct aagacttctg aatacatagg   26940
```

```
aaatcctcag taacaggtta ttgctctgcc ttgaacacag tgataaaagc tgggaggatg   27000
cagcctaatc tgtctgtgtg aatgagttgt attgattccc tttttggcag ctgcaaactc   27060
caagcattag aataaatat gttcactgag aaccccgaag aaagaaagaa agaaaaaaaa    27120
aaagaattgt aggtgttgat ggacggtttg tggcccctga atatctgggg gatgttcacc   27180
cagggatcac gtgtaactgc tgggacccc  agccccatgt ccactgcatc cagcctgctg   27240
ttgaattccg cggatcnnnn nnnnnnnnnn nnnnnnnnnn nnnnnnnnnn nnnnnnnnnn   27300
nnnnnnnnnn nnnnnnnnnn nnnnnnnnnn nnnnnnnnnn nnnnnnnnnn nnnnncaat   27360 tcgagctcgg tacccaaag  gtccgtctag tcaaggctat ggttttcca  gtggtcatgt   27420 atggatgtga gagttggact gtgaagaaag ctgagtgcca aagaattatt cttttgtact   27480
gggtgttgga gaagactctt gagagtccct tgaactgcaa ggagatccaa ccagtccgtt   27540
ctaaaggaga tcagtcctga atgttcattg gaaggactga tgctgaagct gaaactccaa   27600
tactttggcc acctgacgtg aagagttgac tcattggaaa agaccatgat gctgagagga   27660 attggggca  ggaggagaag gggacgacag aggatgagat ggctggatgg catcaccaac   27720
tcgatgngac atgagtttgg ttaaactcca ggagttggtg atggacttgg aggcctggtg   27780
tgctgggatt catggggtcg cagagtcgga catgactgag cgactgaact gaactgaact   27840
gagctgaaga gctcacctgt accagagctc ctcaggtcct cctgcaggcc tggctgtaat   27900
ggcccccagg tcaccgtcct gcctccttca tcccatcctt tcacgacagg ctgggagtgg   27960
ggtgaggtga gttgtcttgt atctagaatt tctgcatgcg accctcagag tgcaatttag   28020
ctccagagaa ctgagctcca agagttcatt ttttccttt  cttctttatg atactaccct   28080
cttctgagca gagacctcat gtcagggaga aggggactct gccttcctca gccttttgtt   28140
cctccaagac ccacacgggg agggtcgcct gcttcactga gccggaaggt tcaattgctc   28200
atgtcctcca gaaacacccc ccccccaga  gaccccagaa ataagtggac acagcacctt   28260
gtttcccaga caagtgggac acacgttatg aaccacctca gtgattaaaa tagtaacctc   28320
tgtgtatgtg tatttactgg agaaggaaac ggcaacctac tccactattc ctgcctagaa   28380
aattccatgg gagagaagcc aggcaggcta cagtccacgg ggtcacagag actgaacata   28440
cacaagcaca tggaagtgta tttttgcagta tttttaaatt tgttcagttc aacatggagt   28500
acaagaattc aaatcgtgaa gtcaattgac caagaaacca gaagaaatca ctgtgttgtg   28560
atctctgtgg aggtaacatg ggtacctgtg ctctgaccct cacagcctct ggctctctct   28620
ctacatgtac atacacatat atttccatgt atgtatgtat tcggaagatt tcacatacgt   28680
ctcaccagtc cacagccccc gcgttccctg atgcccagaa catctgtgat agctgtgagt   28740
attgtcacca gataagatct tccaggttcc tgcactcaca ttggttatca ggtctctctg   28800
atccagcatt tctcagctaa gattccttgt gactcctggc tgcagaatct tctgcaaaag   28860
tcccacagag aggagtgtga tcactgtaca caggagggcc gtggttctct agtgtgagaa   28920
aagctaactc agcccgtcac agggacgtga atgtacctga acagtaatc  agttatgctg   28980 agaaatcaca gctctgctag aggcagcaca tggggtagcc agcaggggc  agcagagcac   29040 ggccaggagc cgcaggtcag aggctgggct gcccaagcgg ggcttcaggg gaaccagccc   29100
tgcgggtcca caggtgtcca gggagcagcg cttggcagga agtcaggacc ggacaggcca   29160 tccccctcagg actagtgacc acctctgagg gtcacatcca cagtgaaccc cagagcacca   29220
tgcctcagtc cacggccagg acgctgccag gctgaccgcc ccactgggga gtccagggga   29280
gaccacaggc cgggggggctt gggacagtga tcatgtggtc agacacagag aaggtgacag   29340
```

```
tgacctcagt ccctgaggac aagtctgatg tgcagacgtg agaagccgag gaggaagctg    29400
gggacagaca gggctgatgg tgtggtgacc ccgcctctca gtgagggggcc cccggggtgt    29460 aatttgcata aacccaagcc ctcactgccc ccacaaagct ctgagaggga ataaaggggc    29520
tcggagagcc cagcactgct gcgggctcag aggcagagct cggggcgcgt ccaccatggc    29580
ctgggcccct ctcgtactgc ccctcctcac tctctgcgca ggtgcggccc cccagcctcg    29640
gtccccaagt gaccaggcct caggctggcc tgtcagctca gcacaggggc tgctgcaggg    29700
aatcggggcc gctggagga gacgctcttc ccacactccc cttcctctcc tctcttctag    29760
gtcacctggc ttcttctcag ctgactcagc cgcctgcggt gtccgtgtcc ttgggacaga    29820
cggccagcat cacctgccag ggagacgact tagaaagcta ttatgctcac tggtaccagc    29880
agaagccaag ccaggccccc tgtgctggtc atttatgagt ctagtgagag accctcaggg    29940
atccctgacc ggttctctgg ctccagctca gggaacacgg ccaccctgac catcagcggg    30000
gcccagactg aggacgaggc cgactattac tgtcagtcat atgacagcag cggtgatcct    30060
cacagtgaca cagacagacg gggaagtgag acacaaacct tccagtcctg ctcacgctct    30120
cctccagccc cggaggact gtgggcacag cagggacagg cctggcccgg ttcccccgga    30180
gctgagcccc caggcggccc cgcctcccgg ccctccaggc aggctctgca caggggcgtt    30240
agcagtggac gatgggctgg caggccctgc tgtgtcgggg tctgggctgt ggagtgacct    30300
ggagaacgga ggcctggatg aggactaaca gagggacaga gactcagtgc taatggcccc    30360
tgggtgtcca tgtgatgctg gctggaccct cagcagccaa aatctcctgg attgaccca    30420 gaacttccca gatccagatc cacgtggctt tagaaaggct taggaggtga acaagtgggg    30480
tgagggctac catggtgacc tggaccagaa ctcctgagac ccatggcacc ccactccagt    30540
actcttccct ggaaaatccc atggacggag gagcctggaa ggcttcagcc catggggtcg    30600
ctaagagtca gacacgactg agcgacgtca cttttccctt tcactttcat gcattggaga    30660
aggaaatggc aacccagtcc agtgttcctg cctggaaaat cccagggaca ggggagcctg    30720
gtgggctgcc atccatgggg ccacacagag tcagacacga ctgaagcaac ttagcagcag    30780
cagcagcagc ccaataaaac tcagcttaag taatggcatc taaatggacc ctattgccaa    30840
ataaggtcca ctcgcgtgca ctctgtttag gacttcagtt cctgattgtg gagggttccc    30900
acaagacgtg tgtgtatatt ggtgttgccg gaaaacagtg tcaatgtgag catcccagac    30960
tcatcaccct cctactccca ctattccatt gtctctgcag gtattaagca taaaggttaa    31020
gggtcttatt agatggaaga ggagtgaata ctcgtctgtg cttaacacat accaagtacc    31080
atcaaggtcc ttcctattta ttaacgtgtg ttttaatcag aaatatgcta tgtagaagca    31140 tccgacgat agcccatgtt acagacgggg aagctgaggc atgaagttct cagcaccttg    31200
tttcacgtca gacctgaaac ggggcagagc cggcagcaaa caaggttcct cttcccaagc    31260
gcccgctctt caccgcttc ctatggcttc tcactgtgct tcctaaacta agctctcccc    31320
aaccctgtgg agacaggatt agagacttta ggagaaaaga ccaggaacat cccacacccg    31380
acccgagtga gccactaaga caaggctttg taaggacaga accagcaggt gtcctcagcg    31440
agccagggag agacctcgca ccaaaaacaa tattgtagca tcctgaccct ggacttctga    31500
cctccagaaa tgtgaaaaag aaacgtgtgg ggtttaatca actcaccggt gttatttggt    31560
tatgactgcc tgagttaaga aggagttggg aacacttgag tgtaggtgtt tatggaacat    31620
aagtcttgtt tctctgaaat aaattcccaa gggtataatt cctaggttgt agggtaactg    31680
```

```
ccacaaatct aggcagctta ttaaaaaaca aagatatcac tttgccagca aaggttcata    31740
tagtcaaatt atggttttta tagtagtcat gtatggatgt aaaagttgga tcataaagaa    31800
ggctgagcac cagagaattg atcccttcaa atcgtggtgc tggagaagac tcttgagagt    31860
cccttggaca gcaaggagat ccaaccagtc aatcctaaag gaaatgaact gtgaatattc    31920
actggaagga ctgatgctga agctgaagat ccaatacttt ggccacctga tgcgaagagt    31980
tgactcattg gaaaagaccc tgatgctgga agcttgaggg caggaggag aagagggcgg     32040 cagaggatga gacggttgga tggcatcact gactcaatgg acatgagttt gagccaactc    32100
tgggagacag tgaaggatag ggaaggctgg cgtggtacag tgcatgcggt cacaaagagt    32160
ctgacacatc ttagtgactc aacaacgaca gcaacacagg catcacacgc ttagtgtgat    32220
aagcggcaga actgttttcc aggggtccgn nnnnnnnnnn nnnnnnnnnn nnnnnnnnnn    32280
nnnnnnnnnn nnnnnnnnnn nnnnnnnnnn nnnnnnnnnn nnnnnnnnnn nnnnnnnnnn    32340
nnnnnnnnng tacgattcga gctcggaccc tgacattgtg agtcacgtca tgagcagctg    32400
ttttccggtc ttcagggatt gtggacgatt tctgtttggg tttgctcatg ataatttagt    32460
tacagcttag gttctttctt tccaggccac gagcgacatg ttttcaggtg agatgacgtg    32520 gtggggatg ggcggccaag cccccactgg gggggaggg attctgttgt gggcaggagt      32580
tggcagcatc cctgaactga tgacctgcga tccaggtgac aagaaccggg ggatattatt    32640
cctctgcctt ctcatgtcat gtcctcggtt cttcatgatg aaaacatatg acaatacagg    32700
ggagttagat ttgggcgggc acaactctgg gtggggacc cggtggcatt gtgcccagca     32760
gggccatcaa gatgagggcg acctgggtgg tccccttctc ccctgggtc ttagtttcc      32820 cctcatggaa atgggatcag gcagcagcca tggaacaccg cgaccgtggc ttctctcacc    32880
tcctcgtctg tgattttggg tcgggatacc aggcatgaag acctgggcg ggggacatc      32940 actcctctgc agcagggagg ccgcagagtc ctccgtccat gaggacttcg tccctgggct    33000
gaccctgcgg actgctggag gctgaagctg gaggcacagg cgggctgcga ggccagggtc    33060
ctgaggacga cagagccagt ggggctgcag ctctgagcag atggcccctc gccccgggcc    33120
ctgagcttgt gtgtccagct gcaggttcgc tcaggtgagc cactacgtta tggggggaggc   33180 gccctgggca gggatcgggg gtgctgactc ctccgagatt ccgaccttct gggagcactc    33240
tggccacact ctaagcctgg caagagctgg gttcatcagt ctaactctcc tcctgaagtc    33300
caatggactc tctccatgcg gcagtcactg gatggcctct ttatcccga tggtgtcctt     33360 ttccgctgac ctggctctcc tgaccacctc ccagccccc accatacagg aagatggcac     33420
ctggtccctg cagagctaag tccacccctg gcctggcttc agatgcctac agtcctcctg    33480
cgggaggccc cgctcccac taggcccaa ggctgccgtg tgagtctcag tctcacctgg      33540
aaccctcctc atttctcccc agtcctcagc tcccaacccc agaggtatcc cctgccctt     33600 tcaaggccct tgtcccttcc tggggggatg ggtgtatgg gagggcaagc ctgatcccc      33660 gagcctgtgc cgctgacaat gtccgtctct ggatcatcgc tcccctggct ctcagagctc    33720
cctggtccct ggggatgggt tgcggtgatg acaagtggat ggactctcag gtcacacctg    33780
tcccttccct aaggaactga cccttaaccc cgacactcgg ccagacccag aaagcacttc    33840
agacatgtcg gctgataaat gagaaggtct ttattcagga gaaacaggaa cagggaggga    33900
ggagaggccc ctggtgtgag gcgacctggg taggggctca ggggtccatg gagaggtggg    33960 ggaggggtg tgggccagag ggccccgag ggtggggtc cagggccta agaacacgct        34020 gaggtcttca ctgtcttcgt cacggtgctc ccctcgtgcg tgacctcgca gctgtaactg    34080
```

```
cctttcgatt tccagtcgct gcccgtcagg ctcagtagct gctggccgcg tatttgctgt    34140
tgctctgttt ggaggcccgg gtggtctcca cgttgcgggt gatggtgctg ccgtctgcct    34200
tccaggccac ggtcacgcta cccgggtaga agtcgctgat gagacacacc agggtggcct    34260
tgttggcgct gagctcctcg gtgggggcg ggaacagggt gaccgagggt gcggacttgg     34320
gctgacccgt gtggacagag gagagggtgt aagacgccgg ggaggttctg accttgtccc    34380
cacggtagcc ctgtttgcct tctctgtgcc ctccgaccct tgccctcagc ccctgggcgg    34440
cagacagccc ctcagaagcc attgcaatcc actctccaag tgaccagcca acgtggcct    34500 cagagtcccc ggctgcgacc agggctgctc tcctccgtcc tcctggcccc gggagtctgt    34560
gtctgctctt ggcactgacc ccttgagccc tcagcccctg ccagacccct ccgtgacctt    34620
ccgctcatgc agcccaggtg cctcctccgt gaacccgggt cccccgccc acctgccagg     34680 acggtcctga tgggagatgt ggggacaagc gtgctagggt catgtgcgga gccgggcccg    34740
ggcctccctc tcctcgccca gcccagcctc agctctcctg gccaaagccc ggggctcctc    34800
tgaggtcctg cctgtctacc gtccgccctg cctgagtgca gggcccctcg cctcacctgc    34860
cttcagggga cggtgccccc acacagcacc tccaaagacc ccgattctgt gggagtcaga    34920
gccctgttca tatctcctaa gtccaatgct cgcttcgagg ccagcggagg ccgaccctcg    34980
gacaggtgtg acccctgggt cccagggat caggtctccc agactgacga gtttctgccc    35040
catgggaccc gctcctttct gaccgctgtc ctgagatcct ctggtcagct tgccccgtct   35100
cagctgtgtc cacccggccc ctcagcccag agcgggcgag accctctct ctctgccctc     35160 cagggccttc cctcaggctg ccctctgtgt tcctggggcc tggtcatagc cccgccgag    35220 cccccaagct cctgtctggc ctccggctg gggcatggag ctcacagcac agagcccggg    35280
gcttggagat gcccctagtc agcaccagcc tctggcccgc accccagcgt ctgccctgca    35340 agagggaac aagtccctgc attcctggac caaacaccag ccccggcgcc ccgactggcc     35400
ccattggacg gtcggccact ggatgctcct gctggttacc ccaagaccaa cccgcctccc    35460
ctcccggccc cacggagaaa ggtgggatc ggcccttaag gccgggggga cagagaggaa     35520
gctgccccca gagcaagaga agtgactttc ccgagagagc agaggtgag agaggctggg    35580 gtagggtgag agccacttac ccaggacggt gacccaggtc ccgccgccta agacaaaata    35640
cagagactaa gtctcggacc aaaacccgcc gggacacgc ctggggcctg tccccgggg     35700 gggctgggcc gagcgggaac ctgctgggcg tgacgggcgc agggctgcag ccggtggggc    35760
tgtgtcctcc gctgaggggt gttgtggagc cagccttcca gaggcaggg gaccttgtgt     35820 cctggaggtg ccctgtgccc agcccctgg ccgaggcagc agccacacac gcccttgggg     35880
tcacccagtg cccctcact cggaggctgt cctggccacc actgacgcct tagcgctgag    35940
ggagacgtgg agcgccgcgt ctgtgcgggg cggcagagga gtaccggcct ggcttggacc    36000
tgcccagccg ctcctggcct cactgtaagg cctctgggtg ttccttcccc acagtcctca    36060
cagtccagcc aggcagcttc cttcctgggg ctgtggacac cgggctattc ctcaggcccc    36120
aagtggggaa ccctgccctt tttctccacc cacggagatg cagttcagtt tgttctcttc    36180
aatgaacatt ctctgctgtc agatcactgt cttttctgtac atctgtttgt ccatccatcg    36240
atccaacatc catccatcca tccatcaccc agccatccat ctgtcatcca acatccatcc    36300
ttccatccat tgtccatcca tctgtccatc ttgcatctgt ctgtccaaca gtggccatca    36360
agcacccgtc tgccaagccc tgtgtcacac gctgggactt ggtgggggga gccctcgccc    36420
```

-continued

```
tcccaccctc ccatctctcc tgaaacttct ggggtcaagt ctaacaaggt cccatcccgt      36480
ctagtctgag gtccccccgc agcctcctct tccactctct ctgcttctga cccacactgt      36540
gcactcggac gaccacccag ggcccttgca tccctgtttc cttcctgacc tcttttttt      36600 ggctctggat ttatacacat tctgcctcct ggaggcgtct cagcttgagt gtcccacaga      36660
cgcctcagac tcagcatctt ccatcgaaac tgctcccagg tccttgcaga cctggtcccc      36720
cacattgttc tcaattcggt agatttctcc acaagccaga ggcctggact catcccataa      36780
tgcctgcccc tcattgagtc agcctctgtg tcctaccata accaaacatc cccttaaaaa      36840
tctcagaaga acaaaaaaag cacccagatg gcactgtcag agtttatgat gacaagaatc      36900
ctcagttcag ttcagtcact cagtcgtgtc cgactctttg cgaccccatg aatcgcagca      36960
cgccaggcct ccctgtccat caccaactcc cggagttcac tcagactcac gtccattgag      37020
tcagtgatgc catccagcca tctcatcctc tctcgtcccc ttctcctcct gccccaatc       37080 cctcccagca tcagagtttt ttccaatgag tcaactcttc gcgtgaggtg accaaagtac      37140
tggagtttca gcttcagcat cattccttcc aaagaaatcc cagggctgat ctccttcaga      37200
atggactggt tggatctcct tacagtccaa gggactctca agagtcttct ccaacaccac      37260
agttcaaaag cctcaattct ttggcgctca gccttcttca cagtccaact ctcacatcca      37320
tacatgacca caggaaaaac cataaccttg actagatgga cctttgttgg caaagtaatg      37380
tctctgcttt taatatgct atctaggttg ctcataactt tccttccaag aagtaagtgt       37440
cttttaattt catggctgca atcaacatct gcagtgattt tggagcccca aaaaataaag      37500
tctgccactg tttccactgt ttccccatct atttcccatg aagtgatggg accagatgcc      37560
atgatctttg ttttctgaat gttgagcttt aagccaactt ttcactctcc actttcactt      37620
tcatcaagag gcttttttagt tcctcttcac tttctgccat aagggtggtg tcatctgcat     37680
atctgaggtt attgatattt ctcctggcaa tcttgattcc agtttgtgtt cttccagtc       37740 cagtgtttct catgatgtac tctgcatata agttaaataa gcagggtgat aatatacagc      37800
cttgacgtac tccttttcct atttggaacc agtctgttgt tccatgtcca gttctaactg      37860
ttgcttcctg acctgcatac agatttctca agaggcaggt caggtggtct ggtattccca      37920
tctctttcag aattttccac agttgattgt gatccacaca gtcaaaggct ttggcatagt      37980
caataaagca gaaatagatg ttttttctgaa actctcttgc ttttttccatg atccagcaga    38040 tgttggcaat ttgatctctg gttcctctgc cttttctaaa accagcttga acatcaggaa      38100
gttcacggtt catgtattgc tgaagcctgg cttggagaat tttgagcatt cctttgctag     38160
cgtgtgagat gagtgcaatt gtgcggcagt ttgagcattc tttggcattg cctttctttg     38220
ggattggaat gaaaactgac ctgttccagg cctgtggcca ctgttgagtt ttcccaattt      38280
gctggcatat tgagtgcagc actttcacag catcatcttt caggatttga aatcgctcca      38340
ctggaattcc atcacctcca ctagctttgt ttgtagtgat gctctctaag gcccacttga      38400
cttcacattc caggatgtct ggctctagat gagtgatcac accatcgtga ttatctgggt      38460
cgtgaagatc ttttttgtac agttcttctg tgtattcttg ccacctcttc ttaatatctt     38520
ctgcttctgt taggcccata ccgtttctgt cctcgcctat cgagccctcg cctccctacg     38580
tagagactct aagcaggaag gtgacccgtg ctgcactggg tccagcatgc ttttaattca     38640
gcagtggaac ttctgggtca tgattgtgtt taagggatgc gcatacgatt tttgaagcaa     38700
aatttaacag gacagcagtg taaagtcagt acttatttct gattaaagaa agcaaatatc     38760
cagcctgtta ctaagttaat taactaaaga aacatcttca acttaataaa cagtatctcc     38820
```

-continued

```
tgaaacttac agcatgcttc acatttaaag gcaaaaccat tttagaggcc agggttccca   38880
cgcttacgtt tattatttaa tatatgctac agattcaagc ccatgacaca aaatgggggg   38940
aagagtgtga gtgttaggaa aaatgagata aaattggttt ttgcaggtga tgggctagtt   39000
tactttaaaa aaaaaaacaa aacaagctca agatgaactg aaggactatt agaactggta   39060
caagagttaa cctgtgatcg aatacaagca ggctgggcaa aactcagcag gttttcttct   39120
atacaggcag taatgattga gaatacgaaa cggcggaagc gcttacaacc tcgataacag   39180
ttctattaaa agccctagga atgaacttaa cacggnnnnn nnnnnnnnnn nnnnnnnnnn   39240
nnnnnnnnnn nnnnnnnnnn nnnnnnnnnn nnnnnnnnnn nnnnnnnnnn nnnnnnnnnn   39300
nnnnnnnnnn nnnnngctcc ccccaccctc ccctcctccc ccccaccac cagtgcccca    39360
ggtctcgtgc ccagagagct gaagatgcca gcaggcccgc tgcctgcctc gctcgcgtgg   39420
cccgggctcg ctgccggtct gcctgcccag cacacagatg cagcccagc tctcgctgcc    39480
acccgcctcc cccaggcagg actctcccac aacaccaagg gcgtctctgg gttcaggatg   39540
gccctcgttg aggtgtaaag tgcttcccgg ggctgagacg aatgggccgg agatccaaac   39600
gaggccaagg ccgccacggc gcctggcgca gggcacccat ggtgcagagc ggcccagctc   39660
cctccctccc tccctccctc cctgcttctt tatgctcccg gctatgtcta ttttttactct  39720
gcaatttaga aatgataccg aaggacaaac accgttcccc ctgtgtgtct gctctaaacc   39780
ctttatctac ttatctatta gcgtgtccaa gttttgctgc taagtgaatg aaggaacact   39840
acccacaagc agcaacgtcc ccacgaccct cgcctgttca actgggaatg taaatgtgct   39900
ttcaaaggac ctaagtttct atgttcaaaa ccgttgtgtg tttcttttgg gagtgaacct   39960
aggccactcg ttgttctgcc tttcaaagca ttcttaacaa ctctccagaa cccagggctt   40020
ggcttacgtt tccagaaatt ccaaagacag acacttggaa acctgatgaa gaaggcctgt   40080
gagcacagca ggggccgggg tacctgaggt aggtggggg ctcggtgctg atggacacgg    40140
ccttgtactt ctcatcgttg ccgtccagga tctcctccac ctcggaggct ttcagcaggg   40200
tcacgctggt ggccagggtc gtgtatccat gatctgcaac cagagacggg gctgcgtca    40260
gcccgcgggc gggcagcagg caggagcagc caggagacga agcacaccga ggtcctcaca   40320
tgcaggaggt gggggaagcg gctgtggacc tcacgactgc ccgatgtggg cctcttccaa   40380
agggccggcc tggaccctgg ctttctccag aggccctgct gggccgtccg cacaggctcc   40440
agccacaggg cctcttggga caggagggct ccagagtgag ccggccggcg ggaagaggtc   40500
tgacaccgct gcagtccaca acacgaagcg aggtggagat gggatgaggg atgagaaaca   40560
cttttctttt aaaacaagag cccagagagt tggaaagagc tgctgcacac gcaacatgaa   40620
ctcctggccc cggtgccagc ggcgctggga gcccgagttc tcgcaatcc gaccacagct    40680
tgcctaggga gccgggtgga gacggagggt tagggaagg cggctcccca gggagcgcga    40740
ggcccggggt cgccaaggct cgccagggc aagcgcagct agggggcgcag ggttagtgac   40800
cggcactgca cccggcgcag gagggccagg gaggggctga aaggtcacag cagtgtgtgg   40860
acaagaggct ccggctcctg cgttaaaaga acgcggtgga cagaccacga cagcgccacg   40920
gacacactca taccggacgg actgcggagt gcacgcgcgc gcacacacac acacacacca   40980
cacacacaca cacacggccc gggacacact cataccggac ggactgcgga gtgcacgcgc   41040
acacacacac ccaccacaca cacacccacc acacacacac ccaccacaca cacacacaca   41100
cacacacacc cccacacaca cccacacaca cccacacaca cccacacaca cacacccaca   41160
```

```
cacacacaca cacacacaca cacacacacg gcccggtggc cccaggcgca cacagcacgg    41220
agcaaacatg cacagagcac agagcgagcg ctagcggacc ggctgccaga ccaggcgcca    41280
cgcgatggat tgggggcggg gacggggagg ggcgggagca aacggnnnnn nnnnnnnnn    41340 nnnnnnnnnn nnnnnnnnnn nnnnnnnnnn nnnnnnnnnn nnnnnnnnnn nnnnnnnnnn    41400
nnnnnnnnnn nnnnnnnnnn nnnnngtatt aaagaagccg ggagcgagaa tatgacggca    41460
agaggatgta ggtgggggcg gggcaagagt aaagagagcg gacggtagag gggatgcgat    41520
tgtgatgcgg aagcgagacg aggagtgatg ccgtattaga ttgatagcaa gaggaacagt    41580
aggagggggg gggagagga gggggaggtg ggggtggtg ggtgggaagg gaactttaaa    41640 aaaagaggg gagagttgga gggggaata acgggcggt aaaaagaac aatttgaaat    41700 taccagggtg gggcggccag gggggtgatt cattcttgga gggggcaaca tatgggggt    41760 ggctgtcgcg gattaggaga aaataaatat cagggtgat taagtgtttg gcgttgggga    41820
ataatgaagt aagaatcaaa tatgaatcgc gttggcatcg ttagccatcg ggggaaacat    41880
ttcccatgca aggaacaagg atgtgagaat gcgtccgtct gaaccaccgt cccggggtcc    41940
cagtaggact cgccgagctg atagttgccg gagcaacagt taaggagca gaagctgcta    42000 caaaccacc acctgccaaa gtagggtctc caattacgga gtgcgcctcc tgggtgtcgg    42060
tccaaacctt tggaaggac ctggaaataa gtgctaccca ccagatatta atataaaccc    42120
acctggccag gagaggcagg cgctgctggc acaggaagtg tccccagact cagtcatcaa    42180
ggtaaataat attttgggac ctccctggaa atccagtggt taggactctg cggttcaatc    42240
cctggtcggg gaactaagat cccacaagtc acaagacatg gccaaattta aaaagaaaa    42300 aaagagagag aaatatttag tgcaataggt tttagaattg aaattaagct cctgcccacc    42360
cccacccccc aatctggatg aataaagcat tgaaatagta agtgaagtca ggctctgaca    42420
tgcactgatg tgactcacct taagcaaccc ccaccctagg actggtcggg gttccaggag    42480
tttcaggggt gccaggaaga tggagtccag cccctgccct ctcccccac cacgtcctcc    42540 actggagccg cctaccccac ctcccacccc tccgcaccct gctaccccc accctgccc    42600 ccaggtctcc cctgtcctgt gtctgagctc cacactttct gggcagtgtc tccctctaca    42660
gctggtttct gctgcccgct accgggcccg tccctctgt tcagttcagt tcagtcgctc    42720
agtcatgtct gactctttgt gaccccatgg actgcagcac accaggcctc cctgccatc    42780 accaacccc agaacttact caaactcatg tccatcgagc cagtgatgcc atccaaccat    42840
ctcatcctct gtcgacccct tctcctggcc tcaatctttc ccagcatcag ggtcttttcc    42900
aatgagtcag ttctttgcat caggtagcca aagtattgga gtttcagctt cagcatcatt    42960
tcttccaatg aatattcagg actcatttcc tttgggatga actggttgga tctccttgca    43020
gtccaaggga ctctcaagag tcttctccaa caccacagtt caaaagcatc aattcttcag    43080
tgctcagctc tctttatagt ccaactctca catccatacg tgaccactgg aaaaaccata    43140
gcctcgacta gatggaactt tgtgggcaaa gtaatgtctc tgcttttgaa tatgctgtct    43200
aggttggtca taacttttct tccaaggagc aagcgtcttt taatttcatg gctgcagtca    43260
ccatctgcag tgattttggg agcccaagaa aataaagtct gtcactgttt ccactgttc    43320 cccgtctatt taacggaggg aaatttccca gagcccccag gttccaggct gggcccacc    43380 ccactcccat gtcccagaga gcctggtcct cccaggctcc cggctggcgc tggtaagtcc    43440
caggatatag tctttacatc aagttgctgt gtgtcttagg aaagaaactc tccctctctg    43500
tgcctctgtt ccctcatccg cagaagtgac tgccaggtcg gggagtctgt gacgtctcca    43560
```

```
gaagccggag gattttctcc ccatttgctg aaagagagct cggggtgggg gaagcttctg    43620 caccccctagg atcaccagag gagccagggt cttcagggtt cccggggacc cctcagtggg    43680
ggctcaggaa ccacagagcc agaccctgat tccaaaaacc tggtcacacc tccagatgac    43740
cctttgtccc ttggctccgc ctcaaatgct ccaagcccca acagtgaagc gcttaagaga    43800
aggatccacc aggcttgagt ttggggagga gggaagtggg gagctggggg agggcctggg    43860
cctgggagac aggaatccac catggcttca ggcagggtct ctggggcctg cggggtggag    43920
agcgggcagg agcagacaga ggtgactgga cacgacacac ccctccactc caagggaggt    43980
gggcaggggc ggggcacaga ggaacaagag accctgagaa ggggtccacc gagcagactg    44040
ctggacccag acatctctga gccagctgga atccagctct aagccatgct cagcccaggc    44100
agggtatagg gcaggactga gtggagtggc cagagctgca gctgcatggg ctgggaaggc    44160
cctgcccgtc ccctgagggt cccccagggt ctagccagac tccaatttcc gaccgcagca    44220
cacacaggag gaagtggtcg gggtggagtt ggcccagagg tctgggcagg tgcagggtgg    44280
gggaaggggg gcagctggag tcacccgctg aattcaggga cagtcccttt ttctccctga    44340
aacctggggc tgtcccgggg gccaccgcag cctccaggca gcgggggac ccagccccca    44400 atatgtgaga agagcaggtc ccaggctgga gagagcgaag caccatggtg gggagaagtt    44460
agactggatc ggggccccta ggggctcccc cggacctgca cggcagccgt cagggcaccc    44520
gcaccccatt gctgttcagt gctggccagt gtccaaggcc agggatgtgt gtgtgtgtgt    44580
gtgcgtgcgt gcgtgcgtgt gtgtgtgcgt gtgtgcgcgt gcgtgcgtgt gtgtgtgtgt    44640
gcgtgcgtgt gcgtgcgtag acgtgtgcgt gcgtgcgtgc gtgcgtgcgt gtgtgtgcgc    44700
acgcgcgcag cccagcctca gcactggacc aggcagcctg ggattcctcc aaaactgcct    44760
tgtgagtttg gtcaaaccgt gaggctctga tcaccgccat ccattcgccc cctcctgccc    44820
ccctcatcac cgtggttgtt gtcattatcg agagctgtgg agggtctggg aggtcatccc    44880
acctgccagc taaaccgtga ggctgccgca atcgcactga tgcgggcaga cccgagacgc    44940
tgtgccggag acgaaggcca gcttgtcacc ccgccagagc ggcagtcggg ccacaagcat    45000
catccaagca gtggttctct gagcccgacg gggtgatgca aaggagccag gagacacctg    45060
cgcgtccaag ctgggggacc ccaggtctgt tatgccggac agtaaacacg ttcagctccg    45120
gagggagagg gttcccctac cttccagggt ttctcattcc acaaacatcc aaagacaatc    45180
cataccgaag gcgatccgtg cctttgctcc tgagacgtgc ggaagcacag agatccacag    45240
acactgtctc ccaggatcct atgtatgtaa aggaaccgaa gtcccaggct gtgtgtctgg    45300
taccacatcc cacggaacag gctggactga ttttcaccaa atgtagcaga aacgttaagg    45360
agtatcagct tcaaaatatg agggccagac atgtctgaga agtcccttcc agaaaagtcc    45420
ctttggggtc cttccccaga gttgctgaaa cagagaaccg gaagggctgc agagctgaac    45480
ttaaacaact ggatcgcaaa ggtccgtctc atcagagcga tggttttttcc agtggtcatg    45540 tatggatgag agagttggac cataaagaaa gctgagcgcc gaagaatcga tgcttttgaa    45600
ctctggtgtt ggagaagact cttgagagtc ccttggactg caaggagatc caaccagtca    45660
atcctaaagg aaatcaatcc tgaatattca tgggaaggac tgatgctgaa gctgaaactc    45720
caatactttg gccacttgat gcaaagaact gactcactgg aaaaaccctg atgctgggaa    45780
aggttgaagg caggaggaga aggggtcgac agaggatgag atggttgggt ggcatcaccc    45840
acccatggac tcaatggaca tgggtttgag taaactctgg gagttggtga tggacagaga    45900
```

```
atcctggcat gctgcggtcc atggggtcat agagagtcag acacaactga gcgactgaca   45960
gaactgaagc aactggcaag ccggagggta ggtgccggct gcgatgagcg ggaacgtgca   46020
acctgccacg tggagctctt cctacaccca gagtcctgac ggcactggga ccctagccct   46080
ccacggcctc tccagggcca cgagacaccc tcacagagca gagaagcgga acagagctgg   46140
tgtgcagaac caggccccgg gggtggggcg gggctggtgg gcaggcttta gtgagaagcc   46200
cttgagccct ggaaccagag cagagcagaa cagttggcag aggccccct gggagaggcc    46260 ccccgcccag agtaccggcc ctgggccctg ggggagaggg cggtgctggg ggcagggaca   46320
gaaggcccag gcagaggatg ggccccgtgg gacggggcgc accaaaacag cccctgccag   46380
caaggggaag ctggggcact tcgacccccc tccaaggagg agcccacacc agcgcatctg   46440
cccaaggtgc ccttggccct gggggcacat gaggcccagg ccaggccagg ggcccatga    46500 ggcccccagg ggtcagtgca gtgtccccag gcagccctgg cctctcatcc tgctgggcct   46560
ggcctcttat cccgtgggcg cccacggcct gctgccccg acagcggcgc ctcagagcac    46620 agcccccgc atggaagccc cgtcaggaaa gagcccttgg agcctgcagg acaggtaagg    46680
gccgagggag tcatggtgca gggaagtggg gcttcccttc gatgggaccc aggggtgaat   46740
gaccgcaggg gcggggaacg agaagggaaa ccagctggag agaaggagcc tgggcagacg   46800
tggctgcacg cacagcgctg accctgggcc cagtgtgcct ttgtgttggg ttttatttt    46860 aattttgtat tgagatgcta tttatctcgt ggagcttttg ccgccctgag attttgtacc   46920
cgtggctggt gtccctcttg cctcaccccg gcctctgtag cagggcagac acggcgcaac   46980
ggggcagggc gtgcccagga ggcactgtca ttttgggggc agcggcccca caaggcaggt   47040
ctgccttcct cccctcttac aggcagcgac agaggtccag agaggtgagg caagctgccc   47100
aatgtcacac agcacacggg cgcagtccca ggactgtaga atcccggga ctagacaggc    47160 accagagtgt cctgtgtttt taaaaaaacg gcccaagaga agaggcaagt ctgcaaggcg   47220
tcccgggaag gcagcagggg cttggctcgg tctcccccaa ggaggccagc tcctcagcga   47280
ggttcctaag tgtctaacgg agccaagcct gaaccaaggg ggtcacgtgc agctatggga   47340
cactgacctg ggatggggga gctccaggca aaggagtag ggaggccaag gaggagagag    47400
gggtgcacag gcctgcaggg agcttccaga gctggggaaa acggggttca gaccacgggg   47460
tcatgtccac ccctccttta tcctgggatc cggggcaggt attgagggat ttatgtgcgg   47520
ggctgtcagg gtccagttcg tgctgtggaa aaattgtttc agatcagaga ccagcgtgag   47580
gtcaggttag aggatggaga agaagctgtg aaaaggtgat ggagagcggg gggacggtcc   47640
tcggtgatca ggcaccgaga tcgcccatgg aatccgcagg cgaatttaca gtgacgtcgt   47700
cagagggctg tcggggagga acaggcactg tcatgaactg gctacaaaaa tctaaaatgt   47760 gcacccttt cggcaatatg cagcaagtca taaagaaaa cgcatttctt taaaattgcg     47820
taattccgct tttaggaatt catctggggg cggggggaaca atcaaaaaga tgtgaccaaa   47880
ggtttacaag ccaggaagtc aactcgttaa tgatgggaga aaaccggaaa taacctgaat   47940
atccaacaga aagggtgtga tgaagcgcag catggcacat ccaccgcaag gaatcctaac   48000
acaaacttcc aaaacaatat ttctgacgtt gggttttaa agcatgcgtg cactttcaaa    48060
agcttgtcag aaaacataga aatatgccaa taatgtgtct ctagccaaat ttttaatt     48120 ttgctttata attttataaa gttataattg tatgaaatat aatgataaaa ttataaacta   48180
taaaaaagtt atgaaaatgt tcacaagaag atatacatgt aatttatct tctacaatac    48240 tttttaatac cagaataacg tgcttttaaa aaagattgag cacagaagcg tataaagtaa   48300
```

```
aaattgagag tttctgctca ccaaccacac gtcttacctt aaaacccatt ctccagcgag   48360
agacagtgtc atgtgggtct gtacacttct ggcctttctc ctaggcatgt atgtccctga   48420
aaactcacac acacggctaa tggtgctggg attttagttt tcaaaacgga ctcatactct   48480
gcctatgagc ctgcaactat ttattcagtc tgttgagatt ttctatatca gcccacatgg   48540
atcccgcatg ttctctgaat ggctctgtat gaattcaaag tttggaagaa gcagcgtgtc   48600
tttaatcatt cgcctattaa tggacgtttg gggtgtttcc actacaaaan nnnnnnnnnn   48660
nnnnnnnnnn nnnnnnnnnn nnnnnnnnnn nnnnnnnnnn nnnnnnnnnn nnnnnnnnnn   48720
nnnnnnnnnn nnnnnnnnnn nnnnnnnnng atacaattcg agctcggtac cctggcttga   48780
actatatgaa cagagaacga tgagaacagt ttctcaaact tggaacagtt aacattttgg   48840
gctaaatgat tcttttttgt gtggagttgg cctatgaata gaggatatta gcagcatcat   48900
ttaaccttta ctcactacat acctgtagca actacatcct ctccatttgt gtcaatcaaa   48960
actgtctccg gacatggaca agtgtgcccc tgggatgggt ggaatgacct tttgttaaga   49020
accactgggt cagagattca tagattttg tcttgttgac ttttaaaaa tacatcttgg   49080 tttttatttt attggtttct gctcttatct ttatgattac cttccttta cttgggcttt   49140 ccctgataga ttttcccttc tggctcagct ggtaaagaat ctgcctgcaa tgcaggagac   49200
ctgggttcag tccctgggtt gggaggatcc cctggagagg agaagggcta cccaccccag   49260
tattctggcc tggaggattc catggagtgt atagtccatg gggtcgcaga gtcggacatg   49320
actgagtgac tttcacacac acatatgtcc ctggtagctc agctagtaaa gaatcccacc   49380
cgcaatgcag gagacccggg tccaattcct gggtccggaa gattcccttt tgtttactcc   49440
ataagatctt atctggggac aaaactaaca gctatgccag accttctgga catcagggaa   49500
cgtgaggggt gtggactgga cagatgtgtg tgttctccca aacacaaaca tacatctgta   49560
tacatgtaca tggagagagg gggagggagg ctgtgagtct ccaggggacc gtgcaaccat   49620
gtgacattca tggaggcgtt tgcgggtgat cactacacag tttcttcttc tggtttcttg   49680
gtcaattgac ttcacaattc caattcctat acttcatttt agactgaggg aattttacac   49740
tattgtaaga catatgtata catgagttat gttcagcgcc atgagggctc attttgtgtg   49800
tccactttgc ctggaaacaa agttggactg atttacttct aggggtgcct ggggtgttt   49860 ctggaggaca ggagcatttg aacccaaggg ctcggtgaag catgagcctc tctgcaggtg   49920
gacccaggag gaacgcaagg ccgaggaagg cagactctcc tcctccctaa cccgaggtct   49980
ctgctcagaa aagggacaat ataatgacta gaagaaaaga aagaacatca gctgtgggag   50040
gtttgttctc tggagcagat tcacacgttg aggctcatgt gcaggaattc taggtgaaac   50100
agagcagtca cccatgtgtg ttggaaaatt ttaaattaca tttgcagtta cgactttgtt   50160
taagccagac agggtagcac agcaaagtca ccatgtggtc acctgtgttt tgtaaaggag   50220
agagaacttg ctggcacatt caggaaaggc cgtgtctcag ctttggaggc acactgagag   50280
gccacaagca gatggtgagg accagggtct cgggcagagg gatcaattca ctgctcttca   50340
cttttgccac atctgtgtgc tgtccatcct ggccagagta gttcagtctt cagatgctgg   50400
agttcccatt ggtagaaatc caatctgggt catttttaaa cctctcttgg ttctacttaa   50460
tggttttaaa atctctttgg ctcaagaaaa aaaataaaca taattttaaa gggtggtttg   50520
gggccttgac tataaagtac attatctggg ccatttcaga gcatggttga attaatacat   50580
ttcgtgctta ctatagctcc tattttcttg attctttaca ggtaattttt gttaggaatc   50640
```

| | |
|---|---|
| gggtactgtg aatattttct tgttgaatac gggatctttg tatttttttcc taattttttt | 50700 |
| tttttttttca tttttggttt taccttcagg aaagtcacta ggactcagga aagtcctttg | 50760 |
| tccgcctgtt atttcagtct cttacctggg gccagggcag cgtttcctct gggctaagtt | 50820 |
| tccccacaac cggggccagt tctcctcact cttcaccctg aggccttaat gaggagctcc | 50880 |
| cctgcgtctg agcagccggc cctcctgtga cgtgcgtgtg tctctggcca tcggcgtccg | 50940 |
| gtgtccttgg aggttccgtc ctcccttcgc tcactgtgcc ccgcactcga gctctcaggc | 51000 |
| tccaagcagt gtccgcagtg tgcagaccct ctgtgtagct ctctcctcct caggactctt | 51060 |
| ccctctagat gtgtgttttc ttttggctcc ttggacctcc gctctgaacg caggcctggt | 51120 |
| gctgagtgtg atctctggag ggaagcctgg gaggctggac gggtccgccc tgcggtgtgg | 51180 |
| tgacaggtgt gggctcgggg cggggcctgc acgtcgtcct gacccgagcc gggactgggc | 51240 |
| tccgggcctc aggcatcact gactgaatct ccctcacaga ggggtcaggg cctgggcggg | 51300 |
| ggaaccgtct ctgcaatgac agcccctccc agggagggca cagcggggag ctgccgaggc | 51360 |
| tccagcccta gtgggaggtc ggggagccca ggggagcggg ctgacggccc cacaccggcc | 51420 |
| cagggctggt tcgttctgtt tctcgagctc aacagaagct ccgaggagct gggcagttct | 51480 |
| ctgaattcgt cccggagttt tggctgctga gtgtcctgtc agcaccgtat ggacatccag | 51540 |
| agtccattag cagtggtctc tgtccctctg tctgtccttc atcaggctct ttgtccaggt | 51600 |
| caccacacgg ccaacaccag acagtctgg tcccgccagc ccatcgtccc tgcggacgcc | 51660 |
| cctgtgcagc ctgccgaagg gccgggaggc cgggggaacc gggccaggcc tgtccctgct | 51720 |
| gtgtccacag tcctcccggg gctggaggag agcgtgagca ggacgggagg gtttgtgtct | 51780 |
| cacttccccg tctgtctgtg tcactgtgag gattatcact gctgtcagct gactgacagt | 51840 |
| aatagtcggc ctcgtcctcg gtctgggccc cgctgatggt cagcgtggct gttttgcctg | 51900 |
| agctggagcc agagaaccgg tcagagatcc ctgagggccg ctcactatct ttataaatga | 51960 |
| ccctcacagg gccctggccc ggcttctgct ggtaccactg agtatattgt tcatccagca | 52020 |
| ggtcccccga gcaggtgatc ttggccgtct gtcccaaggc cactgacact gaagtcggct | 52080 |
| gggtcagttc ataggagacc acggagccgg aagagaggag ggagaggga tgagaaagaa | 52140 |
| ggaccccttc cccgggcatc ccaccctgag gcggtgcctg gagtgcactc tgggttcggg | 52200 |
| gcaggcccca gcccagggtc ctgtgtggcc ggagcctgcg ggcagggccg ggggccgca | 52260 |
| cctgtgcaga gagtgaggag gggcagcagg agaggggtcc aggccatggt ggatgcgccc | 52320 |
| cgagctctgc ctctgagccc gcagcagcac tgggctctct gagaccctt attccctctc | 52380 |
| agagctttgc aggggccagt gagggtttgg gtttatgcaa attcaccccc ggggggccct | 52440 |
| cactgagagg cggggtcacc acaccatcag ccctgtctgt ccccagcttc ctcctcggct | 52500 |
| tctcacgtct gcacatcaga cttgtcctca gggactgagg tcactgtcac cttccccgtc | 52560 |
| tctgaccaca tgaccactgt cccaagcccc ccggcctgtg gtctcccctg gactcccag | 52620 |
| tggggcggtc agcctggcag catcctggcc gtggactgag gcatggtgct ctggggttca | 52680 |
| ctgtggatgt gaccctcaga ggtggtcact agtcctgagg ggatggcctg tccagtcctg | 52740 |
| acttcctgcc aagcgctgct ccttggacag ctgtggaccc gcaggctgc ttcccctgaa | 52800 |
| gctccccttg ggcagcccag cctctgacct gctgctcctg gccacgctct gctgccccct | 52860 |
| gctggtggag gacgatcagg gcagcggctc ccctcccgca ggtcacccca aggcccctgt | 52920 |
| cagcagagag ggtgtggacc tgggagtcca gccctgcctg gcccagcact agaggccgcc | 52980 |
| tgcaccggga agttgctgtg ctgtgaccct gtctcagggc ggagatgacc gcgccgtccc | 53040 |

```
tttggtttgt tagtggagtg gagggtccgg gatgactcta gccgtaaact gccaggctcc    53100
gtagcaacct gtgcgatgcc cccggggacc cagggctcct tgtgctggtg taccaaggtt    53160
ggcactagtc ccaccccagg agggcacttc gctgatggtg ttcctggcag ttgagtgcat    53220
ttgagaactt acatcatttt catcatcaca tcttcatcac cagtatcatc accaccatca    53280
ccattccatc atctcttctc tcttttctt ttatgtcatc tcacaatctc acacccctca    53340
agagtttgca ttggtagcat atttacttta gcacagtgtg cctcttttta ggaaactggg    53400
ggtctcctgc tgataccct gggaacccat ccagaaattg tactgatggc tgaaccctg    53460
cgtttggatt cttgccgagg agaccctagg gcctcaaagt tctctgaatc actcccatag    53520
ttaacaacac tcattgggcc tttttatact ttaatttgga aaaatatcct tgaagttagt    53580
acctacctcc acatttaca gcaggtaaag ctgcttcgca tttgagagca agtccccaga    53640
tcaataaaga gaatgggatg aacccaggat ggggcccagg ggtcctggat tcagactcca    53700
gccgttagg acagaacttg actaggtacg aagtgagcgg ggtggggggg caatctgggg    53760
ggaactgtgg caccccagg gctcgggcc atccccacca catcctggct ttcatcagta    53820
gccccctcag cctgcgtgtg gaggaggcca gggaagctat ggtccaggtc atgctggaga    53880
atatgtgggg ctggggtgct gctgggtcct agggggtctgg ccaggtcctg ctgcctctgc    53940
tgggcagtga taattggtcc tcatcctcct gagaagtcac gagtgacagg tgtctcatgg    54000
ccaagctatt ggaggaggca gtgagcactc ccacccctgc agacatctct ggaggcatca    54060
gtggtcctgt aggtggtcct ggggcttggg ccggggacc tgagattcag ccattgactc    54120
tcagaggggc cagctgtggg tgcagcggca gggctgggcg gtggaggata cctcaccaga    54180
gccaaaataa gagatcaccc aacggataga aattgactca cacccttggg tctggcacat    54240
tctgtcttga aatttcttgt ggacaggaca cagtccctgg ataaagggat ttctatcttg    54300
cgtgtgcaat agagctgtcg acacgcttgg ctgggacatg taatcctttg aacatggtat    54360
taaattctgt tcactaacat ctgaaaggat ttttgcatca ataaacctaa ggtatattgc    54420
cctgtcattt ccttgtcttg tagtgtctct gagtaggctg gaaggggtaa ccagcttcac    54480
aaatcgagtt aggaaattcc cttattcttc cactgtctaa tagactttca taagattagt    54540
gttaattcct ctttaaatcg ctgctataat catcactgtg ccaccggta ctgaattttt    54600
tgttaggatg atttttaaac aagcatttta atgattttc cttttatttt cggctgtgct    54660
gggtctcgtt gctgtgtgcc ggcgttctct cgctgtggcc agtgggggcg ctgctctcgc    54720
gttgcgaagc tcgggcttct gactgcagtg gcttctctcg ttgcagagcg cgggctccag    54780
ggcgctcagg ctcgcgtggc tgcggcacgt gggctcagta gtcctggggc acaggtgcag    54840
cagcctctca ggacgttttg ttcccagatg gtgggtcggt cgaaccggtg tccctgcgt    54900
tgcaaggtgg attcttcacc gctggaccac cagcgacgtt ccctggaggt ttttaattat    54960
ggatttaagc tctcattaga tgtctcctca catttcctat ttcttttga gtcagtttga    55020
tactttgttt gtgtctgtaa gtttgtccat tttatccaag tcatctaatg tgttgataga    55080
caattattgg ttagtcatct aattgttggt ttacaatttt gagagcattg tcctgcaatt    55140
ccttctatct gcaagattgg taataatatc tcccaagagg agtcacaaac tgaaatgaga    55200
ttanatacag gcttttttt taaagaatg aacttatgtt gttgcctttc tcatagatct    55260
tacttcttag catgactgta cttactgact ggggcgtttt catgtctgtg tggagagcta    55320
ccattagtac ttcttatcgc ccaaagacat cgggctcctg ggcacagtga aaacactcct    55380
```

```
ttctgtggct attttgcaaa atatggccta gcctagcgtc ataagggatc acagctgaca    55440
actgctggaa cagagggaca tgcgaagcaa cgtgagggct ggaacctgga gggtcctctc    55500
tggggacagt ttaaccagct ataatggaca ttccagcatc tgggacatgg agctgtgaac    55560
tggaccaatg actgtcattt ttggaagaga atcccagga gagaagggtc caggggaatc    55620
tgaggccgca tgcagtgcct caggacaggg gacaccttct ccagcagagc aggggggccc    55680
gcccaggccg cctgcagtga ttccaccagg aggagatgca tccctgcaga cctctgacag    55740
cacggccctc tcctgagaca cagggtcaca cccggggccc tggaaccctt tgagaccta    55800 aacctttcct ttcctgacca ccctgacagc agtctagctc agaacagaca tcttcatttt    55860
cagcaggaaa atccttttcc tcgtttgagg gagcgactgg caccggagga gctgagtctt    55920
ttaaacacag gctgcctgaa cctcagggat gacctgcagc tgctcagagg aggctggagt    55980
gtgatagctc actctaatgt tactaaaagg aacatattgg accccctc tctgaaaaat    56040 ttccctcctg cctctcatct cttagtccac tttatcgccg ttttactgct tttctattta    56100
ctactcttaa cgccaaccta tcttatttcc cctcccagtt taacacggtt ttccctccac    56160
ccgctctctt taatctcaga agattctgcc tattcctcta ttatcacacg cccctacttt    56220
ttattttttt tcttacccgc cttttattcc ctcccctcct cactctctat ttaattacat    56280
cttaactaca ccgcctgcgc tatcttcgaa tgtatccaaa tattttcc ttatataaca    56340 ctccaggccg agcggctaac ttattataat ttctttatag cgcctaccta atttcccttt    56400
atttctaatt atctatatat acccatgcaa tttcgnnnnn nnnnnnnnnn nnnnnnnnn     56460 nnnnnnnnnn nnnnnnnnnn nnnnnnnnnn nnnnnnnnnn nnnnnnnnnn nnnnnnnnnn    56520
nnnnnnnnnn nnnntgggt gtacgttata gagtaaacgc gcatgaagaa gtgggtcaat    56580
ctatggctgt gagaggcaga aaataatatt atcatatata atttatgtta taacacactg    56640
aggtggtggg ctcgtagaat agtgcggacg gggagaaagg tgggaaggag aagacacaag    56700
agagagatgt tcgcctcgcg ggatggatgg gcggagggat agaagaataa aaagaggaga    56760
ggtatagagg ggggcggggg gcataacgtg tggtgggta aatagtaggc ggtaattatg    56820
aaaaaaagaa agacgggggg ggcggtaaca tagaatacgc aaaaaagtca tatactgaac    56880
ggggattagg gagaagaggt gggggcgtg gggtgcgggg gaaagaggtg tgtgtataat    56940
tggtatggag tgttatttga atatatatta atgtaatagg gagtgtaatt agtgaaattg    57000
tgggagtatt atattggggt gtgggggaca tggcaaagtg atgatcggga taaaaaaagt    57060
aaagcaagag gggagggaa aataagggg gggagaaggt cgaagaaaat aagaggaaga    57120
agaaagaacg ggggtggcgg gcggggggg cgccgctctt gtatctggct ttttttgttgt    57180 gtcggtggtt gttcgcgtct tgttgggtcc ggggcgggtg tgcggaaaaa aaaaaaggcg    57240
ggaggcccgg ggcccggtca cgcggcaccc ccgcgggtcc ctggcttctc cttcggcagc    57300
tccgggggtc ggtgagcctg cgccctccgg gccgccggcc cgagctgtgt gcgccctgga    57360
gaatcggagc cgctgtggca gcacgcgcgag ggcgcgcgca agggccacgg gacgaccttt    57420
caaaggccgc ggcggagcgc ggcaagccga accgagggcg gtctggcgat cggccgagcc    57480 ctgctcccc ctcccgcgtg gccccagggt cgcgggtgga ctgggcgggg tacaaagcac    57540 tcaccccgt cccgccccca gaaagcctcc caggactctc acagagcacc cgccaggagg    57600
catccggttc cccctcggc tcagttcagt tgctcagtcg tgtccaactc tttgcgaccc    57660 catgactgc agcaccccaa gcttccctgt ccatcaccaa ctcccggagt ttactcaaac    57720
tcatctattg agtcagtgat gccatccaac cgtctcatcc tctgttgtcc ccttctcctc    57780
```

```
ccactttcaa tctttcccag catcagggtc ttttcttatg agccagttct tcacatcagg   57840
tggtcagagt attggagttt cagcttcagc atcagtcctt ccaatgaaca ctcaggactg   57900
atttccttta ggatggactg gctggatgca gcgccagaca ccgaccgcgt ttaccccgtg   57960
tgtcctttcc aatggctgtc ccctgcgggc ctaggggcat tggtgcgggt ttgaatcctg   58020
tggccttgaa ttttacgcct tagttccagg tccagggcag ggccatccgg attcaggatg   58080
cttcccagcc cttcaggaat ggcaggtttt catggtcctt tctgagtgag ttctgagtgg   58140
tcatattggt gcccttggca gggagggctc ctgactttcc tatcttcaca tcactgtccc   58200 caaccccaa gagaggcctc ttggcccagg gactgcaggg aggatgaagt caggagcaga   58260
agcatggggt aggggctca ggtgggcaga ggaggcccct ctgtgaggag aacggcaag   58320 cgaggaggga acaggggcac cggcagtgcc tggcaagctg ggtgatgtca cgactacgtc   58380
ccgaccacac agtcctctca gccagcccga aagcagggc cctccctga cccccatctg   58440 ggcctgggct tcagttttct cctccctgca atggggtgac tgtttgcctc caggagaggg   58500
gagcatgtaa aggtggccac tctcttctgg cagacatgcc aggcctgggc cagcctccac   58560 cccttttgctc ctgcagcccc tgctgacctg ctcctgtttg ccacccggc ccctcctggg   58620 ctgatcaggg cccccctcct gcaggaagcc ctctgggaca agcccagctt gctgtaactg   58680 tggcttcca ctgtgacctg caacgtggga ggctgttact taaaactccc atgactggtg   58740
gattgccggt ccccagaaca aggccacgca tccctggagg ccctcgagac catttaaggt   58800
agttaaacat ttttactta tgcatttca tgtgtatcag aaagaaaaaa aatgtatcat   58860
cagttcatca aatccatgat ttcttgacca atattgctaa gatgaggctg aaataggcat   58920 ttccatttttt aaaaaactga atcactctga agaaacagat ggcaggcttc ctggtggtc   58980 cggtggttaa cagtccatgc ttccagtgct gggggcatgg gttcgatccc tgaaaatttt   59040
aaaaaggaag aaaaagatgg ctcccccgtc cctgggattc tccaggcaag aacactggag   59100
tgggttgcca tttccttctc cagtgcatga aagggaaaag ggaaagtgaa gtcgctcagt   59160
cgtgtgcgac tcttagcaac cccatggact gcagcctacc agactcctcc gtccatggga   59220
ttttccaggc aagagtactg gagtggggtg ccattgcctt ctccaggcaa acggcctgct   59280
actgctactg ctgctaaatc gcttcagtcg tgtccaactc tgtgcgaccc catagacggc   59340
agcccaccag gctcccccgt ccctgggatt ctccaggcaa gaacactgga gtggggtgcc   59400
attgccttca gcctgctgct gctgctgcta agtcgcttca gtcgtgtccg actctgtgtg   59460
accgcataga cggcagccca ccaggctccc ccgtccctgg gattctccag gcaagaacac   59520
tggagtgggt tgccatttcc ttctccaatg catgaaagtg aaaagttaaa gtgaaattgc   59580
tcagtcgtgt ccgactctta gtgacccaat ggactgcagc ctaccagggt cctccatcca   59640
tgggattttc caggcaagag tactggagtg gggtgccatt cggcctaggg agtgagaaat   59700
cacggctgtc ttccctcttc tcgccctcta ggggtctctg tggagcctcc ctggagaggc   59760
cgcggcggct ccggggactg gaggggggagg ggggggttgag tcagccggtg ccctcccct   59820 cgctgcccgt ctcctccctt tttaggcaca agctgggcgc ccttttttagg cgcagcctca   59880 ccctgcgggc cactgcccgt gtttcggctc cccggagata aaacagattg cctgcacccc   59940
gggtcatcac aaggattgta tgaccgtttc ccagtgtgct caccacccctc cctctgattc   60000 tcagagacgc gccctcgcct caggaggctg ctcatcccag gccaagggc ggcgtggggt   60060 ccccagcgcc ccgcacagac actgccttct gaccacctcc tcccaacagc ttacctgcca   60120
```

```
agaaggcctc ctgacccctc atcctgcccg gtggtttgga gaaagcctca tctgcccct    60180 ccttctcggg gcctcagttt ccccctctgt gaactggcgg attctgccaa gctgacgtcc    60240
tggccagccg cctccccgtg gccagtgtcc cccgggacac agctgaatgt ccctgctcgg    60300
gatgcacctt cccaagttgg cctgtcagga ggcggggcg agcagggaaa cccgactcct    60360
ctcagacggc ccatcgcatt ggggacgctg aggcccggag cagcggcacc tcctggcca    60420 gggtcattct cccgccccgc ccgtccctc cgggcctccg agaccgcagc ccggcccgcc    60480
ccgggaagga ccggatccgc gggccgggcc accccccttc cctggccgcg ggcgcggggc    60540
gagtgcagaa caaaagcggg gggcggggcc ggggcggggg cggggcggag gatataaggg    60600
gcggcggccg gcggcacccc agcaggccct gcaccccgg ggggatggc tcgggccgcc    60660 ggcctccgcg gggcggcctc gcgcgccttt ttgtttttgg tgagggtgat ggggcggtc    60720 gcggggtact atttttcat ttataattgg gtattagcta gcgagtggaa ccacacctt    60780 attccactat agccaatttt tgcgggggca tcttacatta cagactcgcc cgcctcttat    60840
ttcggtacag catatcagat cgtctcttta ctcagacact agtgattatt gtctatagta    60900
cacaaaaaga acggttgtgt cggcgtaatg gttgcatttt ccctcctcgt ttctcctgac    60960
cacctcaatt acaccaacac tctactattt aaatcacgta ttgtacgcca ccctccgccc    61020
gcgaactaaa agaatgtgca gatattctga agataaaatc gttcattgtt acgcccgcg    61080 cgcttcgcgt atattactct tagaacttct tattcgcccg agcagttatt caccccccgc    61140
aactagatgt cgccttaata tttgttctaa ccgttttgga ttctaacgat aggcgggaaa    61200
ggtagacatt cgaccgctac gacaactaaa atcgacgagc acaggctatt tatatcgcga    61260
ccacacgcgc gcggtataca naccgtaaaa ttatctaaca tcgagagtaa gggcacagag    61320
cgaaatacaa gcggcgtggt gggaggtgtg tctgtagtga attcgcacct cgcgccgccg    61380
cctctgtgcg tcgnnnnnnn nnnnnnnnnn nnnnnnnnnn nnnnnnnnnn nnnnnnnnnn    61440
nnnnnnnnnn nnnnnnnnnn nnnnnnnnnn nnnnnnnnnn nnnnnnnnnn nnngatataa    61500
tattaataaa cagcggatag atgtgtgtaa gggaggaggt gcataagaga ttaaagagag    61560
gcgggcggag agaaatagag tagaggagga tgagagaaaa aagaaagcaa gcgtaggtac    61620
aacggcgggt gggtagtatg ataaagtgag tgtatatatt tgagtaaagg aagggtagat    61680
ggagtataaa gaagtaagga gaggagaggg cggcggagag agagagtgca aagaaaataa    61740
gtgggcaaag gcggggtggg tgagaagcag tagaagagaa gatagagaag ggggaaaaag    61800
aggaaaatga ggattagaac aagtaggaca ggatagatgt gaaaaatgag atcaggtcaa    61860
ggtggagaaa aagtagaaac tggggcgtga ttgtaaaaaa gggaggccgc gatggggcag    61920
caccataagc gaagagatga attaatgaaa gcaaggcagg gagaatcaaa tgagttgggt    61980
ggaggaagga ggctgtgact tccttcgctg ccggaaagag aactagaata gcctcgggct    62040 gtgggggag gtaaagataa agtgacttct gggccctggg ggaggcccag gagtttctac    62100
cgagctgagc tgggtgcctc tcccaaatgc ccaaccccct gagagtcgac gggagagcac    62160
agcctggcca aacctgggca gggcacacgt gtccttcacc ccacagtggt cacgagccca    62220
gcgtggtccc tgcgtctggc gggaaacaca gaccctcaca ccccacacaa gggtccggcc    62280
gctttcaaat aacagcagcc gtgccctctg gccggtgac ccggacacag agagatgaag    62340
tccgcatctc tcagagtgcg ctgtcctccg cccggtcagg cccgggtccc ctgcttctct    62400
gaggtcacca ggagggattg catgtgggtc tcagggacac aggttcagtg atgtgacaga    62460
gggtagtggg tcccagcagg gccggtcttt ggacccgttt ttctgaaaag ccagttggcg    62520
```

```
acctggggtc acagcaaagc tgatcctgtt tggccaggag tctcccagtg acggcctccc   62580
ccagaacatc gggcccagtg ggggctccag ggggtagact tgcctcccag ctcacgcccg   62640
tgtcttgaca agtccatgat ttggtaaaat taatttgtgt tggatggagt tgatttagtg   62700
gtgtgtgagt ttctgtggcg cagcaaagtc aatcagttac gcatacacat gtatccagct   62760
cttcctacga ttctgttccc atataggtca ttatggggtg tcaggtagag cttcctgtgc   62820
tacgcagtac ggccttattc agttcagctc agtcgtgtcc gactccttgt gaccccatgg   62880
actgcagcac gccaggctcc cctgtccatc accaactcct ggagcttatt caaactcatg   62940
tccatcgagc cggtgatgcc atccaaccat ctcatcctct gtcgttccct ctcctcctgc   63000
cttcagtctt tcccagcacc ccctagagaa gggaatggca aaccacttcg gtattcttgc   63060
cctgagaacc ccatgaacag tacggaaagt ccttattagt tttctatttt atatatagca   63120
gtgcacacgt gtcagcccca atctcgcaat ttatcacccc cctccgccgc cgattggtag   63180
tcatgtttgt tttctacatc tgcgactcta tttctgtttt gtaaacaagt tcatttacac   63240 cacttttta gattctgcac atacgtggca agcccacagc aaacatgctc aatggtgaaa    63300
gactgaaagc atttcctcta agatcaaaaa caagacgagg atgtccactc actccgtttt   63360
tactcaacac agccctgaac gtcctagcca tggcaatcag agaagagaaa gaaattaagg   63420
aatccaaatt ggaaaagaag aagtaaaact cactctttgc aaatgacatg acacttatac   63480
ccagaaaatc ctagagatgc taccagataa ctattagagc tcatcagtga atttgttgca   63540
ggatacaaaa ttaatacaca gaaatctcct gcattcctat agactgacaa caaaagatct   63600
gagagagaaa ttaaggaaac catcccacgg catgaaaaag agtaaaatac ctaggaataa   63660
agctacctaa agaggcaaaa gacctgtact cagaaaacta taaaatactg acaaaggaaa   63720
tcagacgaca cagagagaga gagataccac gctcttggat gagaagaatc gatagtgtga   63780
caatgactat actacccaga gaaacataca gattcagtac aaccccctatc aaattcccaa   63840 tggcatttt cacagaatca gaattagaac aaaaagtttt acaagtttca gggaaacaag    63900
aaagatccta aagagccaga gcaatcttga gaaagaaaaa tggagctgga agagtcaggc   63960
tccctgagtt ctgactgtgt atacaaagct ggcatgattt ttaacagcag gggtgtaaat   64020
gaacttgttc acaaaacaga tggtggggtg ggcttccctg gtggctcagc tggtaaagaa   64080
tcctcctgca acgcaggaga cctgggttcg atccctaggc tgggaagatc ccctggaaaa   64140
gggaaaggct acccactcca gtattctggc ctggaaaatt ccaaggacca tatagtccat   64200
gggtttgcaa agagtcggac acgactgagc gacttccaat cctggaaacg tcccattgtg   64260
gacggtgaac tggggttgtc caagctcagg gtaaccgttt gctgagtgac tgacactcct   64320
tctcatgggt taaaatgtgg ggcccaaggc caggaccaga cccgcagtc agccaggcag    64380 accctgtgca gccccagcga gtgtgtggcc gccgtggagt tcctggcccc catgggcctc   64440
gactggagcc cctggagtga gcccattccc tcccagcccg tgagaggctg ggtgcagccc   64500
taaccatttc ccacccagtg acagatccgc ctgtgtggaa acctgctctt gtccccaggg   64560
aacctggcag gactcaggga gaatgtctca gggcggccac agatcagggg ctggggggc    64620 agggctgggt ccagcagagg ccctgtgccc actcccgga aagagcagct gatggtcagc   64680
atgacccacc agggcaccga cgcgtgcttg cacacaggcc gccccctcat ggtgacactc   64740
ttttcctgtg gccacatctc gcccctcag gtccctcctg ctcccagct cctggcctga   64800 gaacctcttc cccgccccgg ggacgtcagg gctggtgtcc actgagcatc ccatgcccgg   64860
```

```
gactgtgctg atcaccagca cctgcacccc ctctcgggtc tcaccaggat gggcaactcc    64920
tgcccatcca gcacccagcc tcctgggtac acatcggggg aggagggaga agcctgggcc    64980 agaccccag tgggctccct aaggaggaca gaaaggctgc cgtgggccag ccgagagcag     65040
ctctctgaga cgtgtgggac cccagaccac ctgtgagcca cccgcagtgt ctctgctcac    65100
acgggccacc agcccagcac tagtgtggac gagggtgagt gggtgaggcc caggtgcacc    65160
agggcaagtg ggtgaggccc gagtggacag ggtgagtggg tgaggcccag gtagaccagg    65220
gcccatgtgg gtgaggcccg ggtggaccag agtgagcggg tgaggcccag gtggacaggg    65280
cgagcgggtg aggcccaggt ggacagggcg agcgggtgag gcccgggtgg acagggcgag    65340
cgggtgaggc ccggtggac agggcgagcg ggtgaggccc gggtggacag ggcgagtggg    65400
tgaggcccgg gtggaccagg gcgagtgggt gaggcccggg tggacagggc gagtgggtga    65460
ggcccgggtg gaccagggcg agtgggtgag gcccaggtgg acagggtgag tgggtgaggc    65520
ccaggtagac cagggcccag agcaaagccc cggctcagca gtgatttcct gagcgcccac    65580
tgcttgcagg gacctcagcg atggtaaggc agccctgttg ggggctcccg actggggaca    65640
gcatgcagag agcgagtggt cccctggaga acagccagg gcatggccgg gcgccctgcc     65700
aggctgcccc aggggccaca gctgagcccc gaggcggcca ggggccggga cagccctgat    65760
tctgggttgg gggctggggg ccagagtgcc ctctgtgcag ctgggccggt gacagtggcg    65820
cctcgctccc tgggggcccg ggaggacgg tcaggtggaa aatggacgtt tgcgggtctc     65880
tggggttgac agttgtcgcc attggcactg gctgttggg gccagcagc ctcaggccag      65940 cacccccggg gctccccacg ggcccgcac cctcacccca gcagctggc ctggcgaaac      66000 caagaggccc tgacgcccga aatagccagg aaaccccgac cgaccgccca gccctggcag    66060
caggtgcctc cctctccccg gggtggggg aggggttgct ccagttctgg aagcttccac     66120
cagcccagct ggagaaaggc ccacatccca gcacccaggc cgcccaggcc cctgtgtcca    66180
ggcctggccg cctgagacca cgtccgtcag aagcggcatc tcttatccca cgatcctgtg    66240
tctgggatcc tggaggtcat ggcccctctc ggggcccag gagcccatct aagtgccagg     66300
ctcagagctg aggctgccgc gggacacaga ggagctgggg ctggcctagg gcaccgcggt    66360
cacacttccc ctgccgcccc tcacttggga ctctttgcgg ggagggactg agccaagtat    66420
ggggatgggg agaaaaatgg ggaccctcac gatcactgcc ctgggagccc tggtgcgtct    66480
ggagtaacaa tgcggtgact cgaagcacag ctgttcccca cgaggcctca cagggtcctt    66540
ctccagggga cgggacctca gatgccagt cactcatcca ttccccacga ggcctcacag     66600
ggtccttctc caggggacgg gacctcagat ggccagtcac tcatccattc ccatgaggt     66660 ctcacagggt ccttctccag gggacggac ctcagatggc cagtcactca tccattcccc     66720
acgaggcctc acagggtcct tctccagggg acggacccc agatgggcca gtcactcatc    66780
catccgtctg tgcacccatc cgtccaacca tcacccttcc ctccatccat ctgaaagctt    66840
ccctgaggcc tccccgggga cccagcctgc atgcggccct cagctgctca tcccaggcca    66900
gtcaggcccg gcacagtcaa ggccaaagtc agacctggaa ggtgcctgct tcaccacggg    66960 aggaggggg ctgtgacac agggcgcccc atgcctgcc cagcctgccc ccgtgctcg       67020 gccgagatgc tgagggcaac gggggggcag gaggtgggac agacaggcca gcgtgggggg    67080
ccagctgccg cctggctgcg ggtgagcaga ctgcccccct caccccaggt acaggtctcc    67140
ctgatgtccc ctgccctccc tgcctccctg tccggctcca atcagagagg tcccggcatt    67200
ccagggctcc gtggtcctca tgggaataaa aggtggggaa caagtacccg gcacgctctc    67260
```

-continued

```
ctgagcccac ccccaaacac acacaaaaaa atccctccac cggtgggact tcaccagctc   67320
gttctcaggg gagctgccag ggggtccccc agccccagga agccaggggc caggcctgca   67380
agtccacagc cataacacca tgtcagctga cacagagaga cagtgtctgg tggacaggtg   67440
cccccacctg cgagcctgga gagtgtggcc ctcgcctgcc ccagccgcgg tcagtcggct   67500
cagcaaccgc tgtccactcc cagcgccctg gcctcccctg tgggcccagg tcaagtcctg   67560
ggggtgaagc taagtcaggg agcctcatcc atgcccagcc cggagcccac agcgccatca   67620
agaaatgctt cttccctcca tcaggaaaca ttagtgggaa agacaagagc tgggggggttc   67680 tggggtcctg gggatcaga tgaaggggtc tgggagcagc agcagcctca ggcaccccaa   67740
aacaaggccc aggagctgga ctcccagggc tgaggggcag agggaaggaa ggcctcctgg   67800
ggggttggca tgagcaaagg cacccaggtg ggggctgagc accctcggc tggcacacac   67860 aggcccccac tgcagtacct tcccctcgg agaccctggg ctcccgtctc ccgcctggcc   67920
tgccatcctc ctcaccaccc agaaatccct gagtgcggtg ccatgtgact gggccctgcc   67980
ctggggagga aggagattca gacagacagg atgccagggc agagaggggc gagcagagga   68040
tgctgggagg gggcccgggg aggcctgggg ggcagggggg caggagttct ccagggtgga   68100
cggcgctgtg ctatgctcgg tgagcacaga ggccccgggt gtcccaggcc tgggaaccca   68160
gcagaggggc agggacgggg ctcaaaggac ccaaaggccg agccctgacc agacctgtgg   68220
gtccagaagg cagctgcgcc ctgaggccac tgagtggccc cgtgtcccga accaccgctg   68280
aaacatggga cacacgttcc caggcggagc cactcctgcc ttccgggagg ctcccagcgg   68340
gctcatcgct ccatcccaca gggagggaaa ccgaggccca gatgacgaac atcccggcga   68400
gcaggtcaaa gccagcccct ggggtccct ctcccggcct ggggcctccc ctctgcaggg   68460
tgggaaaccg aggccacaca ggggctccat ggggctgccc tctgccaggc cctggacacc   68520
ccgcgggtga cccccgcctc tatcatccca gccctgccag gccctggaca ccccgtggat   68580
gacccccgcc tctatcatcc cagccctggg ggacagatgg gaggcccaag cgtggacccc   68640
ctggccaccc cctaccccac agccgggagg agccgggagc tggtggccaa gggcctagag   68700
gagccagann nnnnnnnnn nnnnnnnnnn nnnnnnnnn nnnnnnnnn nnnnnnnnnn   68760 nnnnnnnnnn nnnnnnnnnn nnnnnnnnn nnnnnnnnn nnnnnnnca atatagaggg   68820 ggtgggataa aggtaatat gatgtttagg tagttagagt taaattagaa gggtttggat   68880
aaagattaat aaaattacaa gcgtacatat cgtgtgagtg tgggtgataa tatttgtgta   68940 tgtgggaat agaagtgagt gtgagtagta ttcaagatgt aagtgtgcga atacaggtct   69000
gagcgatttg aatggaagtg aaaaaagcg tgtgtgtgga ggaggcggga gaggaagata   69060
gtgtggggga agaaaagaag gctagtgggt aaagaaatat cagtaggcgg ttgacgaaag   69120
aagaactagg aagaattaat ataaaaataa agggaggatt aaaaaataaa gagggaggag   69180
gtaacggaaa tagttagtta agaaaagaat ggagagtgga ggtaagataa ataagggagt   69240
aatgggagtg aggaggaata aataaaaaaa tggtgaggga aaatagagta gaatgagaac   69300
aagaatgaaa aagggagtga aggggtgaa aaaagtgaa gttgaaaaaa gaggaaaaaa   69360
aaggagaaga taaaaaaata aaataaaaaa aggaaaaaaa agaaaaaaag aaagaagggt   69420
taaaggacga aaagaaggga agagaaaaaa aatagtttaa gtgggggagg gtaaaaaaga   69480
attaataaag taaatatggt tgtggtcgaa aaaaaaaaaa aaattgttgt gttgatgaga   69540
agaaaagaaa aagaagaaa gggaaaagca aaaagaaagg agagaaaaag acaaccccac   69600
```

```
cgcccgggcg catggagggt gaggatggcg cacgcccgcg gatggcacag catcacagca   69660
atcctaaaac gttttcagac cggtgcatct tcaccgcgcg cgcgcccgc ccggccctcc    69720 tcccgccctg accgcggacc cccacccgca ccggggagcc tacccccacc ccggggacgc   69780
tccgccacgc taaggtcagg actgccgtga agacgcgccg gggtgaaaac gttttatctt   69840
catgacataa gcgagtggtt ttgaaacagg tttacaaacc ctcgtgaaga cgcacccta   69900 gcgttaggtt ttgttttttt accatgtgac gatgcaacta ttttcttcct ctcttccaca   69960
gtggctagtc gcctccagag cgaggggtat ctcttgtaca gagaccctcg gaacatccgg   70020
aggtagtttc ccacctaggg gtaaagcgag aaggctcatt acgagggccg gggctcctcg   70080
gggaagggca gggccctggc gcagaggctc tgccacctca gtgacacgca gaccacgcgc   70140
ggcctgcagg cgccgggctc tgaaagcagg caaagcccga tctgctgaca tcagggttc    70200 cgcagcagcg aaggtctggc ccgcacctgg cccactggga gggggtaagc tctgcctccc   70260
gacgacagca ccaagttcag gaagggccac gcagacactg gtgagacacg gcccccccgg   70320
agctgcccga gaagctctga ctttgcacta aagatctctg gcgcggtcca aaaatgtaag   70380
gcctctcttc cttttatctt aagactttga tatttttacg atgtaataaa taccaagaag   70440
ggcttttaat ttcagacaga tgtaggataa ttttccccgt agcccttgct gctttgttta   70500
gtaacgaaac tcaaccaga aataccaaag gaattttcca aagagtttca aaagcgctta    70560
tcagcaatca ctagactgct gcatacatca tcactgcccc aaacaatagc ctgcctgtgc   70620
cagttactca aagtactact tacttgacga aaacaaatct agtcctaacg tttttacaaa   70680
gaaactccac tcttccgcca acttttcaga acaaccact cgatcacgtg gcaggggacc    70740
gtggctggac tgggtgctgg ctccttctgt gaccaggcaa cactgccccc ttctcggcct   70800
ccctacgcct cttgacaaat gttcatcagc tgtaaagttc accccacgag ggacccactt   70860
ctgctatttc ccacgtacct accccattat aggagttttc tttgtgacag tttctgcatt   70920
tttcatggat ttagaggttt acataatcag ggctgctgaa cagcatgaga gacgtggcca   70980
caaggtccct cctgcacctt gccgcagggg cagggcgagt tatctggctt gagcgtggtt   71040
accatcaggg ggtaaacaca gtttccagga cgttttttgac aagacactga cccgatgcc   71100 cccactacca ccgtgcaggt cctgcaggcc tcccagcctc ccaggccctt cccgaggtcc   71160
cttcggaact taggggactc ggtctgcccc cctgggtttt ccctgcacca gcttttgccc   71220
cctctggacc caggtttccc aaatggaaaa cgaaggtgtg ggtatggaag ctccctgggc   71280
tcctctcagc tgtgcctctg catggtgatg acggctgccc atcgggggg gcaggactgg    71340 ggcagctgcg gacaccctcc caaggctgct accccgagt ggtgtggggc gctgtgggca    71400
cgctctgctc agcgcacctc ctggaaacca gcgcctgccg tctgcccggg caaccggcc    71460 cgggagccaa gcaccactgc cgtcagagga gctgctggct gtgagtggac gccagtctag   71520
ctctgaaccc tgcccaggcc tcctgaggtc tgaacattgt aaaatcaggc cccgacggc    71580 aactgcctct ccctcctgcc gtctggtctc cataaactgc atctcaggac aaatcttctc   71640
actcaccagg gctgaaacag aagactgcag ctatctttct caaatctaag gtgtgctaca   71700
gggcaagtcg cagaaactgt ctggcctaag catctcatca gatgcctgag acaagagctg   71760
tggacgccaa gctggagcca gagctcctcg cgttctgccc acctggcacc gcgttccacc   71820
cagtaaacgc aggcttgatt ttcaaaagta ccaccgactc agagccaatg ctaaaccgac   71880 cactttttcct gccccattaga ttgggtgaag gtttctttaa tcaatctgcc agtcaccaca   71940
tgccgcctct gtgcccacag gctggcgaag acctttctga gctacggcat gtggcaggca   72000
```

```
gcggcacctc tcttcagtac ggccagctgt caagggagc gttctgtga tgatgtgaaa    72060
atacattgca tccggccccg tgttcatga acacgggtga ggaaaggaaa cacacaaagt    72120
tctgatgcga ctgacagcac gggtctcata actcaataca agtcagacaa accacaggga    72180
gtcacaggga atcccaatag cctcatctag tgtgaccatc atgaggctta atttattcag    72240
tgtattcaat cataaagagg gggaaaaatt gtaaaaaaaa aaaaaagaa agagtgaaat    72300
gtgtaatact gaaaactgtt gctaggagaa gcaagcattg gcgtttgtaa ctgctttgac    72360
tccccaagac ccacactcgc ctcgctacaa aagggaggca ctgctgctca gtacttgcac    72420
acccgaactg cggatttgta atttaaaaat gtgtgtgtgg acacagcaca agccagagac    72480
tgccaaaggt tgagggacac tggaagaact taatatactt ggtgcatgct gccagtgaca    72540
gtcagtcacc agctgattca atagagtgcc gaaaggtcac cttttaggta aggatgaagg    72600
ggttctgggc tcgtttactt gcactaactc agagttagtc cgagatatcc gaagtgccag    72660
gtgcctccca tttgctgatg gatctagctc agggacggct gggccctagc catccaaaaa    72720
tcaagcattg ttctcccaac ctgtcttctc gctgataatg gaaggtcaga acgcccaccc    72780
gcccacctca aagtcaaaga acaccaagcg ggtgagtccc cactaagctc ggtgtttcca    72840
atcagcggtt tcaggattcc agctggggca atgagggagg gagcgtgcga gggatccaac    72900
acctcgcccc gtgcgcagca agggataacc caacaccccg tttctgtacg tccggctgga    72960
gttgtggaac tcagcgcgga cccggggcca ccgcgacccc cgggaccctg ccgcgcggc    73020
gcatccccgc tgccgggaca cgggtaagcg tccccaaact gccggacgcg gggcggggcc    73080
ttctccgcca cgccccgata ggccacgccc aaggacaagg atggtcgtgc ccagacggcc    73140
ggggcgggn nnnnnnnnn nnnnnnnnnn nnnnnnnnnn nnnnnnnnnn nnnnnnnnnn    73200
nnnnnnnnnn nnnnnnnnnn nnnnnnnnnn nnnnnnnnnn nnnnnncg gagggggggg    73260
ggcggggcgg gggctgccgc cgcgcgtata ggacggtggt cgcccggcct ggggtccggc    73320
cgggaatgac cccgcctctc cccgcatccc gcagccgccc cgccgcgccc tctgccgcgc    73380
acccgcctgc gcaccgccg ccctcggccg cggccccggc cccgccccg tcgggccagc    73440
ccggcctgat ggcgcagatg gcgaccaccg ccgccggagt ggccgtgggc tcggctgtgg    73500
gccacgtcgt gggcagcgct ctgaccggag ccttcagtgg ggggagctca gagcccgccc    73560
agcctgcggc ccagcaggtg agcaagggct caggggaaac tgaggcccga cacagagccg    73620
cagcaagaag gatcctactg gtcactcggc tgttggcctg gggtcatcac aggcgggctc    73680
tcccaaccca tccctgagg ccaaggtccc tagaaccccg tgggcagaca ccaaccagcc    73740
ctttaaatat ggggaaacca aggtgcttag gggtcagaga tagccctagg tcgcccaacc    73800
ctagtagaag ggagggctgt tggagttcct gagtgcccgc tctcccaccc ccgggaggc    73860
ccctttcctga gccaagggt gactggtagt cagtgacttt gggcctgccg acctgtaccc    73920
cactgggcac cccaccagtc ctgagccaca tttgggctta gtgacggggt cagggatcat    73980
gaggatcaat gtggctgagc caggaaggtg ttagaacctg tcggcctgga gttcatacca    74040
gcactgccct gggcttttct agacccatgt cccgcctcct gccccacctg cccctgttcc    74100
cgcaccccac cagcagcggc aggggcttcg agagggctgt gggctcaccc tatttcaggg    74160
atggagccgc taagacctgg ggcacactgc ccgctaggga cccctgaggc accagggccg    74220
ggggctctgc ggaggggcag ccgccacccc cagctttgga gtcctctccc gggtgccag    74280
cccgagctga tccggctgcc tcccacgctg tgccccaggg cccggagcgc gccgccccgc    74340
```

```
agccctgca gatggggccc tgtgcctatg agatcaggca gttcctggac tgctccacca    74400
cccagagcga cctgaccctg tgtgagggct tcagcgaggc cctgaagcag tgcaagtaca    74460
accacggtga gcggctgctg cccgactggc gccagggtgg aagggcggt ccacggctcc     74520 cactccttcg gggtgctccc gctattccca ggtgctcctg cacttcccat gtgctcccga    74580
ttctccctgg tgctccctct cctcctggct gctcctttgc ctcccaggtg ctcccacttc    74640
tccctggtgc tcctgctcct ccggcggct cctgtacctt cggcctgacc tcctccctct     74700
acaggtctga gctccctgcc ctaagagacc agagcagatt gggtggccag ccctgcaccc    74760
acctgcaccc cctcccacc gacagccgga ccatgacgtc agattgtacc caccgagctg     74820
ggacccagag tgaggagggg gtccctcacc ccacagatga cctgagatga aaacgtgcaa    74880
ttaaaagcct ttattttagc cgaacctgct gtgtctcctc ttgttggact gtctgcgggg    74940
ggcggggggg agggagatgg aagtcccact gcggggtggg gtgccacccc ttcagctgct    75000 gcccctgtg gggagggtga ccttgtcatc ctgcgtaatc cgacgggcag cgcagaccgg     75060
atggtgaggc actaactgct gacctcaagc ctcaagggcg tccgactccg gccagctgga    75120
gaccctggag gagcgtgccg cctccttctc gtctctgggg gccctcggt ggcctcacgc     75180 tctgtcggtc accttgcccc tcttgctgat gcaatttccc cgtaattgca gattcagcag    75240
gaggaatgct tcgggccttt gcacctgacc gcatgagcag aggtcacggc cagccccctt    75300
ggatctcagt ccagctcggc cgcttggccg tgacgttcca ggtcacaggg cctgccggca    75360
cagaggagca ggcccttcag tgccgtcgag cactcggagc tgctgcctcc gctgagttca    75420
ctcagtgtct acgcacagag cgcccactgt gtaccaggcc ctattccacg ttccccagtc    75480
accgagcccc cagggctggt ggggacctgc cctcgggtac actgtgtccc gtcacgtggc    75540
tttacgtgtg tctctgaggg aggctggcat tgcggtccac ctctcagcac aaacatctgt    75600
cccctgggaa gggggtccca tttctgggtg cgagcagccc cctgggtcc gtgtctcctc     75660 cttacctggc tcaaggcccc ggctcctggg tcctggacag cagggagccc acccctcggg    75720
gctgtggagg gggaccttgc ttctggaggc cacgccgagg gcccaggcgc cgcctccggc    75780
cgtcgccctg agggagcagg cccgacgcca gcgcggctcc tctgtgaggc ccgggaaacc    75840
ctgcctgagg gtgcgggtgg gcaggtgccc ctgccccag gctctcctgt gtgagtgaca     75900
ctcaccagcc agctctggat gccacccatc cgggttctcc aggaggcact catagcgggt    75960
ggggtcccct ccctcccccc tctgtggagg gagggagtct gatcactggg aggctggtgg    76020
tccgtacccg ccccccgac tctggacgtg tttactaccc ccgcctgggc tcaggacagg     76080
gcattggatg gaaggacag ggctgggtcc tggccaggct gggggctctg cagggcatgg     76140
gtgcccctgt ctcttcttat attccaacgt cactgcaggg gggcgcaaat cttggacccc    76200
acttactgat gatctgcatc aggacatagg tcccccctcc tgcagcgggg ggctggccac    76260
ggagggcgct ggggaaggcc cctcctccag cccctcggcg aggctcacca ggtgcccatc    76320
ctcagccagc agggcgacgc tcgctgggag ggcgagagg gaggcagggc agggctggta     76380 cgaccccgc tggggcgggg gggccctcag ccggtcctcc agcacccttg ctgccccccc     76440
tcaccgtcag ggggcacctg gccgctctgc ctcaggtggg cggtgagggt cccaaggcca    76500
caccaggtgt tcaccagctc ccagcagctg gctgtgggag aggggcagag gtgggcgcat    76560
ggcacccgcc ttccccccag accaggatgc tctgccttcc tccgcccat ctccccagac     76620 atctgaagga ctcttgcctc caccatgcag ccccgcctcc accagaagct caggttcccc    76680 gcccccctc cccgaagctg caggaccct gaccagcgaa gagatgggac agttggaaca     76740
```

```
cacgctcccc cagcagcggc acagcagctg tgtggcccag aagagcccgc ctgtttccct    76800
caagcaactc cccatggatg tcatcccatg dacacccct tccccacacc gcctcctcgt    76860
tctccccctc caaggcagag ggaacgcacc cccacctgtc tgctaggaca ggggacccca    76920
cttacctccg aacatcacct tgataaacat ggccgtggtg gggacagatc cctccgaccc    76980
ccaacttccg acctggggaa ggagctgggg tggagctcga ctgcagggtg gggccctgtg    77040
ggaggtgtac gggtggagag ggtgatgggt ggtgggctc aagcgagct ccttgctcag    77100 tccaggcggt ccctgcagct agtccaggat cctcagcctt ctcccctca ctggatcagg    77160 gaagactgag gttccctccc ctgccccccc acccagcttc caagctggtc tctgtggcag    77220
tgggagctgc caagaggtct gagcggccag tatccgggta acggggtttg tggagggtcc    77280
gggcattccc ggtgcagggc tctagtgggg gctggagcct cgggcccaga gctgtccaga    77340
gaccagtgcc ctcccaccgc cgccgcccgc aaggagagac agagctccca ggcggggagt    77400
cggaggttcc tggaggggga gcatcctcaa ctctgcaggc ccccttccca ggcgcactcc    77460
cggcctcccc gtcttctgtc ccctgctctt gttgaagtat gattggcata cagttcacag    77520
ccactcttcg gagtgttctc cacactaagg atacagaaca tgtccctcgt cccccaaac     77580 tcccagccag gctgtcacga agagggaggc ggccgacggg gcagggcctt gcactcctgc    77640
gtgtggggtc cacaggggtc gtccccgtgt cggtggcccc ttcctctcac gccaggaggg    77700
tccccttgcc tggaggtgcc gtggatccgc tcgctgcctg ctctttgggt tgtttcccgc    77760
atggggtgat gatgaagagg ccagtacaga cactcgccag caggtctctg ggtgaacagg    77820
catttatttc tctttcctga gggcagatcc tgggagtggg gtgccggacc gtccggggag    77880
agtatgcttc tgtttctaag aagctgccgt gttctccagt gtgctgcacc atgtcacggc    77940
ccctctgtgc gtctggactc aggagacctc cttctcagcg gccctccccc ccaggtggtc    78000
aggccatctg tgcccttctg ggggcagagc tcagcgccgg aggcgggagg aggcccagat    78060
cccagcgcag cccaccagcg ttgctctgct tccctcggca ttcatagctg gagaaagggc    78120
aaggagcacc ggctgaagcc ccacctggag gacgcacttc gatggcagca ggtgctcaga    78180
ggtggccccg ggcagcattc cccagacgca caggccagtg cttcttccc aggacaccac    78240 tgtgtctggg gacccgagtc ctgcagcacg gtcgggagcg gctgtgccca gattccggcc    78300
tgcacccttg gctccagcca ccaccctgt ttgtcaaggg gttttttgtct ttcgagccgc    78360 cgaggaggga gtcttttgtc tgcagtgtca cagaagtgcc ataaagaggg gcccacagtg    78420 ggagcttat aacattggtg cggagggctg taacaggtca gggaggcact tgagggagcc    78480
ttctagggcg atggagatgt tctaaaattt ggtctgggta caggctacag agatgtgtgg    78540
gtgtgtgtgt gtgtgtgtgt aaaaccctcg agccacacgt gtgaggtctg tgcatgtgac    78600
cgtacacagg agacctcggt ggaaagcagc cacctgctct gactgcacct gtggatttcc    78660
agctcctgcc ctcaggcggc cctgcgggcc ccactgctg acgggagac ggcaccgccc    78720 tcccccgctg tcagggtggg ggggctgacg atttgcatgt cgtgtcaggg tccagcggcc    78780
tcccttgcgt ggaggtcccg aagcacctgg agcgccgccc gcagaacagc ggactcctgc    78840
ctgcctccct gcctctggcc atggcctgcc cgcctctggc cctctttctg ctcggggccc    78900
tcctggcagg tgagccctcc caaggcctgg ctcacctagg ggtgtgtaag acagcacggg    78960
gctctagaag taaatcgcgg ggaagtaaat cgtagtgggc agggggatg gtttccgaag    79020 gggccctgag ggggacagga gacctggcct cagtttcccc actggtgagt gaccagatag    79080
```

```
ccagggtacc tttggactct gactctgggg ggctctcaga gactggtctc ctactcagtt    79140
tttcagaggg gaagctggtg tggccttgtc actgccctgc agggcctcag ggacaagcta    79200
tccctgagga ggtctccagc agtcagtggc cggaggctga gccgatggat atagtaacag    79260
cccaggcggc tcttgggggg tggtcagcct gtagccaggt tttggacgag ccgaagtgac    79320
ctaagtgatg ggggtctgca gagcaaggga tgagggtggg cagcaggagg acccagagcc    79380
caccagccca ccctctgaat tctggaccct tagctgcatg tggctccttg ggaagacggg    79440
gcttaagggt tgcccgctct gtggcccaca cagtgctgat tccacagcac tggctgtgag    79500
cttttgggag cagattctcc cggggagtct gacccaggct ttgtggggca ggggctggag    79560
ggaaggggcc caggccagac ctgagtgtgt gtctctcagc ctcccagcca gccctgacca    79620
agccagaagc actgctggtc ttcccaggac aagtggccca actgtcctgc acgatcagcc    79680
cccattacgc catcgtcggg gacctcggcg tgtcctggta tcagcagcga gcaggcagcg    79740 cccccccgcct gctcctctac taccgctcag aggagcacca acaccgggcc ccggcattc    79800 cggaccgctt ctctgcagct gcggatgcag cccacaacac ctgcatcctg accatcagcc    79860
ccgtgcagcc cgaagatgac gccgattatt actgctttgt gggtgactta ttctaggggt    79920
gtgggatgag tgtcttccgt ctgcctgcca cttctactcc tgaccttggg accctctctc    79980
tgagcctcag ttttcctcct ctgtgaaatg ggttaataac actcaccatg tcaacaataa    80040
ctgctctgag ggttatgaga tccctgtggc tcggggtgtg ggggtaggga tggtcctggg    80100
gattactgca gaagaggaag cacctgagac ccttggcgtg gggcccagcc tccccaccag    80160
cccccagggg cccagactgg tggctcttgc cttcctgtga cggaggagc tggagtgaga    80220 gaaaaaggaa ccagcctttg ctggtcccgg ctctgcatgg ctggttgggt tccaacactc    80280
aacgagggga ctggaccggg tcttcgggag cccctgccta ctcctgggtg gggcaagggg    80340
gcaggtgtga gtgtgtgtgt ggggtgcaga cactcagagg cacctgaagg caggtgggca    80400
gagggcaggg gaggcatggg cagcagccct cctggggtag agaggcaggc ttgccaccag    80460
aagcagaact tagccctggg aggggggtgg ggggggttgaa gaacacagct ctcttctctc    80520
ccggttcctc taagaggcgc cacatgaaca gggggactac ccatcagatg nnnnnnnnn    80580 nnnnnnnnnn nnnnnnnnnn nnnnnnnnnn nnnnnnnnnn nnnnnnnnnn nnnnnnnnnn    80640
nnnnnnnnnn nnnnnnnnnn nnnnnnnnnn agagggtggg tgggtggaat ttaatatagt    80700
ggtgcgcgtg gagcgtgggc ggcgcatttta aggcggtcat ctaaaatagt ggataggggg    80760
tggtgtgaca ataacgggtg gtggatgtgg tttacggggg gtgcaatagt tctgagtttg    80820
ttagtgtctt cttgatgggg ttgcggcgtg tggacctacg ccttgagtat gtgggggggg    80880
aaaagcagtg agggtagtag ggatgggaaa tattggtgga ggttctttgt tggtgtattt    80940
tttggtatta tgttgggtgg tggagtggtg ggttgggtgt aatttcgctt gcgttatgtg    81000
ttttttttct tttcgtgtc gtgggttggg ttggttggtg ctttgtggtg gtggtgggtt    81060
gtggtataaa aaaaaatgtg tggttgtgct cagcttagcc ctataacggt cggctttgtt    81120
tcttgtttgt tctgtgggcg tgagcggatg gctcgggcct ccgtgctccg cggcgcggcc    81180
tcgcgcgccc tcctgctccc gctgctgctg ctgctgctgc tcccgccgcc gccgctgctg    81240
ctggcccggg cccgcggcc gccggtgagt gccgccgtc ctccagcccc cccgcccgc    81300 cccgccctcc acgccgaggg gcgccggctc gcagagctgg atccaagggg gtgcccggga    81360
gtggcccggc gcggccgtt acccccgaaac gctgtctggg tgcccggggg gtgtggtgga    81420
tagtgagctt cccgtccctg gaagtatgca agtgaagccg gcgccgggat cgctcgggct    81480
```

```
ggctggtgag cgggcgggac tcggtcgggc gctagacgca cgccgccagc ccccagctc    81540 ccagacctgc ccactccgcg cccgcccggc cgcgatcccg ggtgtgtgtg tgtgttgcag    81600
gggagggaca gcgggagtgg ctacagggct cccgactcac cgcagggaca agacccgcg    81660 ggtccccagc tggcgtcagc cgccaggtgt gtggcctcgg tgagcacacc tccaggcggg    81720
agggttgagg gaagcgctgt ggggagggca tgcgggtct gagcctggaa gagacggatg    81780
ctaccgcctg ggacctgtga gtggcgggat tgggaggcta tggaatcagg aggcagccta    81840
agcgtgagag ctccggtgtg gcctggcggg ggtggtaggg gggggacgcc cctgtgtgtg    81900
ccagcctgcg tgtgccctaa aggctgcgcc ctcccccact gctggggctt cgggggacca    81960
gtcacagcct aggctactgc aggcgcacag ctccccggga gcccggccca cgcgggtgtg    82020
ccgctgagcc tccagcctgt cggggcaggg gtggggggca gggatggggt cgttagcggg    82080
gttgggggca gacgcccagg cagactctct gggcacagct ccggtgacaa gggaggtctg    82140
gcaagcctgg gcccctctg tccagccacg ccagctctgc cctggccagt cttgccccct    82200
ggcagtgctg gggatggaag ggggagcggg tacctcagtc tgggggccct gcctcctccc    82260
cagccccgcc cggccccta ggcctagggg cagagtctag gggtcaccct ggggagctgc    82320
tgaatccgcg ggtttaggaa ccggagggac ctgggctttt gaaccacgtg ccctaggtg    82380 agccctccgg cgcctcggta gccctcaccc ccagccttgt ccaggtgggc gggtgggagg    82440
cgacagtgcc cactgctggg ctgaacagcg tctgcaggga ggccaggaga gctgggcaca    82500
cggacacgtt ccatcacctg gagctgccac tgtgccactt gtgcggggtc aggcggggtc    82560
tgagccgggc tgtcatctgt cacgccacag atatgcaggg ggcactcggg gtcgcctcgg    82620
acatgcttat ccctggacgg ctgttggcag ggccgggaag gctctgtaaa tatttatcca    82680
tcccagctca cagctttcag ggttgatgaa agccccgccg cccgcccact gtggggggacc    82740 ccgccttccc ttctggagcc agcggggtga ggggtgggg gagatggacc tgcctgccca    82800
ggagcaggcg gtgtgactct ggcaggtcac ttgacctctc tgagcctcag ggagggcccg    82860
ggatggtgtg cggatgctct ctgccttcct cccagcctga ccagtgtcct cccctcgggg    82920
tcgcctcctg cccaccgcag aggggtggc tatgggacc tgggccgatg gcaggcaggc    82980
cggagagggc atgcccggct cagccgtgcc cagcacttcc cagtccaggg gcccccgcca    83040
ctcccagccg ctggctgcct cccatttcc cgattgcagg ttggccccga ggctgaccgg    83100
agcctctggc tcagctggga gactgaattc cccaagcaat tcctcaagga tgtgtgaggc    83160 tgtggtgtg tgcctatccg ggagaggtgg ggtgagcgga ctgggcacct ccgcccaggg    83220
caggcccagg gagacgctgg ctgacgagca ggcaggcctg caaggaggac gagcagccat    83280
ctcaggaatg tgggttttgg agacaagcca cagctgggg ggtgggggg ccatgggtgg    83340 ggaggcctga tccccaggtc taggtccagc tctgggctcc ctcgccgtgt gaccctgggc    83400
caagacctgc acctctctgg gccccgtctc ttccctggg aggtggggcg atgcctgctc    83460
cccaatcccc cagggctgtg gatgaggcag acgaggtgtg tgctcatccc cacctcactg    83520
ccttccagca gccccgggcg gggggggtgg tggggactgg cgcacccagg tgaggatcag    83580
gccttggagc taggagggc ccccagccc caggccagaa aggacacggg gagacagaat    83640
gcaggagggc ggcagagcag gggccagcgg tggggaaact gaggccaaga gcctgtggac    83700
gatgtgctcc aggaaaggac ctcgctgcct ggggcctgga tcctagagcc tccaggagcc    83760
gtgaccatga cgtgggcagg gaaccggagg ccccggcttg caggtggacc cggcgcgagt    83820
```

```
cactcttcct ctctggccct gagagcttcc ttccagctgc cgctcctgtg ttctaatgtc    83880
aagtctggag gcctgggggg caggtggggg ctgactgcca ggtggggggag ggcaggaatt   83940 tggcagagca gcgtcccaga gtgggagaag ccagcccatg gaggggactc tctccatgcc   84000
tgctgcccca aagggcgtta tagagagagg tcggttaccc cttcgccatg gccccgttcc   84060
cattgaacag atgggaaagt ggaggctgag agaaggctgt gacttgccca gggtctccgt   84120
ggcatggaac tgggcctgct gagtctcagg ccggggatct cgctgctgca ctgagcacgc   84180
caggatgcag gggtctgggc ctggacctag cgcctcgtgg gggcaagaga ggaaggcacg   84240
ctgggcctgc ctgtcaccct ccacccccacc gtggcttgtt gctcaggcct tcctgggggc   84300
agaggagagg ggagatttca ctcgctggca ggctaggccc tgggctctct ggggctccgg   84360
gggaacaatg cagccctggt ctttctgagg agggtccttg gacctccacc agggttgagg   84420
aaaggatttc tgttcctcct ggaggtcacg gagccgacat ggggaggagc aggggcaggc   84480
ccggggccca catcctcagt gtgagacctg gacgtgtgtc ctcccacctg acgctggggg   84540 tgggggggtgg gggccggggg ggatccagtg aaccctgccc ccaaattgtc tggaagacag   84600
cgggtacttg gtcatttccc cttcctcctc ttcgtttgcc ctggtgggga cagtccctcc   84660
cctggggaag gggacccca gcctgaagaa cagagcagag ctgggtcag gggtgtgctg    84720 ggagcgcaga gagcctcctg ctctgcctgc tggtcattcc tggtggctct ggagtcggca   84780
gctggtgggg agcggctggg gtgctcgtct gagctctggg gtgcccaggg cctgggagag   84840
ttgccagagg ctgaggccga gggtgggggcc ctggcggccc ggctcctgcc ccaaatatgg   84900
ctcgggaagg ccacagcggc actgagcaga caggccgggc cagacgggcg ctgaggctcc   84960
cggcctctcc cccagctccg ctgtgaccct cacctgcggc ccggggtgcc agggcccccg   85020
cttggttctg ccgtgtcttt gcaggctgat cccacgggct ctccctgcct ctctgagctt   85080
ccgccttttc caggcagggg aaccgcgacc tccaggctgg gacgcgggga gggtgtatgc   85140
gccaggtcag aatcacccct ccaccggag agcgtggtcc aggggccctg gcagggtggg    85200
gaccgagcat ctgggaactg ccagccaccc ccacccatgc agaggggaca tacagaccac   85260
acggaggctg tgcctccgct gcagcaactg gagaacaccc agccgcggcc aaacataaat   85320
aactaaataa taaaagtttt aaagatcgtt acttaaaaaa acaagtgtgc cccagtgatc   85380
ggaccccagt tcccggtgcc ctgagtggtg ccggccctgt gctgagcatg gcctggttgg   85440
ttcaccccca gatccacact aaagggtggg atcaccccta ctagtcaggt gagcagatgc   85500 aggggggggag ggcggcagcc cctccatgct ggtgggtggc cgtggtgggt gtcctgggca   85560
ggagccagct cacggagctg gagaggacag acctgggggg ttgggggcgc ccaggaagaa   85620 acgcagggg agaggtgtct gccggggtg ggggtccctt cgaggctgtg cgtgaagagg    85680
gcaggcgggc ctgcagcccc acctacccgt ccccggccca aacggcggga gtaagtgacc   85740
ctgggcacct ggggccctcc aggaggggggc gggaggcctt gggatcagca tctgacgcc    85800 agtcagcccg cgcagagcg ccatgctccc cgacggcctc cgctggagtg aggctgcgct    85860
gacacccaca ccgctgaccc gggcctctct cccgctcagg atgcccccg ccgccacccc    85920 gtgagcagag ggcacagcc ctggcccgac gcccctcccg acagtgacgc ccccgccctg    85980
gccacccagg aggccctccc gcttgctggc cgccccagac ctccccgctg cggcgtgcct   86040
gacctgcccg atgggccgag tgcccgcaac cgacagaagc ggttcgtgct gtcgggcggg   86100
cgctgggaga agacgacct cacctacagg tagggccagt ggccacgagc tggccttttga   86160 tctccacctg ctgtctgaga cacgctggag ctgggggggag ggcagatccc tatggccaac   86220
```

```
aggctggagt gtcccccaac tcccgtgccc actgctcaac accccaaacc cacacttaga  86280
tgcactccca tgccctccct tgggagcacg gtctccacac ccacctggcc accccacaca  86340
cccgtggggc acggccgtta gtcacccacg caacctctgc gggcaccgtg ctgcgggcca  86400
ggccctggga ctctcagtga gggaggcaga cacggcccct cctccggggg agcgaggtgc  86460
tccccacgcc cggttcagct ctagcaccgc actcgggacc ctcacaggga gggacccact  86520
ggggcaggcc aggtgacggc tcgggtgacc tcggcccctg gcgctgagac tacacttcct  86580
gcagtgggcg gcgaagatgg gtgtggtgtc ccacgtcgtt gcagcgggga ctcctggggc  86640
ctcggaagtg tcctgggcgg ggagcctggg gagcaggaag ggcaggtctt ggggtccaag  86700
gcctccccac ggtcaggtct ggagggggc ctcgggctc ttgggtcctt tccgccagt  86760 gcagaccctc gcggccacct aagggcacac agaccacaca aagctgtgcc catgcagtgt  86820
ggggagtggt gcgcaccctc agagcacact gggcccacat cacgcacgcc tgcccctca  86880 ctgtgcatcc ggggaaactc ctggccccga cagccagcgg ggctgacgct accccgtgag  86940
ccagacccag gccccctca ccgccctgt cctccccagg atcctccggt tccatggca  87000 gctgctgcgg gaacaggtgc ggcagacggt ggcggaggcc ctccaggtgt ggagcgatgt  87060
cacaccgctc accttcaccg aggtgcacga gggccgcgcc gacatcgtga tcgacttcac  87120
caggtgagcg ggggcctgag ggcaccccca ccctgggaag gaaacccatc tgccggcagc  87180
cactgactct gcccctaccc accccccgac aggtactggc acgggacaa tctgcccttt  87240 gatggacctg ggggcatcct ggcccacgcc ttcttcccca agaccaccg agaagggat  87300 gtccacttcg actatgatga gacctggacc atcggggaca accagggtag gggctggggc  87360
cccactttcc ggaggggccc tgtcgaggcc ccggagccgg gccgggctc tgcgtccgct  87420 ggggagctcg cgcattgccg ggctgtctcc ctcttccagg cacggatctc ctgcaggtgg  87480
cggcacacga gtttggccac gtgctcgggc tgcagcacac gacagctgcg aaggccctga  87540 tgtcccccctt ctacaccttc cgctacccac tgagcctcag cccagacgac cgcaggggca  87600
tccagcagct gtacgccgg cctcagctag ctcccacgtc caggcctccg gacctgggcc  87660
ctggcaccgg ggcggacacc aacgagatcg cgccgctgga ggtgaggccc tgctccccct  87720
gcccacggct gcctctgcag ctccaacatg ggctcctcct aacccttcgc tctcaccca  87780 gccggacgcc ccaccggatg cctgccaggt ctcctttgac gcagccgcca ccatccgtgg  87840
cgagctcttc ttcttcaagg caggctttgt gtggcggctg cgcggggcc ggctgcagcc  87900 tggctaccct gcgctggcct ctcgccactg gcaggggctg cccagccctg tggatgcagc  87960
cttcgaggac gcccagggcc acatctggtt cttccaaggt gagtgggagc cgggtcacac  88020
tcaggagact gcagggagcc aggaacgtca tggccaaggg tagggacaga cagacgtgat  88080
gagcagatgg acagacggag ggggtcccgg agttttgggg cccaggaaga gcgtgactca  88140
ctcctctggg cacagctggg aggcttcctg gaggaggcg ttctcgaagc gggagtagga  88200
taaaaggtat tgcaccccat gaagcacgtg tgatccttgc ccctagagac aaggctctgg  88260
ggctcagagg tggtgaagtg acccacatga gggcacagct tggagaatgt cgggagggat  88320
gtgagctcag tgtgccagag atgggagcct ggagcatgcc aaggggcagg gcctgctgcc  88380
tgagagctgg cactggggtg ggcagccaag tgcaggatg agcgggcgc ccaggtggcc  88440 tctttgctgc tcagaacgac ctttcccatg tatacctccc agcgccgctg gcattgccca  88500
gtgtccttct tggggggcagg agtaccaagc aggcattatt actggccttt tgtgttttat  88560
```

```
ggacaacgaa actgaggctg ggaaggtccg aggtggtgtt ggtggcggaa ggtggccgct    88620
gggcagccct gttgcagcac acaccccca cccaccgttt ctccaacagg agctcagtac    88680
tgggtgtatg acggtgagaa gccggtcctg ggccccgcgc ccctctccga gctgggcctg    88740
caggggtccc cgatccatgc cgccctggtg tggggctccg agaagaacaa gatctacttc    88800
ttccgaagtg gggactactg gcgcttccag cccagcgccc gccgcgtgga cagccctgtg    88860
ccgcgccggg tcaccgactg gcgaggggtg ccctcggaga tcgacgcggc cttccaggat    88920
gctgaaggtg tgcaggggggc aggccctctg cccagccccc tcccattccg ccctcctcc    88980 tgccaaggac tgtgctaact ccctgtgctc catctttgtg gctgtgggca ccaggcacgg    89040
catggagact gaggcccgtg cccaggtccc ttggatgtgg ctagtgaaat cagtccgagg    89100
ctccagcctc tgtcaggctg ggtggcagct cagaccagac cctgagggca ggcagaaggg    89160
ctcgcccaag ggtagaaaga ccctgggggct tccttggtgg ctcagacagt aaagcgtctg    89220
cctgcaatgc gggagacctg gattcgatcc ctgggtcagg gagatcccct ggagaaggaa    89280
atggcaatgc cctccggtac tgttgcctgg aaaattccat ggacagagca gcctggaagc    89340
tccatggggt cgcgaagagt cagacacaat ggagcgactt cactgtctta agggccacct    89400
gaggtcctca ggtttcaagg aacccagcag tggccaaggc ctgtgcccat ccctctgtcc    89460
acttaccagg ccctgaccct cctgtctcct caggcttcgc ctacttcctg cgtggccgcc    89520
tctactggaa gtttgacccc gtgaaggtga agcccggga gggcttcccc cggctcgtgg    89580
gccccgactt cttcagctgt actgaggctg ccaacacttt ccgctgatca ccgcctggct    89640
gtcctcaggc cctgacacct ccacacagga gaccgtggcc gtgcctgtgg ctgtaggtac    89700
caggcagggc acggagtcgc ggctgctatg ggggcaaggc agggcgctgc caccaggact    89760
gcagggaggg ccacgcgggt cgtggccact gccagcgact gtctgagact gggcaggggg    89820
gctctggcat ggaggctgag ggtggtcttg ggctggctcc acgcagcctg tgcaggtcac    89880
atggaaccca gctgcccatg gtctccatcc acacccctca gggtcgggcc tcagcagggc    89940
tgggggagct ggagccctca ccgtcctcgc tgtggggtcc catagggggc tggcacgtgg    90000
gtgtcagggt cctgcgcctc ctgcctccca caggggttgg ctctgcgtag gtgctgcctt    90060
ccagtttggt ggttctggag acctattccc caagatcctg gccaaaaggc caggtcagct    90120
ggtgggggtg cttcctgcca gagaccctgc accctggggg ccccagcata cctcagtcct    90180
atcacgggtc agatcctcca aagccatgta aatgtgtaca gtgtgtataa agctgttttg    90240 ttttcattt tttaaccgac tgtcattaaa cacggtcgtt ttctacctgc ctgctggggt    90300
gtctctgtga gtgcaaggcc agtatagggt ggaactggac cagggagttg ggaggcttgg    90360
ctggggaccc gctcagtccc ctggtcctca gggctgggtg ttggttcagg gctccccctg    90420
ctccatctca tcctgcttga atgcctacag tggcttcaca gtctgctccc catctcccca    90480
gcggcctctc agaccgtcgt ccaccaagtg ctgctcacgt tttccgatcc agccactgtc    90540
aggacacaga accgaactca aggttactgt ggctgactcc tcactctctg gggtctactt    90600
gcctgccacc ctcagagagc caaggatccg cctgtgatgc aggagtgagt gaagtcgctc    90660
agccgagtcc gactctttgc aaccccatag gactgtagcc taccaggctc ctctgtctat    90720 gggattttc aggcaagagt gctggagtgg gttgccattt ccttctccag gggatcttcc    90780
caaccctggt ctcccgcata gcaggcagac tctttactgt ctgagccacc aggcaatgca    90840
ggagacctag gttcagtctc tgggtgggga agatcccctg gagaagggaa tgacaacctg    90900
cttcagtatt cttgattggg gaatcccatg gacaaaggag cctggaggcc tacagcccat    90960
```

-continued

```
agggtgcaaa gagacacgac tgagcaagtc acacacacag agccctacgt ggatgctcat   91020
agcggcacct catagctgcc atgtatcagg tgttggcatg ggcagccatc agcagggggc   91080
catttctgac ccactgcctt gttccaccgg atacacgggt gccttcctgt gtgtcgggcc   91140
cactcggctg tcagcgccca agggcagggc tgtcggagg cacagggcac agagttaagg    91200
aggggatggg gacgttagct cctccccagc tctcagcgga tgcagcaggc aaaacaaacg   91260
ctaggaatcc tgccaaaccc ggtagtctct gcccatgctc gccccatccc cagagccaca   91320
agaacgggag ctgggggtg gcccggagct gggatactgg tccctgggcc cgcccatgtg    91380
ctcggccgca cagcgtcctc cgggcgggga aactgaggca cgggcgcctc cggcttcctc   91440
cccgccttcc gggcctcgcc tcgttcctcc tcaccagggc agtattccag ccccggctgt   91500
gagacggaga agggcgccgt tcgagtcagg gccgcggctg ttatttctgc cggtgagcgg   91560
ccttccctgg tacctccact tgagaggcgg ccgggaaggc cgagaacgg gccgaggctc     91620 cttaagggg cccgtggggg cgcgcccggc ccttttgtcc gggtggcggc ggcggcgacg     91680
cgcgcgtcag cgtcaacgcc cgcgcctgcg cactgagggc ggcctgcttg tcgtctgcgg   91740
cggcggcggc ggcggcggcg gaggaggcga accccatctg gcttggcaag agactgagnn   91800
nnnnnnnnnn nnnnnnnnnn nnnnnnnnnn nnnnnnnnnn nnnnnnnnnn nnnnnnnnnn   91860
nnnnnnnnnn nnnnnnnnnn nnnnnnnnnn nnnnnnnct gcaggtgccg gcggtgacgc    91920
ggacgtacac cgcggcctgc gtcctcacca ccgccgccgt ggtaaccgcc cccggggtt    91980 gccaaggtta cgattggacc ctccccgccc cgaccctgct cccctagggt gggtgggtcg   92040
gggggcagtt tctaagatct cctggttccg cagcagctgg aactcctcag tcccttccag   92100
ctctacttca acccgcacct cgtgttccgg aagttccagg tgaggccgcc ccgcccttg    92160 cacttgctgg cccaaccccct cccgcccagc gctggcctga ccgccccca ccccgcccac   92220 cccacgcagg tttggaggct catcaccaac ttcctcttct tcgggcccct gggattcagc   92280
ttcttcttca acatgctctt cgtgtatcct gcgccgtggt ggaagcggga ggagggcggg   92340 gcggggacc gggcgggagg cagcgggccc cgggaagctg agaccctcca aggggcacgc    92400
ttcctatacc aaagccgcag gttccgctac tgccgcatgc tggaggaggg ctccttccgc    92460
ggccgcacgg ccgacttcgt cttcatgttt ctcttcgggg gcgtcctgat gactgtatcc   92520
ttcccgggct cggggaccta tgggtccggg cctctgctgg ccctgaggcc ctgcttgagc   92580
gcatgccaca gagggagagt tgcgaccccg agctgagggt gttttgagc gtacatcacg    92640 tgctcagctg caggtgcccc tgtcgaactc cagggctaca cccaaaatac cacagggcag   92700
ggtgcccagg ggctgagtcc tgaatgcagg tagccaggag gatctagggc tgggcccggg   92760
ggctggggtg aagtggagag gcaggccga tcagggggcc cctggaggcc accgtttggt   92820
cttagagtgg gaagcgaaac caacctgctt gagggtttca ggggtttagg aagtcagagg   92880
ggccctgggc agggcacaag accttgactc tggcccagct actggggctc ctgggtagcc   92940
tcttcttcct gggccaggcc ctcacggcca tgctggtgta cgtgtggagc cgccgcagcc   93000
ctggggtgag ggtcaacttc tttggcctcc tcaccttcca ggcgccgttc ctgccctggg   93060
cgctcatggg cttttcaatg ctgctgggca actccatcct ggtggacctg ctgggtgagc   93120
ctgctgtcca gggagcctgc ccaagctgg gtgtgctggg ccagagccct ggtcctctcc    93180 ccgccccac ccctcttccc cactcctggc gccccatcc ttccagcccc tccaacaagt    93240
cagcctatag gttttactta ttcgagcctg acccatttgc tgacgcttgt gtggggcccg   93300
```

-continued

```
acccggtagg gatgggtggc tcagggtgcc tgctcacagc tccacttctt ctgacgtcct    93360
caggcctgac ctcctcccag gttctgccta ctctgggcca agcctggccc cacgctgggc    93420
tggctggccg tgcagggcat cagacccca tgctttgggg gcttcagggc tgtggagggt    93480
ggcctcggca ttggcgcctc tcccacaggg attgcggtgg gccacgtcta ctacttcctg    93540
gaggacgtct tccccaacca gcctggaggc aagaggctgc tgctgacccc cagcttcctg    93600
tgagtgctga cagccttccc cacccccttc cccagatggc tctctacccc atgagggggg    93660
gggaccctgc cagctgccgc tcagcgtggg ctcctcccca caggaaactg ctactggatg    93720
ccccagagga ggaccccaat tacctgcccc tccccgagga gcagccagga ccctgcagc    93780 agtgaggacg acctcaccca gagccgggtc cccaccccc acccctggcc tgcaacgcag    93840
ctccctgtcc tggaggccgg gcctgggccc agggccccg ccctgaataa acaagtgacc    93900
tgcagcctgt tcgccacagc actggctctc ctgccgcggc cagcctctcc acgcggggca    93960
ggtgctgctg gccgagagcc agggccacca agcctgacgt gctctccgac ccagaacatt    94020
ggcacagctg gaggcccaga gagggtccag aacctgccca ctcgccagca gaactctgag    94080
cacagagggc agccctgctg gggttctcat ccctgccctg cctgtgccgt aattcagctt    94140
ccactgatgg ggctcacatc tcaggggcgg ggctgggact gggatgctgg gttgtgctga    94200
gctttggccg tgggggccct cctgtcccga actagcaacc cccaagggga cctctgcttc    94260
atttcccagc caggccactg aaggacgggc caggtgcaga agaggccag gccctttctg    94320 tgactccgaa gcctcaagtg tcagtgtttg cagagtccag tggctgaggc agaggcctct    94380
gggaagctct gccctgccg tttgcagctg aggccggcag gagcctcacc tggtccccag    94440
ctcacgggca ttggaggacc agtccgcacg gtggtttact cctgggtcgg caccagccgc    94500
cgccggctgt ccctttcaca gaggataaaa gtactcgctc tggagttgga ctttaatgtt    94560
gtcatgaaac ctctggccca gcagcgggct ccgcagtggg tggcaggtga aggcccctcc    94620
ccgggcctct ccaggcaggt gccgcctggc cagcagggaa ggcaggcagt gtcatccccc    94680
actggctctg gggctcaggc tacctcctgc tgtggccgga acatctcccc cagtggtgga    94740
gcccagtgtc cgtgaggcca gctgggcctg aaaccttcct ctctgaagcc ccgctgtccc    94800
cttgccctgt atggagggca gaggctggag cgcaagttcc taggatgtgc ttgcgagacc    94860
cccgagccca ggggcgaggc ccatctcagc ccacccccga actggaaacc cttggagctc    94920
tgcccctcgt ggtgtgaggc ccctgctatg cgaccctcag ccctgccagc aacggaaggt    94980
gcagggcccg ggcccacggg cttaacgcaa ctgggcctgg gtcacctgcg gggcctggtc    95040
ccaggaggaa gacccaggtg ccaccctcct gggtgccacg tccaggtcac gtgggaccc    95100 gtccatgtca cagaagatgc agggtcaccc ggtgagctgg cgccgggccc tgccagagca    95160
ccagccgcgg gtggaggtgg gccccagctc tcctgtcagg cacgtggtgc tgggaggtgc    95220
ggccggagca gtgcccacca gctgcagcag gacaggtggg cacaggccca ccagcagtgc    95280
ccgcacggga tgggcccctg caagggccag agaagccacg ctcctggctg ggggctgggc    95340
tgggactgac aggtggccct gccctctgcg ccccactact tcccagccac ccgggactcc    95400
aaggacttgc tgagctgggc aggtgggacg ccgaggggag tcaaactgct cgtggggca    95460 ggaggggcgg tccacagggc tgagccctga gctgaaccct ggccctgctc gtggttgtgg    95520
gggtgggggg gtccagtggc gcccagccc tgctgaggcc cagctgggac gtgcgcgccg    95580
gagggcgagg ggccagccca tgccatgctg tcccccgttc tcagtccat gctaccactt    95640 tgaagaaaca gaacctgttg cctttttatt tagaaagtgt tgcttgccct gcctggggct    95700
```

```
tctatacaaa aaacaaacac agctcaacgt ggcctctcct gaccagagac gggcggtggg    95760
gactggggct cagcagacgg aatgtgtccc cggcggcggg agaccaggag gcccctggcc    95820
cgctcctcag gacggctggg ctgtccccac ctggtcccct ccgagccaga agatggagga    95880
gaggtgggct gatctccaga tgctccctgg gagccaagcg ccacggggtg gtcaccaggc    95940
cggggccgtg ttggccagac gcctcatccg cctgtgggag ggggagggca gcaaccccg    96000 gatctctcag gcaaccgagt gaggaggcag gagcccccag cccctccctc ggccgctctg    96060
ctgcgtgggg ccctgaagtc gtcctctgtc tcgccccct ccccagggag agtgagcctg    96120
ttctgggctg tggtcagacc tgcccgaggg ccagcctcgc ccggggccct gtcctgcctg    96180
gaaggggctg gggcagcacc ttgtgttccg gtcctggtcc cggatcttct tctccatctc    96240
tgcatccgtc agggtctcca gcagcgggca ccactggtca gcgtcgcctg tgttccggat    96300
ggcaatctcc accgtgggca gggggttctc actgtggagg acgagagagg tagacggctc    96360
acagagcagc tgcaggagag gcccctagaa agcagtgtcc accccgctgc gggcagacag    96420
gacatggagc ctggtttctg caccccggctc ccgacacagg gcggccgggc acgctgccaa    96480
catggcatct ccgggtctgc atgtgggag gggtccacag gacagtgctg caggtccagc    96540
cattcccagt ggacttgctg ggaggaggag ggccgtccgc cccgctcagt gtccaggaga    96600
aaggagagca aaggagtcca tccacccagg agtggagtcc cagggcccct gccctgacca    96660
gcctgcaggg ggccctcgg cccacatcac aggggcccag aatccataag ccctgactgc    96720
tccaccccgg ggccctcaa agacgcgcct agactccgtc cgagggccac ctgcacaccc    96780
tctggcgaag tggactcagg gctgggggtc agcctcggtg aggccgcaaa ggctggggac    96840
tcctggccga gctgctgcct ctgccaggag ccagcccag cctgccggcg agcctcagcc    96900
acgccctcac ccaccctgcc cgcggcgcca cgctggcctc cgggtcctct cctctggcct    96960
cctgctgggc cactggtgct cagccccagc agtcggcctg ccaggagccc tgcagagtca    97020
gcccccagag ggaggagggg gcccggggga acagcacagg aacaaacaga cccctggcct    97080
tagttttagc tcctcatctg gaaaatgggg acagtgtcct tgctgcgagg ggtttcagag    97140
gaccactgcc atgcaacacc cagcacacac ccactgcgtg ggggctcggg cccgagccgg    97200
tgcccccgag tcccaggctg gtggctgggc cgccccagcc accctgccga cagctgcttc    97260
ccagccgggc ggtgctgcgg cagtccagaa gccagcactg cagacccaaa tgtcactcct    97320
cacgttgcgg gctcccagct gccttccttg ggggcagcag acacgaaagt caccaagccc    97380
acgccgacgg gagcaaacac gtcttcctct taaacaagtg cgggtcccgg aggccctgtg    97440
tttacctccc tgtggctccg ggaagattgc atcccagggg gttgttctaa accaagggct    97500
gctcgggcca ggcctggaag gaggggcctg gagccaggag cccaccctta cgggcattcg    97560
gcttcctggg tctcaaggcc ggctgggacc ctgcattccc accacccgcc aggtgcaagc    97620
agggaggccg tgtcggagga ggcagagggc ctggagggtc gtcttcgacg tgacctcact    97680
tttacaacct cacaggtgcg gcaggccagc tgggaggcat ggctgtgccc tcctggtaga    97740
tgagaacaag actgcaggga gtgatccccc tgaacttccc caaccaggag gagacaaaac    97800
tcggtgtcgc cctcctgctt aagatcaact gactctggac aaggggccca gcccaccga    97860 tggggaaagg gcagtccttc aacaagcgg tgctggacg ggacccggca ggccatggtt    97920
tctcagctat gacaccagca gcacaagcac cccgagaaaa acagctaagc tgggcactgt    97980
cacacaagtg aactccaaac ccaagaaaac cacaaaaagc ctgcggatct tcagatatgt    98040
```

```
gggaagggac ctgtatctgg aatgtataac gaactcctga aaagtgaaag tgttagtcac   98100
tcagtctgtt cagctctttg caaccccatg gacggtagcc tgccaggctc ctctgcccat   98160
gggattctct aggcaagaat actggagtgg gttgccatgc cttcctccag gggatcttcc   98220
caacccaggg attgaacctg tgtctctctt gcactggcag gcgggttctt taccagtagc   98280
gccacctgag tagaaacact ccaggtgccc tgagtgtcag agcaggaggg actcggccca   98340
ggcctgtgag ggaccctct ccgagtcccc tgctgcacag cagtgagagg tgcgttctga   98400
gtcagcctcc agggatgagg gacttggtgt cgacatcact cccaggacct caggatctgc   98460
tctgggaagc gaggctcccc aggctggccc caggcccgct ggcctcagct cgtgagccgt   98520
gcgtggacag gtgccatgag caggcctccc acgggactcg gggcgcggcc tggaccccgg   98580
ggctgccagt ggtcgcgggg ggcccgtgt ggcggctgtt ccctctcttg ctccgagtcc    98640
taggaacatg gtgggcgctg cctcctgggg tttctggaga agcagctgag atgcaaacag   98700
ccccacgcgc tccctcagct gttccctgtc acgggtggcc ccttggtgac ggcctccatg   98760
cagggacggt gacagctcga gcagccgcgt aaaaccacac ggggacggtg gcagctcgag   98820
cagccgcgta aagcctgaca tccaatttgg aagcctcccg cagtggaaga ggggcccggg   98880
gacggggctg cccggggcga gctccaccgg gtcggggtc acgaggagcc cacccgcgtc    98940
cccgccacca gcacctggga ccagatacc tccccgctct gagggcggcc tgaacgccgc    99000
cccctcccac gggggcgccc accgcctgct cgtggactga caagaggcg gcagtggcct    99060 ccagaccccc tcggggagg gcagacctgt ccgagactga gcacaagtcc agggaatgag   99120
caagggtctc agtaatgtcc ccaccggac gggacgggag gaggcgacag aggccgctga   99180 ggtgcgggc agccctcagt agctggcatc aaggccccag gcagtcccgg ggcatccccg   99240
caggggggcg gggcgaccac cggcccgagc ccaggcagtc ccggggcatc cctgcagcgg   99300 gcggggggcga ccaccggccc gagccctacc tgaaggcgta ggtcttctga tgccagctca   99360
gctgtccccg gatgctgtag gcgatggtgg tgacgaactc cccgcccagc ccagctcgg   99420 agcacagctt cagagcgaac ttctcgggcg agttctcctt ctccgacatg tcccactcga   99480
actggtccac caaggagatg ttccccacgt ggatgttcag ctggcccggg agcacagaca   99540
tgagccagag cggccccctc tggggccagg ccgcaccctc accccccttt ctcccccggaa   99600 catccccgcc tcgttcttgg ccgcgcccct gtgctgctac ttgggggtaag gaaaacaacc   99660 cccatctctc tgaaaagggt taactagcga ggaagatgcg ctggtaactg gaaaactccc   99720
tacaaagaaa gcttggatct gatggcttca ctggtgaatt ccaccaaaca tttcaagcac   99780
taacaccaat ccttatcaaa tcctgccaaa aaactgaaaa ggaaggaaca catcataact   99840
ccctgccttg ataccaaagc cagacaaaga tactacgaga aaggaaaggt gcagaccggc   99900
acttactgtg gacattgatg tgaaacctca gcagacacga gcaaaactac attcaccagc   99960
acgtcagaag aatcacacac cgttataaat gatgggatga tgcacacaacc acattataaa  100020 cggtggggct tactctggtg atgtaaggac ggctcagtaa gaaaaccggt caatgccatg   100080
aaccacttga acagagtgaa ggacaaaaac cacacagtca tcttgataat tggaggaaaa   100140
tcattagaca aacttcaacg tgctttcacg ataaaagcac tcagtaaact aagatcagat   100200
ggaaaccaca tcaacaagat taattcagtc aaaaaattca ctgcaagtat cacccacaat   100260
ggcagaagac tggtaacttt tcctctaaga tcaggaacga gccaaagata cccagtcttg   100320 ccactttgt tcaatatagc gttggaattt ctactcagtg cagtgcagtc gctcagtcgt    100380
gtccgactct tttcgacccc atggatcaca gcacgccagg cctccctgtc catcaccaac   100440
```

```
tcccggagtt cacccaaact catgtgcact gagtcagtga tgccatccag ccatctcatc   100500
ctctgtcgtc cccttctcct cctgcctcca atcccttcca gcagttaggc aagaaaaata   100560
aatcaaaggt atccacctgg aatggaagaa gtaaaactat ctctggtccg agatgttaca   100620
atcttatatg cagagtttaa gatgctaaca aaatactatt agaactaatg aatgaattca   100680
gcaaggtacc aggatacaaa gtcaacgtgc aaaaatcagc cgcatttcta catgctaaca   100740
ctgcacaatc tgaagaagaa aggatgaaca aattacaata acataaaaaa gaataaaatc   100800
cttagaaatt aacttgatca agagatgta caatgaacaa tataaaacat actgaaagaa   100860
attgaagata taaataaatg gaaaaacatc ctatgtccat ggattggaag acttaaaatt   100920
attaagctgt caaggctatg gttttccag tggtcatgta tggatgtgag agttggacta   100980
taaagaaagc tgagcaccga agaagtgatg cttttgaact gtggtgttgg agaagactct   101040
tgagaggtcc ttggactgca aggagatcca accagtccat cctaaaggag atcagtcctg   101100
ggtgttcatt ggaaggactg atgttaaagc tgaaactcca atactttggc cacctgatgc   101160
gaagagctga ctcatttgaa aagaccctga tgctgggtaa gattgagggc gggaggggaa   101220
ggggacaaca gaggatgaga tggttggatg gcatcaccga ctcaatggac atgggtttgg   101280
gtggactctg gaagttggtg atggacaggg aggcctggcg tgctgcggtt catggggttg   101340
tgaggagtcg gacacgactg agcgactgaa ctgaactgaa catgaatacc caaagcaatc   101400
tacaaagcca aatgtaatcc ctatcaaaat cccaatagca tttctgcaga aacaggaaaa   101460
aaaatcttaa aattcatatg gaatctaagg aaaagcaaag gatgtctggt caaaacaatg   101520
acgaaaagaa caacaaagct ggaagactca cacttcctga tttcagaact tactgcaaag   101580
atacaataat gaaacactg tgggactaac gtaaaagcag acacgtgggc caacgggaca   101640
gcccagaaat aaactctcaa ataagcagtc aaatgatttt caacagagat gccaagacca   101700
ctcagtgaag gaaagtgttt gcaaccaacg gttttgggaa aaaagaaccc acatgcgaaa   101760
gaatgaagtg ggacccttac ccagccccat ctacagaaat caactcaaaa cagacagaac   101820
atatggctca agccataaaa cgctcagaaa aacagagcaa agctttatga tgttggattt   101880
ggcggtgatt tctcagatat gacgtcaaag gcataggtga taagcgaaaa aataaactgg   101940
acttcaccaa aatacaacac ttctatgcat ccaaggacac taccgacagc ataacaaggc   102000
agcccaggga aaggaggaaa catccgcaaa tcacagcatc tgggaacaga ccgctgcctg   102060
tgagatacag ggaaccgata aaaacaagaa aacagcaaaa cccggactca aaatgggaa    102120 ggactccagc agacacagga gacagacaag ccgccagcag gtcactaatc agcaagcaag   102180
gcccgcaaag gcccgtatcc aaggctgtgg ttttttccagt ggtcatgtag gaaagagagc   102240
tggatcgtaa gaaagctgag cgctgaagaa ttgattgaac tgtggtgttg gagaagactc   102300
ttgagagtcc cttggactgc aagatcaaac cagtccattc tgaaggagat cagtcccgaa   102360
tagtcactga aggactgatg ctgtagctcc aatactttgg ccacctgatt cgaagaactg   102420
actcattggc aaagaccctg atgctgggaa agattgaagg caggaggaga aggggacgac   102480
agaggatgag atggttggat ggcatcactg actccatgga catgagcttg ggcaagctcc   102540
gggagagagt gaaggacagg gaagcctggc gtgctgcagc ccgtgggtcc caaatctttg   102600
gaccaagcga ctgaacaata acaaatcaac agggaaatgc aaatcaaaac cacagtgaga   102660
tactgtccac caccaggcag gcgttcttca gcggggttcg gggcaggtgg tgccctcttc   102720
tctcgtaacg cccccaggac cgcgggggct gctgagacag catgggggtgt gcttggccta   102780
```

```
gcctgcccat gacaagagtg gcagtgtgct cgcctcactg cgcccttccc tgctctgccc    102840
accagctggg ccaccctgg gaccacccag cttccgctcc gtggacggca aggccgcagc     102900
agcgcccgga cacgcccaga acgtggtgcc ctcctcagaa gtcggcctgt gcccttcctg    102960
ggacaagccg cccaagagac agtcttccag agccctgccc cacaacacgg accccagaca    103020
ggctcctgtg gaggcctcca cgcacctccg cacctcgcaa gccccgagga caaggcaggc    103080
ccgctgcggt tgaggagccg cctaccttga taatgacgcg ctggtctgac tggtcttcca    103140
ggatgctgtc cgtggggtag gactcgatct gctgtctgat ggcagaggca atggctggca    103200
cgaatgtcag tgggttcaga tccaggtcgt cacagagaat ctctgagaac atctccgggg    103260
tcatcagctt ctctgaaacg atgacggagc gggggaaccc ccagtggacc acagggccta    103320
cggtcagcgt gctcagcccc ggcctccccc agccttgcct cctctgccac cgccccccg    103380 ggtgacgaca ggaccccctg gcagcacgca gacagagctg agtgcacgcc agccaggggcg    103440 gcggacggac cattcatgtt ccaggtaaag gcatcccgca gcttctgccc gtcaatctcc    103500
atgtccagtc ggatggggac cagcacctcg ggctgggacg cgttctcgtg gatcacggct    103560
gggtcgtggt cgtcgaagct ggaagggagag cggccgcgtg ctcagcaaag cgggctgggc    103620
ccctgtgccc agggcctccc tctctgcacc actggtcgct gagacctgcc cagagaggac    103680
ctgtccacta cgggccgggc cggcagaaac agggctggcg ggggtccacg cggggcggga    103740
ggggagctgc cgactcggca gcgggacaag ctcagaggtt ccctgcagga agagaggttt    103800
aagccccaga gcaggcagga ttctcccagc agctgtgggg aagaaagggt atgtccagaa    103860
gaagaaaccc tggaacaaag gccgaggggc aggaggttg aggagctgct ggagagcag     103920 tgaaggggg ctggcggct gggggtgct ggggagcctc ggtggccaag cacccagggc       103980
tccccacctg cagcctggac cccgaggag cccagagga cggagagcaa ggcagctccg      104040
cactcacacc tgcccttag gatggggaag agggaagaga cgggggctgc gggggcaag     104100 gaaaccaggc acgccccgct tagacccggg ggcgagaacc actttccaag aacgcagggg    104160
cgccaatgat gaacaatggg tagcagcccg caggcgggag gcccggtggc cgaggcccct    104220
caccagagcg ggaaggtccg cttcttgtcg cggcccatgc ggttcctgtt gatggtggtg    104280
gagcagggca cggcgtccag gtggtgcgag ctgttgggca gggtgggcac ccactggctg    104340
ttcctcttgg cctctgttc cctgggagac acagacgccc gtccgctcag cctatgggcc    104400
aaaagccgcc cccagccgc caggttgtgg ccagtggacg cccgccatgc ccctctgggc    104460
ccaggccccc atggggacct ctgtgcgccc agctccgcgg tggttattcc ccaggctcca    104520
agcggcacct gctcggggtc accagttta ggggaggagg agagggcagg ggccccagcc    104580
cagtctgtga gctgtcaccc ccaggctcca agcggcacct gctcggggtc accagttta    104640 ggggaggagg agagggcagg ggccccagcc cagtctgtga gctgtcaccc ccaggctcca    104700
agcggcacct gctcggggtc accagttta ggggaggagg agagggcagg ggccccagcc    104760
cagtctgtga gctgtcaccc ccaggctcca agcggcacct gctcggggtc accagttta    104820 ggggaggagg agagggcagg ggccccagcc cagtctgtga gctgtcaccc gtgctatgtg    104880
ctgggctggg cactcaggaa agagggtcag ggttcacggg ggggtggcgc gcagatttcc    104940
aggagagccc cgagggcagc agagaggagg ctcaggtcaa tggttgggca ggggccagg     105000 gctggagaca cagagagggt cccgattcgg ggggtgccc tcagcaggtg gctgggagtc    105060 cctggggtt tgcacacttt cgatcaggct gttatttcag acgcttggtc cagcctgaga    105120
caggtaatgc ctctggcctc cgggccttca gggatggaaa gatactctag aaagcgggac    105180
```

```
tcaaagtaac tcaaggaact cgcgtcccac agtggggagc ccttctctcc aatttacatg   105240
gggcgtttac tacgaggaaa ataccgaagg ccgttttgag ctgaggctcc cgggccgggc   105300
tgtccgtttg tgagactgct cgtcacccct gggccacatc cctggtggcc aagggggcaa   105360
tcagtgcggt gactgcacga cacacctctg cagccctgcc ccacagctgt caccatcggt   105420
gacgtccacc ccctggagaa cctgaccact gcccggtttc ccgctaaaac agcgcccttc   105480
caggatgggg ggcagaggga gaggccttgg ccttttcact cctcttctgc agcgggggcc   105540
cctcgcaccc cagtgcccgg gcccaggagc gcccctttggg gtggggcagg agggatcca   105600 cacaccaagg ggagccagga cccccccaaa tctgctgccc tgccctgata cccgagacct   105660
ggggaaacgg gggactgggg ctgatgcggg caggaccaag aactgaggcg gtgagacggg   105720
gtccccacca caggccatct ggctggcagt ttctactccg ggcctgcagg ccaagaggga   105780
aaaggtgccc cactcagatc aggcgcctcc cgtccccagg gagggcctac aaggtcagat   105840
cctttgtaac ttccacgggc aaaactggct tgctgggcct gtgcgggccg catgggcgtg   105900
gaccaccaca ccttccccca ctgagtctcc agccggagct gtcacccagg tcccccagg    105960 ccagccccac cccgccacct tgcagtagcc tctcgtatcc aggccgaggc tgcccggtcg   106020 accccctcctg cctgatggcc tcaagtggac aatgcgagtc acgttgcagc acgtgagtgg   106080
gacgggcagc gccacgcggg gtccgggcat ccgagtccca ccactcagcc tcccttccgc   106140
tgcagagagg tctgtccaag agccctgggg gccatccagc cctgtccga cctggccggt    106200 gtggaagagg gggtgtgcca cccctcctgg ggggctggct gggcgctggg caggcccctc   106260
ctaagagtgg agcccactgg tggttttcct gcagcccac ctccacacag cagttctcac    106320
tgcccagtaa caggaggcta ctggcctagc tctctccctc gtgtgatgga ctcaaccagg   106380
agcgttcacg gccccacaca gggttctcgg ctgctgcatg aggatctcaa agccccatcc   106440
acgtgcatgt aatctcctcc ggtaacttct ctagggaagc ccggctatcc tgccatcctc   106500
accgcaccac cagggcgaga aaagccatct ccagcgctca catccacaat gggccaggcc   106560
gtgagcacac caccttcttc gggaggttgt gggggcgggn nnnnnnnnn nnnnnnnnn    106620 nnnnnnnnnn nnnnnnnnnn nnnnnnnnnn nnnnnnnnnn nnnnnnnnnn nnnnnnnnnn   106680
nnnnnnnnnn nnnnnnnnng cgcgccccc cccccgcgg cgccggcacc ccgggcggcg     106740 gccccggcg ctgggagcag gtgcgggggcc gcggccgctc gtgagcctcc agcccggagg   106800
acgggccccg ggggccggcc cggtgcccag gccctgggag cccggaggc cagagtgcca    106860 gagggccgga ggaccgggga aggcccgaga gaggtgggaa gcacgggggtt ccagccctag  106920 gccatttcag ccccaaagcc atcggtgaaa ccattgctgg ccccagataa aagcgtcgcc    106980 aacttttttca ccccggcgga gactttagcg ggtagctgcc ccctaggggg aatggaaaaa   107040
ccaggattta ccaggtgggt ggaggtcaca actgcccaga tcctgagaaa gagggggtcag  107100 tggggcggga agattagtgg ggagaggagc tttcagaacc caagggaatg aaacgaggct    107160
tgaggttggt tatccagcag ccgccccctg ccccgtgagt gagcgaaggc tgggcccctt   107220
attgtcacat cttccagctc ttcgctagaa aacctagagt tttaaatact gtggcagctg   107280
agtcaaacaa taaggaaaag cccgactctt tgagagccag gcacaaggcg tctgtgacag   107340
ggtctccagg ctgcccattt gcagtctctg aaacggaggg ttttttcgaga aggaggtctt   107400 ggggtgcctg ccagaattgg agggggggc gcgggaagtg aggacccaga agagagggct    107460
tggcccgctg caaggaggtc actggacact ggagctgaag cgccagccga aactggaaac   107520
```

```
tcgaaatctg tctccgtgcc agccacaagg cctatgattt tccttggcga cgttcagcat    107580
cttaggagga gctggcgggg gaggcgggta gttcgtgggc ggttgcagca gggcaggaag    107640
gtgaggaacc tgaggctggt cagagagctg gttggagtga tgcccatcgg tggacccgct    107700
ggagaaggcc tgagtagaga aggtctaagc ttaacgggga aggggtgggc cagggtggaa    107760
atggggtggg aagtttgagg aggggagca gtggagatgg gggttgtgag gaatgggagt     107820
gagcttagac gtcttgagga tactgcagtt ctgtgctttt tttcacacct ggctgaaaat    107880
tcactgaaaa caaacaacc cttgctctgt gacagcctag aggggtggga gggaggctta     107940
agagggaggg gacgtgcgtg tgcctatggg cgattcatgt gggtgtacgg cagaaagcaa    108000
cacagtatgt aattaccctc caattaaaga tcaagtacaa cttaaaaacc ccaaacacaa    108060
cattgtaagt cagctagact ccagtaaaca tttcagtaag aagattcaac tgggaatgag    108120
ttccgccgtg actatcctga tgaatttccc gtgtcttctt gaggccattc ctctttgaac    108180
ttccgtgttt ggggaagcgt gccttttgtat ggagtcctga ggagtaaatg agacgggctt    108240
gtagaaggcc tagtagtgcc ttgcacgcgg cagatgctca ataacctcga gttgtcacca    108300
ttatggtacc tcaagagtct ccttggagct tgcacggttt ctgaatgggg tcctgcgggg    108360
ctcccttggg gctcccacat ggggttgggg ggctgagtgg ggtgtccccg ctccttgctt    108420
gtccctgtg gaacacccc ttccacccga gcagctctgc ttttgtctct tgtgtttgtt     108480
tatatctcct agattgttgt tcagtcgctc agtcgtgtcc aactctccga ccccatggac    108540
tgcagcacac caggccttct gccttcacca tctcccggag cttgctcaaa ctcctgtcca    108600
ttgagttgct gatgccgtcc aaccatctcg tcctctgtcg tccccttctc cttttgacct    108660
cagtcttcc cagcatcagg gtcttttcca atgagtcagc tctttgactc aggtggccaa     108720
gtattggagc ttcagcttca ttatcagtcc ttccaatgaa tattcagggt tgatttcttt    108780
taggattgag tgacttgatc tccttgcagt ccaagggact ctcaagagtc ttcaacacca    108840
cagttcaaaa gcatcagttc ttcggcactc agccttcttt atgatccaac gcccacatcg    108900
gtacatgact actggaaaaa ctttggctca gagataattg acttgattga atacaaagtt    108960
ctttggcaaa aaataaaagt gtggcaagca gtactgacac aaaagcaagt ggcttttcct    109020
ccgttgagtc atttatttat tcagtgggtg tgtgcgtgta gagacggagc ggctgtgctg    109080
ggagctgggg cttccacttc agaggagccc cggacctgcc ctcggggagt tcacaggcag    109140
tgctgcgggg ggtcctgcca ggacgcctgc cctgcgagtg cccagtgctg tgatggatgc    109200
gtgtcccgca tctgcggcca ctggggccac gtgcccgaga ttgtccgggt ctgagggtgc    109260
agagaagagg aggcatttgg actgagtctg gaaaaatgag catgtggcca cgtgagaagc    109320
cagtggtgag gggaccagtc aggcggagga aagagcggct catacgagtt gtggagctgg    109380
aagcatgagg gtgtgtggaa gcagaggccg gggacagggc cgcagggccg ccatggagg     109440
gcgtgggctg ctgcaggctc ctgagaaggg ggacgctgcc atcatgaccg ggtttaggtg    109500
tttgaccctg gtgtccacgt agaggacaga tgtgtggggg gggagctgga gatgggcatc    109560
catcgggagt cagcctggag agaggcagag accccgtcag tgggccctca ggacgtggat    109620
ggggcggatg ttgggaagat ctgactcctg ggttccggct ggggctccgg gctgaggggg    109680
tgccgcccac cgagcacagg aggcaaacag atgccctctc ccagcaagac cccagcccca    109740
gcaccctccg gggccggact ccgcccctct tccagaatgg ctcccttgct gtcctcgccc    109800
atctttccgg tgccctgagc ctctagagtc tggacaccag cgtccgcctt gcgcttgttt    109860
ctgggaagtc tctggcttgt ctctgactca cccaggaccg tcttcgaggg caaggttgtg    109920
```

```
tccttggttc catctgctttt ggggtccggc tcctcgctgc ttgacctgct gatgtgacag   109980
tgtctcttgt tttcttttca gaatccgaga gcagctgtgt gtgtcccaga cagacccagc   110040
cgctgggatg acgggcccct ctgtggagat ccccccggcc gccaagctgg gtgaggcttt   110100
cgtgtttgcc ggcgggctgg acatgcaggc agacctgttc gcggaggagg acctggggc    110160 cccctttctt caggggaggg ctctggagca gatggccgtc atctacaagg agatccctct   110220
cggggagcaa ggcagggagc aggacgatta ccggggggac ttcgatctgt gctccagccc   110280
tgttccgcct cagagcgtcc ccccgggaga cagggcccag gacgatgagc tgttcggccc   110340
gaccttcctc cagaaaccag acccgactgc gtaccggatc acgggcagcg gggaagccgc   110400
cgatccgcct gccagggagg cggtgggcag gggtgacttg gggctgcagg ggccgcccag   110460
gaccgcgcag cccgccaagc cctacgcgtg tcgggagtgc ggcaaggcct tcagccagag   110520
ctcgcacctg ctccggcacc tggtgattca caccggggag aagccgtatg agtgcggcga   110580
gtgcggcaag gccttcagcc agagctcgca cctgctccgg caccaggcca tccacaccgg   110640
ggagaagccg tacgagtgcg gcgagtgcgg caaggccttc cggcagagct cggccctggc   110700
gcagcacgcg aagacgcaca gcgggaggcg gccgtacgtc tgccgcgagt gcggcaagga   110760
cttcagccgc agctccagcc tgcgcaagca cgagcgcatc cacaccgggg agaagcccta   110820
cgcgtgccag gagtgcggca aggccttcaa ccagagctcg gcctgagcc agcaccgcaa    110880 gatccactcg ctgcagaggc cgcacgcctg cgagctgtgc gggaaggcct tctgccaccg   110940
ctcgcacctg ctgcggcacc agcgcgtcca cacgggcaag aagccgtacg cctgcgcgga   111000
ctgcggcaag gccttcagcc agagctccaa cctcatcgag caccgcaaga cgcacacggg   111060
cgagaggccc taccggtgcc acaagtgcgc caaggccttc agccagagct cggcgctcat   111120
cgagcaccag cgcacccaca cgggcgagag gccttacgag tgcggccagt gcggcaaggc   111180
cttccgccac agctcggcgc tcatccagca ccagcgcacg cacacgggcc gcaagcccta   111240
cgtgtgcaac gagtgcggca aggccttccg ccaccgctcg gcgctcatcg agcactacaa   111300
gacgcacacg cgcgagcggc cctacgagtg caaccgctgc ggcaaggcct tccggggcag   111360
ctcgcacctc ctccgccacc agaaggtcca cgcggcggac aagctctagg gtccgcccgg   111420
ggcgagggca cgccggcccct ggcgcccccg gcccagcggg tggacctggg gggccagccg   111480
gacggcggaa tccggccgg ctcttctctg ccgtgacccc ggggggttgg ttttgccctc    111540
cattcgcttt ttctaaagtg cagacgaata cacgtcagag ggacgaagtg gggttaagcc   111600
cccgggagac gtccggcgag ctctaacgtc agacacttga agaagtgaag cggactcgca   111660
gcccgtacag cccggggaag atgagtccaa agtcgagggt caccttggcc actgcagggt   111720 cgctcggcg tgggcggag cggtgcagg agggctcctc ctgggcttgg ggtggcaggc    111780
gaggaccccg cgcctctcag ccctcggcct gggttggctg agggcgggcc tggctgtagg   111840
ccctccagcg gaggtggagg cgctgccgg ctcagccagg cacaggaccc tgccacgagg   111900
agtagccctc cgccagaccc ggcgtccagg ctggggcgcc tgcggggcct ccgttctgtg   111960
gctgggcagc ctgcgccctg tccagggatg aaggggttcc ggtctgaagg gctgggttca   112020
gggtccagct ctggccctc ctgccttggt gtcctggagg aagccccaag gctccgtttc    112080
cctctccagg aggtggggac gttgggaatg ccacattccc ctgggggtg tgtgtgtgtg    112140 ttcaaggctc ccattcagac tgggactggg cactcacgag ctttggcaac tgcaactga    112200 ggacggagac ccagggtgac accccacctc ctgctgcggc ccccccggca ggggagacac   112260
```

```
aggcccgtct ggttcccaag atggcagggc ccctccccct ccagcttgtg ccctgggtgt    112320
ggtgcctggg gctacagcga ccctttccgg ttccccgggc cagttcagct gggcatcctc    112380
agggcggggc tctgagggtg ccatgtttcc agagctcctc ctcctcccac cagtagcagg    112440
cgggcggcca gctcccaggc agccccctgg catcgcctag gtgcacacct gcccgctgtg    112500
acccagcaag gcttgaaggt ggccatccca gttaagtccc ctgcccctgg cccaggaatg    112560
ggctcgggca gggccgcatc tggctgcccc agaagcgtct gtccctggcc tctgggagtt    112620
ggcggtggtc tctggtactg tccctcgcag ggccccttag cactgctcgg ggaggaggtg    112680
ggctgaactg atttgaagt tttacatgtc tgcggccgca gtcctacgag cccgtcaggg    112740
tcatgctggt tatttcagca gatggggctt ggctcggcag ctaggatggt cctgaataaa    112800
aatgggaagg ccagagctgt tcctccatca gcaggcttgg cagctgggga cgttgaaagg    112860
acaggtctgc tggtctgggg agaccagctc tgtgcagccc ctgctgtccg tgggggtact    112920
aaaccagccc ctgtgtgcgc ccatctgagt ggcagcccgc ctggaggatc gcccatcact    112980
tgtgagaatt gagagaatgc tgacaccccc gcttggtgca gggggacagg gcccctaag     113040 atctacctcc ttgccccacc cccgggaccc cctcagcctt ggccaggact gtccttactg    113100
ggcagggcag tcatccactt ccaaccttg ccgtctcctc cgcgcgctgt gctcccagcc    113160
aaattgtttt attttttcc aagcatcact ttgcacacgt caccactctc cttaaaacca    113220
cccttccgga gtcctcctgct cgtaaatcgc cggtttcagc caacctgggt cgcccccaa    113280 gcccagcaag cctgctgagc ccgcgcctc ccagctactt cacgctcgcc tcaagcttct    113340
aaacgcggac cttctccccc ccaccccat cccttccttt tctgatttat gtaacacggc     113400
aggtaagact cctctcctga agggttgaca gactcacaca aaaccgtggt cagaccaggc    113460
aagtgctttt tttcagaagt gtgagcggaa cctagtcttc agctcatgct ctttccttgt    113520
tttcttatgt gttctaagtc ctttgacttg ggctcccaga cagcgacgtt gtaagaggcc    113580
gtcctggtag catttgaatt gtcctcgagt ttcgttgtcg gattttgttt tattgtctta    113640 gttttcccctt cttttagcag acgttgttga ctgtcgtaaa gctccagttc ttggttctgt    113700
ttactaatca aattgttttg tcaaagtaca tgtattctgc tcttttcttt atctttttgt    113760
ttgcttaata ttaacacttt acatttctaa gattaattat ttaggtaatt aataattttt    113820
aacatttcta gtaaacgtgg gtacttgggt ctgtgtttgt tttcttgtag ttacagcttt    113880
ttctgctcta tactgttgac gtctgggttt ttttttgctc ttaggaattt cccttttgacc   113940 ccattattat tattttaatt agtattttt aataattaaa aattagtgtt tttaaattaa    114000
ccctaatcct aaccccagtg atgactgctt cagtcattgc tgttacttat tatgtgctgg    114060
tgtcaggatt tttaagtgtc catagacatt ctctgagcct gaatatatta tcagtttat     114120 acagcatttg tgtactctca agaaacgtgt tttcactctg tcagttcggt tgttacctc     114180 agtctttatg ttattttgct ccagtccgca cttgctctaa cttgtcttcc cttcgaggtg    114240
tgaggacgcc tggcagccgg tgagcatgcc ggggtccggg gtcgtgggcc caggcgccca    114300
gcaaagccct gtgggtgtgt gcacggctgg gctgctccgg gaggaagcct gtggccccac    114360
ggtagttagg agcgctggtt tacctggtca caccacggtc tggttttgtg tgcttttccc    114420
tgacgtgttt ctgttttgcc ttggtttcta ttctgttta tgagtgccgt ttacgctttg     114480
ttagtcatgc cgttatctcg atagacaggg tgtacgtgat caagtgatta ccgtatttgg    114540
agcagatgtc tatttaacag agatgaactg agaacctgtg cctttgcatg ccctcttgc    114600 ctctttaat gcttctagct tcaacttctc ttttccaaac attataatgg aaaccccttg    114660
```

```
cttttttttt tttaatttgc atttgcatga gagtttattt agctcggcat tttatttta   114720
aaatttgtgt atatattttt gctatatatc tgtaacttat aaacagcaaa ttattggatt   114780
ttgctttctg attctttctg taattcttct tacataagaa gttctcctat gagtaacatt   114840
gctgtttaga gtgaggcatg atttatttcc agcttagtat gtattgggtc ggttaacccc   114900
caaaggtcat gctcatcccc gccccatctc tgtgagttat tgtccgagtg tggagcgccc   114960
tgtctaggcc gacgagagac ccaccatcgg gcacacctgc ccctcctggt ctggtcagtg   115020
ccgggctctg tcctgagtcc actcctgatg tcacaggctg gtgcttcagc gacctcggct   115080
gtgacacgga gggtgtgatg gcactgccca gccccatggg gcttggagga ctaaaggatg   115140
cacacctgcc tggcagactg agggcacagg tgtttctcac actgtcagcg ttttgaaata   115200
ttcctttgat tttctaccct aactcccaaa ggccgttcaa cataagctag aatgctacgt   115260
ggtgcttgat tacattttag aaaagtttca gcaaatacca cgagatgcag caagaactg    115320
gacctcacag atcaggccgc ctgcataagg gagcccacac agtcgtggga gacggggacc   115380
ctctcccacg tcctgtctgt cccaggatgg tcccctcacc cgcccctct ctcccctcgc    115440
cctcctgtgg tgggggccgg ccaccatcac agctgcagag cctcaagaag ggggtcgccc   115500
tggccactcc cgtggcagga gggacacgag ggcaggagct taccgcgggt gcagtggtct   115560
cggatcagct cagctggccg ctgcggggtc ggggggacac ttcagtggga ggcaggagcc   115620
cccactacag ctgccaggac ttctcagagg tgacaagggg gttcagtcac ctcagcccag   115680
gtggaaacca aatggcctct tgcgcggctc ctggggccac gcggaggttc gctgggatca   115740
caggtatctg gatgtgtgcg ccatggacat gcaccaccttt cgggggtaa ggggtgggga   115800
aaggcagccc cttctttttg ggggaccccc tcttcagtgt ctgataacca ggaaaccaaa   115860
tcagaaggtg gtctgggggt gctgagcagg gtgtctccta caccacaggc cacacactca   115920
cacagcctcc aggactccag tggggctgag cgctggagac tcacccacgt ttgctacccc   115980
cccacccaag gccatcccag aacagctgcc tgcgtcctca cggctggccc ctccctctg    116040
gtctaaccca gtgtgggtgg gccggcctgg ggtctccacc tgcctcctgc tgttccctgg   116100
gctgctggct gtctgcagat gcggggcct ggcccggaga agcccatca gagcccagag     116160
gacgggagtg gagcggggag gtgagccccg gagtctcgag gggccagagg caaaatactg   116220
ggctgtgtcc ctggaaggca gtttcccatg aaaccttcaa tataggccgc cccagacgat   116280
cagcctcatc tgctacgtgg attcctcccc gtagcgaatg gtgattgggt tctacatgga   116340
cccgggactt ctgtttgaat tataatcttt cccccactgc ccctccaggg atctggaaaa   116400
tggaggcctg ggctagacgg aagcttcctc caagattctt tattgaaggg attcgaagag   116460
aaacaggtgg tcagtaatct gtgggggatg gaggggtgag cgctacgtgt aacggtttta   116520
ctgttgctac gggaccagtt ttgatgtctt tccccttcaa gaagcagacc caaacaccga   116580
gatgctgagg ttagcagcac agagcgggtt catccacaag gcaaccaggc agggagacca   116640
gagacgctct ggaatctgcc tccctatggg cacgggctgg gtgctcacgg atgaagacca   116700
agcagcaggt ggcgtggggc gtggggagcc tgcggaaagc gatggacaag gtgcgggacc   116760
gcggtccgcg cggtggaccc aagctccgcc tctgcgctgc agcgcgagct gggggcgag    116820
cttccaggga cccgcgaccg cgcccagtgg gagggtccgc ggtccaccca gtcctaacag   116880
ctcagctcca gctagacgcc gctgagtccg gctttctaga gagcaacccc ggcgggtatt   116940
ttatggttct ggcttcctga ttggaggaca cgcgagtctt agaacaccct tgattagtgc   117000
```

```
gggcaggcgg aatggatttg actgatcacg atctgcagtt tcaccatctc aggggccgcc   117060
ctcaccccca cctatcctgc caaagggggg gcctcggtgc tgagatcggg gccacacgtg   117120
cactagacgg tcggtcagcg ctgctgctga gcggacccgg ggccatcctc acaccgccac   117180
tggcccctgt gctcaataaa aggaaggaaa gcgggaaaag cgctttctgg ccgcggtggc   117240
ctcgcgcgtt cctccatcgc catctgctgg cagagcccgg catggcaccc gctgcacaga   117300
aacctcggtg tccgtttggg tgccccatcc ttgaccccga gagagcaccc tccgtccaaa   117360
atgaaaaaca gctgctccca agagtcatta taatcacagc caattgtgtt aattcgtcct   117420
cggatccact cacagttcca cggaacattc tgctaacctc tgacaactcc tacataaagc   117480
aatactgaga agaaaagaac gtggttgata aatacaaagg catacaacaa taaggagcaa   117540
agaaaaaaga cagtcctcgc agttctgttt tgttcatctc tcatgagtag gatggcagat   117600
aaaacacaga atgcccagtg aataatttta gtctaagtat gtccccaata ctgcctaatc   117660
ttcaaatcta accttatttt taaaatatat attttttgct ggtcactcat cagttcatgc   117720
accaaagcct ttgtttcttg actcctaact ttttgacccc tctggggtga ggagcacccc   117780
taacctcgag agcccatcac acagtcccct tgggactaga cccttctttg cccatcacag   117840
ctgaccggaa gggccagccc atggccagcg ctcgcgcccc ctggcggaca gactctgcgc   117900 ggcagcccg ggagcccagg tgcgaccccg cggtctctgg cgccctctag tgtggaaaga   117960
tctcctcctg gtgttcccag tcattgggct gtatttatt agagaagatg ctcgcgtgac   118020
gatgatgatg gtcctttacc gggaggcacg tttgggcgc gtcggctcag gggccgagct   118080
attagcctgc atcgcgccca caggcatcgc gtccccctga gccgggtcag ctgtgggctg   118140
tcctgacacg ggtttccccc agtctctggc ccgctgtccc tcccaggtca gtgtccagcg   118200
ttgcccttct ggttgtggac ttgtgcagcg gtctcagcag atggagggc gaccctaaag   118260 gatgtattga ggcatctcag cactgtcctc cgcccaggtt tgctggtcag cagtgaagtg   118320
accgggaaaa ggggctgtct tggggtcctt tcagaggcct gggttagacc aaagttttct   118380
agaagattca ccattgcagg gagtcaaaga caaaactagg gtggtcagca atctgtgggg   118440
gattcggcgg tgagggaatt ctgaatgcta catgtaatgg ttttactatt gttagggaac   118500
atttttcccc cctacaaaca gcaggccaaa atactgagat gtcaggtttg catcaaagag   118560
cgggttcatc cacaaggcaa ccagagaacg ctctggaatc tgcctccctg cgggcacagg   118620
ctgggtgctc acggatgaag accaagcagc aggtggcgtg gggagtgggg agcctgggga   118680
aagcgatgga caaggtgcga ggacctccgg cgcgagctgg aggcggagct tccagggaca   118740
cgcggccacg cccagtggga gggtcagcgg tccatccagt cctaacagct cagctccaac   118800
tagacgctgc tgagtctggc tttctagaga acactccggg cgggtatttt attgttttgg   118860
cttcgtgact ggaggacgtt caagtcttaa aacacccttg attagtgcgg ggaggcggaa   118920
tggatttgac tgatcacgac ccgcagtttc accatctcag gggccgccct caccccctcc   118980
taccctacca aaggtggggg catcggtgct gagatctggg gtgacacata aaatcaggtg   119040
aagtcttagg acagggggcc gattccaggt cctaggtgc agaaaaaacc tacctggccc   119100
cgggctagac agcgtggagg gcgtggcccg ggctggtgca cagaagtggc ccccaactgg   119160
tcagaaggtg tgggagccca gggctggtct actgcagaag gggtcgcctg gtggacagag   119220
tggggcctga gtgcctgctg aactggtccg tcagggctgc tgagcagaca cgggccatca   119280
tcactggctc ctgtgctcga tagaagggag ggaaaccagg aaagcaaagg cgctttatgg   119340
ccgcttttgt gtttcgcgtt cctctagcac cgtctgccgg cagaacgcgg cattacatcc   119400
```

```
gctggccaaa cctcggggtc cggcttggat gtcccatcc ttgtctcgga gatctcacct   119460
ctcagcagtt cccctgggga caatgtcgag aagatgcgac cttgacccgg agctcggtgg   119520
agagggtgcc ctgggttctt tccgcagttg cttggagtgg aggtgcctca tgttgggctg   119580
ggaacgggag gaaggaaaca ggtcatgatt gagatgctct agacagactg tccctgctct   119640
tgccaaattt cagaagattg tctttaataa atattccatt ttttgtatgc ccttaggtct   119700
atttccagac actttaaata tattgaaaga ctttaaatat ttatataaaa atattattta   119760
tagactgtat aaaaggaaca gttagaactg gacttggaac aacagactgg ttccaaatag   119820
gaaaaggagt acgtcaaggc tgtatattgt caccctgctt atttaactta tatgcagagt   119880
acatcatgag aaacgctggg ctggaagaaa cacaagctgg aatcaagatt gccgggagaa   119940
atatcaataa cctcagatat gcagatgaca ccacccttat ggcagaaagt gaagaggaac   120000
tcaaaagcct cttgatgaag gtgaaagagg agagcgaaaa agttggctta agctcaaca   120060 tttagaaaac gaagatcatg gcatctggtc ccatcacttc atggaaatag atggggaaac   120120
agttgagaca gtgtcagact ttattttttgg gggctccaat gaaattaaaa gacgcttact   120180
tcttggaagg aaagttatga ccaacctaga cagcatatta aaaagcagag acactacttt   120240
gccagcaaag gtccgtctag tcaaggctat ggttttttcca gtggtcatgt atggatgtga   120300
gagttggact gtgaagaagg ctgagcaccg aagaagtgat gcttttgaac tgtggtgttg   120360
gagaagactc ttgagaggcc cttggactgc aaggagatcc aaccagtcca tcgtaaagga   120420
gatcaccccc tgggtggtca ttggaaggac tgatgttgaa gctgaaactc cagtactttg   120480
gctacctaat gcgaagagct gactcattgg aaaagaccct gatgctggga aagattgaag   120540
gtgggaggag aagggggacaa cagaggatga gatggttgga ttgcatcact gactcgatgg   120600
acgtgagtct gagtgaagtc tgggagttgg tgatggccag ggaggccctg gcgtgctggc   120660
ggttcatggg gtcgcaaaga gtcggccatg actgagtgac tgaactgaac tgatccagaa   120720
atttaaaatt aatatataaa ccaaatccat gcagacaatt ataagcatat attataaatg   120780
cataattata agcaagtata tgttatattt ataatagttt ataatgtatt tataagcaag   120840
tatatattat tataagcata attgtaagta gaagtaactt tgggctttcc tggtggctca   120900
gacagtaaag aatctgcctg cagtacagga gaccgggttc gatccctggt ttggggaaat   120960
tccctggaga agggaatggc aaccaactcc aacatgtttg cctggagaat tccatggaca   121020
gaggagcccg gaaggttgca gtccatgggg ttgcaaagag ctggatacaa cagagtgact   121080
aacacatgta tataaataaa tttacctata tattgtatat atatttataa acatattcag   121140
atattataaa taattagaaa catattatac atgtatttaa atactgttat aaacataaat   121200
ttaaaaaata atttttcagcc ctttggcttg ggggtgtgtt tgtggacgtc tttgtgctac   121260
tgttcctgaa gtggagctct cccctcccaa accagctttt gaaatgactg ggaaagcaat   121320
ggaatacata agcatcagga agatagcaac agagctgtca ttcttcacag agggtgtgct   121380
tgagtgtgta gcaagtcccg cagaatgtag acagattaat atagtctatt aaaaatagtg   121440
tagcaaattt acgaggtgcg atttcaagta taaagactta ctgggtctct cagttcagtt   121500
cagtcgcttg gttgtgtccg actcttttg accccatgga ccgcagcacg ccaggcctcc   121560
ctgtccatca ccaactcctg gagttcactc aaactcatgt ccatcgagtc ggtgatgcca   121620
tccaaccatc tcatcctctg gcgtccccctt ctcctcccac cttcaatctt tcccagcatc   121680
agggtctttc ccagtgagtc agttcttgc atcaggtggc cagagtagtg gagtttcagc   121740
```

```
ttcagcatcg gtccttccaa tgaatattct ggactgattt cctttaggat tgactggttg 121800
gatctccttg cagttcaagg gactctcaag agtcttctcc aacagcacag tctatgaata 121860
gaatagcaaa tgaatagaga ataacattta cgaggatata ttttaccatt gcataaaata 121920
tatcagcttg tagagaacag acttgttccc aggggagagg gtgggtaggg atggagtggg 121980
agtttgngat cancagaagc gagctgttat atagaagatg gataaaaagg atacacaaca 122040
atgtcctact gtgtggcacc gggacctata ttcagtagct tgtgagaaac cataatcgac 122100
aagactgagg aaaagtatat atatatgtat gtacttgagt tgctttgctg tacagaagaa 122160
attaacacaa cattgtaaat cgatatttca atagaatcca ccccccaaa tatataagtt 122220 tcctggagat ggagacggca acccactcca tttcttgcac ccaatattct tgcctggagg 122280
atcccatgga tagaggatcg caaagactcg gacataaccc agcgactaac actttccctt 122340
tcaaatgtgt aggtttacta gcgtgaatct acagagatgc ccaagacatt cgtttatgag 122400
gaaaactcca cacgcagctt cactgagaat tattaaacct attaaaggga gagagcgcca 122460
ggatattcat ggattgaaag attcgatgtg gtcaagttgc cagttttccc caaactgatt 122520
ggtaaattcc ccaggagctg gctcaaggcg caaaattccc tttacctttt tttaagagac 122580
gaagccaagg agccgattct ggttgagaga cgctcaggtc ctcctgcggg agagcagccc 122640
tcttcctccc ggtcgcctgg gcagtttcga ggccacgacc agaaggactt ggctccctgt 122700
gtcgcgcact cagaagtctc cctctccgtc caaggactc agaagctggg cgtcctgccc 122760
gcagcagagg aggcagcctg gaggggcccc gcgggcacag cggtccgggt ttcagccgag 122820
ttgcccgccc cgcccctcta cctgggcgct gccgccggc tcggggccg gccgtgccct 122880 ccgtggccgc aaggcgtcgc tgtccccccg ctggaagtgc tgacccggag gaagggccc 122940 agacggaggg actcggagcc tccgagtgac accctgggac tccagcgct ggagcctggc 123000 gtcaccccag gcaggggcag tggggggcccg gggcggggtc aggggcctcc cccggttctc 123060
atttgacacc gcggggggtgc gctgggcaca gtgtccaggg gccacgttcc gagcaggggc 123120
gcgatgcagg cccgggcgcg gcctgtcccg ggcgcgagtc cagctgctt gcagaggtgg 123180 cggcaggtcg cagtgaccct cacagagacg ccccactctg cggctccagg tgggcctgtg 123240 cccccccagaa gtgctgacct gtgcaccggg aaggcacagg gcccccccagc catgtctgcg 123300 atggaagagc cggaaccgcg ccatgcccgt cctcgctgac cggcaggcac ccgccgtgtg 123360
tccacacgct gagccatctg gctcccttg cttgacatac acccaggacc tgagtgtgca 123420
ggaagttaga aggggcaggt gtggtgacac gatgccatcc agcatcacct gagaacctgg 123480
acaaacctca ggggcccagc ctgctctgtg aggccccgag ggccggcccc tccccggacc 123540
cctgccttga atccggccac actgcccgcc ttcctgctcc tgcggcttgt cagacacgcc 123600
tgagcccagg gcctgtgcac tcgctgtccc ttctgccagg actgctcctc cccaggctct 123660
tgctggggct cccccttcttc attcggggt ggcctctctt gttcagtggc tcagctgtgc 123720
ccagtctttg caaccccatg gactgcagca cgccaggctt ccctgtcctt cactagctcc 123780
tggagtttgc tcaaactcat gtccattgag tcagtgatgc tatccaacca tctcatcctt 123840
tgctgcccac ttcttctcct gctctcaatc tttcccagca tcagggtctt ttccaatgag 123900
ttagctctct gcatcaggag gccaaagtat tggagcttca gcatcagtcc ttccagtgaa 123960
tatgcgaggt tgatttccct tagaattgac tggttggatc tccttcctgt ccagagaact 124020
ctcaagagtc ttctccagca ccacagtcgg agagcatcag ttcttcagtg atcaggtttc 124080
tttatagccc agctctcaca tcggtacatg actattggaa aacccatagc tttgattaga 124140
```

```
tggaccttca ttggcaaagt gatgggcctt cattggccct gcttttaat acaccatcta  124200 ggtttgtcgt agctttcctt ccaaagagca aacatctttt aatttcctgg ctgcagtaac  124260
catccatagt gattttggag cccaagaaaa taaaatctgc cactgtttcc acttttccc   124320 cttctatttg ctatgaagtg aggggactgg atgccatgat cttagtttaa accagcagtt  124380
gtcaccccga ccgcttcctt tcctaaagag ctcatcacac ctcccactgg aatgcaatgt  124440
gttgcctgtc cgcctgcttc acctcctggg actttgctgc aggtcttggt ctctgaggcc  124500
cctgccgtat ccccagggcc cagagcagtg ctgggcttcg agtccgatca gggactatgt  124560
gtgtggactg gatggtgctt gcttcttctg gggaacgaga gacctgggcc tggggaacga  124620
ggggacctgg tgtgaccgga tctcctccct cgggagagga gccaagcgag tggacacagg  124680
tcagtgtgtc ttgctcctgt gtggcaggtg tcccgtctgt gtctgtcatc ttggcatttc  124740
ggtgtttctg tgaacccagc ccctcccctc ctgataccc  atcccatcag cacagaggag  124800
actgggcttg gggactctct ggtcctgaga ttcctctccg catgtgactc ccccctcctg  124860
gggggagcag gcaccgtgtg tgaggagggt ggaagctttt caagaccccc agcttttctg  124920 tcccagggg ctctggcagg ccttgggag ctggaatgag ctggaatctg gccagtggg    124980 ggtttccctg gtggtaaaga acccgcctgc ccatgcacga ggcataagag acgcgggttc  125040
gatcactggg tcgggaagat cccctacagg agggcatggc aacccactcc agtattcttt  125100
cctgaagaat cccttggaca gaggagcctg gtgggctaca gtctctgggg tggcaaggag  125160
tcggacacga ctgaagcgac ttaccatgca cgcacgcggg gtcaggggtc agggccgcgc  125220
tgcttacctg ctgtgtgacc ttagccaggt cacacccccc aggctgtgaa agagaacagt  125280
cttcccagac tcgggcatcc aggtctttac agacgtgcct gtgagctttg tgactctggc  125340
tctgtggccg ctagagggcg ctgtccgccg ggccctatgt gcgtgcacgc atgtgagcat  125400
gttcgcatac gtgtgtgcat ctgtcggggg cgcacggtgc ggggacacgg gcacgcggtc  125460
aggaacgcag cccggacacc tccacgtggc ccgcgagtac cgtcaggtgg gggctgtggc  125520
tccgctgtgt gggtgacccg ccctcccccc gcgaacgtgg tgcatagtga ccgcctggct  125580
gggctcctga gctcagccat cctgcccccc gggtcagctc ccgacaggcc cagctctagg  125640
ccccaggcgt ggaccgaggc ccccaggccc cggcctgtga gatgggacct ccgtctgggg  125700
ggctcattct gctcccggag gcctggcagg cccctcctct ttggcattgc ataccctcgc  125760
attggggtgg gtaagcacag taccccatgc ctgtggcccc gtgggagcgg cctgctcagg  125820
gaggccggag cctcagctac agggctgtca caccgggctg cagaggaaga agacgggagc  125880
gaggcctaca ggaacctagc caggccctgg cccactgagc cgacaggagc ctggccagag  125940
gcctgcacag gacggggtgg cgggggggt gggtgggt gctgggcccc gtggccttga     126000
ctgcagaccc cgagggctcc tcagcttaga acggccaagc ctgagtcttg ggggtgcagg  126060
tcaggggg                                                          126068
```

<210> SEQ ID NO 32
<211> LENGTH: 10012
<212> TYPE: DNA
<213> ORGANISM: Sus sp.

<400> SEQUENCE: 32

```
gccacgccca ctccatcatg cggggagggg atgggcagac cctccagaaa gaagctccct   60
ggggtgcagg ttaacagctt tcccagacac agccagtact agagtgaggt gaataagaca  120
```

```
tcctccttgc ttgtgaaatt taggaagtgc ccccaaacat cagtcattaa gataaataat    180
attgaatgca cttttttttt tttattttt tttttgctt tttagggcct aatctgcagc      240
atatggaagt tcccaggcta caagtcgaac cagagctgca gctgccagcc tacatcacag    300
ccacagcaac accagatccg agccacatct gtgactaaca ctgcagttca cagcaacgcc    360
agatccttaa cccattgagt gaggccaggg atcaaaccca catcctcatg gatactagtc    420
tggttcgtaa accactgagc cacaagggga actcctgaat gcaatatttt tgaaaattga    480
aattaaatct gtcactcttt cacttaagag tcccctttaga ttggggaaaa tttaaatatc   540
tgtcatctta gtgcatcttt gctcatatga tgtgaataaa atcccaaaat ccatatgaat    600
gaagcatcaa aatgtacatg aagtcagcct gaccctgcac tgccctcact tgcctcatgt    660 acccccacc tcaaaggaag atgcagaaag gagtccagcc cctacaccgc cacctgcccc     720
caccactgga gcccctcagg tctcccacct ccttttctga gcttcagtct tcctgtggca    780
ttgcctacct ctacagctgc cccctactag gccctccccc tggggctgag ctccaggcac    840
tggactggga aagttagagg ttaaagcatg gaaaattccc aaagccacca gttccaggct    900 gcccccacc ccaccgccac gtccaaaaag gggcatcttc ccagatctct ggctggtatt     960
ggtaggaccc aggacatagt ctttataccca attctgctgt gtgtcttagg aaagaaactc  1020
tccctctctg tgcttcagtt tcctcatcaa taaaaggagc aggccaggtt ggagggtctg   1080
tgacgtctgc tgaagcagca ggattctctc tccttttgct ggaggagaac tgatccttca   1140
cccccaggat caacagagaa gccaaggtct tcagccttcc tggggacccc tcagagggaa   1200
ctcagggcca cagagccaga ccctgatgcc agaacctttg tcatatgccc agacggagac   1260 ttcatcccc tcctcctcag accctccagg ccccaacagt gagatgctga agatattaag    1320
agaagggcaa gtcagcttaa gtttgggggt agaggggaac agggagtgag gagatctggc   1380
ctgagagata ggagccctgg tggccacagg aggactcttt gggtcctgtc ggatggacac   1440
agggcggccc gggggcatgt tggagcccgg ctggttctta ccagaggcag ggggcaccct   1500
ctgacacggg agcagggcat gttccataca tgacacaccc ctctgctcca gggcaggtgg   1560
gtggcggcac agaggagcca gggactctga gcaaggggtc caccagtggg gcagttggat   1620
ccagacttct ctgggccagc gagagtctag ccctcagccg ttctctgtcc aggaggggggg  1680 tggggcaggc ctgggcggcc agagctcatc cctcaagggt tcccagggtc ctgccagacc   1740
cagatttccg accgcagcca ccacaagagg atgtggtctg ctgtggcagc tgccaagacc   1800
ttgcagcagg tgcagggtgg gggggtgggg gcacctgggg gcagctgggg tcactgagtt   1860
cagggaaaac ccctttttc ccctaaacct ggggccatcc ctaggggaaa ccacaacttc    1920
tgagccctgg gcagtggctg ctgggaggga agagcttcat cctggaccct gggggggaac   1980
ccagctccaa aggtgcaagg ggcccaggtc caaggctaga gtgggccaag caccgcaatg   2040
gccagggagt gggggaggtg gagctggact ggatcagggc ctccttggga ctccctacac   2100
cctgtgtgac atgttagggt acccacaccc catcaccagt cagggcctgg cccatctcca   2160
gggccaggga tgtgcatgta agtgtgtgtg agtgtgtgtg tgtggtgtag tacaccccttt  2220 ggcatccggt tccgaggcct tgggttcctc caaagttgct ctctgaatta ggtcaaactg   2280
tgaggtcctg atcgccatca tcaacttcgt tctccccacc tcccatcatt atcaagagct   2340
ggggagggtc tgggatttct tcccacccac aagccaaaag ataagcctgc tggtgatggc   2400
agaagacaca ggatcctggg tcagagacaa aggccagtgt gtcacagcga gagaggcagc   2460
cggactatca gctgtcacag agaggcctta gtccgctgaa ctcaggcccc agtgactcct   2520
```

-continued

```
gttccactgg gcactggccc cctccacag cgccccagg ccccagggag aggcgtcaca    2580
gcttagagat ggccctgctg aacagggaac aagaacaggt gtgccccatc cagcgcccca    2640
ggggtgggac aggtgggctg gatttggtgt gaagcccttg agccctggaa cccaaccaca    2700
gcagggcagt tggtagatgc catttgggga gaggccccag gagtaagggc catgggccct    2760
tgagggggcc aggagctgag gacagggaca gagacggccc aggcagagga cagggccatg    2820
aggggtgcac tgagatggcc actgccagca ggggcagctg ccaacccgtc cagggaactt    2880
attcagcagt cagctggagg tgccattgac cctgagggca gatgaagccc aggccaggct    2940
aggtgggctg tgaagacccc aggggacaga gctctgtccc tgggcagcac tggcctctca    3000
ttctgcaggg cttgacggga tcccaaggcc tgctgcccct gatggtagtg cagtaccgc    3060 ccagagcagg accccagcat ggaaacccca acgggacgca gcctgcggag cccacaaaac    3120
cagtaaggag ccgaagcagt catggcacgg ggagtgtgga cttccctttg atggggccca    3180
ggcatgaagg acagaatggg acagcggcca tgagcagaaa atcagccgga ggggatgggc    3240
ctaggcagac gctggcttta tttgaagtgt tggcattttg tctggtgtgt attgttggta    3300 ttgatttat tttagtatgt cagtgacata ctgacatatt atgtaacgac atattattat    3360
gtgttttaag aagcactcca agggaacagg ctgtctgtaa tgtgtccaga aagagagca    3420 agagcttggc tcagtctccc ccaaggaggt cagttcctca acaggggtcc taatgtttc    3480 ctggagccag gcctgaatca aggggtcat atctacacgt ggggcagacc catgaccat    3540 tttcggagca ataagatggc agggaggata ccaagctggt cttacagatc cagggctttg    3600
acctgtgacg cgggcgctcc tccaggcaaa gggagaagcc agcaggaagc tttcagaact    3660
ggggagaaca gggtgcagac ctccagggtc ttgtacaacg cacccttat cctggggtcc    3720 aggaggggtc actgagggat ttaagtgggg gaccatcaga accaggtttg tgttttggaa    3780
aaatggctcc aaagcagaga ccagtgtgag gccagattag atgatgaaga agaggcagtg    3840
gaaagtcgat gggtggccag gtagcaagag ggcctatgga gttggcaagt gaatttaaag    3900
tggtggcacc agagggcaga tggggaggag caggcactgt catggactgt ctatagaaat    3960
ctaaaatgta tacccttttt agcaatatgc agtgagtcat aaaagaacac atatatattt    4020
aaattgtgta attccacttc taaggattca tcccaagggg ggaaaataat caaagatgta    4080
accaaaggtt tacaaacaag aactcatcat taatcttcct tgttgttatt tcaacgatat    4140
tattattatt actattatta ttattattat tttgtctttt tgcattttct agggccactc    4200
ccacggcata gagaggttcc caggctaggg gtcaaatcgg agctacagct gccggcctac    4260
gccagagcca cagcaacgca ggatctgagc cacagcaatg caggatctac accacagctc    4320
atggtaacgc tggatcctta acccaatgag tgaggccagg gatcgaacct gtaacttcat    4380
ggttcctagt cggattcatt aaccactgag ccacgacagg aactccaaca ttattaatga    4440
tgggagaaaa ctgaagtaa cctaaatatc cagcagaaag ggtgtggcca aatacagcat    4500
ggagtagcca tcataaggaa tcttacacaa gcctccaaaa ttgtgtttct gaaattgggt    4560
ttaaagtacg tttgcatttt aaaaagcctg ccagaaaata cagaaaaatg tctgtgatat    4620
gtctctggct gataggattt tgcttagttt aattttggc tttataattt tctatagtta    4680
tgaaaatgtt cacaagaaga tatatttcat tttagcttct aaaataatta taacacagaa    4740
gtaatttgtg cttaaaaaaa atattcaaca cagaagtata taagtaaaaa attgaggagt    4800
tcccatcgtg gctcagtgat taacaaaccc aactagtatc catgaggata tggatttgat    4860
```

-continued

```
ccctggcctt gctcagtggg ttgaggatcc agtgttgctg tgagctgtgg tgtaggttgc    4920
agacacagca ctctggcgtt gctgtgactc tggcgtaggc cggcagctac agctccattt    4980
ggacccttag cctgggaacc tccatatgcc tgagatacgg ccctaaaaag tcaaaagcca    5040
aaaaaatagt aaaaattgag tgtttctact taccacccct gcccacatct tatgctaaaa    5100
cccgttctcc agagacaaac atcgtcaggt gggtctatat atttccagcc ctcctcctgt    5160
gtgtgtatgt ccgtaaaaca cacacacaca cacacacacg cacacacaca cacacgtatc    5220
taattagcat tggtattagt ttttcaaaag ggaggtcatg ctctacccttt taggcggcaa    5280
atagattatt taaacaaatc tgttgacatt ttctatatca acccataaga tctcccatgt    5340
tcttggaaag gctttgtaag acatcaacat ctgggtaaac cagcatggtt tttagggggt    5400
tgtgtggatt tttttcatat tttttagggc acacctgcag catatggagg ttcccaggct    5460
aggggttgaa tcagagctgt agctgccggc ctacaccaca gccacagcaa cgccagatcc    5520
ttaacccact gagaaaggcc agggattgaa cctgcatcct catggatgct ggtcagattt    5580
atttctgctg agccacaaca ggaactccct gaaccagaat gcttttaacc attccacttt    5640
gcatggacat ttagattgtt tccatttaaa aatacaaatt acaaggagtt cccgtcgtgg    5700
ctcagtggta acgaattgga ctaggaacca tgaggtttcg ggttcgatcc ctggccttgc    5760
tcggtgggtt aaggatccag cattgatgtg agatatggtg taggtcgcag acgtggctcg    5820
gatcccacgt tgctgtggct ctggcgtagg ccggcaacaa cagctccgat tcgaccccta    5880
gcctgggaac ctccatgtgc cacaggagca gccctagaaa aggcaaaaag acaaaaaaat    5940
aaaaaattaa aatgaaaaaa taaaataaaa atacaaatta caagagacgg ctacaaggaa    6000
atccccaagt gtgtgcaaat gccatatatg tataaaatgt actagtgtct cctcgcggga    6060
aagttgccta aaagtgggtt ggctggacag agaggacagg ctttgacatt tcataggta    6120
gtagcaatgg gcttctcaaa atgctgttcc agtttacact caccatagca aatgacagtg    6180
cctcttcctc tccaccctg ccaataatgt gacaggtgga tcttttttcta ttttgtgtat    6240
ctgacaagca aaaaatgaga acaggagttc ctgtcgtggt gcagtggaga caaatctgac    6300
taggaaccat gaaatttcgg gttcaatccc tggcctcact cagtaggtaa aggatccagg    6360
gttgcagtga gctgtggggt aggtcgcaga cacagtgcaa atttggccct gttgtggctg    6420
tggtgtaggc cggcagctat agctccaatt ggacccctag cctgggaacc tccttatgcc    6480
gtgggtgagg ccctaaaaaa aagagtgcaa aaaaaaaaaa taagaacaaa aatgatcatc    6540
gtttaattct ttatttgatc attggtgaaa cttattttcc ttttatattt ttattgactg    6600
atttttatttc tcctatgaat ttaccggtca tagttttgcc tgggtgtttt tactccggtt    6660
ttagttttgg ttggttgtat tttcttagag agctatagaa actcttcatc tatttggaat    6720
agtaattcct cattaagtat ttgtgctgca aaaaattttc cctgatctgt tttatgcttt    6780
tgtttgtggg gtctttcacg agaaagcctt tttagttttt acacctcagc ttggttgttt    6840
ttcttgattg tgtctgtaat ctgcggccaa cataggaaac acattttac tttagtgttt    6900
ttttcctatt ttcttcaagt acgtccattg ttttggtgtc tgattttact ttgcctgggg    6960
tttgttttttg tgtggcagga atataaactt atgtattttc caaatggaga gccaatggtt    7020
gtatatttgt tgaattcaaa tgcaacttta tcaaacacca aatcatcgat ttatcacaac    7080
tcttctctgg tttattgatc taatgatcaa ttcctgttcc acgctgtttt aattatttta    7140
gctttgtgga ttttggtgcc tggtagagaa caaagcctcc attattttca ttcaaaatag    7200
tcccgtctat tatctgccat tgttgtagta ttagacttta aaatcaattt actgattttc    7260
```

```
aaaagttatt cctttggtga tgtggaatac tttatacttc ataaggtaca tggattcatt  7320 tgtgggaat  tgatgtcttt gctattgtgg ccatttgtca agttgtgtaa tattttaccc   7380
atgccaactt tgcatattgt atgtgagttt attcccaggg ttttaatag  gatgtttatt   7440 gaagttgtca gtgtttccac aatttcatcg cctcagtgct tactgtttgc ataaaaggaa  7500
acctactcac ttttgcctat tgctcttgta ttcaatcatt ttagttaact cttgtgttaa  7560
ttttgagagt ttttcagctg actgtctggg ttttcttta  atagactagc cctttgtctg  7620
taaagaataa ttttatcgaa ttttcttaa  cactcacact ctccccaccc ccaccccgc   7680 tcatctcctt tcattgggtc aaatctgtag aatacaataa agtaagagt  gggaaccta   7740 gcctttaagt cgattttgcc tttaaatgtg aatgttgcta tgtttcggga cattctcttt  7800
atcaagttgc ggatgtttcc ttagataatt aacttaataa agactggat  gtttgctttc  7860 ttcaaatcag aattgtgttg aatttatatt gctattctgt ttaattttgt ttcaaaaaat  7920
ttacatgcac accttaaaga taaccatgac caaatagtcc tcctgctgag agaaaatgtt  7980
ggccccaatg ccacaggtta cctcccgact cagataaact acaatgggag ataaaatcag  8040
atttggcaaa gcctgtggat tcttgccata actctcagag catgacttgg gtgttttttc  8100
cttttctaag tattttaatg gtattttgt  gttacaatag gaaatctagg acacagagag  8160
tgattcaatg aggggaacgc attctgggat gactctaggc ctctggtttg gggagagctc  8220
tattgaagta aagacaatga gaggaagcaa gtttgcaggg aactgtgagg aatttagatg  8280
gggaatgttg ggtttgaggt ttctataggg cacgcaagca gagatgcact caggaggaag  8340
aaggagcata aatctagagg caaaaagaga ggtcaggact ggaaatagag atgcgagaca  8400
ccagggtggc agtcagagag cacagtgtgg gtcagaagac agtggaagaa cacaagggac  8460
agagagggat ctccaacttc actgggatga gggccttgtt ggccttgacc tgagagattt  8520
ccaggagttg agggtgggaa ggagagggct cctgcacatg tcctgacatg aaacggtgcc  8580
cagcatatgg gtgcttggaa gacattgttg gacagatgga tggatgatgg atgatggatg  8640
aatggatgga tggaagatga tggataaatg gatgatggat ggatgaacag aaggacaaag  8700
agatggacag aaagacagtg atctgagaga gcagagaagg cttcatgaaa ggacaggaac  8760
tgaactgtct cagtgggtgg agacaatggt gtaggggggtt tccacatgga ggcaccaggg  8820
gtcaggaata atctagtgtc cacaggccca ggaaggaagc tgtctgcagg aaattgtggg  8880
gaagaacctc agagtcctta aatgaggtca ggagtggtca ggagggtctg atcaggtaag  8940
gactcatgtc catcatcaca tggtcaccta agggcatgta gctctcagca tctccatcag  9000
gacagtctca gaatggggggc ggggtcacac actgggtgac tcaaggcgtg ggtcatgcct  9060
gcctcggacg tgggcctggg catggggaca cctccagacc atgggcccgc ccagggctgc  9120
actggcctct ggtgggctag ctacccgtcc aagcaacaca ggacacagcc ctacctgctg  9180
caaccctgtg cccgaaacgc ccatctggtt cctgctccag cccggcccca gggaacagga  9240
ctcaggtgct agcccaatgg ggttttgttc gagcctcagt cagcgtggta tttctccggc  9300
agcgagactc agttcaccgc cttaggttaa gtggttctca tgaatttcct agcagtcctg  9360
cactctgcta tgccgggaaa gtcacttttg tcgctggggg ctgtttcccc gtgcccttgg  9420
agaatcaagg attgcccaac tttctctgtg ggggaggtgg ctggtcttgg ggtgaccagc  9480
aggaagggcc ccaaaagcag gagcagctgc ctccagaata caactgtcgg ctacagctca  9540
aacaggaggc ctggactggg gtttaaccac cagggcggca cgaaggagcg aggctgggag  9600
```

-continued

| | |
|---|---|
| ggtgaggaca tgggagcctg aggaggagct ggagacttca gcaggccccc agctccgggc | 9660 |
| ttcgggctct gagatgctcg gacgcaaggt gagtgacccc acctgtggct gacctgacct | 9720 |
| caggggaca aggctcagcc tgagactctg tgtccccatc gcctgcacag gggattcccc | 9780 |
| tgatggacac tgagccaacg acctcccgtc tctccccgac ccccaggtca gcccaaggcc | 9840 |
| gcccccacgg tcaacctctt cccgccctcc tctgaggagc tcggcaccaa caaggccacc | 9900 |
| ctggtgtgtc taataagtga cttctacccg aagggcgaat ccagcacac tggcggccgt | 9960 |
| tactagtgga tccgagctcg gtaccaagct tgatgcatag cttgagtatc ta | 10012 |

<210> SEQ ID NO 33
<211> LENGTH: 4614
<212> TYPE: DNA
<213> ORGANISM: Sus sp.

<400> SEQUENCE: 33

| | |
|---|---|
| agatctttaa accaccgagc aaggccaggg atcgaacccg catcctcatg aatcctagtt | 60 |
| gggttcgtta accgctgaac cacaatggga actcctgtct ttcacattta attcacaacc | 120 |
| tctccaggat tctgggggtg ggtggggaat cctaggtacc cactgggaaa gtaatccaag | 180 |
| gggagaggct cacggactct agggatcggc ggaggaggga aggtatctcc caggaaactg | 240 |
| gccaggacac attggtcctc cgccctcccc ttcctcccac tcctcctcca gacaggactg | 300 |
| tgcccacccc ctgccacctt tctggccaga actgtccatg gcaggtgacc ttcacatgag | 360 |
| cccttcctcc ctgcctgccc tagtgggacc ctccatacct cccctggac cccgttgtcc | 420 |
| tttctttcca gtgtggccct gagcataact gatgccatca tgggctgctg acccacccgg | 480 |
| gactgtgttg tgcagtgagt cacttctctg tcatcagggc tttgtaattg atagatagtg | 540 |
| tttcatcatc attaggaccg ggtggcctct atgctctgtt agtctccaaa cactgatgaa | 600 |
| aaccttcgtt ggcatagtcc cagcttcctg ttgcccatcc ataaatcttg acttagggat | 660 |
| gcacatcctg tctccaagca accacccctc ccctaggcta actataaaac tgtcccaatg | 720 |
| gcccttgtgt ggtgcagagt tcatgcttcc agatcatttc tctgctagat ccatatctca | 780 |
| ccttgtaagt catcctataa taaactgatc cattgattat ttgcttctgt tttttccatc | 840 |
| tcaaaacagc ttctcagttc agttcgaatt ttttattccc tccatccacc catactttcc | 900 |
| tcagcctggg gaacccttgc ccccagtccc atgcccttcc tccctctctg cccagctcag | 960 |
| cacctgccca ccctcaccct tcctgtcact ccctaggact ggaccatcca ctggggccag | 1020 |
| gacactccag cagccttggc ttcatgggct ctgaaatcca tggcccatct ctattcctca | 1080 |
| ctggatggca ggttcagaga tgtgaaaggt ctaggaggaa gccaggaagg aaactgttgc | 1140 |
| atgaaaggcc ggcctgatgg ttcagtactt aaataatatg agctctgagc tccccaggaa | 1200 |
| ccaaagcatg gagggagtat gtgcctcaga atctctctga gattcagcaa agcctttgct | 1260 |
| agagggaaaa tagtggctca accttgaggg ccagcatctt gcaccacagt taaaagtggg | 1320 |
| tatttgtttt acctgaggcc tcagcattat gggaaccggg ctctgacaca aacacaggtg | 1380 |
| cagcccggca gcctcagaac acagcaacga ccacaagctg ggacagctgc cctgaacgg | 1440 |
| ggagtccacc atgcttctgt ctcgggtacc accaggtcac catccctggg ggaggtagtt | 1500 |
| ccatagcagt agtcccctga tttcgcccct cgggcgtgta gccaggcaag ctcctgcctc | 1560 |
| tggacccagg gtggaccctt gctccccact accctgcaca tgccagacag tcaagaccac | 1620 |
| tcccacctct gtctgaggcc cccttgggtg tcccagggcc cccgagctgt cctctactca | 1680 |
| tggttcttcc acctgggtac aaaagaggcg aggacacttt ttctcaggtt tgcggctcag | 1740 |

```
aaaggtacct tcctagggtt tgtccactgg gagtcacctc ccttgcatct caatgtcagt    1800 gggggaaaact gggtcccatg gggggattag tgccactgtg aggcccctga agtctggggc    1860
ctctagacac tatgatgatg agggatgtgg tgaaaaaccc caccccagcc cttcttgccg    1920
ggaccctggg ctgtggctcc cccattgcac ttggggtcag aggggtggat ggtggctatg    1980
gtcaggcatg tttcccatga gctgggggca ccctgggtga ctttctcctg tgaatcctga    2040
attagcagct ataacaaatt gcccaaactc ttaggcttaa acaacacac atttattcct     2100 ctgggtccca gggtcagaag tccaaaatga gtcctatagg ctaaatttga ggtgtctctg    2160
ggttgagctc ctcctggaag cctttttccag cctctagagt cccaagtcct ggctctggg    2220 cccctccctc aagcttcaaa gccacagaag cttctaatct ctctcccttc ccctctgacc    2280
tctgctccca tcctcatacc ctgtcccctc actctgaccc tcctgcctcc ctctttccct    2340
tataaagacc ctgcatgggg ccacggagat aatccagggt aatcgcccct cttccagccc    2400
ttaactccat cccatctgca aaatcccgt cacccataa tggacctact gatggtctgg     2460
gggttaggac gtggacaact tggggcctta ttcatctgat cacaactcca gttcccagac    2520
ccccagaccc ccgggcatta gggaaacttc tcccagttcc tctccctctg tgtcctgccc    2580
agtctccagg atgggccact cccgagggcc cttcagctca ggctcccct cctttctccc     2640 tggcctcttg tggcccccatc tcctcctccg ctcacaggga gagaactttg atttcagctt    2700
tggctctggg gctttgcttc cttctggcca ttggctgaag ggcgggtttc tccaggtctt    2760
acctgtcagt catcaaaccg cccttggagg aagaccctaa tatgatcctt accctacaga    2820
tggagactcg aggcccagag atcctgagtg acctgctcac attcacagca gggactgaac    2880
cccagtcacc tacccaactc cagggctcag cgcttttttt tttttttttc ttttttgcctt   2940 ttcgagggcc gctcccgcaa catatggaga tttccaggct aggggtctaa ttggagcagt    3000
cgacactggc ctaagccaaa gccacagcaa caagggcaag ccgcttctgc agcctatacc    3060
acagctcacg gcaatgccgg atccttaacc cactgagcaa agccagggat tgaacctgca    3120
acctcatgtt tcctagtcaa atttgttaac cactgaccca tgacgggaac tcccagggct    3180
cagctcttga ctccaggttc gcagctgccc tcaaagcaat gcaaccctgg ctggccccgc    3240
ctcatgcatc cggcctcctc cccaaagagc tctgagccca cctgggccta ggtcctcctc    3300
cctgggactc atggcctaag ggtacagagt tactggggct gatgaaggga ccaatgggga    3360
caggggcctc aaatcaaagt ggctgtctct ctcatgtccc ttcctctcct cagggtccaa    3420
aatcagggtc agggccccag ggcaggggct gagagggcct cttctgaag gccctgtctc     3480 agtgcaggtt atgggggtct gggggagggt caatgcaggg ctcacccttc agtgccccaa    3540
agcctagaga gtgagtgcct gccagtggct tccaggccc aatcccttga ctgcctggga     3600
atgctcaaat gcaggaactg tcacaacacc ttcagtcagg ggctgctctg ggaggaaaaa    3660
cactcagaat tggggttca gggaaggccc agtgccaagc atagcaggag ctcaggtggc     3720
tgcagatggt gtgaacccca ggagcaggat ggccggcact ccccccagac cctccagagc    3780
cccaggttgg ctgccctctt cactgccgac acccctgggt ccacttctgc cctttcccac    3840
ctaaaacctt tagggctccc actttctccc aaatgtgaga catcaccacg ctcccaggg    3900 agtgtccaga agggcatctg gctgagaggt cctgacatct gggagcctca ggccccacaa    3960
tggacagacg ccctgccagg atgctgctgc agggctgtta gctaggcggg gtggagatgg    4020
ggtactttgc ctctcagagg ccccggcccc accatgaaac ctcagtgaca ccccatttcc    4080
```

```
ctgagttcac ataccgtgtat cctactccag tcaccttccc cacgaacccc tgggagccca    4140
ggatgatgct ggggctggag ccacgaccag cccacgagtg atccagctct gccaatcagc    4200
agtcatttcc caagtgttcc agccctgcca ggtcccacta cagcagtaat ggaggcccca    4260
gacaccagtc cagcagttag agggctggac tagcaccagc tttcaagcct cagcatctca    4320
aggtgaatgg ccagtgcccc tccccgtggc catcacagga tcgcagatat gaccctaggg    4380
gaagaaatat cctgggagta aggaagtgcc catactcaag gatggcccct ctgtgaccta    4440
acctgtccct gaggattgta cttccaggcg ttaaaacagt agaacgcctg cctgtgaacc    4500
cccgccaagg gactgcttgg ggaggccccc taaaccagaa cacaggcact ccagcaggac    4560
ctctgaactc tgaccaccct cagcaagtgg cacccccgc agcttccaag gcac          4614
```

<210> SEQ ID NO 34
<211> LENGTH: 1151
<212> TYPE: DNA
<213> ORGANISM: Sus sp.

<400> SEQUENCE: 34

```
aacaagatgc taccccacca acaaaattca ccggagaaga caaggacagg gggttcctgg    60
ggtcctgaca gggtcaccaa agagggttct ggggcagcag caactccagc cgcctcagaa    120
cagagcctgg aagctgtacc ctcagagcag aggcggagag agaaagggcc tcttggtggg    180
tcagcaggag cagaggctca gaggtggggg ttgcagcccc cccttcaaca ggccaacaca    240
gtgaagcagc tgacccctcc accttggaga ccccagactc ctgtctccca cgccaccttg    300 gttttttaagg taatttttat tttatatcag agtatggttg acttacaatg ttgtgttggt    360
ttcaggtgta cagcagagtg attcacttct acatagactc atatctattc tttctcagat    420
tcttttccca tataggttat tacagaatat tgagtagatc cctgctgatt acccattttt    480
ataattgtat atgttaatcc caaactccta atttatccct ccccagacta tgattcttta    540
tatctctatc tgttttcctaa tctgtctcct ctaagtcacc ctaggagagc agaggggtca    600
cgtctgtcct gtcctggccc agccacctct ctccacccag gaatcccttg catttggtgc    660
caagggcccg gccccgccct aaagagaaag gagaacggga tgtggacagg acaccgggca    720
gagagggaca agcagaggat gccagggtag ggaggtctcc agggtggatg gtggtctgtc    780
cgcaggcagg atgaggcagg aagggtgtgg atgtactcgg tgaggctggc gcatggcctg    840
gagtgtcctg agccctggga ggcctcagcc ctggatcaga tctgtgattc caaagggcca    900
ctgcatccag agaccgttga gtgggccatt gtcctgaacc atttatagaa cacaggacaa    960
gcggtacctg actaagctgc tcacagattc catgaggctg atgccagggt tgtcacccca    1020
tctcacaggc agggaaactg atgcatatac tgcagagcca ggcagaggcc ctcccagtgc    1080
cccctcccag cctgtggccc cctccagtg gctggacact gaggccacac tgggggcaccc    1140 tgtggagatc t                                                         1151
```

<210> SEQ ID NO 35
<211> LENGTH: 630
<212> TYPE: DNA
<213> ORGANISM: Sus sp.

<400> SEQUENCE: 35

```
agatctggcc aggccagaga agcccatgtg gtgacctccc tccatcactc cacgccctga    60
cctgccaggg agcagaaagt aggcccaggg tggacccggt ggccaccgtc accccatgg    120 ctgggagaag ggagggcctg ggcaaagggc ctgggaagcc tgtggtggga ccccagaccc    180
```

```
cagggtggac agggagggtc ccacacccac agccatttgc ttccctctgt ggttcagtg      240 tcctcatctc atctgtgggg aggggctga taatgaatct cccccattgg ggtgggcttg      300
gggattaaag ggccagtgtc tgtgatatgc ctggaccata gtgaccctca ccctccccag     360
ccattgctgt caccttccgg gctcttgccc aggcctgcct acatgctgt gtgaccctgg      420 gcaagatgat cccccttcct gggccccagc cttcctctct gctccggaag tgcttcctgg     480
ggaaacctgt gggctggatc ctataggaaa cctgtccaat tcctggatgc acagagggc     540 agggaggccc tgggcctgga ggggcaggga ggctcgaggt gggagcaggg taggggccag    600
tccagggcaa ggaggtgggt gggtagggtg                                       630

<210> SEQ ID NO 36
<211> LENGTH: 947
<212> TYPE: DNA
<213> ORGANISM: Sus sp.

<400> SEQUENCE: 36
gatctgtgtt ccatctcaga gctatcttag cagagaggtg caggggcctc cagggccacc     60
aaagtccagg ctcagccaga ggcaatgggg tatcgatgag ctacaggaca caggcgtcag     120
cccagtgtca gggagaatca ccttgtttgt tttctgagtt cctcttaaaa tagagttaat     180
tggtcttggc cttacggttt acaataacaa ctgcaccctg taaacaacgt gaagagtaca     240
gaacaacaaa tgggggaaaa catatttcac ctgaaagagc caccgctcat attttgatgg    300
atttccttct agtttaatcc tgttttaatt gtaaactgtt aaaacaaaca taaataaaga     360
aaatgcatct gtaaagttta aaagtcatat ctatggtgat ggttgcaaaa cactgtgaat    420
gttcactttg aaatcgtgaa ctctacgtga tatgcatgtc ccgttaatta acctcacagg    480
ctcagaatgt ggttcattat ttctttaatt ttcctttaat tttatgtcct ctgtgtgtgc    540 ccttaaaacca actactttc agctctgcct gttttgacc ttcacataga tgacatttgt     600
gagtgttttc tttctcaaca ctgggtctga taccccaccca cgctgtctgc tgtcactgcg    660
gacgtggagg gccaccaccc agctatggcc ccagccaggc caacactgga tgaatctgcc    720
cccagagcag ggccaccaac actggagtg cagagagggt ttcttcaggg ccatcattat     780
ccaaggcatt gtttctactg taagctttca aaatgcttcc cctgattatt aaaagaaata    840
ataagatggg gggaaagtac aagaagggaa gtttccagcc cagcctgaag atcgtgctgg    900
ttgtatctgg agcctgtctt cctgacaggc ctctattccc agagtta                    947

<210> SEQ ID NO 37
<211> LENGTH: 2067
<212> TYPE: DNA
<213> ORGANISM: Sus sp.

<400> SEQUENCE: 37
ggatcctagg gaagggaggg cggggccctg gacaaagggg gcctaaagga cattctcacc     60
tatcccactg gaccctgct gtgctctgag ggagggagca gagaggggt ctgaggcctt      120 ttcccagctc ctctgagtcc ctcctccgag cacctggacg gaagcccctc ctcagggagt    180
cctcagaccc ctccctcca gccaggttgg cctgtgtgga gtcccagta agaatagaat     240 gctcagggct tcgagctgag ccctggctac ttgggggggt gctgggatt ggggtgctg     300 ggcggggagc tggggtgtca ctagatgcca gtaggctgtg ggctcgggtc tggggggtct   360
gcacatgtgc agctgtggga aggccctatt ggtggtaccc tcagacacat atggcccctc   420
```

```
aatttctgag accagagacc ccagtctggc cttcccagaa cagctgcccc tggtgggggga      480
gatgtagggg ggccttcagc ccaggacccc caacggcagg gcctgaggcc cccatccect      540
tgtcctgggc ccagagcctc agctatcagg cctatcagag atcctggctg cccagctcag      600
gttccccagg agccagaggg aggccagggg ttactaggaa atccggaaag ggtcttttgag     660
gctgggcccc accctctcag cttttcacagg agaaacagag gcccacaggg ggcaaaggac     720
ttgccagact cacaatgagc ccagcagctg gactcaaggc ccagtgttcg gccccacaac      780
agcactcacg tgcccttgat cgtgaggggc cccctctcag ccaggcattc agacctgtga     840
cctgcatcta agattcagca tcagccattc tgagctgaag agccctcagg gtctgcagtc     900
aaggccacag ggccagacct ccaacggcca gacatcccag ccagattcct ttctggtcaa     960
tgggccccag tctggcttgg ctcctgcagg cccagtgccg ccttcttccc ctgggcctgt    1020
ggagtccagc ctttcagttt cccacccaca tcctcagcca caatccaggc tcagaggcaa    1080
tgtccgtggg cagcccctgt gtgacccctc tgtgggtgat cctcagtcct acccttagca    1140
gacagcgcat gagggggccct cttgaacctg agggatactc catgtcggag gggagaagct   1200
ggccttcccc accccacctt ccaggccttg gggagcagag aaagaccccca gacctgggtc    1260
ccttctaaca ggccaggccc cagcccagct ctccaccagc cccaggggcc tcgggtccac     1320
gcctggggac tggaggggtgg gcctgtcagg cgctgaccca gaggcaggac agccaagttc   1380
aggatcccag ccaggtggtc cccgtgcacc atgcaggggg gtcacccaca caggggtgtt     1440
gccacccctca cctgactgtc ctcatgggcc acatggaggt atcctgggtt cattactggt     1500
caacataccc gtgtccctgc agtgccccct ctggcgcacg cgtgcacgcg cacacgcaca     1560
cactcataca gaggctccag ccaacagtgc cctctagtag gcactgctgt cacttctcta     1620
aaaggtcgca atcatacttg taaagaccca agattgttca gaaatcccag atggagaagt     1680
ctggaaagat ctttttctcc tttcacgggc tggggaaatg tgacctggcc aaggtcacac     1740
agcaagtggt ggaaccctgg ccctgatc cagctcattc cagttcccaa ggccctgcca     1800
gagcccagag gctgggccct ctggggcaga ggagctgggg tcctcccccc tacacagagc    1860
acacagcccc gcaagagaga agagacacct tggggagagg aatctccaga ccagagatcc    1920
cagtatgggt ctcctctatg ctgacgggat gggatgtcaa gaggggaggg ggctgggctt     1980
tagggaaaca cacaaaaatc gctgagaaca ctgacaggtg cgacacaccc accctaatg     2040
ctaacctgtg gcccattact cagatct                                        2067
```

<210> SEQ ID NO 38  
<211> LENGTH: 4898  
<212> TYPE: DNA  
<213> ORGANISM: Sus sp.

<400> SEQUENCE: 38

```
gatcttctcc taagaccaag gaaaactggt cataccaggt ccacttgtcc cctgtggcca       60
ttgtccctcc ttccccagaa gaaacaagca ctttccactc cacaagtagc tcctgatcag      120
cttggaagcc cggtgctgct ctgggccctg ggacacggc aggggcatca gagaccaaat       180
cctgaacaa agttccagtg ggtgaggcag gccggacaag caacacgtta ccataata        240
tgaggcaaaa tataatgtga gttctttatg aaaggaaggg gttgcaggtg caactgttgg     300
cttaggtgga tggtcacccc tgaatggagg aggggttcc cagggcatgt gcctggggag     360
aagggctcct ggcaggaggg acagcaagtg caagggccct gtgatcaaat gtgcctggca   420
agttgcagga acagctagaa ggccagcaag gttggaacca aggaagggt caggggaggg    480
```

```
gcagggccct cagggccttg cccagcagcc tgagcatctg gagatttgtc caaagtttca    540
aatgtacctg ggcaacctca tgcccatata ccattcctaa cttctgcact taacatctct    600
aggactggga cccagccagt caagcggggg gacccagaga gctccggtgt gaacaccgag    660
gtgctggtgg gtctgcgtgt gtggacatag ggcagtcccg gtccttcctt cactaacacg    720
gcccgggaag ccctgtgcct ccctggtgcg cgggtcggcg cttccggagg gtacaggccc    780
acctggagcc cgggcacagt gcatgcaagt cgggttcacg gcaacctgag ctggctctgc    840
agggcagtgg gactcacagc caggggtaca gggcagaccg gtcctgcctc tgcgcccctc    900
cctggcctgt ggcccctgga cgtgatcccc aacagttagc atgccccgcc ggtgctgaga    960
acctggacga ggtccgcagg cgtcactggg cggtcactga gcccgcccca ggcccctct   1020
gccccttcct ggggtgaccg tggactcctg gatgaccctg gacccagac ttcccagggt   1080
gtctcgcgga ggttcctcag ccaggatctc tgcgtctcct ccttccatag aggggacggc   1140
gccccttgt ggccaaggag gggacggtgg gtcccggagc tggggcggag aacacaggga   1200
gcccctccca gacccgctc tgggcagaac ctgggaaggg atgtggccat cggggatcc   1260
ctccaggcca tctcctcaga tgggggctgg tcgactagct tctgagtcct ccaaggaacc   1320
gggtccttct agtcatgact ctgcccagat gaagaaggag agcacttctc tccatcagga   1380
ggatctgagc ttctcttaat tagaatcagc tccttggctt ctaccccta aaaaaaggta   1440
cagaaacttt gcaccttgat ccagtatcag gggaatttat caatcaatgt gggagaaatt   1500
ggcatcttta ccacactgaa tctttcaatc catgaatatc ctctctctct tccatgcata   1560
ggttttaata attctcaatg gagtttaatg taagttttcc tcatagacaa ttgcctttgg   1620
acatctcttt agactcatct ctagtaaact gatattctta atgcaattat aaaatgtatc   1680
ctgcttaatg ttatttcta ttcatttgct gttatataga gatacaatga gtttccacat   1740
ttgaaactgg atctggtaaa ttggctaccc ttttttata gattctatta attttatac   1800
attctgtggg acttgctaca tacttaatca tgtcacctgt gaagaatgac aatttggttg   1860
ctaccctccc aattcttata tgtctcattt cttttcctct gctggtactc tggcagcagc   1920
agggaagata atgggcctcc ttatcttgtc acaaaaggat gtttttaaag atttcgttat   1980
aaaacataac gctttctggt tttctttaaa gattctctca ccagcttaag aaaattttct   2040
tatactctgt atgataaatg ggttttgac aatcatttgt tgcattttac ctagtgtttt   2100
ctctgcatct ttatatgctt tttctccttt aatcctgaaa attgtttcga ttttctaac   2160
attgaaccaa tcttacattc ctggaatgga tggaccagac tagtccacat gtttattctg   2220
cccaatggct agattttgtg ttcaatattt tgttcagaat gtttgcatct atattcttga   2280
gtgagacaga gctgccttg ttaggtttca caaccgaggt tgtgttagct tcataaaatg   2340
agacgtttat tctctaaaag aattgtttcg cttctctgga tgaatttgtg taaggttaga   2400
attgcttacc agtgaagatc tcggggccag ttcttcttta ggggaagatt ttcaacaatt   2460
aagctcaatg cctttagaag aactgagagt ttctattatt tcttgagtta aatatatgta   2520
tttaattaga ctttctagga atagtctcat ttcatctcaa ataattgaca tatgctatta   2580
aagcagattc tcatgaacca ttgtaggtat tccaggtcta gaaaaatgtt ccccttttgca   2640
tccctaatgt gtttaatttt caccttcttt cttttgttct tgagaaattc accaaatcat   2700
ttcaatttc agtcatatcc caaagcaacc aactctctac cttcttgttt tatcatccct   2760
gctggatttt tgttatctac ttcttcagta tttgttcttc cctttcttct attcctcatt   2820
```

```
ccattttttcc cttgttttct aactttctga gatatatgct tagttccttc atttgaagcc    2880
tttttatttt ctttttttttt ttttggtctt tttgtctttt gttgttgttg ttgtgctatt    2940
tcttgggccg ctcccgcggc atatggaggt tcccaggcta ggagtcgaat cggagctgta    3000
gccaccggcc tacgccagag ccacagcaat gcgggatccg agccgcgtct gcaacctaca    3060
ccacagctca tggcaacgcc ggatcgttaa cccactgagc aagggcagga accgaacccg    3120
caacctcatg gttcctagtc ggattcgtaa ccactgtgcc acaacaggaa ctccgccttt    3180
ttatttctta taaaaatttc tatgtacatt ttaaggttat aggtttcctt ctatgtaccc    3240
cattggctgt atcctcaggg ttctgtggag tgatttcatt attgttcaag ttcaatatgt    3300
cttctgattt tccaatttga atacctctct aaatcagtag gtgaatattt cttttctttt    3360
ttcttttctt ttcttcttttt ttttttttctt tcagccaggt ccatggcatg cagaaattcc    3420
caggccagga atcaaactct caccatggca gtgacaatgt cggatccttt acccactagg    3480
ccaccaggga actctgggag catatgtttt tatttcccga catctgagga tgcctagtat    3540
gtcttcatta ttgatttcta gtttgccact gatttctagt attttgctca tagagtgtat    3600
gctcaatggt tttggtcatt tgaaatgtat ttagtcctgc tttatgaccc agtatgtggt    3660
cagttttgtc aatgttcctt ttctgcttga agagaaccta catgctgtaa ctctgggtgc    3720
atgttctgta tataagtcta taggctgagc cggggagcc ttctaatctg ccgttatctt    3780
cttcgagtta ttctaggtac tatttcttag ccataaaacct ttaaattctg atatcaatat    3840
aatgacccca gccgcttag ggtcggcact tcatgttatc ttttttccatc catttaatcc    3900
ctccccactg ttttggccac acccgtggga tatgggagtt cctgggccaa ggatcagatc    3960
tgagccgcag ctgccaccta tgccacagca gcagcaatga tggatctta acccactgca    4020
ccacactggg gattgaaccc aagcctcagc agcaacccaa gctactgcag agacaacacc    4080
agatccttaa cctgctgtgc catagcggga atttccatcc atttactttc aagccagctg    4140
aataacctag cccaccatgc ctggacatgg gtgctctgct tcaaatgatt ttgttcagtc    4200
agcatccatc tctgaaatgt gtgccaagca tttatatgca tgcaagagtc atgttggcac    4260
ttctatcatt tccaacagtt cagtagcctt tgtatcatga catttcttgg ccttttctct    4320
acaatatttg aggctgagca gactggccgt gcccctgtcc atgcttccag agcctgtgtg    4380
cagacttctg ctctagacag agacagctaa ccatcctgca gtgcccagaa acccaactc    4440
aaagaccctc aagtaaggaa ggatttattg gctcacgtaa tctggaatcc aggcatgggg    4500
tattcagggc cacctgaacc agaggccctg gccctgttct ctaagcttct tcctgccctg    4560
ccctcgttct ggaagtgacc ctgaaggaca gcaatgaagg gcagctcccc cagggacaga    4620
tgactgagag gtccatttca gtccaacttt ggcctagatt gagaggcagc aagaaatatg    4680
gacctacagt gagtcacagg atttaccagt ggtttggctg ggttgtcagt gttacaggct    4740
aaacatttgg gtccctccaa aattaacatg ttgccactct aaccaccaaa atcatggtat    4800
ttggggtgg ggcccttgga ggtaattagg tttagaaaga atgaagaggg ggcccttgtg    4860
atgggactag tgcctttata gagagagaag agagaggg                           4898
```

<210> SEQ ID NO 39
<211> LENGTH: 1913
<212> TYPE: DNA
<213> ORGANISM: Sus sp.

<400> SEQUENCE: 39

```
cacctcatcc ccaaccacct ggatggtggc aagtggcagg ctgagaggct gcatatgagc    60
```

```
tcatcaagag ggtccccacc ccacagaggc tgacccagct gccactgcca cctagtggct    120
gatcggccaa gagcaggagc cccaggggca gctccattcc ctggggcggc cagggaacca    180
cctggtggta ggacaattcc attgcacctc atccatcagg aaaaggtttg ccttccctgg    240
cagtaatgca tcttcccata acatggtccc tggcctcttg gaatggcttg ccaccgtca     300 tggcctcacc cacaaagcct tgtgtctcag caaggaactt attccacagc aaaggacttg    360
cagcctggaa tgaactggtc tgactacata ccccattgcc cagaagtagg tggtctattg    420
caaagtggag tggcttaccc aagactcagt tgtgcccaag ttgagagata gcatcctaaa    480
atatgggctt atgtctcact ggctgaggtt tattctttga atcaaagaca attatatggt    540
gtggtccccc cagagataga atacatgagt ctgggaatca agggatagaa gtaagaagag    600
attttgtcac cattaatccc aataactcgc caaagaata tttgctttct gtcctggcag     660
ctctgctgct ttggcaataa cttcctagaa tataatgtct ccaccagggg actccacaac    720
ggttccattg atttgaagcc aatgggcaga ggaggggctg ccttactggt cggactggtc    780
agccctgatt actaaggaga atcaggcaa cttcaacaaa actaaggcag ggggacttt      840 gtctagaacc caaagcacta agcatcttag tacttttag ttctcagagc ctccaagaac     900
aaagatttag cccctcagca ccaccaggta agaacaggt aaatccagct gaggacaaga    960
gaaatattga atggatagag gaagaaagaa attatagata tcaactatgg cctcatgact    1020
agagtctcca gattaagcgg aataaaaata cagatgatta gatctgaaca tcaggccaaa    1080
caacgaacaa cagtttaagt gcgacctagg caatatttgg gacatactta tactaaaatt    1140
ttttcgctat ttgagcatcc tgtatttat ctggcaactt tattcatccc tagcgaaaaa     1200
ggaactgtgg taacttagtg tatttttact ttgctcatta ttgtgtatat acctacttgt    1260
atttatcaat catatttact ctgttctcag tattacttta tatagcagtt ggtggtgatg    1320
gttagcaaca tattcagtgg aactgtgact gaatttgagg agaaattaac agagttggct    1380
gtggctacaa taacccttcg ggacatgtgt cccctcattt tggggagatg gttagatctc    1440
tgggtaaatg ttagggcatc tgagccagaa accaagattt tgccagctgg tgcaatgtca    1500
gattttacca gcagagggtg ccagaggaat gcggcaaaac ccgagtgcca gaaagcacct    1560
ccctgttttc cagcttttct tccttttat ttattttatt tacggcccag gagtccgtaa     1620
tagcgctgag gatgcccag gctcttctca gcagccctga ctgactagtt cagcaatgcg    1680
ctcaggcccc atctggccac cgggcagcct cttctgtggt agctccagcc tcagccagtg    1740
caaaaggcta ccctacactg gcgccacttc tacaatcagc actggccaca ccctccacgc    1800
catccggcac ggagccaggt gatctgccgg ccagattgca gttcgtgctg cctgagtcca    1860
ggtgattaca ctggctgcat ctttctttc tggaccattc attccatttt ttt           1913
```

<210> SEQ ID NO 40
<211> LENGTH: 394
<212> TYPE: DNA
<213> ORGANISM: Artificial Sequence
<220> FEATURE:
<223> OTHER INFORMATION: Synthetic

<400> SEQUENCE: 40

```
ctctgcactc actaccgccg gacgcgcact gccgtgctgc ccatggacca cgctggggag     60
gggtgagcgg acagcacgtt aggaagtgtg tgtgtgcgcg tgggtgcaag tcgagccaag    120
gccaagatcc aggggctggg ccctgtgccc agaggagaat ggcaggtgga gtgtagctgg    180
```

```
attgaaaggt ggcctgaagg gtggggcatc ctgtttggag gctcactctc agccccaggg    240
tctctggttc ctgccggggt gggggcgca aggtgcctac cacaccctgc tagcccctcg    300
tccagtcccg ggcctgcctc ttcaccacgg aagaggataa gccaggctgc aggcttcatg    360
tgcgccgtgg agaacccagt tcggcccttg gagg                                394

<210> SEQ ID NO 41
<211> LENGTH: 333
<212> TYPE: DNA
<213> ORGANISM: Artificial Sequence
<220> FEATURE:
<223> OTHER INFORMATION: Synthetic

<400> SEQUENCE: 41
ggctgaagtc tgaggcctgg cagatgagct tggacgtgcg ctggggagta ctggagaagg    60
actcccgggt ggggacgaag atgttcaaga cgggggggctg ctcctctacg actgcaggca    120
ggaacggggc gtcactgtgc cggcggcacc cggccccgcc ccgccacag ccacaggggg    180 agcccagctc acctggccca gagatggaca cggacttggt gccactgggg tgctggacct    240
cgcacaccag gaaggcctct gggtcctggg ggatgctcac agagggtagg agcacccggg    300
aggaggccaa gtacttgccg cctctcagga cgg                                 333

<210> SEQ ID NO 42
<211> LENGTH: 399
<212> TYPE: DNA
<213> ORGANISM: Artificial Sequence
<220> FEATURE:
<223> OTHER INFORMATION: Synthetic

<400> SEQUENCE: 42
gaagtgaagc cagccagttc ctcctgggca ggtggccaaa attacagttg acccctcctg    60
gtctggctga accttgcccc atatggtgac agccatctgg ccagggccca ggtctccctc    120
tgaagccttt ggaggagag ggagagtggc tggcccgatc acagatgcgg aaggggctga    180
ctcctcaacc ggggtgcaga ctctgcaggg tgggtctggg cccaacacac ccaaagcacg    240
cccaggaagg aaaggcagct tggtatcact gcccagagct aggagaggca ccgggaaaat    300
gatctgtcca agacccgttc ttgcttctaa actccgaggg ggtcagatga agtggttttg    360
tttcttggcc tgaagcatcg tgttccctgc aagaagcgg                           399

<210> SEQ ID NO 43
<211> LENGTH: 23
<212> TYPE: DNA
<213> ORGANISM: Artificial Sequence
<220> FEATURE:
<223> OTHER INFORMATION: Synthetic primer

<400> SEQUENCE: 43
gtctttggtt tttgctgagg gtt                                             23

<210> SEQ ID NO 44
<211> LENGTH: 12673
<212> TYPE: DNA
<213> ORGANISM: Artificial Sequence
<220> FEATURE:
<223> OTHER INFORMATION: Synthetic

<400> SEQUENCE: 44
taaacaaata ggggttccgc gcacatttcc ccgaaaagtg ccacctgacg tcgctgagca    60
ggccctggcc tccctggccg agggcggttt gcgtattaga ggcctaaatg gccgaattca    120
```

```
gcggataaca atttcacaca ggaaacagct atgaccatga ttatctagta actataacgg    180
tcctaaggta gcgagcgatc gcttaattaa cctgcaggga tatcccatgg gggccgccag    240
tgtgatggat atctgcagaa ttcgcccttg atattaagag aagggcaagt cagcttaagt    300 ttggggggtag aggggaacag ggagtgagga gatctggcct gagagatagg agccctggtg    360
gccacaggag gactctttgg gtcctgtcgg atggacacag gcggcccgg gggcatgttg    420 gagcccggct ggttcttacc agaggcaggg ggcaccctct gacacgggag cagggcatgt    480
tccatacatg acacacccct ctgctccagg gcaggtgggt ggcggcacag aggagccagg    540
gactctgagc aaggggtcca ccagtggggc agttggatcc agacttctct gggccagcga    600
gagtctagcc ctcagccgtt ctctgtccag gagggggggtg gggcaggcct gggcggccag    660
agctcatccc tcaagggttc ccagggtcct gccagaccca gatttccgac cgcagccacc    720
acaagaggat gtggtctgct gtggcagctg ccaagacctt gcagcaggtg cagggtgggg    780
gggtgggggc acctgggggc agctgggggtc actgagttca gggaaaaccc cttttttccc    840
ctaaacctgg ggccatccct aggggaaacc acaacttctg agccctgggc agtggctgct    900
gggagggaag agcttcatcc tggacccctgg ggggaaccc agctccaaag gtgcaagggg    960
cccaggtcca aggctagagt gggccaagca ccgcaatggc cagggagtgg gggaggtgga    1020
gctggactgg atcagggcct ccttgggact ccctacaccc tgtgtgacat gttagggtac    1080 ccacaccccca tcaccagtca gggcctggcc catctccagg gccagggatg tgcatgtaag    1140
tgtgtgtgag tgtgtgtgtg tggtgtagta caccccttgg catccggttc cgaggccttg    1200
ggttcctcca aagttgctct ctgaattagg tcaaactgtg aggtcctgat cgccatcatc    1260
aacttcgttc tccccacctc ccatcattat caagagctgg ggagggtctg ggatttcttc    1320
ccacccacaa gccaaaagat aagcctgctg gtgatggcag aagacacagg atcctgggtc    1380
agagacaaag gccagtgtgt cacagcgaga gaggcagccg gactatcagc tgtcacagag    1440
aggccttagt ccgctgaact caggccccag tgactcctgt tccactgggc actggccccc    1500
ctccacagcg ccccccaggcc ccagggagag gcgtcacagc ttagagatgg ccctgctgaa    1560
cagggaacaa gaacaggtgt gccccatcca gcgcccagg ggtgggacag gtgggctgga    1620
tttggtgtga agcccttgag ccctggaacc caaccacagc agggcagttg gtagatgcca    1680
tttgggagag gccccagga gtaagggcca tgggcccttg aggggccag gagctgagga    1740 cagggacaga gacggcccag gcagaggaca gggccatgag gggtgcactg agatggccac    1800
tgccagcagg ggcagctgcc aacccgtcca gggaacttat tcagcagtca gctggaggtg    1860
ccattgaccc tgagggcaga tgaagcccag gccaggctag gtgggctgtg aagaccccag    1920
gggacagagc tctgtccctg gcagcactg gcctctcatt ctgcagggct tgacgggatc    1980
ccaaggcctg ctgcccctga tggtagtggc agtaccgccc agagcaggac cccagcatgg    2040 aaacccccaac gggacgcagc ctgcggagcc cacaaaacca gtaaggagcc gaagcagtca    2100
tggcacgggg agtgtggact tccctttgat ggggcccagg catgaaggac agaatgggac    2160
agcggccatg agcagaaaat cagccggagg ggatgggcct aggcagacgc tggctttatt    2220
tgaagtgttg gcattttgtc tggtgtgtat tgttggtatt gatttatttt tagtatgtca    2280
gtgacatact gacatattat gtaacgacat attattatgt gttttaagaa gcactccaag    2340
ggaacaggct gtctgtaatg tgtccagaga agagagcaag agcttggctc agtctccccc    2400
aaggaggtca gttcctcaac aggggtccta aatgtttcct ggagccaggc ctgaatcaag    2460
```

```
ggggtcatat ctacacgtgg ggcagaccca tggaccattt tcggagcaat aagatggcag   2520
ggaggatacc aagctggtct tacagatcca gggctttgac ctgtgacgcg ggcgctcctc   2580
caggcaaagg gagaagccag caggaagctt tcagaactgg ggagaacagg gtgcagacct   2640
ccagggtctt gtacaacgca cccttttatcc tggggtccag gaggggtcac tgagggattt   2700
aagtggggga ccatcagaac caggtttgtg ttttggaaaa atggctccaa agcagagacc   2760
agtgtgaggc cagattagat gatgaagaag aggcagtgga aagtcgatgg gtggccaggt   2820
agcaagaggg cctatggagt tggcaagtga atttaaagtg gtggcaccag agggcagatg   2880
gggaggagca ggcactgtca tggactgtct atagaaatct aaaatgtata cccttttttag   2940 caatatgcag tgagtcataa aagaacacat atatatttcc tttggccggc cggcgcgcca   3000
cgcgtataac ttcgtatagc atacattata cgaagttatc ttaagggcta tggcagggcc   3060
tgccgccccg acgttggctg cgagccctgg gccttcaccc gaacttgggg ggtggggtgg   3120
ggaaaaggaa gaaacgcggg cgtattggcc ccaatggggt ctcggtgggg tatcgacaga   3180
gtgccagccc tgggaccgaa ccccgcgttt atgaacaaac gacccaacac cgtgcgtttt   3240
attctgtctt tttattgccg tcatagcgcg ggttccttcc ggtattgtct ccttccgtgt   3300
ttcactcgag ttagaagaac tcgtcaagaa ggcgatagaa ggcgatgcgc tgcgaatcgg   3360
gagcggcgat accgtaaagc acgaggaagc ggtcagccca ttcgccgcca agctcttcag   3420
caatatcacg ggtagccaac gctatgtcct gatagcggtc cgccacaccc agccggccac   3480
agtcgatgaa tccagaaaag cggccatttt ccaccatgat attcggcaag caggcatcgc   3540
catgggtcac gacgagatcc tcgccgtcgg gcatgcgcgc cttgagcctg gcgaacagtt   3600
cggctggcgc gagcccctga tgctcttcgt ccagatcatc ctgatcgaca agaccggctt   3660
ccatccgagt acgtgctcgc tcgatgcgat gtttcgcttg gtggtcgaat gggcaggtag   3720
ccggatcaag cgtatgcagc cgccgcattg catcagccat gatggatact ttctcggcag   3780
gagcaaggtg agatgacagg agatcctgcc ccggcacttc gcccaatagc agccagtccc   3840
ttcccgcttc agtgacaacg tcgagcacag ctgcgcaagg aacgcccgtc gtggccagcc   3900
acgatagccg cgctgcctcg tcctgcagtt cattcagggc accggacagg tcggtcttga   3960
caaaaagaac cgggcgcccc tgcgctgaca gccggaacac ggcggcatca gagcagccga   4020
ttgtctgttg tgcccagtca tagccgaata gcctctccac ccaagcggcc ggagaacctg   4080
cgtgcaatcc atcttgttca atggccgatc ccattccaga tctgttagcc tcccccatct   4140
cccgtgcaaa cgtgcgcgcc aggtcgcaga tcgtcggtat ggagcctggg gtggtgacgt   4200
gggtctggat catcccggag gtaagttgca gcagggcgtc ccggcagccg gcgggcgatt   4260
ggtcgtaatc caggataaag acgtgcatgg gacggaggcg tttggtcaag acgtccaagg   4320
cccaggcaaa cacgttgtac aggtcgccgt tgggggccag caactcgggg cccgaaaaca   4380
gggtaaataa cgtgtccccg atatgggggtc gtgggcccgc gttgctctgg ggctcggcac   4440
cctggggcgg cacggccgtc cccgaaagct gtccccaatc ctcccgccac gacccgccgc   4500
cctgcagata ccgcaccgta ttggcaagca gcccgtaaac gcggcgaatc gcggccagca   4560
tagccaggtc aagccgctcg ccggggcgct ggcgtttggc caggcggtcg atgtgtctgt   4620
cctccggaag ggcccccaac acgatgtttg tgccgggcaa ggtcggcggg atgagggcca   4680
cgaacgccag cacggcctgg ggggtcatgc tgcccataag gtatcgcgcg gccgggtagc   4740
acaggagggc ggcgatggga tggcggtcga agatgagggt gagggccggg ggcggggcat   4800
gtgagctccc agcctccccc ccgatatgag gagccagaac ggcgtcggtc acggcataag   4860
```

```
gcatgcccat tgttatctgg gcgcttgtca ttaccaccgc cgcgtccccg gccgatatct    4920
caccctggtc aaggcggtgt tgtgtggtgt agatgttcgc gattgtctcg gaagccccca    4980
gcacccgcca gtaagtcatc ggctcgggta cgtagacgat atcgtcgcgc gaacccaggg    5040
ccaccagcag ttgcgtggtg gtggttttcc ccatcccgtg gggaccgtct atataaaccc    5100
gcagtagcgt gggcattttc tgctccgggc ggacttccgt ggcttcttgc tgccggcgag    5160
ggcgcaacgc cgtacgtcgg ttgctatggc cgcgagaacg cgcagcctgg tcgaacgcag    5220
acgcgtgctg atggccgggg tacgaagcca tggtggctct agaggtcgaa aggcccggag    5280
atgaggaaga ggagaacagc gcggcagacg tgcgcttttg aagcgtgcag aatgccgggc    5340
ttccggagga ccttcgggcg cccgccccgc ccctgagccc gccctgagc ccgccccgg     5400 acccacccct tcccagcctc tgagcccaga aagcgaagga gccaaagctg ctattggccg    5460
ctgccccaaa ggcctacccg cttccattgc tcagcggtgc tgtccatctg cacgagacta    5520
gtgagacgtg ctacttccat ttgtcacgtc ctgcacgacg cgagctgcgg ggcgggggg     5580 aacttcctga ctaggggagg agtagaaggt ggcgcgaagg ggccaccaaa gaacggagcc    5640
ggttggcgcc taccggtgga tgtggaatgt gtgcgaggcc agaggccact tgtgtagcgc    5700
caagtgccca gcggggctgc taaagcgcat gctccagact gccttgggaa aagcgcctcc    5760 cctaccggt agggatccgc gttacataac ttacggtaaa tggcccgcct ggctgaccgc    5820
ccaacgaccc ccgcccattg acgtcaataa tgacgtatgt tcccatagta acgccaatag    5880
ggactttcca ttgacgtcaa tgggtggagt atttacggta aactgcccac ttggcagtac    5940
atcaagtgta tcatatgcca agtacgcccc ctattgacgt caatgacggt aaatggcccg    6000
cctggcatta tgcccagtac atgaccttat gggactttcc tacttggcag tacatctacg    6060
tattagtcat cgctattacc atggtgatgc ggttttggca gtacatcaat gggcgtggat    6120
agcggtttga ctcacgggga tttccaagtc tccaccccat tgacgtcaat gggagtttgt    6180
tttggcacca aaatcaacgg gactttccaa aatgtcgtaa caactccgcc ccattgacgc    6180
tttggcacca aaatcaacgg ttaacaagct tataacttcg tatagcatac attatacgaa    6240
gttattacgt agcggccgcg tcgacgataa attgtgtaat tccacttcta aggattcatc    6300
ccaagggggg aaaataatca agatgtaac caaaggttta caaacaagaa ctcatcatta    6360
atcttccttg ttgttatttc aacgatatta ttattattac tattattatt attattattt    6420 tgtcttttg cattttctag ggccactccc acgcataga gaggttccca ggctaggggt    6480
caaatcggag ctacagctgc cggcctacgc cagagccaca gcaacgcagg atctgagcca    6540
cagcaatgca ggatctacac cacagctcat ggtaacgctg atccttaac ccaatgagtg     6600 aggccaggga tcgaacctgt aacttcatgg ttcctagtcg gattcattaa ccactgagcc    6660
acgacaggaa ctccaacatt attaatgatg ggagaaaact ggaagtaacc taaatatcca    6720
gcagaaaggg tgtggccaaa tacagcatgg agtagccatc ataaggaatc ttacacaagc    6780
ctccaaaatt gtgtttctga aattgggttt aaagtacgtt tgcattttaa aaagcctgcc    6840
agaaaataca gaaaaatgtc tgtgatatgt ctctggctga taggattttg cttagtttta    6900
attttggctt tataatttc tatagttatg aaaatgttca caagaagata tatttcattt    6960
tagcttctaa aataattata acacagaagt aatttgtgct ttaaaaaaat attcaacaca    7020
gaagtatata aagtaaaaat tgaggagttc ccatcgtggc tcagtgatta acaaacccaa    7080
ctagtatcca tgaggatatg gatttgatcc ctggccttgc tcagtgggtt gaggatccag    7140
tgttgctgtg agctgtggtg taggttgcag acacagcact ctggcgttgc tgtgactctg    7200
```

```
gcgtaggccg gcagctacag ctccatttgg acccttagcc tgggaacctc catatgcctg    7260
agatacggcc ctaaaaagtc aaagccaaaa aaatagtaa aaattgagtg tttctactta     7320
ccaccctgc ccacatctta tgctaaaacc cgttctccag agacaaacat cgtcaggtgg     7380
gtctatatat ttccagccct cctcctgtgt gtgtatgtcc gtaaaacaca cacacacaca    7440
cacacacgca cacacacaca cacgtatcta attagcattg gtattagttt ttcaaaaggg    7500
aggtcatgct ctaccttta ggcggcaaat agattattta acaaatctg ttgacatttt      7560
ctatatcaac ccataagatc tcccatgttc ttggaaaggc tttgtaagac atcaacatct    7620
gggtaaacca gcatggtttt tagggggttg tgtggatttt tttcatattt tttagggcac    7680
acctgcagca tatggaggtt cccaggctag gggttgaatc agagctgtag ctgccggcct    7740
acaccacagc cacagcaacg ccagatcctt aacccactga gaaaggccag ggattgaacc    7800
tgcatcctca tggatgctgg tcagatttat ttctgctgag ccacaacagg aactccctga    7860
accagaatgc ttttaaccat tccactttgc atggacattt agattgtttc catttaaaaa    7920
tacaaattac aaggagttcc cgtcgtggct cagtggtaac gaattggact aggaaccatg    7980
aggtttcggg ttcgatccct ggccttgctc ggtgggttaa ggatccagca ttgatgtgag    8040
atatggtgta ggtcgcagac gtggctcgga tcccacgttg ctgtggctct ggcgtaggcc    8100
ggcaacaaca gctccgattc gaccectagc ctgggaacct ccatgtgcca caggagcagc    8160
cctagaaaag gcaaaagac aaaaaataa aaattaaaa tgaaaaaata aataaaaat        8220
acaaattaca agagacggct acaaggaaat ccccaagtgt gtgcaaatgc catatatgta    8280
taaaatgtac tagtgtctcc tcgcgggaaa gttgcctaaa agtgggttgg ctggacagag    8340
aggacaggct ttgacattct cataggtagt agcaatgggc ttctcaaaat gctgttccag    8400
tttacactca ccatagcaaa tgacagtgcc tcttcctctc caccttgcc aataatgtga     8460
caggtggatc ttttctatt ttgtgtatct gacaagcaaa aaatgagaac aggagttcct     8520
gtcgtggtgc agtggagaca aatctgacta ggaaccatga aatttcgggt tcaatccctg    8580
gcctcactca gtaggtaaag gatccagggt tgcagtgagc tgtggggtag gtcgcagaca    8640
cagtgcaaat ttggccctgt tgtggctgtg gtgtaggccg gcagctatag ctccaattgg    8700
accccctagcc tgggaacctc cttatgccgt gggtgaggcc ctaaaaaaaa gagtgcaaaa   8760
aaaaaaata agaacaaaaa tgatcatcgt ttaattcttt atttgatcat tggtgaaact    8820
tattttcctt ttatatttt attgactgat tttatttctc ctatgaattt accggtcata    8880
gttttgcctg ggtgttttta ctccggtttt agttttggtt ggttgtattt tcttagagag    8940
ctatagaaac tcttcatcta tttggaatag taattcctca ttaagtattt gtgctgcaaa    9000
aaattttccc tgatctgttt tatgcttttg tttgtgggt cttcacgag aaagcctttt      9060
tagttttac acctcagctt ggttgttttt cttgattgtg tctgtaatct gcggccaaca    9120
taggaaacac attttactt tagtgttttt ttcctatttt cttcaagtac gtccattgtt    9180
ttggtgtctg attttacttt gcctggggtt tgttttgtg tggcaggaat ataaacttat    9240
gtattttcca aatggagagc caatggttgt atatttgttg aattcaaatg caactttatc    9300
aaacaccaaa tcatcgattt atcacaactc ttctctggtt tattgatcta atgatcaatt    9360
cctgttccac gctgttttaa ttattttagc tttgtggatt ttggtgcctg gtagagaaca    9420
aagcctccat tattttcatt caaaatagtc ccgtctatta tctgccattg ttgtagtatt    9480
agactttaaa atcaatttac tgattttcaa aagttattcc tttggtgatg tggaatactt    9540
tatacttcat aaggtacatg gattcatttg tggggaattg atgtctttgc tattgtggcc    9600
```

```
atttgtcaag ttgtgtaata ttttacccat gccaactttg catattgtat gtgagtttat    9660
tcccagggtt tttaatagga tgtttattga agttgtcagt gtttccacaa tttcatcgcc    9720
tcagtgctta ctgtttgcat aaaaggaaac ctactcactt ttgcctattg ctcttgtatt    9780
caatcatttt agttaactct tgtgttaatt ttgagagttt ttcagctgac tgtctggggt    9840
tttctttaat agactagccc tttgtctgta aagaataatt ttatcgaatt tttcttaaca    9900
ctcacactct ccccacccc acccccgctc atctcctttc attgggtcaa atctgtagaa    9960
tacaataaaa gtaagagtgg gaaccttagc ctttaagtcg attttgcctt taaatgtgaa   10020
tgttgctatg tttcgggaca ttctctttat caagttgcgg atgtttcctt agataattaa   10080
cttaataaaa gactggatgt ttgctttctt caaatcagaa ttgtgttgaa tttatattgc   10140
tattctgttt aattttgttt caaaaaattt acatgcacac cttaaagata accatgacca   10200
aatagtcctc ctgctgagag aaaatgttgg ccccaatgcc acaggttacc tcccgactca   10260
gataaactac aatgggagat aaaatcagat ttggcaaagc ctgtggattc ttgccataac   10320
tctcagagca tgacttgggt gttttttcct tttctaagta ttttaatggt attttgtgt    10380 tacaatagga aatctaggac acagagagtg attcaatgag gggaacgcat tctgggatga   10440
ctctaggcct ctggtttggg gagagctcta ttgaagtaaa gacaatgaga ggaagcaagt   10500
ttgcagggaa ctgtgaggaa tttagatggg gaatgttggg tttgaggttt ctatagggca   10560
cgcaagcaga gatgcactca ggaggaagaa ggagcataaa tctagtggcg ctgccggcaa   10620
gcttgctgga ggaggccaat tgggagctgc tggaatgcat ggaggcggcg ctctcgaggc   10680
tggaggaggc cagctgattt aaatcggtcc gcgtacgatg catattaccc tgttatccct   10740
accgcggtta ctggccgtcg ttttacaacg tcgtgactgg gaaaaccctg gcgatgctct   10800
tctcccggtg aaaacctctg acacatggct cttctaaatc cggagtttaa acgcttcctt   10860
catgtgagca aaaggccagc aaaaggccag gaaccgtaaa aaggccgcgt tgctggcgtt   10920
tttccatagg ctccgccccc ctgacgagca tcacaaaaat cgacgctcaa gtcagaggtg   10980
gcgaaacccg acaggactat aaagatacca ggcgtttccc cctggaagct ccctcgtgcg   11040
ctctcctgtt ccgaccctgc cgcttaccgg atacctgtcc gcctttctcc cttcgggaag   11100
cgtggcgctt tctcatagct cacgctgtag gtatctcagt tcggtgtagg tcgttcgctc   11160
caagctgggc tgtgtgcacg aaccccccgt tcagcccgac cgctgcgcct tatccggtaa   11220
ctatcgtctt gagtccaacc cggtaagaca cgacttatcg ccactggcag cagccactgg   11280
taacaggatt agcagagcga ggtatgtagg cggtgctaca gagttcttga agtggtggcc   11340
taactacggc tacactagaa ggacagtatt tggtatctgc gctctgctga agccagttac   11400
cttcggaaaa agagttggta gctcttgatc cggcaaacaa accaccgctg gtagcggtgg   11460
tttttttgtt tgcaagcagc agattacgcg cagaaaaaaa ggatctcaag aagatccttt   11520
gatcttttct acgggtctg acgctcagtg gaacgaaaac tcacgttaag ggattttggt    11580 catgctagg tggcaaacag ctattatggg tattatgggt ctaccggtgc atgagattat    11640
caaaaaggat cttcacctag atccttttaa attaaaaatg aagttttaaa tcaatctaaa   11700
gtatatatga gtaaacttgg tctgacagtt accaatgctt aatcagtgag gcacctatct   11760
cagcgatctg tctatttcgt tcatccatag ttgcctgact ccccgtcgtg tagataacta   11820
cgatacggga gggcttacca tctggcccca gtgctgcaat gataccgcga gacccacgct   11880
caccggctcc agatttatca gcaataaacc agccagccgg aagggccgag cgcagaagtg   11940
```

| | |
|---|---|
| gtcctgcaac tttatccgcc tccatccagt ctattaattg ttgccgggaa gctagagtaa | 12000 |
| gtagttcgcc agttaatagt ttgcgcaacg ttgttgccat tgctacaggc atcgtggtgt | 12060 |
| cacgctcgtc gtttggtatg gcttcattca gctccggttc ccaacgatca aggcgagtta | 12120 |
| catgatcccc catgttgtgc aaaaaagcgg ttagctcctt cggtcctccg atcgttgtca | 12180 |
| gaagtaagtt ggccgcagtg ttatcactca tggttatggc agcactgcat aattctctta | 12240 |
| ctgtcatgcc atccgtaaga tgcttttctg tgactggtga gtactcaacc aagtcattct | 12300 |
| gagaatagtg tatgcggcga ccgagttgct cttgcccggc gtcaatacgg gataataccg | 12360 |
| cgccacatag cagaacttta aaagtgctca tcattggaaa acgttcttcg ggcgaaaac | 12420 |
| tctcaaggat cttaccgctg ttgagatcca gttcgatgta acccactcgt gcacccaact | 12480 |
| gatcttcagc atcttttact ttcaccagcg tttctgggtg agcaaaaaca ggaaggcaaa | 12540 |
| atgccgcaaa aaagggaata agggcgacac ggaaatgttg aatactcata ctcttccttt | 12600 |
| ttcaatatta ttgaagcatt tatcagggtt attgtctcgg gagcggatac atatttgaat | 12660 |
| gtatttagaa aaa | 12673 |

<210> SEQ ID NO 45
<211> LENGTH: 12263
<212> TYPE: DNA
<213> ORGANISM: Artificial Sequence
<220> FEATURE:
<223> OTHER INFORMATION: Synthetic

<400> SEQUENCE: 45

| | |
|---|---|
| taaacaaata ggggttccgc gcacatttcc ccgaaaagtg ccacctgacg tcgctgagca | 60 |
| ggccctggcc tccctggccg agggcggttt gcgtattaga ggcctaaatg gccgaattca | 120 |
| gcggataaca atttcacaca ggaaacagct atgaccatga ttatctagta actataacgg | 180 |
| tcctaaggta gcgagcgatc gcttaattaa cctgcaggga taaccactga cccatgacgg | 240 |
| gaactcccag ggctcagctc ttgactccag gttcgcagct gccctcaaag caatgcaacc | 300 |
| ctggctggcc ccgcctcatg catccggcct cctccccaaa gagctctgag cccacctggg | 360 |
| cctaggtcct cctccctggg actcatggcc taagggtaca gagttactgg ggctgatgaa | 420 |
| gggaccaatg gggacagggg cctcaaatca agtggctgt ctctctcatg tcccttcctc | 480 |
| tcctcagggt ccaaaatcag ggtcagggcc ccagggcagg ggctgagagg gcctcttttct | 540 |
| gaaggccctg tctcagtgca ggttatgggg gtctggggga gggtcaatgc agggctcacc | 600 |
| cttcagtgcc ccaaagccta gagagtgagt gcctgccagt ggcttcccag gcccaatccc | 660 |
| ttgactgcct gggaatgctc aaatgcagga actgtcacaa caccttcagt caggggctgc | 720 |
| tctggggaga aaaacactca gaattggggg ttcaggaag gcccagtgcc aagcatagca | 780 |
| ggagctcagg tggctgcaga tggtgtgaac cccaggagca ggatggccgg cactcccccc | 840 |
| agaccctcca gagccccagg ttggctgccc tcttcactgc cgacacccct gggtccactt | 900 |
| ctgccctttc ccacctaaaa cctttagggc tcccactttc tcccaaatgt gagacatcac | 960 |
| cacggctccc agggagtgtc cagaagggca tctggctgag aggtcctgac atctgggagc | 1020 |
| ctcaggcccc acaatggaca gacgcccgc caggatgctg ctgcagggct gttagctagg | 1080 |
| cggggtggag atggggtact tgcctctca gaggcccgg ccccaccatg aaacctcagt | 1140 |
| gacaccccat ttccctgagt tcacataccct gtatcctact ccagtcacct tcccacgaa | 1200 |
| cccctgggag cccaggatga tgctgggggct ggagccacga ccagcccacg agtgatccag | 1260 |
| ctctgccaat cagcagtcat ttcccaagtg ttccagccct gccaggtccc actacagcag | 1320 |

```
taatggaggc cccagacacc agtccagcag ttagagggct ggactagcac cagcttttcaa    1380 gcctcagcat ctcaaggtga atggccagtg cccctccccg tggccatcac aggatcgcag    1440
atatgaccct aggggaagaa atatcctggg agtaaggaag tgcccatact caaggatggc    1500
ccctctgtga cctaacctgt ccctgaggat tgtacttcca ggcgttaaaa cagtagaacg    1560
cctgcctgtg aaccccgcc aagggactgc ttggggaggc cccctaaacc agaacacagg    1620
cactccagca ggacctctga actctgacca ccctcagcaa gtgggcaccc cccgcagctt    1680
ccaaggcacc ccagggctca ccacagcggc ccctcctggc agcccctcac ccaggcccag    1740
accctctaag atggcacatc taagccaatc cacctccttg tcattcctcc tgtccccacc    1800 caggacccttt ctcagatgaa accttcgctc cagccgctgg gccctctctc ctgcccctct    1860
ggcagttctc cagggactcc gcctcccact ctctgtctct ccctgcactc ctaggaacaa    1920
gcgacctcca ggaagcccag tccaattatc ccctctgtgt cctccccaat ctctgcctct    1980
gggtggattt gagcaccaca tcctgttctc ttcgacctga aactccttgg ccccggtgtc    2040
cgctctcctg ggccctcttt tctctcctcc cctcttccgt gccccgtttg tttggtgtta    2100
caggcaggcc ccggggagcc gtccctccag ctgctcttcc ttgtctgtct caggagccag    2160
aaactggcag catctaaaaa gggctcctgt ttcttcatct gcccagcctc ctagcccaac    2220
cagggctctg gcctcactcc agagggtggg ctccagaggg caggggttgc accctcttag    2280
tgcctcagag gctcagctgg gtgcaggatg ggggggccct cagggagccc ctcagtgact    2340
gctgatcact tactgcagga ctgttcccag ctcttcccaa tcattggaat gacaatacct    2400
agttctgctc catcatagtg atgcaggaaa aatgttactg aaatcctggt tcttgtttag    2460
caatcgaaga atgaattccg cgaacacaca ggcagcaagc aagcgaagcc tttattaaag    2520
gaaagcagat agctcccagg gctgcaggga gcggggagaa gagctcccca ctctctattg    2580
tcctataggg cttttttaccc cttaaagttg gggggataca aaaaaaatag aagaaaaagg    2640
gagttcccgt cagggcacag cagaaacaaa tccaactagg aaccatgagg ttggggggttc    2700 gattcctggc ctctctcagt gggttaagga tgcagcgttg ccgtgagcta tgatacaggt    2760
cacagatgca gctcagatct actagtcaat tgacaggcgc cggagcagga gctaggcctt    2820
tggccggccg gcgcgccaga tctcttaagg gctatggcag ggcctgccgc cccgacgttg    2880
gctgcgagcc ctgggccttc acccgaactt gggggtgggg gtggggaaaa ggaagaaacg    2940
cgggcgtatt ggccccaatg gggtctcggt ggggtatcga cagagtgcca gccctgggac    3000 cgaacccccgc gtttatgaac aaacgaccca acaccgtgcg ttttattctg tcttttattt    3060
gccgtcatag cgcgggttcc ttccggtatt gtctccttcc gtgtttcact cgagttagaa    3120
gaactcgtca agaaggcgat agaaggcgat gcgctgcgaa tcgggagcgg cgataccgta    3180
aagcacgagg aagcggtcag cccattcgcc gccaagctct tcagcaatat cacgggtagc    3240
caacgctatg tcctgatagc ggtccgccac acccagccgg ccacagtcga tgaatccaga    3300
aaagcggcca ttttccacca tgatattcgg caagcaggca tcgccatggg tcacgacgag    3360
atcctcgccg tcgggcatgc gcgccttgag cctggcgaac agttcggctg gcgcgagccc    3420
ctgatgctct tcgtccagat catcctgatc gacaagaccg gcttccatcc gagtacgtgc    3480
tcgctcgatg cgatgtttcg cttggtggtc gaatgggcag gtagccggat caagcgtatg    3540
cagccgccgc attgcatcag ccatgatgga ctttctctcg gcaggagcaa ggtgagatga    3600
caggagatcc tgccccggca cttcgcccaa tagcagccag tcccttcccg cttcagtgac    3660
```

-continued

```
aacgtcgagc acagctgcgc aaggaacgcc cgtcgtggcc agccacgata gccgcgctgc   3720
ctcgtcctgc agttcattca gggcaccgga caggtcggtc ttgacaaaaa gaaccgggcg   3780
cccctgcgct gacagccgga cacggcggc atcagagcag ccgattgtct gttgtgccca    3840
gtcatagccg aatagcctct ccacccaagc ggccggagaa cctgcgtgca atccatcttg   3900
ttcaatggcc gatcccattc cagatctgtt agcctccccc atctcccgtg caaacgtgcg   3960
cgccaggtcg cagatcgtcg gtatggagcc tggggtggtg acgtgggtct ggatcatccc   4020
ggaggtaagt tgcagcaggg cgtcccggca gccggcgggc gattggtcgt aatccaggat   4080
aaagacgtgc atgggacgga ggcgtttggt caagacgtcc aaggcccagg caaacacgtt   4140
gtacaggtcg ccgttggggg ccagcaactc ggggccccga acagggtaa ataacgtgtc     4200
cccgatatgg ggtcgtgggc ccgcgttgct ctgggctcg gcaccctggg gcggcacggc    4260
cgtccccgaa agctgtcccc aatcctcccg ccacgacccg ccgccctgca gataccgcac   4320
cgtattggca agcagcccgt aaacgcggcg aatcgcggcc agcatagcca ggtcaagccg   4380
ctcgccgggg cgctggcgtt tggccaggcg gtcgatgtgt ctgtcctccg gaagggcccc   4440
caacacgatg tttgtgccgg gcaaggtcgg cgggatgagg gccacgaacg ccagcacggc   4500
ctgggggtc atgctgccca taaggtatcg cgcggccggg tagcacagga gggcggcgat    4560
gggatggcgg tcgaagatga gggtgagggc cggggcggg gcatgtgagc tcccagcctc    4620
ccccccgata tgaggagcca gaacggcgtc ggtcacggca taaggcatgc ccattgttat   4680
ctgggcgctt gtcattacca ccgccgcgtc cccggccgat atctcaccct ggtcaaggcg   4740
gtgttgtgtg gtgtagatgt tcgcgattgt ctcggaagcc cccagcaccc gccagtaagt   4800
catcggctcg ggtacgtaga cgatatcgtc gcgcgaaccc agggccacca gcagttgcgt   4860
ggtggtggtt ttccccatcc cgtggggacc gtctatataa acccgcagta gcgtgggcat   4920
tttctgctcc gggcggactt ccgtggcttc ttgctgccgg cgagggcgca acgccgtacg   4980
tcggttgcta tggccgcgag aacgcgcagc ctggtcgaac gcagacgcgt gctgatggcc   5040
ggggtacgaa gccatggtgg ctctagaggt cgaaaggccc ggagatgagg aagaggagaa   5100
cagcgcggca gacgtgcgct tttgaagcgt gcagaatgcc gggcttccgg aggaccttcg   5160
ggcgcccgcc ccgcccctga gccgcccct gagcccgccc ccggacccac cccttcccag    5220
cctctgagcc cagaaagcga aggagccaaa gctgctattg gccgctgccc caaaggccta   5280
cccgcttcca ttgctcagcg gtgctgtcca tctgcacgag actagtgaga cgtgctactt   5340
ccatttgtca cgtcctgcac gacgcgagct gcggggcggg ggggaacttc ctgactaggg   5400
gaggagtaga aggtggcgcg aaggggccac caaagaacgg agccggttgg cgcctaccgg   5460
tggatgtgga atgtgtgcga ggccagaggc cacttgtgta gcgccaagtg cccagcgggg   5520
ctgctaaagc gcatgctcca gactgccttg ggaaaagcgc ctcccctacc cggtagggat   5580
ccgcgttaca taacttacgg taaatggccc gcctggctga ccgcccaacg accccgcccc   5640
attgacgtca ataatgacgt atgttcccat agtaacgcca atagggactt tccattgacg   5700
tcaatgggtg gagtatttac ggtaaactgc ccacttggca gtacatcaag tgtatcatat   5760
gccaagtacg ccccctattg acgtcaatga cggtaaatgg cccgcctggc attatgccca   5820
gtacatgacc ttatgggact ttcctacttg gcagtacatc tacgtattag tcatcgctat   5880
taccatggtg atgcggtttt ggcagtacat caatgggcgt ggatagcggt ttgactcacg   5940
gggatttcca agtctccacc ccattgacgt caatgggagt ttgttttggc accaaaatca   6000
acgggtaaca agcttataac ttcgtatagc atacattata cgaagttatt acgtagcggc   6060
```

```
cgcgtcgacg atatcgctgc cggagccccc ggggccgctg ccggaagatc tggcattgct   6120
gtgactgtgg tgtaggccgg cagctggagc tctgattaga cccctcacct gggaatctcc   6180
atatgctgca cgtgcggccc taaaaagaca aagacaaaa aaaaaaaaaa aaaaaaaaa    6240 tcaaaaaaaa acatagggggg ttaccaacgt ggggtccaga agatgtggt tttctcccat   6300 tggccttgcc cagttaccta tatcagtcct tgtccaacag gggttttagg ggtggaaatg   6360
ccccataaat tttacggttt ctttgccctt ctcttccttt agactgagtc accattgctc   6420
tcattccttt tctatcagtt gaggagtggg ttagagatta aggtccatgt ggtggaggta   6480
cacttcttat agtaaacaag gcctatgggg aattactctc tggagccctt aaaccacaaa   6540
tgataatcca tgccacatca aagatgcatc gaagcccatg ctcctacact gactacctga   6600
gttagcattc tgcctcaaca ggactgacca tccccagctc tggggcagat atcctctctc   6660
tgccacaagg gcagtgaccc ccatgctgtc tgagggtcac gctttacccc ccccccaccc   6720
ctgccgtgac cccccagacc accccaggag gtgggcacta atatccctca ttaccccata   6780
gatgaggaaa cagaggttcc cccggggtcc cacaggtgct cagggtcaca tgcaccgtgg   6840
gcacccaggc cccatcccaa ggccaccctc cctcctcagg aagctgtgct gcgctgggcc   6900
agaaggtact gcacacgact cctcagcctc cggtggtggg aggcagcctc aagcctctga   6960
gtgggggggc acccgggctc ctcaatctat actgactcct gggggtggga gaaggggagg   7020
gggagctgtg gcctctgagt ccactaagca aatcagggtg ggcaatgcgg gcccatttca   7080
aggaggagag aaccgaggct ctgacagcag gccggggtc cagggacctg cccagggtca   7140
taggctgaac tgctggctga cctgccttgg gttctttcct tggctcctca gccctgtgtg   7200
atgtgacagg tcattcattc actcactcgc tcattcattc agcaaaccct cagtgagccc   7260
tgctgggagc aggtgctagg ggcaaggaga caggacctct tgccctggaa cagctgaagc   7320 actggggac aggcagtggc agggaggtgc gtgatcaccg ctgaccccat tccatcctcc   7380
agcccccagg tcagttttcca cccaccattg accccaccat gtcctccatc cccaaggtca   7440
gtttcccgcc caaggagcat ctccttacac actaggaca aaatttcacg gctgtcactg   7500
ggcatctctc cacgctcatc acagcccctct agcagccttg aagtcctgta gagcccttcc   7560
catttcacag aagggacaag actatgaggg ccacaccgtg agccatgagc cttaggctgt   7620
gagccgggac agcccctgca ggactggtgg cctcagggca ctgggtgggg aggtgcaca   7680 gtgggtgggc cccttgtgga atagagagga gtgtcaggtc agggaggggg gcttggcctg   7740
gccctggcct gctggtgtg caaccctagg cagcccctcc ttcccaggcc tcctacttcc   7800
tggaggccaa gcctcaggga ggtaattgag tcaggtgggg gagggggggt tgtggctttc   7860
ttcacagcag aaaaacagag cccacaatag tgtccactga gacagagggg tcctggggga   7920
ggggaggggt gggaggtgac tgctgagccc tgtgggaggg agggagcaac tactgagctg   7980
agctgggtga ctctcccatc tgccccgccc cctgtgggc cagcagagtc accgagagaa   8040
catgacccag ccaggcctgg acaggggac acccatgtcc tttaccccac agggttcact   8100
gagcctatct gccccaagcc tgtgtctccc tgggacggag accctcactc ccaaccacaa   8160
aggtctaaac tcaagttccc aacagccttg aaaatacagc ttccggggc ctccaaggag   8220 cagtcagccg tccactgcca ggctcgctgg ctcagtgaca caggacacat cctgatgacg   8280
gtccacctgt ctccaagcag gttctcctct gccgatgggg caacgagctc ctcctgtggc   8340
tccctggctg gatgcgtggg aggcggggtg gggggcagg cggtgttcct ggccgcacac   8400
```

```
aaggagcacc cccaccagca tccgaagacg ggggcccggt ctttccccaa aacactgctt    8460
gcgggagact ttgtgacgtt tccaggggcc atgctcccct cgggcagctt gggggacttc    8520
tgctcctatg tggtcacctg cagggactcc ccccaggcct tggggacaaa caaagtgatg    8580
agagggaggg ttagtgggtc ggggcagggc cagtctttgg accggtttat ctgaaaagcc    8640
agttggtcac cgggaaccac agcaaaccta aacccatttg gccaggcatc tcccagggac    8700
agtctccccc aggatgcggg gcccaggggg gctccagggg tgacctgcgt cctggatttc    8760
cctgatgctc ccagttcgtg cctctgtcca agcatgattt ttaatagtgc cccttccact    8820
cccagaaatg tccaagtgtg gcaataaat tctggtcacc tgagctcagt gtaactgttt    8880
gctgaatgac acttactgta acaggttaaa atggaggcc caaggccacg cagagccatc    8940
gaaggctctg tgtgtcccag ccctgataga agcatcagga tggggactgt ggcctcacca    9000
ggggccacat ccaggcggtc accatggggt tcctggtctc cgtgggcctt gactggagcc    9060
cctggtgtga gctcacccca tcccagcctg tgagaggcct ggatgtgggc ctgacatcat    9120
ttcccaccca gtgacagcac tgcatgtgat ggggcctctg gcagccttt tcccggggg     9180 aaactggcag gaatcaggac caccaggaca ggggtcaggg gagaggcgat gctgggcacc    9240
agagcctgga ccaccctcgg gttctcagcg atgggcaacc cctgccaccc agggcccgc    9300 cttcctgggg agacatcggg gtttccaggc catcctggga ggagggtggg agcctcagct    9360
agaccccagc tggcttgccc ccccatgccc cggccaagag agggtcttgg agggaagggg    9420
gaccccagac cagcctggcg agcccatcct cagggtctct ggtcagacag gggctcagct    9480
gagctccagg gtagaccaag gccctgcgtg atgaggcca gtgtggtcac tgcccagagc    9540
aaagccacct ctcagcagcc ctttcctgag caccttctgt gtgcggggac atcagcagtg    9600
gcaacacagc catgctgggg actcaggct agagacaggg gaccagccta tggagagtgg    9660
gtagtgtcct gcagggcagg cttgtgccct ggagaaaaca aaccagggtg aggccaggga    9720
cgctggccgg gttcacaggg tgatggctga gcacagagtg ccaggggctg gactgtcctg    9780
actctgggtt ggtggctgag ggcctgtgtc cctctatgcc tctggttgg tgataatgga    9840 aacttgctcc ctggagagac aggacgaatg gttgatggga aatgaatgtt tgcttgtcac    9900
ttggttgact gttgttgccg ttagcattgg gcttcttggg ccaggcagcc tcaggccagc    9960
actgctgggc tccccacagg cccgacaccc tcagccctgt gcagctggcc tggcgaaacc    10020
aagaggccct gatgcccaaa atagccggga aaccccaacc agcccagccc tggcagcagg    10080
tgcctcccat ttgcctgggc tggggagggg gtggctctgg ttctggaagt ttctgccagt    10140
ccagctggag aagggacctg tatcccagca cccaggccgc ccaagcccct gcaccagggc    10200
ctgggccagg cagagttgac atcaatcaat tgggagctgc tggaatgcat ggaggcggcg    10260
ctctcgaggc tggaggaggc cagctgattt aaatcggtcc gcgtacgatg catattaccc    10320
tgttatccct accgcggtta ctggccgtcg ttttacaacg tcgtgactgg gaaaccctg     10380 gcgatgctct tctcccggtg aaaacctctg acacatggct cttctaaatc cggagtttaa    10440
acgcttcctt catgtgagca aaaggccagc aaaaggccag gaaccgtaaa aaggccgcgt    10500
tgctggcgtt tttccatagg ctccgccccc ctgacgagca tcacaaaaat cgacgctcaa    10560
gtcagaggtg gcgaaacccg acaggactat aaagatacca ggcgtttccc cctggaagct    10620
ccctcgtgcg ctctcctgtt ccgaccctgc cgcttaccgg atacctgtcc gcctttctcc    10680
cttcgggaag cgtggcgctt tctcatagct cacgctgtag gtatctcagt tcggtgtagg    10740
tcgttcgctc caagctgggc tgtgtgcacg aaccccccgt tcagcccgac cgctgcgcct    10800
```

```
tatccggtaa ctatcgtctt gagtccaacc cggtaagaca cgacttatcg ccactggcag    10860
cagccactgg taacaggatt agcagagcga ggtatgtagg cggtgctaca gagttcttga    10920
agtggtggcc taactacggc tacactagaa ggacagtatt tggtatctgc gctctgctga    10980
agccagttac cttcggaaaa agagttggta gctcttgatc cggcaaacaa accaccgctg    11040
gtagcggtgg ttttttttgtt tgcaagcagc agattacgcg cagaaaaaaa ggatctcaag    11100
aagatccttt gatcttttct acggggtctg acgctcagtg gaacgaaaac tcacgttaag    11160
ggattttggt catgcctagg tggcaaacag ctattatggg tattatgggt ctaccggtgc    11220
atgagattat caaaaaggat cttcacctag atccttttaa attaaaaatg aagttttaaa    11280
tcaatctaaa gtatatatga gtaaacttgg tctgacagtt accaatgctt aatcagtgag    11340
gcacctatct cagcgatctg tctatttcgt tcatccatag ttgcctgact ccccgtcgtg    11400
tagataacta cgatacggga gggcttacca tctggcccca gtgctgcaat gataccgcga    11460
gacccacgct caccggctcc agatttatca gcaataaacc agccagccgg aagggccgag    11520
cgcagaagtg gtcctgcaac tttatccgcc tccatccagt ctattaattg ttgccgggaa    11580
gctagagtaa gtagttcgcc agttaatagt ttgcgcaacg ttgttgccat tgctacaggc    11640
atcgtggtgt cacgctcgtc gtttggtatg gcttcattca gctccggttc ccaacgatca    11700
aggcgagtta catgatcccc catgttgtgc aaaaaagcgg ttagctcctt cggtcctccg    11760
atcgttgtca gaagtaagtt ggccgcagtg ttatcactca tggttatggc agcactgcat    11820
aattctctta ctgtcatgcc atccgtaaga tgcttttctg tgactggtga gtactcaacc    11880
aagtcattct gagaatagtg tatgcggcga ccgagttgct cttgcccggc gtcaatacgg    11940
gataataccg cgccacatag cagaacttta aaagtgctca tcattggaaa acgttcttcg    12000
gggcgaaaac tctcaaggat cttaccgctg ttgagatcca gttcgatgta acccactcgt    12060
gcacccaact gatcttcagc atcttttact ttcaccagcg tttctgggtg agcaaaaaca    12120
ggaaggcaaa atgccgcaaa aaagggaata agggcgacac ggaaatgttg aatactcata    12180
ctcttccttt ttcaatatta ttgaagcatt tatcagggtt attgtctcgg gagcggatac    12240
atatttgaat gtatttagaa aaa                                            12263
```

<210> SEQ ID NO 46
<211> LENGTH: 12639
<212> TYPE: DNA
<213> ORGANISM: Artificial Sequence
<220> FEATURE:
<223> OTHER INFORMATION: Synthetic

<400> SEQUENCE: 46

```
taaacaaata ggggttccgc gcacatttcc ccgaaaagtg ccacctgacg tcgctgagca      60
ggccctggcc tccctggccg agggcggttt gcgtattaga ggcctaaatg gccgaattca     120
gcggataaca atttcacaca ggaaacagct atgaccatga ttatctagta actataacgg     180
tcctaaggta gcgagcgatc gcttaattaa cctgcaggga tatcccatgg gggccgccag     240
tgtgatggat atctgcagaa ttcgcccttg atattaagag aagggcaagt cagcttaagt     300
ttgggggtag aggggaacag ggagtgagga gatctggcct gagagatagg agccctggtg     360
gccacaggag gactctttgg gtcctgtcgg atggacacag gcggcccgg gggcatgttg      420 gagcccggct ggttcttacc agaggcaggg ggcaccctct gacacgggag cagggcatgt     480
tccatacatg acacacccct ctgctccagg gcaggtgggt ggcggcacag aggagccagg     540
```

-continued

```
gactctgagc aaggggtcca ccagtggggc agttggatcc agacttctct gggccagcga      600
gagtctagcc ctcagccgtt ctctgtccag gagggggtg gggcaggcct gggcggccag       660
agctcatccc tcaagggttc ccagggtcct gccagaccca gatttccgac cgcagccacc      720
acaagaggat gtggtctgct gtggcagctg ccaagacctt gcagcaggtg cagggtgggg      780
gggtggggc acctggggc agctgggtc actgagttca gggaaaaccc ctttttttccc        840
ctaaacctgg ggccatccct aggggaaacc acaacttctg agccctgggc agtggctgct      900
gggagggaag agcttcatcc tggaccctgg ggggaaccc agctccaaag gtgcaagggg       960
cccaggtcca aggctagagt gggccaagca ccgcaatggc cagggagtgg gggaggtgga     1020
gctggactgg atcagggcct ccttgggact ccctacaccc tgtgtgacat gttagggtac     1080
ccacacccca tcaccagtca gggcctggcc catctccagg gccagggatg tgcatgtaag     1140
tgtgtgtgag tgtgtgtgtg tggtgtagta caccccttgg catccggttc cgaggccttg     1200
ggttcctcca aagttgctct ctgaattagg tcaaactgtg aggtcctgat cgccatcatc     1260
aacttcgttc tccccacctc ccatcattat caagagctgg ggagggtctg ggatttcttc     1320
ccacccacaa gccaaaagat aagcctgctg gtgatggcag aagacacagg atcctgggtc     1380
agagacaaag gccagtgtgt cacagcgaga gaggcagccg gactatcagc tgtcacagag     1440
aggccttagt ccgctgaact caggccccag tgactcctgt tccactgggc actggccccc     1500
ctccacagcg ccccccaggcc ccaggagag gcgtcacagc ttagagatgg ccctgctgaa    1560
cagggaacaa gaacaggtgt gccccatcca gcgccccagg ggtgggacag gtgggctgga    1620
tttggtgtga agcccttgag ccctggaacc caaccacagc agggcagttg gtagatgcca     1680
tttggggaga ggccccagga gtaagggcca tgggcccttg aggggccag gagctgagga      1740
cagggacaga gacggcccag gcagaggaca gggccatgag gggtgcactg agatggccac    1800
tgccagcagg ggcagctgcc aacccgtcca gggaacttat tcagcagtca gctggaggtg    1860
ccattgaccc tgagggcaga tgaagcccag gccaggctag gtgggctgtg aagaccccag    1920
gggacagagc tctgtccctg gcagcactg gcctctcatt ctgcagggct tgacgggatc     1980
ccaaggcctg ctgcccctga tggtagtggc agtaccgccc agagcaggac cccagcatgg    2040
aaaccccaac gggacgcagc ctgcggagcc cacaaaacca gtaaggagcc gaagcagtca    2100
tggcacgggt agtgtggact tccctttgat ggggcccagg catgaaggac agaatgggac    2160
agcggccatg agcagaaaat cagccggagg ggatgggcct aggcagacgc tggctttatt    2220
tgaagtgttg gcattttgtc tggtgtgtat tgttggtatt gattttattt tagtatgtca    2280
gtgacatact gacatattat gtaacgacat attattatgt gttttaagaa gcactccaag    2340
ggaacaggct gtctgtaatg tgtccagaga agagagcaag agcttggctc agtctccccc    2400
aaggaggtca gttcctcaac aggggtccta aatgtttcct ggagccaggc ctgaatcaag    2460
ggggtcatat ctacacgtgg ggcagaccca tggaccatt tcggagcaat aagatggcag    2520
ggaggatacc aagctggtct tacagatcca gggctttgac ctgtgacgcg ggcgctcctc    2580
caggcaaagg gagaagccag caggaagctt tcagaactgg ggagaacagg gtgcagacct    2640
ccagggtctt gtacaacgca ccctttatcc tggggtccag gaggggtcac tgagggattt    2700
aagtggggga ccatcagaac caggtttgtg ttttggaaaa atggctccaa agcagagacc    2760
agtgtgagg cagattagat gatgaagaag aggcagtgga aagtcgatgg gtggccaggt    2820
agcaagaggg cctatggagt tggcaagtga atttaaagtg gtggcaccag agggcagatg    2880
gggaggagca ggcactgtca tggactgtct atagaaatct aaaatgtata ccctttttag    2940
```

```
caatatgcag tgagtcataa aagaacacat atatatttcc tttggccggc cggcgcgcca    3000
cgcgtataac ttcgtatagc atacattata cgaagttatc ttaagggcta tggcagggcc    3060
tgccgccccg acgttggctg cgagccctgg gccttcaccc gaacttgggg ggtggggtgg    3120
ggaaaaggaa gaaacgcggg cgtattggcc ccaatgggt ctcggtgggg tatcgacaga    3180
gtgccagccc tgggaccgaa ccccgcgttt atgaacaaac gacccaacac cgtgcgtttt    3240
attctgtctt tttattgccg tcatagcgcg ggttccttcc ggtattgtct ccttccgtgt    3300
ttcactcgag ttagaagaac tcgtcaagaa ggcgatagaa ggcgatgcgc tgcgaatcgg    3360
gagcggcgat accgtaaagc acgaggaagc ggtcagccca ttcgccgcca agctcttcag    3420
caatatcacg ggtagccaac gctatgtcct gatagcggtc cgccacaccc agccggccac    3480
agtcgatgaa tccagaaaag cggccatttt ccaccatgat attcggcaag caggcatcgc    3540
catgggtcac gacgagatcc tcgccgtcgg gcatgcgcgc cttgagcctg gcgaacagtt    3600
cggctggcgc gagcccctga tgctcttcgt ccagatcatc ctgatcgaca agaccggctt    3660
ccatccgagt acgtgctcgc tcgatgcgat gtttcgcttg gtggtcgaat gggcaggtag    3720
ccggatcaag cgtatgcagc cgccgcattg catcagccat gatggatact ttctcggcag    3780
gagcaaggtg agatgacagg agatcctgcc ccggcacttc gcccaatagc agccagtccc    3840
ttcccgcttc agtgacaacg tcgagcacag ctgcgcaagg aacgcccgtc gtggccagcc    3900
acgatagccg cgctgcctcg tcctgcagtt cattcagggc accggacagg tcggtcttga    3960 caaaagaac cgggcgcccc tgcgctgaca gccggaacac ggcggcatca gagcagccga    4020
ttgtctgttg tgcccagtca tagccgaata gcctctccac ccaagcggcc ggagaacctg    4080
cgtgcaatcc atcttgttca atggccgatc ccattccaga tctgttagcc tcccccatct    4140
cccgtgcaaa cgtgcgcgcc aggtcgcaga tcgtcggtat ggagcctggg gtggtgacgt    4200
gggtctggat catcccggag gtaagttgca gcagggcgtc ccggcagccg gcgggcgatt    4260
ggtcgtaatc caggataaag acgtgcatgg gacggaggcg tttggtcaag acgtccaagg    4320
cccaggcaaa cacgttgtac aggtcgccgt tgggggccag caactcgggg gcccgaaaca    4380
gggtaaataa cgtgtccccg atatgggtc gtgggccgc gttgctctgg ggctcggcac    4440
cctggggcgg cacggccgtc cccgaaagct gtccccaatc ctcccgccac gacccgccgc    4500
cctgcagata ccgcaccgta ttggcaagca gcccgtaaac gcggcgaatc gcggccagca    4560
tagccaggtc aagccgctcg ccggggcgct ggcgtttggc caggcggtcg atgtgtctgt    4620
cctccggaag ggcccccaac acgatgtttg tgccgggcaa ggtcggcggg atgagggcca    4680
cgaacgccag cacggcctgg ggggtcatgc tgcccataag gtatcgcgcg gccgggtagc    4740
acaggagggc ggcgatggga tggcggtcga agatgagggt gagggccggg ggcggggcat    4800
gtgagctccc agcctccccc ccgatatgag gagccagaac ggcgtcggtc acggcataag    4860
gcatgcccat tgttatctgg gcgcttgtca ttaccaccgc cgcgtccccg gccgatatct    4920
caccctggtc aaggcggtgt tgtgtggtgt agatgttcgc gattgtctcg gaagcccca    4980 gcacccgcca gtaagtcatc ggctcgggta cgtagacgat atcgtcgcgc gaacccaggg    5040
ccaccagcag ttgcgtggtg gtggttttcc ccatcccgtg ggaccgtct atataaaccc    5100 gcagtagcgt gggcattttc tgctccgggc ggacttccgt ggcttcttgc tgccggcgag    5160
ggcgcaacgc cgtacgtcgg ttgctatggc cgcgagaacg cgcagcctgg tcgaacgcag    5220
acgcgtgctg atggccgggg tacgaagcca tggtggctct agaggtcgaa aggcccggag    5280
```

-continued

```
atgaggaaga ggagaacagc gcggcagacg tgcgcttttg aagcgtgcag aatgccgggc    5340
ttccggagga ccttcgggcg cccgccccgc ccctgagccc gcccctgagc ccgccccgg     5400
acccaccct  tcccagcctc tgagcccaga aagcgaagga gccaaagctg ctattggccg    5460
ctgccccaaa ggcctacccg cttccattgc tcagcggtgc tgtccatctg cacgagacta    5520
gtgagacgtg ctacttccat tgtcacgtc  ctgcacgacg cgagctgcgg ggcggggggg    5580
aacttcctga ctaggggagg agtagaaggt ggcgcgaagg ggccaccaaa gaacggagcc    5640
ggttggcgcc taccggtgga tgtggaatgt gtgcgaggcc agaggccact tgtgtagcgc    5700
caagtgccca gcggggctgc taaagcgcat gctccagact gccttgggaa aagcgcctcc    5760
cctacccggt agggatccgc gttacataac ttacggtaaa tggcccgcct ggctgaccgc    5820
ccaacgaccc ccgcccattg acgtcaataa tgacgtatgt tcccatagta acgccaatag    5880
ggactttcca ttgacgtcaa tgggtggagt atttacggta aactgcccac ttggcagtac    5940
atcaagtgta tcatatgcca agtacgcccc ctattgacgt caatgacggt aaatggcccg    6000
cctggcatta tgcccagtac atgaccttat gggactttcc tacttggcag tacatctacg    6060
tattagtcat cgctattacc atggtgatgc ggttttggca gtacatcaat gggcgtggat    6120
agcggtttga ctcacgggga tttccaagtc tccaccccat tgacgtcaat gggagtttgt    6180
tttggcacca aaatcaacgg gactttccaa aatgtcgtaa caactccgcc ccattgacgc    6180
tttggcacca aaatcaacgg ttaacaagct tagatctgcg gccgcgtcga cgataaattg    6240
tgtaattcca cttctaagga ttcatcccaa ggggggaaaa taatcaaaga tgtaaccaaa    6300
ggtttacaaa caagaactca tcattaatct tccttgttgt tatttcaacg atattattat    6360
tattactatt attattatta ttatttttgtc ttttgcatt ttctagggcc actcccacgg    6420
catagagagg ttcccaggct aggggtcaaa tcggagctac agctgccggc ctacgccaga    6480
gccacagcaa cgcaggatct gagccacagc aatgcaggat ctacaccaca gctcatggta    6540
acgctggatc cttaacccaa tgagtgaggc cagggatcga acctgtaact tcatggttcc    6600
tagtcggatt cattaaccac tgagccacga caggaactcc aacattatta atgatgggag    6660
aaaactggaa gtaacctaaa tatccagcag aaagggtgtg gccaaataca gcatggagta    6720
gccatcataa ggaatcttac acaagcctcc aaaattgtgt ttctgaaatt gggttttaaag   6780
tacgtttgca ttttaaaaag cctgccagaa aatacagaaa aatgtctgtg atatgtctct    6840
ggctgatagg attttgctta gttttaattt tggctttata attttctata gttatgaaaa    6900
tgttcacaag aagatatatt tcattttagc ttctaaaata attataacac agaagtaatt    6960
tgtgctttaa aaaatattc  aacacagaag tatataaagt aaaaattgag gagttcccat    7020
cgtggctcag tgattaacaa acccaactag tatccatgag gatatggatt tgatccctgg    7080
ccttgctcag tgggttgagg atccagtgtt gctgtgagct gtggtgtagg ttgcagacac    7140
agcactctgg cgttgctgtg actctggcgt aggccggcag ctacagctcc atttggaccc    7200
ttagcctggg aacctccata tgcctgagat acggccctaa aaagtcaaaa gccaaaaaaa    7260
tagtaaaaat tgagtgtttc tacttaccac ccctgcccac atcttatgct aaaacccgtt    7320
ctccagagac aaacatcgtc aggtgggtct atatatttcc agccctcctc ctgtgtgtgt    7380
atgtccgtaa acacacaca  cacacacaca cacgcacaca cacacacacg tatctaatta    7440
gcattggtat tagttttttca aaagggaggt catgctctac cttttaggcg gcaaatagat    7500
tatttaaaca aatctgttga cattttctat atcaacccat aagatctccc atgttcttgg    7560
aaaggctttg taagacatca acatctgggt aaaccagcat ggttttttagg gggttgtgtg    7620
gattttttttc atattttttta gggcacacct gcagcatatg gaggttccca ggctagggt    7680
```

-continued

```
tgaatcagag ctgtagctgc cggcctacac cacagccaca gcaacgccag atccttaacc    7740
cactgagaaa ggccagggat tgaacctgca tcctcatgga tgctggtcag atttatttct    7800
gctgagccac aacaggaact ccctgaacca gaatgctttt aaccattcca ctttgcatgg    7860
acatttagat tgtttccatt taaaaataca aattacaagg agttcccgtc gtggctcagt    7920
ggtaacgaat tggactagga accatgaggt ttcgggttcg atccctggcc ttgctcggtg    7980
ggttaaggat ccagcattga tgtgagatat ggtgtaggtc gcagacgtgg ctcggatccc    8040
acgttgctgt ggctctggcg taggccggca acaacagctc cgattcgacc cctagcctgg    8100
gaacctccat gtgccacagg agcagcccta gaaaaggcaa aaagacaaaa aaataaaaaa    8160
ttaaaatgaa aaataaaat aaaaatacaa attacaagag acggctacaa ggaaatcccc    8220
aagtgtgtgc aaatgccata tatgtataaa atgtactagt gtctcctcgc gggaaagttg    8280
cctaaaagtg ggttggctgg acagagagga caggctttga cattctcata ggtagtagca    8340
atgggcttct caaaatgctg ttccagttta cactcaccat agcaaatgac agtgcctctt    8400
cctctccacc cttgccaata atgtgacagg tggatctttt tctattttgt gtatctgaca    8460
agcaaaaaat gagaacagga gttcctgtcg tggtgcagtg gagacaaatc tgactaggaa    8520
ccatgaaatt tcgggttcaa tccctggcct cactcagtag gtaaaggatc cagggttgca    8580
gtgagctgtg gggtaggtcg cagacacagt gcaaatttgg ccctgttgtg gctgtggtgt    8640
aggccggcag ctatagctcc aattggaccc ctagcctggg aacctcctta tgccgtgggt    8700
gaggccctaa aaaaaagagt gcaaaaaaaa aaaataagaa caaaaatgat catcgtttaa    8760 ttctttatt gatcattggt gaaacttatt ttcctttat atttttattg actgatttta    8820
tttctcctat gaatttaccg gtcatagttt tgcctgggtg ttttactcc ggttttagtt    8880 ttggttggtt gtattttctt agagagctat agaaactctt catctatttg aatagtaat    8940 tcctcattaa gtatttgtgc tgcaaaaaat tttccctgat ctgttttatg cttttgtttg    9000
tggggtcttt cacgagaaag cctttttagt ttttacacct cagcttggtt gtttttcttg    9060
attgtgtctg taatctgcgg ccaacatagg aaacacattt ttactttagt gttttttttcc   9120 tattttcttc aagtacgtcc attgttttgg tgtctgattt tactttgcct ggggtttgtt    9180
tttgtgtggc aggaatataa acttatgtat tttccaaatg gagagccaat ggttgtatat    9240
ttgttgaatt caaatgcaac tttatcaaac accaaatcat cgattatca caactcttct    9300 ctggtttatt gatctaatga tcaattcctg ttccacgctg ttttaattat tttagctttg    9360 tggatttgg tgcctggtag agaacaaagc ctccattatt ttcattcaaa atagtcccgt    9420
ctattatctg ccattgttgt agtattagac tttaaaatca atttactgat tttcaaaagt    9480
tattcctttg gtgatgtgga atactttata cttcataagg tacatggatt catttgtggg    9540
gaattgatgt ctttgctatt gtggccattt gtcaagttgt gtaatatttt acccatgcca    9600
actttgcata ttgtatgtga gtttattccc agggtttttta ataggatgtt tattgaagtt    9660
gtcagtgttt ccacaatttc atcgcctcag tgcttactgt tgcataaaa ggaaacctac     9720 tcacttttgc ctattgctct tgtattcaat cattttagtt aactcttgtg ttaatttgta    9780 gagttttttca gctgactgtc tggggttttc tttaatagac tagcccttg tctgtaaaga    9840 ataatttat cgaattttc ttaacactca cactctcccc accccaccc ccgctcatct      9900 cctttcattg ggtcaaatct gtagaataca ataaagtaa gagtgggaac cttagccttt     9960
aagtcgattt tgcctttaaa tgtgaatgtt gctatgtttc gggacattct ctttatcaag   10020
```

```
ttgcggatgt tccttagat aattaactta ataaaagact ggatgtttgc tttcttcaaa    10080
tcagaattgt gttgaattta tattgctatt ctgtttaatt ttgtttcaaa aaatttacat    10140
gcacacctta aagataacca tgaccaaata gtcctcctgc tgagagaaaa tgttggcccc    10200
aatgccacag gttacctccc gactcagata aactacaatg ggagataaaa tcagatttgg    10260
caaagcctgt ggattcttgc cataactctc agagcatgac ttgggtgttt tttccttttc    10320
taagtatttt aatggtattt ttgtgttaca ataggaaatc taggacacag agagtgattc    10380
aatgagggga acgcattctg ggatgactct aggcctctgg tttggggaga gctctattga    10440
agtaaagaca atgagaggaa gcaagtttgc agggaactgt gaggaattta gatggggaat    10500
gttgggtttg aggtttctat agggcacgca agcagagatg cactcaggag gaagaaggag    10560
cataaatcta gtggcgctgc cggcaagctt gctggaggag gccaattggg agctgctgga    10620
atgcatggag gcggcgctct cgaggctgga ggaggccagc tgatttaaat cggtccgcgt    10680
acgatgcata ttaccctgtt atccctaccg cggttactgg ccgtcgtttt acaacgtcgt    10740
gactgggaaa accctggcga tgctcttctc ccggtgaaaa cctctgacac atggctcttc    10800
taaatccgga gtttaaacgc ttccttcatg tgagcaaaag gccagcaaaa ggccaggaac    10860
cgtaaaaagg ccgcgttgct ggcgtttttc cataggctcc gcccccctga cgagcatcac    10920
aaaaatcgac gctcaagtca gaggtggcga acccgacag gactataaag ataccaggcg    10980
tttccccctg gaagctccct cgtgcgctct cctgttccga ccctgccgct taccggatac    11040
ctgtccgcct ttctcccttc gggaagcgtg gcgctttctc atagctcacg ctgtaggtat    11100
ctcagttcgg tgtaggtcgt tcgctccaag ctgggctgtg tgcacgaacc ccccgttcag    11160
cccgaccgct gcgccttatc cggtaactat cgtcttgagt ccaacccggt aagacacgac    11220
ttatcgccac tggcagcagc cactggtaac aggattagca gagcgaggta tgtaggcggt    11280
gctacagagt tcttgaagtg gtggcctaac tacggctaca ctagaaggac agtatttggt    11340
atctgcgctc tgctgaagcc agttaccttc ggaaaaagag ttggtagctc ttgatccggc    11400
aaacaaacca ccgctggtag cggtggtttt tttgtttgca agcagcagat tacgcgcaga    11460
aaaaaaggat ctcaagaaga tcctttgatc ttttctacgg ggtctgacgc tcagtggaac    11520
gaaaactcac gttaagggat tttggtcatg cctaggtggc aaacagctat tatgggtatt    11580
atgggtctac cggtgcatga gattatcaaa aaggatcttc acctagatcc ttttaaatta    11640
aaaatgaagt tttaaatcaa tctaaagtat atatgagtaa acttggtctg acagttacca    11700
atgcttaatc agtgaggcac ctatctcagc gatctgtcta tttcgttcat ccatagttgc    11760
ctgactcccc gtcgtgtaga taactacgat acgggagggc ttaccatctg gccccagtgc    11820
tgcaatgata ccgcgagacc cacgctcacc ggctccagat ttatcagcaa taaaccagcc    11880
agccggaagg gccgagcgca gaagtggtcc tgcaacttta tccgcctcca tccagtctat    11940
taattgttgc cgggaagcta gagtaagtag ttcgccagtt aatagtttgc gcaacgttgt    12000
tgccattgct acaggcatcg tggtgtcacg ctcgtcgttt ggtatggctt cattcagctc    12060
cggttcccaa cgatcaaggc gagttacatg atcccccatg ttgtgcaaaa aagcggttag    12120
ctccttcggt cctccgatcg ttgtcagaag taagttggcc gcagtgttat cactcatggt    12180
tatggcagca ctgcataatt ctcttactgt catgccatcc gtaagatgct tttctgtgac    12240
tggtgagtac tcaaccaagt cattctgaga atagtgtatg cggcgaccga gttgctcttg    12300
cccggcgtca atacgggata ataccgcgcc acatagcaga actttaaaag tgctcatcat    12360
tggaaaacgt tcttcggggc gaaaactctc aaggatctta ccgctgttga tccagttc    12420
```

```
gatgtaaccc actcgtgcac ccaactgatc ttcagcatct tttactttca ccagcgtttc     12480
tgggtgagca aaaacaggaa ggcaaaatgc cgcaaaaaag ggaataaggg cgacacggaa     12540
atgttgaata ctcatactct tccttttttca atattattga agcatttatc agggttattg    12600
tctcgggagc ggatacatat ttgaatgtat ttagaaaaa                            12639
```

<210> SEQ ID NO 47
<211> LENGTH: 12297
<212> TYPE: DNA
<213> ORGANISM: Artificial Sequence
<220> FEATURE:
<223> OTHER INFORMATION: Synthetic

<400> SEQUENCE: 47

```
taaacaaata ggggttccgc gcacatttcc ccgaaaagtg ccacctgacg tcgctgagca       60
ggccctggcc tccctggccg agggcggttt gcgtattaga ggcctaaatg gccgaattca      120
gcggataaca atttcacaca ggaaacagct atgaccatga ttatctagta actataacgg     180
tcctaaggta gcgagcgatc gcttaattaa cctgcaggga taaccactga cccatgacgg     240
gaactcccag ggctcagctc ttgactccag gttcgcagct gccctcaaag caatgcaacc     300
ctggctggcc ccgcctcatg catccggcct cctccccaaa gagctctgag cccacctggg     360
cctaggtcct cctccctggg actcatggcc taagggtaca gagttactgg ggctgatgaa     420
gggaccaatg gggacagggg cctcaaatca agtggctgt ctctctcatg tcccttcctc      480
tcctcagggt ccaaaatcag ggtcagggcc ccagggcagg ggctgagagg gcctcttcct     540
gaaggccctg tctcagtgca ggttatgggg gtctggggga gggtcaatgc agggctcacc    600
cttcagtgcc ccaaagccta gagagtgagt gcctgccagt ggcttcccag gcccaatccc     660
ttgactgcct gggaatgctc aaatgcagga actgtcacaa caccttcagt caggggctgc    720
tctgggagga aaaacactca gaattggggg ttcaggaag gcccagtgcc aagcatagca      780
ggagctcagg tggctgcaga tggtgtgaac cccaggagca ggatggccgg cactccccc     840 agaccctcca gagccccagg ttggctgccc tcttcactgc cgacacccct gggtccactt    900
ctgccctttc ccacctaaaa cctttagggc tcccactttc tcccaaatgt gagacatcac    960
cacggctccc agggagtgtc cagaagggca tctggctgag aggtcctgac atctgggagc    1020 ctcaggccc acaatggaca gacgccctgc caggatgctg ctgcagggct gttagctagg     1080
cggggtggag atgggtact ttgcctctca gaggccccgg ccccaccatg aaacctcagt     1140 gacacccat ttccctgagt tcacatacct gtatcctact ccagtcacct tccccacgaa    1200
cccctgggag cccaggatga tgctggggct ggagccacga ccagcccacg agtgatccag    1260
ctctgccaat cagcagtcat ttcccaagtg ttccagccct gccaggtccc actacagcag    1320
taatggaggc cccagacacc agtccagcag ttagagggct ggactagcac cagcttttcaa    1380 gcctcagcat ctcaaggtga atggccagtg ccctccccg tggccatcac aggatcgcag     1440
atatgaccct aggggaagaa atatcctggg agtaaggaag tgcccatact caaggatggc    1500
ccctctgtga cctaacctgt ccctgaggat tgtacttcca ggcgttaaaa cagtagaacg    1560
cctgcctgtg aaccccgcc aagggactgc ttggggaggc cccctaaacc agaacacagg     1620
cactccagca ggacctctga actctgacca ccctcagcaa gtgggcaccc ccgcagctt    1680 ccaaggcacc ccagggctca ccacagcggc ccctcctggc agcccctcac ccaggcccag    1740
accctctaag atggcacatc taagccaatc cacctccttg tcattcctcc tgtccccacc    1800
```

```
caggacccctt ctcagatgaa accttcgctc cagccgctgg gccctctctc ctgcccctct    1860
ggcagttctc cagggactcc gcctcccact ctctgtctct ccctgcactc ctaggaacaa    1920
gcgacctcca ggaagcccag tccaattatc ccctctgtgt cctccccaat ctctgcctct    1980
gggtggattt gagcaccaca tcctgttctc ttcgacctga aactccttgg ccccggtgtc    2040
cgctctcctg ggccctcttt tctctcctcc cctcttccgt gccccgtttg tttggtgtta    2100
caggcaggcc ccggggagcc gtccctccag ctgctcttcc ttgtctgtct caggagccag    2160
aaactggcag catctaaaaa gggctcctgt ttcttcatct gcccagcctc ctagcccaac    2220
cagggctctg gcctcactcc agagggtggg ctccagaggg caggggttgc accctcttag    2280
tgcctcagag gctcagctgg gtgcaggatg ggggggccct cagggagccc ctcagtgact    2340
gctgatcact tactgcagga ctgttcccag ctcttcccaa tcattggaat gacaatacct    2400
agttctgctc catcatagtg atgcaggaaa aatgttactg aaatcctggt tcttgtttag    2460
caatcgaaga atgaattccg cgaacacaca ggcagcaagc aagcgaagcc tttattaaag    2520
gaaagcagat agctcccagg gctgcaggga gcggggagaa gagctcccca ctctctattg    2580
tcctataggg cttttaccc cttaaagttg gggggataca aaaaaaatag aagaaaagg    2640 gagttcccgt cagggcacag cagaaacaaa tccaactagg aaccatgagg ttgggggttc    2700
gattcctggc ctctctcagt gggttaagga tgcagcgttg ccgtgagcta tgatacaggt    2760
cacagatgca gctcagatct actagtcaat tgacaggcgc cggagcagga gctaggcctt    2820
tggccggccg gcgcgccacg cgtataactt cgtatagcat acattatacg aagttatctt    2880
aagggctatg gcagggcctg ccgccccgac gttggctgcg agccctgggc cttcacccga    2940
acttgggggg tggggtgggg aaaaggaaga aacgcgggcg tattggcccc aatgggtct    3000 cggtggggta tcgacagagt gccagccctg ggaccgaacc ccgcgtttat gaacaaacga    3060
cccaacaccg tgcgttttat tctgtctttt tattgccgtc atagcgcggg ttccttccgg    3120
tattgtctcc ttccgtgttt cactcgagtt agaagaactc gtcaagaagg cgatagaagg    3180
cgatgcgctg cgaatcggga gcggcgatac cgtaaagcac gaggaagcgg tcagcccatt    3240
cgccgccaag ctcttcagca atatcacggg tagccaacgc tatgtcctga tagcggtccg    3300
ccacacccag ccggccacag tcgatgaatc cagaaaagcg gccattttcc accatgatat    3360
tcggcaagca ggcatcgcca tgggtcacga cgagatcctc gccgtcgggc atgcgcgcct    3420
tgagcctggc gaacagttcg gctggcgcga gcccctgatg ctcttcgtcc agatcatcct    3480
gatcgacaag accggcttcc atccgagtac gtgctcgctc gatgcgatgt ttcgcttggt    3540
ggtcgaatgg gcaggtagcc ggatcaagcg tatgcagccg ccgcattgca tcagccatga    3600
tggatacttt ctcggcagga gcaaggtgag atgacaggag atcctgcccc ggcacttcgc    3660
ccaatagcag ccagtcccctt cccgcttcag tgacaacgtc gagcacagct gcgcaaggaa    3720 cgccccgtcgt ggccagccac gatagccgcg ctgcctcgtc ctgcagttca ttcagggcac    3780
cggacaggtc ggtcttgaca aaaagaaccg ggcgcccctg cgctgacagc cggaacacgg    3840
cggcatcaga gcagccgatt gtctgttgtg cccagtcata gccgaatagc ctctccaccc    3900
aagcggccgg agaacctgcg tgcaatccat cttgttcaat ggccgatccc attccagatc    3960
tgttagcctc ccccatctcc cgtgcaaacg tgcgcgccag gtcgcagatc gtcggtatgg    4020
agcctggggt ggtgacgtgg gtctggatca tcccggaggt aagttgcagc agggcgtccc    4080
ggcagccggc gggcgattgg tcgtaatcca ggataaagac gtgcatggga cggaggcgtt    4140
tggtcaagac gtccaaggcc caggcaaaca cgttgtacag gtcgccgttg ggggccagca    4200
```

-continued

```
actcggggc   ccgaaacagg   gtaaataacg   tgtccccgat   atgggtcgt   gggcccgcgt    4260 tgctctgggg   ctcggcaccc   tggggcggca   cggccgtccc   cgaaagctgt   ccccaatcct    4320
cccgccacga   cccgccgccc   tgcagatacc   gcaccgtatt   ggcaagcagc   ccgtaaacgc    4380
ggcgaatcgc   ggccagcata   gccaggtcaa   gccgctcgcc   ggggcgctgg   cgtttggcca    4440
ggcggtcgat   gtgtctgtcc   tccggaaggg   ccccccaacac   gatgtttgtg   ccgggcaagg    4500
tcggcgggat   gagggccacg   aacgccagca   cggcctgggg   ggtcatgctg   cccataaggt    4560
atcgcgcggc   cgggtagcac   aggagggcgg   cgatgggatg   gcggtcgaag   atgagggtga    4620
gggccggggg   cggggcatgt   gagctcccag   cctcccccc   gatatgagga   gccagaacgg    4680
cgtcggtcac   ggcataaggc   atgcccattg   ttatctgggc   gcttgtcatt   accaccgccg    4740 cgtcccggc   cgatatctca   ccctggtcaa   ggcggtgttg   tgtggtgtag   atgttcgcga    4800
ttgtctcgga   agcccccagc   acccgccagt   aagtcatcgg   ctcgggtacg   tagacgatat    4860
cgtcgcgcga   acccagggcc   accagcagtt   gcgtggtggt   ggttttcccc   atcccgtggg    4920
gaccgtctat   ataaacccgc   agtagcgtgg   gcattttctg   ctccgggcgg   acttccgtgg    4980
cttcttgctg   ccggcgaggg   cgcaacgccg   tacgtcggtt   gctatggccg   cgagaacgcg    5040
cagcctggtc   gaacgcagac   gcgtgctgat   ggccggggta   cgaagccatg   gtggctctag    5100
aggtcgaaag   gcccggagat   gaggaagagg   agaacagcgc   ggcagacgtg   cgcttttgaa    5160
gcgtgcagaa   tgccgggctt   ccggaggacc   ttcgggcgcc   cgccccgccc   ctgagcccgc    5220
ccctgagccc   gccccccggac   ccaccccttc   ccagcctctg   agcccagaaa   gcgaaggagc    5280
caaagctgct   attggccgct   gccccaaagg   cctacccgct   tccattgctc   agcggtgctg    5340
tccatctgca   cgagactagt   gagacgtgct   acttccattt   gtcacgtcct   gcacgacgcg    5400
agctgcgggg   cgggggggaa   cttcctgact   aggggaggag   tagaaggtgg   cgcgaagggg    5460
ccaccaaaga   acggagccgg   ttggcgccta   ccggtggatg   tggaatgtgt   gcgaggccag    5520
aggccacttg   tgtagcgcca   agtgcccagc   ggggctgcta   aagcgcatgc   tccagactgc    5580
cttgggaaaa   gcgcctcccc   tacccggtag   ggatccgcgt   tacataactt   acggtaaatg    5640
gcccgcctgg   ctgaccgccc   aacgaccccc   gcccattgac   gtcaataatg   acgtatgttc    5700
ccatagtaac   gccaataggg   actttccatt   gacgtcaatg   ggtggagtat   ttacggtaaa    5760
ctgcccactt   ggcagtacat   caagtgtatc   atatgccaag   tacgcccct   attgacgtca    5820 atgacggtaa   atggcccgcc   tggcattatg   cccagtacat   gaccttatgg   actttccta    5880 cttggcagta   catctacgta   ttagtcatcg   ctattaccat   ggtgatgcgg   ttttggcagt    5940
acatcaatgg   gcgtggatag   cggtttgact   cacggggatt   tccaagtctc   cacccccattg    6000 acgtcaatgg   gagtttgttt   tggcaccaaa   atcaacggt   aacaagctta   taacttcgta    6060
tagcatacat   tatacgaagt   tattacgtag   cggccgcgtc   gacgatatcg   ctgccggagc    6120
cccgggggcc   gctgccggaa   gatctggcat   tgctgtgact   gtggtgtagg   ccggcagctg    6180
gagctctgat   tagacccctc   acctgggaat   ctccatatgc   tgcacgtgcg   ccctaaaaa    6240 gacaaaagac   aaaaaaaaaa   aaaaaaaaa   aaaatcaaaa   aaaacatag   ggggttacca    6300 acgtggggtc   cagaaagatg   tggttttctc   ccattggcct   tgcccagtta   cctatatcag    6360
tccttgtcca   acaggggttt   tagggggtgga   aatgccccat   aaattttacg   gtttctttgc    6420
ccttctcttc   ctttagactg   agtcaccatt   gctctcattc   cttttctatc   agttgaggag    6480
tgggttagag   attaaggtcc   atgtggtgga   ggtacacttc   ttatagtaaa   caaggcctat    6540
```

-continued

```
ggggaattac tctctggagc ccttaaacca caaatgataa tccatgccac atcaaagatg    6600
catcgaagcc catgctccta cactgactac ctgagttagc attctgcctc aacaggactg    6660
accatcccca gctctggggc agatatcctc tctctgccac aagggcagtg accccccatgc   6720
tgtctgaggg tcacgcttta ccccccccc  accctgccg  tgaccccccca gaccacccca    6780
ggaggtgggc actaatatcc ctcattaccc catagatgag gaaacagagg ttcccccggg    6840
gtcccacagg tgctcagggt cacatgcacc gtgggcaccc aggccccatc ccaaggccac    6900
cctccctcct caggaagctg tgctgcgctg gccagaagg  tactgcacac gactcctcag    6960
cctccgtgg  tgggaggcag cctcaagcct ctgagtgggg gggcacccgg gctcctcaat    7020
ctatactgac tcctgggggt gggagaaggg gaggggagc  tgtggcctct gagtccacta    7080
agcaaatcag ggtgggcaat gcgggcccat ttcaaggagg agagaaccga ggctctgaca    7140
gcaggccggg ggtccaggga cctgcccagg gtcataggct gaactgctgg ctgacctgcc    7200
ttgggttctt tccttggctc ctcagccctg tgtgatgtga caggtcattc attcactcac    7260
tcgctcattc attcagcaaa ccctcagtga gccctgctgg gagcaggtgc taggggcaag    7320
gagacaggac ctcttgccct ggaacagctg aagcactggg ggacaggcag tggcagggag    7380
gtgcgtgatc accgctgacc ccattccatc ctccagcccc caggtcagtt ccacccacc    7440
attgacccca ccatgtcctc catccccaag gtcagtttcc cgcccaagga gcatctcctt    7500
acacactagg gacaaaattt cacggctgtc actgggcatc tctccacgct catcacagcc    7560
ctctagcagc cttgaagtcc tgtagagccc ttcccatttc acagaaggga caagactatg    7620
agggccacac cgtgagccat gagccttagg ctgtgagccg ggacagcccc tgcaggactg    7680
gtggcctcag ggcactgggt ggggagggtg cacagtgggt gggccccttg tggaatagag    7740
aggagtgtca ggtcagggga gggggcttgg cctggccctg gcctgcctgg tgtgcaaccc    7800
taggcagccc ctccttccca ggcctcctac ttcctggagg ccaagcctca gggaggtaat    7860
tgagtcaggt ggggggagggg gggttgtggc tttcttcaca gcagaaaaac agagcccaca    7920
atagtgtcca ctgagacaga ggggtcctgg gggaggggag gggtgggagg tgactgctga    7980
gcccgtgtgg gggagggag  caactactga gctgagctgg gtgactctcc catctgcccc    8040
gcccctgtg  gggccagcag agtcaccgag agaacatgac ccagccaggc ctggacaggg    8100
ggacacccat gtcctttacc ccacagggtt cactgagcct atctgcccca agcctgtgtc    8160
tccctgggac ggagaccctc actcccaacc acaaaggtct aaactcaagt tcccaacagc    8220
cttgaaaata cagcttccgg gggcctccaa ggagcagtca gccgtccact gccaggctcg    8280
ctggctcagt gacacaggac acatcctgat gacggtccac ctgtctccaa gcaggttctc    8340
ctctgccgat ggggcaacga gctcctcctg tggctccctg gctggatgcg tgggaggcgg    8400
ggtgggggg  caggcggtgt tcctggccgc acacaaggag cacccccacc agcatccgaa    8460
gacgggggcc cggtctttcc ccaaaacact gcttgcggga gactttgtga cgtttccagg    8520
ggccatgctc ccttcgggca gcttggggga cttctgctcc tatgtggtca cctgcaggga    8580
ctccccccag gccttgggga caaacaaagt gatgagaggg agggttagtg ggtcggggca    8640
gggccagtct ttgaccggt  ttatctgaaa agccagttgg tcaccgggaa ccacagcaaa    8700
cctaaaccca tttggccagg catctcccag ggacagtctc cccaggatg  cggggcccag    8760
gggggctcca ggggtgacct gcgtcctgga tttccctgat gctcccagtt cgtgcctctg    8820
tccaagcatg atttttaata gtgccccttc cactcccaga aatgtccaag tgtgggcaat    8880
aaattctggt cacctgagct cagtgtaact gtttgctgaa tgacacttac tgtaacaggt    8940
```

```
taaaatggga ggcccaaggc cacgcagagc catcgaaggc tctgtgtgtc ccagccctga   9000
tagaagcatc aggatgggga ctgtggcctc accaggggcc acatccaggc ggtcaccatg   9060
gggttcctgg tctccgtggg ccttgactgg agccctggt gtgagctcac cccatcccag    9120
cctgtgagag gcctggatgt gggcctgaca tcatttccca cccagtgaca gcactgcatg   9180
tgatggggcc tctgggcagc cttttcccg ggggaaactg gcaggaatca ggaccaccag    9240 gacagggtc aggggagagg cgatgctggg caccagagcc tggaccaccc tcgggttctc    9300
agcgatgggc aaccctgcc acccagggcc ccgccttcct ggggagacat cggggtttcc    9360
aggccatcct gggaggaggg tgggagcctc agctagaccc cagctggctt gccccccat   9420 gccccggcca agagagggtc ttggagggaa ggggacccc agaccagcct ggcgagccca    9480
tcctcagggt ctctggtcag acaggggctc agctgagctc cagggtagac caaggccctg   9540
cgtggatgag gccagtgtgg tcactgccca gagcaaagcc acctctcagc agcccttctcc  9600 tgagcacctt ctgtgtgcgg ggacatcagc agtggcaaca cagccatgct ggggactcag   9660
ggctagagac aggggaccag cctatggaga gtgggtagtg tcctgcaggg caggcttgtg   9720
ccctggagaa aacaaaccag ggtgaggcca gggacgctgg ccgggttcac agggtgatgg   9780
ctgagcacag agtgccaggg gctggactgt cctgactctg ggttggtggc tgagggcctg   9840
tgtccctcta tgcctctggg ttggtgataa tggaaacttg ctccctggag agacaggacg   9900
aatggttgat gggaaatgaa tgtttgcttg tcacttggtt gactgttgtt gccgttagca   9960
ttgggcttct tgggccaggc agcctcaggc cagcactgct gggctcccca caggcccgac   10020
accctcagcc ctgtgcagct ggcctggcga aaccaagagg ccctgatgcc caaaatagcc   10080
gggaaacccc aaccagccca gccctggcag caggtgcctc ccatttgcct gggctggggg   10140
aggggtggct ctggttctgg aagtttctgc cagtccagct ggagaaggga cctgtatccc   10200
agcacccagg ccgcccaagc ccctgcacca gggcctgggc caggcagagt tgacatcaat   10260
caattgggag ctgctggaat gcatggaggc ggcgctctcg aggctggagg aggccagctg   10320
atttaaatcg gtccgcgtac gatgcatatt accctgttat ccctaccgcg gttactggcc   10380
gtcgttttac aacgtcgtga ctgggaaaac cctggcgatg ctcttctccc ggtgaaaacc   10440
tctgacacat ggctcttcta aatccggagt ttaaacgctt ccttcatgtg agcaaaaggc   10500
cagcaaaagg ccaggaaccg taaaaaggcc gcgttgctgg cgttttttcca taggctccgc   10560 cccccctgacg agcatcacaa aaatcgacgc tcaagtcaga ggtggcgaaa cccgacagga   10620
ctataaagat accaggcgtt tccccctgga agctccctcg tgcgctctcc tgttccgacc   10680
ctgccgctta ccggatacct gtccgccttt ctcccttcgg gaagcgtggc gctttctcat   10740
agctcacgct gtaggtatct cagttcggtg taggtcgttc gctccaagct gggctgtgtg   10800
cacgaacccc ccgttcagcc cgaccgctgc gccttatccg gtaactatcg tcttgagtcc   10860
aacccggtaa gacacgactt atcgccactg gcagcagcca ctggtaacag gattagcaga   10920
gcgaggtatg taggcggtgc tacagagttc ttgaagtggt ggcctaacta cggctacact   10980
agaaggacag tatttggtat ctgcgctctg ctgaagccag ttaccttcgg aaaaagagtt   11040
ggtagctctt gatccggcaa acaaaccacc gctggtagcg tggtttttt tgtttgcaag   11100 cagcagatta cgcgcagaaa aaaaggatct caagaagatc ctttgatctt ttctacgggg   11160
tctgacgctc agtggaacga aaactcacgt taagggattt tggtcatgcc taggtggcaa   11220
acagctatta tgggtattat gggtctaccg gtgcatgaga ttatcaaaaa ggatcttcac   11280
```

-continued

| | |
|---|---|
| ctagatcctt ttaaattaaa aatgaagttt taaatcaatc taaagtatat atgagtaaac | 11340 |
| ttggtctgac agttaccaat gcttaatcag tgaggcacct atctcagcga tctgtctatt | 11400 |
| tcgttcatcc atagttgcct gactcccgt cgtgtagata actacgatac gggagggctt | 11460 |
| accatctggc cccagtgctg caatgatacc gcgagaccca cgctcaccgg ctccagattt | 11520 |
| atcagcaata accagccag ccggaagggc cgagcgcaga agtggtcctg caactttatc | 11580 |
| cgcctccatc cagtctatta attgttgccg gaagctaga gtaagtagtt cgccagttaa | 11640 |
| tagtttgcgc aacgttgttg ccattgctac aggcatcgtg gtgtcacgct cgtcgtttgg | 11700 |
| tatggcttca ttcagctccg gttcccaacg atcaaggcga gttacatgat cccccatgtt | 11760 |
| gtgcaaaaaa gcggttagct ccttcggtcc tccgatcgtt gtcagaagta agttggccgc | 11820 |
| agtgttatca ctcatggtta tggcagcact gcataattct cttactgtca tgccatccgt | 11880 |
| aagatgcttt tctgtgactg gtgagtactc aaccaagtca ttctgagaat agtgtatgcg | 11940 |
| gcgaccgagt tgctcttgcc cggcgtcaat acgggataat accgcgccac atagcagaac | 12000 |
| tttaaaagtg ctcatcattg gaaaacgttc ttcggggcga aaactctcaa ggatcttacc | 12060 |
| gctgttgaga tccagttcga tgtaaccac tcgtgcaccc aactgatctt cagcatcttt | 12120 |
| tactttcacc agcgtttctg ggtgagcaaa aacaggaagg caaaatgccg caaaaaaggg | 12180 |
| aataagggcg acacggaaat gttgaatact catactcttc cttttcaat attattgaag | 12240 |
| catttatcag ggttattgtc tcgggagcgg atacatattt gaatgtattt agaaaaa | 12297 |

<210> SEQ ID NO 48
<211> LENGTH: 12163
<212> TYPE: DNA
<213> ORGANISM: Artificial Sequence
<220> FEATURE:
<223> OTHER INFORMATION: Synthetic

<400> SEQUENCE: 48

| | |
|---|---|
| gcaaaaggcc aggaaccgta aaaaggccgc gttgctggcg ttttttccata ggctccgccc | 60 |
| ccctgacgag catcacaaaa atcgacgctc aagtcagagg tggcgaaacc cgacaggact | 120 |
| ataaagatac caggcgtttc ccctggaag ctccctcgtg cgctctcctg ttccgaccct | 180 |
| gccgcttacc ggatacctgt ccgcctttct cccttcggga agcgtggcgc tttctcaatg | 240 |
| ctcacgctgt aggtatctca gttcggtgta ggtcgttcgc tccaagctgg gctgtgtgca | 300 |
| cgaacccccc gttcagcccg accgctgcgc cttatccggt aactatcgtc ttgagtccaa | 360 |
| cccggtaaga cacgacttat cgccactggc agcagccact ggtaacagga ttagcagagc | 420 |
| gaggtatgta ggcggtgcta cagagttctt gaagtggtgg cctaactacg gctacactag | 480 |
| aaggacagta tttggtatct gcgctctgct gaagccagtt accttcggaa aaagagttgg | 540 |
| tagctcttga tccggcaaac aaaccaccgc tggtagcggt ggtttttttg tttgcaagca | 600 |
| gcagattacg cgcagaaaaa aaggatctca agaagatcct ttgatctttt ctacggggtc | 660 |
| tgacgctcag tggaacgaaa actcacgtta agggattttg gtcatgagat tatcaaaaag | 720 |
| gatcttcacc tagatccttt taaattaaaa atgaagtttt aaatcaatct aaagtatata | 780 |
| tgagtaaact tggtctgaca gttaccaatg cttaatcagt gaggcaccta tctcagcgat | 840 |
| ctgtctattt cgttcatcca tagttgcctg actccccgtc gtgtagataa ctacgatacg | 900 |
| ggagggctta ccatctggcc ccagtgctgc aatgataccg cgagacccac gctcaccggc | 960 |
| tccagattta tcagcaataa accagccagc cggaagggcc gagcgcagaa gtggtcctgc | 1020 |
| aactttatcc gcctccatcc agtctattaa ttgttgccgg gaagctagag taagtagttc | 1080 |

```
gccagttaat agtttgcgca acgttgttgc cattgctaca ggcatcgtgg tgtcacgctc   1140
gtcgtttggt atggcttcat tcagctccgg ttcccaacga tcaaggcgag ttacatgatc   1200
ccccatgttg tgcaaaaaag cggttagctc cttcggtcct ccgatcgttg tcagaagtaa   1260
gttggccgca gtgttatcac tcatggttat ggcagcactg cataattctc ttactgtcat   1320
gccatccgta agatgctttt ctgtgactgg tgagtactca accaagtcat tctgagaata   1380
gtgtatgcgg cgaccgagtt gctcttgccc ggcgtcaata cgggataata ccgcgccaca   1440
tagcagaact ttaaaagtgc tcatcattgg aaaacgttct cgggggcgaa aactctcaag   1500
gatcttaccg ctgttgagat ccagttcgat gtaacccact cgtgcaccca actgatcttc   1560
agcatctttt actttcacca gcgtttctgg gtgagcaaaa acaggaaggc aaaatgccgc   1620
aaaaaaggga ataagggcga cacgaaaatg ttgaatactc atactcttcc ttttcaata   1680 ttattgaagc atttatcagg gttattgtct catgagcgga tacatatttg aatgtattta   1740
gaaaaataaa caaatagggg ttccgcgcac atttccccga aaagtgccac ctgacgtcaa   1800
acagctatga ccatggcggc cgcgtcgaca gggtgtggcc aaatacagca tggagtagcc   1860
atcataagga atcttacaca agcctccaaa attgtgtttc tgaaattggg tttaaagtac   1920
gtttgcattt taaaaagcct gccagaaaat acagaaaaat gtctgtgata tgtctctggc   1980
tgataggatt ttgcttagtt ttaattttgg ctttataatt ttctatagtt atgaaaatgt   2040
tcacaagaag atatatttca ttttagcttc taaaataatt ataacacaga agtaatttgt   2100
gctttaaaaa aatattcaac acagaagtat ataaagtaaa aattgaggag ttcccatcgt   2160
ggctcagtga ttaacaaacc caactagtat ccatgaggat atggatttga tccctggcct   2220
tgctcagtgg gttgaggatc cagtgttgct gtgagctgtg gtgtaggttg cagacacagc   2280
actctggcgt tgctgtgact ctggcgtagg ccggcagcta cagctccatt tggaccctta   2340
gcctgggaac ctccatatgc ctgagatacg gccctaaaaa gtcaaaagcc aaaaaaatag   2400
taaaaattga gtgtttctac ttaccacccc tgcccacatc ttatgctaaa cccgttctc   2460 cagagacaaa catcgtcagg tgggtctata tatttccagc cctcctcctg tgtgtgtatg   2520
tccgtaaaac acacacacac acacacacac gcacacacac acacacgtat ctaattagca   2580
ttggtattag ttttcaaaa gggaggtcat gctctacctt ttaggcggca aatagattat   2640
ttaaacaaat ctgttgacat tttctatatc aacccataag atctcccatg ttcttggaaa   2700
ggctttgtaa gacatcaaca tctgggtaaa ccagcatggt ttttaggggg ttgtgtggat   2760
ttttttcata tttttttaggg cacacctgca gcatatggag gttcccaggc taggggttga   2820
atcagagctg tagctgccgg cctacaccac agccacagca acgccagatc cttaacccac   2880
tgagaaaggc cagggattga acctgcatcc tcatggatgc tggtcagatt tatttctgct   2940
gagccacaac aggaactccc tgaaccagaa tgcttttaac cattccactt tgcatggaca   3000
tttagattgt ttccatttaa aaatacaaat tacaaggagt tcccgtcgtg gctcagtggt   3060
aacgaattgg actaggaacc atgaggtttc gggttcgatc cctggccttg ctcggtgggt   3120
taaggatcca gcattgatgt gagatatggt gtaggtcgca gacgtggctc ggatcccacg   3180
ttgctgtggc tctggcgtag gccggcaaca acagctccga ttcgacccct agcctgggaa   3240
cctccatgtg ccacaggagc agccctagaa aaggcaaaaa gacaaaaaaa taaaaaatta   3300
aaatgaaaaa ataaaataaa aatacaaatt acaagagacg gctacaagga atccccaag   3360 tgtgtgcaaa tgccatatat gtataaaatg tactagtgtc tcctcgcggg aaagttgcct   3420
```

```
aaaagtgggt tggctggaca gagaggacag gctttgacat tctcataggt agtagcaatg    3480
ggcttctcaa aatgctgttc cagtttacac tcaccatagc aaatgacagt gcctcttcct    3540
ctccacccct tgccaataatg tgacaggtgg atcttttcct attttgtgta tctgacaagc    3600
aaaaaatgag aacaggagtt cctgtcgtgg tgcagtggag acaaatctga ctaggaacca    3660
tgaaatttcg ggttcaatcc ctggcctcac tcagtaggta aaggatccag ggttgcagtg    3720
agctgtgggt taggtcgcag acacagtgca aatttggccc tgttgtggct gtggtgtagg    3780
ccggcagcta tagctccaat tggaccccta gcctgggaac ctccttatgc cgtgggtgag    3840
gccctaaaaa aaagagtgca aaaaaaaaa ataagaacaa aaatgatcat cgtttaattc    3900
tttatttgat cattggtgaa acttatttc cttttatatt tttattgact gattttattt    3960
ctcctatgaa tttaccggtc atagttttgc ctgggtgttt ttactccggt tttagttttg    4020
gttggttgta ttttcttaga gagctataga aactcttcat ctatttggaa tagtaattcc    4080
tcattaagta tttgtgctgc aaaaaatttt ccctgatctg ttttatgctt ttgtttgtgg    4140
ggtctttcac gagaaagcct ttttagttt tacacctcag cttggttgtt tttcttgatt    4200
gtgtctgtaa tctgcggcca acataggaaa cacatttta cttagtgtt tttttcctat    4260
tttcttcaag tacgtccatt gttttggtgt ctgatttac tttgcctggg gtttgttttt    4320
gtgtggcagg aatataaact tatgtatttt ccaaatggag agccaatggt tgtatatttg    4380
ttgaattcaa atgcaacttt atcaaacacc aaatcatcga tttatcacaa ctcttctctg    4440
gtttattgat ctaatgatca attcctgttc cacgctgttt taattatttt agctttgtgg    4500
attttggtgc ctggtagaga acaaagcctc cattattttc attcaaaata gtcccgtcta    4560
ttatctgcca ttgttgtagt attagacttt aaaatcaatt tactgatttt caaaagttat    4620
tcctttggtg atgtggaata ctttatactt cataaggtac atggattcat ttgtggggaa    4680
ttgatgtctt tgctattgtg gccatttgtc aagttgtgta atattttacc catgccaact    4740
ttgcatattg tatgtgagtt tattcccagg gttttaata ggatgtttat tgaagttgtc    4800
agtgtttcca caatttcatc gcctcagtgc ttactgtttg cataaaagga aacctactca    4860
cttttgccta ttgctcttgt attcaatcat tttagttaac tcttgtgtta attttgagag    4920
tttttcagct gactgtctgg ggtttctttt aatagactag ccctttgtct gtaaagaata    4980
attttatcga attttctta acactcacac tctccccacc cccaccccg ctcatctcct    5040
ttcattgggt caaatctgta gaatacaata aaagtaagag tgggaacctt agcctttaag    5100
tcgatttttgc cttaaatgt gaatgttgct atgtttcggg acattctctt tatcaagttg    5160
cggatgtttc cttagataat taacttaata aaagactgga tgtttgcttt cttcaaatca    5220
gaattgtgtt gaatttatat tgctattctg tttaattttg tttcaaaaaa tttacatgca    5280
caccttaaag ataaccatga ccaaatagtc ctcctgctga gagaaaatgt tggccccaat    5340
gccacaggtt acctcccgac tcagataaac tacaatggga gataaaatca gatttggcaa    5400
agcctgtgga ttcttgccat aactctcaga gcatgacttg ggtgtttttt ccttttctaa    5460
gtatttttaat ggtatttttg tgttacaata ggaaatctag gacacagaga gtgattcaat    5520
gaggggaacg cattctggga tgactctagg cctctggttt ggggagagct ctattgaagt    5580
aaagacaatg agaggaagca gtttgcagg gaactgtgag gaatttagat ggggaatgtt    5640
gggtttgagg tttctatagg gcacgcaagc agagatgcac tcaggaggaa gaaggagcat    5700
aaatctagag gcaaaagag aggtcaggac tggaaataga gatgcgagac accagggtgg    5760
cagtcagaga gcacagtgtg ggtcagaaga cagtggaaga acacaaggga cagagaggga    5820
```

```
tctccaactt cactgggatg agggccttgt tggccttgac ctgagagatt tccaggagtt    5880
gagggtggga aggagccgcg gtctaggaag ctttctaggg tacctctagg gatccgaaca    5940
atggaagtcc gagctcatcg ctaataactt cgtatagcat acattatacg aagttatatt    6000
cgatgcggcc gcaaggggtt cgcgtcagcg ggtgttggcg ggtgtcgggg ctggcttaac    6060
tatgcggcat cagagcagag atcccggcgc gccctaccgg gtaggggagg cgcttttccc    6120
aaggcagtct ggagcatgcg ctttagcagc ccgctgggca acttggcgct acacaagtgg    6180
cctctggcct cgcacacatt ccacatccac cggtaggcgc caaccggctc cgttctttgg    6240
tggcccttc gcgccacctt ctactcctcc cctagtcagg aagttccccc ccgcccgcca    6300
gctcgcgtcg tgcaggacgt gacaaatgga agtagcacgt ctcactagtc tcgtgcagat    6360
ggacagcacc gctgagcaat ggaagcgggt aggcctttgg ggcagcggcc aatagcagct    6420
ttggctcctt cgctttctgg gctcagaggc tgggaagggg tgggtccggg ggcgggctca    6480
ggggcgggct caggggcggg gcgggcgccc gaaggtcctc cggaagcccg gcattctgca    6540
cgcttcaaaa gcgcacgtct gccgcgctgt tctcctcttc ctcatctccg ggcctttcga    6600
cctgcagcca atatgggatc ggccattgaa caagatggat tgcacgcagg ttctccggcc    6660
gcttgggtgg agaggctatt cggctatgac tgggcacaac agacaatcgg ctgctctgat    6720
gccgccgtgt tccggctgtc agcgcagggg cgcccggttc tttttgtcaa gaccgacctg    6780
tccggtgccc tgaatgaact gcaggacgag gcagcgcggc tatcgtggct ggccacgacg    6840
ggcgttcctt gcgcagctgt gctcgacgtt gtcactgaag cgggaaggga ctggctgcta    6900
ttgggcgaag tgccggggca ggatctcctg tcatctcacc ttgctcctgc cgagaaagta    6960
tccatcatgg ctgatgcaat gcggcggctg catacgcttg atccggctac ctgcccattc    7020
gaccaccaag cgaaacatcg catcgagcga gcacgtactc ggatggaagc cggtcttgtc    7080
aatcaggatg atctggacga agagcatcag gggctcgcgc cagccgaact gttcgccagg    7140
ctcaaggcgc gcatgcccga cggcgaggat ctcgtcgtga cccatggcga tgcctgcttg    7200
ccgaatatca tggtggaaaa tggccgcttt tctggattca tcgactgtgg ccggctgggt    7260
gtggcggatc gctatcagga catagcgttg gctacccgtg atattgctga agagcttggc    7320
ggcgaatggg ctgaccgctt cctcgtgctt tacggtatcg ccgctcccga ttcgcagcgc    7380
atcgccttct atcgccttct tgacgagttc ttctgagggg atcaattctc tagtgaacaa    7440
tggaagtccg agctcatcgc taataacttc gtatagcata cattatacga agttatattc    7500
gatgcggccg caaggggttc gcgtcagcgg gtgttggcgg gtgtcgggc tggcttaact    7560
atgcggcatc agagcagtct agagctcgct gatcagcctc gactgtgcct tctagttgcc    7620
agccatctgt tgtttgcccc tccccgtgc cttccttgac cctggaaggt gccactccca    7680
ctgtcctttc ctaataaaat gaggaaattg catcgcattg tctgagtagg tgtcattcta    7740
ttctgggggg tggggtgggg caggacagca agggggagga ttgggaagac aatagcaggc    7800
atgctgggga tgcggtgggc tctatggctt ctgaggcgga agaaccagc tggggcgcg    7860
cccctcgagg ggaaggtatc tcccaggaaa ctgccagga cattggtc ctccgccctc    7920
cccttcctcc cactcctcct ccagacagga ctgtgcccac ccctgccac ctttctggcc    7980
agaactgtcc atgcaggtg accttcacat gagcccttcc tccctgcctg ccctagtggg    8040
accctccata cctcccctg gacccgttg tctttctt ccagtgtggc cctgagcata    8100
actgatgcca tcatgggctg ctgacccacc cgggactgtg ttgtgcagtg agtcacttct    8160
```

```
ctgtcatcag ggctttgtaa ttgatagata gtgtttcatc atcattagga ccgggtggcc      8220
tctatgctct gttagtctcc aaacactgat gaaaaccttc gttggcatag tcccagcttc      8280
ctgttgccca tccataaatc ttgacttagg gatgcacatc ctgtctccaa gcaaccaccc      8340
ctcccctagg ctaactataa aactgtccca atggcccttg tgtggtgcag agttcatgct      8400
tccagatcat ttctctgcta gatccatatc tcaccttgta agtcatccta taataaactg      8460
atccattgat tatttgcttc tgttttttcc atctcaaaac agcttctcag ttcagttcga      8520
attttttatt ccctccatcc acccatactt tcctcagcct ggggaaccct tgcccccagt      8580
cccatgccct tcctccctct ctgcccagct cagcacctgc ccaccctcac ccttcctgtc      8640
actccctagg actggaccat ccactggggc caggacactc cagcagcctt ggcttcatgg      8700
gctctgaaat ccatggccca tctctattcc tcactggatg gcaggttcag agatgtgaaa      8760
ggtctaggag gaagccagga aggaaactgt tgcatgaaag gccggcctga tggttcagta      8820
cttaaataat atgagctctg agctccccag gaaccaaagc atggagggag tatgtgcctc      8880
agaatctctc tgagattcag caaagccttt gctagaggga aatagtggc tcaaccttga       8940 gggccagcat cttgcaccac agttaaaagt gggtatttgt tttacctgag gcctcagcat      9000
tatgggaacc gggctctgac acaaacacag gtgcagcccg gcagcctcag aacacagcaa      9060
cgaccacaag ctgggacagc tgcccctgaa cggggagtcc accatgcttc tgtctcgggt      9120
accaccaggt caccatccct gggggaggta gttccatagc agtagtcccc tgatttcgcc      9180
cctcgggcgt gtagccaggc aagctcctgc ctctggaccc agggtggacc cttgctcccc      9240
actaccctgc acatgccaga cagtcaagac cactcccacc tctgtctgag gccccctttgg     9300 gtgtcccagg gccccgagc tgtcctctac tcatggttct tccacctggg tacaaaagag       9360
gcgagggaca cttttctcag gtttgcggct cagaaaggta ccttcctagg gtttgtccac      9420
tgggagtcac ctcccttgca tctcaatgtc agtggggaaa actgggtccc atgggggat       9480 tagtgccact gtgaggcccc tgaagtctgg ggcctctaga cactatgatg atgagggatg      9540
tggtgaaaaa ccccaccccca gcccttcttg ccgggaccct gggctgtggc tcccccattg     9600
cacttggggt cagaggggtg gatggtggct atggtcaggc atgtttccca tgagctgggg     9660
gcaccctggg tgactttctc ctgtgaatcc tgaattagca gctataacaa attgcccaaa      9720
ctcttaggct taaaacaaca cacatttatt cctctgggtc ccagggtcag aagtccaaaa      9780
tgagtcctat aggctaaatt tgaggtgtct ctgggttgag ctcctcctgg aagccttttc     9840
cagcctctag agtcccaagt ccttggctct gggcccctcc ctcaagcttc aaagccacag      9900
aagcttctaa tctctctccc ttcccctctg acctctgctc ccatcctcat accctgtccc     9960
ctcactctga ccctcctgcc tccctctttc ccttataaag accctgcatg gggccacgga    10020
gataatccag ggtaatcgcc cctcttccag cccttaactc catcccatct gcaaaatccc    10080
tgtcacccca taatggacct acagatctcc tagagttaac actggccgtc gttttaccgg    10140
tccgtagtca ggtttagttc gtccggcggc gccagaaatc cgcgcggtgg ttttggggg     10200 tcggggggtgt ttggcagcca cagacgcccg gtgttcgtgt cgcgccagta catgcgggtcc   10260 atgcccaggc catccaaaaa ccatgggtct gtctgctcag tccagtcgtg gactgacccc    10320
acgcaacgcc caaaataata accccccacga accataaacc attccccatg ggggacccccg  10380 tccctaaccc acggggcccg tggctatggc aggcctgccg cccgacgttg gctgcgagcc    10440
ctgggccttc acccgaactt gggggtggg gtggggaaaa ggaagaaacg cgggcgtatt    10500
ggccccaatg gggtctcggt ggggtatcga cagagtgcca gccctgggac cgaacccgc    10560
```

-continued

```
gtttatgaac aaacgaccca acacccgtgc gttttattct gtcttttat tgccgacata    10620 gcgcgggttc cttccggtat tgtctccttc cgtgtttcag ttagcctccc ccatctcccg    10680
tgcaaacgtg cgcgccaggt cgcagatcgt cggtatggag cctggggtgg tgacgtgggt    10740
ctggatcatc ccggaggtaa gttgcagcag ggcgtcccgg cagccggcgg gcgattggtc    10800
gtaatccagg ataaagacgt gcatgggacg gaggcgtttg ccaagacgt ccaaggccca    10860 ggcaaacacg ttgtacaggt cgccgttggg ggccagcaac tcgggggccc gaaacagggt    10920
aaataacgtg tccccgatat ggggtcgtgg gcccgcgttg ctctggggct cggcaccctg    10980
gggcggcacg gccgtccccg aaagctgtcc ccaatcctcc cgccacgacc cgccgccctg    11040
cagataccgc accgtattgg caagcagccc gtaaacgcgg cgaatcgcgg tcagcatagc    11100
caggtcaagc cgctcgccgg ggcgctggcg tttggccagg cggtcgatgt gtctgtcctc    11160
cggaagggcc cccaacacga tgtttgtgcc gggcaaggtc ggcgggatga gggccacgaa    11220
cgccagcacg gcctgggggg tcatgctgcc cataaggtat cgcgcggccg ggtagcacag    11280
gagggcggcg atgggatggc ggtcgaagat gagggtgagg gccgggggcg gggcatgtga    11340
gctcccagcc tcccccccga tatgaggagc cagaacggcg tcggtcacgg tataaggcat    11400
gcccattgtt atctgggcgc ttgtcattac caccgccgcg tccccggccg atatctcacc    11460
ctggtcaagg cggtgttgtg tggtgtagat gttcgcgatt gtctcggaag cccccagcac    11520
ccgccagtaa gtcatcggct cgggtacgta gacgatatcg tcgcgcgaac ccagggccac    11580
cagcagttgc gtggtggtgg ttttccccat cccgtgggga ccgtctatat aaacccgcag    11640
tagcgtgggc attttctgct ccgggcggac ttccgtggct tcttgctgcc ggcgagggcg    11700
caacgccgta cgtcggttgc tatggccgcg agaacgcgca gcctggtcga acgcagacgc    11760
gtgctgatgg ccggggtacg aagccatacg cgcttctaca aggcgctggc cgaagaggtg    11820
cgggagtttc acgccaccaa gatgtgcggc acgctgttga cgctgttaag cgggtcgctg    11880
cagggtcgct cggtgttcga ggccacacgc gtcaccttaa tatgcgaagt ggacctggga    11940
ccgcgccgcc ccgactgcat ctgcgtgttc caattcgcca atgacaagac gctgggcggg    12000
gtttgctcga cattgggtgg aaacattcca ggcctgggtg gagaggcttt ttgcttcctc    12060
ttgcaaaacc acactgctcg acattgggtg gaaacattcc aggcctgggt ggagaggctt    12120
tttgcttcct cttgaaaacc acactgctcg actctacggt ccg                     12163
```

<210> SEQ ID NO 49
<211> LENGTH: 4066
<212> TYPE: DNA
<213> ORGANISM: Artificial Sequence
<220> FEATURE:
<223> OTHER INFORMATION: Synthetic

<400> SEQUENCE: 49

```
agggtgtggc caaatacagc atggagtagc catcataagg aatcttacac aagcctccaa      60
aattgtgttt ctgaaattgg gtttaaagta cgtttgcatt ttaaaaagcc tgccagaaaa     120
tacagaaaaa tgtctgtgat atgtctctgg ctgataggat tttgcttagt tttaattttg     180
gctttataat tttctatagt tatgaaaatg ttcacaagaa gatatattc attttagctt     240 ctaaaataat tataacacag aagtaatttg tgctttaaaa aaatattcaa cacagaagta     300
tataaagtaa aaattgagga gttcccatcg tggctcagtg attaacaaac ccaactagta     360
tccatgagga tatggatttg atccctggcc ttgctcagtg ggttgaggat ccagtgttgc     420
```

```
tgtgagctgt ggtgtaggtt gcagacacag cactctggcg ttgctgtgac tctggcgtag      480
gccggcagct acagtccatt ttggacccctt agcctgggaa cctccatatg cctgagatac     540
ggccctaaaa agtcaaaagc caaaaaaata gtaaaaattg agtgtttcta cttaccaccc     600
ctgcccacat cttatgctaa aacccgttct ccagagacaa acatcgtcag gtgggtctat     660
atatttccag ccctcctcct gtgtgtgtat gtccgtaaaa cacacacaca cacacacaca     720
cgcacacaca cacacacgta tctaattagc attggtatta gttttttcaaa agggaggtca    780 tgctctacct tttaggcggc aaatagatta tttaaacaaa tctgttgaca ttttctatat    840
caacccataa gatctcccat gttcttggaa aggctttgta agacatcaac atctgggtaa    900
accagcatgg ttttttagggg gttgtgtgga tttttttcat atttttttagg gcacacctgc   960 agcatatgga ggttcccagg ctaggggttg aatcagagct gtagctgccg gcctacacca   1020
cagccacagc aacgccagat ccttaaccca ctgagaaagg ccagggattg aacctgcatc   1080
ctcatggatg ctggtcagat ttatttctgc tgagccacaa caggaactcc ctgaaccaga   1140
atgcttttaa ccattccact ttgcatggac atttagattg ttttccattta aaaatacaaa   1200 ttacaaggag ttcccgtcgt ggctcagtgg taacgaattg gactaggaac catgaggttt   1260
cgggttcgat ccctggcctt gctcggtggg ttaaggatcc agcattgatg tgagatatgg   1320
tgtaggtcgc agacgtggct cggatcccac gttgctgtgg ctctggcgta ggccggcaac   1380
aacagctccg attcgacccc tagcctggga acctccatgt gccacaggag cagccctaga   1440
aaaggcaaaa agacaaaaaa ataaaaaatt aaaatgaaaa aataaaataa aaatacaaat   1500
tacaagagac ggctacaagg aaatccccaa gtgtgtgcaa atgccatata tgtataaaat   1560
gtactagtgt ctcctcgcgg gaaagttgcc taaagtgggg ttggctggac agagaggaca   1620
ggctttgaca ttctcatagg tagtagcaat gggcttctca aaatgctgtt ccagtttaca   1680
ctcaccatag caaatgacag tgcctcttcc tctccaccct tgccaataat gtgacaggtg   1740
gatctttttc tattttgtgt atctgacaag caaaaaatga aacaggagt tcctgtcgtg   1800 gtgcagtgga gacaaatctg actaggaacc atgaaatttc gggttcaatc cctggcctca   1860
ctcagtaggt aaaggatcca gggttgcagt gagctgtggg gtaggtcgca gacacagtgc   1920
aaatttggcc ctgttgtggc tgtggtgtag gccggcagct atagctccaa ttggaccect   1980 agcctgggaa cctccttatg ccgtgggtga ggccctaaaa aaaagagtgc aaaaaaaaaa   2040
aataagaaca aaaatgatca tcgtttaatt cttttatttga tcattggtga aacttatttt   2100
ccttttatat ttttattgac tgattttatt tctcctatga atttaccggt catagttttg   2160
cctgggtgtt tttactccgg ttttagttttt ggttggttgt attttcttag agagctatag   2220
aaactcttca tctatttgga atagtaattc ctcattaagt atttgtgctg caaaaaattt   2280
tccctgatct gttttatgct tttgtttgtg gggtctttca cgagaaagcc ttttttagttt   2340 ttacacctca gcttggttgt ttttcttgat tgtgtctgta atctgcggcc aacataggaa   2400
acacattttt actttagtgt ttttttccta ttttcttcaa gtacgtccat tgttttggtg   2460 tctgattta ctttgcctgg ggtttgtttt tgtgtggcag aaatataaac ttatgtattt    2520
tccaaatgga gagccaatgg ttgtatattt gttgaattca aatgcaactt tatcaaacac   2580
caaatcatcg atttatcaca actcttctct ggtttattga tctaatgatc aattcctgtt   2640
ccacgctgtt ttaattattt tagctttgtg gattttggtg cctggtagag aacaaagcct   2700 ccattattt cattcaaaat agtcccgtct attatctgcc attgttgtag tattagactt   2760
taaaatcaat ttactgattt tcaaaagtta ttcctttggt gatgtggaat actttatact   2820
```

```
tcataaggta catggattca tttgtgggga attgatgtct ttgctattgt ggccatttgt    2880
caagttgtgt aatattttac ccatgccaac tttgcatatt gtatgtgagt ttattcccag    2940
ggttttaat aggatgttta ttgaagttgt cagtgtttcc acaatttcat cgcctcagtg    3000
cttactgttt gcataaaagg aaacctactc acttttgcct attgctcttg tattcaatca    3060
ttttagttaa ctcttgtgtt aattttgaga gtttttcagc tgactgtctg ggttttctt     3120
taatagacta gcccttttgtc tgtaaagaat aattttatcg aattttttctt aacactcaca   3180
ctctccccac ccccaccccc gctcatctcc tttcattggg tcaaatctgt agaatacaat    3240
aaaagtaaga gtgggaacct tagcctttaa gtcgattttg cctttaaatg tgaatgttgc    3300
tatgtttcgg gacattctct ttatcaagtt gcggatgttt ccttagataa ttaacttaat    3360
aaaagactgg atgtttgctt tcttcaaatc agaattgtgt tgaatttata ttgctattct    3420
gtttaatttt gtttcaaaaa atttacatgc acaccttaaa gataaccatg accaaatagt    3480
cctcctgctg agagaaaatg ttggccccaa tgccacaggt tacctcccga ctcagataaa    3540
ctacaatggg agataaaatc agatttggca aagcctgtgg attcttgcca taactctcag    3600
agcatgactt gggtgttttt tccttttcta agtattttaa tggtattttt gtgttacaat    3660
aggaaatcta ggacacagag agtgattcaa tgaggggaac gcattctggg atgactctag    3720
gcctctggtt tggggagagc tctattgaag taaagacaat gagaggaagc aagtttgcag    3780
ggaactgtga ggaatttaga tggggaatgt tgggtttgag gtttctatag ggcacgcaag    3840
cagagatgca ctcaggagga agaaggagca taaatctaga ggcaaaaaga gaggtcagga    3900
ctggaaatag agatgcgaga caccagggtg gcagtcagag agcacagtgt gggtcagaag    3960
acagtggaag aacacaaggg acagagaggg atctccaact tcactgggat gagggccttg    4020
ttggccttga cctgagagat ttccaggagt tgagggtggg aaggag                   4066
```

<210> SEQ ID NO 50
<211> LENGTH: 2233
<212> TYPE: DNA
<213> ORGANISM: Artificial Sequence
<220> FEATURE:
<223> OTHER INFORMATION: Synthetic

<400> SEQUENCE: 50

```
gggaaggtat ctcccaggaa actggccagg acacattggt cctccgccct ccccttcctc      60
ccactcctcc tccagacagg actgtgccca cccctgcca cctttctggc cagaactgtc      120
catggcaggt gaccttcaca tgagcccttc ctccctgcct gccctagtgg accctccat      180
acctccccct ggacccccgtt gtcctttctt tccagtgtgg ccctgagcat aactgatgcc    240
atcatgggct gctgacccac ccgggactgt gttgtgcagt gagtcacttc tctgtcatca    300
gggctttgta attgatagat agtgtttcat catcattagg accgggtggc ctctatgctc    360
tgttagtctc caaacactga tgaaaacctt cgttggcata gtcccagctt cctgttgccc    420
atccataaat cttgacttag ggatgcacat cctgtctcca agcaaccacc cctcccctag    480
gctaactata aaactgtccc aatggcccctt gtgtggtgca gagttcatgc ttccagatca   540
tttctctgct agatccatat ctcaccttgt aagtcatcct ataataaact gatccattga    600
ttatttgctt ctgttttttc catctcaaaa cagcttctca gttcagttcg aattttttat    660
tccctccatc cacccatact ttcctcagcc tggggaaccc ttgccccag tcccatgccc     720
ttcctccctc tctgcccagc tcagcacctg cccacccctca ccccttcctgt cactccctag  780
```

```
gactggacca tccactgggg ccaggacact ccagcagcct tggcttcatg ggctctgaaa    840
tccatggccc atctctattc ctcactggat ggcaggttca gagatgtgaa aggtctagga    900
ggaagccagg aaggaaactg ttgcatgaaa ggccggcctg atggttcagt acttaaataa   960
tatgagctct gagctcccca ggaaccaaag catggaggga gtatgtgcct cagaatctct  1020
ctgagattca gcaaagcctt tgctagaggg aaaatagtgg ctcaaccttg agggccagca  1080
tcttgcacca cagttaaaag tgggtatttg ttttacctga ggcctcagca ttatgggaac  1140
cgggctctga cacaaacaca ggtgcagccc ggcagcctca gaacacagca acgaccacaa  1200
gctgggacag ctgcccctga acggggagtc caccatgctt ctgtctcggg taccaccagg  1260
tcaccatccc tgggggaggt agttccatag cagtagtccc ctgatttcgc ccctcgggcg  1320
tgtagccagg caagctcctg cctctggacc cagggtggac ccttgctccc cactaccctg  1380
cacatgccag acagtcaaga ccactcccac ctctgtctga ggcccccttg ggtgtcccag  1440
ggcccccgag ctgtcctcta ctcatggttc ttccacctgg gtacaaaaga ggcgagggac  1500
acttttctca ggtttgcggc tcagaaaggt accttcctag ggtttgtcca ctgggagtca  1560
cctcccttgc atctcaatgt cagtggggaa aactgggtcc catgggggga ttagtgccac  1620
tgtgaggccc ctgaagtctg gggcctctag acactatgat gatgagggat gtggtgaaaa  1680
accccacccc agcccttctt gccgggaccc tgggctgtgg ctcccccatt gcacttgggg  1740
tcagaggggt ggatggtggc tatggtcagg catgtttccc atgagctggg ggcaccctgg  1800
gtgactttct cctgtgaatc ctgaattagc agctataaca aattgcccaa actcttaggc  1860
ttaaaacaac acacatttat tcctctgggt cccagggtca gaagtccaaa atgagtccta  1920
taggctaaat ttgaggtgtc tctgggttga gctcctcctg gaagcctttt ccagcctcta  1980
gagtcccaag tccttggctc tgggcccctc cctcaagctt caaagccaca gaagcttcta  2040
atctctctcc cttcccctct gacctctgct cccatcctca taccctgtcc cctcactctg  2100
accctcctgc ctccctcttt cccttataaa gaccctgcat ggggccacgg agataatcca  2160
gggtaatcgc ccctcttcca gcccttaact ccatcccatc tgcaaaatcc ctgtcacccc  2220
ataatggacc tac                                                      2233
```

UNGULATES WITH GENETICALLY MODIFIED IMMUNE SYSTEMS

CROSS-REFERENCE TO RELATED APPLICATIONS

This application is a continuation of U.S. application Ser. No. 15/430,583, filed Feb. 13, 2017, which is a continuation of U.S. application Ser. No. 12/433,477, filed Apr. 30, 2009, which is a continuation of U.S. application Ser. No. 11/789,961, filed Apr. 26, 2007, which claims benefit of U.S. Provisional Application 60/794,963 filed on Apr. 26, 2006 and which is a continuation-in-part of U.S. application Ser. No. 11/257,817, filed Oct. 24, 2005, which claims benefit of U.S. Provisional Application 60/621,433, filed Oct. 22, 2004.

The instant application contains a Sequence Listing which has been submitted in ASCII format via EFS-WEB and is hereby incorporated by reference in its entirety. Said ASCII copy, created on Dec. 13, 2019, is named sequence.txt and is 399,572 bytes.

FIELD OF THE INVENTION

The present invention provides ungulate animals, tissue and organs as well as cells and cell lines derived from such animals, tissue and organs, which lack expression of functional endogenous immunoglobulin loci. The present invention also provides ungulate animals, tissue and organs as well as cells and cell lines derived from such animals, tissue and organs, which express xenogenous, such as human, immunoglobulin loci. The present invention further provides ungulate, such as porcine genomic DNA sequence of porcine heavy and light chain immunogobulins. Such animals, tissues, organs and cells can be used in research and medical therapy. In addition, methods are provided to prepare such animals, organs, tissues, and cells.

BACKGROUND OF THE INVENTION

An antigen is an agent or substance that can be recognized by the body as 'foreign'. Often it is only one relatively small chemical group of a larger foreign substance which acts as the antigen, for example a component of the cell wall of a bacterium. Most antigens are proteins, though carbohydrates can act as weak antigens. Bacteria, viruses and other microorganisms commonly contain many antigens, as do pollens, dust mites, molds, foods, and other substances.

The body reacts to antigens by making antibodies. Antibodies (also called immunoglobulins (Igs)) are proteins that are manufactured by cells of the immune system that bind to an antigen or foreign protein. Antibodies circulate in the serum of blood to detect foreign antigens and constitute the gamma globulin part of the blood proteins. These antibodies interact chemically with the antigen in a highly specific manner, like two pieces of a jigsaw puzzle, forming an antigen/antibody complex, or immune complex. This binding neutralizes or brings about the destruction of the antigen.

When a vertebrate first encounters an antigen, it exhibits a primary humoral immune response. If the animal encounters the same antigen after a few days the immune response is more rapid and has a greater magnitude. The initial encounter causes specific immune cell (B-cell) clones to proliferate and differentiate. The progeny lymphocytes include not only effector cells (antibody producing cells) but also clones of memory cells, which retain the capacity to produce both effector and memory cells upon subsequent stimulation by the original antigen. The effector cells live for only a few days. The memory cells live for a lifetime and can be reactivated by a second stimulation with the same antigen. Thus, when an antigen is encountered a second time, its memory cells quickly produce effector cells which rapidly produce massive quantities of antibodies.

By exploiting the unique ability of antibodies to interact with antigens in a highly specific manner, antibodies have been developed as molecules that can be manufactured and used for both diagnostic and therapeutic applications. Because of their unique ability to bind to antigenic epitopes, polyclonal and monoclonal antibodies can be used to identify molecules carrying that epitope or can be directed, by themselves or in conjunction with another moiety, to a specific site for diagnosis or therapy. Polyclonal and monoclonal antibodies can be generated against practically any pathogen or biological target. The term polyclonal antibody refers to immune sera that usually contain pathogen-specific antibodies of various isotypes and specificities. In contrast, monoclonal antibodies consist of a single immunoglobulin type, representing one isotype with one specificity.

In 1890, Shibasaburo Kitazato and Emil Behring conducted the fundamental experiment that demonstrated immunity can be transmitted from one animal to another by transferring the serum from an immune animal to a non-immune animal. This landmark experiment laid the foundation for the introduction of passive immunization into clinical practice. However, wide scale serum therapy was largely abandoned in the 1940s because of the toxicity associated with the administration of heterologous sera and the introduction of effective antimicrobial chemotherapy. Currently, such polyclonal antibody therapy is indicated to treat infectious diseases in relatively few situations, such as replacement therapy in immunoglobulin-deficient patients, post-exposure prophylaxis against several viruses (e.g., rabies, measles, hepatitis A and B, varicella), and toxin neutralization (diphtheria, tetanus, and botulism). Despite the limited use of serum therapy, in the United States, more than 16 metric tons of human antibodies are required each year for intravenous antibody therapy. Comparable levels of use exist in the economies of most highly industrialized countries, and the demand can be expected to grow rapidly in developing countries. Currently, human antibody for passive immunization is obtained from the pooled serum of donors. Thus, there is an inherent limitation in the amount of human antibody available for therapeutic and prophylactic therapies.

The use of antibodies for passive immunization against biological warfare agents represents a very promising defense strategy. The final line of defense against such agents is the immune system of the exposed individual. Current defense strategies against biological weapons include such measures as enhanced epidemiologic surveillance, vaccination, and use of antimicrobial agents. Since the potential threat of biological warfare and bioterrorism is inversely proportional to the number of immune persons in the targeted population, biological agents are potential weapons only against populations with a substantial proportion of susceptible persons.

Vaccination can reduce the susceptibility of a population against specific threats; provided that a safe vaccine exists that can induce a protective response. Unfortunately, inducing a protective response by vaccination may take longer than the time between exposure and onset of disease. Moreover, many vaccines require multiple doses to achieve a protective immune response, which would limit their usefulness in an emergency to provide rapid prophylaxis after an attack. In addition, not all vaccine recipients mount a protective response, even after receiving the recommended immunization schedule.

Drugs can provide protection when administered after exposure to certain agents, but none are available against many potential agents of biological warfare. Currently, no small-molecule drugs are available that prevent disease following exposure to preformed toxins. The only currently available intervention that could provide a state of immediate immunity is passive immunization with protective antibody (Arturo Casadevall "Passive Antibody Administration (Immediate Immunity) as a Specific Defense Against Biological Weapons" from Emerging Infectious Diseases, Posted Sep. 12, 2002).

In addition to providing protective immunity, modern antibody-based therapies constitute a potentially useful option against newly emergent pathogenic bacteria, fungi, virus and parasites (A. Casadevall and M. D. Scharff, Clinical Infectious Diseases 1995; 150). Therapies of patients with malignancies and cancer (C. Botti et al, Leukemia 1997; Suppl 2:S55-59; B. Bodey, S. E. Siegel, and H. E. Kaiser, Anticancer Res 1996; 16(2):661), therapy of steroid resistant rejection of transplanted organs as well as autoimmune diseases can also be achieved through the use of monoclonal or polyclonal antibody preparations (N. Bonnefoy-Berard and J. P. Revillard, J Heart Lung Transplant 1996; 15(5):435-442; C. Colby, et al Ann Pharmacother 1996; 30(10):1164-1174; M. J. Dugan, et al, Ann Hematol 1997; 75(1-2):41 2; W. Cendrowski, Boll Ist Sieroter Milan 1997; 58(4):339-343; L. K. Kastrukoff, et al Can J Neurol Sci 1978; 5(2):175178; J. E. Walker et al J Neurol Sci 1976; 29(2-4):303309).

Recent advances in the technology of antibody production provide the means to generate human antibody reagents, while avoiding the toxicities associated with human serum therapy. The advantages of antibody-based therapies include versatility, low toxicity, pathogen specificity, enhancement of immune function, and favorable pharmacokinetics.

The clinical use of monoclonal antibody therapeutics has just recently emerged. Monoclonal antibodies have now been approved as therapies in transplantation, cancer, infectious disease, cardiovascular disease and inflammation. In many more monoclonal antibodies are in late stage clinical trials to treat a broad range of disease indications. As a result, monoclonal antibodies represent one of the largest classes of drugs currently in development.

Despite the recent popularity of monoclonal antibodies as therapeutics, there are some obstacles for their use. For example, many therapeutic applications for monoclonal antibodies require repeated administrations, especially for chronic diseases such as autoimmunity or cancer. Because mice are convenient for immunization and recognize most human antigens as foreign, monoclonal antibodies against human targets with therapeutic potential have typically been of murine origin. However, murine monoclonal antibodies have inherent disadvantages as human therapeutics. For example, they require more frequent dosing to maintain a therapeutic level of monoclonal antibodies because of a shorter circulating half-life in humans than human antibodies. More critically, repeated administration of murine immunoglobulin creates the likelihood that the human immune system will recognize the mouse protein as foreign, generating a human anti-mouse antibody response, which can cause a severe allergic reaction. This possibility of reduced efficacy and safety has lead to the development of a number of technologies for reducing the immunogenicity of murine monoclonal antibodies.

Polyclonal antibodies are highly potent against multiple antigenic targets. They have the unique ability to target and kill a plurality of "evolving targets" linked with complex diseases. Also, of all drug classes, polyclonals have the highest probability of retaining activity in the event of antigen mutation. In addition, while monoclonals have limited therapeutic activity against infectious agents, polyclonals can both neutralize toxins and direct immune responses to eliminate pathogens, as well as biological warfare agents.

The development of polyclonal and monoclonal antibody production platforms to meet future demand for production capacity represents a promising area that is currently the subject of much research. One especially promising strategy is the introduction of human immunoglobulin genes into mice or large domestic animals. An extension of this technology would include inactivation of their endogenous immunoglobulin genes. Large animals, such as sheep, pigs and cattle, are all currently used in the production of plasma derived products, such as hyperimmune serum and clotting factors, for human use. This would support the use of human polyclonal antibodies from such species on the grounds of safety and ethics. Each of these species naturally produces considerable quantities of antibody in both serum and milk.

Arrangement of Genes Encoding Immunoglobulins

Antibody molecules are assembled from combinations of variable gene elements, and the possibilities resulting from combining the many variable gene elements in the germline enable the host to synthesize antibodies to an extraordinarily large number of antigens. Each antibody molecule consists of two classes of polypeptide chains, light (L) chains (that can be either kappa (κ) L-chain or lambda (λ) L-chain) and heavy (H) chains. The heavy and light chains join together to define a binding region for the epitope. A single antibody molecule has two identical copies of the L chain and two of the H chain. Each of the chains is comprised of a variable region (V) and a constant region (C). The variable region constitutes the antigen-binding site of the molecule. To achieve diverse antigen recognition, the DNA that encodes the variable region undergoes gene rearrangement. The constant region amino acid sequence is specific for a particular isotype of the antibody, as well as the host which produces the antibody, and thus does not undergo rearrangement.

The mechanism of DNA rearrangement is similar for the variable region of both the heavy- and light-chain loci, although only one joining event is needed to generate a light-chain gene whereas two are needed to generate a complete heavy-chain gene. The most common mode of rearrangement involves the looping-out and deletion of the DNA between two gene segments. This occurs when the coding sequences of the two gene segments are in the same orientation in the DNA. A second mode of recombination can occur between two gene segments that have opposite transcriptional orientations. This mode of recombination is less common, although such rearrangements can account for up to half of all $V_\kappa$ to $J_\kappa$ joins; the transcriptional orientation of half of the human $V_\kappa$ gene segments is opposite to that of the $J_\kappa$ gene segments.

The DNA sequence encoding a complete V region is generated by the somatic recombination of separate gene segments. The V region, or V domain, of an immunoglobulin heavy or light chain is encoded by more than one gene segment. For the light chain, the V domain is encoded by two separate DNA segments. The first segment encodes the first 95-101 amino acids of the light chain and is termed a V gene segment because it encodes most of the V domain. The second segment encodes the remainder of the V domain (up to 13 amino acids) and is termed a joining or J gene segment. The joining of a V and a J gene segment creates a continuous exon that encodes the whole of the light-chain V region. To make a complete immunoglobulin light-chain messenger RNA, the V-region exon is joined to the C-region sequence by RNA splicing after transcription.

A heavy-chain V region is encoded in three gene segments. In addition to the V and J gene segments (denoted $V_H$ and $J_H$ to distinguish them from the light-chain $V_L$ and $J_L$), there is a third gene segment called the diversity or $D_H$ gene segment, which lies between the $V_H$ and $J_H$ gene segments. The process of recombination that generates a complete heavy-chain V region occurs in two separate stages. In the first, a $D_H$ gene segment is joined to a $J_H$ gene segment; then a $V_H$ gene segment rearranges to $DJ_H$ to make a complete $V_H$-region exon. As with the light-chain genes, RNA splicing joins the assembled V-region sequence to the neighboring C-region gene.

Diversification of the antibody repertoire occurs in two stages: primarily by rearrangement ("V(D)J recombination") of Ig V, D and J gene segments in precursor B cells resident in the bone marrow, and then by somatic mutation and class switch recombination of these rearranged Ig genes when mature B cells are activated. Immunoglobulin somatic mutation and class switching are central to the maturation of the immune response and the generation of a "memory" response.

The genomic loci of antibodies are very large and they are located on different chromosomes. The immunoglobulin gene segments are organized into three clusters or genetic loci: the κ, λ, and heavy-chain loci. Each is organized slightly differently. For example, in humans, immunoglobulin genes are organized as follows. The λ light-chain locus is located on chromosome 22 and a cluster of $V_λ$ gene segments is followed by four sets of $J_λ$ gene segments each linked to a single $C_λ$ gene. The κ light-chain locus is on chromosome 2 and the cluster of $V_κ$ gene segments is followed by a cluster of $J_κ$ gene segments, and then by a single $C_κ$ gene. The organization of the heavy-chain locus, on chromosome 14, resembles that of the κ locus, with separate clusters of $V_H$, $D_H$, and $J_H$ gene segments and of $C_H$ genes. The heavy-chain locus differs in one important way: instead of a single C-region, it contains a series of C regions arrayed one after the other, each of which corresponds to a different isotype. There are five immunoglobulin heavy chain isotypes: IgM, IgG, IgA, IgE and IgD. Generally, a cell expresses only one at a time, beginning with IgM. The expression of other isotypes, such as IgG, can occur through isotype switching.

The joining of various V, D and J genes is an entirely random event that results in approximately 50,000 different possible combinations for VDJ(H) and approximately 1,000 for VJ(L). Subsequent random pairing of H and L chains brings the total number of antibody specificities to about $10^7$ possibilities. Diversity is further increased by the imprecise joining of different genetic segments. Rearrangements occur on both DNA strands, but only one strand is transcribed (due to allelic exclusion). Only one rearrangement occurs in the life of a B cell because of irreversible deletions in DNA. Consequently, each mature B cell maintains one immunologic specificity and is maintained in the progeny or clone. This constitutes the molecular basis of the clonal selection; i.e., each antigenic determinant triggers the response of the pre-existing clone of B lymphocytes bearing the specific receptor molecule. The primary repertoire of B cells, which is established by V(D)J recombination, is primarily controlled by two closely linked genes, recombination activating gene (RAG)-1 and RAG-2.

Over the last decade, considerable diversity among vertebrates in both Ig gene diversity and antibody repertoire development has been revealed. Rodents and humans have five heavy chain classes, IgM, IgD, IgG, IgE and IgA, and each have four subclasses of IgG and one or two subclasses of IgA, while rabbits have a single IgG heavy chain gene but 13 genes for different IgA subclasses (Burnett, R. C et al. *EMBO J* 8:4047; Honjo, In Honjo, T, Alt. F. W. T. H. eds, *Immunoglobulin Genes* p. 123 Academic Press, New York). Swine have at least six IgG subclasses (Kacskovics, I et al. 1994 *J Immunol* 153:3565), but no IgD (Butler et al. 1996 Inter. Immunol 8:1897-1904). A gene encoding IgD has only been described in rodents and primates. Diversity in the mechanism of repertoire development is exemplified by contrasting the pattern seen in rodents and primates with that reported for chickens, rabbits, swine and the domesticated Bovidae. Whereas the former group have a large number of $V_H$ genes belonging to seven to 10 families (Rathbun, G. In Hongo, T. Alt. F. W. and Rabbitts, T. H., eds, *Immunoglobulin Genes*, p. 63, Academic press New York), the $V_H$ genes of each member of the latter group belong to a single $V_H$ gene family (Sun, J. et al. 1994 *J. Immunol.* 1553:56118; Dufour, V et al. 1996, *J Immunol.* 156:2163). With the exception of the rabbit, this family is composed of less than 25 genes. Whereas rodents and primates can utilize four to six $J_H$ segments, only a single $J_H$ is available for repertoire development in the chicken (Reynaud et al. 1989 Adv. Immunol. 57:353). Similarly, Butler et al. (1996 Inter. Immunol 8:1897-1904) hypothesized that swine may resemble the chicken in having only a single $J_H$ gene. These species generally have fewer V, D and J genes; in the pig and cow a single VH gene family exists, consisting of less than 20 gene segments (Butler et al, Advances in Swine in Biomedical Research, eds: Tumbleson and Schook, 1996; Sinclair et al, J. Immunol. 159: 3883, 1997). Together with lower numbers of J and D gene segments, this results in significantly less diversity being generated by gene rearrangement. However, there does appear to be greater numbers of light chain genes in these species. Similar to humans and mice, these species express a single κ light chain but multiple λ light chain genes. However, these do not seem to affect the restricted diversity that is achieved by rearrangement.

Since combinatorial joining of more than 100 $V_H$, 20-30 $D_H$ and four to six $J_H$ gene segments is a major mechanism of generating the antibody repertoire in humans, species with fewer $V_H$, $D_H$ or $J_H$ segments must either generate a smaller repertoire or use alternative mechanisms for repertoire development. Ruminants, pigs, rabbits and chickens, utilize several mechanisms to generate antibody diversity. In these species there appears to be an important secondary repertoire development, which occurs in highly specialized lymphoid tissue such as ileal Peyer's patches (Binns and Licence, Adv. Exp. Med. Biol. 186: 661, 1985). Secondary repertoire development occurs in these species by a process of somatic mutation which is a random and not fully understood process. The mechanism for this repertoire diversification appears to be templated mutation, or gene conversion (Sun et al, J. Immunol. 153: 5618, 1994) and somatic hypermutation.

Gene conversion is important for antibody diversification in some higher vertebrates, such as chickens, rabbits and cows. In mice, however, conversion events appear to be infrequent among endogenous antibody genes. Gene conversion is a distinct diversifying mechanism characterized by transfers of homologous sequences from a donor antibody V gene segment to an acceptor V gene segment. If donor and acceptor segments have numerous sequence differences then gene conversion can introduce a set of sequence changes into a V region by a single event. Depending on the species, gene conversion events can occur before and/or after antigen exposure during B cell differentiation (Tsai et al. International Immunology, Vol. 14, No. 1, 55-64, January 2002).

Somatic hypermutation achieves diversification of antibody genes in all higher vertebrate species. It is typified by the introduction of single point mutations into antibody V(D)J segments. Generally, hypermutation appears to be activated in B cells by antigenic stimulation.

Production of Animals with Humanized Immune Systems

In order to reduce the immunogenicity of antibodies generated in mice for human therapeutics, various attempts have been made to replace murine protein sequences with human protein sequences in a process now known as humanization. Transgenic mice have been constructed which have had their own immunoglobulin genes functionally replaced with human immunoglobulin genes so that they produce human antibodies upon immunization. Elimination of mouse antibody production was achieved by inactivation of mouse Ig genes in embryonic stem (ES) cells by using gene-targeting technology to delete crucial cis-acting sequences involved in the process of mouse Ig gene rearrangement and expression. B cell development in these mutant mice could be restored by the introduction of megabase-sized YACs containing a human germline-configuration H- and κ L-chain minilocus transgene. The expression of fully human antibody in these transgenic mice was predominant, at a level of several 100 μg/l of blood. This level of expression is several hundred-fold higher than that detected in wild-type mice expressing the human Ig gene, indicating the importance of inactivating the endogenous mouse Ig genes in order to enhance human antibody production by mice.

The first humanization attempts utilized molecular biology techniques to construct recombinant antibodies. For example, the complementarity determining regions (CDR) from a mouse antibody specific for a hapten were grafted onto a human antibody framework, effecting a CDR replacement. The new antibody retained the binding specificity conveyed by the CDR sequences (P. T. Jones et al. Nature 321: 522-525 (1986)). The next level of humanization involved combining an entire mouse VH region with a human constant region such as gamma (S. L. Morrison et al., Proc. Natl. Acad. Sci., 81, pp. 6851-6855 (1984)). However, these chimeric antibodies, which still contain greater than 30% xenogeneic sequences, are sometimes only marginally less immunogenic than totally xenogeneic antibodies (M. Bruggemann et al., J. Exp. Med., 170, pp. 2153-2157 (1989)).

Subsequently, attempts were carried out to introduce human immunoglobulin genes into the mouse, thus creating transgenic mice capable of responding to antigens with antibodies having human sequences (Bruggemann et al. Proc. Nat'l. Acad. Sci. USA 86:6709-6713 (1989)). Due to the large size of human immunoglobulin genomic loci, these attempts were thought to be limited by the amount of DNA, which could be stably maintained by available cloning vehicles. As a result, many investigators concentrated on producing mini-loci containing limited numbers of V region genes and having altered spatial distances between genes as compared to the natural or germline configuration (See, for example, U.S. Pat. No. 5,569,825). These studies indicated that producing human sequence antibodies in mice was possible, but serious obstacles remained regarding obtaining sufficient diversity of binding specificities and effector functions (isotypes) from these transgenic animals to meet the growing demand for antibody therapeutics.

In order to provide additional diversity, work has been conducted to add large germline fragments of the human Ig locus into transgenic mammals. For example, a majority of the human V, D, and J region genes arranged with the same spacing found in the unrearranged germline of the human genome and the human Cμ and Cδ constant regions was introduced into mice using yeast artificial chromosome (YAC) cloning vectors (See, for example, WO 94/02602). A 22 kb DNA fragment comprising sequences encoding a human gamma-2 constant region and the upstream sequences required for class-switch recombination was latter appended to the foregoing transgene. In addition, a portion of a human kappa locus comprising Vκ, Jκ and Cκ region genes, also arranged with substantially the same spacing found in the unrearranged germline of the human genome, was introduced into mice using YACS. Gene targeting was used to inactivate the murine IgH & kappa light chain immunoglobulin gene loci and such knockout strains were bred with the above transgenic strains to generate a line of mice having the human V, D, J, Cμ, Cδ. and Cγ$_2$ constant regions as well as the human Vκ, Jκ and Cκ region genes all on an inactivated murine immunoglobulin background (See, for example, PCT patent application WO 94/02602 to Kucherlapati et al.; see also Mendez et al., Nature Genetics 15:146-156 (1997)).

Yeast artificial chromosomes as cloning vectors in combination with gene targeting of endogenous loci and breeding of transgenic mouse strains provided one solution to the problem of antibody diversity. Several advantages were obtained by this approach. One advantage was that YACs can be used to transfer hundreds of kilobases of DNA into a host cell. Therefore, use of YAC cloning vehicles allows inclusion of substantial portions of the entire human Ig heavy and light chain regions into a transgenic mouse thus approaching the level of potential diversity available in the human. Another advantage of this approach is that the large number of V genes has been shown to restore full B cell development in mice deficient in murine immunoglobulin production. This ensures that these reconstituted mice are provided with the requisite cells for mounting a robust human antibody response to any given immunogen. (See, for example, WO 94/02602; L. Green and A. Jakobovits, J. Exp. Med. 188:483-495 (1998)). A further advantage is that sequences can be deleted or inserted onto the YAC by utilizing high frequency homologous recombination in yeast. This provides for facile engineering of the YAC transgenes.

In addition, Green et al. Nature Genetics 7:13-21 (1994) describe the generation of YACs containing 245 kb and 190 kb-sized germline configuration fragments of the human heavy chain locus and kappa light chain locus, respectively, which contained core variable and constant region sequences. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See, for example, Mendez et al. Nature Genetics 15:146-156 (1997), Green and Jakobovits J. Exp. Med. 188:483-495 (1998), European Patent No. EP 0 463 151 B1, PCT Publication Nos. WO 94/02602, WO 96/34096 and WO 98/24893.

Several strategies exist for the generation of mammals that produce human antibodies. In particular, there is the "minilocus" approach that is typified by work of GenPharm International, Inc. and the Medical Research Council, YAC introduction of large and substantially germline fragments of the Ig loci that is typified by work of Abgenix, Inc. (formerly Cell Genesys). The introduction of entire or substantially entire loci through the use microcell fusion as typified by work of Kirin Beer Kabushiki Kaisha.

In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (such as a gamma constant region) are formed into a construct for insertion into an animal. See, for example, U.S. Pat. Nos. 5,545,807, 5,545,806, 5,625,825, 5,625,126, 5,633,425, 5,661,016, 5,770,429, 5,789,650, 5,814,318, 5,591,669, 5,612,205, 5,721,367, 5,789,215, 5,643,763; European Patent No. 0 546 073; PCT Publication Nos. WO 92/03918, WO 92/22645, WO 92/22647, WO 92/22670, WO 93/12227, WO 94/00569, WO 94/25585, WO 96/14436, WO 97/13852, and WO 98/24884; Taylor et al. Nucleic Acids Research 20:6287-6295 (1992), Chen et al. International Immunology 5:647-656 (1993), Tuaillon et al. J. Immunol. 154:6453-6465 (1995), Choi et al. Nature Genetics 4:117-123 (1993), Lonberg et al. Nature 368:856-859 (1994), Taylor et al. International Immunology 6:579-591 (1994), Tuaillon et al. J. Immunol. 154:6453-6465 (1995), and Fishwild et al. Nature Biotech. 14:845-851 (1996).

In the microcell fusion approach, portions or whole human chromosomes can be introduced into mice (see, for example, European Patent Application No. EP 0 843 961 A1). Mice generated using this approach and containing the human Ig heavy chain locus will generally possess more than one, and potentially all, of the human constant region genes. Such mice will produce, therefore, antibodies that bind to particular antigens having a number of different constant regions.

While mice remain the most developed animal for the expression of human immunoglobulins in humans, recent technological advances have allowed for progress to begin in applying these techniques to other animals, such as cows. The general approach in mice has been to genetically modify embryonic stem cells of mice to knock-out murine immunoglobulins and then insert YACs containing human immunoglobulins into the ES cells. However, ES cells are not available for cows or other large animals such as sheep and pigs. Thus, several fundamental developments had to occur before even the possibility existed to generate large animals with immunoglobulin genes knocked-out and that express human antibody. The alternative to ES cell manipulation to create genetically modified animals is cloning using somatic cells that have been genetically modified. Cloning using genetically modified somatic cells for nuclear transfer has only recently been accomplished.

Since the announcement of Dolly's (a cloned sheep) birth from an adult somatic cell in 1997 (Wilmut, I., et al (1997) Nature 385: 810-813), ungulates, including cattle (Cibelli, J et al 1998 Science 280: 1266-1258; Kubota, C. et al. 2000 Proc. Nat'l. Acad. Sci 97: 990-995), goats (Baguisi, A. et al., (1999) Nat. Biotechnology 17: 456-461), and pigs (Polejaeva, I. A., et al. 2000 Nature 407: 86-90; Betthauser, J. et al. 2000 Nat. Biotechnology 18: 1055-1059) have been cloned.

The next technological advance was the development of the technique to genetically modify the cells prior to nuclear transfer to produce genetically modified animals. PCT publication No. WO 00/51424 to PPL Therapeutics describes the targeted genetic modification of somatic cells for nuclear transfer.

Subsequent to these fundamental developments, single and double allele knockouts of genes and the birth of live animals with these modifications have been reported. Between 2002 and 2004, three independent groups, Immerge Biotherapeutics, Inc. in collaboration with the University of Missouri (Lai et al. (Science (2002) 295: 1089-1092) & Kolber-Simonds et al. (PNAS. (2004) 101 (19):7335-40)), Alexion Pharmaceuticals (Ramsoondar et al. (Biol Reprod (2003)69: 437-445) and Revivicor, Inc. (Dai et al. (Nature Biotechnology (2002) 20: 251-255) & Phelps et al. (Science (2003) January 17; 299(5605):411-4)) produced pigs that lacked one allele or both alleles of the alpha-1,3-GT gene via nuclear transfer from somatic cells with targeted genetic deletions. In 2003, Sedai et al. (Transplantation (2003) 76:900-902) reported the targeted disruption of one allele of the alpha-1,3-GT gene in cattle, followed by the successful nuclear transfer of the nucleus of the genetically modified cell and production of transgenic fetuses.

Thus, the feasibility of knocking-out immunoglobulin genes in large animals and inserting human immunoglobulin loci into their cells is just now beginning to be explored. However, due to the complexity and species differences of immunoglobulin genes, the genomic sequences and arrangement of Ig kappa, lambda and heavy chains remain poorly understood in most species. For example, in pigs, partial genomic sequence and organization has only been described for heavy chain constant alpha, heavy chain constant mu and heavy chain constant delta (Brown and Butler Mol Immunol. 1994 June; 31(8):633-42, Butler et al Vet Immunol Immunopathol. 1994 October; 43(1-3):5-12, and Zhao et al J Immunol. 2003 Aug. 1; 171(3):1312-8).

In cows, the immunoglobulin heavy chain locus has been mapped (Zhao et al. 2003 J. Biol. Chem. 278:35024-32) and the cDNA sequence for the bovine kappa gene is known (See, for example, U.S. Patent Publication No. 2003/0037347). Further, approximately 4.6 kb of the bovine mu heavy chain locus has been sequenced and transgenic calves with decreased expression of heavy chain immunoglobulins have been created by disrupting one or both alleles of the bovine mu heavy chain. In addition, a mammalian artificial chromosome (MAC) vector containing the entire unarranged sequences of the human Ig H-chain and κL-chain has been introduced into cows (TC cows) with the technology of microcell-mediated chromosome transfer and nuclear transfer of bovine fetal fibroblast cells (see, for example, Kuroiwa et al. 2002 Nature Biotechnology 20:889, Kuroiwa et al. 2004 Nat Genet. June 6 Epub, U.S. Patent Publication Nos. 2003/0037347, 2003/0056237, 2004/0068760 and PCT Publication No. WO 02/07648).

While significant progress has been made in the production of bovine that express human immunoglobulin, little has been accomplished in other large animals, such as sheep, goats and pigs. Although cDNA sequence information for immunoglobulin genes of sheeps, goats and pigs is readily available in Genbank, the unique nature of immunoglobulin loci, which undergo massive rearrangements, creates the need to characterize beyond sequences known to be present in mRNAs (or cDNAs). Since immunoglobulin loci are modular and the coding regions are redundant, deletion of a known coding region does not ensure altered function of the locus. For example, if one were to delete the coding region of a heavy-chain variable region, the function of the locus would not be significantly altered because hundreds of other function variable genes remain in the locus. Therefore, one must first characterize the locus to identify a potential "Achilles heel".

Despite some advancements in expressing human antibodies in cattle, greater challenges remain for inactivation of the endogenous bovine Ig genes, increasing expression levels of the human antibodies and creating human antibody expression in other large animals, such as porcine, for which the sequence and arrangement of immunoglobulin genes are largely unknown.

It is therefore an object of the present invention to provide the arrangement of ungulate immunoglobin germline gene sequence.

It is another object of the present invention to provide novel ungulate immunoglobulin genomic sequences.

It is a further object of the present invention to provide cells, tissues and animals lacking at least one allele of a heavy and/or light chain immunoglobulin gene.

It is another object of the present invention to provide ungulates that express human immunoglobulins.

It is a still further object of the present invention to provide methods to generate cells, tissues and animals lacking at least one allele of novel ungulate immunoglobulin gene sequences and/or express human immunoglobulins.

SUMMARY OF THE INVENTION

The present invention provides for the first time ungulate immunoglobin germline gene sequence arrangement as well as novel genomic sequences thereof. In addition, novel ungulate cells, tissues and animals that lack at least one allele of a heavy or light chain immunoglobulin gene are provided. Based on this discovery, ungulates can be produced that completely lack at least one allele of a heavy and/or light chain immunoglobulin gene. In addition, these ungulates can be further modified to express xenogenous, such as human, immunoglobulin loci or fragments thereof.

In one aspect of the present invention, a transgenic ungulate that lacks any expression of functional endogenous immunoglobulins is provided. In one embodiment, the ungulate can lack any expression of endogenous heavy and/or light chain immunoglobulins. The light chain immunoglobulin can be a kappa and/or lambda immunoglobulin. In additional embodiments, transgenic ungulates are provided that lack expression of at least one allele of an endogenous immunoglobulin wherein the immunoglobulin is selected from the group consisting of heavy chain, kappa light chain and lambda light chain or any combination thereof. In one embodiment, the expression of functional endogenous immunoglobulins can be accomplished by genetic targeting of the endogenous immunoglobulin loci to prevent expression of the endogenous immunoglobulin. In one embodiment, the genetic targeting can be accomplished via homologous recombination. In another embodiment, the transgenic ungulate can be produced via nuclear transfer.

In other embodiments, the transgenic ungulate that lacks any expression of functional endogenous immunoglobulins can be further genetically modified to express an xenogenous immunoglobulin loci. In an alternative embodiment, porcine animals are provided that contain an xenogenous immunoglobulin locus. In one embodiment, the xenogenous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In another aspect of the present invention, transgenic ungulates are provided that expresses a xenogenous immunoglobulin loci or fragment thereof, wherein the immunoglobulin can be expressed from an immunoglobulin locus that is integrated within an endogenous ungulate chromosome. In one embodiment, ungulate cells derived from the transgenic animals are provided. In one embodiment, the xenogenous immunoglobulin locus can be inherited by offspring. In another embodiment, the xenogenous immunoglobulin locus can be inherited through the male germ line by offspring. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In another aspect of the present invention, novel genomic sequences encoding the heavy chain locus of ungulate immunoglobulin are provided. In one embodiment, an isolated nucleotide sequence encoding porcine heavy chain is provided that includes at least one variable region, two diversity regions, at least four joining regions and at least one constant region, such as the mu constant region, for example, as represented in Seq ID No. 29. In another embodiment, an isolated nucleotide sequence is provided that includes at least four joining regions and at least one constant region, such as the mu constant region, of the porcine heavy chain genomic sequence, for example, as represented in Seq ID No. 4. In a further embodiment, nucleotide sequence is provided that includes 5' flanking sequence to the first joining region of the porcine heavy chain genomic sequence, for example, as represented in Seq ID No 1. Still further, nucleotide sequence is provided that includes 3' flanking sequence to the first joining region of the porcine heavy chain genomic sequence, for example, as represented in the 3' region of Seq ID No 4. In further embodiments, isolated nucleotide sequences as depicted in Seq ID Nos 1, 4 or 29 are provided. Nucleic acid sequences at least 80, 85, 90, 95, 98 or 99% homologous to Seq ID Nos 1, 4 or 29 are also provided. In addition, nucleotide sequences that contain at least 10, 15, 17, 20, 25 or 30 contiguous nucleotides of Seq ID Nos 1, 4 or 29 are provided. In one embodiment, the nucleotide sequence contains at least 17, 20, 25 or 30 contiguous nucleotides of Seq ID No 4 or residues 1-9,070 of Seq ID No 29. In another embodiment, the nucleotide sequence contains residues 9,070-11039 of Seq ID No 29. Further provided are nucleotide sequences that hybridize, optionally under stringent conditions, to Seq ID Nos 1, 4 or 29, as well as, nucleotides homologous thereto.

In another embodiment, novel genomic sequences encoding the kappa light chain locus of ungulate immunoglobulin are provided. The present invention provides the first reported genomic sequence of ungulate kappa light chain regions. In one embodiment, nucleic acid sequence is provided that encodes the porcine kappa light chain locus. In another embodiment, the nucleic acid sequence can contain at least one joining region, one constant region and/or one enhancer region of kappa light chain. In a further embodiment, the nucleotide sequence can include at least five joining regions, one constant region and one enhancer region, for example, as represented in Seq ID No. 30. In a further embodiment, an isolated nucleotide sequence is provided that contains at least one, at least two, at least three, at least four or five joining regions and 3' flanking sequence to the joining region of porcine genomic kappa light chain, for example, as represented in Seq ID No 12. In another embodiment, an isolated nucleotide sequence of porcine genomic kappa light chain is provided that contains 5' flanking sequence to the first joining region, for example, as represented in Seq ID No 25. In a further embodiment, an isolated nucleotide sequence is provided that contains 3' flanking sequence to the constant region and, optionally, the 5' portion of the enhancer region, of porcine genomic kappa light chain, for example, as represented in Seq ID Nos. 15, 16 and/or 19.

In further embodiments, isolated nucleotide sequences as depicted in Seq ID Nos 30, 12, 25, 15, 16 or 19 are provided. Nucleic acid sequences at least 80, 85, 90, 95, 98 or 99% homologous to Seq ID Nos 30, 12, 25, 15, 16 or 19 are also provided. In addition, nucleotide sequences that contain at least 10, 15, 17, 20, 25 or 30 contiguous nucleotides of Seq ID Nos 30, 12, 25, 15, 16 or 19 are provided. Further provided are nucleotide sequences that hybridizes, optionally under stringent conditions, to Seq ID Nos 30, 12, 25, 15, 16 or 19, as well as, nucleotides homologous thereto.

In another embodiment, novel genomic sequences encoding the lambda light chain locus of ungulate immunoglobulin are provided. The present invention provides the first reported genomic sequence of ungulate lambda light chain regions. In one embodiment, the porcine lambda light chain nucleotides include a concatamer of J to C units. In a specific embodiment, an isolated porcine lambda nucleotide sequence is provided, such as that depicted in Seq ID No. 28. In one embodiment, a nucleotide sequence is provided that includes 5' flanking sequence to the first lambda J/C unit of the porcine lambda light chain genomic sequence, for example, as represented by Seq ID No 32. Still further, nucleotide sequence is provided that includes 3' flanking sequence to the J/C cluster region of the porcine lambda light chain genomic sequence, for example, approximately 200 base pairs downstream of lambda J/C, such as that represented by Seq ID No 33. Alternatively, nucleotide sequence is provided that includes 3' flanking sequence to the J/C cluster region of the porcine lambda light chain genomic sequence, for example, as represented by Seq ID No 34, 35, 36, 37, 38, and/or 39.

In a further embodiment, nucleic acid sequences are provided that encode bovine lambda light chain locus, which can include at least one joining region-constant region pair and/or at least one variable region, for example, as represented by Seq ID No. 31. In further embodiments, isolated nucleotide sequences as depicted in Seq ID Nos 28, 31, 32, 33, 34, 35, 36, 37, 38, or 39 are provided. Nucleic acid sequences at least 80, 85, 90, 95, 98 or 99% homologous to Seq ID Nos 28, 31, 32, 33, 34, 35, 36, 37, 38, or 39 are also provided. In addition, nucleotide sequences that contain at least 10, 15, 17, 20, 25 or 30 contiguous nucleotides of Seq ID Nos 28, 31, 32, 33, 34, 35, 36, 37, 38, or 39 are provided. Further provided are nucleotide sequences that hybridizes, optionally under stringent conditions, to Seq ID Nos 28, 31, 32, 33, 34, 35, 36, 37, 38, or 39, as well as, nucleotides homologous thereto.

In another embodiment, nucleic acid targeting vector constructs are also provided. The targeting vectors can be designed to accomplish homologous recombination in cells. These targeting vectors can be transformed into mammalian cells to target the ungulate heavy chain, kappa light chain or lambda light chain genes via homologous recombination. In one embodiment, the targeting vectors can contain a 3' recombination arm and a 5' recombination arm (i.e. flanking sequence) that is homologous to the genomic sequence of ungulate heavy chain, kappa light chain or lambda light chain genomic sequence, for example, sequence represented by Seq ID Nos. 1, 4, 29, 30, 12, 25, 15, 16, 19, 28 or 31, as described above. The homologous DNA sequence can include at least 15 bp, 20 bp, 25 bp, 50 bp, 100 bp, 500 bp, 1 kbp, 2 kbp, 4 kbp, 5 kbp, 10 kbp, 15 kbp, 20 kbp, or 50 kbp of sequence homologous to the genomic sequence.

In one embodiment, the 5' and 3' recombination arms of the targeting vector can be designed such that they flank the 5' and 3' ends of at least one functional variable, joining, diversity, and/or constant region of the genomic sequence. The targeting of a functional region can render it inactive, which results in the inability of the cell to produce functional immunoglobulin molecules. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

In one particular embodiment, the targeting vector can contain 5' and 3' recombination arms that contain homologous sequence to the 3' and 5' flanking sequence of the J6 region of the porcine immunoglobulin heavy chain locus. Since the J6 region is the only functional joining region of the porcine immunoglobulin heavy chain locus, this will prevent the expression of a functional porcine heavy chain immunoglobulin. In a specific embodiment, the targeting vector can contain a 5' recombination arm that contains sequence homologous to genomic sequence 5' of the J6 region, including J1-4, and a 3' recombination arm that contains sequence homologous to genomic sequence 3' of the J6 region, including the mu constant region (a "J6 targeting construct"), see for example, FIG. 1. Further, this J6 targeting construct can also contain a selectable marker gene that is located between the 5' and 3' recombination arms, see for example, Seq ID No 5 and FIG. 1. In other embodiments, the targeting vector can contain a 5' recombination arm that contains sequence homologous to genomic sequence 5' of the diversity region, and a 3' recombination arm that contains sequence homologous to genomic sequence 3' of the diversity region of the porcine heavy chain locus. In a further embodiment, the targeting vector can contain a 5' recombination arm that contains sequence homologous to genomic sequence 5' of the mu constant region and a 3' recombination arm that contains sequence homologous to genomic sequence 3' of the mu constant region of the porcine heavy chain locus.

In another particular embodiment, the targeting vector can contain 5' and 3' recombination arms that contain homologous sequence to the 3' and 5' flanking sequence of the constant region of the porcine immunoglobulin kappa light chain locus. Since the present invention discovered that there is only one constant region of the porcine immunoglobulin kappa light chain locus, this will prevent the expression of a functional porcine kappa light chain immunoglobulin. In a specific embodiment, the targeting vector can contain a 5' recombination arm that contains sequence homologous to genomic sequence 5' of the constant region, optionally including the joining region, and a 3' recombination arm that contains sequence homologous to genomic sequence 3' of the constant region, optionally including at least part of the enhancer region (a "Kappa constant targeting construct"), see for example, FIG. 2. Further, this kappa constant targeting construct can also contain a selectable marker gene that is located between the 5' and 3' recombination arms, see for example, Seq ID No 20 and FIG. 2. In other embodiments, the targeting vector can contain a 5' recombination arm that contains sequence homologous to genomic sequence 5' of the joining region, and a 3' recombination arm that contains sequence homologous to genomic sequence 3' of the joining region of the porcine kappa light chain locus.

In another particular embodiment, the targeting vector can contain 5' and 3' recombination arms that contain homologous sequence to the 3' and 5' flanking sequence of the J/C region of the porcine lambda light chain. See FIG. 3. Disruption of the J/C region will prevent the expression of a functional porcine kappa light chain immunoglobulin. In one embodiment, the targeting vector can contain a 5' recombination arm that contains sequence homologous to genomic sequence 5' of the first J/C unit and a 3' recombination arm that contains sequence homologous to genomic sequence 3' of the last J/C unit. Further, this lambda light chain targeting construct can also contain a selectable marker gene that is located between the 5' and 3' recombination arms, see for example FIG. 4.

In a further embodiment, more than one targeting vector can be used to target the ungulate heavy chain, kappa light chain or lambda light chain genes via homologous recombination. For example, two targeting vectors can be used to target the gene of interest. A first targeting vector can contain 5' and 3' recombination arms that contain homologous sequence to the 5' flanking sequence of at least one functional variable, joining, diversity, and/or constant region of the genomic sequence. A second targeting vector can contain 5' and 3' recombination arms that contain homologous sequence to the 3' flanking sequence at least one functional variable, joining, diversity, and/or constant region of the genomic sequence.

In a particular embodiment, the first targeting vector can contain 5' and 3' recombination arms that contain homologous sequence to the 5' flanking sequence of the first J/C unit in the J/C cluster region. See FIG. 5. According to this embodiment, a second targeting vector can contain 5' and 3' recombination arms that contain homologous sequence to the 3' flanking sequence of the last J/C unit in the J/C cluster region. See FIG. 6.

In another embodiment, primers are provided to generate 3' and 5' sequences of a targeting vector. The oligonucleotide primers can be capable of hybridizing to porcine immunoglobulin genomic sequence, such as Seq ID Nos. 1, 4, 29, 30, 12, 25, 15, 16, 19, 28 or 31, as described above. In a particular embodiment, the primers hybridize under stringent conditions to Seq ID Nos. 1, 4, 29, 30, 12, 25, 15, 16, 19, 28 or 31, as described above. Another embodiment provides oligonucleotide probes capable of hybridizing to porcine heavy chain, kappa light chain or lambda light chain nucleic acid sequences, such as Seq ID Nos. 1, 4, 29, 30, 12, 25, 15, 16, 19, 28 or 31, as described above. The polynucleotide primers or probes can have at least 14 bases, 20 bases, 30 bases, or 50 bases which hybridize to a polynucleotide of the present invention. The probe or primer can be at least 14 nucleotides in length, and in a particular embodiment, are at least 15, 20, 25, 28, or 30 nucleotides in length.

In one embodiment, primers are provided to amplify a fragment of porcine Ig heavy-chain that includes the functional joining region (the J6 region). In one non-limiting embodiment, the amplified fragment of heavy chain can be represented by Seq ID No 4 and the primers used to amplify this fragment can be complementary to a portion of the J-region, such as, but not limited to Seq ID No 2, to produce the 5' recombination arm and complementary to a portion of Ig heavy-chain mu constant region, such as, but not limited to Seq ID No 3, to produce the 3' recombination arm. In another embodiment, regions of the porcine Ig heavy chain (such as, but not limited to Seq ID No 4) can be subcloned and assembled into a targeting vector.

In other embodiments, primers are provided to amplify a fragment of porcine Ig kappa light-chain that includes the constant region. In another embodiment, primers are provided to amplify a fragment of porcine Ig kappa light-chain that includes the J region. In one non-limiting embodiment, the primers used to amplify this fragment can be complementary to a portion of the J-region, such as, but not limited to Seq ID No 21 or 10, to produce the 5' recombination arm and complementary to genomic sequence 3' of the constant region, such as, but not limited to Seq ID No 14, 24 or 18, to produce the 3' recombination arm. In another embodiment, regions of the porcine Ig heavy chain (such as, but not limited to Seq ID No 20) can be subcloned and assembled into a targeting vector.

In another aspect of the present invention, ungulate cells lacking at least one allele of a functional region of an ungulate heavy chain, kappa light chain and/or lambda light chain locus produced according to the process, sequences and/or constructs described herein are provided. These cells can be obtained as a result of homologous recombination. Particularly, by inactivating at least one allele of an ungulate heavy chain, kappa light chain or lambda light chain gene, cells can be produced which have reduced capability for expression of ungulate antibodies. In other embodiments, mammalian cells lacking both alleles of an ungulate heavy chain, kappa light chain and/or lambda light chain gene can be produced according to the process, sequences and/or constructs described herein. In a further embodiment, porcine animals are provided in which at least one allele of an ungulate heavy chain, kappa light chain and/or lambda light chain gene is inactivated via a genetic targeting event produced according to the process, sequences and/or constructs described herein. In another aspect of the present invention, porcine animals are provided in which both alleles of an ungulate heavy chain, kappa light chain and/or lambda light chain gene are inactivated via a genetic targeting event. The gene can be targeted via homologous recombination.

In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques. Additional genes for a desired protein or regulatory sequence that modulate transcription of an existing sequence can be inserted. To achieve multiple genetic modifications of ungulate immunoglobulin genes, in one embodiment, cells can be modified sequentially to contain multiple genetic modifications. In other embodiments, animals can be bred together to produce animals that contain multiple genetic modifications of immunoglobulin genes. As an illustrative example, animals that lack expression of at least one allele of an ungulate heavy chain gene can be further genetically modified or bred with animals lacking at least one allele of a kappa light chain gene.

In embodiments of the present invention, alleles of ungulate heavy chain, kappa light chain or lambda light chain gene are rendered inactive according to the process, sequences and/or constructs described herein, such that functional ungulate immunoglobulins can no longer be produced. In one embodiment, the targeted immunoglobulin gene can be transcribed into RNA, but not translated into protein. In another embodiment, the targeted immunoglobulin gene can be transcribed in an inactive truncated form. Such a truncated RNA may either not be translated or can be translated into a nonfunctional protein. In an alternative embodiment, the targeted immunoglobulin gene can be inactivated in such a way that no transcription of the gene occurs. In a further embodiment, the targeted immunoglobulin gene can be transcribed and then translated into a nonfunctional protein.

In a further aspect of the present invention, ungulate, such as porcine or bovine, cells lacking one allele, optionally both alleles of an ungulate heavy chain, kappa light chain and/or lambda light chain gene can be used as donor cells for nuclear transfer into recipient cells to produce cloned, transgenic animals. Alternatively, ungulate heavy chain, kappa light chain and/or lambda light chain gene knockouts can be created in embryonic stem cells, which are then used to produce offspring. Offspring lacking a single allele of a functional ungulate heavy chain, kappa light chain and/or lambda light chain gene produced according to the process, sequences and/or constructs described herein can be breed to further produce offspring lacking functionality in both alleles through mendelian type inheritance.

In one aspect of the present invention, a method is provided to disrupt the expression of an ungulate immunoglobulin gene by (i) analyzing the germline configuration of the ungulate heavy chain, kappa light chain or lambda light chain genomic locus; (ii) determining the location of nucleotide sequences that flank the 5' end and the 3' end of at least one functional region of the locus; and (iii) transfecting a targeting construct containing the flanking sequence into a cell wherein, upon successful homologous recombination, at least one functional region of the immunoglobulin locus is disrupted thereby reducing or preventing the expression of the immunoglobulin gene. In one embodiment, the germline configuration of the porcine heavy chain locus is provided. The porcine heavy chain locus contains at least four variable regions, two diversity regions, six joining regions and five constant regions, for example, as illustrated in FIG. 1. In a specific embodiment, only one of the six joining regions, J6, is functional. In another embodiment, the germline configuration of the porcine kappa light chain locus is provided. The porcine kappa light chain locus contains at least six variable regions, six joining regions, one constant region and one enhancer region, for example, as illustrated in FIG. 2. In a further embodiment, the germline configuration of the porcine lambda light chain locus is provided. The porcine lambda light chain locus contains a variable region and the J/C region. See FIG. 3.

In a further aspect of the present invention, a method is provided to disrupt the expression of an ungulate lambda light chain locus by (i) analyzing the germline configuration of the ungulate lambda light chain genomic locus; (ii) determining the location of nucleotide sequences that flank the 5' end of at least one functional region of the locus; (ii) constructing a 5' targeting construct; (iv) determining the location of nucleotide sequences that flank the 3' end of at least one functional region of the locus; (v) constructing a 3' targeting construct; (vi) transfecting both the 5' and the 3' targeting constructs into a cell wherein, upon successful homologous recombination of each targeting construct, at least one functional region of the immunoglobulin locus is disrupted thereby reducing or preventing the expression of the immunoglobulin gene. See FIGS. 5 and 6.

In one embodiment, the germline configuration of the porcine lambda light chain locus is provided. The porcine lambda light chain locus contains a variable region and a J/C region. See FIG. 3.

In further aspects of the present invention provides ungulates and ungulate cells that lack at least one allele of a functional region of an ungulate heavy chain, kappa light chain and/or lambda light chain locus produced according to the processes, sequences and/or constructs described herein, which are further modified to express at least part of a human antibody (i.e. immunoglobulin (Ig)) locus. In additional embodiments, porcine animals are provided that express xenogenous immunoglobulin. This human locus can undergo rearrangement and express a diverse population of human antibody molecules in the ungulate. These cloned, transgenic ungulates provide a replenishable, theoretically infinite supply of human antibodies (such as polyclonal antibodies), which can be used for therapeutic, diagnostic, purification, and other clinically relevant purposes. In one particular embodiment, artificial chromosomes (ACs), such as yeast or mammalian artificial chromosomes (YACS or MACS) can be used to allow expression of human immunoglobulin genes into ungulate cells and animals. All or part of human immunoglobulin genes, such as the Ig heavy chain gene (human chromosome 414), Ig kappa chain gene (human chromosome #2) and/or the Ig lambda chain gene (chromosome #22) can be inserted into the artificial chromosomes, which can then be inserted into ungulate cells. In further embodiments, ungulates and ungulate cells are provided that contain either part or all of at least one human antibody gene locus, which undergoes rearrangement and expresses a diverse population of human antibody molecules.

In additional embodiments, methods of producing xenogenous antibodies are provided, wherein the method can include: (a) administering one or more antigens of interest to an ungulate whose cells comprise one or more artificial chromosomes and lack any expression of functional endogenous immunoglobulin, each artificial chromosome comprising one or more xenogenous immunoglobulin loci that undergo rearrangement, resulting in production of xenogenous antibodies against the one or more antigens; and/or (b) recovering the xenogenous antibodies from the ungulate. In one embodiment, the immunoglobulin loci can undergo rearrangement in a B cell.

In one aspect of the present invention, an ungulate, such as a pig or a cow, can be prepared by a method in accordance with any aspect of the present invention. These cloned, transgenic ungulates (e.g., porcine and bovine animals) provide a replenishable, theoretically infinite supply of human polyclonal antibodies, which can be used as therapeutics, diagnostics and for purification purposes. For example, transgenic animals produced according to the process, sequences and/or constructs described herein that produce polyclonal human antibodies in the bloodstream can be used to produce an array of different antibodies which are specific to a desired antigen. The availability of large quantities of polyclonal antibodies can also be used for treatment and prophylaxis of infectious disease, vaccination against biological warfare agents, modulation of the immune system, removal of undesired human cells such as cancer cells, and modulation of specific human molecules.

In other embodiments, animals or cells lacking expression of functional immunoglobulin, produced according to the process, sequences and/or constructs described herein, can contain additional genetic modifications to eliminate the expression of xenoantigens. Such animals can be modified to eliminate the expression of at least one allele of the alpha-1,3-galactosyltransferase gene, the CMP-Neu5Ac hydroxylase gene (see, for example, U.S. Ser. No. 10/863,116), the iGb3 synthase gene (see, for example, U.S. Patent Application 60/517,524), and/or the Forssman synthase gene (see, for example, U.S. Patent Application 60/568,922). In additional embodiments, the animals discloses herein can also contain genetic modifications to express fucosyltransferase and/or sialyltransferase. To achieve these additional genetic modifications, in one embodiment, cells can be modified to contain multiple genetic modifications. In other embodiments, animals can be bred together to achieve multiple genetic modifications. In one specific embodiment, animals, such as pigs, lacking expression of functional immunoglobulin, produced according to the process, sequences and/or constructs described herein, can be bred with animals, such as pigs, lacking expression of alpha-1,3-galactosyl transferase (for example, as described in WO 04/028243).

BRIEF DESCRIPTION OF THE DRAWINGS

FIG. 4 represents the design of a targeting vector that disrupts the expression of the JC cluster region of the porcine lambda light chain immunoglobulin gene. "SM" stands for a selectable marker gene, which can be used in the targeting vector.

FIG. 5 illustrates a targeting strategy to insert a site specific recombinase target or recognition site into the region 5' of the JC cluster region of the porcine lambda immunoglobulin locus. "SM" stands for a selectable marker gene, which can be used in the targeting vector. "SSRRS" stands for a specific recombinase target or recognition site.

FIG. 7 illustrates the site specific recombinase mediated transfer of a YAC into a host genome. "SSRRS" stands for a specific recombinase target or recognition site.

DETAILED DESCRIPTION

Figure 1:
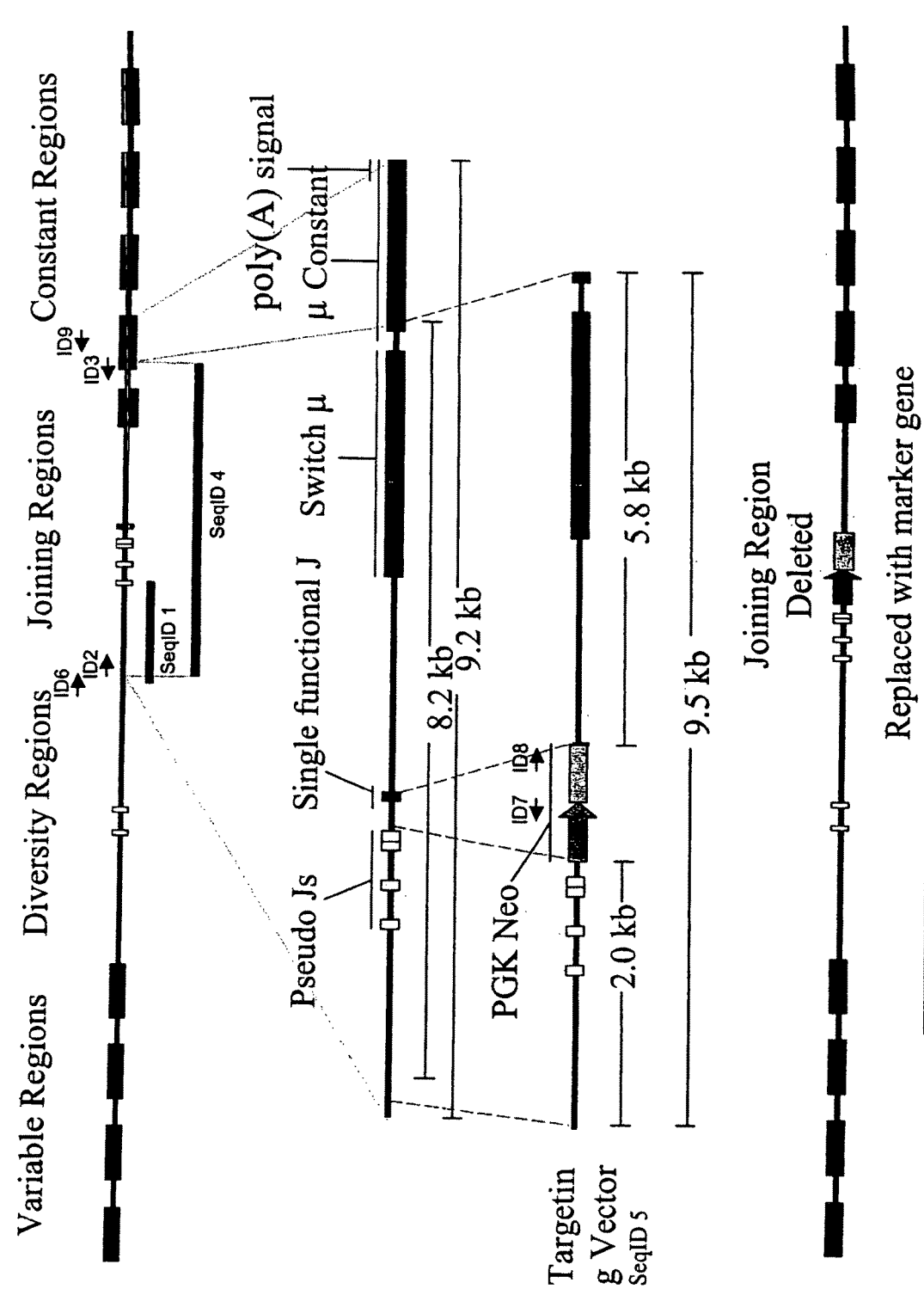
FIG. 1 illustrates the design of a targeting vector that disrupts the expression of the joining region of the porcine heavy chain immunoglobulin gene.

The present invention provides for the first time ungulate immunoglobin germline gene sequence arrangement as well as novel genomic sequences thereof. In addition, novel ungulate cells, tissues and animals that lack at least one allele of a heavy or light chain immunoglobulin gene are provided. Based on this discovery, ungulates can be produced that completely lack at least one allele of a heavy and/or light chain immunoglobulin gene. In addition, these ungulates can be further modified to express xenogenous, such as human, immunoglobulin loci or fragments thereof.

In one aspect of the present invention, a transgenic ungulate that lacks any expression of functional endogenous immunoglobulins is provided. In one embodiment, the ungulate can lack any expression of endogenous heavy and/or light chain immunoglobulins. The light chain immunoglobulin can be a kappa and/or lambda immunoglobulin. In additional embodiments, transgenic ungulates are provided that lack expression of at least one allele of an endogenous immunoglobulin wherein the immunoglobulin is selected from the group consisting of heavy chain, kappa light chain and lambda light chain or any combination thereof. In one embodiment, the expression of functional endogenous immunoglobulins can be accomplished by genetic targeting of the endogenous immunoglobulin loci to prevent expression of the endogenous immunoglobulin. In one embodiment, the genetic targeting can be accomplished via homologous recombination. In another embodiment, the transgenic ungulate can be produced via nuclear transfer.

In other embodiments, the transgenic ungulate that lacks any expression of functional endogenous immunoglobulins can be further genetically modified to express an xenogenous immunoglobulin loci. In an alternative embodiment, porcine animals are provided that contain an xenogenous immunoglobulin locus. In one embodiment, the xenogenous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In another aspect of the present invention, transgenic ungulates are provided that expresses a xenogenous immunoglobulin loci or fragment thereof, wherein the immunoglobulin can be expressed from an immunoglobulin locus that is integrated within an endogenous ungulate chromosome. In one embodiment, ungulate cells derived from the transgenic animals are provided. In one embodiment, the xenogenous immunoglobulin locus can be inherited by offspring. In another embodiment, the xenogenous immunoglobulin locus can be inherited through the male germ line by offspring. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

Definitions

The terms "recombinant DNA technology," "DNA cloning," "molecular cloning," or "gene cloning" refer to the process of transferring a DNA sequence into a cell or organism. The transfer of a DNA fragment can be from one organism to a self-replicating genetic element (e.g., bacterial plasmid) that permits a copy of any specific part of a DNA (or RNA) sequence to be selected among many others and produced in an unlimited amount. Plasmids and other types of cloning vectors such as artificial chromosomes can be used to copy genes and other pieces of chromosomes to generate enough identical material for further study. In addition to bacterial plasmids, which can carry up to 20 kb of foreign DNA, other cloning vectors include viruses, cosmids, and artificial chromosomes (e.g., bacteria artificial chromosomes (BACs) or yeast artificial chromosomes (YACs)). When the fragment of chromosomal DNA is ultimately joined with its cloning vector in the lab, it is called a "recombinant DNA molecule." Shortly after the recombinant plasmid is introduced into suitable host cells, the newly inserted segment will be reproduced along with the host cell DNA.

"Cosmids" are artificially constructed cloning vectors that carry up to 45 kb of foreign DNA. They can be packaged in lambda phage particles for infection into E. coli cells.

As used herein, the term "mammal" (as in "genetically modified (or altered) mammal") is meant to include any non-human mammal, including but not limited to pigs, sheep, goats, cattle (bovine), deer, mules, horses, monkeys, dogs, cats, rats, mice, birds, chickens, reptiles, fish, and insects. In one embodiment of the invention, genetically altered pigs and methods of production thereof are provided.

The term "ungulate" refers to hoofed mammals. Artiodactyls are even-toed (cloven-hooved) ungulates, including antelopes, camels, cows, deer, goats, pigs, and sheep. Perissodactyls are odd toes ungulates, which include horses, zebras, rhinoceroses, and tapirs. The term ungulate as used herein refers to an adult, embryonic or fetal ungulate animal.

As used herein, the terms "porcine", "porcine animal", "pig" and "swine" are generic terms referring to the same type of animal without regard to gender, size, or breed.

A "homologous DNA sequence or homologous DNA" is a DNA sequence that is at least about 80%, 85%, 90%, 95%, 98% or 99% identical with a reference DNA sequence. A homologous sequence hybridizes under stringent conditions to the target sequence, stringent hybridization conditions include those that will allow hybridization occur if there is at least 85, at least 95% or 98% identity between the sequences.

An "isogenic or substantially isogenic DNA sequence" is a DNA sequence that is identical to or nearly identical to a reference DNA sequence. The term "substantially isogenic" refers to DNA that is at least about 97-99% identical with the reference DNA sequence, or at least about 99.5-99.9% identical with the reference DNA sequence, and in certain uses 100% identical with the reference DNA sequence.

"Homologous recombination" refers to the process of DNA recombination based on sequence homology.

"Gene targeting" refers to homologous recombination between two DNA sequences, one of which is located on a chromosome and the other of which is not.

"Non-homologous or random integration" refers to any process by which DNA is integrated into the genome that does not involve homologous recombination.

A "selectable marker gene" is a gene, the expression of which allows cells containing the gene to be identified. A selectable marker can be one that allows a cell to proliferate on a medium that prevents or slows the growth of cells without the gene. Examples include antibiotic resistance genes and genes which allow an organism to grow on a selected metabolite.

Alternatively, the gene can facilitate visual screening of transformants by conferring on cells a phenotype that is easily identified. Such an identifiable phenotype can be, for example, the production of luminescence or the production of a colored compound, or the production of a detectable change in the medium surrounding the cell.

The term "contiguous" is used herein in its standard meaning, i.e., without interruption, or uninterrupted.

"Stringent conditions" refers to conditions that (1) employ low ionic strength and high temperature for washing, for example, 0.015 M NaCl/0.0015 M sodium citrate/0.1% SDS at 50° C., or (2) employ during hybridization a denaturing agent such as, for example, formamide. One skilled in the art can determine and vary the stringency conditions appropriately to obtain a clear and detectable hybridization signal. For example, stringency can generally be reduced by increasing the salt content present during hybridization and washing, reducing the temperature, or a combination thereof. See, for example, Sambrook et aL, Molecular Cloning: A Laboratory Manual, Cold Spring Harbour Laboratory Press, Cold Spring Harbour, N.Y., (1989).

I. Immunoglobulin Genes

In one aspect of the present invention, a transgenic ungulate that lacks any expression of functional endogenous immunoglobulins is provided. In one embodiment, the ungulate can lack any expression of endogenous heavy and/or light chain immunoglobulins. The light chain immunoglobulin can be a kappa and/or lambda immunoglobulin. In additional embodiments, transgenic ungulates are provided that lack expression of at least one allele of an endogenous immunoglobulin wherein the immunoglobulin is selected from the group consisting of heavy chain, kappa light chain and lambda light chain or any combination thereof. In one embodiment, the expression of functional endogenous immunoglobulins can be accomplished by genetic targeting of the endogenous immunoglobulin loci to prevent expression of the endogenous immunoglobulin. In one embodiment, the genetic targeting can be accomplished via homologous recombination. In another embodiment, the transgenic ungulate can be produced via nuclear transfer.

In another aspect of the present invention, a method is provided to disrupt the expression of an ungulate immunoglobulin gene by (i) analyzing the germline configuration of the ungulate heavy chain, kappa light chain or lambda light chain genomic locus; (ii) determining the location of nucleotide sequences that flank the 5' end and the 3' end of at least one functional region of the locus; and (iii) transfecting a targeting construct containing the flanking sequence into a cell wherein, upon successful homologous recombination, at least one functional region of the immunoglobulin locus is disrupted thereby reducing or preventing the expression of the immunoglobulin gene.

In one embodiment, the germline configuration of the porcine heavy chain locus is provided. The porcine heavy chain locus contains at least four variable regions, two diversity regions, six joining regions and five constant regions, for example, as illustrated in FIG. 1. In a specific embodiment, only one of the six joining regions, J6, is functional.

Figure 2:
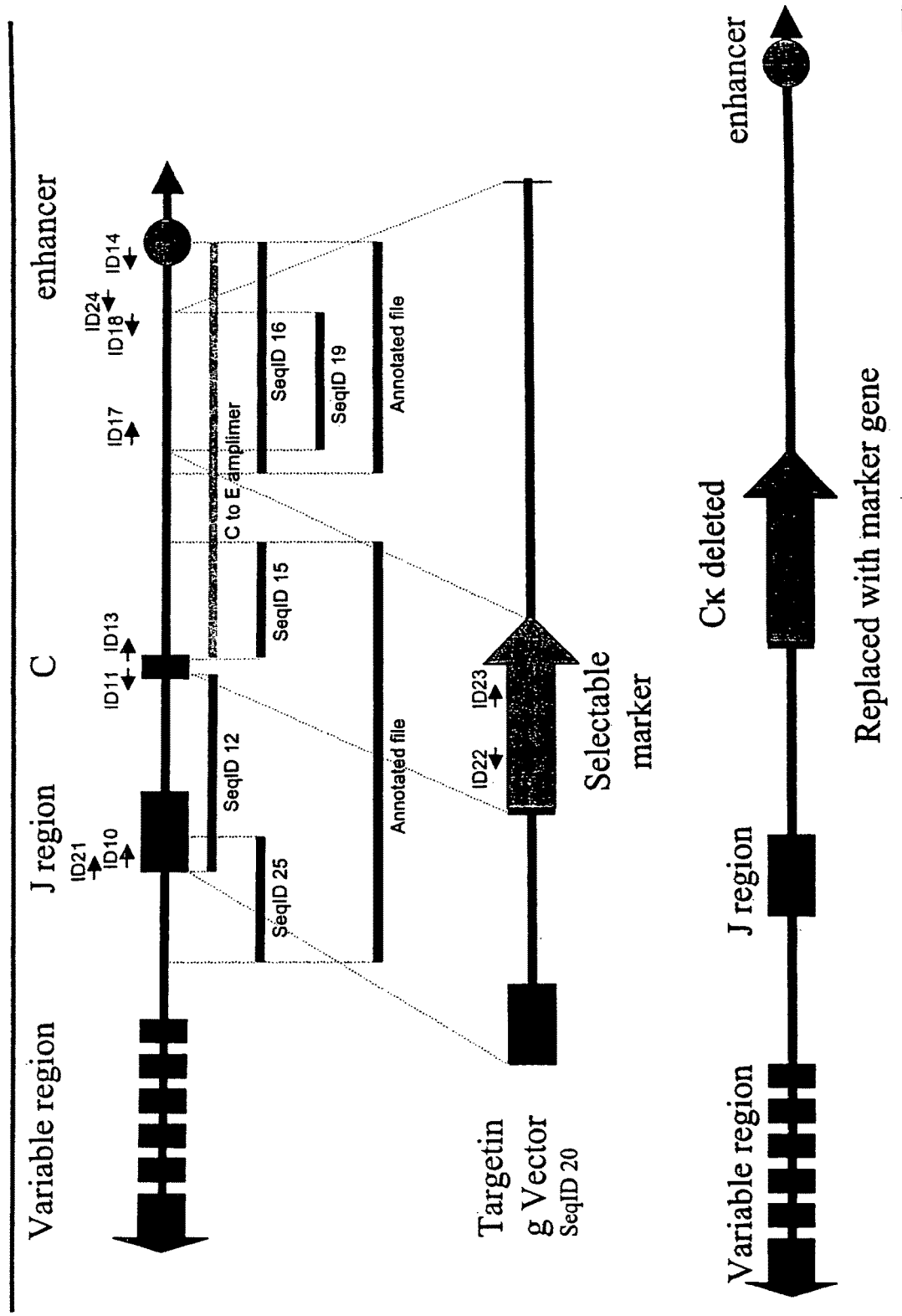
FIG. 2 illustrates the design of a targeting vector that disrupts the expression of the constant region of the porcine kappa light chain immunoglobulin gene.

In another embodiment, the germline configuration of the porcine kappa light chain locus is provided. The porcine kappa light chain locus contains at least six variable regions, six joining regions, one constant region and one enhancer region, for example, as illustrated in FIG. 2.

In a further embodiment, the germline configuration of the porcine lambda light chain locus is provided.

Isolated nucleotide sequences as depicted in Seq ID Nos 1-39 are provided. Nucleic acid sequences at least 80, 85, 90, 95, 98 or 99% homologous to any one of Seq ID Nos 1-39 are also provided. In addition, nucleotide sequences that contain at least 10, 15, 17, 20, 25 or 30 contiguous nucleotides of any one of Seq ID Nos 1-39 are provided. Further provided are nucleotide sequences that hybridize, optionally under stringent conditions, to Seq ID Nos 1-39, as well as, nucleotides homologous thereto.

Homology or identity at the nucleotide or amino acid sequence level can be determined by BLAST (Basic Local Alignment Search Tool) analysis using the algorithm employed by the programs blastp, blastn, blastx, tblastn and tblastx (see, for example, Altschul, S. F. et al (1997) Nucleic Acids Res 25:3389-3402 and Karlin et al, (1900) Proc. Natl. Acad. Sci. USA 87, 2264-2268) which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a preselected threshold of significance. See, for example, Altschul et aL, (1994) (Nature Genetics 6, 119-129). The search parameters for histogram, descriptions, alignments, expect (i.e., the statistical significance threshold for reporting matches against database sequences), cutoff, matrix and filter (low co M'plexity) are at the default settings. The default scoring matrix used by blastp, blastx, tblastn, and tblastx is the BLOSUM62 matrix (Henikoff et aL, (1992) Proc. Natl. Acad. Sci. USA 89, 10915-10919), which is recommended for query sequences over 85 in length (nucleotide bases or amino acids).

Porcine Heavy Chain

In another aspect of the present invention, novel genomic sequences encoding the heavy chain locus of ungulate immunoglobulin are provided. In one embodiment, an isolated nucleotide sequence encoding porcine heavy chain is provided that includes at least one variable region, two diversity regions, at least four joining regions and at least one constant region, such as the mu constant region, for example, as represented in Seq ID No. 29. In another embodiment, an isolated nucleotide sequence is provided that includes at least four joining regions and at least one constant region, such as the mu constant region, of the porcine heavy chain genomic sequence, for example, as represented in Seq ID No. 4. In a further embodiment, nucleotide sequence is provided that includes 5' flanking sequence to the first joining region of the porcine heavy chain genomic sequence, for example, as represented in Seq ID No 1. Still further, nucleotide sequence is provided that includes 3' flanking sequence to the first joining region of the porcine heavy chain genomic sequence, for example, as represented in the 3' region of Seq ID No 4. In further embodiments, isolated nucleotide sequences as depicted in Seq ID Nos 1, 4 or 29 are provided. Nucleic acid sequences at least 80, 85, 90, 95, 98 or 99% homologous to Seq ID Nos 1, 4 or 29 are also provided. Further provided are nucleotide sequences that hybridize, optionally under stringent conditions, to Seq ID Nos 1, 4 or 29, as well as, nucleotides homologous thereto.

In addition, nucleotide sequences that contain at least 10, 15, 17, 20, 25 or 30 contiguous nucleotides of Seq ID Nos 1, 4 or 29 are provided. In one embodiment, the nucleotide sequence contains at least 17, 20, 25 or 30 contiguous nucleotides of Seq ID No 4 or residues 1-9,070 of Seq ID No 29. In other embodiments, nucleotide sequences that contain at least 50, 100, 1,000, 2,500, 4,000, 4,500, 5,000, 7,000, 8,000, 8,500, 9,000, 10,000 or 15,000 contiguous nucleotides of Seq ID No. 29 are provided. In another embodiment, the nucleotide sequence contains residues 9,070-11039 of Seq ID No 29.

In further embodiments, isolated nucleotide sequences as depicted in Seq ID Nos 1, 4 or 29 are provided. Nucleic acid sequences at least 80, 85, 90, 95, 98 or 99% homologous to Seq ID Nos 1, 4 or 29 are also provided. In addition, nucleotide sequences that contain at least 10, 15, 17, 20, 25 or 30 contiguous nucleotides of Seq ID Nos 1, 4 or 29 are provided. Further provided are nucleotide sequences that hybridize, optionally under stringent conditions, to Seq ID Nos 1, 4 or 29, as well as, nucleotides homologous thereto.

In one embodiment, an isolated nucleotide sequence encoding porcine heavy chain is provided that includes at least one variable region, two diversity regions, at least four joining regions and at least one constant region, such as the mu constant region, for example, as represented in Seq ID No. 29. In Seq ID No. 29, the Diversity region of heavy chain is represented, for example, by residues 1089-1099 (D(psuedo)), the Joining region of heavy chain is represented, for example, by residues 1887-3352 (for example: J(psuedo): 1887-1931, J(psuedo): 2364-2411, J(psuedo): 2756-2804, J (functional J): 3296-3352), the recombination signals are represented, for example, by residues 3001-3261 (Nonamer), 3292-3298 (Heptamer), the Constant Region is represented by the following residues: 3353-9070 (J to C mu intron), 5522-8700 (Switch region), 9071-9388 (Mu Exon 1), 9389-9469 (Mu Intron A), 9470-9802 (Mu Exon 2), 9830-10069 (Mu Intron B), 10070-10387 (Mu Exon 3), 10388-10517 (Mu Intron C), 10815-11052 (Mu Exon 4), 11034-11039 (Poly(A) signal).

Seq ID No. 29
tctagaagacgctggagagaggccagacttcctcggaacagctcaaagag
ctctgtcaaagccagatcccatcacacgtgggcaccaataggccatgcca
gcctccaagggccgaactgggttctccacggcgcacatgaagcctgcagc
ctggcttatcctcttccgtggtgaagaggcaggcccgggactggacgagg
ggctagcagggtgtggtaggcaccttgcgcccccaccccggcaggaacc
agagaccctggggctgagagtgagcctccaaacaggatgccccacccttc
aggccacctttcaatccagctacactccacctgccattctcctctgggca
cagggcccagccctggatcttggccttggctcgacttgcacccacgcgc
acacacacacttcctaacgtgctgtccgctcaccccctcccagcgtggtc
catgggcagcacggcagtgcgcgtccggcggtagtgagtgcagaggtccc
ttcccctcccccaggagcccagggGtgtgtgcagatctgggggctcctg
tcccttacaccttcatgcccctcccctcataccccaccctccaggcgggag
gcagcgagacctttgcccagggactcagccaacgggcacacgggaggcca
gccctcagcagctggctcccaaagaggaggtggggaggtaggtccacagct
gccacagagagaaaccctgacggacccacaggggccacgccagccgaa
ccagctccctcgtgggtgagcaatggccaggccccgccggccaccacgg
ctggccttcgcgccagctgagaactcacgtccagtgcagggagactcaaga
cagcctgtgcacacagcctcggatctgctcccatttcaagcagaaaagg
aaaccgtgcaggcagccctcagcatttcaaggattgtagcagcggccaac
tattcgtcggcagtggccgattagaatgaccgtggagaagggcggaaggg
tctctcgtgggctctgcggccaacaggccctggctccacctgcccgctgc
cagcccgagggcttgggccgagccaggaaccacagtgctcaccgggacc
acagtgactgaccaaactcccggccagagcagccccaggccagccgggct
ctcgccctggaggactcaccatcagatgcacaaggggcgagtgtggaag
agacgtgtcgcccgggccatttggaaggcgaagggaccttccaggtgga
caggaggtgggacgcactccaggcaagggactgggtcccaaggcctggg
gaaggggtactggcttgggggttagcctggccagggaacggggagcggg
cggggggctgagcagggaggacctgacctcgtgggagcgaggcaagtcag -continued
gcttcaggcagcagccgcacatcccagaccaggaggctgaggcaggaggg
gcttgcagcggggcggggcctgcctggctccgggggctcctggggacg
ctggctcttgtttccgtgtcccgcagcacagggccagctcgctgggccta
tgcttaccttgatgtctggggccggggcgtcagggtcgtcgtctcctcag
gggagagtcccctgaggctacgctgggg*ggggactatggcagctccacc
aggggcctggggaccaggggcctggaccaggctgcagcccggaggacggg
cagggctctggctctccagcatctggccctcggaaatggcagaaccctg
gcgggtgagcgagctgagagcgggtcagacagacaggggccggccggaaa
ggagaagttgggggcagagcccgccaggggccaggcccaaggttctgtgt
gccagggcctgggtgggcacattggtgtggccatggctacttagattcgt
ggggccagggcatcctggtcaccgtctcctcaggtgagcctggtgtctga
tgtccagctaggcgctggtgggccgcgggtgggcctgtctcaggctaggg
caggggctgggatgtgtatttgtcaaggaggggcaacagggtgcagactg
tgccctggaaacttgaccactgggcagggcgtcctggtcacgtctcc
tcaggtaagacggccctgtgcccctctctcgcgggactggaaaaggaatt
ttccaagattccttggtctgtgtggggccctctggggccccgggggtgg
ctcccctcctgcccagatgggcctcggcctgtggagcacgggctgggca
cacagctcgagtctagggccacagaggcccgggctcagggctctgtgtgg
cccggcgactggcagggggctcgggttttggacacccctaatgggggc
cacagcactgtgaccatcttcacagctggggccgaggagtcgaggtcacc
gtctcctcaggtgagtcctcgtcagccctctctcactctctgggggttt
tgctgcattttgtggggaaagaggatgcctgggtctcaggtctaaaggt
ctagggccagcgccggggcccaggaaggggccgaggggccaggctcggct
cggccaggagcagagcttccagacatctcgcctcctggcggctgcagtca
ggcctttggccgggggggtctcagcaccaccaggcctcttggctcccgag
gtccccggccccggctgcctcaccaggcaccgtgcgcggtgggcccggc
tcttggtcggccacccttctaactgggatccgggcttagttgtcgcaa
tgtgacaacgggctcgaaagctggggccaggggaccctagtctacgacgc
ctcgggtggtgtcccgcacccctccccactttcacggcactcggcgaga
cctggggagtcaggtgttggggacactttggaggtcaggaacgggagctg
gggagagggctctgtcagcgggtccagagatgggccgccctccaaggac
gccctgcgcggggacaagggcttcttggcctggcctggccgcttcacttg
ggcgtcagggggggcttcccggggcaggcggtcagtcgaggcgggttgga
attctgagtctgggttcggggttcggggttcggccttcatgaacagacag
cccaggcgggcgttgtttggcccctgggggcctggttggaatgcgaggt
ctcgggaagtcaggaggagcctggccagcagagggttcccagccctgcg
gccgagggacctggagacgggcagggcattggccgtcgcagggccaggcc
acacccccaGGTTTTTGTggggcgagcctggagattgcacCACTGTGAT
TACTATGCTATGGATCTCTGGGGCCCAGGCGTTGAAGTCGTCGTGTCCTC
AGgtaagaacggccctccagggcctttaatttctgctctcgtctgtgggc -continued

```
ttttctgactctgatcctcgggaggcgtctgtgcccccccgggggatgag
gccggcttgccaggaggggtcagggaccaggagcctgtgggaagttctga
cgggggctgcaggcgggaagggccccaccgggggggcgagcccaggccgc
tgggcggcaggagaccgtgagagtgcgccttgaggagggtgtctgcgga
accacgaacgcccgccgggaagggcttgctgcaatgcggtcttcagacgg
gaggcgtcttctgccctcaccgtctttcaagcccttgtgggtctgaaaga
gccatgtcggagagagaagggacaggcctgtcccgacctggccgagagcg
ggcagcccggggggagagcggggcgatcggcctgggctctgtgaggccag
gtccaagggaggacgtgtggtcctcgtgacaggtgcacttgcgaaacctt
agaagacggggtatgttggaagcggctcctgatgtttaagaaaagggaga
ctgtaaagtgagcagagtcctcaagtgtgttaaggttttaaaggtcaaag
tgttttaaacctttgtgactgcagttagcaagcgtgcggggagtgaatgg
ggtgccagggtggccgagaggcagtacgagggccgtgccgtcctctaatt
cagggcttagttttgcagaataaagtcggcctgttttctaaaagcattgg
tggtgctgagctggtggaggaggccgcgggcagccctggccacctgcagc
aggtggcaggaagcaggtcggccaagaggctattttaggaagccagaaaa
cacggtcgatgaatttatagcttctggtttccaggaggtggttgggcatg
gctttgcgcagcgccacagaaccgaaagtgcccactgagaaaaacaact
cctgcttaatttgcattttctaaaagaagaaacagaggctgacggaaac
tggaaagttcctgttttaactactcgaattgagttttcggtcttagctta
tcaactgctcacttagattcattttcaaagtaaacgtttaagagccgagg
cattcctatcctcttctaaggcgttattcctggaggctcattcaccgcca
gcacctccgctgcctgcaggcattgctgtcaccgtcaccgtgacggcgcg
cacgattttcagttggcccgcttccctcgtgattaggacagacgcgggc
actctgcccagccgtcttggctcagtatctgcaggcgtccgtctcggga
cggagctcaggggaagagcgtgactccagttgaacgtgatagtcggtgcg
ttgagaggagacccagtcgggtgtcgagtcagaaggggcccggggcccga
ggccctgggcaggacggcccgtgccctgcatcacgggcccagcgtcctag
aggcaggactctggtggagagtgtgagggtgcctggggcccctccggagc
tggggccgtgcggtgcaggttgggctctcggcgcggtgttggctgtttct
gcgggatttggaggaattcttccagtgatgggagtcgccagtgaccggc
accaggctggtaagagggaggccgccgtcgtggccagagcagctgggagg
gttcggtaaaaggctcgcccgtttcctttaatgaggacttttcctggagg
gcatttagtctagtcgggaccgttttcgactcgggaagagggatgcgag
gagggcatgtgcccaggagccgaaggcgccgcggggagaagcccagggct
ctcctgtccccacagaggcgacgccactgccgcagacagacagggccttt
ccctctgatgacggcaaaggcgcctcggctcttgcggggtgctgggggg
agtcgccccgaagccgctcacccagaggcctgaggggtgagactgaccga
tgcctcttggccgggcctggggccggaccgagggggactccgtggaggca
gggcgatggtggctgcgggagggaaccgaccctgggccgagcccggcttg
gcgattcccgggcgagggcccctcagccgaggcgagtgggtccggcggaac
```

```
cacccttctggccagcgccacagggctctcgggactgtccggggcgacg
ctgggctgcccgtggcaggccTGGGCTGACCTGGACTTCACCAGACAGAA
CAGGGCTTTCAGGGCTGAGCTGAGCCAGGTTTAGCGAGGCCAAGTGGGC
TGAACCAGGCTCAACTGGCCTGAGCTGGGTTGAGCTGGGCTGACCTGGC
TGAGCTGAGCTGGGCTGGGCTGGGCTGGGCTGGGCTGGGCTGGGCTGGAC
TGGCTGAGCTGAGCTGGGTTGAGCTGAGCTGAGCTGGCCTGGGTTGAGCT
GGGCTGGGTTGAGCTGAGCTGGGTTGAGCTGGGTTGAGCTGGGTTGATCT
GAGCTGAGCTGGGCTGAGCTGAGCTAGGCTGGGGTGAGCTGGGCTGAGCT
GGTTTGAGTTGGGTTGAGCTGAGCTGAGCTGGGCTGTGCTGGCTGAGCTA
GGCTGAGCTAGGCTAGGTTGAGCTGGGCTGGGCTGAGCTGAGCTAGGCTG
GGCTGATTTGGGCTGAGCTGAGCTGAGCTAGGCTGCGTTGAGCTGGCTGG
GCTGGATTGAGCTGGCTGAGCTGGCTGAGCTGGGCTGAGCTGGCCTGGGT
TGAGCTGAGCTGGACTGGTTTGAGCTGGGTCGATCTGGGTTGAGCTGTCC
TGGGTTGAGCTGGGCTGGGTTGAGCTGAGCTGGGTTGAGCTGGGCTCAGC
AGAGCTGGGTTGGGCTGAGCTGGGTTGAGCTGAGCTGGGCTGAGCTGGCC
TGGGTTGAGCTGGGCTGAGCTGAGCTGGGCTGAGCTGGCCTGTGTTGAGC
TGGGCTGGGTTGAGCTGGGCTGAGCTGGATTGAGCTGGGTTGAGCTGAGC
TGGGCTGGGCTGTGCTGACTGAGCTGGGCTGAGCTAGGCTGGGGTGAGCT
GGGCTGAGCTGATCCGAGCTAGGCTGGGCTGGTTTGGGCTGAGCTGAGCT
GAGCTAGGCTGGATTGATCTGGCTGAGCTGGGTTGAGCTGAGCTGGGCTG
AGCTGGTCTGAGCTGGCCTGGGTCGAGCTGAGCTGGACTGGTTTGAGCTG
GGTCGATCTGGGCTGAGCTGGCCTGGGTTGAGCTGGGCTGGGTTGAGCTG
AGCTGGGTTGAGCTGGGCTGAGCTGAGGGCTGGGGTGAGCTGGGCTGAAC
TAGCCTAGCTAGGTTGGGCTGAGCTGGGCTGGTTTGGGCTGAGCTGAGCT
GAGCTAGGCTGCATTGAGCAGGCTGAGCTGGGCTGAGCAGGCCTGGGGTG
AGCTGGGCTAGGTGGAGCTGAGCTGGGTCGAGCTGAGTTGGGCTGAGCTG
GCCTGGGTTGAGGTAGGCTGAGCTGAGCTGAGCTAGGCTGGGTTGAGCTG
GCTGGGCTGGTTTGCGCTGGGTCAAGCTGGGCCGAGCTGGCCTGGGTTGA
GCTGGGCTCGGTTGAGCTGGGCTGAGCTGAGCCGACCTAGGCTGGGATGA
GCTGGGCTGATTTGGGCTGAGCTGAGCTGAGCTAGGCTGCATTGAGCAGG
CTGAGCTGGGCCTGGAGCCTGGCCTGGGGTGAGCTGGGCTGAGCTGCGCT
GAGCTAGGCTGGGTTGAGCTGGCTGGGCTGGTTTGCGCTGGGTCAAGCTG
GGCCGAGCTGGCCTGGGATGAGCTGGGCCGGTTTGGGCTGAGCTGAGCTG
AGCTAGGCTGCATTGAGCAGGCTGAGCTGGGCTGAGCTGGCCTGGGGTGA
GCTGGGCTGAGCTAAGCTGAGCTGGGCTGGTTTGGGCTGAGCTGGCTGAG
CTGGGTCCTGCTGAGCTGGGCTGAGCTGACCAGGGGTGAGCTGGGCTGAG
TTAGGCTGGGCTCAGCTAGGCTGGGTTGATCTGGCAGGGCTGGTTTGCGC
TGGGTCAAGCTCCCGGGAGATGGCCTGGGATGAGCTGGGCTGGTTTGGGC
TGAGCTGAGCTGAGCTGAGCTAGGCTGCATTGAGCAGGCTGAGCTGGGCT
GAGCTGGCCTGGGGTGAGCTGGGCTGGGTGGAGCTGAGCTGGGCTGAACT
```

-continued

```
GGGCTAAGCTGGCTGAGCTGGATCGAGCTGAGCTGGGCTGAGCTGGCCTG
GGGTTAGCTGGGCTGAGCTGAGCTGAGCTAGGCTGGGTTGAGCTGGCTGG
GCTGGTTTGCGCTGGGTCAAGCTGGGCCGAGCTGGCCTGGGTTGAGCTGG
GCTGGGCTGAGCTGAGCTAGGCTGGGTTGAGCTGGGCTGGGCTGAGCTGA
GCTAGGCTGCATTGAGCTGGCTGGGATGGATTGAGCTGGCTGAGCTGGCT
GAGCTGGCTGAGCTGGGCTGAGCTGGCCTGGGTTGAGCTGGGCTGGGTTG
AGCTGAGCTGGGCTGAGCTGGGCTCAGCAGAGCTGGGTTGAGCTGAGCTG
GGTTGAGCTGGGGTGAGCTGGGCTGAGCAGAGCTGGGTTGAGCTGAGCTG
GGTTGAGCTGGGCTCGAGCAGAGCTGGGTTGAGCTGAGCTGGGTTGAGCT
GGGCTCAGCAGAGCTGGGTTGAGCTGAGCTGGGTTGAGCTGGGCTGAGCT
AGCTGGGCTCAGCTAGGCTGGGTTGAGCTGAGCTGGGCTGAACTGGGCTG
AGCTGGGCTGAACTGGGCTGAGCTGGGCTGAGCTGGGCTGAGCAGAGCTG
GGCTGAGCAGAGCTGGGTTGGTCTGAGCTGGGTTGAGCTGGGCTGAGCTG
GGCTGAGCAGAGTTGGGTTGAGCTGAGCTGGGTTCAGCTGGGCTGAGCTA
GGCTGGGTTGAGCTGGGTTGAGTTGGGCTGAGCTGGGCTGGGTTGAGCGG
AGCTGGGCTGAACTGGGCTGAGCTGGGCTGAGCGGAACTGGGTTGATCTG
AATTGAGCTGGGCTGAGCCGGGCTGAGCCGGGCTGAGCTGGGCTAGGTTG
AGCTTGGGTGAGCTTGCCTCAGCTGGTCTGAGCTAGGTTGGGTGGAGCTA
GGCTGGATTGAGCTGGGCTGAGCTGAGCTGATCTGGCCTCAGCTGGGCTG
AGGTAGGCTGAACTGGGCTGTGCTGGGCTGAGCTGAGCTGAGCCAGTTTG
AGCTGGGTTGAGCTGGGCTGAGCTGGGCTGTGTTGATCTTTCCTGAACTG
GGCTGAGCTGGGCTGAGCTGGCCTAGCTGGATTGAACGGGGGTAAGCTGG
GCCAGGCTGGACTGGGCTGAGCTGAGCTAGGCTGAGCTGAGTTGAATTGG
GTTAAGCTGGGCTGAGATGGGCTGAGCTGGGCTGAGCTGGGTTGAGCCAG
GTCGGACTGGGTTACCCTGGGCCACACTGGGCTGAGCTGGGCGGAGCTCG
attaacctggtcaggctgagtcgggtccagcagacatgcgctggccaggc
tggcttgacctggacacgttcgatgagctgccttgggatggttcacctca
gctgagccaggtggctccagctgggctgagctggtgaccctgggtgacct
cggtgaccaggttgtcctgagtccgggccaagccgaggctgcatcagact
cgccagacccaaggcctgggccccggctggcaagccaggggcggtgaagg
ctgggctggcaggactgtcccggaaggaggtgcacgtggagccgcccgga
ccccgaccggcaggacctggaaagacgcctctcactcccctttctcttct
gtccctctcgggtcctcagAGAGCCAGTCTGCCCCGAATCTCTACCCCC
TCGTCTCCTGCGTCAGCCCCCCGTCCGATGAGAGCCTGGTGGCCCTGGGC
TGCCTGGCCCGGGACTTCCTGCCCAGCTCCGTCACCTTCTCCTGGAACTA
CAAGAACAGCAGCAAGGTCAGCAGCCAGAACATCCAGGACTTCCCGTCCG
TCCTGAGAGGCGGCAAGTACTTGGCCTCCTCCCGGGTGCTCCTACCCTCT
GTGAGCATCCCCCAGGACCCAGAGGCCTTCCTGGTGTGCGAGGTCCAGCA
CCCCAGTGGCACCAAGTCCGTGTCCATCTCTGGGCCAGgtgagctgggct
cccccctgtggctgtggcggggcggggccgggtgccgccggcacagtg
acgccccgttcctgcctgcagTCGTAGAGGAGCAGCC
```

```
CCCCGTCTTGAACATCTTCGTCCCCACCCGGGAGTCCTTCTCCAG
TACTCCCCAGCGCACGTCCAAGCTCATCTGCCAGGCCTCAGACTTC
AGCCCCAAGCAGATCTCCATGGCCTGGTTCCGTGATGGGAAACGGGTGGT
GTCTGGCGTCAGCACAGGCCCCGTGGAGACCCTACAGTCCAGTCCGGTGA
CCTACAGGCTCCACAGCATGCTGACCGTCACGGAGTCCGAGTGGCTCAGC
CAGAGCGTCTTCACCTGCCAGGTGGAGCACAAAGGGCTGAACTACGAGA
AGAACGCGTCCTCTCTGTGCACCTCCAgtgagtgcagcccctcgggcc
gggcggcggggcggcgggagccacacacacaccagctgctccc
tgagccttggcttccgggagtggccaaggcggggaggggctgtgc
agggcagctggagggcactgtcagctggggcccagcacccctc
accccggcagggcccgggctccgaggggccccgcagtcgcaggcc
ctgctcttgggggaagccctacttggccccttcagggcgctgacgctccc
cccacccaccccgcctagATCCCAACTCTCCCATCACCGTCTTCGCCAT
CGCCCCCTCCTTCGCTGGCATCTTCCTCACCAAGTCGGCCAAGCTTTCCT
GCCTGGTCACGGGCCTCGTCACCAGGGAGAGCCTCAACATCTCCTGGACC
CGCCAGGACGGCGAGGTTCTGAAGACCAGTATCGTCTTCTCTGAGATCTA
CGCCAACGGCACCTTCGGCGCCAGGGGCGAAGCCTCCGTCTGCGTGGAGG
ACTGGGAGTCGGGCGACAGGTTCACGTGCACGGTGACCCACACGGACCTG
CCCTCGCCGCTGAAGCAGAGCGTCTCCAAGCCCAGAGgtaggccctgccc
tgccctgcctccgccggcctgtgccttggccgccggggcgggagccga
gcctggccgaggagcgccctcggcccccgcggtcccgacccacacccct
cctgctctcctccccagGGATCGCCAGGCACATGCCGTCCGTGTACGTGC
TGCCGCCGCCCCGGAGGAGCTGAGCCTGCAGGAGTGGGCCTCGGTCACC
TGCCTGGTGAAGGGCTTCTCCCCGGCGGACGTGTTCGTGCAGTGGCTGCA
GAAGGGGGAGCCCGTGTCCGCCGACAAGTACGTGACCAGCGCGCCGGTG
CCCGAGCCCGAGCCCAAGGCCCCCGCCTCCTACTTCGTGCAGAGCGTCCT
GACGGTGAGCGCCAAGGACTGGAGCGACGGGGAGACCTACACCTGCGTC
GTGGGCCACGAGGCCCTGCCCCACACGGTGACCGAGAGGACCGTGGACAA
GTCCACCGGTAAACCCACCCTGTACAACGTCTCCCTGGTCCTGTCCGACA
CGGCCAGCACCTGCTACTGACCCCCTGGCTGCCCGCCGCGGCCGGGGCCA
GAGCCCCGGGCGACCATCGCTCTGTGTGGGCCTGTGTGCAACCCGACCC
TGTCGGGGTGAGCGGTCGCATTTCTGAAAATTAGAaataaaAGATCTCGT
GCCG
```

Seq ID No. 1
```
TCTAgAAGACGCTGGAGAGAGGCCagACTTCCTCGGAACAGCTCAAAGAG
CTCTGTCAAAGCCAGATCCCATCACACGTGGGCACCAATAGGCCATGCCA
GCCTCCAAGGGCCGAACTGGGTTCTCCACGGCGCACATGAAGCCTGCAGC
CTGGCTTATCCTCTTCCGTGGTGAAGAGGCAGGCCCGGGACTGGACGAGG
GGCTAGCAGGGTGTGGTAGGCACCTTGCGCCCCCCACCCCGGCAGGAACC
AGAGACCCTGGGGCTGAGAGTGAGCCTCCAAACAGGATGCCCCACCCTTC
AGGCCACCTTTCAATCCAGCTACACTCCACCTGCCATTCTCCTCTGGGCA
```

-continued

CAGGGCCCAGCCCCTGGATCTTGGCCTTGGCTCGACTTGCACCCACGCGC

ACACACACACTTCCTAACGTGCTGTCCGCTCACCCCTCCCCAGCGTGGTC

CATGGGCAGCACGGCAGTGCGCGTCCGGCGGTAGTGAGTGCAGAGGTCCC

TTCCCCTCCCCAGGAGCCCCAGGGGTGTGTGCAGATCTGGGGGCTCCTG

TCCCTTACACCTTCATGCCCCTCCCCTCATACCCACCCTCCAGGCGGGAG

GCAGCGAGACCTTTGCCCAGGGACTCAGCCAACGGGCACACGGGAGGCC

AGCCCTCAGCAGCTGGG

Seq ID No. 4
GGCCAGACTTCCTCGGAACAGCTCAAAGAGCTCTGTCAAAGCCAGATCCC

ATCACACGTGGGCACCAATAGGCCATGCCAGCCTCCAAGGGCCGAACTGG

GTTCTCCACGGCGCACATGAAGCCTGCAGCCTGGCTTATCCTCTTCCGTG

GTGAAGAGGCAGGCCCGGGACTGGACGAGGGGCTAGCAGGGTGTGGTAGG

CACCTTGCGCCCCCACCCCGGCAGGAACCAGAGACCCTGGGGCTGAGAG

TGAGCCTCCAAACAGGATGCCCCACCCTTCAGGCCACCTTTCAATCCAGC

TACACTCCACCTGCCATTCTCCTCTGGGCACAGGGCCCAGCCCCTGGATC

TTGGCCTTGGCTCGACTTGCACCCACGCGCACACACACTTCCTAACGT

GCTGTCCGCTCACCCCTCCCCAGCGTGGTCCATGGGCAGCACGGCAGTGC

GCGTCCGGCGGTAGTGAGTGCAGAGGTCCCTTCCCCTCCCCAGGAGCCC

CAGGGGTGTGTGCAGATCTGGGGGCTCCTGTCCCTTACACCTTCATGCCC

CTCCCCTCATACCCACCCTCCAGGCGGGAGGCAGCGAGACCTTTGCCCAG

GGACTCAGCCAACGGGCACACGGGAGGCCAGCCCTCAGCAGCTGGCTCCC

AAAGAGGAGGTGGGAGGTAGGTCCACAGCTGCCACAGAGAGAAACCCTGA

CGGACCCCACAGGGGCCACGCCAGCCGGAACCAGCTCCCTCGTGGGTGAG

CAATGGCCAGGGCCCCGCCGGCCACCACGGCTGGCCTTGCGCCAGCTGAG

AACTCACGTCCAGTGCAGGGAGACTCAAGACAGCCTGTGCACACAGCCTC

GGATCTGCTCCCATTTCAAGCAGAAAAAGGAAACCGTGCAGGCAGCCCTC

AGCATTTCAAGGATTGTAGCAGCGGCCAACTATTCGTCGGCAGTGGCCGA

TTAGAATGACCGTGGAGAAGGGCGGAAGGGTCTCTCGTGGGCTCTGCGGC

CAACAGGCCCTGGCTCCACCTGCCCGCTGCCAGCCCGAGGGGCTTGGGCC

GAGCCAGGAACCACAGTGCTCACCGGGACCACAGTGACTGACCAAACTCC

CGGCCAGAGCAGCCCCAGGCCAGCCGGGCTCTCGCCCTGGAGGACTCACC

ATCAGATGCACAAGGGGCGAGTGTGGAAGAGACGTGTCGCCCGGGCCAT

TTGGGAAGGCGAAGGGACCTTCCAGGTGGACAGGAGGTGGGACGCACTCC

AGGCAAGGGACTGGGTCCCCAAGGCCTGGGGAAGGGGTACTGGCTTGGGG

GTTAGCCTGGCCAGGGAACGGGGAGCGGGGCGGGGGCTGAGCAGGGAGG

ACCTGACCTCGTGGGAGCGAGGCAAGTCAGGCTTCAGGCAGCAGCCGCAC

ATCCCAGACCAGGAGGCTGAGGCAGGAGGGGCTTGCAGCGGGGCGGGGC

CTGCCTGGCTCCGGGGCTCCTGGGGGACGCTGGCTCTTGTTTCCGTGTC

CCGCAGCACAGGGCCAGCTCGCTGGGCCTATGCTTACCTTGATGTCTGGG

GCCGGGGCGTCAGGGTCGTCGTCTCCTCAGGGGAGAGTCCCCTGAGGCTA

CGCTGGGG*GGGGACTATGGCAGCTCCACCAGGGGCCTGGGGACCAGGGG

CCTGGACCAGGCTGCAGCCCGGAGGACGGGCAGGGCTCTGGCTCTCCAGC

ATCTGGCCCTCGGAAATGGCAGAACCCCTGGCGGGTGAGCGAGCTGAGAG

CGGGTCAGACAGACAGGGGCCGGCCGGAAAGGAGAAGTTGGGGGCAGAGC

CCGCCAGGGGCCAGGCCCAAGGTTCTGTGTGCCAGGGCCTGGGTGGGCAC

ATTGGTGTGGCCATGGCTACTTAGATTCGTGGGGCCAGGGCATCCTGGTC

ACCGTCTCCTCAGGTGAGCCTGGTGTCTGATGTCCAGCTAGGCGCTGGTG

GGCCGCGGGTGGGCCTGTCTCAGGCTAGGGCAGGGCTGGGATGTGTATT

TGTCAAGGAGGGGCAACAGGGTGCAGACTGTGCCCCTGGAAACTTGACCA

CTGGGGCAGGGGCGTCCTGGTCACGTCTCCTCAGGTAAGACGGCCCTGTG

CCCCTCTCTCGCGGGACTGGAAAAGGAATTTTCCAAGATTCCTTGGTCTG

TGTGGGGCCCTCTGGGGCCCCGGGGGTGGCTCCCCTCCTGCCCAGATGG

GGCCTCGGCCTGTGGAGCACGGGCTGGGCACACAGCTCGAGTCTAGGGCC

ACAGAGGCCCGGGCTCAGGGCTCTGTGTGGCCCGGCGACTGGCAGGGGGC

TCGGGTTTTTGGACACCCCCTAATGGGGGCCACAGCACTGTGACCATCTT

CACAGCTGGGGCCGAGGAGTCGAGGTCACCGTCTCCTCAGGTGAGTCCTC

GTCAGCCCTCTCTCACTCTCTGGGGGTTTTGCTGCATTTTGTGGGGGAA

AGAGGATGCCTGGGTCTCAGGTCTAAAGGTCTAGGGCCAGCGCCGGGGCC

CAGGAAGGGGCCGAGGGGCCAGGCTCGGCTCGGCCAGGAGCAGAGCTTCC

AGACATCTCGCCTCCTGGCGGCTGCAGTCAGGCCTTTGGCCGGGGGGGTC

TCAGCACCACCAGGCCTCTTGGCTCCCGAGGTCCCCGGCCCCGGCTGCCT

CACCAGGCACCGTGCGCGGTGGGCCCGGGCTCTTGGTCGGCCACCCTTTC

TTAACTGGGATCCGGGCTTAGTTGTCGCAATGTGACAACGGGCTCGAAAG

CTGGGGCCAGGGGACCCTAGT*TACGACGCCTCGGGTGGGTGTCCCGCAC

CCCTCCCCACTTTCACGGCACTCGGCGAGACCTGGGGAGTCAGGTGTTGG

GGACACTTTGGAGGTCAGGAACGGGAGCTGGGGAGAGGGCTCTGTCAGCG

GGGTCCAGAGATGGGCCGCCCTCCAAGGACGCCCTGCGCGGGGACAAGGG

CTTCTTGGCCTGGCCTGGCCGCTTCACTTGGGCGTCAGGGGGGGCTTCCC

GGGGCAGGCGGTCAGTCGAGGCGGGTTGGAATTCTGAGTCTGGGTTCGGG

GTTCGGGGTTCGGCCTTCATGAACAGACAGCCCAGGCGGGCCGTTGTTTG

GCCCCTGGGGGCCTGGTTGGAATGCGAGGTCTCGGGAAGTCAGGAGGGAG

CCTGGCCAGCAGAGGGTTCCCAGCCCTGCGGCCGAGGGACCTGGAGACGG

GCAGGGCATTGGCCGTCGCAGGGCCAGGCCACACCCCCCAGGTTTTTGTG

GGGCGAGCCTGGAGATTGCACCACTGTGATTACTATGCTATGGATCTCTG

GGGCCCAGGCGTTGAAGTCGTCGTGTCCTCAGGTAAGAACGGCCCTCCAG

GGCCTTTAATTTCTGCTCTCGTCTGTGGGCTTTTCTGACTCTGATCCTCG

GGAGGCGTCTGTGCCCCCCCCGGGGATGAGGCCGGCTTGCCAGGAGGGGT

CAGGGACCAGGAGCCTGTGGGAAGTTCTGACGGGGGCTGCAGGCGGGAAG

GGCCCCACCGGGGGCGAGCCCCAGGCCGCTGGGCGGCAGGAGACCCGTG

AGAGTGCGCCTTGAGGAGGGTGTCTGCGGAACCACGAACGCCCGCCGGGA

AGGGCTTGCTGCAATGCGGTCTTCAGACGGGAGGCGTCTTCTGCCCTCAC

CGTCTTTCAAGCCCTTGTGGGTCTGAAAGAGCCATGTCGGAGAGAGAAGG
GACAGGCCTGTCCCGACCTGGCCGAGAGCGGGCAGCCCCGGGGGAGAGCG
GGGCGATCGGCCTGGGCTCTGTGAGGCCAGGTCCAAGGGAGGACGTGTGG
TCCTCGTGACAGGTGCACTTGCGAAACCTTAGAAGACGGGGTATGTTGGA
AGCGGCTCCTGATGTTTAAGAAAAGGGAGACTGTAAAGTGAGCAGAGTCC
TCAAGTGTGTTAAGGTTTTAAAGGTCAAAGTGTTTTAAACCTTTGTGACT
GCAGTTAGCAAGCGTGCGGGGAGTGAATGGGGTGCCAGGGTGGCCGAGAG
GCAGTACGAGGGCCGTGCCGTCCTCTAATTCAGGGCTTAGTTTTGCAGAA
TAAAGTCGGCCTGTTTTCTAAAAGCATTGGTGGTGCTGAGCTGGTGGAGG
AGGCCGCGGGCAGCCCTGGCCACCTGCAGCAGGTGGCAGGAAGCAGGTCG
GCCAAGAGGCTATTTTAGGAAGCCAGAAAACACGGTCGATGAATTTATAG
CTTCTGGTTTCCAGGAGGTGGTTGGGCATGGCTTTGCGCAGCGCCACAGA
ACCGAAAGTGCCCACTGAGAAAAAACAACTCCTGCTTAATTTGCATTTTT
CTAAAAGAAGAAACAGAGGCTGACGGAAACTGGAAAGTTCCTGTTTTAAC
TACTCGAATTGAGTTTTCGGTCTTAGCTTATCAACTGCTCACTTAGATTC
ATTTTCAAAGTAAACGTTTAAGAGCCGAGGCATTCCTATCCTCTTCTAAG
GCGTTATTCCTGGAGGCTCATTCACCGCCAGCACCTCCGCTGCCTGCAGG
CATTGCTGTCACCGTCACCGTGACGGCGCGCACGATTTTCAGTTGGCCCG
CTTCCCCTCGTGATTAGGACAGACGCGGGCACTCTGGCCCAGCCGTCTTG
GCTCAGTATCTGCAGGCGTCCGTCTCGGGACGGAGCTCAGGGGAAGAGCG
TGACTCCAGTTGAACGTGATAGTCGGTGCGTTGAGAGGAGACCCAGTCGG
GTGTCGAGTCAGAAGGGGCCCGGGGCCCGAGGCCCTGGGCAGGACGGCCC
GTGCCCTGCATCACGGGCCCAGCGTCCTAGAGGCAGGACTCTGGTGGAGA
GTGTGAGGGTGCCTGGGCCCCTCCGGAGCTGGGGCCGTGCGGTGCAGGT
TGGGCTCTCGGCGCGGTGTTGGCTGTTTCTGCGGGATTTGGAGGAATTCT
TCCAGTGATGGGAGTCGCCAGTGACCGGGCACCAGGCTGGTAAGAGGGAG
GCCGCCGTCGTGGCCAGAGCAGCTGGGAGGGTTCGGTAAAAGGCTCGCCC
GTTTCCTTTAATGAGGACTTTTCCTGGAGGGCATTTAGTCTAGTCGGGAC
CGTTTTCGACTCGGGAAGAGGGATGCGGAGGAGGGCATGTGCCCAGGAGC
CGAAGGCGCCGCGGGGAGAAGCCCAGGGCTCTCCTGTCCCCACAGAGGCG
ACGCCACTGCCGCAGACAGACAGGGCCTTTCCCTCTGATGACGGCAAAGG
CGCCTCGGCTCTTGCGGGGTGCTGGGGGGGAGTCGCCCCGAAGCCGCTCA
CCCAGAGGCCTGAGGGGTGAGACTGACCGATGCCTCTTGGCCGGGCCTGG
GGCCGGACCGAGGGGGACTCCGTGGAGGCAGGGCGATGGTGGCTGCGGGA
GGGAACCGACCCTGGGCCGAGCCCGGCTTGGCGATTCCCGGGCGAGGGCC
CTCAGCCGAGGCGAGTGGGTCCGGCGGAACCACCCTTTCTGGCCAGCGCC
ACAGGGCTCTCGGGACTGTCCGGGGCGACGCTGGGCTGCCCGTGGCAGGC
CTGGGCTGACCTGGACTTCACCAGACAGAACAGGGCTTTCAGGGCTGAGC
TGAGCCAGGTTTAGCGAGGCCAAGTGGGGCTGAACCAGGCTCAACTGGCC
TGAGCTGGGTTGAGCTGGGCTGACCTGGGCTGAGCTGAGCTGGGCTGGGC
TGGGCTGGGCTGGGCTGGGCTGGACTGGCTGAGCTGAGCTGGGTT

GAGCTGAGCTGAGCTGGCCTGGGTTGAGCTGGGCTGGGTTGAGCTGAGCT
GGGTTGAGCTGGGTTGAGCTGGGTTGATCTGAGCTGAGCTGGGCTGAGCT
GAGCTAGGCTGGGGTGAGCTGGGCTGAGCTGGTTTGAGTTGGGTTGAGCT
GAGCTGAGCTGGGCTGTGCTGGCTGAGCTAGGCTGAGCTAGGCTAGGTTG
AGCTGGGCTGGGCTGAGCTGAGCTAGGCTGGGCTGATTTGGGCTGAGCTG
AGCTGAGCTAGGCTGCGTTGAGCTGGCTGGGCTGGATTGAGCTGGCTGAG
CTGGCTGAGCTGGGCTGAGCTGGCCTGGGTTGAGCTGAGCTGGACTGGTT
TGAGCTGGGTCGATCTGGGTTGAGCTGTCCTGGGTTGAGCTGGGCTGGGT
TGAGCTGAGCTGGGTTGAGCTGGGCTCAGCAGAGCTGGGTTGGGCTGAGC
TGGGTTGAGCTGAGCTGGGCTGAGCTGGCCTGGGTTGAGCTGGGCTGAGC
TGAGCTGGGCTGAGCTGGCCTGTGTTGAGCTGGGCTGGGTTGAGCTGGGC
TGAGCTGGATTGAGCTGGGTTGAGCTGAGCTGGGCTGGGCTGTGCTGACT
GAGCTGGGCTGAGCTAGGCTGGGGTGAGCTGGGCTGAGCTGATCCGAGCT
AGGCTGGGCTGGTTTGGGCTGAGCTGAGCTGAGCTAGGCTGGATTGATCT
GGCTGAGCTGGGTTGAGCTGAGCTGGGCTGAGCTGGTCTGAGCTGGCCTG
GGTCGAGCTGAGCTGGACTGGTTTGAGCTGGGTCGATCTGGGCTGAGCTG
GCCTGGGTTGAGCTGGGCTGGGTTGAGCTGAGCTGGGTTGAGCTGGGCTG
AGCTGAGGGCTGGGGTGAGCTGGGCTGAACTAGCCTAGCTAGGTTGGGCT
GAGCTGGGCTGGTTTGGGCTGAGCTGAGCTGAGCTAGGCTGCATTGAGCA
GGCTGAGCTGGGCTGAGCAGGCCTGGGGTGAGCTGGGCTAGGTGGAGCTG
AGCTGGGTCGAGCTGAGTTGGGCTGAGCTGGCCTGGGTTGAGGTAGGCTG
AGCTGAGCTGAGCTAGGCTGGGTTGAGCTGGCTGGGCTGGTTTGCGCTGG
GTCAAGCTGGGCCGAGCTGGCCTGGGTTGAGCTGGGCTCGGTTGAGCTGG
GCTGAGCTGAGCCGACCTAGGCTGGGATGAGCTGGGCTGATTTGGGCTGA
GCTGAGCTGAGCTAGGCTGCATTGAGCAGGCTGAGCTGGGCCTGGAGCCT
GGCCTGGGGTGAGCTGGGCTGAGCTGCGCTGAGCTAGGCTGGGTTGAGCT
GGCTGGGCTGGTTTGCGCTGGGTCAAGCTGGGCCGAGCTGGCCTGGGATG
AGCTGGGCCGGTTTGGGCTGAGCTGAGCTGAGCTAGGCTGCATTGAGCAG
GCTGAGCTGGGCTGAGCTGGCCTGGGGTGAGCTGGGCTGAGCTAAGCTGA
GCTGGGCTGGTTTGGGCTGAGCTGGCTGAGCTGGGTCCTGCTGAGCTGGG
CTGAGCTGACCAGGGGTGAGCTGGGCTGAGTTAGGCTGGGCTCAGCTAGG
CTGGGTTGATCTGGCAGGGCTGGTTTGCGCTGGGTCAAGCTCCCGGGAGA
TGGCCTGGGATGAGCTGGGCTGGTTTGGGCTGAGCTGAGCTGAGCTGAGC
TAGGCTGCATTGAGCAGGCTGAGCTGGGCTGAGCTGGCCTGGGGTGAGCT
GGGCTGGGTGGAGCTGAGCTGGGCTGAACTGGGCTAAGCTGGCTGAGCTG
GATCGAGCTGAGCTGGGCTGAGCTGGCCTGGGGTTAGCTGGGCTGAGCTG
AGCTGAGCTAGGCTGGGTTGAGCTGGCTGGGCTGGTTTGCGCTGGGTCAA
GCTGGGCCGAGCTGGCCTGGGTTGAGCTGGGCTGGGCTGAGCTGAGCTAG
GCTGGGTTGAGCTGGGCTGGGCTGAGCTGAGCTAGGCTGCATTGAGCTGG
CTGGGATGGATTGAGCTGGCTGAGCTGGCTGAGCTGGCTGAGCTGGGCTG

```
-continued
AGCTGGCCTGGGTTGAGCTGGGCTGGGTTGAGCTGAGCTGGGCTGAGCTG

GGCTCAGCAGAGCTGGGTTGAGCTGAGCTGGGTTGAGCTGGGGTGAGCTG

GGCTGAGCAGAGCTGGGTTGAGCTGAGCTGGGTTGAGCTGGGCTCGAGCA

GAGCTGGGTTGAGCTGAGCTGGGTTGAGCTGGGCTCAGCAGAGCTGGGTT

GAGCTGAGCTGGGTTGAGCTGGGCTGAGCTAGCTGGGCTCAGCTAGGCTG

GGTTGAGCTGAGCTGGGCTGAACTGGGCTGAGCTGGGCTGAACTGGGCTG

AGCTGGGCTGAGCTGGGCTGAGCAGAGCTGGGCTGAGCAGAGCTGGGTTG

GTCTGAGCTGGGTTGAGCTGGGCTGAGCTGGGCTGAGCAGAGTTGGGTTG

AGCTGAGCTGGGTTCAGCTGGGCTGAGCTAGGCTGGGTTGAGCTGGGTTG

AGTTGGGCTGAGCTGGGCTGGGTTGAGCGGAGCTGGGCTGAACTGGGCTG

AGCTGGGCTGAGCGGAACTGGGTTGATCTGAATTGAGCTGGGCTGAGCCG

GGCTGAGCCGGGCTGAGCTGGGCTAGGTTGAGCTTGGGTGAGCTTGCCTC

AGCTGGTCTGAGCTAGGTTGGGTGGAGCTAGGCTGGATTGAGCTGGGCTG

AGCTGAGCTGATCTGGCCTCAGCTGGGCTGAGGTAGGCTGAACTGGGCTG

TGCTGGGCTGAGCTGAGCTGAGCCAGTTTGAGCTGGGTTGAGCTGGGCTG

AGCTGGGCTGTGTTGATCTTTCCTGAACTGGGCTGAGCTGGGCTGAGCTG

GCCTAGCTGGATTGAACGGGGGTAAGCTGGGCCAGGCTGGACTGGGCTGA

GCTGAGCTAGGCTGAGCTGAGTTGAATTGGGTTAAGCTGGGCTGAGATGG

GCTGAGCTGGGCTGAGCTGGGTTGAGCCAGGTCGGACTGGGTTACCCTGG

GCCACACTGGGCTGAGCTGGGCGGAGCTCGATTAACCTGGTCAGGCTGAG

TCGGGTCCAGCAGACATGCGCTGGCCAGGCTGGCTTGACCTGGACACGTT

CGATGAGCTGCCTTGGGATGGTTCACCTCAGCTGAGCCAGGTGGCTCCAG

CTGGGCTGAGCTGGTGACCCTGGGTGACCTCGGTGACCAGGTTGTCCTGA

GTCCGGGCCAAGCCGAGGCTGCATCAGACTCGCCAGACCCAAGGCCTGGG

CCCCGGCTGGCAAGCCAGGGGCGGTGAAGGCTGGGCTGGCAGGACTGTCC

CGGAAGGAGGTGCACGTGGAGCCGCCCGGACCCCGACCGGCAGGACCTGG

AAAGACGCCTCTCACTCCCCTTTCTCTTCTGTCCCCTCTCGGGTCCTCAG

AGAGCCAGTCTGCCCCGAATCTCTACCCCCTCGTCTCCTGCGTCAGCCCC

CCGTCCGATGAGAGCCTGGTGGCCCTGGGCTGCCTGGCCCGGGACTTCCT

GCCCAGCTCCGTCACCTTCTCCTGGAA
```

Porcine Kappa Light Chain

In another embodiment, novel genomic sequences encoding the kappa light chain locus of ungulate immunoglobulin are provided. The present invention provides the first reported genomic sequence of ungulate kappa light chain regions. In one embodiment, nucleic acid sequence is provided that encodes the porcine kappa light chain locus. In another embodiment, the nucleic acid sequence can contain at least one joining region, one constant region and/or one enhancer region of kappa light chain. In a further embodiment, the nucleotide sequence can include at least five joining regions, one constant region and one enhancer region, for example, as represented in Seq ID No. 30. In a further embodiment, an isolated nucleotide sequence is provided that contains at least one, at least two, at least three, at least four or five joining regions and 3' flanking sequence to the joining region of porcine genomic kappa light chain, for example, as represented in Seq ID No 12. In another embodiment, an isolated nucleotide sequence of porcine genomic kappa light chain is provided that contains 5' flanking sequence to the first joining region, for example, as represented in Seq ID No. 25. In a further embodiment, an isolated nucleotide sequence is provided that contains 3' flanking sequence to the constant region and, optionally, the 5' portion of the enhancer region, of porcine genomic kappa light chain, for example, as represented in Seq ID Nos. 15, 16 and/or 19.

In further embodiments, isolated nucleotide sequences as depicted in Seq ID Nos 30, 12, 25, 15, 16 or 19 are provided. Nucleic acid sequences at least 80, 85, 90, 95, 98 or 99% homologous to Seq ID Nos 30, 12, 25, 15, 16 or 19 are also provided. In addition, nucleotide sequences that contain at least 10, 15, 17, 20, 25 or 30 contiguous nucleotides of Seq ID Nos 30, 12, 25, 15, 16 or 19 are provided. In addition, nucleotide sequences that contain at least 10, 15, 17, 20, 25 or 30 contiguous nucleotides of Seq ID Nos 1, 4 or 29 are provided. In other embodiments, nucleotide sequences that contain at least 50, 100, 1,000, 2,500, 5,000, 7,000, 8,000, 8,500, 9,000, 10,000 or 15,000 contiguous nucleotides of Seq ID No. 30 are provided. Further provided are nucleotide sequences that hybridizes, optionally under stringent conditions, to Seq ID Nos 30, 12, 25, 15, 16 or 19, as well as, nucleotides homologous thereto.

In one embodiment, an isolated nucleotide sequence encoding kappa light chain is provided that includes at least five joining regions, one constant region and one enhancer region, for example, as represented in Seq ID No. 30. In Seq ID No. 30, the coding region of kappa light chain is represented, for example by residues 1-549 and 10026-10549, whereas the intronic sequence is represented, for example, by residues 550-10025, the Joining region of kappa light chain is represented, for example, by residues 5822-7207 (for example, J1:5822-5859, J2:6180-6218, J3:6486-6523, J4:6826-6863, J5:7170-7207), the Constant Region is represented by the following residues: 10026-10549 (C exon) and 10026-10354 (C coding), 10524-10529 (Poly(A) signal) and 11160-11264 (SINE element).

```
                                                  Seq ID No 30
GCGTCCGAAGTCAAAAATATCTGCAGCCTTCATGTATTCATAGAAACAAG

GAATGTCTACATTTTCCAAAGTGGGACCAGAATCTTGGGTCATGTCTAAG

GCATGTGCATTTGCACATGGTAGGCAAAGGACTTTGCTTCTCCCAGCACA

TCTTTCTGCAGAGATCCATGGAAACAAGACTCAACTCCAAAGCAGCAAAG

AAGCAGCAAGTTCTCAAGTGATCTCCTCTGACTCCCTCCTCCCAGGCTAA

TGAAGCCATGTTGCCCCTGGGGGATTAAGGGCAGGTGTCCATTGTGGCAC

CCAGCCCGAAGACAAGCAATTTGATCAGGTTCTGAGCACTCCTGAATGTG

GACTCTGGAATTTTCTCCTCACCTTGTGGCATATCAGCTTAAGTCAAGTA

CAAGTGACAAACAACATAATCCTAAGAAGAGAGGAATCAAGCTGAAGTCA

AAGGATCACTGCCTTGGATTCTACTGTGAATGATGACCTGGAAAATATCC

TGAACAACAGCTTCAGGGTGATCATCAGAGACAAAAGTTCCAGAGCCAGg tagggaaaccctcaagccttgcaaagagcaaaatcatgccattgggttct taacctgctgagtgatttactatatgttactgtgggaggcaaagcgctca aatagcctgggtaagtatgtcaaataaaaagcaaaagtggtgtttcttga aatgttagacctgaggaaggaatattgataacttaccaataattttcaga
```

-continued

```
atgatttatagatgtgcacttagtcagtgtctctccaccccgcacctgac
aagcagtttagaatttattctaagaatctaggtttgctgggggctacatg
ggaatcagcttcagtgaagagtttgttggaatgattcactaaattttcta
tttccagcataaatccaagaacctctcagactagtttattgacactgctt
ttcctccataatccatctcatctccgtccatcatggacactttgtagaat
gacaggtcctggcagagactcacagatgcttctgaaacatcctttgcctt
caaagaatgaacagcacacatactaaggatctcagtgatccacaaattag
tttttgccacaatggttcttatgataaaagtctttcattaacagcaaatt
gttttataatagttgttctgctttataataattgcatgcttcactttctt
ttcttttcttttttttcttttttgcttttttagtgccgcaggtgcagca
tatgaaatttcccaggctaggggtcaaatcagaactacacctactggcct
acgccacagccacagcaactcaggatctaagccatgtcggtgacctacac
tacagctcatggcaatgccagatccttaacccaatgagcgaggccaggga
tcgaacccatgtcctcatggatactagtcaggctcattatccgctgagcc
ataacaggaactcccgagtttgcttttatcaaaattggtacagccttat
tgtttctgaaaaccacaaaatgaatgtattcacataattttaaaaggtta
aataatttatgatatacaagacaatagaaagagaaaacgtcattgcctct
ttcttccacgacaacacgcctccttaattgatttgaagaaataactactg
agcatggtttagtgtacttcttcagcaattagcctgtattcatagccat
acatattcaattaaaatgagatcatgatatcacacaatacataccataca
gcctatagggattttttacaatcatcttccacatgactacataaaaaccta
cctaaaaaaaaaaaaaccctacttcatcctcctattggctgctttgtgc
tccattaaaaagctctatcataattaggttatgatgaggatttccatttt
ctacctttcaagcaacatttcaatgcacagtcttatatacacatttgagc
ctactttctttttctttcttttttggttttttttttttttttttttttt
ggtcttttgtcttttctaaggctgcatatggaggttcccaggctagctg
tctaatcagaactatagctgctggcctacgccacatccacagcaatacaa
gatctgagccatgtctgcaacttacaccacagctcacagcaacggtggat
ccttaaaccactgagcaaggccagggatcaaacccataacttcatggctc
ctagttggatttgttaaccactgagccatgatggcaactcctgagcctac
ttttctaatcatttccaacctaggacacttttttaagtttcattttct
cccccaccccctgttttctgaagtgtgtttgcttccactgggtgacttc
actcccaggatctcatctgcaggatactgcagctaagtgtatgagctctg
aatttgaatcccaactctgccactcaaagggataggagtttccgatgtgg
cccaatgggatcagtggcatctctgcagtgccaggacgcaggttccatcc
ctggcccagcacagtgggttaagaatctggcattgctgcagctgaggcat
agatttcaattgtgcctcagatctgatccttggcccaaggactgcatatg
cctcagggcaaccaaaaagagaaaagggggggtgatagcattagtttcta
gatttggggggataattaaataaagtgatccatgtacaatgtatggcattt
tgtaaatgctcaacaaatttcaactattatggagttcccatcatggctca
gtggaagggaatctgattagcatccatgaggacacaggtccaaccccgac
```

-continued

```
cttgctcagtgggcattgctgtgagctgtggcatgggttacagacgaagc
tcggatctggcattgctgtggctgtggtgtaagccagcaactacagctct
cattcagcccctagcctgggaacctccatatgcctaaaagacaaaaaata
aaatttaaattaaaaataaagaaatgttaactattatgattggtactgct
tgcattactgcaaagaaagtcactttctatactctttaatatcttagttg
actgtgtgctcagtgaactattttggacacttaatttccactctcttcta
tctccaacttgacaactctcttcctctcttctggtgagatccactgctg
actttgctctttaaggcaactagaaaagtgctcagtgacaaaatcaaaga
aagttaccttaatcttcagaattacaatcttaagttctcttgtaaagctt
actatttcagtggttagtattattccttggtcccttacaacttatcagct
ctgatctattgctgattttcaactatttattgttggagttttttccttt
ttccctgttcattctgcaaatgtttgctgagcatttgtcaagtgaagata
ctggactgggccttccaaatataagacaatgaaacatcggagttctcat
tatggtgcagcagaaacgaatccaactaggaaatgtgaggttgcaggttc
gatccctgcccttgctcagtgggttaaggatccagcattaccgtgagctg
tggtgtaggttgcagacgtggctcagatcctgcgttgctgtggctgtggc
ataggctggcagctctagctctgattcgaccgctagcctgggaacctcca
tgcgccccgagtgcagcccttaaaaagcaaaaaaaaagaaagaaagaaa
aagacaatgaaacatcaaacagctaacaatccagtagggtagaaagaatc
tggcaacagataagagcgattaaatgttctaggtccagtgaccttgcctc
tgtgctctacacagtcgtgccacttgctgagggagaaggtctctcttgag
ttgagtcctgaaagacattagttgttcacaaactaatgccagtgagtgaa
ggtgtttccaagcagagggagagtttggtaaaaagctggaagtcacagaa
agactctaaagagtttaggatggtgggagcaacatacgctgagatgggc
tggaaggttaagagggaaacaactatagtaagtgaagctggactcacagc
aaagtgaggacctcagcatccttgatggggttaccatggaaacaccaagg
cacaccttgatttccaaaacagcaggcacctgattcagcccaatgtgaca
tggtgggtacccctctagctctacctgttctgtgacaactgacaaccaac
gaagttaagtctggattttctactctgctgatccttgttttgtttcaca
cgtcatctatagcttcatgccaaaatagagttcaaggtaagacgcgggcc
ttggtttgatatacatgtagtctatcttgtttgagacaatatggtggcaa
ggaagaggttcaaacaggaaaatactctctaattatgattaactgagaaa
agctaaagagtcccataatgacactgaatgaagttcatcatttgcaaaag
ccttccccccccccaggagactataaaaaagtgcaatttttttaaatgaa
cttatttacaaaacagaaatagactcacagacataggaaacgaacagatg
gttaccaagggtgaaagggagtaggagggataaataaggagtctggggtt
agcagatacaccccagtgtacacaaaataaacaacagggacctactatat
agcacagggaactatatgcagtagcttacaataacctataatggaaaaga
atgtgaaaagaatatatgtatgcgtgtgtgtgtaactgaatcacttttgc
tgtaacctgaatctaacataacattgtaaatcaactacagtttttttttt
```

-continued

```
ttttaagtgcagggttttggtgttttttttttttcattttttgtttttgtt
tttgttttttgcttttagggccacacccagacatatgggggttcccagg
ctaggggtctaattagagctacagttgccggcttgcaccacagccacagc
aacatcagatccgagccgcacttgcgacttacaccacagctcatggcaat
accagatccttaacccactgagcaagggcccagggatcgtacccgcaacct
catggttcctagtcagattcatttctgctgcgctacaatgggaactccaa
gtgcagttttttgtaatgtgcttgtctttctttgtaattcatattcatcc
tacttcccaataaataaataaatacataaataataaacataccattgtaa
atcaactacaatttttttttaaatgcagggttttgtgtttttttgttttttgt
tttgtcttttttgccttttctagggccgctcccatggcatatggaggttcc
caggctaggggtcgaatcggagctgtagccacccggcctacgccagagcca
cagcaacgcgggatccgagccgcgtctgcaacctacaccacagctcacgg
caacgccggatcgttaacccactgagcaagggcagggatcgaacctgcaa
cctcatggttcctagtcagattcgttaactactgagccacaacggaaact
cctaaagtgcagttttttaaatgtgcttgtctttctttgtaatttacactc
aacctacttcccaataaataaataaataaacaaataaatcatagacatgg
ttgaattctaaaggaagggaccatcaggccttagacagaaatacgtcatc
ttctagtattttaaaacacactaaagaagacaaacatgctctgccagaga
agcccagggcctccacagctgcttgcaaagggagttaggcttcagtagct
gacccaaggctctgttcctcttcagggaaaagggttttttgttcagtgaga
cagcagacagctgtcactgtgGTGGACGTTCGGCCAAGGAACCAAGCTGG
AACTCAAACgtaagtcaatccaaacgttccttccttggctgtctgtgtct
tacggtctctgtggctctgaaatgattcatgtgctgactctctgaaacca
gactgacattctccagggcaaaactaaagcctgtcatcaaactggaaaac
tgagggcacattttctgggcagaactaagagtcaggcactgggtgaggaa
aaacttgttagaatgatagtttcagaaacttactgggaagcaaagcccat
gttctgaacagagctctgctcaagggtcaggaggggaaccagttttttgta
caggagggaagttgagacgaaccctgtgTATATGGTTTCGGCGCGGGGA
CCAAGCTGGAGCTCAAACgtaagtggcttttttccgactgattctttgctg
tttctaattgttggttggcttttttgtccattttttcagtgttttcatcgaa
ttagttgtcagggaccaaacaaattgccttcccagattaggtaccaggga
ggggacattgctgcatgggagaccagagggtggctaattttttaacgtttc
caagccaaaataactggggaaggggggcttgctgtcctgtgagggtaggtt
tttatagaagtggaagttaaggggaaatcgctatgGTTCACTTTTGGCTC
GGGGACCAAAGTGGAGCCCAAAAttgagtacattttccatcaattatttg
tgagattttgtcctgttgtgtcatttgtgcaagttttttgacattttggt
tgaatgagccattcccagggacccaaaaggatgagaccgaaaagtagaaa
agagccaacttttaagctgagcagacagaccgaattgttgagtttgtgag
gagagtagggtttgtagggagaaaggggaacagatcgctggcttttttctc
tgaattagccttctcatgggactggcttcagaggggggttttttgatgagg
gaagtgttctagagccttaactgtgGGTTGTGTTCGGTAGCGGGACCAAG
CTGGAAATCAAACgtaagtgcacttttctactcctttttctttcttatac
gggtgtgaaattggggacttttcatgtttggagtatgagttgaggtcagt
tctgaagagagtgggactcatccaaaaatctgaggagtaagggtcagaac
agagttgtctcatggaagaacaaagacctagttagttgatgaggcagcta
aatgagtcagttgacttgggatccaaatggccagacttcgtctgtaacca
acaatctaatgagatgtagcagcaaaagagatttccattgaggggaaag
taaaattgttaatattgtgGATCACCTTTGGTGAAGGGACATCCGTGGAG
ATTGAACgtaagtatttttctctactaccttctgaaatttgtctaaatg
ccagtgttgacttttagaggcttaagtgtcagttttgtgaaaaatgggta
aacaagagcatttcatattttattcagtttcaaaagttaaactcagctc
caaaaatgaatttgtagacaaaaagattaatttaagccaaattgaatgat
tcaaaggaaaaaaaaattagtgtagatgaaaaaggaattcttacagctcc
aaagagcaaaagcgaattaattttctttgaactttgccaaatcttgtaaa
tgattttgttctttacaatttaaaaaggttagagaaatgtatttcttag
tctgttttctctcttctgtctgataaattattatatgagataaaaatgaa
aattaataggatgtgctaaaaaatcagtaagaagttagaaaaatatatgt
ttatgttaaagttgccacttaattgagaatcagaagcaatgttattttta
aagtctaaaatgagagataaactgtcaatacttaaattctgcagagattc
tatatcttgacagatatctcctttttcaaaaatccaatttctatggtaga
ctaaatttgaaatgatcttcctcataatggagggaaaagatggactgacc
ccaaaagctcagatttaaagaaatctgtttaagtgaaagaaaataaaaga
actgcattttttaaaggcccatgaatttgtagaaaaatagggaaatatttt
aataagtgtattcttttatttttcctgttattacttgatggtgttttata
ccgccaaggaggccgtggcaccgtcagtgtgatctgtagaccccatggcg
gccttttttcgcgattgaatgaccttggcggtgggtccccagggctctgg
tggcagcgcaccagccgctaaaagccgctaaaaactgccgctaaaggcca
cagcaaccccgcgaccgcccgttcaactgtgctgacacagtgatacagat
aatgtcgctaacagaggagaatagaaatatgacgggcacacgctaatgtg
ggggaaaagagggagaagcctgattttttattttttttagagattctagagata
aaattcccagtattatatccttttaataaaaaattttctattaggagatta
taaagaatttaaagctatttttttaagtggggtgtaattctttcagtagt
ctcttgtcaaatggatttaagtaatagaggcttaatccaaatgagagaaa
tagacgcataaccctttcaaggcaaaagctacaagagcaaaaattgaaca
cagcagccagccatctagccactcagattttgatcagttttactgagttt
gaagtaaatatcatgaaggtataattgctgataaaaaaataagatacagg
tgtgacacatcttttaagtttcagaaatttaatggcttcagtaggattata
tttcacgtatacaaagtatctaagcagataaaaatgccattaatggaaac
ttaatagaaatatattttttaaattccttcattctgtgacagaaattttct
aatctgggtcttttaatcacctacccttgaaagagtttagtaatttgct
atttgccatcgctgtttactccagctaatttcaaaagtgatacttgagaa
```

-continued

```
agattattttggtttgcaaccacctggcaggactattttagggccattt
taaaactcttttcaaactaagtattttaaactgttctaaaccatttaggg
ccttttaaaaatcttttcatgaatttcaaacttcgttaaaagttattaag
gtgtctggcaagaacttccttatcaaatatgctaatagtttaatctgtta
atgcaggatataaaattaaagtgatcaaggcttgacccaaacaggagtat
cttcatagcatatttccctccttttttttctagaattcatatgattttgc
tgccaaggctattttatataatctctggaaaaaaaatagtaatgaaggtt
aaaagaagaaaaatatcagaacattaagaattcggtattttactaactg
cttggttaacatgaaggttttatttttattaaggtttctatctttataaa
aatctgttccttttctgctgatttctccaagcaaaagattcttgatttg
tttttaactcttactctcccacccaagggcctgaatgcccacaaagggg
acttccaggaggccatctggcagctgctcaccgtcagaagtgaagccagc
cagtcctcctgggcaggtggccaaaattacagttgacccctcctggtct
ggctgaaccttgccccatatggtgacagccatctggccagggcccaggtc
tccctctgaagcctttgggaggagagggagagtggctggcccgatcacag
atgcggaaggggctgactcctcaaccggggtgcagactctgcagggtggg
tctgggcccaacacacccaaagcacgcccaggaaggaaaggcagcttggt
atcactgcccagagctaggagaggcaccgggaaaatgatctgtccaagac
ccgttcttgcttctaaactccgaggggtcagatgaagtggttttgtttc
ttggcctgaagcatcgtgttccctgcaagaagcggggaacacagaggaag
gagagaaaagatgaactgaacaaagcatgcaaggcaaaaaaggccttagg
atggctgcaggaagttagttcttctgcattggctccttactggctcgtcg
atcgcccacaaacaacgcacccagtggagaacttccctgttacttaaaca
ccattctctgtgcttgcttcctcagGGGCTGATGCCAAGCCATCCGTCTT
CATCTTCCCGCCATCGAAGGAGCAGTTAGCGACCCCAACTGTCTCTGTGG
TGTGCTTGATCAATAACTTCTTCCCCAGAGAAATCAGTGTCAAGTGGAAA
GTGGATGGGGTGGTCCAAAGCAGTGGTCATCCGGATAGTGTCACAGAGCA
GGACAGCAAGGACAGCACCTACAGCCTCAGCAGCACCCTCTCGCTGCCCA
CGTCACAGTACCTAAGTCATAATTTATATTCCTGTGAGGTCACCCACAAG
ACCCTGGCCTCCCCTCTGGTCACAAGCTTCAACAGGAACGAGTGTGAGGC
TtagAGGCCCACAGGCCCCTGGCCTGCCCCCAGCCCCAGCCCCCCTCCCC
ACCTCAAGCCTCAGGCCCTTGCCCCAGAGGATCCTTGGCAATCCCCCAGC
CCCTCTTCCCTCCTCATCCCCTCCCCCTCTTTGGCTTTAACCGTGTTAAT
ACTGGGGGGTGGGGGAATGAATAaataaaGTGAACCTTTGCACCTGTGAt
ttctctctcctgtctgattttaaggttgttaaatgttgttttcccccatta
tagttaatcttttaaggaactacatactgagttgctaaaaactacaccat
cacttataaaattcacgccttctcagttctccctcccctcctgtcctcc
gtaagacaggcctccgtgaaacccataagcacttctctttacaccctctc
ctgggccggggtaggagacttttttgatgtcccctcttcagcaagcctcag
aaccatttgagggggacagttcttacagtcacat*tcctgtgatctaat
gactttagttaccgaaaagccagtctctcaaaaagaagggaacggctaga
```

```
aaccaagtcatagaaatatatatgtataaaatatatatatatccatatat
gtaaaataacaaaataatgataacagcataggtcaacaggcaacagggaa
tgttgaagtccattctggcacttcaatttaagggaataggatgccttcat
tacattttaaatacaatacacatggagagcttcctatctgccaaagacca
tcctgaatgccttccacactcactacaaggttaaaagcattcattacaat
gttgatcgaggagttcccgttgtggctcagcaggttaagaacgtgactgg
tatccaggaggatgcgggtttggtcccccagcctcgctcagtggattaagg
atccagtgttgctgcaagatcacgggctcagatcccgtgttctatggcta
tggtgtaggctggtagctgcatgcagccctaatttgaccectagcctggg
aactgccatatgccacatgtgaggcccttaaaacctaaaagaaaaaaaaa
gaaagaaatatcttcacccaatttatagataagagagaagctaaggtg
gcaggcccaggatcaaagccctacctgcctatcttgacacctgatacaaa
ttctgtcttctagggtttccaacactgcatagaacagagggtcaaacatg
ctaccctcccagggactcctccttcaaatgacataaattttgttgccca
tctctgggggcaaaactcaacaatcaatggcatctctagtaccaagcaag
gctcttctcatgaagcaaaactctgaagccagatccatcatgacccaagg
aagtaaagacaggtgttactggttgaactgtatccttcaattcaatatgc
tcaatttccaactcccagtccccgtaaatacaacccccctttgggaagaga
gtccttgcagatgtagccacgttaaaaagagattatacagaaaggctagt
gaggatgcagtgaaacgggatctttcatacattgctggtggaaatgtaaa
atgctgcaggcactctagaaaataatttgccagttttttgaaaagctaaa
caaaatagtttagttgcattctgggttattatccccagaaattaaaaa
ttatgtccgcacaaaaacgtgtacataatcattcataacagccttgtac
```

Seq ID No. 12

```
caaggaaccaagctggaactcaaacgtaagtcaatccaaacgttccttcc
ttggctgtctgtgtcttacggtctctgtggctctgaaatgattcatgtgc
tgactctctgaaaccagactgacattctccagggcaaaactaaagcctgt
catcaaactggaaaactgagggcacattttctgggcagaactaagagtca
ggcactgggtgaggaaaaacttgttagaatgatagtttcagaaacttact
gggaagcaaagccatgttctgaacagagctctgctcaagggtcaggagg
ggaaccagttttttgtacaggaggggaagttgagacgaaccctgtgtatat
ggtttcggcgcggggaccaagctggagctcaaacgtaagtggcttttcc
gactgattcttgctgtttctaattgttggttggcttttgtccatttt
cagtgttttcatcgaattagttgtcagggaccaaacaaattgccttccca
gattaggtaccagggaggggacattgctgcatgggagaccagagggtggc
taatttttaacgtttccaagcaaaataactggggagggggcttgctgt
cctgtgagggtaggttttatagaagtggaagttaaggggaaatcgctat
ggttcacttttggctcggggaccaaagtggagcccaaaattgagtacatt
ttccatcaattatttgtgagattttttgtcctgttgtgtcatttgtgcaag
ttttttgacattttggttgaatgagccattcccagggacccaaaaggatga
gaccgaaaagtagaaaagagccaacttttaagctgagcagacagaccgaa
```

-continued ttgttgagtttgtgaggagagtagggtttgtagggagaaaggggaacaga
tcgctggcttttctctgaattagcctttctcatgggactggcttcagag
ggggttttgatgagggaagtgttctagagccttaactgtgggttgtgtt
cggtagcgggaccaagctgaaatcaaacgtaagtgcacttttctactcc
ttttctcttcttatacgggtgtgaaattggggacttttcatgtttggagt
atgagttgaggtcagttctgaagagagtgggactcatccaaaaatctgag
gagtaagggtcagaacagagttgtctcatggaagaacaaagacctagtta
gttgatgaggcagctaaatgagtcagttgacttgggatccaaatggccag
acttcgtctgtaaccaacaatctaatgagatgtagcagcaaaagagatt
tccattgaggggaaagtaaaattgttaatattgtggatcacctttggtga
agggacatccgtggagattgaacgtaagtatttttctctactaccttct
gaaatttgtctaaatgccagtgttgacttttagaggcttaagtgtcagtt
ttgtgaaaaatgggtaaacaagagcatttcatatttattatcagtttcaa
aagttaaactcagctccaaaaatgaatttgtagacaaaaagattaattta
agccaaattgaatgattcaaaggaaaaaaaaattagtgtagatgaaaaag
gaattcttacagctccaaagagcaaaagcgaattaattttctttgaactt
tgccaaatcttgtaaatgattttttgttctttacaatttaaaaaggttaga
gaaatgtatttcttagtctgttttctctcttctgtctgataaattattat
atgagataaaaatgaaaattaataggatgtgctaaaaaatcagtaagaag
ttagaaaaatatatgtttatgttaaagttgccacttaattgagaatcaga
agcaatgttattttttaaagtctaaaatgagagataaactgtcaatactta
aattctgcagagattctatatcttgacagatatctccttttttcaaaaatc
caatttctatggtagactaaatttgaaatgatcttcctcataatggaggg
aaaagatggactgaccccaaaagctcagatttt*aagaaaacctgtttaag
*gaaagaaaataaaagaactgcatttttttaaaggcccatgaatttgtaga
aaaataggaaatattttaataagtgtattcttttattttcctgttattac
ttgatggtgtttttataccgccaaggaggccgtggcaccgtcagtgtgat
ctgtagaccccatggcggccttttttcgcgattgaatgaccttggcggtg
ggtcccagggctctggtggcagcgcaccagccgctaaaagccgctaaaa
actgccgctaaaggccacagcaaccccgcgaccgcccgttcaactgtgct
gacacagtgatacagataatgtcgctaacagaggagaatagaaatatgac
gggcacacgctaatgtggggaaaagagggagaagcctgattttttatttt
tagagattctagagataaaattcccagtattatatccttttaataaaaaa
tttctattaggagattataaagaatttaaagctatttttttaagtgggt
gtaattctttcagtagtctcttgtcaaatggatttaagtaatagaggctt
aatccaaatgagagaaatagacgcataacccttcaaggcaaaagctaca
agagcaaaaattgaacacagcagccagccatctagccactcagatttga
tcagttttactgagtttgaagtaaatatcatgaaggtataattgctgata
aaaaaataagatacaggtgtgacacatctttaagtttcagaaatttaatg
gcttcagtaggattatatttcacgtatacaaagtatctaagcagataaaa -continued atgccattaatggaaacttaatagaaatatattttaaattccttcattc
tgtgacagaaattttctaatctgggtcttttaatcacctaccctttgaaa
gagtttagtaatttgctatttgccatcgctgtttactccagctaatttca
aaagtgatacttgagaaagattattttttggtttgcaaccacctggcagga
ctattttagggccatttaaaactcttttcaaactaagtattttaaactg
ttctaaaccatttagggccttttaaaaatcttttcatgaatttcaaactt
cgttaaaagttattaaggtgtctggcaagaacttccttatcaaatatgct
aatagtttaatctgttaatgcaggatataaaattaaagtgatcaaggctt
gacccaaacaggagtatcttcatagcatatttccctcctttttttctag
aattcatatgattttgctgccaaggctatttttatataatctctggaaaaa
aaatagtaatgaaggttaaaagagaagaaaatatcagaacattaagaatt
cggtattttactaactgcttggttaacatgaaggttttttattttattaag
gtttctatctttataaaaatctgttcccttttctgctgatttctccaagc
aaaagattcttgatttgtttttttaactcttactctcccacccaagggcct
gaatgcccacaaagggacttccaggaggccatctggcagctgctcaccg
tcagaagtgaagccagccagttcctcctgggcaggtggccaaaattacag
ttgaccctcctggtctggctgaaccttgccccatggtgacagccatc
tggccagggcccaggtctccctctgaagcctttgggaggagagggagagt
ggctggcccgatcacagatgcggaaggggctgactcctcaaccggggtgc
agactctgcagggtgggtctgggcccaacacacccaaagcacgcccagga
aggaaaggcagcttggtatcactgcccagagctaggagaggcaccgggaa
aatgatctgtccaagacccgttcttgcttctaaactccgagggggtcaga
tgaagtggttttgtttcttggcctgaagcatcgtgttccctgcaagaagc
ggggaacacagaggaaggagagaaaagatgaactgaacaaagcatgcaag
gcaaaaaggccttaggatggctgcaggaagttagttcttctgcattggc
tccttactggctcgtcgatcgcccacaaacaacgcacccagtggagaact
tccctgttacttaaacaccattctctgtgcttgcttcctcaggggctgat
gccaagccatccgtcttcatcttcccgccatcgaaggagcagttagcgac
cccaactgtctctgtggtgtgcttgatca Seq ID No. 15 gatgccaagccatccgtcttcatcttcccgccatcgaaggagcagttagc
gaccccaactgtctctgtggtgtgcttgatcaataacttcttcccccagag
aaatcagtgtcaagtggaaagtggatggggtggtccaaagcagtggtcat
ccggatagtgtcacagagcaggacagcaaggacagcacctacagcctcag
cagcaccctctcgctgcccacgtcacagtacctaagtcataatttatatt
cctgtgaggtcacccacaagaccctggcctcccctctggtcacAAGCTTC
AACAGGAACGAGTGTGAGGCTTAGAGGCCCACAGGCCCCTGGCCTGCCCC
CAGCCCCAGCCCCCTCCCCACCTCAAGCCTCAGGCCCTTGCCCCAGAGG
ATCCTTGGCAATCCCCCAGCCCCTCTTCCCTCCTCATCCCCTCCCCTCT
TTGGCTTTAACCGTGTTAATACTGGGGGGTGGGGAATGAATAAATAAAG
TGAACCTTTGCACCTGTGATTTCTCTCTCCTGTCTGATTTTAAGGTTGTT -continued AAATGTTGTTTTCCCCATTATAGTTAATCTTTTAAGGAACTACATACTGA
GTTGCTAAAAACTACACCATCACTTATAAAATTCAcgCCTTCTCAGTTCT
CCCCTCCCCTCCTGTCCTCCGTAAGACAGGCCTCCGTGAAACCCATAAGC
ACTTCTCTTTACACCCTCTCCTGGGCCGGGGTAGGAGACTTTTTGATGTC
CCCTcTTCAGCAAGCCTCAGAACCATTTTGAGGGGACAGTTCTTACAGT
CACAT*TCCtGtGATCTAATGACTTTAGTTaCCGAAAAGCCAGTCTCTCA
AAAAGAAGGGAACGGCTAGAAACCAAGTCATAGAAATATATATGTATAAA
ATATATATATATCCATATATGTAAAATAACAAAATAATGATAACAGCATA
GGTCAACAGGCAACAGGGAATGTTGAAGTCCATTCTGGCACTTCAATTTA
AGGGAATAGGATGCCTTCATTACATTTTAAATACAATACACATGGAGAGC
TTCCTATCTGCCAAAGACCATCCTGAATGCTTTCCACACTCACTACAAGG
TTAAAAGCATTCATTACAATGTTGATCGAGGAGTTCCCGTTGTGGCTCAG
CAGGTTAAGAACGTGACTGGTATCCAGGAGGATGCGGGTTTGGTCCCCAG
CCTCGCTCAGTGGATTAAGGATCCAGTGTTGCTGCAAGATCACGGGCTCA
GATCCCGTGTTCTATGGCTATGGTGTAGGCTGGTAGCTGCATGCAGCCCT
AATTTGACCCCTAGCCTGGGAACTGCCATAtGCCACATGTGAGGCCCTTA
AAACCTAAAAGAAAAAaAAAGAAAAGAAATATCTTACACCCAATTTATAG
ATAAGAGAGAAGCTAAGGTGGCAGGCCCAGGATCAAAGCCCTACCTGCCT
ATCTTGACACCTGAtACAAATTCTGTCTTCTAGGGtTTCCAACACTGCAT
AGAACAGAGGGTCAAACATGCTACCCTCCCAGGGACTCCTCCCTTCAAAT
GACATAAATTTTGTTGCCCATCTCTGGGGGCAAAACTCAACAATCAATGG
CATCTCTAGTACCAAGCAAGGCTCTTCTCATGAAGCAAAACTCTGAAGCC
AGATCCATCATGACCCAAGGAAGTAAAGACAGGTGTTACTGGTTAACTG
TATCCTTCAATTCAATATGCTCAATTTCCAACTCCCAGTCCCCGTAAATA
CAACCCCCTTTGGGAAGAGAGTCCTTGCAGATGTAGCCACGTTAAAAGA
GATTATACAGAAAGGCTAGTGAGGATGCAGTGAAACGGGATCTTTCATAC
ATTGCTGGTGGAAATGTAAAATGCTGCAGGCACTCTAGAAAATAATTTGC
CAGTTTTTTGAAAAGCTAAACAAAATAGTTTAGTTGCATTCTGGGTTATT
TATCCCCCAGAAATTAAAAATTTATGTCCGCACAAAAACGTGTACATAATC
ATTCATAACAGCCTTGTACGAAAAGCTT Seq ID No. 16
GGATCCTTAACCCACTAATCGAGGATCAAACACGCATCCTCATGGACAAT
ATGTTGGGTTCTTAGCCTGCTGAGACACAACAGGAACTCCCCTGGCACCA
CTTTAGAGGCCAGAGAAACAGCACAGATAAAATTCCCTGCCCTCATGAAG
CTTATAGTCTAGCTGGGGAGATATCATAGGCAAGATAAACACATACAAAT
ACATCATCTTAGGTAATAATATATACTAAGGAGAAAATTACAGGGGAGAA
AGAGGACAGGAATTGCTAGGGTAGGATTATAAGTTCAGATAGTTCATCAG
GAACACTGTTGCTGAGAAGATAACATTTAGGTAAAGACCGAAGTAGTAAG
GAAATGGACCGTGTGCCTAAGTGGGTAAGACCATTCTAGGCAGCAGGAAC
AGCGATGAAAGCACTGAGGTGGGTGTTCACTGCACAGAGTTGTTCACTGC
ACAGAGTTGTGTGGGGAGGGGTAGGTCTTGCAGGCTCTTATGGTCACAGG AAGAATTGTTTTTACTCCCACCGAGATGAAGGTTGGTGGATTTGAGCAGA
AGAATAATTCTGCCTGGTTTATATATAACAGGATTTCCCTGGGTGCTCTG
ATGAGAATAATCTGTCAGGGGTGGGATAGGGAGAGATATGGCAATAGGAG
CCTTGGCTAGGAGCCCACGACAATAATTCCAAGTGAGAGGTGGTGCTGCA
TTGAAAGCAGGACTAACAAGACCTGCTGACAGTGTGGATGTAGAAAAAGA
TAGAGGAGACGAAGGTGCATCTAGGGTTTTCTGCCTGAGGAATTAGAAAG
ATAAAGCTAAAGCTTATAGAAGATGCAGCGCTCTGGGGAGAAAGACCAGC
AGCTCAGTTTTGATCCATCTGGAATTAATTTTGGCATAAAGTATGAGGTA
TGTGGGTTAACATTATTTGTTTTTTTTTTTTCCATGTAGCTATCCAACTG
TCCCAGCATCATTTATTTTAAAGACTTTCCTTTCCCCTATTGGATTGTT
TTGGCACCTTCACTGAAGATCAACTGAGCATAAAATTGGGTCTATTTCTA
AGCTCTTGATTCCATTCCATGACCTATTTGTTCATCTTTACCCCAGTAGA
CACTGCCTTGATGATTAAAGCCCCTGTTACCATGTCTGTTTTGGACATGG
TAAATCTGAGATGCCTATTAGCCAACCAAGCAAGCACGGCCCTTAGAGAG
CTAGATATGAGAGCCTGGAATTCAGACGAGAAAGGTCAGTCCTAGAGACA
TACATGTAGTGCCATCACCATGCGGATGGTGTTAAAAGCCATCAGACTGC
AACAGACTGTGAGAGGGTACCAAGCTAGAGAGCATGGATAGAGAAACCCA
AGCACTGAGCTGGGAGGTGCTCCTACATTAAGAGATTAGTGAGATGAAGG
ACTGAGAAGATTGATCAGAGAAGAAGGAaAATCAGGAAAATGGTGCTGTC
cTGAAAATCCAAGGGAAGAGATGTTCCAAAGAGGAGAaAACTGATCAGTT
GTCAGCTAGCGTCAATTGGGATGAAAATGGACCATTGGACAGAGGGATGT
AGTGGGTCATGGGTGAATAGATAAGAGCAGCTTCTATAGAATGGCAGGGG
CAAAATTCTCATCTGATCGGCATGGGTTcTAAAGAAAACGGGAAGAAAAA
ATTGAGTGCATGACCAGTCCCTTCAAGTAGAGAGGTgGAAAAGGGAAGGA
GGAAAATGAGGCCACGACAACATGAGAGAAATGACAGCATTTTTAAAAAT
TTTTTATTTTATTTTATTTATTTATTTTTGCTTTTTAGGGCTGCCCCTGC
AAcatatggaggttcccaggttaggggtctaatcagagctatagctgcca
gcctacaccacagccatagcaatgccagatctacatgacctacaccacag
ctcacagcaacgccggatccttaaccccactgagtgaggccagagatcaaa
cccatatccttatggatactagtcaggttcattaccactgagccaaaatg
ggaaATCCTGAGTAATGACAGCATTTTTAATGTGCCAGGAAGCAAAACT
TGCCACCCCGAAATGTCTCTCAGGCATGTGGATTATTTTGAGCTGAAAAC
GATTAAGGCCCAAAAAACACAAGAAGAAATGTGGACCTTCCCCCAACAGC
CTAAAAAATTTAGATTGAGGGCCTGTTCCCAGAATAGAGCTATTGCCAGA
CTTGTCTACAGAGGCTAAGGGCTAGGTGTGGTGGGGAAACCCTCAGAGAT
CAGAGGGACGTTTATGTACCAAGCATTGACATTTCCATCTCCATGCGAAT
GGCTTCTTCCCCTCTGTAGCCCCAAACCACCACCCCCAAAATCTTCTTC
TGTCTTTAGCTGAAGATGGTGTTGAAGGTGATAGTTTCAGCCACTTTGGC
GAGTTCCTCAGTTGTTCTGGGTCTTTCCTCCGGATCCACATTATTCGACT
GTGTTTGATTTTTTCCTGTTTATCTGTCTCATTGGCACCCATTTCATTCT
TAGACCAGCCCAAAGAACCTAGAAGAGTGAAGGAAAATTTCTTCCACCCT GACAAATGCTAAATGAGAATCACCgCAGTAGAGGAAAATGATCTGGTgCT
GCGGGAGATAGAAGAGAAAATcGCTGGAGAGATGTCACTGAGTAGGTGAG
ATGGGAAAGGGGGGCACAGGTGGAGGTGTTGCCCTCAGCTAGGAAGACA
GACAGTTcacagaagagaagcgggtgtccgtGGACATCTTGCCTCATGGA
TGAGGAAACCGAGGCTAAGAAAGACTGCAAAAGAAAGGTAAGGATTGCAG
AGAGGTCGATCCATGACTAAAATCACAGTAACCAACCCCAAACCACCATG
TTTTCTCCTAGTCTGGCACGTGGCAGGTACTGTGTAGGTTTTCAATATTA
TTGGTTTGTAACAGTACCTATTAGGCCTCCATCcCCTCCTCTAATACTAA
CAAAAGTGTGAGACTGGTCAGTGAAAAATGGTCTTCTTTCTCTATGCAAT
CTTTCTCAAGAAGATACATAACTTTTTATTTTATCATaGGCTTGAAGAGC
AAATGAGAAACAgCCTCCAACCTATGACACCGTAACAAAGTGTTTATGAT
CAGTGAAGGCAAGAAACAAAACATACACaGTAAAGACCCTCCATAATAT
TGtGGGCTGGCCCAaCACAGGCCAGGTTGTAAAAGCTTTTTATTCTTTGA
TAGAGGAATGGATAGTAATGTTTCAACCTGGACAGAGAT*CATGTTCACT
GAATCCTTCCAAAAATTCATGGGTAGTTTGAAtTATAAGGAAAATAAGAC
TTAGGATAAATACTTTgTCCA*GATCCCAGAGTTAATgCCAAAATCAGTT
TTCAGACTCCAGGCAGCCTGATCAAGAGCCTAAACTTTAAAGACACAGTC
CCTTAATAACTACTATTCACAGTTGCACTTTCAgGGCGCAAAGACTCATT
GAATCCTACAATAGAATGAGTTTAGATATCAAATCTCTCAGTAATAGATG
AGGAGACTAAATAGCGGGCATGACCTGGTCACTTAAAGACAGAATTGAGA
TTCAAGGCTAGTGTTCTTTCTACCTGTTTTGTTTCTACAAGATGTAGCAA
TGCGCTAATTACAGACCTCTCAGGGAAGGAATTCACAACCCTCAGCAAAA
ACCAAAGACAAATCTAAGACAACTAAGAGTGTTGGTTTAATTTGGAAAAA
TAACTCACTAACCAAACGCCCTCTTAGCACCCCAATGTCTTCCACCATC
ACAGTGCTCAGGCCTCAACCATGCCCCAATCACCCCAGCCCCAGACTGGT
TATTACCAAGTTTCATGATGACTGGCCTGAGAAGATCAAAAAAGCAATGA
CATCTTACAGGGGACTACCCCGAGGACCAAGATAGCAACTGTCATAGCAA
CCGTCACACTGCTTTGGTCA Seq ID No. 19
ggatcaaacacgcatcctcatggacaatatgttgggttcttagcctgctg
agacacaacaggaactcccctggcaccactttagaggccagagaaacagc
acagataaaattccctgccctcatgaagcttatagtctagctggggagat
atcataggcaagataaacacatacaaatacatcatcttaggtaataatat
atactaaggagaaaattacaggggagaaagaggacaggaattgctagggt
aggattataagttcagatagttcatcaggaacactgttgctgagaagata
acatttaggtaaagaccgaagtagtaaggaaatggaccgtgtgcctaagt
gggtaagaccattctaggcagcaggaacagcgatgaaagcactgaggtgg
gtgttcactgcacagagttgttcactgcacagagttgtgtgggagggt
aggtcttgcaggctcttatggtcacaggaagaattgttttactcccaccg
agatgaaggttggtggattttgagcagaagaataattctgcctggtttat
ataacaggatttccctgggtgctctgatgagaataatctgtcagggt
ggataggagagatatggcaataggagccttggctaggagcccacgaca
ataattccaagtgagaggtggtgctgcattgaaagcaggactaacaagac
ctgctgacagtgtggatgtagaaaaagatagaggagacgaaggtgcatct
agggttttctgcctgaggaattagaaagataaagctaaagcttatagaag
atgcagcgctctggggagaaagaccagcagctcagttttgatccatctgg
aattaattttggcataaagtatgaggtatgtgggttaacattatttgttt
ttttttttccatgtagctatccaactgtcccagcatcatttatttttaaa
agactttcctttcccctattggattgttttggcaccttcactgaagatca
actgagcataaaattgggtctatttctaagctcttgattccattccatga
cctatttgttcatctttaccccagtagacactgccttgatgattaaagcc
cctgttaccatgtctgttttggacatggtaaatctgagatgcctattagc
caaccaagcaagcacggcccttagagagctagatatgagagcctggaatt
cagacgagaaaggtcagtcctagagacatacatgtagtgccatcaccatg
cggatggtgttaaaagccatcagactgcaacagactgtgagagggtacca
agctagagagcatggatagagaaacccaagcactgagctgggaggtgctc
ctacattaagagattagtgagatgaaggactgagaagattgatcagagaa
gaaggaaaatcaggaaaatggtgctgtcctgaaaatccaagggaagagat
gttccaaagaggagaaaactgatcagttgtcagctagcgtcaattgggat
gaaaatggaccattggacagagggatgtagtgggtcatgggtgaatagat
aagagcagcttctatagaatggcaggggcaaaattctcatctgatcggca
tgggttctaaagaaaacgggaagaaaaaattgagtgcatgaccagtccct
tcaagtagagaggtggaaaagggaaggaggaaaatgaggccacgacaaca
tgagagaaatgacagcatttttaaaaattttttattttattttatttatt
tattttgcttttagggctgcccctgcaacatatggaggttcccaggtt
aggggtctaatcagagctatagctgccagcctacaccacagccatagcaa
tgccagatctacatgacctacaccacagctcacagcaacgccggatcctt
aacccactgagtgaggccagagatcaaacccatatccttatggatactag
tcaggttcattaccactgagccaaaatgggaaatcctgagtaatgacagc
atttttttaatgtgccaggaagcaaaacttgccaccccgaaatgtctctca
ggcatgtggattattttgagctgaaaacgattaaggcccaaaaaacacaa
gaagaaatgtggacctcccccaacagcctaaaaaatttagattgagggc
ctgttcccagaatagagctattgccagacttgtctacagaggctaagggc
taggtggtggggaaaccctcagagatcagagggacgtttatgtaccaa
gcattgacatttccatctccatgcgaatggccttcttcccctctgtagcc
ccaaaccaccaccccaaaatcttcttctgtctttagctgaagatggtgt
tgaaggtgatagtttcagccactttggcgagttcctcagttgttctgggt
ctttcctccTgatccacattattcgactgtgtttgattttctcctgttta
tctgtctcattggcacccatttcattcttagaccagcccaaagaacctag
aagagtgaaggaaaatttcttccaccctgacaaatgctaaatgagaatca
ccgcagtagaggaaaatgatctggtgctgcgggagatagaagagaaaatc -continued

```
gctggagagatgtcactgagtaggtgagatgggaaggggtgacacaggt
ggaggtgttgccctcagctaggaagacagacagttcacagaagagaagcg
ggtgtccgtggacatcttgcctcatggatgaggaaaccgaggctaagaaa
gactgcaaaagaaaggtaaggattgcagagaggtcgatccatgactaaaa
tcacagtaaccaaccccaaaccaccatgttttctcctagtctggcacgtg
gcaggtactgtgtaggttttcaatattattggtttgtaacagtacctatt
aggcctccatcccctcctctaatactaacaaaagtgtgagactggtcagt
gaaaaatggtcttctttctctatgaatctttctcaagaagatacataact
ttttattttatcataggcttgaagagcaaatgagaaacagcctccaacct
atgacaccgtaacaaaatgtttatgatcagtgaagggcaagaaacaaaac
atacacagtaaagaccctccataatatgtgggtggcccaacacaggcca
ggttgtaaaagctttttattctttgatagaggaatggatagtaatgtttc
aacctggacagagatcatgttcactgaatccttccaaaaattcatgggta
gtttgaattataaggaaaataagacttaggataaatactttgtccaagat
cccagagttaatgccaaaatcagttttcagactccaggcagcctgatcaa
gagcctaaactttaaagacacagtcccttaataactactattcacagttg
cactttcagggcgcaaagactcattgaatcctacaatagaatgagtttag
atatcaaatctctcagtaatagatgaggagactaaatagcgggcatgacc
tggtcacttaaagacagaattgagattcaaggctagtgttctttctacct
gttttgtttctacaagatgtagcaatgcgctaattacagacctctcaggg
aaggaattcacaaccctcagcaaaaaccaaagacaaatctaagacaacta
agagtgttggtttaatttggaaaaataactcactaaccaaacgcccctct
tagcaccccaatgtcttccaccatcacagtgctcaggcctcaaccatgcc
ccaatcacc
```

Seq ID No. 25
```
GCACATGGTAGGCAAAGGACTTTGCTTCTCCCAGCACATCTTTCTGCAGA
GATCCATGGAAACAAGACTCAACTCCAAAGCAGCAAAGAAGCAGCAAGTT
CTCAAGTGATCTCCTCTGACTCCCTCCTCCCAGGCTAATGAAGCCATGTT
GCCCCTGGGGGATTAAGGGCAGGTGTCCATTGTGGCACCCAGCCCGAAGA
CAAGCAATTTGATCAGGTTCTGAGCACTCCTGAATGTGGACTCTGGAATT
TTCTCCTCACCTTGTGGCATATCAGCTTAAGTCAAGTACAAGTGACAAAC
AACATAATCCTAAGAAGAGAGGAATCAAGCTGAAGTCAAAGGATCACTGC
CTTGGATTCTACTGTGAATGATGACCTGGAAAATATCCTGAACAACAGCT
TCAGGGTGATCATCAGAGACAAAAGTTCCAGAGCCAGGTAGGGAAACCCT
CAAGCCTTGCAAAGAGCAAAATCATGCCATTGGGTTCTTAACCTGCTGAG
TGATTTACTATATGTTACTGTGGGAGGCAAAGCGCTCAAATAGCCTGGGT
AAGTATGTCAAATAAAAAGCAAAGTGGTGTTTCTTGAAATGTTAGACCT
GAGGAAGGAATATTGATAACTTACCAATAATTTTCAGAATGATTTATAGA
TGTGCACTTAGTCAGTGTCTCTCCACCCCGCACCTGACAAGCAGTTTAGA
ATTTATTCTAAGAATCTAGGTTTGCTGGGGGCTACATGGGAATCAGCTTC
AGTGAAGAGTTTGTTGGAATGATTCACTAAATTTTCTATTTCCAGCATAA
ATCCAAGAACCTCTCAGACTAGTTTATTGACACTGCTTTTCCTCCATAAT
CCATCTCATCTCCGTCCATCATGGACACTTTGTAGAATGACAGGTCCTGG
CAgAGACTCaCAGATGCTTCTGAAACATCCTTTGCCTTCAAAGAATGAAC
AGCACACATACTAAGGATCTCAGTGATCCACAAATTAGTTTTTGCCACAA
TGGTTCTTATGATAAAAGTCTTTCATTAACAGCAAATTGTTTTATAATAG
TTGTTCTGCTTTATAATAATTGCATGCTTCACTTTCTTTTCTTTTCTTTT
TTTTTCTTTTTTTGCTTTTTAGTGCCGCAGGTgcagcatatgaaatttcc
caggctaggggtcaaatcagaactacacctactggcctacgccacagcca
cagcaactcaggatctaagccatgtcggtgacctacactacagctcatgg
caatgccagatccttaacccaatgagcgaggccagggatcgaacccatgt
cctcatggatactagtcaggctcattatccgctgagccataacaggaact
cccGAGTTTGCTTTTTATCAAATTGGTACAGCCTTATTGTTTCTGAAAA
CCACAAAATGAATGTATTCACATAATTTTAAAAGGTTAAATAATTTATGA
TATACAAGACAATAGAAAGAGAAAACGTCATTGCCTCTTTCTTCCACGAC
AACACGCCTCCTTAATTGATTTGAAGAAATAACTACTGAGCATGGTTTAG
TGTACTTCTTTCAGCAATTAGCCTGTATTCATAGCCATACATATTCAATT
AAAATGAGATCATGATATCACACAATACATACCATACAGCCTATAGGGAT
TTTTACAATCATCTTCCACATGACTACATAAAAACCTACCTAAAAAAAAA
AAAAACCCTACTTCATCCTCCTATTGGCTGCTTTGTGCTCCATTAAAAAG
CTCTATCATAATTAGGTTATGATGAGGATTTCCATTTTCTACCTTTCAAG
CAACATTTCAATGCACAGTCTTATATACACATTTGAGCCTACTTTTCTTT
TTCTTTCTTTTTTGGTTTTTTTTTTTTTTTTTTTGGTCTTTTTGTC
TTTTTCTAAGgctgcatatggaggttcccaggctagctgtctaatcagaac
tatagctgctggcctacgccacatccacagcaatacaagatctgagccat
gtctgcaacttacaccacagctcacagcaacggtggatccttaaaccact
gagcaaggccagggatcaaacccatAACTTCATGGCTCCTAGTTGGATTT
GTTAACCACTGAGCCATGATGGCAACTCCTGAGCCTACTTTCTAATCAT
TTCCAACCCTAGGACACTTTTTTAAGTTTCATTTTTCTCCCCCCACCCCC
TGTTTTCTGAAGTGTGTTTGCTTCCACTGGGTGACTTCACTCCCAGGATC
TCATCTGCAGGATACTGCAGCTAAGTGTATGAGCTCTGAATTTGAATCCC
AACTCTGCCACTCAAAGGGATAGGAGTTTCCGATGTGGCCCAATGGGATC
AGTGGCATCTCTGCAGTGCCAGGACGCaggttccatccctggcccagcac
agtgggttaagaatctggCATTGCTGCAGCTGAGGCATAGATTTCAATTG
TGCCTCAgATCTGATCCTTGGCCCAAGGACTGCATATGCCTCAGGGCAAC
CAAAAAGAGAAAAGGGGGTGATAGCATTAGTTTCTAGATTTGGGGGAT
AATTAAATAAAGTGATCCATGTACAATGTATGGCATTTTGTAAATGCTCA
ACAAATTTCAACTATTATGgagttcccatcatggctcagtggaagggaat
ctgattagcatccatgaggacacaggtCCAACCCCGACCTTGCTCAGTGG
GCATTGCTGTGAGCTGTGGCATGGGTTACAGACGAAGCTCGGATCTGGCA
TTGCTGTGGCTGTGGTGTAAGCCAgCAActacagctctcattcagcccct
agcctgggaacctccatatgccTAAAAGACAAAAAATAAAATTTAAATTA
```

-continued

```
AAAATAAAGAAATGTTAACTATTATGATTGgTACTGCTTGCATTACTGCA
AAGAAAGTCACTTTCTATACTCTTTAATATCTTAGTTGACTGTGTGCTCA
GTGAACTATTTTGGACACTTAATTTCCACTCTCTTCTATCTCCAACTTGA
CAACTCTCTTTCCTCTCTTCTGGTGAGATCCACTGCTGACTTTGCTCTTT
AAGGCAACTAGAAAAGTGCTCAGTGACAAAATCAAAGAAAGTTACCTTAA
TCTTCAGAATTACAATCTTAAGTTCTCTTGTAAAGCTTACTATTTCAGTG
GTTAGTATTATTCCTTGGTCCCTTACAACTTATCAGCTCTGATCTATTGC
TGATTTTCAACTATTTATTGTTGGAGTTTTTCCTTTTTTTCCCTGTTCAT
TCTGCAAATGTTTGCTGAGCATTTGTCAAGTGAAGATACTGGACTGGGCC
TTCCAAATATAAGACAATGAAACATCGGGAGTTCTCATTATGGTGCAGCA
GAaacgaatccaactaggaaatgtgaggttgcaggttcgatccctgccct
tgctcagtgggttaaggatccagcattaccgtgagctgtggtgtaggttg
cagacgtggctcagatcctgcgttgctgtggctgtggcataggctggcag
ctctagctctgattcgaccgctagcctgggaacctccatGCGCCCCGAGT
GCAGCCCTTAAAAAGCAAAAAAAAAGAAAGAAAGAAAAAGACAATGAAA
CATCAAACAGCTAACAATCCAGTAGGGTAGAAAGAATCTGGCAACAGATA
AGAGCGATTAAATGTTCTAGGTCCAGTGACCTTGCCTCTGTGCTCTACAC
AGTCGTGCCACTTGCTGAGGGAGAAGGTCTCTCTTGAGTTGAGTCCTGAA
AGACATTAGTTGTTCACAAACTAATGCCAGTGAGTGAAGGTGTTTCCAAG
CAGAGGGAGAGTTTGGTAAAAAGCTGGAAGTCACAGAAAGACTCTAAAGA
GTTTAGGATGGTGGGAGCAACATACGCTGAGATGGGGCTGGAAGGTTAAG
AGGGAAACAACTATAGTAAGTGAAGCTGGACTCACAGCAAAGTGAGGACC
TCAGCATCCTTGATGGGGTTACCATGGAAACACCAAGGCACACCTTGATT
TCCAAAACAGCAGGCACCTGATTCAGCCCAATGTGACATGGTGGGTACCC
CTCTAGCTCTACCTGTTCTGTGACAACTGACAACCAACGAAGTTAAGTCT
GGATTTTCTACTCTGCTGATCCTTGTTTTTGTTTCACACGTCATCTATAG
CTTCATGCCAAAATAGAGTTCAAGGTAAGACGCGGGCCTTGGTTTGATAT
ACATGTAGTCTATCTTGTTTGAGACAATATGGTGGCAAGGAAGAGGTTCA
AACAGGAAAATACTCTCTAATTATGATTAACTGAGAAAAGCTAAAGAGTC
CCATAATGACACTGAATGAAGTTCATCATTTGCAAAAGCCTTCCCCCCCC
CCCAGGAGACTATAAAAAGTGCAATTTTTTAAATGAACTTATTTACAAA
ACAGAAATAGACTCACAGACATAGGAAACGAACAGATGGTTACCAAGGGT
GAAAGGGAGTAGGAGGGATAAATAAGGAGTCTGGGGTTAGCAGATACACC
CCAGTGTACACAAAATAAACAACAGGGACCTACTATATAGCACAGGGAAC
TATATGCAGTAGCTTACAATAACCTATAATGGAAAAGAATGTGAAAAAGA
ATATATGTATGCGTGTGTGTAACTGAATCACTTTGCTGTAACCTGAAT
CTAACATAACATTGTAAATCAACTACAGTTTTTTTTTTTTAAGTGCAG
GGTTTTGGTGTTTTTTTTTTCATTTTTGTTTTTGTTTTTGTTTTTGC
TTTTTAGGGCCACACCCAGACATATGGGGGTTCCCAGGctAGGGGTcTAa
TTAGAGcTACAGtTGCCGGCTTGCAccacagccacagcaacatcagatcc
```

-continued

```
gagccgcacttgcgacttacaccacagctcatggcaataccagatcctta
acccactgagcaaggcccagggatcgtacccgcaacctcatggttcctag
tcagattcattTCTGCTGCGCTACAATGGGAACTCCAAGTGCAGTTTTTT
GTAATGTGCTTGTCTTTCTTTGTAATTCATATTCATCCTACTTCCCAATA
AATAAATAAATACATAAATAATAAACATACCATTGTAAATCAACTACAAT
TTTTTTTAAATGCAGGGTTTTTGTTTTTTGTTTTTTGTTTTGTCTTTTTG
CCTTTTCTAgggccgctcccatggcatatggaggttcccaggctaggggt
cgaatcggagctgtagccaccggcctacgccagagccacagcaacgcggg
atccgagccgcgtctgcaacctacaccacagctcacggcaacgccggatc
gttaacccactgagcaagggcagggatcgaacctgcaacctcatggttcc
tagtcagattcgttaactactgagccacaacggaaacTCCTAAAGTGCAG
TTTTTAAATGTGCTTGTCTTTCTTTGTAATTTACACTCAACCTACTTCCC
AATAAATAAATAAATAAACAAATAAATCATAGACATGGTTGAATTCTAAA
GGAAGGGACCATCAGGCCTTAGACAGAAATACGTCATCTTCTAGTATTTT
AAAACACACTAAAGAAGACAAACATGCTCTGCCAGAGAAGCCCAGGGCCT
CCACAGCTGCTTGCAAAGGGAGTTAGGCTTCAGTAGCTGACCCAAGGCTC
TGTTCCTCTTCAGGGAAAAGGGTTTTTGTTCAGTGAGACAGCAGACAGCT
GTCACTGTGgtggacgttcggccaaggaaccaagctggaactcaaacGTA
AGTCAATCCAAACGTTCCTTCCTTGGCTGTCTGTGTCTTACGGTCTCTGT
GGCTCTGAAATGATTCATGTGCTGACTCTCTGAAACCAGACTGACATTCT
CCAGGGCAAAACTAAAGCCTGTCATCAAACcGGAAAACTGAGGGCACATT
TTCTGGGCAGAACTAAGAGTCAGGCACTGGGTGAGGAAAAACTTGTTAGA
ATGATAGTTTCAGAAACTTACTGGGAAGCAAAGCCCATGTTCTGAACAGA
GCTCTGCTCAAGGGTCAGGAGGGGAACCAGTTTTTGTACAGGAGGGAAGT
TGAGACGAACCCCTGTGTAtatggtttcggcgcggggaccaagctggagc
tcaaacgTAAGTGGCTTTTTCCGACTGATTCTTTGCTGTTTCTAATTGTT
GGTTGGCTTTTTGTCCATTTTTCAGTGTTTTCATCGAATTAGTTGTCAGG
GACCAAACAAATTGCCTTCCCAGATTAGGTACCAGGGAGGGACATTGCT
GCATGGGAGACCAGAGGGTGGCTAATTTTTAACGTTTCCAAGCCAAAATA
ACTGGGGAAGGGGCTTGCTGTCCTGTGAGGGTAGGTTTTTATAGAAGTG
GAAGTTAAGGGGAAATCGCTATGGTtcacttttggctcggggaccaaagt
ggagcccaaaattgaGTACATTTTCCATCAATTATTTGTGAGATTTTTGT
CCTGTTGTGTCATTTGTGCAAGTTTTTGACATTTTGGTTGAATGAGCCAT
TCCCAGGGACCCAAAAGGATGAGACCGAAAAGTAGAAAAGAGCCAACTTT
TAAGCTGAGCAGACAGACCGAATTGTTGAGTTTGTGAGGAGAGTAGGGTT
TGTAGGGAGAAAGGGGAACAGATCGCTGGCTTTTTCTCTGAATTAGCCTT
TCTCATGGGACTGGCTTCAGAGGGGGTTTTTGATGAGGGAAGTGTTCTAG
AGCCTTAACTGTGGgttgtgttcggtagcgggaccaagctggaaatcaaa
CGTAAGTGCACTTTTCTACTCC
```

Porcine Lambda Light Chain

Figure 3:
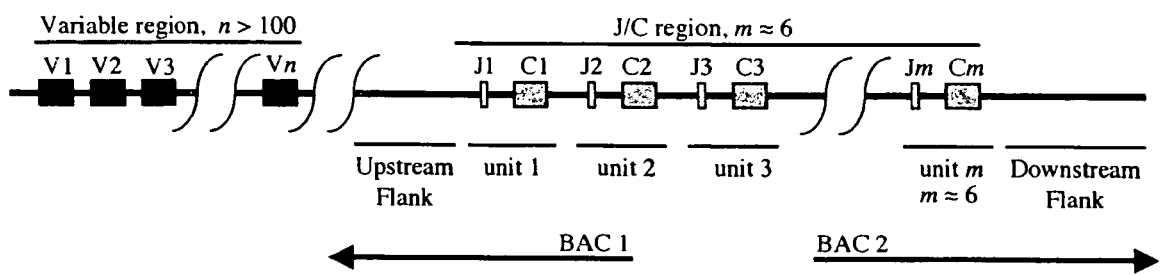
FIG. 3 illustrates the genomic organization of the porcine lambda immunoglobulin locus, including a concatamer of J-C sequences or units as well as flanking regions that include the variable region 5' to the JC cluster region. Bacterial artificial chromosomes (BAC1 and BAC2) represent fragments of the porcine immunoglobulin genome that can be obtained from BAC libraries.

In another embodiment, novel genomic sequences encoding the lambda light chain locus of ungulate immunoglobulin are provided. The present invention provides the first reported genomic sequence of ungulate lambda light chain regions. In one embodiment, the porcine lambda light chain nucleotides include a concatamer of J to C units. In a specific embodiment, an isolated porcine lambda nucleotide sequence is provided, such as that depicted in Seq ID No. 28. See FIG. 3 for a diagram of the organization of the porcine lamba immunoglobulin locus.

In one embodiment, nucleotide sequence is provided that includes 5' flanking sequence to the first lambda J/C region of the porcine lambda light chain genomic sequence, for example, as represented by Seq ID No 32.

Still further, nucleotide sequence is provided that includes 3' flanking sequence to the J/C cluster region of the porcine lambda light chain genomic sequence, for example, approximately 200 base pairs downstream of lambda J/C, such as that represented by Seq ID No 33. Alternatively, nucleotide sequence is provided that includes 3' flanking sequence to the J/C cluster region of the porcine lambda light chain genomic sequence, for example, approximately 11.8 kb downstream of the J/C cluster, near the enhancer (such as that represented by Seq ID No. 34), approximately 12 Kb downstream of lambda, including the enhancer region (such as that represented by Seq ID No. 35), approximately 17.6 Kb downstream of lambda (such as that represented by Seq ID No. 36, approximately 19.1 Kb downstream of lambda (such as that represented by Seq ID No. 37), approximately 21.3 Kb downstream of lambda (such as that represented by Seq ID No. 38), and/or approximately 27 Kb downstream of lambda (such as that represented by Seq ID No. 39).

In still further embodiments, isolated nucleotide sequences as depicted in Seq ID Nos 28, 31, 32, 33, 34, 35, 36, 37, 38, or 39 are provided. Nucleic acid sequences at least 80, 85, 90, 95, 98 or 99% homologous to Seq ID Nos 28, 31, 32, 33, 34, 35, 36, 37, 38, or 39 are also provided. In addition, nucleotide sequences that contain at least 10, 15, 17, 20, 25, 30, 40, 50, 75, 100, 150, 200, 250, 500 or 1,000 contiguous nucleotides of Seq ID Nos 28, 31, 32, 33, 34, 35, 36, 37, 38, or 39 are provided. Further provided are nucleotide sequences that hybridizes, optionally under stringent conditions, to Seq ID Nos 28, 31, 32, 33, 34, 35, 36, 37, 38, or 39, as well as, nucleotides homologous thereto.

```
Seq ID No. 28
CCTTCCTCCTGCACCTGTCAACTCCCAATAAACCGTCCTCCTTGTCATTC

AGAAATCATGCTCTCCGCTCACTTGTGTCTACCCATTTTCGGGCTTGCAT

GGGGTCATCCTCGAAGGTGGAGAGAGTCCCCCTTGGCCTTGGGGAAGTCG

AGGGGGGCGGGGGGAGGCCTGAGGCATGTGCCAGCGAGGGGGTCACCTC

CACGCCCCTGAGGACCTTCTAGAACCAGGGGCGTGGGGCCACCGCCTGAG

TGGAAGGCTGTCCACTTTTCCCCCGGGCCCCAGGCTCCCTCCTCCGTGT

GGACCTTGTCCACCTCTGACTGGCCCAGCCACTCATGCATTGTTTCCCCG

AAACCCCAGGACGATAGCTCAGCACGCGACAGTGTCCCCCTCTGAGGGCC

TCTGTCCATTTCAGGACGACCCGCATGTACAGCGTGACCACTCTGCTCAC

GCCCACTCACCACGTCCTAGAGCCCCACCCCCAGCCCCATCCTTAGGGGC

ACAGCCAGcTCCGACCGCCCCGGGGACACCACCCTCTGCCCCTTcCCCAG

GCCCTCCCTGTCACACGCACCACAGGGCCCTCCGTCCCGAGACCCTGCTC

CCTCATCCCTCGGTCCCCTCAGGTAGCCTTCCACCCGCGTGTGTCCCGAG

-continued
GTCCCAGATGCAGCAAGGCCCCTGGGACAACGCCAGATCTCTGCTCTcCC

CGACCCCTCAGAAGCCAGCCCACGCCTGGCCCCACCACCACTGCCTAACg

TCCAAGTGTCCATAGGCCTCGGGACCTCCAAGTCCAGGTTCTGCCTCTGG

GATTCCGCCATGGGTCTGCCTGGGAAATGATGCACTTGGAGGAGCTCAGC

ATGGGATGCGGGACCTTGTCTCTAGGCGCTcCCTCAGGATCCCACAGCTG

CCCTGTGAGACACACACACACACACACACACACACACACACACACACACACA

CACACAAACACGCATGCACGCACGCCGGCACACACGCTATTGCAGAGATG

GCCACGGTAGCTGTGCCTCGAGGCCGAGTGGAGTGTCTAGAACTCTCGGG

GGTCCCCTCTGCAGACGACACTGCTCCATCCCCCCCGTGCCCTGAAGGGC

TCCTCACTCTCCCATCAGGATCTCTCCAAGCTGCTGACCTGGAGAGGAAG

GGGCCTGGGACAGGCGGGGACACTCAGACCTCCCTGCTGCCCCTCCTCTG

CCTGGGCTTGGACGGCTCCCCCCTTCCCACGGGTGAAGGTGCAGGTGGGG

AGAGGGCACCCCCCTCAGCCTCCCAGACCCAGACCAGCCCCGTGGCAGG

GGCAGCCTGTGAGCCTCCAGCCAGATGCAGGTGGCCTGGGGTGGGGGGTG

GAGGGGGCGGGAGGTTTATGTTTGAGGCTGTATCACTGTGTAATATTTTC

GGCGGTGGGACCCATCTGACCGTCCTCGGTGAGTCTCCCCTTTTCTCTCC

TCCTTGGGGATCCGAGTGAAATCTGGGTCGATCTTCTCTCCGTTCTCCTC

CGACTGGGGCTGAGGTCTGAACCTCGGTGGGGTCCGAAGAGGAGGCCCCT

AGGCCAGGCTCCTCAGCCCCTCCAGCCCGACcgGCCCTCTTGACACAGGG

TCCAGCTAAGGGCAGACATGGAGGCTGCTAGTCCAGGGCCAGGCTCTGAG

ACCCAAGGGCGCTGCCCAAGGAACCCTTGCCCCAGGGACCCTGGGAGCAA

AGCTCCTCACTCAGAGCCTGCAGCCCTGGGGTCTGAGGACAAGGAGGGAC

TGAGGACTGGGCGTGGGGAGTTCAGGCGGGGACACCAGGTCCAGGGAGGT

GACAAAGGCGCTGGGAGGGGGCGGACGGTGCCGGGGACTCCTCCTGGGCC

CTGTGGGCTCGGGGTCCTTGTGAGGACCCTGAGGGACTGAGGGGCCCCTG

GGCCTAGGGACTTGCAgTgAGGGAGGCAGGGAGTGTCCCTTGAGAACGTG

GCCTCCGCGGGCTGGGTCCCCCTCGTGCTCCCAGCC*GGGAGGACACCCC

AGAGCAAGCGCCCCAGGTGGGCGGGAGGGTCTCCTCACAGGGGCAGCTG

ACAGATAGAGGCCCCCGCCAGGCAGATGCTTGATCCTGGCAgTTATACTG

GGTTC**GCACAACTTTCCCTGAACAAGGGGCCCTCCGAACAGACACAGA

CGCAACCCAGTCGACCcaggcTCAGCACAgAAAATGCACTGACACCCAAA

ACCCTCATCTggggGCCTGGCCGGcAtCCCGCCCCAGGACCCAAGGCCCC

TGCCCCCTGGCAGCCCTGGACACGGTCCTCTGTGGGCGGTGGGGTCgGGG

CTGTGGTGACGGTGGCATCGGGGAGCCTGTGCCCCTCCCTGAAAGGGCG

GAGAGGCTCAAGAGGGGACAGAAATGTCCTCCCCTAGGAAGACCTCGGAC

GGGGGCGGGGGGTGGTCTCCGACAGACAGATGCCCGGGACCGACAGACC

TGCCGAGGGAAGAGGGCACCTCGGTCGGGTTAGGCTCCAGGCAGCACGAG

GGAGCGAGGCTGGGAGGGTGAGGACATGGGAGCCTGAGGAGGAGCTGGAG

ACTTCAGCAGGCCCCCAGCTCCGGGCTTCGGGCTCTGAGATGCTCGGACG

CAAGGTGAGTGACCCCACCTGTGGCTGACCTGACCTCAgGGgGACAAGGC

TCAGCCTGGGACTCTGTGTCCCCATCGCCTGcACAGGGGATTCCCCTGAT
```

```
GGACACTGAGCCAACGACCTCCCGTCTCTCCCCGACCCCCAGGTCAGCCC
AAgGCCaCTCCCACGGTCAACCTCTTCCCGCCCTCCTCTGAGGAGCTCGG
CACCAACAAGGCCACCCTGGTGTGTCTAATAAGTGACTTCTACCCGGGCG
CCGTGACGGTGACCTGGAAGGCAGGCGGCACCACCGTCACCCAGGGCGTG
GAGACCACCAAGCCCTCGAAACAGAGCAACAACAAGTACGCGGCCAGCAG
CTACCTGGCCCTGTCCGCCAGTGACTGGAAATCTTCCAGCGGCTTCACCT
GCCAGGTCACCCACGAGGGGACCATTGTGGAGAAGACAGTGACGCCCTCC
GAGTGCGCCTAGGTCCCTGGGCCCCCACCCTCAGGGGCCTGGAGCCACAG
GACCCCCGCGAGGGTCTCCCCGCGACCCTGGTCCAGCCCAGCCCTTCCTC
CTGCACCTGTCAACTCCCAATAAACCGTCCTCCTTGTCATTCAGAAATCA
TGCTCTCCGCTCACTTGTGTCTACCCATTTTCGGGCTTGCATGGGGTCAT
CCTCGAAGGTGGAGAGAGTCCCCCTTGGCCTTGGGgAAATCGAGGGGGGC
GGGGGGAGGCCTGAGGCATGTGCCAGCGAGGGGGGTCACCTCCACGCCCC
TGAGGACCTTCTAGAACCAGGGGCGTGGGGCCACCGCCAGAGTGGAAGGC
TGTCCACTTTTCCCCCGGGCCCCCAGGCTCCCTCCTCCGTGTGGACCTTG
TCCACCTCTGACTGGCCCAGCCACTCATGCATTGTTTCCCCGAAACCCCA
GGACGATAGCTCAGCACGCGACAGTGTCCCCCTCTGAGGGCCTCTGTCCA
TTTCAGGACGACCCGCATGTACAGCGTGACCACTCTGCTCACGCCCACTC
ACCACGTCCTAGAGCCCACCCCCAGCCCCATCCTTAGGGGCACAGCCAG
CTCCGACCGCCCCGGGGACACCACCCTCTGCCCCTTCCCCAGGCCCTCCC
TGTCACACGCACCACAGGGCCCTCCGTCCCGAGACCCTGCTCCCTCATCC
CTCGGTCCCCTCAGGTAGCCTTCCACCCGCGTGTGTCCCGAGGTCCCAGA
TGCAGCAAGGCCCCTGGGACAACGCCAGATCTCTGCTCTCCCCGACCCTC
AGAAGCCAGCCCACGCCTGGCCCACCACCACTGCCTAACGTCCAAGTGTC
CATAGGCTCGGGAcCTCcAaGTCCAGGTTCTGCCTCTGGGATTCCGCCAT
GGGTCTGCCTGGAATGATGCACTTGGAgGAgCTCAgCATGGGATGcGGAA
CTTGTCTAGcGCTCCTCAGATCCACAGcTGCCTGtGAgAcacacacacac
acacacacaccAAAcaCGcATGCACGCACGCCGGCACACACGCTATTA
CAGAGATGGCCACGGTAGCTGTGCCTCGAGGCCGAGTGGAGTGTCTAGAA
CTCTCGGGGGTCCCCTCTGCAGACGACACTGCTCCATCCCCCCCGTGCCC
TGAAGGGCTCCTCACTCTCCCATCAGGATCTCTCCAAGCTGCTGACCTGG
AGAGGAAGGGGCCTGGGACAGGCGGGACACTCAGACCTCCCTGCTGCCC
CTCCTCTGCCTGGGCTTGGACGGCTCCCCCCTTCCCACGGGTGAAGGTGC
AGGTGGGGAGAGGGCACCCCCCTCACCCTCCCAGACCCAGACCAGCCCCC
GTGGCAGGGCAGCCTGTGAGCCTCCAGCCAGATGCAGGTGGCCTGGGGT
GGGGGGTGGAGGGGGCGGGAGGTTTATGTTTGAGGCTGTATTCATCTGTG
TAATATttTCGGCGGTGGGACCCATCTGACCGTCCTCGGTGAGTCTCCCC
TtttctttcctccttgggGATCCGAGTGAAATCTGGGTCGATCTTCTCTC
CGTTCTCCTCCGACTGGGGCTGAGGTCTGAACCTCGGTgGGGTCCGAAGA
GGAGGCCCCTAGGCC*GGCTCcTCAGCCCCTCCAGCCCGACCCGCCCTCT
TGACACAGGGTCCAGCTAAGGGCAGACAT***GGCTGCTAGTCCAGGGCC
AGGCTcTGAGACCCAAGGGCGCTGCCCAAGGAACCCTTGCCCCAGGGACC
CTGGGAGCAAAGCTCCTCACTCAGAGCCTGCAGCCCTGGgGTCTGAGGAC
AAGGAGGGACTGAGGACTGGGCGTGGGGAGTTCAGGCgGGGACACCGGGT
CCAGGGAGGTGACAAAGGCGCTGGGAGGGGGCGGACGGTGCCGGAGACTC
CTCCTGGGCCCTGTGGGCTCGTGGTCCTTGTGAGGACCCTGAGGG*CTGA
GGGGCCCCTGGGCCTAGGGACTTGCAGTGAGGGAGGCAGGGAGTGTCCCT
TGAGAACGTGGCCTCCGCGGGCTGGGTCCCCTCGTGCTCCCAGCAGGGA
GGACACCCCAGAGCAAGCGCCCCAGGTGGGCGGGGAGGGTCTCCTCACAG
GGGCAGCTGACAGATAGAC*GgccCCCGCCAGACAGATGCTTGATCCTGG
TCag***TACTGGGTTCGCcACTTCCCTGAACAGGGGCCCTCCGAACAGA
CACAGACGCAGACCaggCTCAGCACAgAAAATGCACTGACACCCAAACC
CTCATCTGggGGCCTGGCCGGCATCCCGCCCCAGGACCCAAGGCCCCTGC
CCCCTGGCAGCCCTGGACACGGTCCTCTGTGGGCGGTGGGGTCgGGGCTG
TGGTGACGGTGGCATCGGGGAGCCTGTGCCCCCTCCCTGAAAGGGCGGAG
AGGCTCAAGAGGGGACAGAAATGTCCTCCCCTAGGAAGACCTCGGACGGG
GGCGGGGGGTGGTCTCCGACAGACAGATGCCCGGGACCGACAGACCTGC
CGAGGGAAGAGGGCACCTCGGTCGGGTTAGGCTCCAGGCAGCACGAGGGA
GCGAGGCTGGGAGGGTGAGGACATGGGAGCCTGAGGAGGAGCTGGAGACT
TCAGCAGGCCCCCAGCTCCGGGCTTCGGGCTCTGAGATGCTCGGACGCAA
GGTGAGTGACCCCACCTGTGGCTGACCTGACCTGACCtCAGGGGGACAAG
GCTCAGCCTGGGACTCTgTGTCCCCATCGCCTGCACAGGGGATTCCCCTG
ATGGACACTGAGCCAACGACCTCCCGTCTCTCCCCGACCCCCAGGTCAGC
CCAAGGCCACTCCCACGGTCAACCTCTTCCCGCCCTCCTCTGAGGAGCTC
GGCACCAACAAGGCCACCCTGGTGTGTCTA
Seq ID No. 32
GCCACGCCCACTCCATCATGCGGGGAGGGGATGGGCAGACCCTCCAGAAA
GAAGCTCCCTGGGGTGCAGGTTAACAGCTTTCCCAGACACAGCCAGTACT
AGAGTGAGGTGAATAAGACATCCTCCTTGCTTGTGAAATTTAGGAAGTGC
CCCCAAACATCAGTCATTAAGATAAATAATATTGAATGCACTTTTTTTTT
TTTATTTTTTTTTTTGCTTTTTAGGGCCTAATCTGCAGCatatggaagt
tcccaggctacaagtcgaaccagagctgcagctgccagcctacatcacag
ccacagcaacaccagatccgagccacatctgtgactaacactgcagttca
cagcaacgccagatccttaacccattgagtgaggccagggatcaaaccca
catcctcatggatactagtctggttcgtaaaccactgagccaCAAGGGGA
ACTCCTGAATGCAATATTTTTGAAATTGAAATTAAATCTGTCACTCTTT
CACTTAAGAGTCCCCTTAGATTGGGGAAAATTTAAATATCTGTCATCTTA
GTGCATCTTTGCTCATATGATGTGAATAAAATCCCAAAATCCATATGAAT
GAAGCATCAAAATGTACATGAAGTCAGCCTGACCCTGCACTGCCCTCACT
TGCCTCATGTACCCCCACCTCAAAGGAAGATGCAGAAAGGAGTCCAGCC
CCTACACCGCCACCTGCCCCCACCACTGGAGCCCCTCAGGTCTCCCACCT
```

-continued

```
CCTTTTCTGAGCTTCAGTCTTCCTGTGGCATTGCCTACCTCTACAGCTGC
CCCCTACTAGGCCCTCCCCCTGGGGCTGAGCTCCAGGCACTGGACTGGGA
AAGTTAGAGGTTAAAGCATGGAAAATTCCCAAAGCCACCAGTTCCAGGCT
GCCCCCCACCCCACCGCCACGTCCAAAAAGGGGCATCTTCCCAGATCTCT
GGCTGGTATTGGTAGGACCCAGGACATAGTCTTTATACCAATTCTGCTGT
GTGTCTTAGGAAAGAaactctccctctctgtgcttcagtttcctcatcaa
taaaAGGAGCAGGCCAGGTTGGAGGGTCTGTGACGTCTGCTGAAGCAGCA
GGATTCTCTCTCCTTTTGCTGGAGGAGAACTGATCCTTCACCCCCAGGAT
CAACAGAGAAGCCAAGGTCTTCAGCCTTCCTGGGGACCCCTCAGAGGGAA
CTCAGGGCCACAGAGCCAGACCCTGATGCCAGAACCTTTGTCATATGCCC
AGACGGAGACTTCATCCCCCTCCTCCTCAGACCCTCCAGGCCCCAACAGT
GAGATGCTGAAGATATTAAGAAGGGCAAGTCAGcTTAAGTTTGGGGGT
AGAGGGGAACAGGGAGTGAGGAGATCTGGCCTGAGAGATAGGAGCCCTGG
TGGCCACAGGAGGACTCTTTGGGTCCTGTCGGATGGACACAGGGCGGCCC
GGGGGCATGTTGGAGCCCGGCTGGTTCTTACCAGAGGCAGGGGGCACCCT
CTGACACGGGAGCAGGGCATGTTCCATACATGACACACCCCTCTGCTCCA
GGGCAGGTGGGTGGCGGCACAGAGGAGCCAGGGACTCTGAGCAAGGGGTC
CACCAGTGGGGCAGTTGGATCCAGACTTCTCTGGGCCAGCGAGAGTCTAG
CCCTCAGCCGTTCTCTGTCCAGGAGGGGGTGGGGCAGGCCTGGGCGGCC
AGAGCTCATCCCTCAAGGGTTCCCAGGGTCCTGCCAGACCCAGATTTCCG
ACCGCAGCCACCACAAGAGGATGTGGTCTGCTGTGGCAGCTGCCAAGACC
TTGCAGCAGGTGCAGGGTGGGGGGTGGGGCACCTGGGGGCAGCTGGGG
TCACTGAGTTCAGGGAAAACCCCTTTTTTCCCCTAAACCTGGGGCCATCC
CTAGGGGAAACCACAACTTCTGAGCCCTGGGCAGTGGCTGCTGGGAGGGA
AGAGCTTCATCCTGGACCCTGGGGGGGAACCCAGCTCCAAAGGTGCAAGG
GCCCAGGTCCAAGGCTAGAGTGGGCCAAGCACCGCAATGGCCAGGGAGT
GGGGGAGGTGGAGCTGGACTGGATCAGGGCCTCCTTGGGACTCCCTACAC
CCTGTGTGACATGTTAGGGTACCCACACCCCATCACCAGTCAGGGCCTGG
CCCATCTCCAGGGCCAGGGATGTGCATGTAAGTGTGTGTGAGTGTGTGTG
TGTGGTGTAGTACACCCCTTGGCATCCGGTTCCGAGGCCTTGGGTTCCTC
CAAAGTTGCTCTCTGAATTAGGTCAAACTGTGAGGTCCTGATCGCCATCA
TCAACTTCGTTCTCCCCACCTCCCATCATTATCAAGAGCTGGGGAGGGTC
TGGGATTTCTTCCCACCCACAAGCCAAAAGATAAGCCTGCTGGTGATGGC
AGAAGACACAGGATCCTGGGTCAGAGACAAAGGCCAGTGTGTCACAGCGA
GAGAGGCAGCCGGACTATCAGCTGTCACAGAGAGGCCTTAGTCCGCTGAA
CTCAGGCCCCAGTGACTCCTGTTCCACTGGGCACTGGCCCCCCTCCACAG
CGCCCCCAGGCCCCAGGGAGAGGCGTCACAGCTTAGAGATGGCCCTGCTG
AACAGGGAACAAGAACAGGTGTGCCCCATCCAGCGCCCCAGGGGTGGGAC
AGGTGGGCTGGATTTGGTGTGAAGCCCTTGAGCCCTGgAACCCAAcCACA
GCAgGGCAGTTGGTAGATGCCATTTGGGGAGAGGCCCCAGGAGTAAGGGC
CATGGGCCCTTGAGGGGGCCAGGAGCTGAGGACAGGGACAGAGACGGCCC
AGGCAGAGGACAGGGCCATGAGGGGTGCACTGAGATGGCCACTGCCAGCA
GGGGCAGCTGCCAACCCGTCCAGGGAACTTATTCAGCAGTCAGCTGGAGG
TGCCATTGACCCTGAGGGCAGATGAAGCCCAGGCCAGGCTAGGTGGGCTG
TGAAGACCCCAGGGGACAGAGCTCTGTCCCTGGGCAGCACTGGCCTCTCA
TTCTGCAGGGCTTGACGGGATCCCAAGGCCTGCTGCCCCTGATGGTAGTG
GCAGTACCGCCCAGAGCAGGACCCCAGCATGGAAACCCCAACGGGACGCA
GCCTGCGGAGCCCACAAAACCAGTAAGGAGCCGAAGCAGTCATGGCACGG
GGAGTGTGGACTTCCCTTTGATGGGGCCCAGGCATGAAGGACAGAATGGG
ACAGCGGCCATGAGCAGAAAATCAGCCGGAGGGGATGGGCCTAGGCAGAC
GCTGGCTTTATTTGAAGTGTTGGCATTTTGTCTGGTGTGTATTGTTGGTA
TTGATTTTATTTTAGTATGTCAGTGACATACTGACATATTATGTAACGAC
ATATTATTATGTGTTTTAAGAAGCACTCCAAGGGAACAGGCTGTCTGTAA
TGTGTCCAGAGAAGAGAGCAAGAGCTTGGCTCAGTCTCCCCCAAGGAGGT
CAGTTCCTCAACAGGGGTCCTAAATGTTTCCTGGAGCCAGGCCTGAATCA
AGGGGgTCATATCTACACGTGGGGCAGACCCATGGACCATTTTCGGAGCA
ATAAGATGGCAGGGAGGATACCAAGCTGGTCTTACAGATCCAGGGCTTTG
ACCTGTGACGCGGGCGCTCCTCCAGGCAAAGGGAGAAGCCAGCAGGAAGC
TTTCAGAACTGGGGAGAACAGGGTGCAGACCTCCAGGGTCTTGTACAACG
CACCCTTTATCCTGGGGTCCAGGAGGGGTCACTGAGGGATTTAAGTGGGG
GACCATCAGAACCAGGTTTGTGTTTTGGAAAAATGGCTCCAAAGCAGAGA
CCAGTGTGAGGCCAGATTAGATGATGAAGAAGAGGCAGTGGAAAGTCGAT
GGGTGGCCAGGTAGCAAGAGGGCCTATGGAGTTGGCAAGTGAATTTAAAG
TGGTGGCACCAGAGGGCAGATGGGAGGAGCAGGCACTGTCATGGACTGT
CTATAGAAATCTAAAATGTATACCCTTTTTAGCAATATGCAGTGAGTCAT
AAAAGAACACATATATATTTAAATTGTGTAATTCCACTTCTAAGGATTCA
TCCCAAGGGGGAAAATAATCAAAGATGTAACCAAAGGTTTACAAACAAG
AACTCATCATTAATCTTCCTTGTTGTTATTTCAACGATATTATTATTATT
ACTATTATTATTATTATTTtgtcttttgcattttctagggccactc
ccacggcatagagaggttcccaggctaggggtcaaatcggagctacagct
gccggcctacgccagagccacagcaacgcaggatctgagccacagcaatg
caggatctacaccacagctcatggtaacgctggatccttaacccaatgag
tgaggccagggatcgaacctgtaacttcatggttcctagtcggattcatt
aaccactgagccacgacaggaactccAACATTATTAATGATGGGAGAAAA
CTGGAAGTAACCTAAATATCCAGCAGAAAGGGTGTGGCCAAATACAGCAT
GGAGTAGCCATCATAAGGAATCTTACACAAGCCTCCAAAATTGTGTTTCT
GAAATTGGGTTTAAAGTACGTTTGCATTTTAAAAAGCCTGCCAGAAAATA
CAGAAAAATGTCTGTGATATGTCTCTGGCTGATAGGATTTTGCTTAGTTT
TAATTTTGGCTTTATAATTTTCTATAGTTATGAAAATGTTCACAAGAAGA
TATATTTCATTTTAGCTTCTAAAATAATTATAACACAGAAGTAAATTTGTG
CTTTAAAAAAATATTCAACACAGAAGTATATAAAGTAAAAATTGaggagt
```

-continued tcccatcgtggctcagtgattaacaaacccaactagtatccatgaggata
tggatttgatccctggccttgctcagtgggttgaggatccagtgttgctg
tgagctgtggtgtaggttgcagacacagcactctggcgttgctgtgactc
tggcgtaggccggcagctacagctccatttggacccttagcctgggaacc
tccatatgcctgagatacggcccTAAAAAGTCAAAAGCCAAAAAAATAGT
AAAAATTGAGTGTTTCTACTTACCACCCCTGCCCACATCTTATGCTAAAA
CCCGTTCTCCAGAGACAAACATCGTCAGGTGGGTCTATATATTTCCAGCC
CTCCTCCTGTGTGTGTATGTCCGTAAAACACACACACACACACACACACG
CACACACACACACGTATCTAATTAGCATTGGTATTAGTTTTTCAAAAG
GGAGGTCATGCTCTACCTTTTAGGCGGCAAATAGATTATTTAAACAAATC
TGTTGACATTTTCTATATCAACCCATAAGATCTCCCATGTTCTTGGAAAG
GCTTTGTAAGACATCAACATCTGGGTAAACCAGCATGGTTTTTAGGGGGT
TGTGTGGATTTTTTTCATATTTTTAGGGCACACCTGCAgcatatggagg
ttcccaggctaggggttgaatcagagctgtagctgccggcctacaccaca
gccacagcaacgccagatccttaacccactgagaaaggccagggattgaa
cctgcatcctcatggATGCTGGTCAGATTTATTTCTGCTGAGCCACAACA
GGAACTCCCTGAACCAGAATGCTTTTAACCATTCCACTTTGCATGGACAT
TTAGATTGTTTCCATTTAAAAATACAAATTACAaggagttcccgtcgtgg
ctcagtggtaacgaattggactaggaaccatgaggtttcgggttcgatcc
ctggccttgctcggtgggttaaggatccagcattgatgtgagatatggtg
taggtcgcagacgtggctcggatcccacgttgctgtggctctggcgtagg
ccggcaacaacagctccgattcgaccctagccTGggaacctccatgtgc
cacaggagcagccctaGAAAAGGCAAAAAGACAAAAAAATAAAAAATTAA
AATGAAAAATAAAATAAAAATACAAATTACAAGAGACGGCTACAAGGAA
ATCCCCAAGTGTGTGCAAATGCCATATATGTATAAAATGTACTAGTGTCT
CCTCGCGGGAAAGTTGCCTAAAAGTGGGTTGGCTGGACAGAGAGGACAGG
CTTTGACATTCTCATAGGTAGTAGCAATGGGCTTCTCAAAATGCTGTTCC
AGTTTACACTCACCATAGCAAATGACAGTGCCTCTTCCTCTCCACCCTTG
CCAATAATGTGACAGGTGGATCTTTTTCTATTTTGTGTATCTGACAAGCA
AAAAATGAGAACAggagttcctgtcgtggtgcagtgggagacaaatctgac
taggaaccatgaaatttcgggttcaatccctggcctcactcagtaggtaa
aggatccagggttgcagtgagctgtggggtaggtcgcagacacagtgcaa
atttggccctgttgtgctgtggtgtaggccggcagctatagctccaatt
ggaccctagcctgggaacctccttatgccgtgggtgaggccctAAAAAA
AAGAGTGCAAAAAAAAAAATAAGAACAAAAATGATCATCGTTTAATTCT
TTATTTGATCATTGGTGAAACTTATTTTCCTTTATATTTTTATTGACTG
ATTTTATTTCTCCTATGAATTTACCGGTCATAGTTTTGCCTGGGTGTTTT
TACTCCGGTTTTAGTTTTGGTTGGTTGTATTTTCTTAGAGAGCTATAGAA
ACTCTTCATCTATTTGGAATAGTAATTCCTCATTAAGTATTTGTGCTGCA
AAAAATTTTCCCTGATCTGTTTTATGCTTTTGTTTGTGGGGTCTTTCACG
AGAAAGCCTTTTTAGTTTTTACACCCTCAGCTTGGTTGTTTTTCTTGATTG TGTCTGTAATCTGCGGCCAACATAGGAAACACATTTTTACTTTAGTGTTT
TTTTCCTATTTTCTTCAAGTACGTCCATTGTTTTGGTGTCTGATTTACT
TTGCCTGGGGTTTGTTTTTGTGTGGCAGGAATATAAACTTATGTATTTTC
CAAATGGAGAGCCAATGGTTGTATATTTGTTGAATTCAAATGCAACTTTA
TCAAACACCAAATCATCGATTTATCACAACTCTTCTCTGGTTTATTGATC
TAATGATCAATTCCTGTTCCACGCTGTTTTAATTATTTTAGCTTTGTGGA
TTTTGGTGCCTGGTAGAGAACAAAGCCTCCATTATTTTCATTCAAAATAG
TCCCGTCTATTATCTGCCATTGTTGTAGTATTAGACTTTAAAATCAATTT
ACTGATTTTCAAAAGTTATTCCTTTGGTGATGTGGAATACTTTATACTTC
ATAAGGTACATGGATTCATTTGTGGGGAATTGATGTCTTTGCTATTGTGG
CCATTTGTCAAGTTGTGTAATATTTTACCCATGCCAACTTTGCATATTGT
ATGTGAGTTTATTCCCAGGGTTTTTAATAGGATGTTTATTGAAGTTGTCA
GTGTTTCCACAATTTCATCGCCTCAGTGCTTACTGTTTGCATAAAAGGAA
ACCTACTCACTTTTGCCTATTGCTCTTGTATTCAATCATTTTAGTTAACT
CTTGTGTTAATTTTGAGAGTTTTTCAGCTGACTGTCTGGGGTTTTCTTTA
ATAGACTAGCCCTTTGTCTGTAAAGAATAATTTTATCGAATTTTTCTTAA
CACTCACACTCTCCCCACCCCCACCCCCGCTCATCTCCTTTCATTGGGTC
AAATCTGTAGAATACAATAAAAGTAAGAGTGGGAACCTTAGCCTTTAAGT
CGATTTTGCCTTTAAATGTGAATGTTGCTATGTTTCGGGACATTCTCTTT
ATCAAGTTGCGGATGTTTCCTTAGATAATTAACTTAATAAAAGACTGGAT
GTTTGCTTTCTTCAAATCAGAATTGTGTTGAATTTATATTGCTATTCTGT
TTAATTTTGTTTCAAAAAATTTACATGCACACCTTAAAGATAACCATGAC
CAAATAGTCCTCCTGCTGAGAGAAAATGTTGGCCCCAATGCCACAGGTTA
CCTCCCGACTCAGATAAACTACAATGGGAGATAAAATCAGATTTGGCAAA
GCCTGTGGATTCTTGCCATAACTCTCAGAGCATGACTTGGGTGTTTTTTC
CTTTTCTAAGTATTTTAATGGTATTTTTGTGTTACAATAGGAAATCTAGG
ACACAGAGAGTGATTCAATGAGGGGAACGCATTCTGGGATGACTCTAGGC
CTCTGGTTTGGGGAGAGCTCTATTGAAGTAAAGACAATGAGAGGAAGCAA
GTTTGCAGGGAACTGTGAGGAATTTAGATGGGGAATGTTGGGTTTGAGGT
TTCTATAGGGCACGCAAGCAGAGATGCACTCAGGAGGAAGAAGGAGCATA
AATCTAGAGGCAAAAGAGAGGTCAGGACTGGAAATAGAGATGCGAGACA
CCAGGGTGGCAGTCAGAGAGCACAGTGTGGGTCAGAAGACAGTGGAAGAA
CACAAGGGACAGAGAGGGATCTCCAACTTCACTGGGATGAGGGCCTGTT
GGCCTTGACCTGAGAGATTTCCAGGAGTTGAGGGTGGGAAGGAGAGGGCT
CCTGCACATGTCCTGACATGAAACGGTGCCCAGCATATGGGTGCTTGGAA
GACATTGTTGGACAGATGGATGGATGATGGATGATGGATGAATGGATGGA
TGGAAGATGATGGATAAATGGATGATGGATGGATGGACAGAAGGACAAAG
AGATGGACAGAAAGACAGTGATCTGAGAGAGCAGAGAAGGCTTCATGAAA
GGACAGGAACTGAACTGTCTCAGTGGGTGGGACAATGGTAGGGGGTT
TCCACATGGAGGCACCAGGGGTCAGGAATAATCTAGTGTCCACAGGCCCA -continued
```
GGAAGGAAGCTGTCTGCAGGAAATTGTGGGGAAGAACCTCAGAGTCCTTA
AATGAGGTCAGGAGTGGTCAGGAGGGTCTGATCAGGTAAGGACTCATGTC
CATCATCACATGGTCACCTAAGGGCATGTAGCTCTCAGCATCTCCATCAG
GACAGTCTCAGAATGGGGGCGGGGTCACACACTGGGTGACTCAAGGCGTG
GGTCATGCCTGCCTCGGACGTGGGCCTGGGCATGGGACACCTCCAGACC
ATGGGCCCGCCCAGGGCTGCACTGGcctctggtgggctagctacccgtcc
aagcaacacaggacacagccctacctgctgcaaccctgtgcccgaaacgc
ccatctggttcctgctccagcccggccccagggaacaggactcaggtgct
agcccaatggggttttgttcgagcctcagtcagcgtggTATTTCTCCGGC
AGCGAGACTCAGTTCACCGCCTTAGGttaagtggttctcatgaatttcct
agcagtcctgcactctgctatgccgggaaagtcacttttgtcgctggggg
ctgtttccccgtgcccttggagaatcaaggattgcccaacttctctgtg
ggggaggtggctggtcttgggtgaccagcaggaagggccccaaaagcag
gagcagctgcctccagAATACAACTGTCGGCTACAGCTCAAACAGGAGGC
CTGGACTGGGGTTTAACCACCAGGGCGGCACGAAGGAGCGAGGCTGGGAG
GGTGAGGACATGGGAGCCTGAGGAGGAGCTGGAGACTTCAGCAGGCCCCC
AGCTCCGGGCTTCGGGCTCTGAGATGCTCGGACGCAAGGTGAGTGACCCC
ACCTGTGGCTGACCTGACCTCAGGGGGACAAGGCTCAGCCTGAGACTCTG
TGTCCCCATCGCCTGCACAGgggattcccctgatggacactgagccaacg
acctcccgtctctcccgaccccaggtcagcccaaggccgcccccacgg
tcaacctcttcccgccctcctctgaggagctcggcaccaacaaggccacc
ctggtgtgtctaataagtgacttctacccgAAGGGCGAATTCCAGCACAC
TGGCGGCCGTTACTAGTGGATCCGAGCTCGGTACCAAGCTTGATGCATAG
CTTGAGTATCTA
Seq ID No. 33
agatctttaaaccaccgagcaaggccagggatcgaacccgcatcctcatg
aatcctagttgggttcgttaaccgctgaaccacaatgggaactcctGTCT
TTCACATTTAATTCACAACCTCTCCAGGATTCTGGGGGTGGGTGGGGAAT
CCTAGGTACCCACTGGGAAAGTAATCCAAGGGGAGAGGCTCACGGACTcT
AGGGATCGGCGGAGGAGGGAAGGTATCTCCCAGGAAACTGGCCAGGACAC
ATTGGTCCTCCGCCCTCCCCTTCCTCCCACTCCTCCTCCAGACAGGACTG
TGCCCACCCCCTGCCACCTTTCTGGCCAGAACTGTCCATGGCAGGTGACC
TTCACATGAGCCCTTCCTCCCTGCCTGCCCTAGTGGGACCCTCCATACCT
CCCCCTGGACCCCGTTGTCCTTTCTTTCCAGTGTGGCCCTGAGCATAACT
GATGCCATCATGGGCTGCTGACCCACCCGGGACTGTGTTGTGCAGTGAGT
CACTTCTCTGTCATCAGGGCTTTGTAATTGATAGATAGTGTTTCATCATC
ATTAGGACCGGGTGGCCTCTATGCTCTGTTAGTCTCCAAACACTGATGAA
AACCTTCGTTGGCATAGTCCCAGCTTCCTGTTGCCCATCCATAAATCTTG
ACTTAGGGATGCACATCCTGTCTCCAAGCAACCACCCCTCCCCTAGGCTA
ACTATAAAACTGTCCCAATGGCCCTTGTGTGGTGCAGAGTTCATGCTTCC
AGATCATTTCTCTGCTAGATCCATATCTCACCTTGTAAGTCATCCTATAA
```
-continued
```
TAAACTGATCCATTGATTATTTGCTTCTGTTTTTTCCATCTCAAAACAGC
TTCTCAGTTCAGTTCGAATTTTTTATTCCCTCCATCCACCCATACTTTCC
TCAGCCTGGGGAACCCTTGCCCCCAGTCCCATGCCCTTCCTCCCTCTCTG
CCCAGCTCAGCACCTGCCCACCCTCACCCTTCCTGTCACTCCCTAGGACT
GGACCATCCACTGGGGCCAGGACACTCCAGCAGCCTTGGCTTCATGGGCT
CTGAAATCCATGGCCCATCTCTATTCCTCACTGGATGGCAGGTTCAGAGA
TGTGAAAGGTCTAGGAGGAAGCCAGGAAGGAAACTGTTGCATGAAAGGCC
GGCCTGATGGTTCAGTACTTAAATAATATGAGCTCTGAGCTCCCCAGGAA
CCAAAGCATGGAGGGAGTATGTGCCTCAGAATCTCTCTGAGATTCAGCAA
AGCCTTTGCTAGAGGGAAAATAGTGGCTCAACCTTGAGGGCCAGCATCTT
GCACCACAGTTAAAAGTGGGTATTTGTTTTACCTGAGGCCTCAGCATTAT
GGGAACCGGGCTCTGACACAAACACAGGTGCAGCCCGGCAGCCTCAGAAC
ACAGCAACGACCACAAGCTGGGACAGCTGCCCCTGAACGGGGAGTCCACC
ATGCTTCTGTCTCGGGTACCACCAGGTCACCATCCCTGGGGGAGGTAGTT
CCATAGCAGTAGTCCCCTGATTTCGCCCCTCGGGCGTGTAGCCAGGCAAG
CTCCTGCCTCTGGACCCAGGGTGGACCCTTGCTCCCCACTACCCTGCACA
TGCCAGACAGTCAAGACCACTCCCACCTCTGTCTGAGGCCCCCTTGGGTG
TCCCAGGGCCCCCGAGCTGTCCTCTACTCATGGTTCTTCCACCTGGGTAC
AAAAGAGGCGAGGGACACTTTTCTCAGGTTTGCGGCTCAGAAAGGTACCT
TCCTAGGGTTTGTCCACTGGGAGTCACCTCCCTTGCATCTCAATGTCAGT
GGGGAAAACTGGGTCCCATGGGGGATTAGTGCCACTGTGAGGCCCCTGA
AGTCTGGGGCCTCTAGACACTATGATGATGAGGGATGTGGTGAAAAACCC
CACCCCAGCCCTTCTTGCCGGGACCCTGGGCTGTGGCTCCCCCATTGCAC
TTGGGGTCAGAGGGGTGGATGGTGGCTATGGTCAGGCATGTTTCCCATGA
GCTGGGGGCACCCTGGGTGACTTTCTCCTGTGAATCCTGAATTAGCAGCT
ATAACAAATTGCCCAAACTCTTAGGCTTAAAACAACACATTTATTCCT
CTGGGTCCCAGGGTCAGAAGTCCAAAATGAGTCCTATAGGCTAAATTTGA
GGTGTCTCTGGGTTGAGCTCCTCCTGGAAGCCTTTTCCAGCCTCTAGAGT
CCCAAGTCCTTGGCTCTGGGCCCTCCCTCAAGCTTCAAAGCCACAGAAG
CTTCTAATCTCTCTCCCTTCCCCTCTGACCTCTGCTCCCATCCTCATACC
CTGTCCCCTCACTCTGACCCTCCTGCCTCCCTCTTTCCCTTATAAAGACC
CTGCATGGGCCACGGAGATAATCCAGGGTAATCGCCCCTCTTCCAGCCC
TTAACTCCATCCCATCTGCAAAATCCCTGTCACCCCATAATGGACCTACT
GATGGTCTGGGGGTTAGGACGTGGACAACTTGGGGCCTTATTCATCTGAT
CACAACTCCAGTTCCCAGACCCCCAGACCCCCGGGCATTAGGGAAACTTC
TCCCAGTTCCTCTCCCTCTGTGTCCTGCCCAGTCTCCAGGATGGGCCACT
CCCGAGGGCCCTTCAGCTCAGGCTCCCCCTCCTTTCTCCCTGGCCTCTTG
TGGCCCCATCTCCTCCTCCGCTCACAGGGAGAGAACTTTGATTTCAGCTT
TGGCTCTGGGGCTTTGCTTCCTTCTGGCCATTGGCTGAAGGGCGGGTTTC
TCCAGGTCTTACCTGTCAGTCATCAAACCGCCCTTGGAGGAAGACCCTAA
TATGATCCTTACCCTACAGATGGAGACTCGAGGCCCAGAGATCCTGAGTG
```

ACCTGCTCACATTCACAGCAGGGACTGAACCCCAGTCACCTACCCAACTC

CAGGGCTCAGCGCTTTTTTTTTTTTTTTCTTTTTgccttttcgagggcc gctcccgcaacatatggagatttccaggctaggggtctaattggagcagt cgacactggcctaagccaaagccacagcaacaagggcaagccgcttctgc agcctataccacagctcacggcaatgccggatccttaacccactgagcaa agccagggattgaacctgcaacctcatgtttcctagtcaaatttgttaac cactgacccatgacgggaactcccAGGGCTCAGCTCTTGACTCCAGGTTC

GCAGCTGCCCTCAAAGCAATGCAACCCTGGCTGGCCCCGCCTCATGCATC

CGGCCTCCTCCCCAAAGAGCTCTGAGCCCACCTGGGCCTAGGTCCTCCTC

CCTGGGACTCATGGCCTAAGGGTACAGAGTTACTGGGGCTGATGAAGGGA

CCAATGGGACAGGGCCTCAAATCAAAGTGGCTGTCTCTCTCATGTCCC

TTCCTCTCCTCAGGGTCCAAAATCAGGGTCAGGGCCCCAGGGCAGGGGCT

GAGAGGGCCTCTTTCTGAAGGCCCTGTCTCAGTGCAGGTTATGGGGGTCT

GGGGGAGGGTCAATGCAGGGCTCACCCTTCAGTGCCCCAAAGCCTAGAGA

GTGAGTGCCTGCCAGTGGCTTCCCAGGCCCAATCCCTTGACTGCCTGGGA

ATGCTCAAATGCAGGAACTGTCACAACACCTTCAGTCAGGGGCTGCTCTG

GGAGGAAAAACACTCAGAATTGGGGGTTCAGGGAAGGCCCAGTGCCAAGC

ATAGCAGGAGCTCAGGTGGCTGCAGATGGTGTGAACCCCAGGAGCAGGAT

GGCCGGCACTCCCCCAGACCCTCCAGAGCCCAGGTTGGCTGCCCTCTT

CACTGCCGACACCCCTGGGTCCACTTCTGCCCTTTCCCACCTAAAACCTT

TAGGGCTCCCACTTTCTCCCAAATGTGAGACATCACCACGGCTCCCAGGG

AGTGTCCAGAAGGGCATCTGGCTGAGAGGTCCTGACATCTGGGAGCCTCA

GGCCCCACAATGGACAGACGCCCTGCCAGGATGCTGCTGCAGGGCTGTTA

GCTAGGCGGGGTGGAGATGGGGTACTTTGCCTCTCAGAGGCCCCGGCCCC

ACCATGAAACCTCAGTGACACCCCATTTCCCTGAGTTCACATACCTGTAT

CCTACTCCAGTCACCTTCCCCACGAACCCCTGGGAGCCCAGGATGATGCT

GGGGCTGGAGCCACGACCAGCCCACGAGTGATCCAGCTCTGCCAATCAGC

AGTCATTTCCCAAGTGTTCCAGCCCTGCCAGGTCCCACTACAGCAGTAAT

GGAGGCCCCAGACACCAGTCCAGCAGTTAGAGGGCTGGACTAGCACCAGC

TTTCAAGCCTCAGCATCTCAAGGTGAATGGCCAGTGCCCCTCCCCGTGGC

CATCACAGGATCGCAGATATGACCCTAGGGGAAGAAATATCCTGGGAGTA

AGGAAGTGCCCATACTCAAGGATGGCCCCTCTGTGACCTAACCTGTCCCT

GAGGATTGTACTTCCAGGCGTTAAAACAGTAGAACGCCTGCCTGTGAACC

CCCGCCAAGGGACTGCTTGGGGAGGCCCCCTAAACCAGAACACAGGCACT

CCAGCAGGACCTCTGAACTCTGACCACCCTCAGCAAGTGGCACCCCCGC

AGCTTCCAAGGCAC

Seq ID No. 34
AACAAGATGCTACCCCACCAACAAAATTCACCGGAGAAGACAAGGACAGG

GGGTTCCTGGGGTCCTGACAGGGTCACCAAAGAGGGTTCTGGGGCAGCAG

CAACTCCAGCCGCCTCAGAACAGAGCCTGGAAGCTGTACCCTCAGAGCAG

AGGCGGAGAGAGAAAGGGCCTCTTGGTGGGTCAGCAGGAGCAGAGGCTCA

GAGGTGGGGGTTGCAGCCCCCCCTTCAACAGGCCAACACAGTGAAGCAGC

TGACCCCTCCACCTTGGAGACCCCAGACTCCTGTCTCCCACGCCACCTTG

GTTTTTAAGGTAATTTTTATTTTATATCAGAGTATGGTTGACTTACAATG

TTGTGTTGGTTTCAGGTGTACAGCAGAGTGATTCACTTCTACATAGACTC

ATATCTATTCTTTCTCAGATTCTTTTCCCATATAGGTTATTACAGAATAT

TGAGTAGATCCCTGCTGATTACCCATTTTTATAATTGTATATGTTAATCC

CAAACTCCTAATTTATCCCTCCCCAGACTATGATTCTTTATATCTCTATC

TGTTTCCTAATCTGTCTCCTCTAAGTCACCCTAGGAGAGCAGAGGGGTCA

CGTCTGTCCTGTCCTGGCCCAGCCACCTCTCTCCACCCAGGAATCCCTTG

CATTTGGTGCCAAGGGCCCGGCCCCGCCCTAAAGAGAAAGGAGAACGGGA

TGTGGACAGGACACCGGGCAGAGAGGGACAAGCAGAGGATGCCAGGGTAG

GGAGGTCTCCAGGGTGGATGGTGGTCTGTCCGCAGGCAGGATGAGGCAGG

AAGGGTGTGGATGTACTCGGTGAGGCTGGCGCATGGCCTGGAGTGTCCTG

AGCCCTGGGAGGCCTCAGCCCTGGATCAGATCTGTGATTCCAAAGGGCCA

CTGCATCCAGAGACCGTTGAGTGGCCCATTGTCCTGAACCATTTATAGAA

CACAGGACAAGCGGTACCTGACTAAGCTGCTCACAGATTCCATGAGGCTG

ATGCCAGGGTTGTCACCCCATCTCACAGGCAGGGAAACTGATGCATATAC

TGCAGAGCCAGGCAGAGGCCCTCCCAGTGCCCCTCCCAGCCTGTGGCCC

CCCTCCAGTGGCTGGACACTGAGGCCACACTGGGGCACCCTGTGGAGATC t

Seq ID No. 35
AGATCTGGCCAGGCCAGAGAAGCCCATGTGGTGACCTCCCTCCATCACTC

CACGCCCTGACCTGCCAGGGAGCAGAAAGTAGGCCCAGGGTGGACCCGGT

GGCCACCTGCCACCCCATGGCTGGGAGAAGGGAGGGCCTGGGCAAAGGGC

CTGGGAAGCCTGTGGTGGGACCCCAGACCCCAGGGTGGACAGGGAGGGTC

CCACACCCACAGCCATTTGCTTCCCTCTGTGGGTTCAGTGTCCTCATCTC

ATCTGTGGGGAGGGGCTGATAATGAATCTCCCCCATTGGGGTGGGCTTG

GGGATTAAAGGGCCAGTGTCTGTGATATGCCTGGACCATAGTGACCCTCA

CCCTCCCCAGCCATTGCTGTCACCTTCCGGGCTCTTGCCCAGGCCTGCCT

GACATGCTGTGTGACCCTGGGCAAGATGATCCCCCTTTCTGGGCCCCAGC

CTTCCTCTCTGCTCCGGAAGTGCTTCCTGGGGAAACCTGTGGGCTGGATC

CTATAGGAAACCTGTCCAATTCCTGGATGCACAGAGGGGCAGGGAGGCCC

TGGGCCTGGAGGGGCAGGGAGGCTCGAGGTGGGAGCAGGGTAGGGGCCAG

TCCAGGGCAAGGAGGTGGGTGGGTAGGGTG

Seq ID No. 36:
GATCTGTGTTCCATCTCAGAGCTATCTTAGCAGAGAGGTGCAGGGGCCTC

CAGGGCCACCAAAGTCCAGGCTCAGCCAGAGGCAATGGGGTATCGATGAG

CTACAGGACACAGGCGTCAGCCCAGTGTCAGGGAGAATCACCTTGTTTGT

TTTCTGAGTTCCTCTTAAAATAGAGTTAATTGGTCTTGGCCTTACGGTTT

ACAATAACAACTGCACCCTGTAAACAACGTGAAGAGTACAGAACAACAAA

TGGGGGAAAACATATTTCACCTGAAAGAGCCACCGCTCATATTTTGATGG

-continued
ATTTCCTTCTAGTTTAATCCTGTTTTAATTGTAAACTGTTAAAACAAACA
TAAATAAAGAAAATGCATCTGTAAAGTTTAAAAGTCATATCTATGGTGAT
GGTTGCAAAACACTGTGAATGTTCACTTTGAAATCGTGAACTCTACGTGA
TATGCATGTCCCGTTAATTAACCTCACAGGCTCAGAATGTGGTTCATTAT
TTCTTTAATTTTCCTTTAATTTTATGTCCTCTGTGTGTGCCCTTAAACCA
ACTACTTTTCAGCTCTGCCTGTTTTTGACCTTCACATAGATGACATTTGT
GAGTGTTTTCTTTCTCAACACTGGGTCTGATACCCACCCACGCTGTCTGC
TGTCACTGCGGACGTGGAGGGCCACCACCCAGCTATGGCCCCAGCCAGGC
CAACACTGGATGAATCTGCCCCCAGAGCAGGGCCACCAACACTGGAGGTG
CAGAGAGGGTTTCTTCAGGGCATCATTATCCAAGGCATTGTTTCTACTG
TAAGCTTTCAAAATGCTTCCCCTGATTATTAAAAGAAATAATAAGATGGG
GGGAAAGTACAAGAAGGGAAGTTTCCAGCCCAGCCTGAAGATCGTGCTGG
TTGTATCTGGAGCCTGTCTTCCTGACAGGCCTCTATTCCCAGAGTTA
Seq ID No. 37:
GGATCCTAGGGAAGGGAGGGCGGGGCCTGGACAAAGGGGGCCTAAAGGA
CATTCTCACCTATCCCACTGGACCcctgctgtgctctgagggagggagca
gagaggggtctgaggccttttcccagCTCCTCTGAGTCCCTCCTCCGAG
CACCTGGACGGAAGCCCCTCCTCAGGGAGTCCTCAGACCCCTCCCCTCCA
GCCAGGTTGGCCTGTGTGGAGTCCCCAGTAAGAATAGAATGCTCAGGGCT
TCGAGCTGAGCCCTGGCTACTTGGGGGGTGCTGGGGATTGGGGGTGCTG
GGCGGGGAGCTGGGGTGTCACTAGATGCCAGTAGGCTGTGGGCTCGGGTC
TGGGGGGTCTGCACATGTGCAGCTGTGGGAAGGCCCTATTGGTGGTACCC
TCAGACACATATGGCCCCTCAATTTCTGAGACCAGAGACCCCAGTCTGGC
CTTCCCAGAACAGCTGCCCCTGGTGGGGGAGATGTAGGGGGGCCTTCAGC
CCAGGACCCCCAACGGCAGGGCCTGAGGCCCCCATCCCCTTGTCCTGGGC
CCAGAGCCTCAGCTATCAGGCCTATCAGAGATCCTGGCTGCCCAGCTCAG
GTTCCCCAGGAGCCAGAGGGAGGCCAGGGGTTACTAGGAAATCCGGAAAG
GGTCTTTGAGGCTGGGCCCCACCCTCTCAGCTTTCACAGGAGAAACAGAG
GCCCACAGGGGCAAAGGACTTGCCAGACTCACAATGAGCCCAGCAGCTG
GACTCAAGGCCCAGTGTTCGGCCCCACAACAGCACTCACGTGCCCTTGAT
CGTGAGGGCCCCCTCTCAGCCAGGCATTCAGACCTGTGACCTGCATCTA
AGATTCAGCATCAGCCATTCTGAGCTGAAGAGCCCTCAGGGTCTGCAGTC
AAGGCCACAGGGCCAGACCTCCAACGGCCAGACATCCCAGCCAGATTCCT
TTCTGGTCAATGGGCCCAGTCTGGCTTGCCTCCTGCAGGCCCAGTGCCG
CCTTCTTCCCCTGGGCCTGTGGAGTCCAGCCTTTCAGTTTCCCACCCACA
TCCTCAGCCACAATCCAGGCTCAGAGGCAATGTCCGTGGGCAGCCCTGT
GTGACCCCTCTGTGGGTGATCCTCAGTCCTACCCTTAGCAGACAGCGCAT
GAGGGGCCCTCTTGAACCTGAGGGATACTCCATGTCGGAGGGGAGAAGCT
GGCCTTCCCCACCCCCACTTCCAGGCCTTGGGGAGCAGAGAAAGACCCCA
GACCTGGGTCCCTTCTAACAGGCCAGGCCCCAGCCCAGCTCTCCACCAGC
CCCAGGGGCCTCGGGTCCACGCCTGGGGACTGGAGGGTGGGCCTGTCAGG -continued
CGCTGACCCAGAGGCAGGACAGCCAAGTTCAGGATCCCAGCCAGGTGGTC
CCCGTGCACCATGCAGGGGTGTCACCCACACAGGGGTGTTGCCACCCTCA
CCTGACTGTCCTCATGGGCCACATGGAGGTATCCTGGGTTCATTACTGGT
CAACATACCCGTGTCCCTGCAGTGCCCCCTCTGGcgcacgcgtgcacgcg
cacacgcacacactcatacaGAGGCTCCAGCCAACAGTGCCCTCTAGTAG
GCACTGCTGTCACTTCTAAAAGGTCGCAATCATACTTGTAAAGACCCA
AGATTGTTCAGAAATCCCAGATGGAGAAGTCTGGAAAGATCtTTTTCTCC
TTTCACGGGCTGGGGAAATGTGACCTGGCCAAGGTCACACAGCAAGTGGT
GGAACCCTGGCCCCTGATTCCAGCTCATTCCAGTTCCCAAGGCCCTGCCA
GAGCCCAGAGGCTGGGCCCTCTGGGGCAGAGGAGCTGGGGTCCTCCCCCC
TACACAGAGCACACAGCCCCGCAAGAGAAGAGACCTTGGGGAGAGG
AATCTCCAGACCAGAGATCCCAGTATGGGTCTCCTCTATGCTGACGGGAT
GGGATGTCAAGAGGGGAGGGGCTGGGCTTTAGGGAAACACACAAAAATC
GCTGAGAACACTGACAGGTGCGACACACCCACCCCTAATGCTAACCTGTG
GCCCATTACTCAgatct
Seq ID No. 38
GATCTTCTCCTAAGACCAAGGAAAACTGGTCATACCAGGTCCACTTGTCC
CCTGTGGCCATTGTCCCTCCTTCCCCAGAAGAAACAAGCACTTTCCACTC
CACAAGTAGCTCCTGATCAGCTTGGAAGCCCGGTGCTGCTCTGGGCCCTG
GGGACACGCAGGGGCATCAGAGACCAAATCCTGGAACAAAGTTCCAGTG
GGTGAGGCAGGCCGGACAAGCAACACGTTATACCATAATATGAGGCAAAA
TATAATGTGAGTTCTTTATGAAAGGAAGGGGTTGCAGGTGCAACTGTTGG
CTTAGGTGGATGGTCACCCCTGAATGGAGGAGGGGTTCCCAGGGCATGT
GCCTGGGGAGAAGGCTCCTGGCAGGAGGGACAGCAAGTGCAAGGGCCCT
GTGATCAAATGTGCCTGGCAAGTTGCAGGAACAGCTAGAAGGCCAGCAAG
GTTGGAACCAAGGAAGGGGTCAGGGGAGGGGCAGGGCCCTCAGGGCCTTG
CCCAGCAGCCTGAGCATCTGGAGATTTGTCCAAAGTTTCAAATGTACCTG
GGCAACCTCATGCCCATATACCATTCCTAACTTCTGCACTTAACATCTCT
AGGACTGGGACCCAGCCAGTCAAGCGGGGGACCCAGAGAGCTCCGGTGT
GAACACCGAGGTGCTGGTGGGTCTGCGTGTGTGGACATAGGGCAGTCCCG
GTCCTTCCTTCACTAACACGGCCCGGGAAGCCCTGTGCCTCCCTGGTGCG
CGGGTCGGCGCTTCCGGAGGGTACAGGCCCACCTGGAGCCCGGGCACAGT
GCATGCAAGTCGGGTTCACGGCAACCTGAGCTGGCTCTGCAGGGCAGTGG
GACTCACAGCCAGGGGTACAGGGCAGACCGGTCCTGCCTCTGCGCCCCTC
CCTGGCCTGTGGCCCTGGACGTGATCCCCAACAGTTAGCATGCCCCGCC
GGTGCTGAGAACCTGGACGAGGTCCGCAGGCGTCACTGGGCGGTCACTGA
GCCCGCCCAGGCCCCTCTGCCCCTTCCTGGGGTGACCGTGGACTCCTG
GATGACCCTGGACCCTAGACTTCCCAGGGTGTCTCGCGGAGGTTCCTCAG
CCAGGATCTCTGCGTCTCCTCCTTCCATAGAGGGGACGGCGCCCCCTTGT
GGCCAAGGAGGGGACGGTGGGTCCCGGAGCTGGGCGGAGAACACAGGGA
GCCCCTCCCAGACCCCGCTCTGGGCAGAACCTGGGAAGGGATGTGGCCAT -continued

```
CGGGGGATCCCTCCAGGCCATCTCCTCAGATGGGGGCTGGTCGACTAGCT
TCTGAGTCCTCCAAGGAACCGGGTCCTTCTAGTCATGACTCTGCCCAGAT
GAAGAAGGAGAGCACTTCTCTCCATCAGGAGGATCTGAGCTTCTCTTAAT
TAGAATCAGCTCCTTGGCTTCTACCCCTTAAAAAAAGGTACAGAAACTTT
GCACCTTGATCCAGTATCAGGGGAATTTATCAATCAATGTGGGAGAAATT
GGCATCTTTACCACACTGAATCTTTCAATCCATGAATATCCTCTCTCTCT
TCCATGCATAGGTTTTAATAATTCTCAATGGAGTTTAATGTAAGTTTTCC
TCATAGACAATTGCCTTTGGACATCTCTTTAGACTCATCTCTAGTAAACT
GATATTCTTAATGCAATTATAAAATGTATCCTGCTTAATGTTATTTTCTA
TTCATTTGCTGTTATATAGAGATACAATGAGTTTCCACATTTGAAACTGG
ATCTGGTAAATTGGCTACCCTTTTTTTATAGATTCTATTAATTTTTATAC
ATTCTGTGGGACTTGCTACATACTTAATCATGTCACCTGTGAAGAATGAC
AATTTGGTTGCTACCCTCCCAATTCTTATATGTCTCATTTCTTTCCCTCT
GCTGGTACTCTGGCAGCAGCAGGGAAGATAATGGGCCTCCTTATCTTGTC
ACAAAAGGATGTTTTTAAAGATTTCGTTATAAAACATAACGCTTTCTGGT
TTTCTTTAAAGATTCTCTCACCAGCTTAAGAAAATTTTCTTATACTCTGT
ATGATAAATGGGTTTTTGACAATCATTTGTTGCATTTTACCTAGTGTTTT
CTCTGCATCTTTATATGCTTTTTCTCCTTTAATCCTGAAAATTGTTTCGA
TTTTTCTAACATTGAACCAATCTTACATTCCTGGAATGGATGGACCAGAC
TAGTCCACATGTTTATTCTGCCCAATGGCTAGATTTTGTGTTCaatattt
tgttcagaatgtttgcatctatattcttGAGTGAGACAGAGCTGCCCTTG
TTAGGTTTCACAACCGAGGTTGTGTTAGCTTCATAAAATGAGACGTTTAT
TCTCTAAAAGAATTGTTTCGCTTCTCTGGATGAATTTGTGTAAGGTTAGA
ATTGCTTACCAGTGAagatctCGGGgCCAGTTCTTCTTTAGGGGAAGATT
TCAACAATTAAGCTCAATGCCTTTAGAAGAACTGAGAGTTTCTATTATT
TCTTGAGTTAAATATATGTATTTAATTAGACTTTCTAGGAATAGTCTCAT
TTCATCTCAAATAATTGACATATGCTATTAAAGCAGATTCTCATGAACCA
TTGTAGGTATTCCAGGTCTAGAAAAATGTTCCCCTTTGCATCCCTAATGT
GTTTAATTTTCACCTTCTTTCTTTTGTTCTTGAGAAATTCACCAAATCAT
TTTCAATTTCAGTCATATCCCAAAGCAACCAACTCTCTACCTTCTTGTTT
TATCATCCCTGCTGGATTTTGTTATCTACTTCTTCAGTATTTGTTCTTC
CCTTTCTTCTATTCCTCATTCCATTTTTCCCTTGTTTTCTAACTTTCTGA
GATATATGCTTAGTTCCTTCATTTGAAGCCTTTTATTTTCTTTTTTTTT
TTTTGGTCTTTTTGTCTTtGTTGTTGTTGTTGTGCTATTtCTTGGGCCG
CTCCCGCGGCATATGGAGGTTCCCAGGCTAGGAGTCGAATCGGAGCTGTA
GCCACCGGCCTACGCCAGAGCCACAGCAATGCGGGATCCGAGCCGCGTCT
GCAACCTACACCACAGCTCATGGCAACGCCGGATCGTTAACCCACTGAGC
AAGGGCAGGAACCGAACCCGCAACCTCATGGTTCCTAGTCGGATTCGTAA
CCACTGTGCCACAACAGGAACTCCGCCTTTTTATTTTCTATAAAAATTTC
TATGTACATTTTAAGGTTATAGGTTTCCTTCTATGTACCCCATTGGCTGT
ATCCTCAGGGTTCTGTGGAGTGATTTCATTATTGTTCAAGTTCAATATGT
CTTCTGATTTTCCAATTTGAATACCTCTCTAAATCAGTAGGTGAATATTT
CTTTTTCTTTTTCTTTTCTTTTCTTCTTTTTTTTTTTCTTTCAGCCAGGT
CCATGGCATGCAGAAATTCCCAGGCCAGGAATCAAACTCTCACCATGGCA
GTGACAATGTCGGATCCTTTACCCACTAGGCCACCAGGGAACTCTGGGAG
CATATGTTTTATTTCCCGACATCTGAGGATGCCTAGTATGTCTTCATTA
TTGATTTCTAGTTTGCCACTGATTTCTAGTATTTTGCTCATAGAGTGTAT
GCTCAATGGTTTTGGTCATTTGAAATGTATTTAGTCCTGCTTTATGACCC
AGTATGTGGTCAGTTTTGTCAATGTTCCTTTTCTGCTTGAAGAGAACCTA
CATGCTGTAACTCTGGGTGCATGTTCTGTATATAAGTCTATAGGCTGAGC
CGGGGGAGCCTTCTAATCTGCCGTTATCTTCTTCGAGTTATTCTAGGTAC
TATTTCTTAGCCATAAACCTTTAAATTCTGATATCAATATAATGACCCCA
GCCCGCTTAGGGTCGGCACTTCATGTTATCTTTTTCCATCCATTTAATCC
CTCCCCACTGTTTTGGCCACACCCGTGGGATATGGGAGTTCCTGGGCCAA
GGATCaGATCTGAGCCGCAGCTGCCACCTATGCCACAGCAgcagcaatga
tggatctttaacccactgcaccacactggggattgaacccaagcctcagc
agcaacccaagctactgcagagacaacaccagatccttaacctgctgtgc
catagcgggaaTTTCCATCCATTTACTTTCAAGCCAGCTGAATAACCTAG
CCCACCATGCCTGGACATGGGTGCTCTGCTTCAAATGATTTTGTTCAGTC
AGCATCCATCTCTGAAATGTGTGCCAAGCATTTATATGCATGCAAGAGTC
ATGTTGGCACTTCTATCATTTCCAACAGTTCAGTAGCCTTTGTATCATGA
CATTTCTTGGCCTTTTCTCTACAATATTTGAGGCTGAGCAGACTGGCCGT
GCCCCTGTCCATGCTTCCAGAGCCTGTGTGCAGACTTCTGCTCTAGACAG
AGACAGCTAACCATCCTGCAGTGCCCAGAAAACCCAACTCAAAGACCCTC
AAGTAAGGAAGGATTTATTGGCTCACGTAATCTGGAATCCAGGCATGGGG
TATTCAGGGCCACCTGAACCAGAGGCCCTGGCCCTGTTCTCTAAGCTTCT
TCCTGCCCTGCCCTCGTTCTGGAAGTGACCCTGAAGGACAGCAATGAAGG
GCAGCTCCCCCAGGGACAGATGACTGAGAGGTCCATTTCAAGTCCAACTT
GGCCTAGATTGAGAGGCAGCAAGAAATATGGACCTACAGTGAGTCACAGG
ATTTACCAGTGGTTTGGCTGGGTTGTCAGTGTTACAGGCTAAACATTTGG
GTCCCTCCAAAATTAACATGTTGCCACTCTAACCACCAAAATCatggtat
ttgggggtggggcccttggaggtaattaggtttagaaAGAATGAAGAGGG
GGCCCTTGTGATGGGACTAGTGCCTTTATAGAGAGAAGAGAGAGGG
```

Seq ID No. 39
```
CACCTCATCCCCAACCACCTGGATGGTGGCAAGTGGCAGGCTGAGAGGCT
GCATATGAGCTCATCAAGAGGGTCCCCACCCCACAGAGGCTGACCCAGCT
GCCACTGCCACCTAGTGGCTGATCGGCCAAGAGCAGGAGCCCCAGGGGCA
GCTCCATTCCCTGGGGCGGCCAGGGAACCACCTGGTGGTAGGACAATTCC
ATTGCACCTCATCCATCAGGAAAAGGTTTGCCTTCCCTGGCAGTAATGCA
TCTTCCCATAACATGGTCCCTGGCCTCTTGGAATGGCTTGGCCACCGTCA
TGGCCTCACCCACAAAGCCTTGTGTCTCAGCAAGGAACTTATTCCACAGC
AAAGGACTTGCAGCCTGGAATGAACTGGTCTGACTACATACCCCATTGCC
```

-continued

```
CAGAAGTAGGTGGTCTATTGCAAAGTGGAGTGGCTTACCCAAGACTCAGT
TGTGCCCAAGTTGAGAGATAGCATCCTAAAATATGGGCTTATGTCTCACT
GGCTGAGGTTTATTCTTTGAATCAAAGACAATTATATGGTGTGGTCCCCC
CAGAGATAGAATACATGAGTCTGGGAATCAAGGGATAGAAGTAAGAAGAG
ATTTTGTCACCATTAATCCCAATAACTCGCCCAAAGAATATTTGCTTTCT
GTCCTGGCAGCTCTGCTGCTTTGGCAATAACTTCCTAGAATATAATGTCT
CCACCAGGGGACTCCACAACGGTTCCATTGATTTGAAGCCAATGGGCAGA
GGAGGGGCTGCCTTACTGGTCGGACTGGTCAGCCCTGATTACTAAGGAGA
AATCAGGCAACTTCAACAAAACTAAGGCAGGGGGACTTTGTCTAGAACC
CAAAGCACTAAGCATCTTAGTACTTTTTAGTTCTCAGAGCCTCCAAGAAC
AAAGATTTAGCCCCTCAGCACCACCAGGTAAAGAACAGGTAAATCCAGCT
GAGGACAAGAGAAATATTGAATGGATAGAGGAAGAAAGAAATTATAGATA
TCAACTATGGCCTCATGACTAGAGTCTCCAGATTAAGCGGAATAAAAATA
CAGATGATTaGATCTGAACATCAGGCCAAACAACGAACAACAGTTTAAGT
GCGACCTAGGCAATATTTGGGACATACTTATACTAAAATTTTTTCGCTAT
TTGAGCATCCTGTATTTTATCTGGCAACTTTATTCATCCCTAGCGAAAAA
GGAACTGTGGTAACTTAGTGTATTTTTACTTTGCTCATTATTGTGTATAT
ACCTACTTGTATTTATCAATCATATTTACTCTGTTCTCAGTATTACTTTA
TATAGCAGTTGGTGGTGATGGTTAGCAACATATTCAGTGGAACTGTGACT
GAATTTGAGGAGAAATTAACAGAGTTGGCTGTGGCTACAATAACCCTTCG
GGACATGTGTCCCCTCATTTTGGGGAGATGGTTagatctCTGGGTAAATG
TTAGGGCATCTGAGCCAGAAACCAAGATTTTGCCAGCTGGTGCAATGTCA
GATTTTACCAGCAGAGGGTGCCAGAGGAATGCGGCAAAACCCGAGTGCCA
GAAAGCACCTCCCTGTTTTCCAGCTTTTCTTCCTTTTTATTTATTTTATT
TACGGCCCAGGAGTCCGTAATAGCGCTGAGGATGGCCCAGGCTCTTCTCA
GCAGCCCTGACTGACTAGTTCAGCAATGCGCTCAGGCCCCATCTGGCCAC
CGGGCAGCCTCTTCTGTGGTAGCTCCAGCCTCAGCCAGTGCAAAAGGCTA
CCCTACACTGGCGCCACTTCTACAATCAGCACTGGCCACACCCTCCACGC
CATCCGGCACGGAGCCAGGTGATCTGCCGGCCAGATTGCAGTTCGTGCTG
CCTGAGTCCAGGTGATTACACTGGCTGCATCTTTTCTTTCTGGACCAtTC
attccatttttttt
```

Bovine Lambda Light Chain

In a further embodiment, nucleic acid sequences are provided that encode bovine lambda light chain locus, which can include at least one joining region-constant region pair and/or at least one variable region, for example, as represented by Seq ID No. 31. In Seq ID No 31, bovine lambda C can be found at residues 993-1333, a J to C pair can be found at the complement of residues 33848-35628 where C is the complement of 33848-34328 and J is the complement of 35599-35628, V regions can be found at (or in the complement of) residues 10676-10728, 11092-11446, 15088-15381. 25239-25528, 29784-30228, and 51718-52357. Seq ID No. 31 can be found in Genbank ACCESSION No. AC117274. Further provided are vectors and/or targeting constructs that contain all or part of Seq ID No. 31, for example at least 100, 250, 500, 1000, 2000, 5000, 10000, 20000, 500000, 75000 or 100000 contiguous nucleotides of Seq ID No. 31, as well as cells and animals that contain a disrupted bovine lambda gene.

Seq ID No 31

```
  1 tgggttctat gccacccagc ttggtctctg atggtcactt gaggccccca tctcatggca
 61 aagagggaac tggattgcag atgagggacc gtgggcagac atcagaggga cacagaaccc
121 tcaaggctgg ggaccagagt cagagggcca ggaagggctg gggacccttgg gtctagggat
181 ccgggtcagg gactcggcaa aggtggaggg ctccccaagg cctccatggg gcggacctgc
241 agatcctggg ccggccaggg acccaggaa agtgcaaggg gaagacgggg gaggagaagg
301 tgctgaactc agaactgggg aaagagatag gaggtcagga tgcagggac acggactcct
361 gagtctgcag gacacactcc tcagaagcag gagtccctga agaagcagag agacaggtac
421 cagggcagga aacctccaga cccaagaaga ctcagagagg aacctgagct cagatctgcg
481 gatgggggga ccgaggacag gcagacaggc tccccctcga ccagcacaga ggctccaagg
541 gacacagact tggagaccaa cggacgcctt cgggcaaagg ctcgaacaca catgtcagct
601 caaaatatac ctggactgac tcacaggagg ccagggaggc cacatcatcc actcagggga
661 cagactgcca gccccaggca gacccatca accgtcagac gggcaggcaa ggagagtgag
721 ggtcagatgt ctgtgtggga aaccaagaac cagggagtct caggacagcg ctggcagggg
781 tccaggctca ggctttccca ggaagatggg gaggtgcctg agaaaacccc acccaccttc
841 cctggcacag gccctctggc tcacagtggt gcctggactc ggggtcctgc tgggctctca
901 aaggatcctg tgtccccctg tgacacagac tcaggggctc ccatgacggg caccagacct
961 ctgattgtgg tcttcttccc ctcgcccact ttgcaggtca gcccaagtcc acaccctcgg
```

-continued

```
1021 tcaccctgtt cccgccctcc aaggaggagc tcagcaccaa caaggccacc ctggtgtgtc
1081 tcatcagcga cttctacccg ggtagcgtga ccgtggtcta gaaggcagac ggcagcacca
1141 tcacccgcaa cgtggagacc acccgggcct ccaaacagag caacagcaag tacgcggcca
1201 gcagctacct gagcctgatg ggcagcgact ggaaatcgaa aggcagttac agctgcgagg
1261 tcacgcacga ggggagcacc gtgacgaaga cagtgaagcc tcagagtgtt cttagggccc
1321 tgggccccca ccccggaaag ttctaccctc ccaccctggt tcccctagc ccttcctcct
1381 gcacacaatc agctcttaat aaaatgtcct cattgtcatt cagaaatgaa tgctctctgc
1441 tcattttgt tgatacattt ggtgccctga gctcagttat cttcaaagga acaaatcct
1501 cttagccttt gggaatcagg agagagggtg gaagcttggg ggtttgggga gggatgattt
1561 cactgtcatc cagaatcccc cagagaacat tctggaacag gggatggggc cactgcagga
1621 gtggaagtct gtccaccctc cccatcagcc gccatgcttc ctcctctgtg tggaccgtgt
1681 ccagctctga tggtcacggc aacacactct ggttgccacg ggcccagggc agtatctcgg
1741 ctcccctccac tgggtgctca gcaatcacat ctggaagctg ctcctgctca gcggccctc
1801 tgtccactta gatgatgacc ccctgaagt catgcgtgtt ttggctgaaa ccccaccctg
1861 gtgattccca gtcgtcacag ccaagactcc ccccgactcg acctttccaa gggcactacc
1921 ctctgcccct cccccagggc tcccctcac agtcttcagg ggaccggcaa gccccccaacc
1981 ctggtcactc atctcacagt tccccccaggt cgccctcctc ccacttgcat ggcaggaggg
2041 tcccagctga cttcgaggtc tctgaccagc ccagctctgc tctgcgaccc cttaaaactc
2101 agcccaccac ggagcccagc accatctcag gtccaagtgg ccgttttggt tgatgggttc
2161 cgtgagctca gcccagaat caggttaggg aggtcgtggc gtggtcatct ctgaccttgg
2221 gtggtttctt aggagctcag aatgggagct gatacacgga taggctgtgc taggcactcc
2281 cacgggacca cacgtgagca ccgttagaca cacacacaca cacacacaca cacacacaca
2341 cacacacgag tcactacaaa cacggccatg ttggttggac gcatctctag gaccagaggc
2401 gcttccagaa tccgccatgg cctcactctg cggagaccac agctccatcc cctccgggct
2461 gaaaaccgtc tcctcaccct cccaccgggg tgaccccaa agctgctcac gaggagcccc
2521 cacctcctcc aggagaagtt ccctgggacc cggtgtgaca cccagccgtc cctcctgccc
2581 ctcccccgcc tggagatggc cggcgcccca tttcccaggg gtgaactcac aggacgggag
2641 gggtcgctcc cctcacccgc ccggagggtc aaccagcccc tttgaccagg agggggggcgg
2701 acctgggct ccgagtgcag ctgcaggcgg gccccgggg gtggcgggc tggcggcagg
2761 gtttatgctg gaggctgtgt cactgtgcgt gtttgctcgg tggagggacc cagctggcca
2821 tccggggtga gtctcccctt tccagctttc cggagtcagg agtgacaaat gggtagattc
2881 ttgtgttttt cttacccatc tggggctgag gtctccgtca ccctaggcct gtaaccctcc
2941 ccctttagc ctgttccctc tgggcttctt cacgtttcct tgagggacag tttcactgtc
3001 acccagcaaa gcccagagaa tatccagatg gggcaggcaa tatgggacgg caagctagtc
3061 caccctctta ccttgggctc cccgcggcct ccggataatg tctgagctgc ctccctggat
3121 gcttcacctt ctgagactgt gaggcaagaa accccctccc caaaagggag gagacccgac
3181 cccagtgcag atgaacgtgc tgtgagggga ccctgggagt aagtggggtc tggcggggac
3241 cgtgatcatt gcagactgat gccccaggca gggtgagagg tcatggccgc cgacaccagc
3301 agctgcaggg agcacaggcc ggggggcaagt catgcagaca ggacaggacg tgtgaccctg
3361 aagagtcaga gtgacacgcg ggggggggc ccggagctcc cgagattagg gcttgggtcc
3421 taacgggatc caggagggtc cacgggccca ccccagccct ctccctgcac ccaatcaact
```

-continued

```
3481 tgcaataaaa cgtcctctat tgtcttacaa aaaccctgct ctctgctcat gtttttcctt
3541 gccccgcatt taatcgtcaa cctctccagg attctggaac tggggtgggg nnnnnnnnnn
3601 nnnnnnnnnn nnnnnnnnnn nnnnnnnnnn nnnnnnnnnn nnnnnnnnnn nnnnnnnnnn
3661 nnnnnnnnnn nnnnnnnnnn nnnnnnnnnn agcttatgtg gtgggcaggg gggtagtaag
3721 atcaaaagtg cttaaattaa taaagccggc atgatatacg agtttggata aaaatagat
3781 ggaaaagtaa gaaaggacag gaggggggtg aggcggaaga aaggggaag aaggaaaaaa
3841 aaataagaga gaggaacaaa gaaagggagg ggggccggtg atgggggtgg gatagaatat
3901 aataattgga gtaaagagta gcgggtggct gttaattccg gggggaata gagaaaaaaa
3961 aaaaaaaatg tgcgggtggg cggtaagtat ggagatttta taaatattat gtgtggaata
4021 atgagcgggg gtggacgggc aaggcgagag taaaaagggg cgagagaaaa aaattaggat
4081 ggaatatatg gggtaaattt taaatagagg gtgatatatg ttagattgag caagatataa
4141 atatagatgg tgggggaaaa gagacaaggg tgagcgccaa aacgccctcc cgtatcattt
4201 gccttccttc ctttaccacc tcgttcaaac tcttttttcga gaaccctgaa gcggtcaggc
4261 ccggggctgg gggtggggata cccggggagg ggctgcgcct cctcctttgc agaggggggtc
4321 gaggagtggg agctgaggca ggagactggc aggctggaga gatggctgtt gacttcctgc
4381 ctgtttgaac tcacagtcac agtgccagac ccactgaatt gggctaaata ccatattttt
4441 ctggggagag agtgtagagc gagcgactga ggcgagctca tgtcatctac agggccgcca
4501 gctgcaggga cttttgtgtgt gtcgtgctcg ttgctcagtt gtgtccgact ctttatgact
4561 tcatggactg taacctgcca ggctcctctg tccgtggaat tctccaggca agaatactgg
4621 agtgggtagc cattctcatc tccgggggat cttcctgacc caagaatcaa acctgagtct
4681 cccgcattgc aggcagcttc tttcttgtct gagccaccag ggaagcccct taagtggagg
4741 atctaaatag agtgtttagg agtataagag aaaggaagga cgtctataca agatccttcg
4801 gttcctgtaa ctacgactcg agttaacaag ccctgtgtga gtgagttgcc agtaattatt
4861 gctaacctgt ttctttcact cactgagcca ggtatcctgt gagacggcat acttacctcc
4921 tcttctgcat tcctcgggat ggagctgtgc ggtggcctct aggactacca catcgaccag
4981 gtcagaccca gggacagagg attgctgaga tgcactgaga agtttgtcag cctaggtctt
5041 cacccacaca gactgtgctg tcgtctacca cgtaattctt cctgtccaaa gaactggtta
5101 aacgctcctg aagcgtattc tggtctgctt caaaaagtgc ctctttcctt tataagttcc
5161 gccaatcctg gactttgtcc caggccagtc tactttattt gtgggaaagg ttttttttggt
5221 cttttttgtt ttaaactctg cagaaattgc ttacactttt ggtgtgcaat ggctcactct
5281 tacgttcta gctgtattca aagggggttgc ttttctttgt ttttaaagct ttttgaacgt
5341 ggaccatttt taaagtcttt attaaacgtc taacatcgtt tctggtttat tttctggtgg
5401 tctggccatg aggcctacgg gtcttagctc ccctaccagg gtccaaccca catcccttgc
5461 actggacggc aaggtcttaa ccttttgaacc accagagagc ttctgaaagg ggctgctttt
5521 ctccaatcct ctttgctccc tgcctgctgg tagggattca gcacccctgc aatagccctg
5581 tctgttctta ggggctcagt agcctttctg cctgggtgtg gagctggggt tgtaagagag
5641 cttcatggat ttggacacga cctacgactc agaggtaaga ctccatctta gcgctgtaat
5701 gacctctttc caacaaccac ccccaccacc ctggaccact gatcaggaga gatgattctc
5761 tctcttatca tcaacgtggt cagtcccaaa cttgcacccg gcctgtcata gatgtagcag
5821 gtaagcaata aatatttgtt gaatgttaag tgaattgaaa taacataagt gaaaaagaaa
```

```
5881 acacttaaaa acatgtgttt ttataattac acagtaaaca tataatcatt gtagaaaaaa
5941 atcgaaagag tggcgggggc caagtgaaaa ccaccatccc tggtatgtcc acccgcccgg
6001 gtagcccccag gtaagaggtg cggacacgga tggccctgta gacacagaga cacacgctca
6061 tatgctgggt cttgtcttgt gacctcttgg ggatgatgtt attttcacga tgccattcaa
6121 accttctacc acaccatttt tagagggtcg ttcatcgtaa atcagttcac tgctttgttt
6181 tctgattttg aaagtgtcac attcttcgag aaatgagaag gaacaggcgc gcataaggaa
6241 gaaagtaaac acgtggcctt gcttccaggg ggcactcagc gtgttggtgt gcacgctggc
6301 agtcttttct ctgtgacagt catggccttt tcccaaaggt gggctcagat aagaccgcct
6361 cccatcccct gtccctgtcc ccgtcccccta cggtggaacc cacccacggc acgtctccga
6421 ggcccttgg ggctgtggac gttaggctgt gtggacatgc tgctggtggg gacccagggc
6481 tgggcagcac gttgtccctg gtcccgggc cagtgaggag ctcccaagga gcagggctgc
6541 tgggccaaag gcagtgcgt cccgaggcca tggacaaggg gatacatttc ctgctgaagg
6601 gctggactgc gtctccctgg ggcccttgg agtcatgggc agtggggagg cctctgctca
6661 ccccgttgcc cacccatggc tcagtctgca gccaggagcg cctggggctg ggacgccgag
6721 gccggagccc ctccctgctg tgctgacggg ctcggtgacc ctgccgcccc ctccctgggg
6781 ccctgctgac cgcggggggcc accccggcca gttctgagat tcccctgggg tccagccctc
6841 caggatccca ggacccagga tggcaaggat gttgaggagg cagctagggg gcagcatcag
6901 gcccagaccg gggctgggca ggggctgggc gcaggcgggt ggggggtct gcacncccccc
6961 acctgcnagc tgcncnnncn tttgntnncg tcctccctgn tcctggtctg tcccgcccgg
7021 ggggccccccc ctggtcttgt ttgttcccccc tccccgtccc ttccccccctt tttccgtcct
7081 cctcccttct tttattcgcc cctgtggtc gttttttttc cgtccctctt ttgttttttt
7141 gtctttttct tttttccccct cttctcccctt gctctctttt tcattcgtcg gttttttctgc
7201 tcccttccct ctcccccccg cttttttttcc ctgtctgctt tttgtgttct ccctctctac
7261 cccccctgca gcctattttt tttatatatc catttcccccc tagtatttgg cccccgctta
7321 cttctcccta atttttattt tccttttcttt aactaaaatc accgtgtggt tataagttt
7381 aaccttttt gcaccgccca caatgcaatc ttcacgcacg ccccccccgt cagcctcctt
7441 aaatacctt gcctactgcc ccccctccttg tataataacg cgtcacgtgg tcaaccatta
7501 tcacctctcc accaccttac cacattttcc ttcnnnnnnn nnnnnnnnn nnnnnnnnn
7561 nnnnnnnnnn nnnnnnnnnn nnnnnnnnnn nnnnnnnnnn nnnnnnnnnn nnnnnnnnn
7621 nnnnnnnnnn nnntgaaaaa agaaaaggct gggcaggttt taatatgggg gggttggagt
7681 ggaatgaaaa tgcattggag tggttgcaac aaatggaaag gtctcaggag cgctcctccc
7741 ccatcaggag ctggaaagaa gtggaagcaa agcaaggaat tcgtgtgatg gccagaggtc
7801 aggggcaggg agctgcaaag actgccggct gtttgtgact gnccgtctcc gggtgcattt
7861 gttagcaggg aggcattaca ctcatgtctt ggtttgctaa ctaattctta ctattgttta
7921 gttgcaaggt catgtctgac tctttgcaac ccagggactg cagcccgcca ggctcctctg
7981 tccatgggat ttcgcaggca agaatactgg aggtggtagc cattttcttc accatgggat
8041 cttcccgagc cagaaatgga acccgagtcg cctcctgtgc atggggtctg ctgcctaaca
8101 ggcagatatt tgacgtctga gccaacaggg aggacagacg gtaattatac caaccattga
8161 aagaggaatt acacactaat ctttatcaaa atctttcaaa cagtagagga gaaaggatac
8221 tctctagttt attccataaa gttggaatta cgcttatcaa taaagacatt acaagaaaag
8281 aaagtgaagc cccaaatgcc ttataaatat acaagaaaaa atctttttaag atattagcca
```

-continued

```
8341 acttaatcaa caaaaaatgt atcaaaagtc caagtaacat tcaccccagg aatgcaagtg
8401 tggttcagcc taagacaatc agtcatgagt ataccacgga aacaaattaa agagaaaaga
8461 cattaaatct cacaaatggt gcagaaaaag atttggcaat atcgaacatc ttttcatgac
8521 caaaggaaaa aaaagaaaca aaacaccaga aaattctgtg tagaaagaat atatctcaac
8581 ccaatgaagg gcatttatga aaacccaca gcatacatca cactccatga gaaagactga
8641 aagctttccc cactgccatt gaactctgtc ctggaaattc tagtcacagc gacagaacaa
8701 gagaaagaaa taacggccgt ctaaactggt aggaagaaat caaagcgtct ctattctctg
8761 ggcgcataat acaatataga caaatttcta aagtccacaa aaattcctag agctcataat
8821 gaatccagaa atgcgtcagg gctcaagatt cagatgcaaa aatcgtctgg gttttgatgc
8881 accaacaaac aattccatta acaataatac caaggaatta atttaactta aagagaaaa
8941 gacctgttta cagagagtta taaacattt ggtgatgaaa ttaaataaga gtaaatcata
9001 tagaaacacc gttcgtgttt tggagaccta atgtcataaa cgtggcaaca cagagacgcc
9061 tcacggggaa ccctgagcct ccttctccaa acaggcctgc tcatcatttc acaggtaacc
9121 tgagacccta aagcttgact ctgaggcact ttgagggcat gaagagagca gtagctcctc
9181 ccatgggacc gacagtcaag gcccagggaa tgaccacctg gacagatgac ttcccggcct
9241 catcagcagt cggtgcagag tggccaccag ggggcagcag agagtcgctc aacactgcac
9301 ctggagatga ggcaacctgg gcatcaggtg cccatgcagg ggctggatac ccacacctca
9361 cacctgagga caggggccgg ctttctgtgg tgtcgccctc tcaggatgca cagactccac
9421 cctcttcgct tgcattgaca gcctctgtcc ttcctggagg acaagctcca ccttccccat
9481 ctctccccag ggggctgggg ccaacagtgt tctctcttgt ccactccagg aacacagagc
9541 caagagattt atttgtctta attagaaaaa ctatttgtat tcctgcattt ccccagtaac
9601 tgaaggcaac tttaaaaaat gtatttcctg gacttccctg gtgggccagt ggctagactc
9661 tgagctccca gtgcatgggg cctgggttca atccctgctc aggaaactac atcccacagg
9721 ctgcaaataa gatcctgcat gccacccgat gcaggcaaag aaacaagtgt tcggtatgca
9781 tgtatttcac gtgaggtgtt tctataattt acagccagta ttctgtctta cacttagtca
9841 ttcctttgag cacatgatcg gtcgatggcc cagaccacac acaggaatac tgaggcccag
9901 cacccaccgg ctgcccagaa cctcatggcc aagggtggac acttacagga cctcagggga
9961 cctttaagaa cgccccgtgc tcttggcagc ggagcagtgt taagcatggc tctgtccctc
10021 gggagctgtg tctgggctgc gtgcatcacc tgtggtgtgg gcctggtgag ggtcaccgtc
10081 caggggccct cgagggtcag aagaaccttc ccttaaaagt tctagaggtg gagctagaac
10141 cagacccaca tgtgaactgc acccaaaaac agtgaaggat gagacacttc aaagtcctgg
10201 gtgaaattaa gggccttccc ctgaaccagg atggagcaga ggaaggactt ggcttccagg
10261 aaaccctgac gtctccaccg tgactctggc cggggtcatg cagggccca ggatcctttg
10321 gtgcaaagga ctcagggttc ctggaaaata cagtctccac ctctgagccc tcagtgagaa
10381 gggcttctct cccaggagtg gggcaaggac ccagattggg gtggagctgt cccccagac
10441 cctgagacca gcaggtgcag gagcagcccc gggctgaggg gagtgtgagg gacgttcccc
10501 ccgctctcaa ccgctgtagc cctgggctga gcctctccga ccacggctgc aggcagcccc
10561 cacccacc cccgaccctg gctcggactg atttgtatcc ccagcagcaa ggggataaga
10621 caggcctggg aggagccctg cccagcctgg gtttggcgag cagactcagg gcgcctccac
10681 catggcctgg accccctcct cctcggcctc ctggctcact gcacaggtga gccccagggt
```

```
-continued
10741 ccacccaccc cagcccagaa ctcggggaca ggcctggccc tgactctgag ctcagtggga
10801 tctgcccgtg agggcaggag gctcctgggg ctgctgcagg gtgggcagct ggaggggctg
10861 aaatcccct  ctgtgctcac tgctaggtca gccctgaggg ctgtgcctgc cagggaaagg
10921 gggtctcct  ttactcagag actccatcca ccaggcacat gagccggggg tgctgagact
10981 gacggggagg gtgtccctgg gggccagaga atctttggca cttaatctgc atcaggcagg
11041 gggcttctgt tcctaggttc ttcacgtcca gctacctctc ctttcctctc ctgcaggcgc
11101 tgtgtcctcc tacgagctga ctcagtcacc cccggcatcg atgtccccag acagacggc
11161 caggatcacg tgttggggc  ccagcgttgg aggtganaat gttgagtggc accagcagaa
11221 gccaggccag gcctgtgcgc tggtctccta tggtgacgat aaccgaccca cggggtccc
11281 tgaccagttc tctggcgcca actcagggaa catgccacc  ctgcccatca gcggggcccg
11341 ggccaaggat gaggccgact attactgtca gctgtgggac agcagcagta acaatcctca
11401 cagtgacaca ggcagacggg aagggagatg caaacccct  gcctggcccg cgcggcccag
11461 cctcctcgga gcagctgcag gtcccgctga ggcccggtgc cctctgtgct cagggcctct
11521 gttcatcttg ctgagcagcg gcaagtgggc attggttcca agtcctgggg gcatatcagc
11581 acccttgagc cagagggtta ggggttaggg ttaggggttag gctgtcctga gtcctaggac
11641 agccgtgtcc cctgtccatg ctcagcttct ctcaggactg gtgggaagat tccagaacca
11701 ggcaggaaac cgtcagtcgc ttgtggccgc tgagtcaggc agccattctg gtcagcctac
11761 cggatcgtcc agcactgaga cccggggcct ccctggaggg caggaggtgg gactgcagcc
11821 cggcccccac accgtcaccc caaaccctcg agaaccgcg  ctccccagga cgcctgcccc
11881 tttgcaacct gacatccgaa cattttcatc agaacttctg caaaatattc acaccgctcc
11941 tttatgcaca ttcctcagaa gctaaaagtt atcatggctt gctaaccact ctccttaaat
12001 attcttctct aacgtccatc ttccctgctc cttagacgcg ttttcattcc acatgtctta
12061 ctgcctttgg tctgctcgtg tatttctttt ttttttttt  ttttattgga atatatttgc
12121 gttacaatgt tgaatttgaa ttggtttctg ttgtacaaca atgtgaatta gttatacatg
12181 tcctgaggag gggcggctgc gtgggtgcag gagggccgag aggagctact ccacgttcaa
12241 ggtcaggagg ggcggccgtg aggagatacc cctcgtccaa ggtaagagaa acccaagtaa
12301 gacggtaggt gttgcgagag ggcatcagag ggcagacaca ctgaaaccat aatcacagaa
12361 actagccaat gtgatcacac ggaccacagc ctggtctaac tcagtgaaac taagccatgc
12421 ccatggggcc aaccaagatg ggcgggtcat gtgcccatgg ggccaaccaa gatgggcggg
12481 tcatggtgaa gaggtctgat ggaatgtggt ccactggaga agggaaaggc aaaccacttc
12541 agtattcttg ccttgagagc cccatgaaca gtatgaaaag gcaaaatgat aggatactga
12601 aagaggaact ccccaggtca gtaggtgccc aatatgctac tggagatcag tggagaaata
12661 actccagaaa gaatgaaggg atggagccaa agcaaaaaca atacccagtt gtggatgtga
12721 ctggtgatag aagcaagggc caatgatgta aagagcaata ttgcatagga acctggaatg
12781 ttaagtccaa gannnnnnnn nnnnnnnnnn nnnnnnnnnn nnnnnnnnnn nnnnnnnnnn
12841 nnnnnnnnnn nnnnnnnnnn nnnnnnnnnn nnnnnnnnnn nnnnnnnnnn nnagaatttt
12901 gagcattact ttactagcgt gtgagacgag tgcaattgtg cggtagtttg agcattcttt
12961 ggcattgcct ttctttggga ttggaatgaa aactgacctg ttccaggcct gtggccactg
13021 ctgagttttc caaatttgct ggcgtattga gtgcatcact ttaacagcat catcttttag
13081 gatttgaaat agctcaactg gaattctatc actttagcta attccattca ttagctttgt
13141 ttgtagtgat gcttcctaag gccccctgg  ctttatcttc ctggatgtct ggctctggtg
```

-continued

```
13201 agtgatcaca ccgctgtgat tatctgggtc atgaaggtct ttttgtatag ttcttcttag
13261 gaacagatat tatgatctcc atccttgcat ctcgttatat ctagagaagc actgactccc
13321 ttcatggtga cgtcagatcc tcatgactaa caaatggcct tttgtaagat gagtgcctca
13381 tggtattgag ctcccccgtc accaagacct tatgactgac ctcccccact gccccaggtg
13441 cctctcgaag cgtctgagat gccgcctccc aggctgcact cctcattttg ccccaataa
13501 aacttaactt gcagctctcc agctgtgcat ctgtgtttag ttgacagtac aaatataatg
13561 gaaaatttaa attaaatata atctatgggg agaaatccaa acatcttatg agggagagag
13621 agggagagaa aggaaagaag aagaagcagg aggaggagga gagtagagaa acaggggag
13681 ggcggcaggg agacagaggg gaggacaccg aggggaaagg gaggaaggcg agtgcagtga
13741 gagagaggcc agagttcatc agagtctgga ctcgcagccc aatcccacgg gtgtgtcccg
13801 aagcagggga gagcctgagc caggcggaga cagagctgtg tctccagtcc tcgtggccgt
13861 gacctggagc tgtgtggtca gccccctga ccccagcctg gccctgctgg tggtcggagg
13921 cagtgatcct ggacacagtg tctgagcgtc tgtctgaaat ccctgtggag gcgccactca
13981 ggacggacct cgcctggccc cacctggatc tgcaggtcca ggcccgagtg gggcttcctg
14041 cctggaactg agcagctgga ggggcgtctg caccccagca gtggagcggc cccaggggcg
14101 ctcagagctg ccggggggac acagagcttg tctgagaccc agggctcgtc tccgaggggt
14161 cccctaaggt gtcttctggc cagggtcaga gccgggatga gcacaggtct gagtcagact
14221 ttcagagctg gtggctgcat ccctggggac agagggctgg gtcctaacct gggggtcaga
14281 gggcaggacg ggagcccagc tgaccctggg ggactggcct cctctgtggt ctcccctggg
14341 cagtcacagc ttcccccggac gtggactctg aggaggacag ctggggcctg gctgtcagga
14401 gggggttcga gaggccacac tcagaggagg agaccctggc ctgcttgggt tgtgactgag
14461 tttttggggt cctctaggag actctggccc tgcaggccc gcaaggtcat ctctagtgga
14521 gcaggactcc acaagattga tgaactgaat cctctaggag aggtgtggtt tgaggggc
14581 agcattctag aaccaacagc gtgtgcaggt agctggcacc gggtctagtg gcggcgggca
14641 gggcactcag ggccgactag gggtctgggg gattcaatgg tgcccacagc actgggtctt
14701 ccatcagaat cccagacttc acaaggcagt ttcggggatt aggtcaggac gtgagggcca
14761 cagagaggtg gtgatggcct agacaagtcc ttcacagaga gagctccagg ggccatgata
14821 agatggatgg gtctgtattg tcagttccc cacatcaaca ccgtggtccc gccagcccat
14881 aatgctctgt ggatgcccct gtgcagagcc tacctggagg cccgggaggc ggggccgcct
14941 gggggctcag ctccggggta accgggccag gcctgtccct gctgtgtcca cagtcctccc
15001 ggggttggag gagagtgtga gcaggacagg agggtttgtg tctcacttcc ctggctgtct
15061 gtgtcactgg gaacattgta actgccactg gcccacgaca gacagtaata gtcggcttca
15121 tcctcggcac ggaccccact gatggtcaag atggctgttt tgccggagct ggagccagag
15181 aactggtcag ggatccctga gcgccgctta ctgtctttat aaatgaccag cttaggggcc
15241 tggcccggct tctgctggta ccactgagta tattgttcat ccagcagctc ccccgagcag
15301 gtgatcttgg ccgtctgtcc caaggccact gacactgaag tcaactgtgt cagttcatag
15361 gagaccacgg agcctggaag agaggaggga gagggatga aaggaagga ctccttcccc
15421 aagtgagaag ggcgcctccc ctgaggttgt gtctgggctg agctctgggt tgaggcagg
15481 ctcagtcctg agtgctgggg gaccagggcc ggggtgcagt gctgggggc cgcacctgtg
15541 cagagagtga ggaggggcag caggagaggg gtccaggcca tggtggacgt gccccgagct
```

-continued

```
15601 ctgcctctga gcccccagca gtgctgggct ctctgagacc ctttattccc tctcagagct 15661 ttgcaggggc cagtgagggt ttgggtttat gcaaattcac ccccgggggg cccctcactc 15721 agaggcgggg tcaccacacc atcagccctg tctgtcccca gcttcctcct cggcttctca 15781 cgtctgcaca tcagacttgt cctcagggac tgaggtcact gtcaccttcc ctgtgtctga 15841 ccacatgacc actgtcccaa gcccccctgc ctgtggtcct gggctcccca gtggggcggt 15901 cagcttggca gcgtcctggc cgtggactgc ggcatggtgt cctggggttc actgtgtatg 15961 tgaccctcag aggtggtcac tagttctgag gggatggcct gtccagtcct gacttcctgc 16021 caagcgctgc tccctggaca cctgtggacg cacagggctg gttccctga agccccgctt 16081 gggcagccca gcctctgacc tgctgctcct ggccgcgctc tgctgccccc tgctggctac 16141 cccatgtgct gcctctagca gagctgtgat ttctcagcat aactgattac tgtctccagt 16201 actttcatgt ccctgtgacg ggctgagtta gcatttctca cactagagaa ccacagtcct 16261 cctgtgtaaa gtgatcacac tcctctctgt gggacttttg taaaagattc tgcagccagg 16321 agtcatgggt ggtcttagct gagaaatgct ggatcagaga gacctgataa ccgatgtgaa 16381 gagggggaacc tggaagatct tcagttcagt tcatttcagt cattcagttg tgtccgactg 16441 tttgggatcc catggactgc cacacgccag tcctccctgt ccatcaccaa cttctgaagc 16501 ttgttcaaac tcatgtccat caagttggag atgcctttca accatctcat cctctgtcat 16561 cccttctcc tcccgccttc aatcttccct agcattaggg tcttttccgt gagtcagttc 16621 ttcgcatcag gtggccaagt tttggagttt cagtttcagc atcagtcctt tcaatgaata 16681 gtaaggactg atttcccttta ggatggactg gtttgatatc cttgcagttc aagggactct 16741 caagagtctt ctccaacact gcagttaaaa gccatcaatt cttcggtgct cagctttctt 16801 tttggtacaa ctctcacatt catacatgac taccgaaaat acattagtcg tgtagaacca 16861 gtttgggct tcccacgtgg ctctagtggt aaagaatatg cctgccaact cagaagatgt 16921 aagagatgcg gttcaatctc tgggtcggga agatcccctg gagaagggca tgacaaccca 16981 ctccagtatt tttgcctgga gaatcccatg gacagagaag cctggtggac tgcagtccat 17041 ggagtctcac agagtcagac acgactgaag caacttagct acttggaaaa gagcatgcac 17101 gaagctgtct aaaaacagg tcaagaagtc ttgtgttttg aaggtttact gagaaagttg 17161 atgcactgct ccaacacttc ctctcagttg aaaagatcag aagcgttaga tcaaatggtg 17221 gtcaatacct tggatgcgct ccaacaggtt atatctgcag atggaaatga aggcagttta 17281 tggggtaact ggaggacaag atgagatcat acacttggaa cactgtctgg catcaaaggc 17341 gtgtacagta aacattagct gttattagca aaataaattc agcttgaatc acccaaatca 17401 gatggcattc ttaaagccac tgagtggtaa atcaggggt gtgcagccaa aacgtccatt 17461 ttgactcatt atgatttcca tgtcacaaga ctagaaagtc actttctcct cagcagaaga 17521 gaaggtagaa cattttaacc ttttttgga gtgtcaaggg aattttgttt acactgtaaa 17581 gtcagtgaaa atattgaagc ttttcatttg tggaaaatat taaatatgta aaattgaaat 17641 tttaaaattt attcctgggt agttttgttt ttccagtagt catgcatgga tgtgagagtt 17701 ggactataaa gaaagctgag cgctgaagaa ttaatgcttt tgaactgtgg cactggagaa 17761 gactcttgag agtcccttgg tctgcaagga gatcaaacca gtccatccta aaggaaatca 17821 gtcctgaata ttcactgaa ggactgatgc tgaagctgaa actccaaatac tttggccacc 17881 tgatgtgaag aactgactca tatgaaaaga ctcagatgct gggaaagatt gaaggtggga 17941 ggagaagggg acgacagagg atgagatggc tgaatggcat caccgactcg atggacatga 18001 gtctgaataa gctctgggag ttgttgatgg acagggaggc cctggagtgc tgcagtccat
```

-continued

```
18061 gggattgcaa agagttggac atgactgagt gactgaactg aactgagttt ggtaacagat
18121 atgagaatta tataatttaa atctaaactc ttggtatttc ttttttggc ggttccaaaa
18181 gagctgtccc ttctgttaac tatataaatc cttttttgaga attactaaat tgataatgtt
18241 cacaagttat ccaattctc attactctta gttgtcagta taagaaatcc catttgattt
18301 atcatgttat agtatctgca actctaatag ttcagttctg acaaattttt attttattta
18361 aaaatattgg catacagtaa aatttcaaac aatatacaat tctcccttc agtttaaaaa
18421 acaaaacaaa acaaaagtaa tattagttaa aaaaatccgg gaagaatcca agcatttaaa
18481 attgcatcac atttctatgc tagacaagct gatataaagt tataattaat aaaggattgg
18541 actattaaac tctttacata tgaggtaaca tggctctcta gcaaaacatt taaaaatatg
18601 ttgtgggtaa attattgttg tccttaaaga aataaaaaga cataagcgta agcaattggn
18661 nnnnnnnnnn nnnnnnnnnn nnnnnnnnnn nnnnnnnnnn nnnnnnnnnn nnnnnnnnnn
18721 nnnnnnnnnn nnnnnnnnnn nnnnnnnnnn nnnnnnnna aaatggataa ggggggagga
18781 catgggtagg ggagcgcgat ggaggaagta aggtggtcga gggagttggg gggggaataa
18841 gtgggtaaaa gggaagcggg cggaaggagg gggaagcagg agagaggggt gggcgtcaga
18901 tcgggggggag gggtatgagg gagagggaat ggtagacggg gggtgggaag cataaaggaa
18961 aagataggg ggggaaaagt tagaagaaga atgagggggat aggcggaaag ggaagagaaa
19021 tgggagaaga acagaaaaat agggggaggg ggggcgtaaa gagggggggg gagggcaggt
19081 gtggagatga cagatacggg gaatgccccg gtataaaaga gtatatggcg tggggcgaga
19141 aggctgtcat cctgtgggag gggggacgcg gagaacccctt cgggctatag ggaggattcg
19201 ggggggatcgt tcgggaaggc agtcagcaca gcacccacca agggtgcagg gatggatctg
19261 gggtcccaaa gaagaggccc aatcccgcgt cttggcagca aggagccctg gagactggga
19321 agtgtccagg acactgaccc aggggttcga ggaacccaga agtgtgtctg tgaagatgtg
19381 ttttgtgggg ggacaggtcc agagctttga gcagaaaagc ggccatggcc tgtggagggc
19441 caaccacgct gatctttttt aaaaggtttt tgttttgatg tggaccatt ttaaagtctt
19501 cattgaattt gctacaatat tgtttctggt ttatgctctg gtttcttcgg ctgcaaggtt
19561 tgtgtgatcg tatctcctca accaggactg aacccacagc ccctgcactg gaaggcgaag
19621 tcttaaccca gatcgccagg aacgtccctc ccctcactga tctaatccaa gaccctcatt
19681 aaggaaaaac cgagattcaa agctcccccca ggaggactcg gtggggagga gagagccaag
19741 cactcagcac tcagtccagc acgcgccct ccctgtccag ggcgagggct cggccgaagg
19801 accaccggag accctgtcgg attcaccagt aggattgtga ggaatttcaa cttactttt
19861 aaatctgtct ctcaaggctg ttacaagcgg actttaccag taacttaaaa gttgaagggg
19921 acttcccagg cggcacttgc ggtgaagaac ccgccggctg gttttaggag acataagaga
19981 tgtgggttag atccctggtt caggaggatt cccctggaga aggaaatggc aacccactcc
20041 agtattcttg cctggaaagc ctcacggaca gaggaggctg gcgggctaca gtccacgggg
20101 tcgcacacga ctgaatcgac ttagcttcaa gttgagacag gaagaggcag tgactggtgg
20161 caaaacaccg cacccatgct cccaggggac ctgcagcgct ctggttcatg agctgtgcta
20221 acaaaaatca acccaacgag aggcccagac agagggaagc tgagttcatc aaacacgggc
20281 atgatgtgga ggagataatc caggaaggga cctgccaagc ccatgacaga ccggtgtcct
20341 gtctgagggc cgtcctggca gagcagtgca gggccctccg agaccgcccg agctccagac
20401 ccggctgggg gctacagggt ggggctgagc tgcaaggact ctgctgtgag ccccacgtca
```

-continued

```
20461 gggaggatca ccttgtttgt tttctgagtt tctcttaaaa tagcctttat gggtcctggt
20521 ctttggtttt aaaataacaa ctgttctccg taaacaacgt gaaaaaaaac aaacaggagg
20581 aaaacaacgc agcccgggca tttcacccgg aagagccgcc tctaacactt tgacgggttg
20641 ccttctattt taaccctgtt ttcattgtaa actgtaaaaa ccacatcata aataaattaa
20701 aggtctctgt gaagtttaaa aagtaagcat ggcggtggcg atggctgtgc cacaccgtga
20761 acgctcgttt caaaacggta aattctaggg accccctggt ggtccagtgg gtgagatttt
20821 gcttccattg caggagccgt gggtttgatc cctggttggg gaactaagat cccacatgct
20881 gtatggagtg gccaaaaaga atttttttgta aatggtgagt tttaggtgac gtgaattttcc
20941 cattgatgca cttcacaggc tcagatgcag ccaggccctc aggaagcccg agtccaccgg
21001 tcctttactt ttccttagag ttttatggct tctgtttctg cccttaaacc caccatgttt
21061 caacctcatc tgattttgga ctttataata aagttaggct gtgtttcagg aaactttgct
21121 cagtattctg taataatcta aatggaaaga atttgaaaaa agagcagaca cttgtacatg
21181 cataactgaa tcactttggt gtacacctga aactcgagtg cagccgctca gtcgtgtccg
21241 accctgcgac cccacggact gcagcacgcg ggcttccctg cccatcacca actcccggag
21301 ttcactcaaa cacatgtccg tcgactcggt gatgccgtcc aaccgtctca tcctctgtcg
21361 tccccttctc ctcccgcctt caatcttttc cagcatcagg gtcttttcaa atgagtcagt
21421 tcttcacacc aggtggccag agtattggag tttcagcttc agcatcagcc cttccaacga
21481 cccccatac ctgaagctaa cacagtgcta atccactgtg ctgcaacatg aaagaaaaac
21541 acatttttta agtttaggct gtgtgtgtct tccttctctc aacactgcgt ctgaccccac
21601 ccacactgcc cagcactgca ttccccgtgg acaggaggcc ccctgcccca cagctgcgtg
21661 ccggccggtc actgccgagc agacctgccc gcccagagtg gggcccctgg cactggggac
21721 aaggcagggg cctctccagg gccggtcact gtccactgtt cctactggtt ttgttttcaa
21781 aagtggaggc agcgtaatat ttccctgatt ataaaagaa gtacacaggt tctccacaaa
21841 taaaacaggg gaaaagtata aagaatggaa gttcccagca cagcctggag atcacgccgg
21901 gtgcacctgg ggtgtccttc caggctggac ctcacatttc acgcagacat cagaaggctg
21961 cgagatctac ccagaaggct gggtagatgg gggataggtc agtgacaaac agtagacaga
22021 gagatataca gacagatgat ggatagacag acgctaagac accgagcgag gggacagacg
22081 gatggaagac accatccttt gtcactgacc acacacccac atgggtgtgg tgagccggct
22141 gtcatacttg tgaacctgct gctctcacaa caccagctgg gtccctccag ccccagcgtc
22201 ccacacagca gactcccggc tccatcccca ggcaggaatc ccaccaccaa ctggggtgga
22261 ccctccccgc aggaaggtcg tgctgtctaa ggccttgaga gcaagttaca gacctacttc
22321 tgggaagaca gcgcacaacc gcctaccccg cagagcccag gaggacccct gagtcctagg
22381 gaagggacca cgcggcctgg acggggagcg gccccaggac gctgccccca acctgtccca
22441 cctcactcct gctctgctct gaggcggggc gcagagaggg gccctgaggc ctcttcccag
22501 ttcttgggag cacccactgg gcctgaacca ggccagaagc cccctcctca aggtgtcccc
22561 agaccactcc cctccacctc cggttgctct gtctcctggc agcagggagc cccagtgaga
22621 agagacagct ccaggctgtg atcttggccc ctggctgctc tggcagtgtg ggggtgggg
22681 gtcgctggga ggccatgagt gctggggtc ggggctgtga aagcacctcg aggtcagtgg
22741 gctgttggtc gggctctgcg aggtccgcac gggtagagct gtgccaggac acaggaggcc
22801 tggtcagtgg tcccaagagt cagggccaaa ggaagggggtt cgggcccctc tggttcctca
22861 gcttctgagg ccggggaccc cagtctggcc ttggtagggg ggcgattgga gggtacaacg
```

```
22921 atccaaaaga aaacacacat ctacgaggga agagtcctga ggaggagaga gctacacaga
22981 gggtctgcac actgcggaca ctgcttggag tctgagagct cgagtgcggg gcacagtgag
23041 cgaagggagg acggaacctc caaggacacc ggacgccgat ggccagagac acacgcacgt
23101 cccatgaggg ccggctgctc agacgcaggg gagctcctca ttaaggcctc tcgctgaata
23161 gtgaggagaa ctggccccgt gtgtggggaa acttagccca gaagaaacgc tgccctggcc
23221 ccaaggatca nnnnnnnnnn nnnnnnnnnn nnnnnnnnnn nnnnnnnnnn nnnnnnnnnn
23281 nnnnnnnnnn nnnnnnnnnn nnnnnnnnnn nnnnnnnnnn nnnnnnnnnn tgccctttgc
23341 ctccagggag ggaggaagcg tggatcttgg gtttgccttg ggtttaaagg atccacccac
23401 tcccttttta gccactccct gtgctggcaa tttcttaaga ctggaggtcg caaagagttg
23461 gacacactga gcgagtgaac tgcactgagc ctaagaaaag tctttgaatt cctccaaaca
23521 aaacacactt gtcttgggta ctttccttgg ttttgttaca aatgtctggt ccctctgttc
23581 tcctggccag ctcctggggt tcattttgac ctgacgaagt caaagggagc ctggaccctc
23641 aaaatctgta ggacccagca cccctccatt acacctctgt tccccgcgca acgggcacgt
23701 gtttcgccgt ctggcgtaat gtgtaagcga cggtgtgata ctcgggagtc ttactctgtt
23761 tcttttttctt ctggggtgac accaccatcc gcacgactct gtctgaatgt gaacatttgg
23821 gtgatttgat gtggcccaga ctcccccaac gaatgtacct tcaggttggt tttcttcttt
23881 tatattttgc ttttgtgaat agacacagga tcccatcagt tgtatgtagt gagaaagtaa
23941 aaacccactc agccttagct ggatggagat ctagtagtaa gatagcacgt tagccggaaa
24001 tggaaatttc agccagaatc tgaaaagcgt gtcctggaag gagaagaggg actcaggccc
24061 gagcacactg ctccacgctg gagcctcagg ctctgacagc tgtacctgcc ggggtcttca
24121 tgggacaggc catgcaggcc acgatcccgt tgagaagttt cttgcctttc catcacattg
24181 gcaattgcac gctttgctct tgcttctaca tggagttta cttttatccc agacagtttg
24241 gtttcttctc tgattttcgc caattgtaca gatcgttaca gtatttctta accacataga
24301 attcggcagg ggggtgggg ggacagggta gggtggggtg agagtgaggg gaggggggctg
24361 caccgagcag catctggggt cgtagctccc tgacggggat agacctcgtg cccctgcagt
24421 gacagcacag agtcctcctc tctgaactgc cagggacgct cctgcaattg acttaatgaa
24481 aggcatctaa ttaggaattt tggggtgaca ttttacattt aagtgtgtga gcagtgatta
24541 tagttcatat cattttatag tttcgtgatt ttactagctt aaagggtttt tggggtttct
24601 ttttgttta aaagctaaaa tctgttttt aattccatgg aatacaaaaa aaaaaagtct
24661 gtagaatatt ttaaagagtg aaggctttgt tcggaatgtg agcgctttgc tccactgaac
24721 cgaacggtaa taacatttgt agaagagacg cagagtgaaa ggtacctctt tttattgagt
24781 gacatgacag cacccatcgc gtgagttatt ggctggagtt tagagacagg ccatgttggg
24841 ctaaactcct tattgctgtt ctcagccttt gagtaataat cagaagcttt ctctgaagag
24901 agtgggtca gctgtcagac tcctaggtgt ctacctgcag cagggctggg attaaatgca
24961 gcagccagta gatacgggat ggggcaagag gtcaccttgt cctttgttg ctgctgggag
25021 agaggcttgt cctggtgcca gtggggccaa agctgtgact tgtgaccac aggatgtctc
25081 tgaccctgcc ttgggttccc tgagggtgga gggacagcag ggtctcccg gttccttggc
25141 cggagaagga cccccaccc cttgctctct gacatccccc caggacttgc cccggagtag
25201 gttcttcagg atgggcatcc gggccccacc ctgactcctg gagctggccg gctagagctt
25261 gctgcagaat gaggccttgg ccattgcggc cctgaaggag ctgcccgtca agctcttccc
```

-continued

```
25321 gaggctgttt acggcggcct tgccaggag gcacacccat gccgtgaagg cgatggtgca
25381 ggcctggccc ttcccctacc tcccgatggg ggccctgatg aaggactacc agcctcatct
25441 ggagaccttc caggctgtac ttgatggcct ggacctcctg cttgctgagg aggtccgccg
25501 taggtaaggt cgacctggca gactggtggg gcctggggtg tgagcaagat gcagccaggc
25561 caggaagatg aggggtcacc tgggaacagg cgttgggtgt acaggactgg ttgaggctca
25621 gagggacaa aaggcacgtg ggcctccccc ccagtgtccc ttaaagtggg aaccaagggg
25681 gccccggaag ccggaggagc tgtggtgtgt ggagtgcaga gccctcgcgg ggtcctgatg
25741 cccgtcggac tctgcacagc tcagcgtgtg ccccgcggcc cggtaggcgg tggaagctgc
25801 aggtgctgga cttgcgccgg aacgcccacc agggacttct ggaccttgtg gtccggcatc
25861 aaggccagcg tgtgctcact gctggagccc gagtcagccc agcccatgca gaagaggagc
25921 agggtagagg gttccagggg tggggctga agcctgtgcc gggccctttg gaggtgctgg
25981 tcgacctgtg cctcaaggag gacacgctgg acgagaccct ctgctacctg ctgaagaagg
26041 ccaagcagag gaggagcctg ctgcacctgc gctgccagaa gctgaggatc ttcgccatgc
26101 ccatgcagag catcaggagg atcctgaggc tggtgcagct ggactccatc caggacctgg
26161 aggtgaactg cacctggaag ctggctgggc cggatgggca acctgcgcgg ctgctgctgt
26221 cgtgcatgcg cctgttgccg cgcaccgccc ccgaccggga ggagcactgc gttggccagc
26281 tcaccgccca gttcctgagc ctgcccacc tgcaggagct ctacctggac tccatctcct
26341 tcctcaaggg cccgctgcac caggtgctca ggtgaggcgt ggcgccagct ccaaagacca
26401 gagcaggcct ctcttgtttc gtgcccgctg gggacattgc cagggtgccc ggccactcgg
26461 aagtcctcac gatgccaccg ctctgaccct gggcatcttg tcaggtcact tccctggtta
26521 gggtcagagg cgtggcctag gttaaatgct gtcaaagggg actccttct gggagtccgc
26581 atagtggggg cttggtgtga tgcccttggg aattctttcc gagagagtga tgtcttagct
26641 gagataatga cagataacta agcgagaagg acggtccatc aggtgtgagg tttgaagtcc
26701 aaagctctgt ctctccctcc cacctgcccc ttctgtcctg agctgtttta ggctccaggt
26761 gagctgtggg aagtgggtga ttctggagat gacaagaagg gatcaggagg ggaaaattgt
26821 ggctcctaag cagtccagag aagagaaaaa gtcaaataag cattattgtt aaagtggctc
26881 cagtctcttt aagtccaaat tataattata attttcctct aagacttctg aatacatagg
26941 aaatcctcag taacaggtta ttgctctgcc ttgaacacag tgataaaagc tgggaggatg
27001 cagcctaatc tgtctgtgtg aatgagttgt attgattccc ttttttggcag ctgcaaactc
27061 caagcattag gaataaatat gttcactgag aaccccgaag aaagaaagaa agaaaaaaaa
27121 aaagaattgt aggtgttgat ggacggtttg tggccccctga atatctgggg gatgttcacc
27181 cagggatcac gtgtaactgc tgggaccccc agcccatgt ccactgcatc cagcctgctg
27241 ttgaattccg cggatcnnnn nnnnnnnnnn nnnnnnnnnn nnnnnnnnnn nnnnnnnnnn
27301 nnnnnnnnnn nnnnnnnnnn nnnnnnnnnn nnnnnnnnnn nnnnnnnnnn nnnnnncaat
27361 tcgagctcgg tacccccaaag gtccgtctag tcaaggctat ggttttttcca gtggtcatgt
27421 atggatgtga gagttggact gtgaagaaag ctgagtgcca agaattatt cttttgtact
27481 gggtgttgga gaagactctt gagagtccct tgaactgcaa ggagatccaa ccagtccgtt
27541 ctaaaggaga tcagtcctga atgttcattg aaggactga tgctgaagct gaaactccaa
27601 tactttggcc acctgacgtg aagagttgac tcattggaaa agaccatgat gctgagagga
27661 attgggggca ggaggagaag gggacgacag aggatgagat ggctggatgg catcaccaac
27721 tcgatgngac atgagtttgg ttaaactcca ggagttggtg atggacttgg aggcctggtg
```

```
27781 tgctgggatt catggggtcg cagagtcgga catgactgag cgactgaact gaactgaact
27841 gagctgaaga gctcacctgt accagagctc ctcaggtcct cctgcaggcc tggctgtaat
27901 ggcccccagg tcaccgtcct gcctccttca tcccatcctt tcacgacagg ctgggagtgg
27961 ggtgaggtga gttgtcttgt atctagaatt tctgcatgcg accctcagag tgcaatttag
28021 ctccagagaa ctgagctcca agagttcatt tttccttttt cttctttatg atactaccct
28081 cttctgagca gagacctcat gtcagggaga aggggactct gccttcctca gccttttgtt
28141 cctccaagac ccacacgggg agggtcgcct gcttcactga gccggaaggt tcaattgctc
28201 atgtcctcca gaaacacccc cccccccaga gacccccaga ataagtgga acagcacctt
28261 gtttcccaga caagtgggac acacgttatg aaccacctca gtgattaaaa tagtaacctc
28321 tgtgtatgtg tatttactgg agaaggaaac ggcaacctac tccactattc ctgcctagaa
28381 aattccatgg gagagaagcc aggcaggcta cagtccacgg ggtcacagag actgaacata
28441 cacaagcaca tggaagtgta ttttgcagta tttttaaatt tgttcagttc aacatggagt
28501 acaagaattc aaatcgtgaa gtcaattgac caagaaacca gaagaaatca ctgtgttgtg
28561 atctctgtgg aggtaacatg ggtacctgtg ctctgaccct cacagcctct ggctctctct
28621 ctacatgtac atacacatat atttccatgt atgtatgtat tcggaagatt tcacatacgt
28681 ctcaccagtc cacagccccc gcgttccctg atgcccagaa catctgtgat agctgtgagt
28741 attgtcacca gataagatct tccaggttcc tgcactcaca ttggttatca ggtctctctg
28801 atccagcatt tctcagctaa gattccttgt gactcctggc tgcagaatct tctgcaaaag
28861 tcccacagag aggagtgtga tcactgtaca caggagggcc gtggttctct agtgtgagaa
28921 aagctaactc agcccgtcac agggacgtga atgtacctga gacagtaatc agttatgctg
28981 agaaatcaca gctctgctag aggcagcaca tggggtagcc agcaggggc agcagagcac
29041 ggccaggagc cgcaggtcag aggctgggct gcccaagcgg ggcttcaggg gaaccagccc
29101 tgcgggtcca caggtgtcca gggagcagcg cttggcagga agtcaggacc ggacaggcca
29161 tcccctcagg actagtgacc acctctgagg gtcacatcca cagtgaaccc cagagcacca
29221 tgcctcagtc cacggccagg acgctgccag gctgaccgcc ccactgggga gtccagggga
29281 gaccacaggc cgggggggctt gggacagtga tcatgtggtc agacacagag aaggtgacag
29341 tgacctcagt ccctgaggac aagtctgatg tgcagacgtg agaagccgag gaggaagctg
29401 gggacagaca gggctgatgg tgtggtgacc ccgcctctca gtgaggggcc cccgggggtg
29461 aatttgcata aacccaagcc ctcactgccc ccacaaagct ctgagaggga ataaaggggc
29521 tcggagagcc cagcactgct gcgggctcag aggcagagct cggggcgcgt ccaccatggc
29581 ctgggcccct ctcgtactgc ccctcctcac tctctgcgca ggtgcggccc cccagcctcg
29641 gtccccaagt gaccaggcct caggctggcc tgtcagctca gcacaggggc tgctgcaggg
29701 aatcggggcc gctgggagga gacgctcttc ccacactccc cttcctctcc tctcttctag
29761 gtcacctggc ttcttctcag ctgactcagc cgcctgcggt gtccgtgtcc ttgggacaga
29821 cggccagcat cacctgccag ggagacgact tagaaagcta ttatgctcac tggtaccagc
29881 agaagccaag ccaggccccc tgtgctggtc atttatgagt ctagtgagag accctcaggg
29941 atccctgacc ggttctctgg ctccagctca gggaacacgg ccaccctgac catcagcggg
30001 gcccagactg aggacgaggc cgactattac tgtcagtcat atgacagcag cggtgatcct
30061 cacagtgaca cagacagacg gggaagtgag acacaaacct tccagtcctg ctcacgctct
30121 cctccagccc cgggaggact gtgggcacag cagggacagg cctggcccgg ttcccccgga
```

-continued

```
30181 gctgagcccc caggcggccc cgcctcccgg ccctccaggc aggctctgca caggggcgtt 30241 agcagtggac gatgggctgg caggccctgc tgtgtcgggg tctgggctgt ggagtgacct 30301 ggagaacgga ggcctggatg aggactaaca gagggacaga gactcagtgc taatggcccc 30361 tgggtgtcca tgtgatgctg gctggaccct cagcagccaa aatctcctgg attgacccca 30421 gaacttccca gatccagatc cacgtggctt tagaaaggct taggaggtga acaagtgggg 30481 tgagggctac catggtgacc tggaccagaa ctcctgagac ccatggcacc ccactccagt 30541 actcttccct ggaaaatccc atggacggag gagcctggaa ggcttcagcc catggggtcg 30601 ctaagagtca gacacgactg agcgacgtca cttttccctt tcactttcat gcattggaga 30661 aggaaatggc aacccagtcc agtgttcctg cctggaaaat cccagggaca ggggagcctg 30721 gtgggctgcc atccatgggg ccacacagag tcagacacga ctgaagcaac ttagcagcag 30781 cagcagcagc ccaataaaac tcagcttaag taatggcatc taaatggacc ctattgccaa 30841 ataaggtcca ctcgcgtgca ctctgtttag gacttcagtt cctgattgtg gagggttccc 30901 acaagacgtg tgtgtatatt ggtgttgccg gaaaacagtg tcaatgtgag catcccagac 30961 tcatcaccct cctactccca ctattccatt gtctctgcag gtattaagca taaaggttaa 31021 gggtcttatt agatggaaga ggagtgaata ctcgtctgtg cttaacacat accaagtacc 31081 atcaaggtcc ttcctattta ttaacgtgtg ttttaatcag aaatatgcta tgtagaagca 31141 tccggacgat agcccatgtt acagacgggg aagctgaggc atgaagttct cagcaccttg 31201 tttcacgtca gacctgaaac ggggcagagc cggcagcaaa caaggttcct cttcccaagc 31261 gcccgctctt caccccgcttc ctatggcttc tcactgtgct tcctaaacta agctctcccc 31321 aaccctgtgg agacaggatt agagacttta ggagaaaaga ccaggaacat cccacacccg 31381 acccgagtga gccactaaga caaggctttg taaggacaga accagcaggt gtcctcagcg 31441 agccagggag agacctcgca ccaaaaacaa tattgtagca tcctgaccct ggacttctga 31501 cctccagaaa tgtgaaaaag aaacgtgtgg ggtttaatca actcaccggt gttatttggt 31561 tatgactgcc tgagttaaga aggagttggg aacacttgag tgtaggtgtt tatggaacat 31621 aagtcttgtt tctctgaaat aaattcccaa gggtataatt cctaggttgt agggtaactg 31681 ccacaaatct aggcagctta ttaaaaaaca aagatatcac tttgccagca aaggttcata 31741 tagtcaaatt atggtttta tagtagtcat gtatggatgt aaaagttgga tcataaagaa 31801 ggctgagcac cagagaattg atcccttcaa atcgtggtgc tggagaagac tcttgagagt 31861 cccttggaca gcaaggagat ccaaccagtc aatcctaaag gaaatgaact gtgaatattc 31921 actggaagga ctgatgctga agctgaagat ccaatacttt ggccacctga tgcgaagagt 31981 tgactcattg gaaaagaccc tgatgctgga aagcttgagg gcaggaggag aagagggcgg 32041 cagaggatga gacggttgga tggcatcact gactcaatgg acatgagttt gagccaactc 32101 tgggagacag tgaaggatag ggaaggctgg cgtggtacag tgcatgcggt cacaaagagt 32161 ctgacacatc ttagtgactc aacaacgaca gcaacacagg catcacacgc ttagtgtgat 32221 aagcggcaga actgttttcc aggggtccgn nnnnnnnnn nnnnnnnnn nnnnnnnnn 32281 nnnnnnnnn nnnnnnnnn nnnnnnnnn nnnnnnnnn nnnnnnnnn nnnnnnnnn 32341 nnnnnnnng tacgattcga gctcggaccc tgacattgtg agtcacgtca tgagcagctg 32401 ttttccgtc ttcagggatt gtggacgatt tctgtttggg tttgctcatg ataatttagt 32461 tacagcttag gttctttctt tccaggccac gagcgacatg ttttcaggtg agatgacgtg 32521 gtgggggatg ggcggccaag cccccactgg gggggaggg attctgttgt gggcaggagt 32581 tggcagcatc cctgaactga tgacctgcga tccaggtgac aagaaccggg ggatattatt
```

-continued

```
32641 cctctgcctt ctcatgtcat gtcctcggtt cttcatgatg aaacatatg acaatacagg
32701 ggagttagat ttgggcgggc acaactctgg gtgggggacc cggtggcatt gtgcccagca
32761 gggccatcaa gatgagggcg acctgggtgg tccccttctc ccctggggtc ttagtttttcc
32821 cctcatggaa atgggatcag gcagcagcca tggaacaccg cgaccgtggc ttctctcacc
32881 tcctcgtctg tgattttggg tcgggatacc aggcatgaag acctggggcg gggggacatc
32941 actcctctgc agcagggagg ccgcagagtc ctccgtccat gaggacttcg tccctgggct
33001 gaccctgcgg actgctggag gctgaagctg gaggcacagg cgggctgcga ggccagggtc
33061 ctgaggacga cagagccagt ggggctgcag ctctgagcag atggcccctc gccccgggcc
33121 ctgagcttgt gtgtccagct gcaggttcgc tcaggtgagc cactacgtta tggggaggc
33181 gccctgggca gggatcgggg gtgctgactc ctccgagatt ccgaccttct gggagcactc
33241 tggccacact ctaagcctgg caagagctgg gttcatcagt ctaactctcc tcctgaagtc
33301 caatggactc tctccatgcg gcagtcactg gatggcctct ttatccccga tggtgtcctt
33361 ttccgctgac ctggctctcc tgaccacctc ccagcccccc accatacagg aagatggcac
33421 ctggtccctg cagagctaag tccaccccctg gcctggcttc agatgcctac agtcctcctg
33481 cgggaggccc cgctccccac taggccccaa gcctgccgtg tgagtctcag tctcacctgg
33541 aaccctcctc atttctcccc agtcctcagc tcccaacccc agaggtatcc cctgcccctt
33601 tcaaggccct tgtcccttcc tggggggatg gggtgtatgg gagggcaagc ctgatccccc
33661 gagcctgtgc cgctgacaat gtccgtctct ggatcatcgc tcccctggct ctcagagctc
33721 cctggtccct ggggatgggt tgcggtgatg acaagtggat ggactctcag gtcacacctg
33781 tcccttccct aaggaactga cccttaaccc cgacactcgg ccagacccag aaagcacttc
33841 agacatgtcg gctgataaat gagaaggtct ttattcagga gaaacaggaa cagggaggga
33901 ggagaggccc ctggtgtgag gcgacctggg taggggctca ggggtccatg gagaggtggg
33961 ggagggggtg tgggccagag ggcccccgag ggtgggggtc cagggcccta agaacacgct
34021 gaggtcttca ctgtcttcgt cacggtgctc ccctcgtgcg tgacctcgca gctgtaactg
34081 cctttcgatt tccagtcgct gcccgtcagg ctcagtagct gctggccgcg tatttgctgt
34141 tgctctgttt ggaggcccgg gtggtctcca cgttgcgggt gatggtgctg ccgtctgcct
34201 tccaggccac ggtcacgcta cccgggtaga agtcgctgat gagacacacc agggtggcct
34261 tgttggcgct gagctcctcg gtgggggcg ggaacagggt gaccgagggt gcggacttgg
34321 gctgacccgt gtggacagag gagagggtgt aagacgccgg ggaggttctg accttgtccc
34381 cacggtagcc ctgtttgcct tctctgtgcc ctccgaccct tgccctcagc ccctgggcgg
34441 cagacagccc ctcagaagcc attgcaatcc actctccaag tgaccagcca aacgtggcct
34501 cagagtcccc ggctgcgacc agggctgctc tcctccgtcc tcctggcccc gggagtctgt
34561 gtctgctctt ggcactgacc ccttgagccc tcagcccctg ccagacccct ccgtgacctt
34621 ccgctcatgc agcccaggtg cctcctccgt gaacccgggt ccccccgccc acctgccagg
34681 acggtcctga tgggagatgt ggggacaagc gtgctagggt catgtgcgga gccgggcccg
34741 ggcctccctc tcctcgccca gcccagcctc agctctcctg gccaaagccc ggggctcctc
34801 tgaggtcctg cctgtctacc gtccgccctg cctgagtgca gggcccctcg cctcacctgc
34861 cttcagggga cggtgccccc acacagcacc tccaaagacc ccgattctgt gggagtcaga
34921 gccctgttca tatctcctaa gtccaatgct cgcttcgagg ccagcggagg ccgaccctcg
34981 gacaggtgtg accccctgggt cccaggggat caggtctccc agactgacga gtttctgccc
```

```
35041 catgggaccc gctcctttct gaccgctgtc ctgagatcct ctggtcagct tgccccgtct 35101 cagctgtgtc caccceggccc ctcagcccag agcgggcgag accectctct ctctgccctc 35161 cagggccttc cctcaggctg ccctctgtgt tcctggggcc tggtcatagc ccccgccgag 35221 cccccaagct cctgtctggc ctcccggctg gggcatggag ctcacagcac agagcccggg 35281 gcttggagat gcccctagtc agcaccagcc tctggcccgc acccagcgt ctgccctgca 35341 agaggggaac aagtccctgc attcctggac caaacaccag cccccggcgcc ccgactggcc 35401 ccattggacg gtcggccact ggatgctcct gctggttacc ccaagaccaa cccgcctccc 35461 ctccceggccc cacggagaaa ggtggggatc ggcccttaag gccgggggga cagagaggaa 35521 gctgcccca gagcaagaga agtgactttc ccgagagagc agagggtgag agaggctggg 35581 gtagggtgag agccacttac ccaggacggt gacccaggtc ccgccgccta agacaaaata 35641 cagagactaa gtctcggacc aaaacccgcc gggacagcgc ctggggcctg tccccgggg 35701 gggctgggcc gagcgggaac ctgctgggcg tgacgggcgc agggctgcag ccggtggggc 35761 tgtgtcctcc gctgagggggt gttgtggagc cagccttcca gaggccaggg gaccttgtgt 35821 cctggaggtg ccctgtgccc agcccctgg ccgaggcagc agccacacac gcccttgggg 35881 tcacccagtg ccccctcact cggaggctgt cctggccacc actgacgcct tagcgctgag 35941 ggagacgtgg agcgccgcgt ctgtgcgggg cggcagagga gtaccggcct ggcttggacc 36001 tgcccagccg ctcctggcct cactgtaagg cctctgggtg ttccttcccc acagtcctca 36061 cagtccagcc aggcagcttc cttcctgggg ctgtggacac cgggctattc ctcaggcccc 36121 aagtggggaa ccctgccctt tttctccacc cacggagatg cagttcagtt tgttctcttc 36181 aatgaacatt ctctgctgtc agatcactgt ctttctgtac atctgtttgt ccatccatcg 36241 atccaacatc catccatcca tccatcaccc agccatccat ctgtcatcca acatccatcc 36301 ttccatccat tgtccatcca tctgtccatc ttgcatctgt ctgtccaaca gtggccatca 36361 agcacccgtc tgccaagccc tgtgtcacac gctgggactt ggtggggga gccctcgccc 36421 tcccaccctc ccatctctcc tgaaacttct ggggtcaagt ctaacaaggt cccatcccgt 36481 ctagtctgag gtcccccgc agcctcctct tccactctct ctgcttctga cccacactgt 36541 gcactcggac gaccacccag ggcccttgca tccctgtttc cttcctgacc tctttttttt 36601 ggctctggat ttatacacat tctgcctcct ggaggcgtct cagcttgagt gtcccacaga 36661 cgcctcagac tcagcatctt ccatcgaaac tgctcccagg tccttgcaga cctggtcccc 36721 cacattgttc tcaattcggt agatttctcc acaagccaga ggcctggact catcccataa 36781 tgcctgcccc tcattgagtc agcctctgtg tcctaccata accaaacatc cccttaaaaa 36841 tctcagaaga acaaaaaaag cacccagatg gcactgtcag agtttatgat gacaagaatc 36901 ctcagttcag ttcagtcact cagtcgtgtc cgactctttg cgacccatg aatcgcagca 36961 cgccaggcct ccctgtccat caccaactcc cggagttcac tcagactcac gtccattgag 37021 tcagtgatgc catccagcca tctcatcctc tctcgtcccc ttctcctcct gccccaatc 37081 cctcccagca tcagagtttt ttccaatgag tcaactcttc gcgtgaggtg accaaagtac 37141 tggagtttca gcttcagcat cattccttcc aaagaaatcc cagggctgat ctccttcaga 37201 atggactggt tggatctcct tacagtccaa gggactctca agagtcttct ccaacaccac 37261 agttcaaaag cctcaattcc ttggcgctca gccttcttca cagtccaact ctcacatcca 37321 tacatgacca caggaaaaac cataaccttg actagatgga cctttgttgg caaagtaatg 37381 tctctgcttt ttaatatgct atctaggttg ctcataactt tccttccaag aagtaagtgt 37441 cttttaattt catggctgca atcaacatct gcagtgattt tggagcccca aaaaataaag
```

-continued

```
37501 tctgccactg tttccactgt ttccccatct atttcccatg aagtgatggg accagatgcc
37561 atgatctttg ttttctgaat gttgagcttt aagccaactt ttcactctcc actttcactt
37621 tcatcaagag gcttttagt tcctcttcac tttctgccat aagggtggtg tcatctgcat
37681 atctgaggtt attgatattt ctcctggcaa tcttgattcc agtttgtgtt tcttccagtc
37741 cagtgtttct catgatgtac tctgcatata agttaaataa gcagggtgat aatatacagc
37801 cttgacgtac tcctttcct atttggaacc agtctgttgt tccatgtcca gttctaactg
37861 ttgcttcctg acctgcatac agatttctca agaggcaggt caggtggtct ggtattccca
37921 tctctttcag aattttccac agttgattgt gatccacaca gtcaaaggct ttggcatagt
37981 caataaagca gaaatagatg tttttctgaa actctcttgc tttttccatg atccagcaga
38041 tgttggcaat ttgatctctg gttcctctgc cttttctaaa accagcttga acatcaggaa
38101 gttcacggtt catgtattgc tgaagcctgg cttggagaat tttgagcatt cctttgctag
38161 cgtgtgagat gagtgcaatt gtgcggcagt ttgagcattc tttggcattg cctttctttg
38221 ggattggaat gaaaactgac ctgttccagg cctgtggcca ctgttgagtt ttcccaattt
38281 gctggcatat tgagtgcagc actttcacag catcatcttt caggatttga aatcgctcca
38341 ctggaattcc atcacctcca ctagctttgt ttgtagtgat gctctctaag gcccacttga
38401 cttcacattc caggatgtct ggctctagat gagtgatcac accatcgtga ttatctgggt
38461 cgtgaagatc ttttttgtac agttcttctg tgtattcttg ccacctcttc ttaatatctt
38521 ctgcttctgt taggcccata ccgtttctgt cctcgcctat cgagccctcg cctccctacg
38581 tagagactct aagcaggaag gtgacccgtg ctgcactggg tccagcatgc ttttaattca
38641 gcagtggaac ttctgggtca tgattgtgtt taagggatgc gcatacgatt tttgaagcaa
38701 aatttaacag dacagcagtg taaagtcagt acttatttct gattaaagaa agcaaatatc
38761 cagcctgtta ctaagttaat taactaaaga aacatcttca acttaataaa cagtatctcc
38821 tgaaacttac agcatgcttc acatttaaag gcaaaaccat tttagaggcc agggttccca
38881 cgcttacgtt tattatttaa tatatgctac agattcaagc ccatgacaca aaatgggggg
38941 aagagtgtga gtgttaggaa aaatgagata aaattggttt ttgcaggtga tgggctagtt
39001 tactttaaaa aaaaaaacaa aacaagctca agatgaactg aaggactatt agaactggta
39061 caagagttaa cctgtgatcg aatacaagca ggctgggcaa aactcagcag gttttcttct
39121 atacaggcag taatgattga gaatacgaaa cggcggaagc gcttacaacc tcgataacag
39181 ttctattaaa agccctagga atgaacttaa cacggnnnnn nnnnnnnnnn nnnnnnnnnn
39241 nnnnnnnnnn nnnnnnnnnn nnnnnnnnnn nnnnnnnnnn nnnnnnnnnn nnnnnnnnnn
39301 nnnnnnnnnn nnnnngctcc ccccacccte ccctcctccc ccccaccac cagtgcccca
39361 ggtctcgtgc ccagagagct gaagatgcca gcaggcccgc tgcctgcctc gctcgcgtgg
39421 cccgggctcg ctgccggtct gcctgcccag cacacagatg cagcccagc tctcgctgcc
39481 acccgcctcc cccaggcagg actctcccac aacaccaagg gcgtctctgg gttcaggatg
39541 gccctcgttg aggtgtaaag tgcttcccgg ggctgagacg aatgggccgg agatccaaac
39601 gaggccaagg ccgccacggc gcctggcgca gggcacccat ggtgcagagc ggcccagctc
39661 cctccctccc tccctccctc cctgcttctt tatgctcccg gctatgtcta tttttactct
39721 gcaatttaga aatgataccg aaggacaaac accgttcccc ctgtgtgtct gctctaaacc
39781 cttatctac ttatctatta gcgtgtccaa gttttgctgc taagtgaatg aaggaacact
39841 acccacaagc agcaacgtcc ccacgaccct cgcctgttca actgggaatg taaatgtgct
```

-continued

```
39901 ttcaaaggac ctaagtttct atgttcaaaa ccgttgtgtg tttcttttgg gagtgaacct
39961 aggccactcg ttgttctgcc tttcaaagca ttcttaacaa ctctccagaa cccagggctt
40021 ggcttacgtt tccagaaatt ccaaagacag acacttggaa acctgatgaa gaaggcctgt
40081 gagcacagca ggggccgggg tacctgaggt aggtgggggg ctcggtgctg atggacacgg
40141 ccttgtactt ctcatcgttg ccgtccagga tctcctccac ctcggaggct ttcagcaggg
40201 tcacgctggt ggccagggtc gtgtatccat gatctgcaac cagagacggg gctgcggtca
40261 gcccgcgggc gggcagcagg caggagcagc caggagacgc agcacaccga ggtcctcaca
40321 tgcaggaggt gggggaagcg gctgtggacc tcacgactgc ccgatgtggg cctcttccaa
40381 agggccggcc tggaccctgg ctttctccag aggccctgct gggccgtccg cacaggctcc
40441 agccacaggg cctcttggga caggagggct ccagagtgag ccggccggcg ggaagaggtc
40501 tgacaccgct gcagtccaca acacgaagcg aggtggagat gggatgaggg atgagaaaca
40561 cttttctttt aaaacaagag cccagagagt tggaaagagc tgctgcacac gcaacatgaa
40621 ctcctggccc cggtgccagc ggcgctggga gcccgagttc tcggcaatcc gaccacagct
40681 tgcctaggga gccgggtgga gacggagggt taggggaagg cggctcccca gggagcgcga
40741 ggcccggggt cgccaaggct cgccagggc aagcgcagct aggggcgcag ggttagtgac
40801 cggcactgca cccggcgcag gagggccagg gaggggctga aaggtcacag cagtgtgtgg
40861 acaagaggct ccggctcctg cgttaaaaga acgcggtgga cagaccacga cagcgccacg
40921 gacacactca taccggacgg actgcggagt gcacgcgcgc gcacacacac acacacacca
40981 cacacacaca cacacgcccc gggacacact cataccggac ggactgcgga gtgcacgcgc
41041 acacacacac ccaccacaca cacacccacc acacacacac caccacaca cacacacaca
41101 cacacacacc cccacacaca cccacacaca cccacacaca cccacacaca cacacccaca
41161 cacacacaca cacacacaca cacacacacg cccggtggc cccaggcgca cacagcacgg
41221 agcaaacatg cacagagcac agagcgagcg ctagcggacc ggctgccaga ccaggcgcca
41281 cgcgatggat tgggggcggg gacggggagg ggcgggagca aacggnnnnn nnnnnnnnn
41341 nnnnnnnnnn nnnnnnnnnn nnnnnnnnnn nnnnnnnnnn nnnnnnnnnn nnnnnnnnnn
41401 nnnnnnnnnn nnnnnnnnnn nnnnngtatt aaagaagccg ggagcgagaa tatgacggca
41461 agaggatgta ggtgggggcg gggcaagagt aaagagagcg acggtagag gggatgcgat
41521 tgtgatgcgg aagcgagacg aggagtgatg ccgtattaga ttgatagcaa gaggaacagt
41581 aggagggggg ggggagagga gggggaggtg ggggtggtg ggtgggaagg gaactttaaa
41641 aaaaagaggg gagagttgga gggggaata aacgggcggt aaaaagaac aatttgaaat
41701 taccaggtg gggcggccag gggggtgatt cattcttgga gggggcaaca tatgggggt
41761 ggctgtcgcg gattaggaga aaataaatat cagggtgat taagtgtttg gcgttgggga
41821 ataatgaagt aagaatcaaa tatgaatcgc gttggcatcg ttagccatcg ggggaaacat
41881 ttcccatgca aggaacaagg atgtgagaat gcgtccgtct gaaccaccgt cccggggtcc
41941 cagtaggact cgccgagctg atagttgccg gagcaacagt taagggagca gaagctgcta
42001 caaaaccacc acctgccaaa gtagggtctc caattacgga gtgcgcctcc tgggtgtcgg
42061 tccaaaccctt tggaaggac ctggaaataa gtgctaccca ccagatatta atataaaccc
42121 acctggccag gagaggcagg cgctgctggc acaggaagtg tccccagact cagtcatcaa
42181 ggtaaataat atttttgggac ctccctggaa atccagtggt taggactctg cggttcaatc
42241 cctggtcggg gaactaagat cccacaagtc acaagacatg gccaaattta aaaagaaaa
42301 aaagagagag aaatatttag tgcaataggt tttagaattg aaattaagct cctgcccacc
```

-continued

```
42361 cccaccccc aatctggatg aataaagcat tgaaatagta agtgaagtca ggctctgaca
42421 tgcactgatg tgactcacct taagcaaccc ccaccctagg actggtcggg gttccaggag
42481 tttcaggggt gccaggaaga tggagtccag cccctgccct ctcccccac cacgtcctcc
42541 actggagccg cctacccac ctcccacccc tccgcaccct gctaccccc accctgccc
42601 ccaggtctcc cctgtcctgt gtctgagctc cacactttct gggcagtgtc tccctctaca
42661 gctggttct gctgcccgct accgggcccg tccctctgt tcagttcagt tcagtcgctc
42721 agtcatgtct gactcttgt gaccccatgg actgcagcac accaggcctc cctggccatc
42781 accaacccc agaacttact caaactcatg tccatcgagc cagtgatgcc atccaaccat
42841 ctcatcctct gtcgacccct tctcctggcc tcaatcttc ccagcatcag ggtcttttcc
42901 aatgagtcag ttctttgcat caggtagcca aagtattgga gtttcagctt cagcatcatt
42961 tcttccaatg aatattcagg actcatttcc tttgggatga actggttgga tctccttgca
43021 gtccaaggga ctctcaagag tcttctccaa caccacagtt caaaagcatc aattcttcag
43081 tgctcagctc tctttatagt ccaactctca catccatacg tgaccactgg aaaaaccata
43141 gcctcgacta gatggaactt tgtgggcaaa gtaatgtctc tgcttttgaa tatgctgtct
43201 aggttggtca taacttttct tccaaggagc aagcgtcttt taatttcatg gctgcagtca
43261 ccatctgcag tgattttgg agcccaagaa aataaagtct gtcactgttt ccactgtttc
43321 cccgtctatt taacggaggg aaatttccca gagccccag gttccaggct gggccccacc
43381 ccactcccat gtcccagaga gcctggtcct cccaggctcc cggctggcgc tggtaagtcc
43441 caggatatag tctttacatc aagttgctgt gtgtcttagg aaagaaactc tccctctctg
43501 tgcctctgtt ccctcatccg cagaagtgac tgccaggtcg gggagtctgt gacgtctcca
43561 gaagccggag gattttctcc ccatttgctg aaagagagct cggggtgggg gaagcttctg
43621 caccctagg atcaccagag gagccagggt cttcagggtt cccggggacc cctcagtggg
43681 ggctcaggaa ccacagagcc agacctgat tccaaaaacc tggtcacacc tccagatgac
43741 cctttgtccc ttggctccgc ctcaaatgct ccaagcccca acagtgaagc gcttaagaga
43801 aggatccacc aggcttgagt ttggggagga gggaagtggg gagctggggg agggcctggg
43861 cctgggagac aggaatccac catggcttca ggcagggtct ctggggcctg cggggtggag
43921 agcgggcagg agcagacaga ggtgactgga cacgacacac ccctccactc caaggaggt
43981 gggcaggggc ggggcacaga ggaacaagag accctgagaa ggggtccacc gagcagactg
44041 ctggacccag acatctctga gccagctgga atccagctct aagccatgct cagcccaggc
44101 agggtatagg gcaggactga gtggagtggc cagagctgca gctgcatggg ctgggaaggc
44161 cctgcccgtc ccctgagggt cccccaggt ctagccagac tccaatttcc gaccgcagca
44221 cacacaggag gaagtggtcg gggtggagtt ggcccagagg tctgggcagg tgcagggtgg
44281 gggaaggggg gcagctggag tcaccgctg aattcaggga cagtcccttt ttctccctga
44341 aacctggggc tgtcccgggg gccaccgcag cctccaggca gcgggggac ccagcccca
44401 atatgtgaga agagcaggtc ccaggctgga gagagcgaag caccatggtg gggagaagtt
44461 agactggatc ggggccccta ggggctcccc cggacctgca cggcagccgt cagggcaccc
44521 gcaccccatt gctgttcagt gctggccagt gtccaaggcc agggatgtgt gtgtgtgtgt
44581 gtgcgtgcgt gcgtgcgtgt gtgtgtgcgt gtgtgcgcgt gcgtgcgtgt gtgtgtgtgt
44641 gcgtgcgtgt gcgtgcgtag acgtgtgcgt gcgtgcgtgc gtgcgtgcgt gtgtgtgcgc
44701 acgcgcgcag cccagcctca gcactggacc aggcagcctg ggattcctcc aaaactgcct
```

-continued

```
44761 tgtgagtttg gtcaaaccgt gaggctctga tcaccgccat ccattcgccc cctcctgccc
44821 ccctcatcac cgtggttgtt gtcattatcg agagctgtgg agggtctggg aggtcatccc
44881 acctgccagc taaaccgtga ggctgccgca atcgcactga tgcgggcaga cccgagacgc
44941 tgtgccggag acgaaggcca gcttgtcacc ccgccagagc ggcagtcggg ccacaagcat
45001 catccaagca gtggttctct gagcccgacg gggtgatgca aaggagccag gagacacctg
45061 cgcgtccaag ctgggggacc ccaggtctgt tatgccggac agtaaacacg ttcagctccg
45121 gagggagagg gttcccctac cttccagggt ttctcattcc acaaacatcc aaagacaatc
45181 cataccgaag gcgatccgtg cctttgctcc tgagacgtgc ggaagcacag agatccacag
45241 acactgtctc ccaggatcct atgtatgtaa aggaaccgaa gtcccaggct gtgtgtctgg
45301 taccacatcc cacggaacag gctggactga ttttcaccaa atgtagcaga aacgttaagg
45361 agtatcagct tcaaaatatg agggccagac atgtctgaga agtcccttcc agaaaagtcc
45421 ctttggggtc cttccccaga gttgctgaaa cagagaaccg gaagggctgc agagctgaac
45481 ttaaacaact ggatcgcaaa ggtccgtctc atcagagcga tggttttttcc agtggtcatg
45541 tatggatgag agagttggac cataaagaaa gctgagcgcc gaagaatcga tgcttttgaa
45601 ctctggtgtt ggagaagact cttgagagtc ccttggactg caaggagatc caaccagtca
45661 atcctaaagg aaatcaatcc tgaatattca tgggaaggac tgatgctgaa gctgaaactc
45721 caatactttg gccacttgat gcaaagaact gactcactgg aaaaaccctg atgctgggaa
45781 aggttgaagg caggaggaga agggtcgac agaggatgag atggttgggt ggcatcaccc
45841 acccatggac tcaatggaca tgggtttgag taaactctgg gagttggtga tggacagaga
45901 atcctggcat gctgcggtcc atggggtcat agagagtcag acacaactga gcgactgaca
45961 gaactgaagc aactggcaag ccggagggta ggtgccggct gcgatgagcg ggaacgtgca
46021 acctgccacg tggagctctt cctacaccca gagtcctgac ggcactggga ccctagccct
46081 ccacggcctc tccagggcca cgagacaccc tcacagagca gagaagcgga acagagctgg
46141 tgtgcagaac caggccccgg gggtggggcg gggctggtgg gcaggcttta gtgagaagcc
46201 cttgagccct ggaaccagag cagagcagaa cagttggcag aggccccct gggagaggcc
46261 ccccgcccag agtaccggcc ctgggccctg ggggagaggg cggtgctggg ggcagggaca
46321 gaaggcccag gcagaggatg ggccccgtgg gacggggcgc accaaaacag cccctgccag
46381 caagggggaag ctggggcact ttcgaccccc tccaaggagg agcccacacc agcgcatctg
46441 cccaaggtgc ccttggccct gggggcacat gaggcccagg ccaggccagg gggcccatga
46501 ggccccagg ggtcagtgca gtgtccccag gcagccctgg cctctcatcc tgctgggcct
46561 ggcctcttat cccgtgggcg cccacggcct gctgcccccg acagcggcgc ctcagagcac
46621 agccccccgc atggaagccc cgtcaggaaa gagcccttgg agcctgcagg acaggtaagg
46681 gccgaggag tcatggtgca gggaagtggg gcttcccttc gatgggaccc aggggtgaat
46741 gaccgcaggg gcggggaacg agaagggaaa ccagctggag agaaggagcc tgggcagacg
46801 tggctgcacg cacagcgctg accctgggcc cagtgtgcct ttgtgttggg ttttattttt
46861 aattttgtat tgagatgcta tttatctcgt ggagcttttg ccgccctgag attttgtacc
46921 cgtggctggt gtccctcttg cctcaccccg gcctctgtag cagggcagac acggcgcaac
46981 ggggcagggc gtgcccagga ggcactgtca ttttgggggc agcggcccca caaggcaggt
47041 ctgccttcct ccctcttac aggcagcgac agaggtccag agaggtgagg caagctgccc
47101 aatgtcacac agcacacggg cgcagtccca ggactgtaga atcccgggga ctagacaggc
47161 accagagtgt cctgtgtttt taaaaaaacg gcccaagaga agaggcaagt ctgcaaggcg
```

-continued

```
47221  tcccgggaag gcagcagggg cttggctcgg tctcccccaa ggaggccagc tcctcagcga
47281  ggttcctaag tgtctaacgg agccaagcct gaaccaaggg ggtcacgtgc agctatggga
47341  cactgacctg ggatggggga gctccaggca aagggagtag ggaggccaag gaggagagag
47401  gggtgcacag gcctgcaggg agcttccaga gctggggaaa acggggttca gaccacgggg
47461  tcatgtccac ccctccttta tcctgggatc cggggcaggt attgagggat ttatgtgcgg
47521  ggctgtcagg gtccagttcg tgctgtggaa aaattgtttc agatcagaga ccagcgtgag
47581  gtcaggttag aggatggaga agaagctgtg aaaggtgat ggagagcggg gggacggtcc
47641  tcggtgatca ggcaccgaga tcgcccatgg aatccgcagg cgaatttaca gtgacgtcgt
47701  cagagggctg tcggggagga acaggcactg tcatgaactg gctacaaaaa tctaaaatgt
47761  gcacccttt cggcaatatg cagcaagtca taaaagaaaa cgcatttctt taaaattgcg
47821  taattccgct tttaggaatt catctggggg cggggaaca atcaaaaaga tgtgaccaaa
47881  ggtttacaag ccaggaagtc aactcgttaa tgatgggaga aaaccggaaa taacctgaat
47941  atccaacaga aagggtgtga tgaagcgcag catggcacat ccaccgcaag gaatcctaac
48001  acaaacttcc aaaacaatat ttctgacgtt gggttttaa agcatgcgtg cactttcaaa
48061  agcttgtcag aaaacataga aatatgccaa taatgtgtct ctagccaaat tttttaattt
48121  ttgctttata attttataaa gttataattg tatgaaatat aatgataaaa ttataaacta
48181  taaaaagtt atgaaatgt tcacaagaag atatacatgt aattttatct tctacaatac
48241  tttttaatac cagaataacg tgcttttaaa aaagattgag cacagaagcg tataaagtaa
48301  aaattgagag tttctgctca ccaaccacac gtcttacctt aaaacccatt ctccagcgag
48361  agacagtgtc atgtgggtct gtacacttct ggcctttctc ctaggcatgt atgtccctga
48421  aaactcacac acacggctaa tggtgctggg attttagttt tcaaaacgga ctcatactct
48481  gcctatgagc ctgcaactat ttattcagtc tgttgagatt ttctatatca gcccacatgg
48541  atcccgcatg ttctctgaat ggctctgtat gaattcaaag tttggaagaa gcagcgtgtc
48601  tttaatcatt cgcctattaa tggacgtttg gggtgtttcc actacaaaan nnnnnnnnn
48661  nnnnnnnnnn nnnnnnnnnn nnnnnnnnnn nnnnnnnnnn nnnnnnnnnn nnnnnnnnnn
48721  nnnnnnnnnn nnnnnnnnnn nnnnnnnng atacaattcg agctcggtac cctggcttga
48781  actatatgaa cagagaacga tgagaacagt ttctcaaact tggaacagtt aacatttgg
48841  gctaaatgat tcttttttgt gtggagttgg cctatgaata gaggatatta gcagcatcat
48901  ttaacccttta ctcactacat acctgtagca actacatcct tccatttgt gtcaatcaaa
48961  actgtctccg gacatggaca agtgtgcccc tgggatgggt ggaatgacct tttgttaaga
49021  accactgggt cagagattca tagatttttg tcttgttgac tttttaaaaa tacatcttgg
49081  tttttatttt attggtttct gctcttatct ttatgattac cttccttta cttgggctt
49141  ccctgataga ttttcccttc tggctcagct ggtaaagaat ctgcctgcaa tgcaggagac
49201  ctgggttcag tccctgggtt gggaggatcc cctggagagg agaagggcta cccaccccag
49261  tattctggcc tggaggattc catggagtgt atagtccatg ggtcgcaga gtcggacatg
49321  actgagtgac tttcacacac acatatgtcc ctggtagctc agctagtaaa gaatcccacc
49381  cgcaatgcag gagacccgg tccaattcct gggtccggaa gattcccttt tgtttactcc
49441  ataagatctt atctggggac aaaactaaca gctatgccag accttctgga catcagggaa
49501  cgtgaggggt gtggactgga cagatgtgtg tgttctccca aacacaaaca tacatctgta
49561  tacatgtaca tggagagagg gggagggagg ctgtgagtct ccaggggacc gtgcaaccat
```

```
49621 gtgacattca tggaggcgtt tgcgggtgat cactacacag tttcttcttc tggtttcttg
49681 gtcaattgac ttcacaattc caattcctat acttcatttt agactgaggg aattttacac
49741 tattgtaaga catatgtata catgagttat gttcagcgcc atgagggctc attttgtgtg
49801 tccactttgc ctggaaacaa agttggactg atttacttct agggtgcct gggggtgttt
49861 ctggaggaca ggagcatttg aacccaaggg ctcggtgaag catgagcctc tctgcaggtg
49921 gacccaggag gaacgcaagg ccgaggaagg cagactctcc tcctccctaa cccgaggtct
49981 ctgctcagaa aagggacaat ataatgacta gaagaaaaga aagaacatca gctgtgggag
50041 gtttgttctc tggagcagat tcacacgttg aggctcatgt gcaggaattc taggtgaaac
50101 agagcagtca cccatgtgtg ttggaaaatt ttaaattaca tttgcagtta cgactttgtt
50161 taagccagac agggtagcac agcaaagtca ccatgtggtc acctgtgttt tgtaaaggag
50221 agagaacttg ctggcacatt caggaaaggc cgtgtctcag ctttggaggc acactgagag
50281 gccacaagca gatggtgagg accagggtct cgggcagagg gatcaattca ctgctcttca
50341 cttttgccac atctgtgtgc tgtccatcct ggccagagta gttcagtctt cagatgctgg
50401 agttcccatt ggtagaaatc caatctgggt catttttaaa cctctcttgg ttctacttaa
50461 tggttttaaa atctctttgg ctcaagaaaa aaaataaaca taatttaaa gggtggtttg
50521 gggccttgac tataaagtac attatctggg ccatttcaga gcatggttga attaatacat
50581 ttcgtgctta ctatagctcc tattttcttg attctttaca ggtaatttt gttaggaatc
50641 gggtactgtg aatattttct tgttaatac gggatctttg tatttttcc taattttttt
50701 tttttttca tttttggttt taccttcagg aaagtcacta ggactcagga aagtcctttg
50761 tccgcctgtt atttcagtct cttacctggg gccagggcag cgtttcctct gggctaagtt
50821 tccccacaac cggggccagt tctcctcact cttcaccctg aggccttaat gaggagctcc
50881 cctgcgtctg agcagccggc cctcctgtga cgtgcgtgtg tctctggcca tcggcgtccg
50941 gtgtccttgg aggttccgtc ctcccttcgc tcactgtgcc ccgcactcga gctctcaggc
51001 tccaagcagt gtccgcagtg tgcagaccct ctgtgtagct ctctcctcct caggactctt
51061 ccctctagat gtgtgttttc ttttggctcc ttggacctcc gctctgaacg caggcctggt
51121 gctgagtgtg atctctggag ggaagcctgg gaggctggac gggtccgccc tgcggtgtgg
51181 tgacaggtgt gggctcgggg cggggcctgc acgtcgtcct gacccgagcc gggactgggc
51241 tccgggcctc aggcatcact gactgaatct ccctcacaga ggggtcaggg cctgggcggg
51301 ggaaccgtct ctgcaatgac agcccctccc agggagggca cagcggggag ctgccgaggc
51361 tccagcccta gtgggaggtc ggggagccca ggggagcggc ctgacggccc cacaccggcc
51421 cagggctggt tcgttctgtt tctcgagctc aacagaagct ccgaggagct gggcagttct
51481 ctgaattcgt cccggagttt tggctgctga gtgtcctgtc agcaccgtat ggacatccag
51541 agtccattag cagtggtctc tgtccctctg tctgtccttc atcaggctct ttgtccaggt
51601 caccacacgg ccaacaccag gacagtctgg tcccgccagc ccatcgtccc tgcggacgcc
51661 cctgtgcagc ctgccgaagg gccgggaggc cgggggaacc gggccaggcc tgtccctgct
51721 gtgtccacag tcctcccggg gctggaggag agcgtgagca ggacgggagg gtttgtgtct
51781 cacttccccg tctgtctgtg tcactgtgag gattatcact gctgtcagct gactgacagt
51841 aatagtcggc ctcgtcctcg gtctgggccc cgctgatggt cagcgtggct gttttgcctg
51901 agctggagcc agagaaccgg tcagagatcc ctgagggccg ctcactatct ttataaatga
51961 ccctcacagg gccctggccc ggcttctgct ggtaccactg agtatattgt tcatccagca
52021 ggtcccccga gcaggtgatc ttggccgtct gtcccaaggc cactgacact gaagtcggct
```

-continued

```
52081  gggtcagttc ataggagacc acggagccgg aagagaggag ggagagggga tgagaaagaa
52141  ggaccccttc cccgggcatc ccaccctgag gcggtgcctg gagtgcactc tgggttcggg
52201  gcaggcccca gcccagggtc ctgtgtggcc ggagcctgcg ggcagggccg gggggccgca
52261  cctgtgcaga gagtgaggag gggcagcagg agaggggtcc aggccatggt ggatgcgccc
52321  cgagctctgc ctctgagccc gcagcagcac tgggctctct gagacccttt attccctctc
52381  agagctttgc aggggccagt gaggggtttgg gtttatgcaa attcaccccc gggggcccct
52441  cactgagagg cggggtcacc acaccatcag ccctgtctgt cccagcttc ctcctcggct
52501  tctcacgtct gcacatcaga cttgtcctca gggactgagg tcactgtcac cttccccgtc
52561  tctgaccaca tgaccactgt cccaagcccc ccggcctgtg gtctcccctg gactcccccag
52621  tggggcggtc agcctggcag catcctggcc gtggactgag gcatggtgct ctggggttca
52681  ctgtggatgt gaccctcaga ggtggtcact agtcctgagg ggatggcctg tccagtcctg
52741  acttcctgcc aagcgctgct ccttggacag ctgtggaccc gcagggctgc ttcccctgaa
52801  gctccccttg ggcagcccag cctctgacct gctgctcctg gccacgctct gctgccccct
52861  gctggtggag gacgatcagg gcagcggctc ccctcccgca ggtcacccca aggcccctgt
52921  cagcagagag ggtgtggacc tgggagtcca gccctgcctg gcccagcact agaggccgcc
52981  tgcaccggga agttgctgtg ctgtgaccct gtctcagggc ggagatgacc gcgccgtccc
53041  tttggtttgt tagtggagtg gagggtccgg gatgactcta gccgtaaact gccaggctcc
53101  gtagcaacct gtgcgatgcc cccggggacc cagggctcct tgtgctggtg taccaaggtt
53161  ggcactagtc ccaccccagg agggcacttc gctgatggtg ttcctggcag ttgagtgcat
53221  ttgagaactt acatcatttt catcatcaca tcttcatcac cagtatcatc accaccatca
53281  ccattccatc atctcttctc tcttttcttt ttatgtcatc tcacaatctc acacccctca
53341  agagtttgca ttggtagcat atttacttta gcacagtgtg cctcttttta ggaaactggg
53401  ggtctcctgc tgatacccct gggaacccat ccagaaattg tactgatggc tgaaccctg
53461  cgtttggatt cttgccgagg agaccctagg gcctcaaagt tctctgaatc actcccatag
53521  ttaacaacac tcattgggcc tttttatact ttaatttgga aaaatatcct tgaagttagt
53581  acctacctcc acattttaca gcaggtaaag ctgcttcgca tttgagagca agtccccaga
53641  tcaataaaga gaatgggatg aacccaggat ggggcccagg ggtcctggat tcagactcca
53701  gccgtttagg acagaacttg actaggtacg aagtgagcgg ggtgggggg caatctgggg
53761  ggaactgtgg cacccccagg gctcggggcc atccccacca catcctggct ttcatcagta
53821  gcccctcag cctgcgtgtg gaggaggcca gggaagctat ggtccaggtc atgctggaga
53881  atatgtgggg ctgggtgct gctgggtcct aggggtctgg ccaggtcctg ctgcctctgc
53941  tgggcagtga taattggtcc tcatcctcct gagaagtcac gagtgacagg tgtctcatgg
54001  ccaagctatt ggaggaggca gtgagcactc ccaccctgc agacatctct ggaggcatca
54061  gtggtcctgt aggtggtcct ggggcttggg ccggggacc tgagattcag ccattgactc
54121  tcagagggc cagctgtggg tgcagcggca gggctgggcg gtggaggata cctcaccaga
54181  gccaaaataa gagatcaccc aacggataga aattgactca cacccttgg tctggcacat
54241  tctgtcttga aatttcttgt ggacaggaca cagtccctgg ataaagggat ttctatcttg
54301  cgtgtgcaat agagctgtcg acacgcttgg ctgggacatg taatcctttg aacatggtat
54361  taaattctgt tcactaacat ctgaaaggat ttttgcatca ataaacctaa ggtatattgc
54421  cctgtcattt ccttgtcttg tagtgtctct gagtaggctg gaagggtaa ccagcttcac
```

```
54481 aaatcgagtt aggaaattcc cttattcttc cactgtctaa tagactttca taagattagt 54541 gttaattcct ctttaaatcg ctgctataat catcactgtg gccaccggta ctgaattttt 54601 tgttaggatg attttttaaac aagcatttta atgattttc ctttatttt cggctgtgct 54661 gggtctcgtt gctgtgtgcc ggcgttctct cgctgtggcc agtgggggcg ctgctctcgc 54721 gttgcgaagc tcgggcttct gactgcagtg gcttctctcg ttgcagagcg cgggctccag 54781 ggcgctcagg ctcgcgtggc tgcggcacgt gggctcagta gtcctgggc acaggtgcag 54841 cagcctctca ggacgttttg ttcccagatg gtgggtcggt cgaaccggtg tccctgcgt 54901 tgcaaggtgg attcttcacc gctggaccac cagcgacgtt ccctggaggt ttttaattat 54961 ggatttaagc tctcattaga tgtctcctca catttcctat ttcttttga gtcagtttga 55021 tactttgttt gtgtctgtaa gtttgtccat tttatccaag tcatctaatg tgttgataga 55081 caattattgg ttagtcatct aattgttggt ttacaatttt gagagcattg tcctgcaatt 55141 ccttctatct gcaagattgg taataatatc tcccaagagg agtcacaaac tgaaatgaga 55201 ttanatacag gcttttttttt taaaagaatg aacttatgtt gttgcctttc tcatagatct 55261 tacttcttag catgactgta cttactgact ggggcgtttt catgtctgtg tggagagcta 55321 ccattagtac ttcttatcgc ccaaagacat cgggctcctg ggcacagtga aaacactcct 55381 ttctgtggct attttgcaaa atatggccta gcctagcgtc ataagggatc acagctgaca 55441 actgctggaa cagagggaca tgcgaagcaa cgtgagggct ggaacctgga gggtcctctc 55501 tggggacagt ttaaccagct ataatggaca ttccagcatc tgggacatgg agctgtgaac 55561 tggaccaatg actgtcattt ttggaagaga aatcccagga gagaagggtc caggggaatc 55621 tgaggccgca tgcagtgcct caggacaggg gacaccttct ccagcagagc agggggggccc 55681 gcccaggccg cctgcagtga ttccaccagg aggagatgca tccctgcaga cctctgacag 55741 cacggccctc tcctgagaca cagggtcaca cccggggccc tggaacccctt tgagaccctta 55801 aacctttcct ttcctgacca ccctgacagc agtctagctc agaacagaca tcttcatttt 55861 cagcaggaaa atccttttcc tcgtttgagg gagcgactgg caccggagga gctgagtctt 55921 ttaaacacag gctgcctgaa cctcagggat gacctgcagc tgctcagagg aggctggagt 55981 gtgatagctc actctaatgt tactaaaagg aacatattgg acacccctc tctgaaaaat 56041 ttccctcctg cctctcatct cttagtccac tttatcgccg ttttactgct tttctattta 56101 ctactcttaa cgccaaccta tcttatttcc cctcccagtt taacacggtt ttccctccac 56161 ccgctctctt taatctcaga agattctgcc tattcctcta ttatcacacg cccctacttt 56221 ttatttttt tcttacccgc cttttattcc ctcccctcct cactctctat ttaattacat 56281 cttaactaca ccgcctgcgc tatcttcgaa tgtatccaaa tattttccc ttatataaca 56341 ctccaggccg agcggctaac ttattataat ttctttatag cgcctaccta atttccctt 56401 atttctaatt atctatatat acccatgcaa tttcgnnnnn nnnnnnnnnn nnnnnnnnnn 56461 nnnnnnnnnn nnnnnnnnnn nnnnnnnnnn nnnnnnnnnn nnnnnnnnnn nnnnnnnnnn 56521 nnnnnnnnnn nnnntgggt gtacgttata gagtaaacgc gcatgaagaa gtgggtcaat 56581 ctatggctgt gagaggcaga aaataatatt atcatatata atttatgtta taacacactg 56641 aggtggtggg ctcgtagaat agtgcggacg gggagaaagg tgggaaggag aagacacaag 56701 agagagatgt tcgcctcgcg ggatggatgg gcggagggat agaagaataa aaagaggaga 56761 ggtatagagg ggggcggggg gcataacgtg tggtggggta aatagtaggc ggtaattatg 56821 aaaaaagaa agacgggggg ggcggtaaca tagaatacgc aaaaaagtca tatactgaac 56881 ggggattagg gagaagaggt gggggcgtg gggtgcgggg gaaagaggtg tgtgtataat
```

-continued

```
56941 tggtatggag tgttatttga atatatatta atgtaataggg gagtgtaatt agtgaaattg
57001 tgggagtatt atattggggt gtgggggaca tggcaaagtg atgatcggga taaaaaaagt
57061 aaagcaagag gggaggggaa aataaggggg gggagaaggt cgaagaaaat aagaggaaga
57121 agaaagaacg ggggtggcgg gcggggggg cgccgctctt gtatctggct ttttgttgt
57181 gtcggtggtt gttcgcgtct tgttgggtcc ggggcgggtg tgcggaaaaa aaaaaaggcg
57241 ggaggcccgg ggcccggtca cgcggcaccc ccgcgggtcc ctggcttctc cttcggcagc
57301 tccggggtc ggtgagcctg cgccctccgg gccgccggcc cgagctgtgt gcgccctgga
57361 gaatcggagc cgctgtggca gcacgcggag ggcgcgcgca agggccacgg gacggacctt
57421 caaaggccgc ggcggagcgc ggcaagccga accgagggcg gtctggcgat cggccgagcc
57481 ctgctccccc ctcccgcgtg gccccagggt cgcgggtgga ctggggcggg tacaaagcac
57541 tcaccccgt cccgccccca gaaagcctcc caggactctc acagagcacc cgccaggagg
57601 catccggttc cccctcggc tcagttcagt tgctcagtcg tgtccaactc tttgcgaccc
57661 catggactgc agcaccccaa gcttccctgt ccatcaccaa ctcccggagt ttactcaaac
57721 tcatctattg agtcagtgat gccatccaac cgtctcatcc tctgttgtcc ccttctcctc
57781 ccactttcaa tctttcccag catcagggtc ttttcttatg agccagttct tcacatcagg
57841 tggtcagagt attggagttt cagcttcagc atcagtcctt ccaatgaaca ctcaggactg
57901 atttcccttta ggatggactg gctggatgca gcgccagaca ccgaccgcgt ttaccccgtg
57961 tgtcctttcc aatggctgtc cctgcgggc ctagggggcat tggtgcgggt ttgaatcctg
58021 tggccttgaa ttttacgcct tagttccagg tccagggcag ggccatccgg attcaggatg
58081 cttcccagcc cttcaggaat ggcaggtttt catggtcctt tctgagtgag ttctgagtgg
58141 tcatattggt gcccttggca ggggagggctc ctgactttcc tatcttcaca tcactgtccc
58201 caaccccca gagaggcctc ttggcccagg gactgcaggg aggatgaagt caggagcaga
58261 agcatgggt aggggggctca ggtgggcaga ggaggcccct ctgtgaggag gaacggcaag
58321 cgaggaggga acaggggcac cggcagtgcc tggcaagctg ggtgatgtca cgactacgtc
58381 ccgaccacac agtcctctca gccagcccga gaagcagggc cctcccctga cccccatctg
58441 ggcctgggct tcagttttct cctccctgca atggggtgac tgtttgcctc caggagaggg
58501 gagcatgtaa aggtggccac tctcttctgg cagacatgcc aggcctgggc cagcctccac
58561 ccctttgctc ctgcagcccc tgctgacctg ctcctgtttg ccacaccggc ccctcctggg
58621 ctgatcaggg ccccctcct gcaggaagcc ctctgggaca agcccagctt gctgtaactg
58681 tggctttcca ctgtgacctg caacgtggga ggctgttact taaaactccc atgactggtg
58741 gattgccggt ccccagaaca aggccacgca tccctggagg ccctcgagac catttaaggt
58801 agttaaacat ttttacttta tgcattttca tgtgtatcag aaagaaaaaa aatgtatcat
58861 cagttcatca aatccatgat ttcttgacca atattgctaa gatgaggctg aaataggcat
58921 ttccatttttt aaaaaactga atcactctga agaaacagat ggcaggcttc cctggtggtc
58981 cggtggttaa cagtccatgc ttccagtgct ggggcatgg gttcgatccc tgaaaattt
59041 aaaaaggaag aaaaagatgg ctcccccgtc cctgggattc tccaggcaag aacactggag
59101 tgggttgcca tttccttctc cagtgcatga aagggaaaag ggaaagtgaa gtcgctcagt
59161 cgtgtgcgac tcttagcaac cccatggact gcagcctacc agactcctcc gtccatggga
59221 ttttccaggc aagagtactg gagtgggggtg ccattgcctt ctccaggcaa acggcctgct
59281 actgctactg ctgctaaatc gcttcagtcg tgtccaactc tgtgcgaccc catagacggc
```

-continued

```
59341 agcccaccag gctcccccgt ccctgggatt ctccaggcaa gaacactgga gtggggtgcc
59401 attgccttca gcctgctgct gctgctgcta agtcgcttca gtcgtgtccg actctgtgtg
59461 accgcataga cggcagccca ccaggctccc ccgtccctgg gattctccag gcaagaacac
59521 tggagtgggt tgccatttcc ttctccaatg catgaaagtg aaaagttaaa gtgaaattgc
59581 tcagtcgtgt ccgactctta gtgacccaat ggactgcagc ctaccagggt cctccatcca
59641 tgggattttc caggcaagag tactggagtg gggtgccatt cggcctaggg agtgagaaat
59701 cacggctgtc ttccctcttc tcgccctcta ggggtctctg tggagcctcc ctggagaggc
59761 cgcggcggct ccggggactg gaggggagg ggggttgag tcagccggtg gccctcccct
59821 cgctgcccgt ctcctccctt tttaggcaca agctgggcgc ccttttttagg cgcagcctca
59881 ccctgcgggc cactgcccgt gtttcggctc cccggagata aaacagattg cctgcacccc
59941 gggtcatcac aaggattgta tgaccgtttc ccagtgtgct caccaccctc cctctgattc
60001 tcagagacgc gccctcgcct caggaggctg ctcatcccag gccaagggc ggcgtgggt
60061 ccccagcgcc ccgcacagac actgccttct gaccacctcc tcccaacagc ttacctgcca
60121 agaaggcctc ctgacccctc atcctgcccg gtggtttgga gaaagcctca tctggcccct
60181 ccttctcggg gcctcagttt ccccctctgt gaactggcgg attctgccaa gctgacgtcc
60241 tggccagccg cctccccgtg ccagtgtcc cccgggacac agctgaatgt ccctgctcgg
60301 gatgcacctt cccaagttgg cctgtcagga ggcggggcg agcaggaaaa cccgactcct
60361 ctcagacggc ccatcgcatt ggggacgctg aggcccggag cagcggcacc ctcctggcca
60421 gggtcattct cccgccccgc ccgtccctc cgggcctccg agaccgcagc ccggcccgcc
60481 ccgggaagga ccggatccgc gggccgggcc acccccttc cctggccgcg ggcgcggggc
60541 gagtgcagaa caaaagcggg gggcggggcc ggggcggggg cgggcggag gatataaggg
60601 gcggcggccg gcggcacccc agcaggccct gcaccccgg ggggatggc tcgggccgcc
60661 ggcctccgcg gggcggcctc gcgcgccttt tgttttttgg tgagggtgat gggggcggtc
60721 gcggggtact atttttttcat ttataattgg gtattagcta gcgagtggaa ccacaccctt
60781 attccactat agccaatttt tgcgggggca tcttacatta cagactcgcc cgcctcttat
60841 ttcggtacag catatcagat cgtctcttta ctcagacact agtgattatt gtctatagta
60901 cacaaaaaga acggttgtgt cggcgtaatg gttgcatttt ccctcctcgt ttctcctgac
60961 cacctcaatt acaccaacac tctactattt aaatcacgta ttgtacgcca ccctccgccc
61021 gcgaactaaa agaatgtgca gatattctga agataaaatc gttcattgtt acgccccgcg
61081 cgcttcgcgt atattactct tagaacttct tattcgcccg agcagttatt caccccccgc
61141 aactagatgt cgccttaata tttgttctaa ccgttttgga ttctaacgat aggcgggaaa
61201 ggtagacatt cgaccgctac gacaactaaa atcgacgagc acaggctatt tatatcgcga
61261 ccacacgcgc gcggtataca naccgtaaaa ttatctaaca tcgagagtaa gggcacagag
61321 cgaaatacaa gcggcgtggt gggaggtgtg tctgtagtga attcgcacct cgcgccgccg
61381 cctctgtgcg tcgnnnnnnn nnnnnnnnnn nnnnnnnnnn nnnnnnnnnn nnnnnnnnnn
61441 nnnnnnnnnn nnnnnnnnnn nnnnnnnnnn nnnnnnnnnn nnnnnnnnnn nnngatataa
61501 tattaataaa cagcggatag atgtgtgtaa gggaggaggt gcataagaga ttaaagagag
61561 gcgggcggag agaaatagag tagaggagga tgagagaaaa agaaagcaa gcgtaggtac
61621 aacgcgggt gggtagtatg ataaagtgag tgtatatatt tgagtaaagg aagggtagat
61681 ggagtataaa gaagtaagga gaggagaggg cggcggagag agagagtgca aagaaaataa
61741 gtgggcaaag gcggggtggg tgagaagcag tagaagagaa gatagagaag gggaaaaag
```

-continued

```
61801  aggaaaatga ggattagaac aagtaggaca ggatagatgt gaaaaatgag atcaggtcaa
61861  ggtggagaaa aagtagaaac tggggcgtga ttgtaaaaaa gggaggccgc gatggggcag
61921  caccataagc gaagagatga attaatgaaa gcaaggcagg gagaatcaaa tgagttgggt
61981  ggaggaagga ggctgtgact tccttcgctg ccggaaagag aactagaata gcctcgggct
62041  gtgggggag gtaaagataa agtgacttct gggccctggg ggaggcccag gagtttctac
62101  cgagctgagc tgggtgcctc tcccaaatgc ccaacccct gagagtcgac gggagagcac
62161  agcctggcca aacctgggca gggcacacgt gtccttcacc ccacagtggt cacgagccca
62221  gcgtggtccc tgcgtctggc gggaaacaca gaccctcaca ccccacacaa gggtccggcc
62281  gctttcaaat aacagcagcc gtgccctctg gccggtgac ccggacacag agagatgaag
62341  tccgcatctc tcagagtgcg ctgtcctccg cccggtcagg cccgggtccc ctgcttctct
62401  gaggtcacca ggagggattg catgtgggtc tcagggacac aggttcagtg atgtgacaga
62461  gggtagtggg tcccagcagg gccggtcttt ggacccgttt ttctgaaaag ccagttggcg
62521  acctggggtc acagcaaagc tgatcctgtt tggccaggag tctcccagtg acggcctccc
62581  ccagaacatc gggcccagtg ggggctccag ggggtagact tgcctcccag ctcacgcccg
62641  tgtcttgaca agtccatgat ttggtaaaat taatttgtgt tggatggagt tgatttagtg
62701  gtgtgtgagt ttctgtggcg cagcaaagtc aatcagttac gcatacacat gtatccagct
62761  cttcctacga ttctgttccc atataggtca ttatgggtg tcaggtagag cttcctgtgc
62821  tacgcagtac ggccttattc agttcagctc agtcgtgtcc gactccttgt gaccccatgg
62881  actgcagcac gccaggctcc cctgtccatc accaactcct ggagcttatt caaactcatg
62941  tccatcgagc cggtgatgcc atccaaccat ctcatcctct gtcgttccct ctcctcctgc
63001  cttcagtctt tcccagcacc ccctagagaa gggaatggca aaccacttcg gtattcttgc
63061  cctgagaacc ccatgaacag tacggaaagt ccttattagt tttctatttt atatatagca
63121  gtgcacacgt gtcagcccca atctcgcaat ttatcacccc cctccgccgc cgattggtag
63181  tcatgttttgt tttctacatc tgcgactcta tttctgtttt gtaaacaagt tcatttacac
63241  cacttttta gattctgcac atacgtggca agcccacagc aaacatgctc aatggtgaaa
63301  gactgaaagc atttcctcta agatcaaaaa caagacgagg atgtccactc actccgtttt
63361  tactcaacac agccctgaac gtcctagcca tggcaatcag agaagagaaa gaaattaagg
63421  aatccaaatt ggaaagaag aagtaaaact cactctttgc aaatgacatg acacttatac
63481  ccagaaaatc ctagagatgc taccagataa ctattagagc tcatcagtga atttgttgca
63541  ggatacaaaa ttaatacaca gaaatctcct gcattcctat agactgacaa caaaagatct
63601  gagagagaaa ttaaggaaac catcccacgg catgaaaaag agtaaaatac ctaggaataa
63661  agctacctaa agaggcaaaa gacctgtact cagaaaacta taaaatactg acaaaggaaa
63721  tcagacgaca cagagagaga gagataccac gctcttggat gagaagaatc gatagtgtga
63781  caatgactat actacccaga gaaacataca gattcagtac aaccccctatc aaattcccaa
63841  tggcattttt cacagaatca gaattagaac aaaagtttt acaagtttca gggaaacaag
63901  aaagatccta aagagccaga gcaatcttga gaaagaaaaa tggagctgga agagtcaggc
63961  tccctgagtt ctgactgtgt atacaaagct ggcatgattt ttaacagcag gggtgtaaat
64021  gaacttgttc acaaaacaga tggtggggtg ggcttccctg gtggctcagc tggtaaagaa
64081  tcctcctgca acgcaggaga cctgggttcg atccctaggc tgggaagatc ccctggagaa
64141  gggaaaggct acccactcca gtattctggc ctggaaaatt ccaaggacca tatagtccat
```

-continued

```
64201  gggtttgcaa agagtcggac acgactgagc gacttccaat cctggaaacg tcccattgtg
64261  gacggtgaac tggggttgtc caagctcagg gtaaccgttt gctgagtgac tgacactcct
64321  tctcatgggt taaaatgtgg ggcccaaggc caggaccaga ccccgcagtc agccaggcag
64381  accctgtgca gccccagcga gtgtgtggcc gccgtggagt tcctggcccc catgggcctc
64441  gactggagcc cctggagtga gcccattccc tcccagcccg tgagaggctg ggtgcagccc
64501  taaccatttc ccacccagtg acagatccgc ctgtgtggaa acctgctctt gtccccaggg
64561  aacctggcag gactcaggga gaatgtctca gggcggccac agatcagggg ctgggggggc
64621  agggctgggt ccagcagagg ccctgtgccc actccccgga aagagcagct gatggtcagc
64681  atgacccacc agggcaccga cgcgtgcttg cacacaggcc gcccctcat ggtgacactc
64741  ttttcctgtg gccacatctc gcccctcag gtccctcctg ctcccagct cctggcctgg
64801  gaacctcttc cccgccccgg ggacgtcagg gctggtgtcc actgagcatc ccatgccgg
64861  gactgtgctg atcaccagca cctgcacccc ctctcgggtc tcaccaggat gggcaactcc
64921  tgcccatcca gcacccagcc tcctgggtac acatcggggg aggagggaga agcctgggcc
64981  agaccccag tgggctccct aaggaggaca gaaaggctgc cgtgggccag ccgagagcag
65041  ctctctgaga acgtgggac cccagaccac ctgtgagcca cccgcagtgt ctctgctcac
65101  acgggccacc agcccagcac tagtgtggac gagggtgagt gggtgaggcc caggtgcacc
65161  agggcaagtg ggtgaggccc gagtggacag ggtgagtggg tgaggcccag gtagaccagg
65221  gcccatgtgg gtgaggcccg ggtggaccag agtgagcggg tgaggcccag gtggacaggg
65281  cgagcgggtg aggcccaggt ggacagggcg agcgggtgag gcccggtgg acaggcgag
65341  cgggtgaggc ccgggtggac agggcgagcg ggtgaggccc gggtggacag gcgagtgggt
65401  tgaggcccgg gtggaccagg gcgagtgggt gaggcccggg tggacagggc gagtgggtga
65461  ggcccgggtg gaccagggcg agtgggtgag gcccaggtgg acagggtgag tgggtgaggc
65521  ccaggtagac cagggcccag agcaaagccc cggctcagca gtgatttcct gagcgcccac
65581  tgcttgcagg gacctcagcg atggtaaggc agccctgttg ggggctcccg actggggaca
65641  gcatgcagag agcgagtggt cccctggaga aacagccagg gcatggccgg gcgccctgcc
65701  aggctgcccc aggggccaca gctgagcccc gaggcggcca ggggccggga cagccctgat
65761  tctgggttgg gggctggggg ccagagtgcc ctctgtgcag ctgggccggt gacagtggcg
65821  cctcgctccc tgggggcccg ggagggacgg tcaggtggaa aatggacgtt tgcgggtctc
65881  tggggttgac agttgtcgcc attggcactg ggctgttggg gcccagcagc ctcaggccag
65941  cacccccggg gctccccacg ggccccgcac cctcacccca cgcagctggc ctggcgaaac
66001  caagaggccc tgacgcccga aatagccagg aaaccccgac cgaccgccca gccctggcag
66061  caggtgcctc cctctccccg gggtggggg aggggttgct ccagttctgg aagcttccac
66121  cagcccagct ggagaaaggc ccacatccca gcacccaggc cgcccaggcc cctgtgtcca
66181  ggcctggccg cctgagacca cgtccgtcag aagcggcatc tcttatccca cgatcctgtg
66241  tctgggatcc tggaggtcat ggcccctctc ggggcccag agcccatct aagtgccagg
66301  ctcagagctg aggctgccgc gggacacaga ggagctgggg ctggcctagg gcaccgcggt
66361  cacacttccc ctgccgcccc tcacttggga ctctttgcgg ggagggactg agccaagtat
66421  gggatgggg agaaaaatgg ggaccctcac gatcactgcc ctggagcccc tggtgcgtct
66481  ggagtaacaa tgcggtgact cgaagcacag ctgttcccca cgaggcctca cagggtcctt
66541  ctccagggga cgggacctca gatggccagt cactcatcca ttccccacga ggcctcacag
66601  ggtccttctc caggggacgg gacctcagat ggccagtcac tcatccattc cccatgaggt
```

-continued

```
66661 ctcacagggt ccttctccag gggacgggac ctcagatggc cagtcactca tccattcccc
66721 acgaggcctc acagggtcct tctccagggg acgggacccc agatgggcca gtcactcatc
66781 catccgtctg tgcacccatc cgtccaacca tcacccttcc ctccatccat ctgaaagctt
66841 ccctgaggcc tccccgggga cccagcctgc atgcggccct cagctgctca tcccaggcca
66901 gtcaggcccg gcacagtcaa ggccaaagtc agacctggaa ggtgcctgct tcaccacggg
66961 aggagggggg ctgtggacac agggcgcccc atgccctgcc cagcctgccc ccgtgctcg
67021 gccgagatgc tgagggcaac ggggggggcag gaggtgggac agacaggcca gcgtgggggg
67081 ccagctgccg cctggctgcg ggtgagcaga ctgccccct caccccaggt acaggtctcc
67141 ctgatgtccc ctgccctccc tgcctccctg tccggctcca atcagagagg tcccggcatt
67201 ccagggctcc gtggtcctca tgggaataaa aggtggggaa caagtacccg gcacgctctc
67261 ctgagcccac ccccaaacac acacaaaaaa atccctccac cggtgggact tcaccagctc
67321 gttctcaggg gagctgccag ggggtccccc agccccagga agccaggggc caggcctgca
67381 agtccacagc cataacacca tgtcagctga cacagagaga cagtgtctgg tggacaggtg
67441 cccccacctg cgagcctgga gagtgtggcc ctcgcctgcc ccagccgcgg tcagtcggct
67501 cagcaaccgc tgtccactcc cagcgccctg gcctcccctg tgggcccagg tcaagtcctg
67561 ggggtgaagc taagtcaggg agcctcatcc atgcccagcc cggagcccac agcgccatca
67621 agaaatgctt cttccctcca tcaggaaaca ttagtgggaa agacaagagc tgggggttc
67681 tggggtcctg ggggatcaga tgaaggggtc tgggagcagc agcagcctca ggcaccccaa
67741 aacaaggccc aggagctgga ctcccagggc tgaggggcag agggaaggaa ggcctcctgg
67801 ggggttggca tgagcaaagg cacccaggtg ggggctgagc acccctcggc tggcacacac
67861 aggcccccac tgcagtacct tccccctcgg agaccctggg ctcccgtctc ccgcctggcc
67921 tgccatcctg ctcaccaccc agaaatccct gagtgcggtg ccatgtgact gggccctgcc
67981 ctggggagga aggagattca gacagacagg atgccagggc agagaggggc gagcagagga
68041 tgctgggagg gggcccgggg aggcctgggg ggcaggggg caggagttct ccagggtgga
68101 cggcgctgtg ctatgctcgg tgagcacaga ggccccgggt gtcccaggcc tgggaaccca
68161 gcagaggggc agggacgggg ctcaaaggac ccaaaggccg agccctgacc agacctgtgg
68221 gtccagaagg cagctgcgcc ctgaggccac tgagtggccc cgtgtcccga accaccgctg
68281 aaacatggga cacacgttcc caggcggagc cactcctgcc ttccgggagg ctcccagcgg
68341 gctcatcgct ccatcccaca gggagggaaa ccgaggccca gatgacgaac atcccggcga
68401 gcaggtcaaa gccagcccct ggggtcccct ctcccggcct ggggcctccc ctctgcaggg
68461 tgggaaaccg aggccacaca ggggctccat ggggctgccc tctgccaggc cctggacacc
68521 ccgcgggtga ccccgcctc tatcatccca gccctgccag gccctggaca ccccgtggat
68581 gaccccgcc tctatcatcc cagccctggg ggacagatgg gaggcccaag cgtggacccc
68641 ctggccaccc cctacccac agccgggagg agccgggagc tggtggccaa gggcctagag
68701 gagccagann nnnnnnnnn nnnnnnnnn nnnnnnnnn nnnnnnnnn nnnnnnnnn
68761 nnnnnnnnnn nnnnnnnnnn nnnnnnnnnn nnnnnnnnnn nnnnnnnnca atatagaggg
68821 ggtgggataa agggtaatat gatgtttagg tagttagagt taaattagaa gggttggat
68881 aaagattaat aaaattacaa gcgtacatat cgtgtgagtg tgggtgataa tatttgtgta
68941 tgtggggaat agaagtgagt gtgagtagta ttcaagatgt aagtgtgcga atacaggtct
69001 gagcgatttg aatggaagtg aaaaaaagcg tgtgtgtgga ggaggcggga gaggaagata
```

-continued

```
69061  gtgtggggga agaaaagaag gctagtgggt aaagaaatat cagtaggcgg ttgacgaaag
69121  aagaactagg aagaattaat ataaaaataa agggaggatt aaaaaataaa gagggaggag
69181  gtaacggaaa tagttagtta agaaaagaat ggagagtgga ggtaagataa ataagggagt
69241  aatgggagtg aggaggaata aataaaaaaa tggtgaggga aaatagagta gaatgagaac
69301  aagaatgaaa aagggagtga aggggggtgaa aaaaagtgaa gttgaaaaaa gaggaaaaaa
69361  aaggagaaga taaaaaaata aaataaaaaa aggaaaaaaa agaaaaaaag aaagaagggt
69421  taaaggacga aaagaaggga agagaaaaaa aatagtttaa gtggggagg gtaaaaaaga
69481  attaataaag taaatatggt tgtggtcgaa aaaaaaaaaa aaattgttgt gttgatgaga
69541  agaaagaaa aaagaagaaa gggaaaagca aaaagaaagg agagaaaaag acaaccccac
69601  cgcccggcg catggaggt gaggatgcg cacgcccgcg gatggcacag catcacagca
69661  atcctaaaac gttttcagac cggtgcatct tcaccgcgcg cgcgccccgc ccggccctcc
69721  tcccgccctg accgcggacc cccacccgca ccggggagcc taccccacc ccggggacgc
69781  tccgccacgc taaggtcagg actgccgtga agacgcgccg gggtgaaaac gttttatctt
69841  catgacataa gcgagtggtt ttgaaacagg tttacaaacc ctcgtgaaga cgcacccctta
69901  gcgttaggtt ttgttttttt accatgtgac gatgcaacta ttttcttcct ctcttccaca
69961  gtggctagtc gcctccagag cgaggggtat ctcttgtaca gagaccctcg gaacatccgg
70021  aggtagttc ccacctaggg gtaaagcgag aaggctcatt acgagggccg gggctcctcg
70081  gggaagggca gggccctggc gcagaggctc tgccacctca gtgacacgca gaccacgcgc
70141  ggcctgcagg cgccgggctc tgaaagcagg caaagcccga tctgctgaca tcaggggttc
70201  cgcagcagcg aaggtctggc ccgcacctgg cccactggca gggggtaagc tctgcctccc
70261  gacgacagca ccaagttcag gaagggccac gcagacactg gtgagacacg gccccccggg
70321  agctgcccga gaagctctga ctttgcacta aagatctctg gcgcggtcca aaaatgtaag
70381  gcctctcttc ctttttatctt aagactttga tattttacg atgtaataa taccaagaag
70441  ggcttttaat ttcagacaga tgtaggataa ttccccgt agcccttgct gctttgttta
70501  gtaacgaaac tcaaaccaga aataccaaag gaattttcca aagagtttca aaagcgctta
70561  tcagcaatca ctagactgct gcatacatca tcactgcccc aaacaatagc ctgcctgtgc
70621  cagttactca aagtactact tacttgacga aaacaaatct agtcctaacg tttttacaaa
70681  gaaactccac tcttccgcca acttttcaga aacaaccact cgatcacgtg gcaggggacc
70741  gtggctgac tgggtgctgg ctccttctgt gaccaggcaa cactgccccc ttctcggcct
70801  ccctacgcct cttgacaaat gttcatcagc tgtaaagttc accccacgag ggacccactt
70861  ctgctatttc ccacgtacct acccccattat aggagttttc tttgtgacag tttctgcatt
70921  tttcatggat ttagaggttt acataatcag ggctgctgaa cagcatgaga gacgtggcca
70981  caaggtccct cctgcacctt gccgcagggg cagggcgagt tatctggctt gagcgtggtt
71041  accatcaggg ggtaaacaca gttccagga cgttttgac aagacactga cccggatgcc
71101  cccactacca ccgtgcaggt cctgcaggcc tcccagcctc ccaggccctt cccgaggtcc
71161  cttcggaact tagggactc ggtctgcccc cctggttttt ccctgcacca gcttttgccc
71221  cctctggacc caggttccc aaatggaaaa cgaaggtgtg gtatggaag ctccctgggc
71281  tcctctcagc tgtgcctctg catggtgatg acggctgccc atcgggggg gcaggactgg
71341  ggcagctgcg gacaccctcc caaggctgct accccgagt ggtgtgggc gctgtgggca
71401  cgctctgctc agcgcacctc ctggaaacca gcgcctgccg tctgcccggg gcaaccggcc
71461  cgggagccaa gcaccactgc cgtcagagga gctgctggct gtgagtggac gccagtctag
```

-continued

```
71521  ctctgaaccc tgcccaggcc tcctgaggtc tgaacattgt aaaatcaggc cccggacggc
71581  aactgcctct ccctcctgcc gtctggtctc cataaactgc atctcaggac aaatcttctc
71641  actcaccagg gctgaaacag aagactgcag ctatctttct caaatctaag gtgtgctaca
71701  gggcaagtcg cagaaactgt ctggcctaag catctcatca gatgcctgag acaagagctg
71761  tggacgccaa gctggagcca gagctcctcg cgttctgccc acctggcacc gcgttccacc
71821  cagtaaacgc aggcttgatt ttcaaaagta ccaccgactc agagccaatg ctaaaccgac
71881  cacttttcct gcccattaga ttgggtgaag gtttctttaa tcaatctgcc agtcaccaca
71941  tgccgcctct gtgcccacag gctggcgaag acctttctga gctacggcat gtggcaggca
72001  gcggcacctc tcttcagtac ggccagctgt caaggggagc gtttctgtga tgatgtgaaa
72061  atacattgca tccggccccg tgtttcatga acacgggtga ggaaaggaaa cacacaaagt
72121  tctgatgcga ctgacagcac gggtctcata actcaataca agtcagacaa accacaggga
72181  gtcacaggga atcccaatag cctcatctag tgtgaccatc atgaggctta atttattcag
72241  tgtattcaat cataaagagg gggaaaaatt gtaaaaaaaa aaaaaagaa agagtgaaat
72301  gtgtaatact gaaaactgtt gctaggagaa gcaagcattg gcgtttgtaa ctgctttgac
72361  tccccaagac ccacactcgc ctcgctacaa aagggaggca ctgctgctca gtacttgcac
72421  acccgaactg cggatttgta atttaaaaat gtgtgtgtgg acacagcaca agccagagac
72481  tgccaaaggt tgagggacac tggaagaact taatatactt ggtgcatgct gccagtgaca
72541  gtcagtcacc agctgattca atagagtgcc gaaaggtcac cttttaggta aggatgaagg
72601  ggttctgggc tcgtttactt gcactaactc agagttagtc cgagatatcc gaagtgccag
72661  gtgcctccca tttgctgatg gatctagctc agggacggct gggccctagc catccaaaaa
72721  tcaagcattg ttctcccaac ctgtcttctc gctgataatg gaaggtcaga acgcccaccc
72781  gcccacctca aagtcaaaga acaccaagcg ggtgagtccc cactaagctc ggtgtttcca
72841  atcagcggtt tcaggattcc agctggggca atgagggagg gagcgtgcga gggatccaac
72901  acctcgcccc gtgcgcagca agggataacc caacaccccg tttctgtacg tccggctgga
72961  gttgtggaac tcagcgcgga cccggggcca ccgcgacccc cgggaccctg gccgcgcggc
73021  gcatccccgc tgccgggaca cgggtaagcg tccccaaact gccggacgcg gggcggggcc
73081  ttctccgcca cgccccgata ggccacgccc aaggacaagg atggtcgtgc ccagacggcc
73141  ggggcgggnn nnnnnnnnnn nnnnnnnnnn nnnnnnnnnn nnnnnnnnnn nnnnnnnnnn
73201  nnnnnnnnnn nnnnnnnnnn nnnnnnnnnn nnnnnnnnnn nnnnnnncg gaggggggg
73261  ggcggggcgg gggctgccgc cgcgcgtata ggacggtggt cgcccggcct ggggtccggc
73321  cgggaatgac cccgcctctc cccgcatccc gcagccgccc cgccgcgccc tctgccgcgc
73381  acccgcctgc gcacccgccg ccctcggccg cggccccggc cccgccccg tcgggccagc
73441  ccggcctgat ggcgcagatg gcgaccaccg ccgccggagt ggccgtgggc tcggctgtgg
73501  gccacgtcgt gggcagcgct ctgaccggag ccttcagtgg ggggagctca gagcccgccc
73561  agcctgcggc ccagcaggtg agcaagggct caggggaaac tgaggcccga cacagagccg
73621  cagcaagaag gatcctactg gtcactcggc tgttggcctg gggtcatcac aggcgggctc
73681  tcccaaccca tccccctgagg ccaaggtccc tagaaccccg tgggcagaca ccaaccagcc
73741  ctttaaatat ggggaaacca aggtgcttag gggtcagaga tagccctagg tcgcccaacc
73801  ctagtagaag ggagggctgt tggagttcct gagtgccgc tctcccaccc ccgggaggc
73861  cccttcctga gcccaagggt gactggtagt cagtgactttt gggcctgccg acctgtaccc
```

```
73921  cactgggcac cccaccagtc ctgagccaca tttgggctta gtgacggggt cagggatcat
73981  gaggatcaat gtggctgagc caggaaggtg ttagaacctg tcggcctgga gttcatacca
74041  gcactgccct gggcttttct agacccatgt cccgcctcct gccccacctg ccctgttcc
74101  cgcaccccac cagcagcggc aggggcttcg agagggctgt gggctcaccc tatttcaggg
74161  atggagccgc taagacctgg ggcacactgc ccgctaggga ccctgaggc accagggccg
74221  gggctctgc ggagggcag ccgccacccc cagctttgga gtcctctccc gggtgcccag
74281  cccgagctga tccggctgcc tcccacgctg tgccccaggg cccgagcgc ccgccccgc
74341  agccctgca gatggggccc tgtgcctatg agatcaggca gttcctggac tgctccacca
74401  cccagagcga cctgaccctg tgtgagggct tcagcgaggc cctgaagcag tgcaagtaca
74461  accacggtga gcggctgctg cccgactggc gccagggtgg aagggcggt ccacggctcc
74521  cactccttcg gggtgctccc gctattccca ggtgctcctg cacttcccat gtgctcccga
74581  ttctccctgg tgctccctct cctcctggct gctccttgc ctcccaggtg ctcccacttc
74641  tccctggtgc tcctgctcct ccggcggct cctgtacctt cggcctgacc tctcccctct
74701  acaggtctga gctccctgcc ctaagagacc agagcagatt gggtggccag ccctgcaccc
74761  acctgcaccc ccctcccacc gacagccgga ccatgacgtc agattgtacc caccgagctg
74821  ggacccagag tgaggagggg gtccctcacc ccacagatga cctgagatga aaacgtgcaa
74881  ttaaaagcct ttattttagc cgaacctgct gtgtctcctc ttgttggact gtctgcgggg
74941  ggcgggggg agggagatgg aagtcccact gcggggtggg gtgccacccc ttcagctgct
75001  gccccctgtg gggagggtga ccttgtcatc ctgcgtaatc gacgggcag cgcagaccgg
75061  atggtgaggc actaactgct gacctcaagc ctcaagggcg tccgactccg gccagctgga
75121  gaccctggag gagcgtgccg cctccttctc gtctctgggg cccctcggt ggcctcacgc
75181  tctgtcggtc accttgcccc tcttgctgat gcaatttccc cgtaattgca gattcagcag
75241  gaggaatgct tcgggccttt gcacctgacc gcatgagcag aggtcacggc cagccccctt
75301  ggatctcagt ccagctcggc cgcttggccg tgacgttcca ggtcacaggg cctgccggca
75361  cagaggagca ggcccttcag tgccgtcgag cactcggagc tgctgcctcc gctgagttca
75421  ctcagtgtct acgcacagag cgcccactgt gtaccaggcc ctattccacg ttccccagtc
75481  accgagcccc cagggctggt ggggacctgc cctcgggtac actgtgtccc gtcacgtggc
75541  tttacgtgtg tctctgaggg aggctggcat tgcggtccac ctctcagcac aaacatctgt
75601  cccctgggaa ggggtccca tttctgggtg cgagcagccc cctggggtcc gtgtctcctc
75661  cttacctggc tcaaggcccc ggctcctggg tcctggacag cagggagccc acccctcggg
75721  gctgtggagg gggaccttgc ttctggaggc cacgccgagg gccaggcgc cgcctccggc
75781  cgtcgccctg agggagcagg cccgacgcca gcgcggctcc tctgtgaggc ccgggaaacc
75841  ctgcctgagg gtgcgggtgg gcaggtgccc ctgccccag gtctcctgt gtgagtgaca
75901  ctcaccagcc agctctggat gccacccatc cgggttctcc aggaggcact catagcgggt
75961  ggggtccct ccctccccc tctgtggagg gagggagtct gatcactggg aggctggtgg
76021  tccgtacccg cccccccgac tctggacgtg tttactaccc ccgcctgggc tcaggacagg
76081  gcattggatg ggaaggacag ggctgggtcc tggccaggct ggggctctg cagggcatgg
76141  gtgcccctgt ctcttcttat attccaacgt cactgcaggg gggcgcaaat cttggacccc
76201  acttactgat gatctgcatc aggacatagg tccccctcc tgcagcgggg ggctggccac
76261  ggagggcgct ggggaaggcc cctcctccag cccctcggcg aggctcacca ggtgcccatc
76321  ctcagccagc agggcgacgc tcgctgggag ggcggagagg gaggcagggc agggctggta
```

-continued

```
76381 cgacccccgc tggggcgggg gggccctcag ccggtcctcc agcaccttg ctgccccccc 76441 tcaccgtcag ggggcacctg gccgctctgc ctcaggtggg cggtgagggt cccaaggcca 76501 caccaggtgt tcaccagctc ccagcagctg gctgtgggag aggggcagag gtgggcgcat 76561 ggcacccgcc ttcccccag accaggatgc tctgccttcc tcccgcccat ctccccagac 76621 atctgaagga ctcttgcctc caccatgcag ccccgcctcc accagaagct caggttcccc 76681 gccccccctc cccgaagctg caggacccct gaccagcgaa gagatgggac agttggaaca 76741 cacgctcccc cagcagcggc acagcagctg tgtggccag aagagcccgc ctgtttccct 76801 caagcaactc cccatggatg tcatcccatg gacacccct tccccacacc gcctcctcgt 76861 tctcccctc caaggcagag ggaacgcacc cccacctgtc tgctaggaca ggggacccca 76921 cttacctccg aacatcacct tgataaacat ggccgtggtg gggacagatc cctccgaccc 76981 ccaacttccg acctggggaa ggagctgggg tggagctcga ctgcagggtg gggccctgtg 77041 ggaggtgtac gggtggagag ggtgatgggt gggtgggctc aagcggagct ccttgctcag 77101 tccaggcggt ccctgcagct agtccaggat cctcagcctt ctcccctca ctggatcagg 77161 gaagactgag gttccctccc ctgccccccc acccagcttc aagctggtc tctgtggcag 77221 tgggagctgc caagaggtct gagcggccag tatccgggta acggggtttg tggagggtcc 77281 gggcattccc ggtgcagggc tctagtgggg gctggagcct cgggcccaga gctgtccaga 77341 gaccagtgcc ctcccaccgc cgccgcccgc aaggagagac agagctccca ggcggggagt 77401 cggaggttcc tggaggggga gcatcctcaa ctctgcaggc ccccttccca ggcgcactcc 77461 cggcctcccc gtcttctgtc ccctgctctt gttgaagtat gattggcata cagttcacag 77521 ccactcttcg gagtgttctc cacactaagg atacagaaca tgtccctcgt cccccaaac 77581 tcccagccag gctgtcacga agagggaggc ggccgacggg gcagggcctt gcactcctgc 77641 gtgtggggtc cacaggggtc gtccccgtgt cggtggcccc ttcctctcac gccaggaggg 77701 tccccttgcc tggaggtgcc gtggatccgc tcgctgcctg ctctttgggt tgtttcccgc 77761 atggggtgat gatgaagagg ccagtacaga cactcgccag caggtctctg ggtgaacagg 77821 catttatttc tctttcctga gggcagatcc tgggagtggg gtgccggacc gtccggggag 77881 agtatgcttc tgtttctaag aagctgccgt gttctccagt gtgctgcacc atgtcacggc 77941 ccctctgtgc gtctggactc aggagacctc cttctcagcg gccctccccc ccaggtggtc 78001 aggccatctg tgcccttctg ggggcagagc tcagcgccgg aggcgggagg aggcccagat 78061 cccagcgcag cccaccagcc ttgctctgct tccctcggca ttcatagctg gagaaagggc 78121 aaggagcacc ggctgaagcc ccacctggag gacgcacttc gatggcagca ggtgctcaga 78181 ggtggccccg ggcagcattc cccagacgca caggccagtg ctttcttccc aggacaccac 78241 tgtgtctggg gacccgagtc ctgcagcacg gtcgggagcg gctgtgccca gattccggcc 78301 tgcacccttg gctccagcca ccacccctgt ttgtcaaggg gtttttgtct ttcgagccgc 78361 cgaggaggga gtcttttgtc tgcagtgtca cagaagtgcc ataaagaggg gcccacagtg 78421 ggagctttat aacattggtg cggagggctg taacaggtca gggaggcact tgagggagcc 78481 ttctagggcg atggagatgt tctaaaattt ggtctgggta caggctacag agatgtgtgg 78541 gtgtgtgtgt gtgtgtgtgt aaaaccctcg agccacacgt gtgaggtctg tgcatgtgac 78601 cgtacacagg agacctcggt ggaaagcagc cacctgctct gactgcacct gtggatttcc 78661 agctcctgcc ctcaggcggc cctgcgggc ccactggctg acggggagac ggcaccgccc 78721 tccccgctg tcagggtggg ggggctgacg atttgcatgt cgtgtcaggg tccagcggcc
```

```
78781  tcccttgcgt ggaggtcccg aagcacctgg agcgccgccc gcagaacagc ggactcctgc
78841  ctgcctccct gcctctggcc atggcctgcc cgcctctggc cctctttctg ctcggggccc
78901  tcctggcagg tgagccctcc caaggcctgg ctcacctagg ggtgtgtaag acagcacggg
78961  gctctagaag taaatcgcgg ggaagtaaat cgtagtgggc aggggggatg gtttccgaag
79021  gggccctgag ggggacagga gacctggcct cagtttcccc actggtgagt gaccagatag
79081  ccagggtacc tttggactct gactctgggg ggctctcaga gactggtctc ctactcagtt
79141  tttcagaggg gaagctggtg tggccttgtc actgccctgc agggcctcag gacaagcta
79201  tccctgagga ggtctccagc agtcagtggc cggaggctga gccgatggat atagtaacag
79261  cccaggcggc ctcttggggg tggtcagcct gtagccaggt tttggacgag ccgaagtgac
79321  ctaagtgatg ggggtctgca gagcaaggga tgagggtggg cagcaggagg acccagagcc
79381  caccagccca ccctctgaat tctggaccct tagctgcatg tggctccttg ggaagacggg
79441  gcttaagggt tgcccgctct gtggcccaca cagtgctgat ccacagcac tggctgtgag
79501  cttttgggag cagattctcc cggggagtct gacccaggct ttgtggggca ggggctggag
79561  ggaagggggcc caggccagac ctgagtgtgt gtctctcagc ctcccagcca gccctgacca
79621  agccagaagc actgctggtc ttcccaggac aagtggccca actgtcctgc acgatcagcc
79681  cccattacgc catcgtcggg gacctcggcg tgtcctggta tcagcagcga gcaggcagcg
79741  ccccccgcct gctcctctac taccgctcag aggagcacca acaccgggcc cccggcattc
79801  cggaccgctt ctctgcagct gcggatgcag cccacaacac ctgcatcctg accatcagcc
79861  ccgtgcagcc cgaagatgac gccgattatt actgctttgt gggtgactta ttctagggg t
79921  gtgggatgag tgtcttccgt ctgcctgcca cttctactcc tgaccttggg accctctctc
79981  tgagcctcag ttttcctcct ctgtgaaatg ggttaataac actcaccatg tcaacaataa
80041  ctgctctgag ggttatgaga tccctgtggc tcggggtgtg ggggtaggga tggtcctggg
80101  gattactgca gaagaggaag cacctgagac ccttggcgtg gggcccagcc tccccaccag
80161  cccccagggg cccagactgg tggctcttgc cttcctgtga cgggaggagc tggagtgaga
80221  gaaaaaggaa ccagcctttg ctggtcccgg ctctgcatgg ctggttgggt tccaacactc
80281  aacgagggga ctggaccggg tcttcgggag cccctgccta ctcctgggtg gggcaagggg
80341  gcaggtgtga gtgtgtgtgt ggggtgcaga cactcagagg cacctgaagg caggtgggca
80401  gagggcaggg gaggcatggg cagcagccct cctggggtag agaggcaggc ttgccaccag
80461  aagcagaact tagccctggg agggggtgg ggggttgaa gaacacagct ctcttctctc
80521  ccggttcctc taagaggcgc cacatgaaca gggggactac ccatcagatg nnnnnnnnn
80581  nnnnnnnnnn nnnnnnnnnn nnnnnnnnnn nnnnnnnnnn nnnnnnnnnn nnnnnnnnnn
80641  nnnnnnnnnn nnnnnnnnnn nnnnnnnnnn agagggtggg tgggtggaat ttaatatagt
80701  ggtgcgcgtg gagcgtgggc ggcgcattta aggcggtcat ctaaaatagt ggataggggg
80761  tggtgtgaca ataacgggtg gtggatgtgg tttacggggg gtgcaatagt tctgagtttg
80821  ttagtgtctt cttgatgggg ttgcggcgtg tggacctacg ccttgagtat gtggggggg
80881  aaaagcagtg agggtagtag ggatgggaaa tattggtgga ggttctttgt tggtgtattt
80941  tttggtatta tgttgggtgg tggagtggtg ggttgggtgt aatttcgctt gcgttatgtg
81001  ttttttttct tttcgtgtc gtgggttggg ttggttggtg ctttgtggtg gtggtgggtt
81061  gtggtataaa aaaaatgtg tggttgtgct cagcttagcc ctataacggt cggctttgtt
81121  tcttgtttgt tctgtgggcg tgagcggatg gctcgggcct ccgtgctccg cggcgcggcc
81181  tcgcgcgccc tcctgctccc gctgctgctg ctgctgctgc tcccgccgcc gccgctgctg
```

```
81241  ctggcccggg ccccgcggcc gccggtgagt gcccgccgtc ctccagcccc cccgccccgc
81301  cccgccctcc acgccgaggg gcgccggctc gcagagctgg atccaagggg gtgcccggga
81361  gtggcccggc gcggccgtt  accccgaaac gctgtctggg tgccccgggg gtgtggtgga
81421  tagtgagctt cccgtccctg gaagtatgca agtgaagccg gcgccgggat cgctcgggct
81481  ggctggtgag cgggcgggac tcggtcgggc gctagacgca cgccgccagc ccccagctc
81541  ccagacctgc ccactccgcg cccgcccggc cgcgatcccg ggtgtgtgtg tgtgttgcag
81601  gggagggaca gcgggagtgg ctacagggct cccgactcac cgcagggaca agacccgcg
81661  ggtccccagc tggcgtcagc cgccaggtgt gtggcctcgg tgagcacacc tccaggcggg
81721  agggttgagg gaagcgctgt ggggagggca tgcggggtct gagcctggaa gagacggatg
81781  ctaccgcctg ggacctgtga gtggcgggat tgggaggcta tggaatcagg aggcagccta
81841  agcgtgagag ctccggtgtg gcctggcggg ggtggtaggg gggggacgcc cctgtgtgtg
81901  ccagcctgcg tgtgccctaa aggctgcgcc ctcccccact gctggggctt cggggggacca
81961  gtcacagcct aggctactgc aggcgcacag ctccccggga gcccggccca cgcgggtgtg
82021  ccgctgagcc tccagcctgt cggggcaggg gtgggggggca gggatggggt cgttagcggg
82081  gttgggggca gacgcccagg cagactctct gggcacagct ccggtgacaa gggaggtctg
82141  gcaagcctgg gcccttctg  tccagccacg ccagctctgc cctggccagt cttgccccct
82201  ggcagtgctg gggatggaag ggggagcggg tacctcagtc tgggggccct gcctcctccc
82261  cagccccgcc cggccccta  ggcctagggg cagagtctag gggtcaccct ggggagctgc
82321  tgaatccgcg ggtttaggaa ccggagggac ctgggctttt gaaccacgtg gccctaggtg
82381  agccctccgg cgcctcggta gccctcaccc ccagccttgt ccaggtgggc gggtgggagg
82441  cgacagtgcc cactgctggg ctgaacagcg tctgcaggga ggccaggaga gctgggcaca
82501  cggacacgtt ccatcacctg gagctgccac tgtgccactt gtgcggggtc aggcggggtc
82561  tgagccgggc tgtcatctgt cacgccacag atatgcaggg ggcactcggg gtcgcctcgg
82621  acatgcttat ccctggacgg ctgttggcag ggccgggaag gctctgtaaa tatttatcca
82681  tcccagctca cagctttcag ggttgatgaa agccccgccg cccgcccact gtgggggacc
82741  ccgccttccc ttctggagcc agcggggtga gggggtgggg gagatggacc tgcctgccca
82801  ggagcaggcg gtgtgactct ggcaggtcac ttgacctctc tgagcctcag ggaggggcccg
82861  ggatggtgtg cggatgctct ctgccttcct cccagcctga ccagtgtcct cccctcgggg
82921  tcgcctcctg cccaccgcag aggggggtggc tatgggggacc tgggccgatg gcaggcaggc
82981  cggagagggc atgcccggct cagccgtgcc cagcacttcc cagtccaggg gcccccgcca
83041  ctcccagccg ctggctgcct cccatttttcc cgattgcagg ttggccccga ggctgaccgg
83101  agcctctggc tcagctggga gactgaattc cccaagcaat tcctcaagga tgtgtgaggc
83161  tgtggtgtgg tgcctatccg ggagaggtgg ggtgagcgga ctgggcacct ccgcccaggg
83221  caggcccagg gagacgctgg ctgacgagca ggcaggcctg caaggaggac gagcagccat
83281  ctcaggaatg tgggttttgg agacaagcca cagctggggg ggtggggggg ccatgggtgg
83341  ggaggcctga tccccaggtc taggtccagc tctgggctcc ctcgccgtgt gaccctgggc
83401  caagacctgg acctctctgg gccccgtctc ttcccctggg aggtggggcg atgcctgctc
83461  cccaatcccc cagggctgtg gatgaggcag acgaggtgtg tgctcatccc cacctcactg
83521  ccttccagca gccccgggcg ggggggggtgg tggggactgg cgcacccagg tgaggatcag
83581  gccttggagc tagggagggc cccccagccc caggccagaa aggacacggg gagacagaat
```

```
83641 gcaggagggc ggcagagcag gggccagcgg tggggaaact gaggccaaga gcctgtggac 83701 gatgtgctcc aggaaaggac ctcgctgcct ggggcctgga tcctagagcc tccaggagcg 83761 gtgaccatga cgtgggcagg gaaccggagg ccccggcttg caggtggacc cggcgcgagt 83821 cactcttcct ctctggccct gagagcttcc ttccagctgc cgctcctgtg ttctaatgtc 83881 aagtctggag gcctggggggg caggtggggg ctgactgcca ggtggggag gcaggaatt 83941 tggcagagca gcgtcccaga gtgggagaag ccagcccatg gaggggactc tctccatgcc 84001 tgctgcccca aagggcgtta tagagagagg tcggttaccc cttcgccatg gccccgttcc 84061 cattgaacag atgggaaagt ggaggctgag agaaggctgt gacttgccca gggtctccgt 84121 ggcatggaac tgggcctgct gagtctcagg ccggggatct cgctgctgca ctgagcacgc 84181 caggatgcag gggtctgggc ctggacctag cgcctcgtgg gggcaagaga ggaaggcacg 84241 ctgggcctgc ctgtcaccct ccacccacc gtggcttgtt gctcaggcct tcctgggggc 84301 agaggagagg ggagatttca ctcgctggca ggctaggccc tgggctctct ggggctccgg 84361 gggaacaatg cagccctggt ctttctgagg agggtccttg gacctccacc agggttgagg 84421 aaaggatttc tgttcctcct ggaggtcacg gagccgacat ggggaggagc aggggcaggc 84481 ccggggccca catcctcagt gtgagacctg gacgtgtgtc ctcccacctg acgctggggg 84541 tgggggggtgg gggccggggg ggatccagtg aaccctgccc ccaaattgtc tggaagacag 84601 cgggtacttg gtcatttccc cttcctcctc ttcgtttgcc ctggtgggga cagtccctcc 84661 cctggggaag ggggaccca gcctgaagaa cagagcagag ctggggtcag gggtgtgctg 84721 ggagcgcaga gagcctcctg ctctgcctgc tggtcattcc tggtggctct ggagtcggca 84781 gctggtgggg agcggctggg gtgctcgtct gagctctggg gtgcccaggg cctgggagag 84841 ttgccagagg ctgaggccga gggtggggcc ctgcggcccc ggctcctgcc ccaaatatgg 84901 ctcgggaagg ccacagcggc actgagcaga caggccgggc cagacgggcg ctgaggctcc 84961 cggcctctcc cccagctccg ctgtgaccct cacctgcgcc cggggtgcc agggcccccg 85021 cttggttctg ccgtgtcttt gcaggctgat cccacgggct ctccctgcct ctctgagctt 85081 ccgccttttc caggcagggg aaccgcgacc tccaggctgg gacgcgggga gggtgtatgc 85141 gccaggtcag aatcacccct ccaccgggag agcgtggtcc aggggccctg gcagggtggg 85201 gaccgagcat ctgggaactg ccagccaccc ccacccatgc agagggaca tacagaccac 85261 acggaggctg tgcctccgct gcagcaactg gagaacaccc agccgcggcc aaacataaat 85321 aactaaataa taaaagtttt aaagatcgtt acttaaaaaa acaagtgtgc cccagtgatc 85381 ggaccccagt tcccggtgcc ctgagtggtg ccggccctgt gctgagcatg gcctggttgg 85441 ttcacccca gatccacact aaagggtggg atccccccta ctagtcaggt gagcagatgc 85501 aggggggggag ggcggcagcc cctccatgct ggtgggtggc cgtggtgggt gtcctgggca 85561 ggagccagct cacggagctg gagaggacag acctgggggg ttggggcgc ccaggaagaa 85621 acgcaggggg agaggtgtct gccggggggtg ggggtccctt cgaggctgtg cgtgaagagg 85681 gcaggcgggc ctgcagcccc acctacccgt ccccggccca aacggcggga gtaagtgacc 85741 ctgggcacct ggggccctcc aggaggggc gggaggcctt ggatcagca tctggacgcc 85801 agtcagcccg cgccagagcg ccatgctccc cgacggcctc cgctggagtg aggctgcgct 85861 gacacccaca ccgctgaccc gggcctctct cccgctcagg atgccccccg ccgccacccc 85921 gtgagcagag ggccacagcc ctggcccgac gccctcccg acagtgacgc ccccgccctg 85981 gccacccagg aggccctccc gcttgctggc cgccccagac ctccccgctg cggcgtgcct 86041 gacctgcccg atgggccgag tgcccgcaac cgacagaagc ggttcgtgct gtcgggcggg
```

-continued

```
86101 cgctgggaga agacggacct cacctacagg tagggccagt ggccacgagc tggcctttga
86161 tctccacctg ctgtctgaga cacgctggag ctgggggag ggcagatccc tatggccaac
86221 aggctggagt gtccccaac tcccgtgccc actgctcaac ccccaaacc cacacttaga
86281 tgcactccca tgccctccct tgggagcacg gtctccacac ccacctggcc accccacaca
86341 cccgtggggc acggccgtta gtcacccacg caacctctgc gggcaccgtg ctgcgggcca
86401 ggccctggga ctctcagtga gggaggcaga cacggcccct cctccggggg agcgaggtgc
86461 tccccacgcc cggttcagct ctagcaccgc actcgggacc ctcacaggga gggacccact
86521 ggggcaggcc aggtgacggc tcgggtgacc tcggcccctg gcgctgagac tacacttcct
86581 gcagtgggcg gcgaagatgg gtgtggtgtc ccacgtcgtt gcagcgggga ctcctgggc
86641 ctcggaagtg tcctgggcgg ggagcctggg gagcaggaag ggcaggtctt ggggtccaag
86701 gcctccccac ggtcaggtct gggaggggc ctcggggctc ttgggtcctt tccgcccagt
86761 gcagaccctc gcggccacct aagggcacac agaccacaca aagctgtgcc catgcagtgt
86821 ggggagtggt gcgcaccctc agagcacact gggcccacat cacgcacgcc tgcccctca
86881 ctgtgcatcc ggggaaactc ctggccccga cagccagcgg ggctgacgct accccgtgag
86941 ccagacccag gcccccctca ccgcccctgt cctccccagg atcctccggt tcccatggca
87001 gctgctgcgg gaacaggtgc ggcagacggt ggcggaggcc ctccaggtgt ggagcgatgt
87061 cacaccgctc accttcaccg aggtgcacga gggccgcgcc gacatcgtga tcgacttcac
87121 caggtgagcg gggcctgag gcaccccca ccctgggaag gaaacccatc tgccggcagc
87181 cactgactct gccctaccc accccccgac aggtactggc acgggacaa tctgcccttt
87241 gatggacctg ggggcatcct ggcccacgcc ttcttcccca agaccaccg agaaggggat
87301 gtccacttcg actatgatga gacctggacc atcggggaca accaggtag gggctgggc
87361 cccactttcc ggaggggccc tgtcgaggcc ccggagccgg gcccgggctc tgcgtccgct
87421 ggggagctcg cgcattgccg ggctgtctcc ctcttccagg cacggatctc ctgcaggtgg
87481 cggcacacga gtttggccac gtgctcgggc tgcagcacac gacagctgcg aaggccctga
87541 tgtcccctt ctacaccttc cgctacccac tgagcctcag cccagacgac cgcaggggca
87601 tccagcagct gtacggccgg cctcagctag ctcccacgtc caggcctccg gacctgggcc
87661 ctggcaccgg ggcgacacc aacgagatcg cgccgctgga ggtgaggccc tgctcccct
87721 gcccacggct gcctctgcag ctccaacatg ggctcctcct aaccccttcgc tctcacccca
87781 gccggacgcc ccaccggatg cctgccaggt ctccctttgac gcagccgcca ccatccgtgg
87841 cgagctcttc ttcttcaagg caggctttgt gtggcggctg cgcgggggcc ggctgcagcc
87901 tggctaccct gcgctggcct ctcgccactg gcaggggctg cccagccctg tggatgcagc
87961 cttcgaggac gcccagggcc acatctggtt cttccaaggt gagtgggagc cgggtcacac
88021 tcaggagact gcagggagcc aggaacgtca tggccaaggg tagggacaga cagacgtgat
88081 gagcagatgg acagacggag ggggtcccgg agttttgggg cccaggaaga gcgtgactca
88141 ctcctctggg cacagctggg aggcttcctg gaggaggcgg ttctcgaagc gggagtagga
88201 taaaaggtat tgcaccccat gaagcacgtg tgatccttgc ccctagagac aaggctctgg
88261 ggctcagagg tggtgaagtg acccacatga gggcacagct tggagaatgt cgggagggat
88321 gtgagctcag tgtgccagag atgggagcct ggagcatgcc aagggggcagg gcctgctgcc
88381 tgagagctgg cactggggtg ggcagccaag tgcagggatg gagcgggcgc ccaggtgcc
88441 tctttgctgc tcagaacgac ctttcccatg tatacctccc agcgccgctg gcattgccca
```

```
-continued
88501 gtgtccttct tgggggcagg agtaccaagc aggcattatt actggccttt tgtgttttat 88561 ggacaacgaa actgaggctg ggaaggtccg aggtggtgtt ggtggcggaa ggtggccgct 88621 gggcagccct gttgcagcac acaccccca cccaccgttt ctccaacagg agctcagtac 88681 tgggtgtatg acggtgagaa gccggtcctg ggcccgcgc cctctccga gctgggcctg 88741 caggggtccc cgatccatgc cgccctggtg tggggctccg agaagaacaa gatctacttc 88801 ttccgaagtg gggactactg gcgcttccag cccagcgccc gccgcgtgga cagccctgtg 88861 ccgcgccggg tcaccgactg gcgaggggtg ccctcggaga tcgacgcggc cttccaggat 88921 gctgaaggtg tgcagggggc aggccctctg cccagccccc tcccattccg ccctcctcc 88981 tgccaaggac tgtgctaact ccctgtgctc catctttgtg gctgtgggca ccaggcacgg 89041 catggagact gaggcccgtg cccaggtccc ttggatgtgg ctagtgaaat cagtccgagg 89101 ctccagcctc tgtcaggctg ggtggcagct cagaccagac cctgagggca ggcagaaggg 89161 ctcgcccaag ggtagaaaga ccctgggggct tccttggtgg ctcagacagt aaagcgtctg 89221 cctgcaatgc gggagacctg gattcgatcc ctgggtcagg agatcccct ggagaaggaa 89281 atggcaatgc cctccggtac tgttgcctgg aaaattccat ggacagagca gcctggaagc 89341 tccatggggt cgcgaagagt cagacacaat ggagcgactt cactgtctta agggccacct 89401 gaggtcctca ggtttcaagg aacccagcag tggccaaggc ctgtgcccat ccctctgtcc 89461 acttaccagg ccctgaccct cctgtctcct caggcttcgc ctacttcctg cgtggccgcc 89521 tctactggaa gtttgacccc gtgaaggtga agccctgga gggcttcccc cggctcgtgg 89581 gccccgactt cttcagctgt actgaggctg ccaacacttt ccgctgatca ccgcctggct 89641 gtcctcaggc cctgacacct ccacacagga gaccgtggcc gtgcctgtgg ctgtaggtac 89701 caggcagggc acggagtcgc ggctgctatg ggggcaaggc agggcgctgc caccaggact 89761 gcagggaggg ccacgcgggt cgtggccact gccagcgact gtctgagact gggcaggggg 89821 gctctggcat ggaggctgag ggtggtcttg ggctggctcc acgcagcctg tgcaggtcac 89881 atggaaccca gctgcccatg gtctccatcc acacccctca gggtcgggcc tcagcagggc 89941 tgggggagct ggagccctca ccgtcctcgc tgtggggtcc catagggggc tggcacgtgg 90001 gtgtcagggt cctgcgcctc ctgcctccca caggggttgg ctctgcgtag gtgctgcctt 90061 ccagtttggt ggttctggag acctattccc caagatcctg gccaaaaggc caggtcagct 90121 ggtgggggtg cttcctgcca gagaccctgc accctggggg ccccagcata cctcagtcct 90181 atcacgggtc agatcctcca aagccatgta atgtgtaca gtgtgtataa agctgttttg 90241 ttttttcattt tttaaccgac tgtcattaaa cacggtcgtt ttctacctgc ctgctgggt 90301 gtctctgtga gtgcaaggcc agtatagggt ggaactggac cagggagttg ggaggcttgg 90361 ctggggaccc gctcagtccc ctggtcctca gggctgggtg ttggttcagg gctcccctg 90421 ctccatctca tcctgcttga atgcctacag tggcttcaca gtctgctccc catctcccca 90481 gcggcctctc agaccgtcgt ccaccaagtg ctgctcacgt tttccgatcc agccactgtc 90541 aggacacaga accgaactca aggttactgt ggctgactcc tcactctctg gggtctactt 90601 gcctgccacc ctcagagagc caaggatccg cctgtgatgc aggagtgagt gaagtcgctc 90661 agccgagtcc gactcttttgc aacccatag gactgtagcc taccaggctc ctctgtctat 90721 gggatttttc aggcaagagt gctggagtgg gttgccattt ccttctccag gggatcttcc 90781 caaccctggt ctcccgcata gcaggcagac tctttactgt ctgagccacc aggcaatgca 90841 ggagacctag gttcagtctc tgggtgggga agatcccctg gagaagggaa tgacaacctg 90901 cttcagtatt cttgattggg gaatcccatg gacaaaggag cctggaggcc tacagcccat
```

-continued

```
90961 agggtgcaaa gagacacgac tgagcaagtc acacacacag agccctacgt ggatgctcat
91021 agcggcacct catagctgcc atgtatcagg tgttggcatg ggcagccatc agcaggggggc
91081 catttctgac ccactgcctt gttccaccgg atacacgggt gccttcctgt gtgtcgggcc
91141 cactcggctg tcagcgccca agggcagggc tgtcgggagg cacagggcac agagttaagg
91201 agggatggg gacgttagct cctccccagc tctcagcgga tgcagcaggc aaaacaaacg
91261 ctaggaatcc tgccaaaccc ggtagtctct gcccatgctc gccccatccc cagagccaca
91321 agaacgggag ctggggggtg gcccggagct gggatactgg tccctgggcc cgcccatgtg
91381 ctcggccgca cagcgtcctc cgggcgggga aactgaggca cgggcgcctc cggcttcctc
91441 cccgccttcc gggcctcgcc tcgttcctcc tcaccagggc agtattccag ccccggctgt
91501 gagacggaga agggcgccgt tcgagtcagg gccgcggctg ttatttctgc cggtgagcgg
91561 ccttccctgg tacctccact tgagaggcgg ccgggaaggc cgagaaacgg gccgaggctc
91621 ctttaagggg cccgtggggg cgcgcccggc ccttttgtcc gggtggcggc ggcggcgacg
91681 cgcgcgtcag cgtcaacgcc cgcgcctgcg cactgagggc ggcctgcttg tcgtctgcgg
91741 cggcggcggc ggcggcggcg gaggaggcga accccatctg gcttggcaag agactgagnn
91801 nnnnnnnnnn nnnnnnnnnn nnnnnnnnnn nnnnnnnnnn nnnnnnnnnn nnnnnnnnnn
91861 nnnnnnnnnn nnnnnnnnnn nnnnnnnnnn nnnnnnnnct gcaggtgccg gcggtgacgc
91921 ggacgtacac cgcggcctgc gtcctcacca ccgccgccgt ggtaaccgcc cccgggggtt
91981 gccaaggtta cgattggacc ctccccgccc cgaccctgct ccctagggt gggtgggtcg
92041 gggggcagtt tctaagatct cctggttccg cagcagctgg aactcctcag tcccttccag
92101 ctctacttca acccgcacct cgtgttccgg aagttccagg tgaggccgcc ccgccccttg
92161 cacttgctgg cccaaccccct cccgcccagc gctggcctga ccgccccca ccccgcccac
92221 cccacgcagg tttggaggct catcaccaac ttcctcttct cgggcccct gggattcagc
92281 ttcttcttca acatgctctt cgtgtatcct gcgccgtggt ggaagcggga ggagggcggg
92341 gcggggggacc gggcgggagg cagcgggccc cgggaagctg agaccctcca aggggcacgc
92401 ttcctatacc aaagccgcag gttccgctac tgccgcatgc tggaggaggg ctccttccgc
92461 ggccgcacgg ccgacttcgt cttcatgttt ctcttcgggg gcgtcctgat gactgtatcc
92521 ttcccgggct cggggaccta tgggtccggg cctctgctgg ccctgaggcc ctgcttgagc
92581 gcatgccaca gagggagagt tgcgaccccg agctgagggt gttttttgagc gtacatcacg
92641 tgctcagctg caggtgcccc tgtcgaactc cagggctaca cccaaaatac cacagggcag
92701 ggtgcccagg ggctgagtcc tgaatgcagg tagccaggag gatctagggc tgggcccggg
92761 ggctggggtg aagtggagag gcaggccga tcagggggcc cctggaggcc accgtttggt
92821 cttagagtgg gaagcgaaac caacctgctt gagggtttca ggggtttagg aagtcagagg
92881 ggccctgggc agggcacaag accttgactc tggcccagct actggggctc ctgggtagcc
92941 tcttcttcct gggccaggcc ctcacggcca tgctggtgta cgtgtggagc cgccgcagcc
93001 ctgggggtgag ggtcaacttc tttggcctcc tcaccttcca ggcgccgttc ctgccctggg
93061 cgctcatggg cttttcaatg ctgctgggca actccatcct ggtggacctg ctgggtgagc
93121 ctgctgtcca gggagcctgc ccaagctgg gtgtgctggg ccagagccct ggtcctctcc
93181 ccgccccac ccctcttccc cactcctggc gccccatcc ttccagcccc tccaacaagt
93241 cagcctatag gttttactta ttcgagcctg acccattttgc tgacgcttgt gtggggcccg
93301 accggtagg gatgggtggc tcagggtgcc tgctcacagc tccacttctt ctgacgtcct
```

```
93361 caggcctgac ctcctcccag gttctgccta ctctgggcca agcctggccc cacgctgggc
93421 tggctggccg tgcagggcat cagaccccca tgctttgggg gcttcagggc tgtggagggt
93481 ggcctcggca ttggcgcctc tcccacaggg attgcggtgg gccacgtcta ctacttcctg
93541 gaggacgtct tccccaacca gcctggaggc aagaggctgc tgctgacccc cagcttcctg
93601 tgagtgctga cagccttccc cacccccttc cccagatggc tctctacccc atgaggggg
93661 gggaccctgc cagctgccgc tcagcgtggg ctcctcccca caggaaactg ctactggatg
93721 ccccagagga ggaccccaat tacctgcccc tccccgagga gcagccagga cccctgcagc
93781 agtgaggacg acctcaccca gagccgggtc ccccaccccc acccctggcc tgcaacgcag
93841 ctccctgtcc tggaggccgg gcctgggccc agggcccccg ccctgaataa acaagtgacc
93901 tgcagcctgt tcgccacagc actggctctc ctgccgcggc cagcctctcc acgcgggca
93961 ggtgctgctg gccgagagcc agggccacca agcctgacgt gctctccgac ccagaacatt
94021 ggcacagctg gaggcccaga gagggtccag aacctgccca ctcgccagca gaactctgag
94081 cacagagggc agccctgctg gggttctcat ccctgccctg cctgtgccgt aattcagctt
94141 ccactgatgg ggctcacatc tcaggggcgg ggctgggact gggatgctgg gttgtgctga
94201 gctttggccg tgggggccct cctgtcccga actagcaacc cccaagggga cctctgcttc
94261 atttcccagc caggccactg aaggacgggc caggtgcaga gagggccag gcccttttctg
94321 tgactccgaa gcctcaagtg tcagtgtttg cagagtccag tggctgaggc agaggcctct
94381 gggaagctct gcccctgccg tttgcagctg aggccggcag gagcctcacc tggtccccag
94441 ctcacgggca ttggaggacc agtccgcacg gtggttact cctgggtcgg caccagccgc
94501 cgccggctgt ccctttcaca gaggataaaa gtactcgctc tggagttgga cttaatgtt
94561 gtcatgaaac ctctggccca gcagcgggct ccgcagtggg tggcaggtga aggcccctcc
94621 ccgggcctct ccaggcaggt gccgcctggc cagcagggaa ggcaggcagt gtcatccccc
94681 actggctctg gggctcaggc tacctcctgc tgtggccgga acatctcccc cagtggtgga
94741 gcccagtgtc cgtgaggcca gctgggcctg aaaccttcct ctctgaagcc ccgctgtccc
94801 cttgcctgt atggagggca gaggctggag cgcaagttcc taggatgtgc ttgcgagacc
94861 cccgagccca ggggcgaggc ccatctcagc ccaccccga actggaaacc cttggagctc
94921 tgcccctcgt ggtgtgaggc cctgctatg cgaccctcag cctgccagc aacggaaggt
94981 gcagggcccg ggcccacggg cttaacgcaa ctgggcctgg gtcacctgcg gggcctggtc
95041 ccaggaggaa gacccaggtg ccacctcct gggtgccacg tccaggtcac gtggggaccc
95101 gtccatgtca cagaagatgc agggtcaccc ggtgagctgg cgccgggccc tgccagagca
95161 ccagccgcgg gtggaggtgg gccccagctc tcctgtcagg cacgtggtgc tgggaggtgc
95221 ggccggagca gtgcccacca gctgcagcag acaggtggg cacaggccca ccagcagtgc
95281 ccgcacggga tgggcccctg caagggccag agaagccacg ctcctggctg ggggctgggc
95341 tgggactgac aggtggccct gccctctgcg ccccactact tcccagccac ccgggactcc
95401 aaggacttgc tgagctgggc aggtgggacg ccgaggggag tcaaactgct cgtggggca
95461 ggaggggcgg tccacagggc tgagccctga gctgaaccct ggccctgctc gtggttgtgg
95521 gggtggggg gtccagtggc gccctagccc tgctgaggcc cagctgggac gtgcgcgccg
95581 gagggcgagg ggccagccca tgccatgctg tccccgttc tcagctccat gctaccactt
95641 tgaagaaaca gaacctgttg ccttttatt tagaaagtgt tgcttgccct gcctgggct
95701 tctatacaaa aaacaaacac agctcaacgt ggcctctcct gaccagagac gggcggtggg
95761 gactgggct cagcagacgg aatgtgtccc cggcggcggg agaccaggag gcccctggcc
```

-continued

```
95821 cgctcctcag gacggctggg ctgtccccac ctggtccccc ccgagccaga agatggagga 95881 gaggtgggct gatctccaga tgctccctgg gagccaagcg ccacggggtg gtcaccaggc 95941 cggggccgtg ttggccagac gcctcatccg cctgtgggag ggggagggca gcaaccccccg 96001 gatctctcag gcaaccgagt gaggaggcag gagccccccag cccctccctc ggccgctctg 96061 ctgcgtgggg ccctgaagtc gtcctctgtc tcgccccccct ccccaggggag agtgagcctg 96121 ttctgggctg tggtcagacc tgcccgaggg ccagcctcgc ccgggggccct gtcctgcctg 96181 gaaggggctg gggcagcacc ttgtgttccg gtcctggtcc cggatcttct tctccatctc 96241 tgcatccgtc agggtctcca gcagcgggca ccactggtca gcgtcgcctg tgttccggat 96301 ggcaatctcc accgtgggca gggggttctc actgtggagg acgagagagg tagacggctc 96361 acagagcagc tgcaggagag gcccctagaa agcagtgtcc acccccgctgc gggcagacag 96421 gacatggagc ctggtttctg cacccggctc ccgacacagg gcggccgggc acgctgccaa 96481 catggcatct ccgggtctgc atgtggggag gggtccacag gacagtgctg caggtccagc 96541 cattcccagt ggacttgctg ggaggaggag ggccgtccgc cccgctcagt gtccaggaga 96601 aaggagagca aaggagtcca tccacccagg agtggagtcc cagggcccct gccctgacca 96661 gcctgcaggg ggcccctcgg cccacatcac aggggcccag aatccataag ccctgactgc 96721 tccaccccgg ggccctcaa agacgcgcct agactccgtc cgagggccac ctgcacaccc 96781 tctggcgaag tggactcagg gctgggggtc agcctcggtg aggccgcaaa ggctggggac 96841 tcctggccga gctgctgcct ctgccaggag ccaggcccag cctgccggcg agcctcagcc 96901 acgccctcac ccaccctgcc cgcggcgcca cgctggcctc cgggtcctct cctctggcct 96961 cctgctgggc cactggtgct cagcccccagc agtcggcctg ccaggagccc tgcagagtca 97021 gcccccagag ggaggagggg gcccggggga acagcacagg aacaaacaga cccctggcct 97081 tagttttagc tcctcatctg gaaaatgggg acagtgtcct tgctgcgagg ggtttcagag 97141 gaccactgcc atgcaacacc cagcacacac ccactgcgtg ggggctcggg cccgagccgg 97201 tgcccccgag tcccaggctg gtggctgggc cgccccagcc accctgccga cagctgcttc 97261 ccagccgggc ggtgctgcgg cagtccagaa gccagcactg cagacccaaa tgtcactcct 97321 cacgttgcgg gctcccagct gccttccttg ggggcagcag acacgaaagt caccaagccc 97381 acgccgacgg gagcaaacac gtcttcctct taaacaagtc gggtcccgg aggccctgtg 97441 tttacctccc tgtggctccg ggaagattgc atcccagggg gttgttctaa accaagggct 97501 gctcgggcca ggcctggaag gaggggcctg gagccaggag cccacccctta cgggcattcg 97561 gcttcctggg tctcaaggcc ggctgggacc ctgcattccc accacccgcc aggtgcaagc 97621 agggaggccg tgtcggagga ggcagagggc ctggagggtc gtcttcgacg tgacctcact 97681 tttacaacct cacaggtgcg gcaggccagc tgggaggcat ggctgtgccc tcctggtaga 97741 tgagaacaag actgcaggga gtgatccccc tgaacttccc caaccaggag gagacaaaac 97801 tcggtgtcgc cctcctgctt aagatcaact gactctggac aaggggccca gcccacccga 97861 tggggaaagg gcagtccttc caacaagcgg tgctgggacg ggacccggca ggccatggtt 97921 tctcagctat gacaccagca gcacaagcac cccgagaaaa acagctaagc tgggcactgt 97981 cacacaagtg aactccaaac ccaagaaaac cacaaaaagc ctgcggatct tcagatatgt 98041 gggaagggac ctgtatctgg aatgtataac gaactcctga aaagtgaaag tgttagtcac 98101 tcagtctgtt cagctctttg caaccccatg gacggtagcc tgccaggctc ctctgcccat 98161 gggattctct aggcaagaat actggagtgg gttgccatgc cttcctccag gggatcttcc
```

-continued

```
98221 caacccaggg attgaacctg tgtctctctt gcactggcag gcgggttctt taccagtagc 98281 gccacctgag tagaaacact ccaggtgccc tgagtgtcag agcaggaggg actcggccca 98341 ggcctgtgag gggaccctct ccgagtcccc tgctgcacag cagtgagagg tgcgttctga 98401 gtcagcctcc agggatgagg gacttggtgt cgacatcact cccaggacct caggatctgc 98461 tctgggaagc gaggctcccc aggctggccc caggcccgct ggcctcagct cgtgagccgt 98521 gcgtggacag gtgccatgag caggcctccc acgggactcg gggcgcggcc tggaccccgg 98581 ggctgccagt ggtcgcgggg ggccccgtgt ggcggctgtt ccctctcttg ctccgagtcc 98641 taggaacatg gtgggcgctg cctcctgggg tttctggaga agcagctgag atgcaaacag 98701 ccccacgcgc tccctcagct gttccctgtc acgggtggcc ccttggtgac ggcctccatg 98761 cagggacggt gacagctcga gcagccgcgt aaaaccacac ggggacggtg gcagctcgag 98821 cagccgcgta aagcctgaca tccaatttgg aagcctcccg cagtggaaga ggggcccggg 98881 gacggggctg cccggggcga gctccaccgg gtcgggggtc acgaggagcc cacccgcgtc 98941 cccgccacca gcacctggga ccagataccc tccccgctct gagggcggcc tgaacgccgc 99001 cccctcccac gggggcgccc accgcctgct cgtggactga acaagaggcg gcagtggcct 99061 ccagacccc tcggggagg gcagacctgt ccgagactga gcacaagtcc agggaatgag 99121 caagggtctc agtaatgtcc ccaccgggac gggacgggag gaggcgacag aggccgctga 99181 ggtgcggggc agccctcagt agctggcatc aaggcccag gcagtcccgg ggcatccccg 99241 caggggcgg gggcgaccac cggcccgagc ccaggcagtc ccggggcatc cctgcagcgg 99301 gcggggcga ccaccggccc gagccctacc tgaaggcgta ggtcttctga tgccagctca 99361 gctgtccccg gatgctgtag gcgatggtgg tgacgaactc cccgcccagc cccagctcgg 99421 agcacagctt cagagcgaac ttctcgggcg agttctcctt ctccgacatg tcccactcga 99481 actggtccac caaggagatg ttccccacgt ggatgttcag ctggcccggg agcacagaca 99541 tgagccagag cggccccctc tggggccagg ccgcaccctc accacccctt ctcccggaa 99601 catccccgcc tcgttcttgg ccgcgcccct gtgctgctac ttggggtaag gaaaacaacc 99661 cccatctctc tgaaaagggt taactagcga ggaagatgcg ctggtaactg gaaaactccc 99721 tacaaagaaa gcttggatct gatggcttca ctggtgaatt ccaccaaaca tttcaagcac 99781 taacaccaat ccttatcaaa tcctgccaaa aaactgaaaa ggaaggaaca catcataact 99841 ccctgccttg ataccaaagc cagacaaaga tactacgaga aaggaaaggt gcagaccggc 99901 acttactgtg gacattgatg tgaaacctca gcagacacga gcaaaactac attcaccagc 99961 acgtcagaag aatcacacac cgttataaat gatgggatga tgacacaacc acattataaa 100021 cggtggggct tactctggtg atgtaaggac ggctcagtaa gaaaaccggt caatgccatg 100081 aaccacttga acagagtgaa ggacaaaaac cacacagtca tcttgataat tggaggaaaa 100141 tcattagaca aacttcaacg tgctttcacg ataaaagcac tcagtaaact aagatcagat 100201 ggaaaccaca tcaacaagat taattcagtc aaaaaattca ctgcaagtat cacccacaat 100261 ggcagaagac tggtaacttt tcctctaaga tcaggaacga gccaaagata cccagtcttg 100321 ccactttgt tcaatatagc gttggaattt ctactcagtg cagtgcagtc gctcagtcgt 100381 gtccgactct tttcgacccc atggatcaca gcacgccagg cctccctgtc catcaccaac 100441 tcccggagtt cacccaaact catgtgcact gagtcagtga tgccatccag ccatctcatc 100501 ctctgtcgtc cccttctcct cctgcctcca atcccttcca gcagttaggc aagaaaaata 100561 aatcaaaggt atccacctgg aatggaagaa gtaaaactat ctctggtccg agatgttaca 100621 atcttatatg cagagtttaa gatgctaaca aaatactatt agaactaatg aatgaattca
```

-continued

```
100681 gcaaggtacc aggatacaaa gtcaacgtgc aaaaatcagc cgcatttcta catgctaaca
100741 ctgcacaatc tgaagaagaa aggatgaaca aattacaata acataaaaaa gaataaaatc
100801 cttagaaatt aacttgatca aagagatgta caatgaacaa tataaaacat actgaaagaa
100861 attgaagata taaataaatg gaaaaacatc ctatgtccat ggattggaag acttaaaatt
100921 attaagctgt caaggctatg gtttttccag tggtcatgta tggatgtgag agttggacta
100981 taaagaaagc tgagcaccga agaagtgatg cttttgaact gtggtgttgg agaagactct
101041 tgagaggtcc ttggactgca aggagatcca accagtccat cctaaaggag atcagtcctg
101101 ggtgttcatt ggaaggacta tgttaaagc tgaaactcca atactttggc cacctgatgc
101161 gaagagctga ctcatttgaa aagaccctga tgctgggtaa gattgagggc gggaggggaa
101221 gggacaaca gaggatgaga tggttggatg gcatcaccga ctcaatggac atgggtttgg
101281 gtggactctg gaagttggtg atggacaggg aggcctggcg tgctgcggtt catggggttg
101341 tgaggagtcg acacgactg agcgactgaa ctgaactgaa catgaatacc caaagcaatc
101401 tacaaagcca aatgtaatcc ctatcaaaat cccaatagca tttctgcaga aacaggaaaa
101461 aaaatcttaa aattcatatg gaatctaagg aaaagcaaag gatgtctggt caaaacaatg
101521 acgaaaagaa caacaaagct ggaagactca cacttcctga tttcagaact tactgcaaag
101581 atacaataat gaaaacactg tgggactaac gtaaaagcag acacgtgggc caacgggaca
101641 gcccagaaat aaactctcaa ataagcagtc aaatgatttt caacagagat gccaagacca
101701 ctcagtgaag gaaagtgttt gcaaccaacg gttttgggaa aaaagaaccc acatgcgaaa
101761 gaatgaagtg ggacccttac ccagccccat ctacagaaat caactcaaaa cagacagaac
101821 atatggctca agccataaaa cgctcagaaa acagagcaa agctttatga tgttggattt
101881 ggcggtgatt tctcagatat gacgtcaaag gcataggtga taagcgaaaa aataaactgg
101941 acttcaccaa aatacaacac ttctatgcat ccaaggacac taccgacagc ataacaaggc
102001 agcccaggga aaggaggaaa catccgcaaa tcacagcatc tgggaacaga ccgctgcctg
102061 tgagatacag ggaaccgata aaaacaagaa aacagcaaaa cccggactca aaatgggaa
102121 ggactccagc agacacagga gacagacaag ccgccagcag gtcactaatc agcaagcaag
102181 gcccgcaaag gcccgtatcc aaggctgtgg ttttccagt ggtcatgtag aaagagagc
102241 tggatcgtaa gaaagctgag cgctgaagaa ttgattgaac tgtggtgttg gagaagactc
102301 ttgagagtcc cttggactgc aagatcaaac cagtccattc tgaaggagat cagtcccgaa
102361 tagtcactga aggactgatg ctgtagctcc aatactttgg ccacctgatt cgaagaactg
102421 actcattggc aaagaccctg atgctgggaa agattgaagg caggaggaga aggggacgac
102481 agaggatgag atggttggat ggcatcactg actccatgga catgagcttg gcaagctcc
102541 gggagagagt gaaggacagg gaagcctggc gtgctgcagc ccgtgggtcc caaatctttg
102601 gaccaagcga ctgaacaata acaaatcaac agggaaatgc aaatcaaaac cacagtgaga
102661 tactgtccac caccaggcag gcgttcttca gcggggttcg gggcaggtgg tgccctcttc
102721 tctcgtaacg cccccaggac cgcggggggct gctgagacag catgggggtgt gcttggccta
102781 gcctgcccat gacaagagtg gcagtgtgct cgcctcactg cgcccttccc tgctctgccc
102841 accagctggg ccaccccctgg gacccccagc cttccgctcc gtggacggca aggccgcagc
102901 agcgcccgga cacgcccaga acgtggtgcc ctcctcagaa gtcggcctgt gcccttcctg
102961 ggacaagccg cccaagagac agtcttccag agccctgccc cacaacacgg accccagaca
103021 ggctcctgtg gaggcctcca cgcacctccg cacctcgcaa gccccgagga caaggcaggc
```

```
103081 ccgctgcggg tgaggagccg cctaccttga taatgacgcg ctggtctgac tggtcttcca
103141 ggatgctgtc cgtggggtag gactcgatct gctgtctgat ggcagaggca atggctggca
103201 cgaatgtcag tgggttcaga tccaggtcgt cacagagaat ctctgagaac atctccgggg
103261 tcatcagctt ctctgaaacg atgacggagc ggggggaaccc ccagtggacc acagggccta
103321 cggtcagcgt gctcagcccc ggcctccccc agccttgcct cctctgccac cgccccccg
103381 ggtgacgaca ggacccctg gcagcacgca gacagagctg agtgcacgcc agccagggcg
103441 gcggacggac cattcatgtt ccaggtaaag gcatcccgca gcttctgccc gtcaatctcc
103501 atgtccagtc ggatggggac cagcacctcg ggctgggacg cgttctcgtg gatcacggct
103561 gggtcgtggt cgtcgaagct ggaagggggag cggccgcgtg ctcagcaaag cgggctgggc
103621 ccctgtgccc agggcctccc tctctgcacc actggtcgct gagacctgcc cagagaggac
103681 ctgtccacta cgggccgggc cggcagaaac agggctgcg ggggtccacg cggggcggga
103741 ggggagctgc cgactcggca gcgggacaag ctcagaggtt ccctgcagga agagaggttt
103801 aagccccaga gcaggcagga ttctcccagc agctgtgggg aagaaagggt atgtccagaa
103861 gaagaaaccc tggaacaaag gccgaggggc aggagggttg aggagctgct tggagagcag
103921 tgaaggggg ctgggcggct gggggggtgct ggggagcctc ggtggccaag cacccagggc
103981 tccccacctg cagcctggac cccgagggag ccccagagga cggagagcaa ggcagctccg
104041 cactcacacc tgcccttttag gatggggaag aggaagaga cggggctgc gggggcaag
104101 gaaaccaggc acgcccgct tagacccggg ggcgagaacc actttccaag aacgcagggg
104161 cgccaatgat gaacaatggg tagcagcccg caggcgggag gcccggtggc cgaggcccct
104221 caccagagcg ggaaggtccg cttcttgtcg cggcccatgc ggttcctgtt gatggtggtg
104281 gagcagggca cggcgtccag gtggtgcgag ctgttgggca gggtgggcac ccactggctg
104341 ttcctcttgg ccttctgttc cctgggagac acagacgccc gtccgctcag cctatgggcc
104401 aaaagccgcc cccagccgc caggttgtgg ccagtggacg cccgccatgc ccctctgggc
104461 ccaggccccc atggggacct ctgtgcgccc agctccgcgg tggttattcc ccaggctcca
104521 agcggcacct gctcggggtc accagtttta ggggaggagg agagggcagg ggcccagcc
104581 cagtctgtga gctgtcaccc ccaggctcca agcggcacct gctcggggtc accagtttta
104641 ggggaggagg agagggcagg ggcccagcc cagtctgtga gctgtcaccc ccaggctcca
104701 agcggcacct gctcggggtc accagtttta ggggaggagg agagggcagg ggcccagcc
104761 cagtctgtga gctgtcaccc ccaggctcca agcggcacct gctcggggtc accagtttta
104821 ggggaggagg agagggcagg ggcccagcc cagtctgtga gctgtcaccc gtgctatgtg
104881 ctgggctggg cactcaggaa agagggtcag ggttcacggg ggggtggcgc gcagatttcc
104941 aggagagccc cgagggcagc agagaggagg ctcaggtcaa tggttgggca gggggccagg
105001 gctggagaca cagagagggt cccgattcgg ggggggtgccc tcagcaggtg gctgggagtc
105061 cctgggggtt tgcacacttt cgatcaggct gttatttcag acgcttggtc cagcctgaga
105121 caggtaatgc ctctggcctc cgggccttca gggatgggaaa gatactctag aaagcgggac
105181 tcaaagtaac tcaaggaact cgcgtcccac agtggggagc ccttctctcc aatttacatg
105241 gggcgtttac tacgaggaaa ataccgaagg ccgttttgag ctgaggctcc cgggccgggc
105301 tgtccgtttg tgagactgct cgtcaccct gggccacatc cctggtggcc aagggggcaa
105361 tcagtgcggt gactgcacga cacacctctg cagccctgcc ccacagctgt caccatcggt
105421 gacgtccacc ccctggagaa cctgaccact gcccggtttc ccgctaaaac agcgcccttc
105481 caggatgggg ggcagaggga gaggccttgg cctttttcact cctcttctgc agcgggggcc
```

-continued

```
105541 cctcgcaccc cagtgcccgg gcccaggagc gcccctcggg gtggggcagg gagggatcca 105601 cacaccaagg ggagccagga cccccccaaa tctgctgccc tgccctgata cccgagacct 105661 ggggaaacgg gggactgggg ctgatgcggg caggaccaag aactgaggcg gtgagacggg 105721 gtccccacca caggccatct ggctggcagt ttctactccg ggcctgcagg ccaagaggga 105781 aaaggtgccc cactcagatc aggcgcctcc cgtccccagg gagggcctac aaggtcagat 105841 cctttgtaac ttccacgggc aaaactggct tgctgggcct gtgcgggccg catgggcgtg 105901 gaccaccaca cctttcccca ctgagtctcc agccggagct gtcacccagg tcccccagg 105961 ccagcccac cccgccacct tgcagtagcc tctcgtatcc aggccgaggc tgcccggtcg 106021 acccctcctg cctgatggcc tcaagtggac aatgcgagtc acgttgcagc acgtgagtgg 106081 gacgggcagc gccacgcggg gtccgggcat ccgagtccca ccactcagcc tcccttccgc 106141 tgcagagagg tctgtccaag agccctgggg gccatccagc ccctgtccga cctggccggt 106201 gtggaagagg gggtgtgcca cccctcctgg ggggctggct gggcgctggg caggcccctc 106261 ctaagagtgg agcccactgg tggttttcct gcagccccac ctccacacag cagttctcac 106321 tgcccagtaa caggaggcta ctggcctagc tctctccctc gtgtgatgga ctcaaccagg 106381 agcgttcacg gccccacaca gggttctcgg ctgctgcatg aggatctcaa agccccatcc 106441 acgtgcatgt aatctcctcc ggtaacttct ctagggaagc ccggctatcc tgccatcctc 106501 accgcaccac cagggcgaga aaagccatct ccagcgctca catccacaat gggccaggcc 106561 gtgagcacac caccttcttc gggaggttgt ggggcgggn nnnnnnnnn nnnnnnnnn 106621 nnnnnnnnn nnnnnnnnn nnnnnnnnn nnnnnnnnn nnnnnnnnn nnnnnnnnn 106681 nnnnnnnnn nnnnnnnng cgcgccccc cccccgcgg cgccggcacc ccgggcggcg 106741 gcccccggcg ctgggagcag gtgcggggcc gcggccgctc gtgagcctcc agcccggagg 106801 acgggccccg ggggccggcc cggtgcccag gccctgggag ccccggaggc cagagtgcca 106861 gagggccgga ggacccggga aggcccgaga gaggtgggaa gcacggggtt ccagccctag 106921 gccatttcag ccccaaagcc atcggtgaaa ccattgctgg ccccagataa aagcgtcgcc 106981 aactttttca ccccggcgga gactttagcg ggtagctgcc ccctaggggg aatggaaaaa 107041 ccaggattta ccaggtgggt ggaggtcaca actgcccaga tcctgagaaa gaggggtcag 107101 tggggcggga agattagtgg ggagaggagc tttcagaacc caagggaatg aaacgaggct 107161 tgaggttggt tatccagcag ccgcccctg ccccgtgagt gagcgaaggc tgggcccctt 107221 attgtcacat cttccagctc ttcgctagaa aacctagagt tttaaatact gtggcagctg 107281 agtcaaacaa taaggaaaag cccgactctt tgagagccag gcacaaggcg tctgtgacag 107341 ggtctccagg ctgcccattt gcagtctctg aaacggaggg ttttcgaga aggaggtctt 107401 ggggtgcctg ccagaattgg agggggggc gcgggaagtg aggacccaga agagagggct 107461 tggcccgctg caaggaggtc actggacact ggagctgaag cgccagccga aactggaaac 107521 tcgaaatctg tctccgtgcc agccacaagg cctatgattt tccttggcga cgttcagcat 107581 cttaggagga gctggcgggg gaggcgggta gttcgtgggc ggttgcagca gggcaggaag 107641 gtgaggaacc tgaggctggt cagagagctg gttggagtga tgcccatcgg tggacccgct 107701 ggagaaggcc tgagtagaga aggtctaagc ttaacgggga agggtgggc cagggtggaa 107761 atggggtggg aagtttgagg agggggagca gtggagatgg gggttgtgag gaatgggagt 107821 gagcttagac gtcttgagga tactgcagtt ctgtgctttt tttcacacct ggctgaaaat 107881 tcactgaaaa caaaacaacc cttgctctgt gacagcctag aggggtggga gggaggctta
```

```
107941 agagggaggg gacgtgcgtg tgcctatggg cgattcatgt gggtgtacgg cagaaagcaa
108001 cacagtatgt aattaccctc caattaaaga tcaagtacaa cttaaaaacc caaacacaa
108061 cattgtaagt cagctagact ccagtaaaca tttcagtaag aagattcaac tgggaatgag
108121 ttccgccgtg actatcctga tgaatttccc gtgtcttctt gaggccattc ctctttgaac
108181 ttccgtgttt ggggaagcgt gcctttgtat ggagtcctga ggagtaaatg agacgggctt
108241 gtagaaggcc tagtagtgcc ttgcacgcgg cagatgctca ataacctcga gttgtcacca
108301 ttatggtacc tcaagagtct ccttggagct tgcacggttt ctgaatgggg tcctgcgggg
108361 ctcccttggg gctcccacat ggggttgggg ggctgagtgg ggtgtcccg ctccttgctt
108421 gtcccctgtg aacacccc ttccacccga gcagctctgc ttttgtctct tgtgtttgtt
108481 tatatctcct agattgttgt tcagtcgctc agtcgtgtcc aactctccga ccccatggac
108541 tgcagcacac caggccttct gccttcacca tctcccggag cttgctcaaa ctcctgtcca
108601 ttgagttgct gatgccgtcc aaccatctcg tcctctgtcg tccccttctc cttttgacct
108661 cagtcttttcc cagcatcagg gtcttttcca atgagtcagc tctttgactc aggtggccaa
108721 gtattggagc ttcagcttca ttatcagtcc ttccaatgaa tattcagggt tgatttcttt
108781 taggattgag tgacttgatc tccttgcagt ccaagggact ctcaagagtc ttcaacacca
108841 cagttcaaaa gcatcagttc ttcggcactc agccttcttt atgatccaac gcccacatcg
108901 gtacatgact actggaaaaa ctttggctca gagataattg acttgattga atacaaagtt
108961 ctttggcaaa aaataaaagt gtggcaagca gtactgacac aaaagcaagt ggcttttcct
109021 ccgttgagtc atttattttat tcagtgggtg tgtgcgtgta gagacggagc ggctgtgctg
109081 ggagctgggg cttccacttc agaggagccc cggacctgcc ctcggggagt tcacaggcag
109141 tgctgcgggg ggtcctgcca ggacgcctgc cctgcgagtc cccagtgctg tgatggatgc
109201 gtgtcccgca tctgcggcca ctggggccac gtgcccgaga ttgtccgggt ctgagggtgc
109261 agagaagagg aggcatttgg actgagtctg gaaaaatgag catgtggcca cgtgagaagc
109321 cagtggtgag gggaccagtc aggcggagga aagagcggct catacgagtt gtggagctgg
109381 aagcatgagg gtgtgtggaa gcagaggccg gggacagggc cgcagggccg gccatggagg
109441 gcgtgggctg ctgcaggctc ctgagaaggg ggacgctgcc atcatgaccg ggtttaggtg
109501 tttgaccctg gtgtccacgt agaggacaga tgtgtggggg gggagctgga gatgggcatc
109561 catcgggagt cagcctggag agaggcagag accccgtcag tgggccctca ggacgtggat
109621 ggggcggatg ttgggaagat ctgactcctg ggttccggct ggggctccgg gctggagggg
109681 tgccgcccac cgagcacagg aggcaaacag atgccctctc ccagcaagac cccagcccca
109741 gcaccctccg gggccggact ccgcccctct tccagaatgg ctcccttgct gtcctcgccc
109801 atctttccgg tgccctgagc ctctagagtc tggacaccag cgtccgcctt gcgcttgttt
109861 ctgggaagtc tctggcttgt ctctgactca cccaggaccg tcttcgaggg caaggttgtg
109921 tccttggttc catctgcttt ggggtccggc tcctcgctgc ttgacctgct gatgtgacag
109981 tgtctcttgt tttcttttca gaatccgaga gcagctgtgt gtgtcccaga cagacccagc
110041 cgctgggatg acgggcccct ctgtggagat cccccgcc gccaagctgg gtgaggcttt
110101 cgtgtttgcc ggcgggctgg acatgcaggc agacctgttc gcggaggagg acctgggggc
110161 ccccttttctt caggggaggg ctctggagca gatggccgtc atctacaagg agatccctct
110221 cggggagcaa ggcagggagc aggacgatta ccggggggac ttcgatctgt gctccagccc
110281 tgttccgcct cagagcgtcc cccgggagag cagggcccag gacgatgagc tgttcggccc
110341 gaccttcctc cagaaaccag acccgactgc gtaccggatc acgggcagcg gggaagccgc
```

-continued

```
110401 cgatccgcct gccagggagg cggtgggcag gggtgacttg gggctgcagg ggccgcccag
110461 gaccgcgcag cccgccaagc cctacgcgtg tcgggagtgc ggcaaggcct tcagccagag
110521 ctcgcacctg ctccggcacc tggtgattca caccggggag aagccgtatg agtgcggcga
110581 gtgcggcaag gccttcagcc agagctcgca cctgctccgg caccaggcca tccacaccgg
110641 ggagaagccg tacgagtgcg gcgagtgcgg caaggccttc cggcagagct cggccctggc
110701 gcagcacgcg aagacgcaca gcgggaggcg gccgtacgtc tgccgcgagt gcggcaagga
110761 cttcagccgc agctccagcc tgcgcaagca cgagcgcatc cacaccgggg agaagcccta
110821 cgcgtgccag gagtgcggca aggccttcaa ccagagctcg gcctgagcc agcaccgcaa
110881 gatccactcg ctgcagaggc cgcacgcctg cgagctgtgc gggaaggcct tctgccaccg
110941 ctcgcacctg ctgcggcacc agcgcgtcca cacgggcaag aagccgtacg cctgcgcgga
111001 ctgcggcaag gccttcagcc agagctccaa cctcatcgag caccgcaaga cgcacacggg
111061 cgagaggccc taccggtgcc acaagtgcgg caaggccttc agccagagct cggcgctcat
111121 cgagcaccag cgcacccaca cgggcgagag gccttacgag tgcggccagt gcggcaaggc
111181 cttccgccac agctcggcgc tcatccagca ccagcgcacg cacgggcc gcaagcccta
111241 cgtgtgcaac gagtgcggca aggccttccg ccaccgctcg gcgctcatcg agcactacaa
111301 gacgcacacg cgcgagcggc cctacgagtg caaccgctgc ggcaaggcct tccggggcag
111361 ctcgcacctc ctccgccacc agaaggtcca cgcggcggac aagctctagg gtccgcccgg
111421 ggcgagggca cgccggccct ggcgccccg gcccagcggg tggacctggg gggccagccg
111481 gacggcggaa tcccggccgg ctcttctctg ccgtgacccc ggggggttgg ttttgccctc
111541 cattcgcttt ttctaaagtg cagacgaata cacgtcagag ggacgaagtg gggttaagcc
111601 cccgggagac gtccggcgag ctctaacgtc agacacttga agaagtgaag cggactcgca
111661 gcccgtacag cccgggggaag atgagtccaa agtcgagggt ccacttggcc actgcagggt
111721 cgctcggcgg tggggcgag cgggtgcagg agggctcctc ctgggcttgg ggtggcaggc
111781 gaggaccccg cgcctctcag ccctcggcct gggttggctg agggcgggcc tggctgtagg
111841 ccctccagcg gaggtggagg cgctgcccgg ctcagccagg cacaggaccc tgccacgagg
111901 agtagccctc cgccagaccc ggcgtccagg ctggggcgcc tgcggggcct ccgttctgtg
111961 gctgggcagc ctgcgccctg tccagggatg aagggggttcc ggtctgaagg gctgggttca
112021 gggtccagct ctggcccctc ctgccttggt gtcctggagg aagccccaag gctccgtttc
112081 cctctccagg aggtggggac gttgggaatg ccacattccc ctggggggtg tgtgtgtgtg
112141 ttcaaggctc ccattcagac tgggactggg cactcacgag ctttggcaac tggcaactga
112201 ggacggagac ccagggtgac accccacctc ctgctgcggc ccccccggca ggggagacac
112261 aggcccgtct ggttcccaag atggcagggc ccctcccccct ccagcttgtg ccctgggtgt
112321 ggtgcctggg gctacagcga ccctttccgg ttccccggc cagttcagct gggcatcctc
112381 agggcggggc tctgagggtg ccatgttttcc agagctcctc ctcctcccac cagtagcagg
112441 cgggcggcca gctcccagcc agcccctgg catcgcctag gtgcacacct gccgctgtg
112501 acccagcaag gcttgaaggt ggccatccca gttaagtccc ctgcccctgg cccaggaatg
112561 ggctcgggca gggccgcatc tggctgcccc agaagcgtct gtccctggcc tctgggagtt
112621 ggcggtggtc tctggtactg tcccctcgcag ggcccttag cactgctcgg ggaggaggtg
112681 ggctgaactg attttgaagt tttacatgtc tgcggccgca gtcctacgag cccgtcaggg
112741 tcatgctggt tatttcagca gatgggggtt ggctcggcag ctaggatggt cctgaataaa
```

```
112801 aatgggaagg ccagagctgt tcctccatca gcaggcttgg cagctgggga cgttgaaagg 112861 acaggtctgc tggtctgggg agaccagctc tgtgcagccc ctgctgtccg tgggggtact 112921 aaaccagccc ctgtgtgcgc ccatctgagt ggcagcccgc ctggaggatc gcccatcact 112981 tgtgagaatt gagagaatgc tgacaccccc gcttggtgca ggggacagg gcccctaag 113041 atctacctcc ttgccccacc cccgggaccc cctcagcctt ggccaggact gtccttactg 113101 ggcagggcag tcatccactt ccaacctttg ccgtctcctc cgcgcgctgt gctcccagcc 113161 aaattgtttt attttttcc aagcatcact ttgcacacgt caccactctc cttaaaacca 113221 cccttccgga gtctcctgct cgtaaatcgc cggtttcagc caacctgggt cgccccccaa 113281 gcccagcaag cctgctgagc cccgcgcctc ccagctactt cacgctcgcc tcaagcttct 113341 aaacgcggac cttctccccc ccaccccat ccctttcttt tctgatttat gtaacacggc 113401 aggtaagact cctctcctga agggttgaca gactcacaca aaaccgtggt cagaccaggc 113461 aagtgctttt tttcagaagt gtgagcggaa cctagtcttc agctcatgct cttcccttgt 113521 tttcttatgt gttctaagtc ctttgacttg ggctcccaga cagcgacgtt gtaagaggcc 113581 gtcctggtag catttgaatt gtcctcgagt ttcgttgtcg gatttgtttt tattgtctta 113641 gttttccctt cttttagcag acgttgttga ctgtcgtaaa gctccagttc ttggttctgt 113701 ttactaatca aattgttttg tcaaagtaca tgtattctgc tcttttcttt atctttttg 113761 ttgcttaata ttaacacttt acatttctaa gattaattat ttaggtaatt aataattttt 113821 aacatttcta gtaaacgtgg gtacttgggt ctgtgtttgt tttcttgtag ttacagcttt 113881 ttctgctcta tactgttgac gtctgggttt tttttgctc ttaggaattt cccttttgacc 113941 ccattattat tatttttaatt agtatttttt aataattaaa aattagtgtt tttaaattaa 114001 ccctaatcct aaccccagtg atgactgctt cagtcattgc tgttacttat tatgtgctgg 114061 tgtcaggatt tttaagtgtc catagacatt ctctgagcct gaatatatta tcagtttat 114121 acagcatttg tgtactctca agaaacgtgt tttcactctg tcagttcggt ttgttacctc 114181 agtctttatg ttattttgct ccagtccgca cttgctctaa cttgtcttcc cttcgaggtg 114241 tgaggacgcc tggcagccgg tgagcatgcc ggggtccggg gtcgtgggcc caggcgccca 114301 gcaaagccct gtgggtgtgt gcacggctgg gctgctccgg gaggaagcct gtggccccac 114361 ggtagttagg agcgctggtt tacctggtca caccacggtc tggttttgtg tgcttttcc 114421 tgacgtgttt ctgttttgcc ttggtttcta ttctgttta tgagtgccgt ttacgctttg 114481 ttagtcatgc cgttatctcg atagacaggg tgtacgtgat caagtgatta ccgtatttgg 114541 agcagatgtc tatttaacag agatgaactg agaacctgtg cctttgcatg ccctcttgc 114601 ctcttttaat gcttctagct tcaacttctc ttttccaaac attataatgg aaaccccttg 114661 ctttttttttt tttaatttgc atttgcatga gagtttattt agctcggcat tttattttta 114721 aaatttgtgt atatatttt gctatatatc tgtaacttat aaacagcaaa ttattggatt 114781 ttgctttctg attctttctg taattcttct tacataagaa gttctcctat gagtaacatt 114841 gctgtttaga gtgaggcatg atttattcc agcttagtat gtattgggtc ggttaaccc 114901 caaaggtcat gctcatcccc gccccatctc tgtgagttat tgtccgagtg tggagcgccc 114961 tgtctaggcc gacgagagac ccaccatcgg gcacacctgc ccctcctggt ctggtcagtg 115021 ccgggctctg tcctgagtcc actcctgatg tcacaggctg gtgcttcagc gacctcggct 115081 gtgacacgga gggtgtgatg gcactgccca gccccatggg gcttggagga ctaaaggatg 115141 cacacctgcc tggcagactg agggcacagg tgtttctcac actgtcagcg ttttgaaata 115201 ttcctttgat tttctaccct aactcccaaa ggccgttcaa cataagctag aatgctacgt
```

-continued

```
115261 ggtgcttgat tacattttag aaaagtttca gcaaatacca cgagatgcag caaagaacta
115321 gacctcacag atcaggccgc ctgcataagg gagcccacac agtcgtggga gacggggacc
115381 ctctcccacg tcctgtctgt cccaggatgg tcccctcacc cgcccctct ctccctcgc
115441 cctcctgtgg tgggggccgg ccaccatcac agctgcagag cctcaagaag gggtcgccc
115501 tggccactcc cgtggcagga gggacacgag ggcaggagct taccgcgggt gcagtggtct
115561 cggatcagct cagctggccg ctgcgggtc gggggacag ttcagtggga ggcaggagcc
115621 cccactacag ctgccaggac ttctcagagg tgacaagggg gttcagtcac ctcagcccag
115681 gtggaaacca aatggcctct tgcgcggctc ctggggccac gcggaggttc gctgggatca
115741 caggtatctg gatgtgtgcg ccatggacat gcaccacctt cggggggtaa ggggtgggga
115801 aaggcagccc ctttcttttg ggggaccccc tcttcagtgt ctgataacca ggaaaccaaa
115861 tcagaaggtg gtctgggggt gctgagcagg gtgtctccta caccacaggc cacacactca
115921 cacagcctcc aggactccag tggggctgag cgctggagac tcacccacgt ttgctacccc
115981 cccacccaag gccatcccag aacagctgcc tgcgtcctca cggctggccc ctcccctctg
116041 gtctaaccca gtgtgggtgg gccggcctgg ggtctccacc tgcctcctgc tgttccctgg
116101 gctgctggct gtctgcagat gcggggccct ggcccggaga agccccatca gagcccagag
116161 gacgggagtg gagcggggag gtgagcccg gagtctcgag gggccagagg caaaatactg
116221 ggctgtgtcc ctggaaggca gtttcccatg aaaccttcaa tataggccgc cccagacgat
116281 cagcctcatc tgctacgtgg attcctcccc gtagcgaatg gtgattgggt tctacatgga
116341 cccgggactt ctgtttgaat tataatcttt ccccactgc ccctccaggg atctggaaaa
116401 tggaggcctg ggctagacgg aagcttcctc caagattctt tattgaaggg attcgaagag
116461 aaacaggtgg tcagtaatct gtgggggatg gagggtgag cgctacgtgt aacggtttta
116521 ctgttgctac gggaccagtt ttgatgtctt tcccccttcaa gaagcagacc caaacaccga
116581 gatgctgagg ttagcagcac agagcgggtt catccacaag gcaaccaggc agggagacca
116641 gagacgctct ggaatctgcc tccctatggg cacgggctgg gtgctcacgg atgaagacca
116701 agcagcaggt ggcgtgggc gtggggagcc tgcggaaagc gatggacaag gtgcgggacc
116761 gcggtccgcg cggtggaccc aagctccgcc tctgcgctgc agcgcgagct gggggcggag
116821 cttccaggga cccgcgaccg cgcccagtgg gagggtccgc ggtccaccca gtcctaacag
116881 ctcagctcca gctagacgcc gctgagtccg gctttctaga gagcaaccc ggcgggtatt
116941 ttatggttct ggcttcctga ttgaggaca cgcgagtctt agaacaccct tgattagtgc
117001 gggcaggcgg aatggatttg actgatcacg atctgcagtt tcaccatctc aggggccgcc
117061 ctcaccccca cctatcctgc caaaggggg gcctcggtgc tgagatcggg gccacacgtg
117121 cactagacgg tcggtcagcg ctgctgctga gcggacccgg ggccatcctc acaccgccac
117181 tggcccctgt gctcaataaa aggaaggaaa gcgggaaaag cgctttctgg ccgcggtggc
117241 ctcgcgcgtt cctccatcgc catctgctgg cagagcccgg catggcaccc gctgcacaga
117301 aacctcggtg tccgtttggg tgccccatcc ttgaccccga gagagcaccc tccgtccaaa
117361 atgaaaaaca gctgctccca agagtcatta taatcacagc caattgtgtt aattcgtcct
117421 cggatccact cacagttcca cggaacattc tgctaacctc tgacaactcc tacataaagc
117481 aatactgaga agaaaagaac gtggttgata aatacaaagg catacaacaa taaggagcaa
117541 agaaaaaaga cagtcctcgc agttctgttt tgttcatctc tcatgagtag gatggcagat
117601 aaaacacaga atgcccagtg aataatttta gtctaagtat gtccccaata ctgcctaatc
```

```
117661 ttcaaatcta accttatttt taaaatatat atttttttgct ggtcactcat cagttcatgc 117721 accaaagcct ttgtttcttg actcctaact ttttgacccc tctggggtga ggagcacccc 117781 taacctcgag agcccatcac acagtcccct tgggactaga cccttctttg cccatcacag 117841 ctgaccggaa gggccagccc atggccagcg ctcgcgcccc ctggcggaca gactctgcgc 117901 ggcagccccg ggagcccagg tgcgaccccg cggtctctgg cgccctctag tgtggaaaga 117961 tctcctcctg tgtgttccag tcattgggct gtattttatt agagaagatg ctcgcgtgac 118021 gatgatgatg gtcctttacc gggaggcacg tttggggcgc gtcggctcag gggccgagct 118081 attagcctgc atcgcgccca caggcatcgc gtcccccctga gccgggtcag ctgtgggctg 118141 tcctgacacg ggtttccccc agtctctggc ccgctgtccc tccaggtca gtgtccagcg 118201 ttgcccttct ggttgtggac ttgtgcagcg gtctcagcag atggaggggc gaccctaaag 118261 gatgtattga ggcatctcag cactgtcctc cgcccaggtt tgctggtcag cagtgaagtg 118321 accgggaaaa ggggctgtct tggggtcctt tcagaggcct gggttagacc aaagttttct 118381 agaagattca ccattgcagg gagtcaaaga caaaactagg gtggtcagca atctgtgggg 118441 gattcggcgg tgagggaatt ctgaatgcta catgtaatgg ttttactatt gttagggaac 118501 attttttcccc cctacaaaca gcaggccaaa atactgagat gtcaggtttg catcaaagag 118561 cgggttcatc cacaaggcaa ccagagaacg ctctggaatc tgcctccctg cgggcacagg 118621 ctgggtgctc acggatgaag accaagcagc aggtggcgtg gggagtgggg agcctgggga 118681 aagcgatgga caaggtgcga ggacctccgg cgcgagctgg aggcggagct tccagggaca 118741 cgcggccacg cccagtggga gggtcagcgg tccatccagt cctaacagct cagctccaac 118801 tagacgctgc tgagtctggc tttctagaga acactccggg cgggtatttt attgttttgg 118861 cttcgtgact ggaggacgtt caagtcttaa aacacccttg attagtgcgg ggaggcgaa 118921 tggatttgac tgatcacgac ccgcagtttc accatctcag gggccgccct cacccctcc 118981 taccctacca aaggtggggg catcggtgct gagatctggg gtgacacata aaatcaggtg 119041 aagtcttagg acagggggcc gattccaggt cctagggtgc agaaaaaacc tacctggccc 119101 cgggctagac agcgtggagg gcgtggcccg ggctggtgca cagaagtggc ccccaactgg 119161 tcagaaggtg tgggagccca gggctggtct actgcagaag gggtcgcctg gtggacagag 119221 tggggcctga gtgcctgctg aactggtccg tcagggctgc tgagcagaca cgggccatca 119281 tcactggctc ctgtgctcga tagaagggag ggaaaccagg aaagcaaagg cgctttatgg 119341 ccgcttttgt gtttcgcgtt cctctagcac cgtctgccgg cagaacgcgg cattacatcc 119401 gctggccaaa cctcggggtc cggcttggat gtccccatcc ttgtctcgga gatctcacct 119461 ctcagcagtt ccctgggga caatgtcgag aagatgcgac cttgacccgg agctcggtgg 119521 agagggtgcc ctgggttctt tccgcagttg cttggagtgg aggtgcctca tgttgggctg 119581 ggaacgggag gaaggaaaca ggtcatgatt gagatgctct agacagactg tccctgctct 119641 tgccaaattt cagaagattg tctttaataa atattccatt ttttgtatgc ccttaggtct 119701 atttccagac actttaaata tattgaaaga ctttaaatat ttatataaaa atattattta 119761 tagactgtat aaaaggaaca gttagaactg gacttggaac aacagactgg ttccaaatag 119821 gaaaaggagt acgtcaaggc tgtatattgt caccctgctt atttaactta tatgcagagt 119881 acatcatgag aaacgctggg ctgaagaaa cacaagctgg aatcaagatt gccgggagaa 119941 atatcaataa cctcagatat gcagatgaca ccacccttat ggcagaaagt gaagaggaac 120001 tcaaaagcct cttgatgaag gtgaaagagg agagcgaaaa agttggctta aagctcaaca 120061 tttagaaaac gaagatcatg gcatctggtc ccatcacttc atggaaatag atggggaaac
```

-continued

```
120121 agttgagaca gtgtcagact ttatttttgg gggctccaat gaaattaaaa gacgcttact
120181 tcttggaagg aaagttatga ccaacctaga cagcatatta aaaagcagag acactacttt
120241 gccagcaaag gtccgtctag tcaaggctat ggttttcca gtggtcatgt atggatgtga
120301 gagttggact gtgaagaagg ctgagcaccg aagaagtgat gcttttgaac tgtggtgttg
120361 gagaagactc ttgagaggcc cttggactgc aaggagatcc aaccagtcca tcgtaaagga
120421 gatcacccc tgggtggtca ttggaaggac tgatgttgaa gctgaaactc cagtactttg
120481 gctacctaat gcgaagagct gactcattgg aaaagaccct gatgctggga aagattgaag
120541 gtgggaggag aaggggacaa cagaggatga gatggttgga ttgcatcact gactcgatgg
120601 acgtgagtct gagtgaagtc tgggagttgg tgatggccag ggaggccctg gcgtgctggc
120661 ggttcatggg gtcgcaaaga gtcggccatg actgagtgac tgaactgaac tgatccagaa
120721 atttaaaatt aatatataaa ccaaatccat gcagacaatt ataagcatat attataaatg
120781 cataattata agcaagtata tgttatattt ataatagttt ataatgtatt tataagcaag
120841 tatatattat tataagcata attgtaagta gaagtaactt tgggctttcc tggtggctca
120901 gacagtaaag aatctgcctg cagtacagga gaccgggttc gatccctggt ttggggaaat
120961 tccctggaga agggaatggc aaccaactcc aacatgtttg cctggagaat tccatggaca
121021 gaggagcccg gaaggttgca gtccatgggg ttgcaaagag ctggatacaa cagagtgact
121081 aacacatgta tataaataaa tttacctata tattgtatat atatttataa acatattcag
121141 atattataaa taattagaaa catattatac atgtatttaa atactgttat aaacataaat
121201 ttaaaaaata attttcagcc ctttggcttg ggggtgtgtt tgtggacgtc tttgtgctac
121261 tgttcctgaa gtggagctct cccctcccaa accagctttt gaaatgactg ggaaagcaat
121321 ggaatacata agcatcagga agatagcaac agagctgtca ttcttcacag agggtgtgct
121381 tgagtgtgta gcaagtcccg cagaatgtag acagattaat atagtctatt aaaaatagtg
121441 tagcaaattt acgaggtgcg atttcaagta taaagactta ctgggtctct cagttcagtt
121501 cagtcgcttg gttgtgtccg actcttttg accccatgga ccgcagcacg ccaggcctcc
121561 ctgtccatca ccaactcctg gagttcactc aaactcatgt ccatcgagtc ggtgatgcca
121621 tccaaccatc tcatcctctg gcgtccctt ctcctcccac cttcaatctt tcccagcatc
121681 agggtctttc ccagtgagtc agttctttgc atcaggtggc cagagtagtg gagtttcagc
121741 ttcagcatcg gtccttccaa tgaatattct ggactgattt cctttaggat tgactggttg
121801 gatctccttg cagttcaagg gactctcaag agtcttctcc aacagcacag tctatgaata
121861 gaatagcaaa tgaatagaga ataacattta cgaggatata ttttaccatt gcataaaata
121921 tatcagcttg tagagaacag acttgttccc aggggagagg gtgggtaggg atggagtggg
121981 agtttgngat cancagaagc gagctgttat atagaagatg gataaaaagg atacacaaca
122041 atgtcctact gtgtggcacc gggacctata ttcagtagct tgtgagaaac cataatcgac
122101 aagactgagg aaaagtatat atatatgtat gtacttgagt tgctttgctg tacagaagaa
122161 attaacacaa cattgtaaat cgatatttca atagaatcca cccccccaaa tatataagtt
122221 tcctggagat ggagacggca acccactcca tttcttgcac ccaatattct tgcctggagg
122281 atcccatgga tagaggatcg caaagactcg gacataaccc agcgactaac actttccctt
122341 tcaaatgtgt aggtttacta gcgtgaatct acagagatgc caagacatt cgtttatgag
122401 gaaaactcca cacgcagctt cactgagaat tattaaacct attaaaggga gagagcgcca
122461 ggatattcat ggattgaaag attcgatgtg gtcaagttgc cagttttccc caaactgatt
```

```
122521 ggtaaattcc ccaggagctg gctcaaggcg caaaattccc tttacctttt tttaagagac
122581 gaagccaagg agccgattct ggttgagaga cgctcaggtc ctcctgcggg agagcagccc
122641 tcttcctccc ggtcgcctgg gcagtttcga ggccacgacc agaaggactt ggctccctgt
122701 gtcgcgcact cagaagtctc cctctccgtc caaggactc agaagctggg cgtcctgccc
122761 gcagcagagg aggcagcctg gaggggcccc gcgggcacag cggtccgggt ttcagccgag
122821 ttgcccgccc cgcccctcta cctgggcgct gccgcccggc tccggggccg gccgtgccct
122881 ccgtggccgc aaggcgtcgc tgtcccccg ctggaagtgc tgacccggag gaaggggccc
122941 agacggaggg actcggagcc tccgagtgac accctgggac tccgagcgct ggagcctggc
123001 gtcaccccag gcaggggcag tgggggcccg gggcggggtc aggggcctcc cccggttctc
123061 atttgacacc gcggggtgc gctgggcaca gtgtccaggg gccacgttcc gagcaggggc
123121 gcgatgcagg cccgggcgcg gcctgtcccg ggcgcgagtc cagctgcttt gcagaggtgg
123181 cggcaggtcg cagtgaccct cacagagacg ccccactctg cggctccagg tgggcctgtg
123241 cccccagaa gtgctgacct gtgcaccggg aaggcacagg gcccccagc catgtctgcg
123301 atggaagagc cggaaccgcg ccatgcccgt cctcgctgac cggcaggcac ccgccgtgtg
123361 tccacacgct gagccatctg gctccccttg cttgacatac acccaggacc tgagtgtgca
123421 ggaagttaga aggggcaggt gtggtgacac gatgccatcc agcatcacct gagaacctgg
123481 acaaacctca ggggcccagc ctgctctgtg aggccccgag ggccggcccc tccccggacc
123541 cctgccttga atccggccac actgcccgcc ttcctgctcc tgcggcttgt cagacacgcc
123601 tgagcccagg gcctgtgcac tcgctgtccc ttctgccagg actgctcctc cccaggctct
123661 tgctggggct ccccttcttc attcgggggt ggcctctctt gttcagtggc tcagctgtgc
123721 ccagtctttg caaccccatg gactgcagca cgccaggctt ccctgtcctt cactagctcc
123781 tggagtttgc tcaaactcat gtccattgag tcagtgatgc tatccaacca tctcatcctt
123841 tgctgcccac ttcttctcct gctctcaatc tttcccagca tcagggtctt ttccaatgag
123901 ttagctctct gcatcaggag gccaaagtat tggagcttca gcatcagtcc ttccagtgaa
123961 tatgcgaggt tgatttccct tagaattgac tggttggatc tccttcctgt ccagagaact
124021 ctcaagagtc ttctccagca ccacagtcgg agagcatcag ttcttcagtg atcaggtttc
124081 tttatagccc agctctcaca tcggtacatg actattggaa aacccatagc tttgattaga
124141 tggaccttca ttggcaaagt gatgggcctt cattggccct gcttttaat acaccatcta
124201 ggtttgtcgt agctttcctt ccaaagagca aacatctttt aatttcctgg ctgcagtaac
124261 catccatagt gattttggag cccaagaaaa taaaatctgc cactgtttcc acttttccc
124321 cttctatttg ctatgaagtg aggggactgg atgccatgat cttagtttaa accagcagtt
124381 gtcaccccga ccgcttcctt tcctaaagag ctcatcacac ctcccactgg aatgcaatgt
124441 gttgcctgtc cgcctgcttc acctcctggg actttgctgc aggtcttggt ctctgaggcc
124501 cctgccgtat ccccagggcc cagagcagtg ctgggcttcg agtccgatca gggactatgt
124561 gtgtggactg atggtgctt gcttcttctg gggaacgaga gacctgggcc tggggaacga
124621 ggggacctgg tgtgaccgga tctcctccct cgggagagga gccaagcgag tggacacagg
124681 tcagtgtgtc ttgctcctgt gtggcaggtg tcccgtctgt gtctgtcatc ttggcatttc
124741 ggtgtttctg tgaacccagc cctcccctc ctgataccc atcccatcag cacagaggag
124801 actgggcttg gggactctct ggtcctgaga ttcctctccg catgtgactc cccctcctg
124861 gggggagcag gcaccgtgtg tgaggagggt ggaagctttt caagaccccc agcttttctg
124921 tcccaggggg ctctggcagg gccttgggag ctggaatgag ctggaatctg ggccagtggg
```

```
124981 ggtttccctg gtggtaaaga acccgcctgc ccatgcacga ggcataagag acgcgggttc 125041 gatcactggg tcgggaagat cccctacagg agggcatggc aacccactcc agtattcttt 125101 cctgaagaat cccttggaca gaggagcctg gtgggctaca gtctctgggg tggcaaggag 125161 tcggacacga ctgaagcgac ttaccatgca cgcacgcggg gtcaggggtc agggccgcgc 125221 tgcttacctg ctgtgtgacc ttagccaggt cacacccccc aggctgtgaa agagaacagt 125281 cttcccagac tcgggcatcc aggtctttac agacgtgcct gtgagctttg tgactctggc 125341 tctgtggccg ctagagggcg ctgtccgccg ggccctatgt gcgtgcacgc atgtgagcat 125401 gttcgcatac gtgtgtgcat ctgtcggggg cgcacggtgc ggggacacgg gcacgcggtc 125461 aggaacgcag cccggacacc tccacgtggc ccgcgagtac cgtcaggtgg gggctgtggc 125521 tccgctgtgt gggtgacccg ccctccccc gcgaacgtgg tgcatagtga ccgcctggct 125581 gggctcctga gctcagccat cctgccccc gggtcagctc ccgacaggcc cagctctagg 125641 ccccaggcgt ggaccgaggc cccaggccc cggcctgtga gatgggacct ccgtctgggg 125701 ggctcattct gctcccggag gcctggcagg cccctcctct ttggcattgc ataccctcgc 125761 attggggtgg gtaagcacag tacccatgc ctgtggcccc gtgggagcgg cctgctcagg 125821 gaggccggag cctcagctac agggctgtca caccgggctg cagaggaaga agacgggagc 125881 gaggcctaca ggaacctagc caggccctgg cccactgagc cgacaggagc ctggccagag 125941 gcctgcacag gacggggtgg cggggggggt ggggtggggt gctgggcccc gtggccttga 126001 ctgcagaccc cgagggctcc tcagcttaga acggccaagc ctgagtcttg ggggtgcagg 126061 tcaggggg
```

Primers

In another embodiment, primers are provided to generate 3' and 5' sequences of a targeting vector. The oligonucleotide primers can be capable of hybridizing to porcine immunoglobulin genomic sequence, such as Seq ID Nos. 1, 4, 29, 30, 12, 25, 15, 16, 19, 28 or 31, as described above. In a particular embodiment, the primers hybridize under stringent conditions to Seq ID Nos. 1, 4, 29, 30, 12, 25, 15, 16, 19, 28 or 31, as described above. Another embodiment provides oligonucleotide probes capable of hybridizing to porcine heavy chain, kappa light chain or lambda light chain nucleic acid sequences, such as Seq ID Nos. 1, 4, 29, 30, 12, 25, 15, 16, 19, 28 or 31, as described above. The polynucleotide primers or probes can have at least 14 bases, 20 bases, 30 bases, or 50 bases which hybridize to a polynucleotide of the present invention. The probe or primer can be at least 14 nucleotides in length, and in a particular embodiment, are at least 15, 20, 25, 28, or 30 nucleotides in length.

In one embodiment, primers are provided to amplify a fragment of porcine Ig heavy-chain that includes the functional joining region (the J6 region). In one non-limiting embodiment, the amplified fragment of heavy chain can be represented by Seq ID No 4 and the primers used to amplify this fragment can be complementary to a portion of the J-region, such as, but not limited to Seq ID No 2, to produce the 5' recombination arm and complementary to a portion of Ig heavy-chain mu constant region, such as, but not limited to Seq ID No 3, to produce the 3' recombination arm. In another embodiment, regions of the porcine Ig heavy chain (such as, but not limited to Seq ID No 4) can be subcloned and assembled into a targeting vector.

In other embodiments, primers are provided to amplify a fragment of porcine Ig kappa light-chain that includes the constant region. In another embodiment, primers are provided to amplify a fragment of porcine Ig kappa light-chain that includes the J region. In one non-limiting embodiment, the primers used to amplify this fragment can be complementary to a portion of the J-region, such as, but not limited to Seq ID No 21 or 10, to produce the 5' recombination arm and complementary to genomic sequence 3' of the constant region, such as, but not limited to Seq ID No 14, 24 or 18, to produce the 3' recombination arm. In another embodiment, regions of the porcine Ig heavy chain (such as, but not limited to Seq ID No 20) can be subcloned and assembled into a targeting vector.

II. Genetic Targeting of the Immunoglobulin Genes

The present invention provides cells that have been genetically modified to inactivate immunoglobulin genes, for example, immunoglobulin genes described above. Animal cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts. In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

In a particular embodiment, the cells can be fibroblasts; in one specific embodiment, the cells can be fetal fibroblasts. Fibroblast cells are a suitable somatic cell type because they can be obtained from developing fetuses and adult animals in large quantities. These cells can be easily propagated in vitro with a rapid doubling time and can be clonally propagated for use in gene targeting procedures.

Targeting Constructs

Homologous Recombination

In one embodiment, immunoglobulin genes can be genetically targeted in cells through homologous recombination. Homologous recombination permits site-specific modifications in endogenous genes and thus novel alterations can be engineered into the genome. In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome).

A number of papers describe the use of homologous recombination in mammalian cells.

Illustrative of these papers are Kucherlapati et al., Proc. Natl. Acad. Sci. USA 81:3153-3157, 1984; Kucherlapati et al., Mol. Cell. Bio. 5:714-720, 1985; Smithies et al, Nature 317:230-234, 1985; Wake et al., Mol. Cell. Bio. 8:2080-2089, 1985; Ayares et al., Genetics 111:375-388, 1985; Ayares et al., Mol. Cell. Bio. 7:1656-1662, 1986; Song et al., Proc. Natl. Acad. Sci. USA 84:6820-6824, 1987; Thomas et al. Cell 44:419-428, 1986; Thomas and Capecchi, Cell 51: 503-512, 1987; Nandi et al., Proc. Natl. Acad. Sci. USA 85:3845-3849, 1988; and Mansour et al., Nature 336:348-352, 1988. Evans and Kaufman, Nature 294:146-154, 1981; Doetschman et al., Nature 330:576-578, 1987; Thoma and Capecchi, Cell 51:503-512, 4987; Thompson et al., Cell 56:316-321, 1989.

The present invention can use homologous recombination to inactivate an immunoglobulin gene in cells, such as the cells described above. The DNA can comprise at least a portion of the gene(s) at the particular locus with introduction of an alteration into at least one, optionally both copies, of the native gene(s), so as to prevent expression of functional immunoglobulin. The alteration can be an insertion, deletion, replacement or combination thereof. When the alteration is introduce into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

Targeting Vectors

In another embodiment, nucleic acid targeting vector constructs are also provided. The targeting vectors can be designed to accomplish homologous recombination in cells. These targeting vectors can be transformed into mammalian cells to target the ungulate heavy chain, kappa light chain or lambda light chain genes via homologous recombination. In one embodiment, the targeting vectors can contain a 3' recombination arm and a 5' recombination arm (i.e. flanking sequence) that is homologous to the genomic sequence of ungulate heavy chain, kappa light chain or lambda light chain genomic sequence, for example, sequence represented by Seq ID Nos. 1, 4, 29, 30, 12, 25, 15, 16, 19, 28 or 31, as described above. The homologous DNA sequence can include at least 15 bp, 20 bp, 25 bp, 50 bp, 100 bp, 500 bp, 1 kbp, 2 kbp, 4 kbp, 5 kbp, 10 kbp, 15 kbp, 20 kbp, or 50 kbp of sequence, particularly contiguous sequence, homologous to the genomic sequence. The 3' and 5' recombination arms can be designed such that they flank the 3' and 5' ends of at least one functional variable, joining, diversity, and/or constant region of the genomic sequence. The targeting of a functional region can render it inactive, which results in the inability of the cell to produce functional immunoglobulin molecules. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20: 251-255, 2002; WO 00/51424.

Various constructs can be prepared for homologous recombination at a target locus. The construct can include at least 50 bp, 100 bp, 500 bp, 1 kbp, 2 kbp, 4 kbp, 5 kbp, 10 kbp, 15 kbp, 20 kbp, or 50 kbp of sequence homologous with the target locus. The sequence can include any contiguous sequence of an immunoglobulin gene.

Various considerations can be involved in determining the extent of homology of target DNA sequences, such as, for example, the size of the target locus, availability of sequences, relative efficiency of double cross-over events at the target locus and the similarity of the target sequence with other sequences.

The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). In a particular embodiment, the targeting DNA and the target DNA can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

Porcine Heavy Chain Targeting

In particular embodiments of the present invention, targeting vectors are provided to target the porcine heavy chain locus. In one particular embodiment, the targeting vector can contain 5' and 3' recombination arms that contain homologous sequence to the 3' and 5' flanking sequence of the J6 region of the porcine immunoglobulin heavy chain locus. Since the J6 region is the only functional joining region of the porcine immunoglobulin heavy chain locus, this will prevent the expression of a functional porcine heavy chain immunoglobulin. In a specific embodiment, the targeting vector can contain a 5' recombination arm that contains sequence homologous to genomic sequence 5' of the J6 region, optionally including J1-4 and a 3' recombination arm that contains sequence homologous to genomic sequence 3' of the J6 region, including the mu constant region (a "J6 targeting construct"), see for example, FIG. 1. Further, this J6 targeting construct can also contain a selectable marker gene that is located between the 5' and 3' recombination arms, see for example, Seq ID No 5 and FIG. 1. In other particular embodiments, the 5' targeting arm can contain sequence 5' of J1, such as depicted in Seq ID No. 1 and/or Seq ID No 4. In another embodiments, the 5' targeting arm can contain sequence 5' of J1, J2 and/or J3, for example, as depicted in approximately residues 1-300, 1-500, 1-750, 1-1000 and/or 1-1500 Seq ID No 4. In a further embodiment, the 5' targeting arm can contain sequence 5' of the constant region, for example, as depicted in approximately residues 1-300, 1-500, 1-750, 1-1000, 1-1500 and/or 1-2000 or any fragment thereof of Seq ID No 4 and/or any contiguous sequence of Seq ID No. 4 or fragment thereof. In another embodiment, the 3' targeting arm can contain sequence 3' of the constant region and/or including the constant region, for example, such as resides 7000-8000 and/or 8000-9000 or fragment thereof of Seq ID No 4. In other embodiments, targeting vector can contain any contiguous sequence or fragment thereof of Seq ID No 4. sequence In other embodiments, the targeting vector can contain a 5' recombination arm that contains sequence homologous to genomic sequence 5' of the diversity region, and a 3' recombination arm that contains sequence homologous to genomic sequence 3' of the diversity region of the porcine heavy chain locus. In a further embodiment, the targeting vector can contain a 5' recombination arm that contains sequence homologous to genomic sequence 5' of the mu constant region and a 3' recombination arm that contains sequence homologous to genomic sequence 3' of the mu constant region of the porcine heavy chain locus.

In further embodiments, the targeting vector can include, but is not limited to any of the following sequences: the Diversity region of heavy chain is represented, for example, by residues 1089-1099 of Seq ID No 29 (D(pseudo)), the Joining region of heavy chain is represented, for example, by residues 1887-3352 of Seq ID No 29 (for example: J(psuedo): 1887-1931 of Seq ID No 29, J(pseudo): 2364-2411 of Seq ID No 29, J(pseudo): 2756-2804 of Seq ID No 29, J (functional J): 3296-3352 of Seq ID No 29), the recombination signals are represented, for example, by residues 3001-3261 of Seq ID No 29 (Nonamer), 3292-3298 of Seq ID No 29 (Heptamer), the Constant Region is represented by the following residues: 3353-9070 of Seq ID No 29 (J to C mu intron), 5522-8700 of Seq ID No 29 (Switch region), 9071-9388 of Seq ID No 29 (Mu Exon 1), 9389-9469 of Seq ID No 29 (Mu Intron A), 9470-9802 of Seq ID No 29 (Mu Exon 2), 9830-10069 of Seq ID No 29 (Mu Intron B), 10070-10387 of Seq ID No 29 (Mu Exon 3), 10388-10517 of Seq ID No 29 (Mu Intron C), 10815-11052 of Seq ID No 29 (Mu Exon 4), 11034-11039 of Seq ID No 29 (Poly(A) signal) or any fragment or combination thereof. Still further, any contiguous sequence at least about 17, 20, 30, 40, 50, 100, 150, 200 or 300 nucleotides of Seq ID No 29 or fragment and/or combination thereof can be used as targeting sequence for the heavy chain targeting vector. It is understood that in general when designing a targeting construct one targeting arm will be 5' of the other targeting arm.

In other embodiments, targeting vectors designed to disrupt the expression of porcine heavy chain genes can contain recombination arms, for example, the 3' or 5' recombination arm, that target the constant region of heavy chain. In one embodiment, the recombination arm can target the mu constant region, for example, the C mu sequences described above or as disclosed in Sun & Butler Immunogenetics (1997) 46: 452-460. In another embodiment, the recombination arm can target the delta constant region, such as the sequence disclosed in Zhao et al. (2003) J imunol 171: 1312-1318, or the alpha constant region, such as the sequence disclosed in Brown & Butler (1994) Molec Immunol 31: 633-642.

Seq ID No. 5

GGCCAGACTTCCTCGGAACAGCTCAAAGAGCTCTGTCAAAGCCAGATCCC

ATCACACGTGGGCACCAATAGGCCATGCCAGCCTCCAAGGGCCGAACTGG

GTTCTCCACGGCGCACATGAAGCCTGCAGCCTGGCTTATCCTCTTCCGTG

GTGAAGAGGCAGGCCCGGGACTGGACGAGGGGCTAGCAGGGTGTGGTAGG

CACCTTGCGCCCCCACCCCGGCAGGAACCAGAGACCCTGGGGCTGAGAG

TGAGCCTCCAAACAGGATGCCCCACCCTTCAGGCCACCTTTCAATCCAGC

TACACTCCACCTGCCATTCTCCTCTGGGCACAGGGCCCAGCCCCTGGATC

TTGGCCTTGGCTCGACTTGCACCCACGCGCACACACACACTTCCTAACGT

GCTGTCCGCTCACCCCTCCCCAGCGTGGTCCATGGGCAGCACGGCAGTGC

GCGTCCGGCGGTAGTGAGTGCAGAGGTCCCTTCCCCTCCCCCAGGAGCCC
CAGGGGTGTGTGCAGATCTGGGGGCTCCTGTCCCTTACACCTTCATGCCC
CTCCCCTCATACCCACCCTCCAGGCGGGAGGCAGCGAGACCTTTGCCCAG
GGACTCAGCCAACGGGCACACGGGAGGCCAGCCCTCAGCAGCTGGCTCCC
AAAGAGGAGGTGGGAGGTAGGTCCACAGCTGCCACAGAGAGAAACCCTGA
CGGACCCCACAGGGGCCACGCCAGCCGGAACCAGCTCCCTCGTGGGTGAG
CAATGGCCAGGGCCCCGCCGGCCACCACGGCTGGCCTTGCGCCAGCTGAG
AACTCACGTCCAGTGCAGGGAGACTCAAGACAGCCTGTGCACACAGCCTC
GGATCTGCTCCCATTTCAAGCAGAAAAGGAAACCGTGCAGGCAGCCCTC
AGCATTTCAAGGATTGTAGCAGCGGCCAACTATTCGTCGGCAGTGGCCGA
TTAGAATGACCGTGGAGAAGGGCGGAAGGGTCTCTCGTGGGCTCTGCGGC
CAACAGGCCCTGGCTCCACCTGCCCGCTGCCAGCCCGAGGGGCTTGGGCC
GAGCCAGGAACCACAGTGCTCACCGGGACCACAGTGACTGACCAAACTCC
CGGCCAGAGCAGCCCCAGGCCAGCCGGGCTCTCGCCCTGGAGGACTCACC
ATCAGATGCACAAGGGGGCGAGTGTGGAAGAGACGTGTCGCCCGGGCCAT
TTGGGAAGGCGAAGGGACCTTCCAGGTGGACAGGAGGTGGGACGCACTCC
AGGCAAGGGACTGGGTCCCCAAGGCCTGGGGAAGGGGTACTGGCTTGGGG
GTTAGCCTGGCCAGGGAACGGGGAGCGGGGCGGGGGGCTGAGCAGGGAGG
ACCTGACCTCGTGGGAGCGAGGCAAGTCAGGCTTCAGGCAGCAGCCGCAC
ATCCCAGACCAGGAGGCTGAGGCAGGAGGGGCTTGCAGCGGGGCGGGGC
CTGCCTGGCTCCGGGGCTCCTGGGGACGCTGGCTCTTGTTTCCGTGTC
CCGCAGCACAGGGCCAGCTCGCTGGGCCTATGCTTACCTTGATGTCTGGG
GCCGGGGCGTCAGGGTCGTCGTCTCCTCAGGGGAGAGTCCCCTGAGGCTA
CGCTGGGG*GGGGACTATGGCAGCTCCACCAGGGGCCTGGGGACCAGGGG
CCTGGACCAGGCTGCAGCCCGGAGGACGGGCAGGGCTCTGGCTCTCCAGC
ATCTGGCCCTCGGAAATGGCAGAACCCCTGGCGGGTGAGCGAGCTGAGAG
CGGGTCAGACAGACAGGGGCCGGCCGGAAAGGAGAAGTTGGGGGCAGAGC
CCGCCAGGGGCCAGGCCCAAGGTTCTGTGTGCCAGGGCCTGGGTGGGCAC
ATTGGTGTGGCCATGGCTACTTAGACGCGTGATCAAGGGCGAATTCCAGC
ACACTGGCGGCCGTTACTAGTggatcccggcgcgccctaccgggtagggg
aggcgcttttcccaaggcagtctggagcatgcgctttagcagccccgctg
ggcacttggcgctacacaagtggcctctggcctcgcacacattccacatc
caccggtaggcgccaaccggctccgttctttggtggccccttcgcgccac
cttctactcctcccctagtcaggaagttccccccgccccgcagctcgcg
tcgtgcaggacgtgacaaatggaagtagcacgtctcactagtctcgtgca
gatggacagcaccgctgagcaatggaagcgggtaggcctttggggcagcg
gccaatagcagctttggctccttcgctttctgggctcagaggctgggaag
gggtgggtccggggcgggctcaggggcgggctcaggggcggggcgggcg
cccgaaggtcctccggaagcccggcattctgcacgcttcaaaagcgcacg
tctgccgcgctgttctcctcttcctcatctccgggccttttcgacctgcag ccaatatgggatcggccattgaacaagatggattgcacgcaggttctccg
gccgcttgggtggagaggctattcggctatgactgggcacaacagacaat
cggctgctctgatgccgccgtgttccggctgtcagcgcaggggcgcccgg
ttcttttttgtcaagaccgacctgtccggtgccctgaatgaactgcaggac
gaggcagcgcggctatcgtggctggccacgacgggcgttccttgcgcagc
tgtgctcgacgttgtcactgaagcgggaagggactggctgctattgggcg
aagtgccggggcaggatctcctgtcatctcaccttgctcctgccgagaaa
gtatccatcatggctgatgcaatgcggcggctgcatacgcttgatccggc
tacctgcccattcgaccaccaagcgaaacatcgcatcgagcgagcacgta
ctcggatggaagccggtcttgtcaatcaggatgatctggacgaagagcat
caggggctcgcgccagccgaactgttcgccaggctcaaggcgcgcatgcc
cgacggcgaggatctcgtcgtgacccatggcgatgcctgcttgccgaata
tcatggtggaaaatggccgcttttctggattcatcgactgtggccggctg
ggtgtggcggatcgctatcaggacatagcgttggctacccgtgatattgc
tgaagagcttggcggcgaatgggctgaccgcttcctcgtgctttacggta
tcgccgctcccgattcgcagcgcatcgccttctatcgccttcttgacgag
ttcttctgagggggatcaattcTCTAGATGCATGCTCGAGCGGCCGCCAGT
GTGATGGATATCTGCAGAATTCGCCCTtCCAGGCGTTGAAGTCGTCGTGT
CCTCAGGTAAGAACGGCCCTCCAGGGCCTTTAATTTCTGCTCTCGTCTGT
GGGCTTTTCTGACTCTGATCCTCGGGAGGCGTCTGTGCCCCCCCCGGGA
TGAGGCCGGCTTGCCAGGAGGGGTCAGGGACCAGGAGCCTGTGGGAAGTT
CTGACGGGGCTGCAGGCGGGAAGGGCCCCACCGGGGGGCGAGCCCCAGG
CCGCTGGGCGGCAGGAGACCCGTGAGAGTGCGCCTTGAGGAGGGTGTCTG
CGGAACCACGAACGCCCGCCGGGAAGGGCTTGCTGCAATGCGGTCTTCAG
ACGGGAGGCGTCTTCTGCCCTCACCGTCTTTCAAGCCCTTGTGGGTCTGA
AAGAGCCATGTCGGAGAGAGAAGGGACAGGCCTGTCCCGACCTGGCCGAG
AGCGGGCAGCCCCGGGGAGAGCGGGGCGATCGGCCTGGGCTCTGTGAGG
CCAGGTCCAAGGGAGGACGTGTGGTCCTCGTGACAGGTGCACTTGCGAAA
CCTTAGAAGACGGGGTATGTTGGAAGCGGCTCCTGATGTTTAAGAAAAGG
GAGACTGTAAAGTGAGCAGAGTCCTCAAGTGTGTTAAGGTTTTAAAGGTC
AAAGTGTTTTAAACCTTTGTGACTGCAGTTAGCAAGCGTGCGGGGAGTGA
ATGGGGTGCCAGGGTGGCCGAGAGGCAGTACGAGGGCCGTGCCGTCCTCT
AATTCAGGGCTTAGTTTTGCAGAATAAAGTCGGCCTGTTTTCTAAAAGCA
TTGGTGGTGCTGAGCTGGTGGAGGAGGCCGCGGGCAGCCCTGGCCACCTG
CAGCAGGTGGCAGGAAGCAGGTCGGCCAAGAGGCTATTTTAGGAAGCCAG
AAAAACACGGTCGATGAATTTATAGCTTCTGGTTTCCAGGAGGTGGTTGGG
CATGGCTTTGCGCAGCGCCACAGAACCGAAAGTGCCCACTGAGAAAAAAC
AACTCCTGCTTAATTTGCATTTTTCTAAAAGAAGAAACAGAGGCTGACGG
AAACTGGAAAGTTCCTGTTTTAACTACTCGAATTGAGTTTTCGGTCTTAG
CTTATCAACTGCTCACTTAGATTCATTTTCAAAGTAAACGTTTAAGAGCC
GAGGCATTCCTATCCTCTTCTAAGGCGTTATTCCTGGAGGCTCATTCACC -continued

```
GCCAGCACCTCCGCTGCCTGCAGGCATTGCTGTCACCGTCACCGTGACGG
CGCGCACGATTTTCAGTTGGCCCGCTTCCCCTCGTGATTAGGACAGACGC
GGGCACTCTGGCCCAGCCGTCTTGGCTCAGTATCTGCAGGCGTCCGTCTC
GGGACGGAGCTCAGGGGAAGAGCGTGACTCCAGTTGAACGTGATAGTCGG
TGCGTTGAGAGGAGACCCAGTCGGGTGTCGAGTCAGAAGGGGCCCGGGGC
CCGAGGCCCTGGGCAGGACGGCCCGTGCCCTGCATCACGGGCCCAGCGTC
CTAGAGGCAGGACTCTGGTGGAGAGTGTGAGGGTGCCTGGGGCCCCTCCG
GAGCTGGGGCCGTGCGGTGCAGGTTGGGCTCTCGGCGCGGTGTTGGCTGT
TTCTGCGGGATTTGGAGGAATTCTTCCAGTGATGGGAGTCGCCAGTGACC
GGGCACCAGGCTGGTAAGAGGGAGGCCGCCGTCGTGGCCAGAGCAGCTGG
GAGGGTTCGGTAAAAGGCTCGCCCGTTTCCTTTAATGAGGACTTTTCCTG
GAGGGCATTTAGTCTAGTCGGGACCGTTTTCGACTCGGGAAGAGGGATGC
GGAGGAGGGCATGTGCCCAGGAGCCGAAGGCGCCGCGGGGAGAAGCCCAG
GGCTCTCCTGTCCCCACAGAGGCGACGCCACTGCCGCAGACAGACAGGGC
CTTTCCCTCTGATGACGGCAAAGGCGCCTCGGCTCTTGCGGGGTGCTGGG
GGGGAGTCGCCCCGAAGCCGCTCACCCAGAGGCCTGAGGGGTGAGACTGA
CCGATGCCTCTTGGCCGGGCCTGGGGCCGGACCGAGGGGGACTCCGTGGA
GGCAGGGCGATGGTGGCTGCGGGAGGGAACCGACCCTGGGCCGAGCCCGG
CTTGGCGATTCCCGGGCGAGGGCCCTCAGCCGAGGCGAGTGGGTCCGGCG
GAACCACCCTTTCTGGCCAGCGCCACAGGGCTCTCGGGACTGTCCGGGGC
GACGCTGGGCTGCCCGTGGCAGGCCTGGGCTGACCTGGACTTCACCAGAC
AGAACAGGGCTTTCAGGGCTGAGCTGAGCCAGGTTTAGCGAGGCCAAGTG
GGGCTGAACCAGGCTCAACTGGCCTGAGCTGGGTTGAGCTGGGCTGACCT
GGGCTGAGCTGAGCTGGGCTGGGCTGGGCTGGGCTGGGCTGGGCTGGGCT
GGACTGGCTGAGCTGAGCTGGGTTGAGCTGAGCTGAGCTGGCCTGGGTTG
AGCTGGGCTGGGTTGAGCTGAGCTGGGTTGAGCTGGGTTGAGCTGGGTTG
ATCTGAGCTGAGCTGGGCTGAGCTGAGCTAGGCTGGGGTGAGCTGGGCTG
AGCTGGTTTGAGTTGGGTTGAGCTGAGCTGGGCTGTGCTGGCTGA
GCTAGGCTGAGCTAGGCTAGGTTGAGCTGGGCTGGGCTGAGCTGAGCTAG
GCTGGGCTGATTTGGGCTGAGCTGAGCTGAGCTAGGCTGCGTTGAGCTGG
CTGGGCTGGATTGAGCTGGCTGAGCTGGCTGAGCTGGGCTGAGCTGGCCT
GGGTTGAGCTGAGCTGGACTGGTTTGAGCTGGGTCGATCTGGGTTGAGCT
GTCCTGGGTTGAGCTGGGCTGGGTTGAGCTGAGCTGGGTTGAGCTGGGCT
CAGCAGAGCTGGGTTGGGCTGAGCTGGGTTGAGCTGAGCTGGGCTGAGCT
GGCCTGGGTTGAGCTGGGCTGAGCTGAGCTGGGCTGAGCTGGCCTGTGTT
GAGCTGGGCTGGGTTGAGCTGGGCTGAGCTGGATTGAGCTGGGTTGAGCT
GAGCTGGGCTGGGCTGTGCTGACTGAGCTGGGCTGAGCTAGGCTGGGGTG
AGCTGGGCTGAGCTGATCCGAGCTAGGCTGGGCTGGTTTGGGCTGAGCTG
AGCTGAGCTAGGCTGGATTGATCTGGCTGAGCTGGGTTGAGCTGAGCTGG
GCTGAGCTGGTCTGAGCTGGCCTGGGTCGAGCTGAGCTGGACTGGTTTGA
GCTGGGTCGATCTGGGCTGAGCTGGCCTGGGTTGAGCTGGGCTGGGTTGA
GCTGAGCTGGGTTGAGCTGGGCTGAGCTGAGGGCTGGGGTGAGCTGGGCT
GAACTAGCCTAGCTAGGTTGGGCTGAGCTGGGCTGGTTTGGGCTGAGCTG
AGCTGAGCTAGGCTGCATTGAGCAGGCTGAGCTGGGCTGAGCAGGCCTGG
GGTGAGCTGGGCTAGGTGGAGCTGAGCTGGGTCGAGCTGAGTTGGGCTGA
GCTGGCCTGGGTTGAGGTAGGCTGAGCTGAGCTGAGCTAGGCTGGGTTGA
GCTGGCTGGGCTGGTTTGCGCTGGGTCAAGCTGGGCCGAGCTGGCCTGGG
TTGAGCTGGGCTCGGTTGAGCTGGGCTGAGCTGAGCCGACCTAGGCTGGG
ATGAGCTGGGCTGATTTGGGCTGAGCTGAGCTGAGCTAGGCTGCATTGAG
CAGGCTGAGCTGGGCCTGGAGCCTGGCCTGGGGTGAGCTGGGCTGAGCTG
CGCTGAGCTAGGCTGGGTTGAGCTGGCTGGGCTGGTTTGCGCTGGGTCAA
GCTGGGCCGAGCTGGCCTGGGATGAGCTGGGCCGGTTTGGGCTGAGCTGA
GCTGAGCTAGGCTGCATTGAGCAGGCTGAGCTGGGCTGAGCTGGCCTGGG
GTGAGCTGGGCTGAGCTAAGCTGAGCTGGGCTGGTTTGGGCTGAGCTGGC
TGAGCTGGGTCCTGCTGAGCTGGGCTGAGCTGACCAGGGGTGAGCTGGGC
TGAGTTAGGCTGGGCTCAGCTAGGCTGGGTTGATCTGGCAGGGCTGGTTT
GCGCTGGGTCAAGCTCCCGGGAGATGGCCTGGGATGAGCTGGGCTGGTTT
GGGCTGAGCTGAGCTGAGCTGAGCTAGGCTGCATTGAGCAGGCTGAGCTG
GGCTGAGCTGGCCTGGGGTGAGCTGGGCTGGTGGAGCTGAGCTGGGCTG
AACTGGGCTAAGCTGGCTGAGCTGGATCGAGCTGAGCTGGGCTGAGCTGG
CCTGGGTTAGCTGGGCTGAGCTGAGCTGAGCTAGGCTGGGTTGAGCTGG
CTGGGCTGGTTTGCGCTGGGTCAAGCTGGGCCGAGCTGGCCTGGGTTGAG
CTGGGCTGGGCTGAGCTGAGCTAGGCTGGGTTGAGCTGGGCTGGGCTGAG
CTGAGCTAGGCTGCATTGAGCTGGCTGGGATGGATTGAGCTGGCTGAGCT
GGCTGAGCTGGCTGAGCTGGGCTGAGCTGGCCTGGGTTGAGCTGGGCTGG
GTTGAGCTGAGCTGGGCTGAGCTGGGCTCAGCAGAGCTGGGTTGAGCTGA
GCTGGGTTGAGCTGGGGTGAGCTGGGCTGAGCAGAGCTGGGTTGAGCTGA
GCTGGGTTGAGCTGGGCTCGAGCAGAGCTGGGTTGAGCTGAGCTGGGTTG
AGCTGGGCTCAGCAGAGCTGGGTTGAGCTGAGCTGGGTTGAGCTGGGCTG
AGCTAGCTGGGCTCAGCTAGGCTGGGTTGAGCTGAGCTGGGCTGAACTGG
GCTGAGCTGGGCTGAACTGGGCTGAGCTGGGCTGAGCTGGGCTGAGCAGA
GCTGGGCTGAGCAGAGCTGGGTTGGTCTGAGCTGGGTTGAGCTGGGCTGA
GCTGGGCTGAGCAGAGTTGGGTTGAGCTGAGCTGGGTTCAGCTGGGCTGA
GCTAGGCTGGGTTGAGCTGGGTTGAGTTGGGCTGAGCTGGGCTGGGTTGA
GCGGAGCTGGGCTGAACTGGGCTGAGCTGGGCTGAGCGGAACTGGGTTGA
TCTGAATTGAGCTGGGCTGAGCCGGGCTGAGCCGGGCTGAGCTGGGCTAG
GTTGAGCTTGGGTGAGCTTGCCTCAGCTGGTCTGAGCTAGGTTGGGTGGA
GCTAGGCTGGATTGAGCTGGGCTGAGCTGAGCTGATCTGGCCTCAGCTGG
GCTGAGGTAGGCTGAACTGGGCTGTGCTGGGCTGAGCTGAGCTGAGCCAG
TTTGAGCTGGGTTGAGCTGGGCTGAGCTGGGCTGTGTTGATCTTTCCTGA
ACTGGGCTGAGCTGGGCTGAGCTGGCCTAGCTGGATTGAACGGGGGTAAG
```

-continued

CTGGGCCAGGCTGGACTGGGCTGAGCTGAGCTAGGCTGAGCTGAGTTGAA

TTGGGTTAAGCTGGGCTGAGATGGGCTGAGCTGGGCTGAGCTGGGTTGAG

CCAGGTCGGACTGGGTTACCCTGGGCCACACTGGGCTGAGCTGGGCGGAG

CTCGATTAACCTGGTCAGGCTGAGTCGGGTCCAGCAGACATGCGCTGGCC

AGGCTGGCTTGACCTGGACACGTTCGATGAGCTGCCTTGGGATGGTTCAC

CTCAGCTGAGCCAGGTGGCTCCAGCTGGGCTGAGCTGGTGACCCTGGGTG

ACCTCGGTGACCAGGTTGTCCTGAGTCCGGGCCAAGCCGAGGCTGCATCA

GACTCGCCAGACCCAAGGCCTGGGCCCCGGCTGGCAAGCCAGGGCGGTG

AAGGCTGGGCTGGCAGGACTGTCCCGGAAGGAGGTGCACGTGGAGCCGCC

CGGACCCCGACCGGCAGGACCTGGAAAGACGCCTCTCACTCCCCTTTCTC

TTCTGTCCCCTCTCGGGTCCTCAGAGAGCCAGTCTGCCCCGAATCTCTAC

CCCCTCGTCTCCTGCGTCAGCCCCCCGTCCGATGAGAGCCTGGTGGCCCT

GGGCTGCCTGGCCCGGGACTTCCTGCCCAGCTCCGTCACCTTCTCCTG

GAA

Porcine Kappa Chain Targeting

In particular embodiments of the present invention, targeting vectors are provided to target the porcine kappa chain locus. In one particular embodiment, the targeting vector can contain 5' and 3' recombination arms that contain homologous sequence to the 3' and 5' flanking sequence of the constant region of the porcine immunoglobulin kappa chain locus. Since the present invention discovered that there is only one constant region of the porcine immunoglobulin kappa light chain locus, this will prevent the expression of a functional porcine kappa light chain immunoglobulin. In a specific embodiment, the targeting vector can contain a 5' recombination arm that contains sequence homologous to genomic sequence 5' of the constant region, optionally including the joining region, and a 3' recombination arm that contains sequence homologous to genomic sequence 3' of the constant region, optionally including at least part of the enhancer region (a "Kappa constant targeting construct"), see for example, FIG. 2. Further, this kappa constant targeting construct can also contain a selectable marker gene that is located between the 5' and 3' recombination arms, see for example, Seq ID No 20 and FIG. 2. In other embodiments, the targeting vector can contain a 5' recombination arm that contains sequence homologous to genomic sequence 5' of the joining region, and a 3' recombination arm that contains sequence homologous to genomic sequence 3' of the joining region of the porcine kappa light chain locus. In other embodiments, the 5' arm of the targeting vector can include Seq ID No 12 and/or Seq ID No 25 or any contiguous sequence or fragment thereof. In another embodiment, the 3' arm of the targeting vector can include Seq ID No 15, 16 and/or 19 or any contiguous sequence or fragment thereof.

In further embodiments, the targeting vector can include, but is not limited to any of the following sequences: the coding region of kappa light chain is represented, for example by residues 1-549 of Seq ID No 30 and 10026-10549 of Seq ID No 30, whereas the intronic sequence is represented, for example, by residues 550-10025 of Seq ID No 30, the Joining region of kappa light chain is represented, for example, by residues 5822-7207 of Seq ID No 30 (for example, J1:5822-5859 of Seq ID No 30, J2:6180-6218 of Seq ID No 30, J3:6486-6523 of Seq ID No 30, J4:6826-6863 of Seq ID No 30, J5:7170-7207 of Seq ID No 30), the Constant Region is represented by the following residues: 10026-10549 of Seq ID No 30 (C exon) and 10026-10354 of Seq ID No 30 (C coding), 10524-10529 of Seq ID No 30 (Poly(A) signal) and 11160-11264 of Seq ID No 30 (SINE element) or any fragment or combination thereof. Still further, any contiguous sequence at least about 17, 20, 30, 40, 50, 100, 150, 200 or 300 nucleotides of Seq ID No 30 or fragment and/or combination thereof can be used as targeting sequence for the heavy chain targeting vector. It is understood that in general when designing a targeting construct one targeting arm will be 5' of the other targeting arm.

Seq ID No. 20 ctcaaacgtaagtggcttttccgactgattctttgctgtttctaattgt tggttggcttttgtccattttcagtgttttcatcgaattagttgtcag ggaccaaacaaattgccttcccagattaggtaccagggaggggacattgc tgcatgggagaccagagggtggctaattttaacgtttccaagccaaaat aactggggaaggggcttgctgtcctgtgagggtaggttttatagaagt ggaagttaaggggaaatcgctatggttcacttttggctcggggaccaaag tggagcccaaaattgagtacattttccatcaattatttgtgagatttttg tcctgttgtgtcatttgtgcaagttttttgacattttggttgaatgagcca ttcccagggacccaaaaggatgagaccgaaaagtagaaaagagccaactt ttaagctgagcagacagaccgaattgttgagtttgtgaggagagtagggt ttgtagggagaaaggggaacagatcgctggcttttctctgaattagcct ttctcatgggactggcttcagagggggtttttgatgagggaagtgttcta gagccttaactgtgggttgtgttcggtagcgggaccaagctggaaatcaa acgtaagtgcacttttctactccttttttctttcttatacgggtgtgaaat tggggactttcatgtttggagtatgagttgaggtcagttctgaagagag tgggactcatccaaaaatctgaggagtaagggtcagaacagagttgtctc atggaagaacaaagacctagttagttgatgaggcagctaaatgagtcagt tgacttgggatccaaatggccagacttcgtctgtaaccaacaatctaatg agatgtagcagcaaaaagagatttccattgagggggaaagtaaaattgtta atattgtggatcacctttggtgaagggacatccgtggagattgaacgtaa gtatttttctctactaccttctgaaatttgtctaaatgccagtgttgac ttttagaggcttaagtgtcagttttgtgaaaaatgggtaaacaagagcat ttcatatttattatcagtttcaaaagttaaactcagctccaaaaatgaat ttgtagacaaaaagattaatttaagccaaattgaatgattcaaaggaaaa aaaaattagtgtagatgaaaaaggaattcttacagctccaaagagcaaaa gcgaattaattttctttgaactttgccaaatcttgtaaatgatttttgtt ctttacaatttaaaaaggttagagaaatgtatttcttagtctgttttctc tcttctgtctgataaattattatatgagataaaaatgaaaattaatagga tgtgctaaaaaatcagtaagaagttagaaaaatatatgtttatgttaaag ttgccacttaattgagaatcagaagcaatgttatttttaaagtctaaaat gagagataaactgtcaatacttaaattctgcagagattctatatcttgac agatatctccttttttcaaaaatccaatttctatggtagactaaatttgaa -continued

```
atgatcttcctcataatggagggaaaagatggactgaccccaaaagctca
gattt*aagaaaacctgtttaag*gaaagaaaataaaagaactgcatttt
ttaaaggcccatgaatttgtagaaaaataggaaatattttaataagtgta
ttcttttattttcctgttattacttgatggtgtttttataccgccaagga
ggccgtggcaccgtcagtgtgatctgtagaccccatggcggccttttttc
gcgattgaatgaccttggcggtgggtccccagggctctggtggcagcgca
ccagccgctaaaagccgctaaaaactgccgctaaaggccacagcaacccc
gcgaccgcccgttcaactgtgctgacacagtgatacagataatgtcgcta
acagaggagaatagaaatatgacgggcacacgctaatgtggggaaaagag
ggagaagcctgattttttattttttagagattctagagataaaattcccag
tattatatccttttaataaaaaatttctattaggagattataaagaattt
aaagctatttttttaagtgggggtgtaattctttcagtagtctcttgtcaa
atggatttaagtaatagaggcttaatccaaatgagagaaatagacgcata
acccttcaaggcaaaagctacaagagcaaaaattgaacacagcagccag
ccatctagccactcagattttgatcagttttactgagtttgaagtaaata
tcatgaaggtataattgctgataaaaaaataagatacaggtgtgacacat
ctttaagtttcagaaatttaatggcttcagtaggattatatttcacgtat
acaaagtatctaagcagataaaaatgccattaatggaaacttaatagaaa
tatattttaaattccttcattctgtgacagaaattttctaatctgggtc
ttttaatcacctacccttttgaaagagtttagtaatttgctatttgccatc
gctgtttactccagctaatttcaaaagtgatacttgagaaagattattt
tggtttgcaaccacctggcaggactattttagggccattttaaaactctt
ttcaaactaagtattttaaactgttctaaaccattttagggcctttttaaaa
atcttttcatgaatttcaaacttcgttaaaagttattaaggtgtctggca
agaacttccttatcaaatatgctaatagtttaatctgttaatgcaggata
taaaattaaagtgatcaaggcttgacccaaacaggagtatcttcatagca
tatttccctctcttttttttctagaattcatatgattttgctgccaaggct
attttatataatctctggaaaaaaaatagtaatgaaggttaaaagagaag
aaaatatcagaacattaagaattcggtattttactaactgcttggttaac
atgaaggttttatttattaaggtttctatctttataaaaatctgttcc
cttttctgctgatttctccaagcaaaagattcttgatttgttttttaact
cttactctcccacccaagggcctgaatgcccacaaaggggacttccagga
ggccatctggcagctgctcaccgtcagaagtgaagccagccagttcctcc
tgggcaggtggccaaaattacagttgacccctcctggtctggctgaacct
tgccccatatggtgacagccatctggccagggcccaggtctccctctgaa
gcctttgggaggagagggagagtggctggcccgatcacagatgcggaagg
ggctgactcctcaaccggggtgcagactctgcagggtgggtctgggccca
acacacccaaagcacgcccaggaaggaaaggcagcttggtatcactgccc
agagctaggagaggcaccgggaaaatgatctgtccaagaccgttcttgc
ttctaaactccgaggggtcagatgaagtggttttgtttcttggcctgaa
gcatcgtgttccctgcaagaagcggggaacacagaggaaggagagaaaag
```

```
atgaactgaacaaagcatgcaaggcaaaaaaggGGGTCTAGCCGCGGTCT
AGGAAGCTTTCTAGGGTACCTCTAGGGATCCCGGCGCGCCCTACCGGGTA
GGGGAGGCGCTTTTCCCAAGGCAGTCTGGAGCATGCGCTTTAGCAGCCCC
GCTGGGCACTTGGCGCTACACAAGTGGCCTCTGGCCTCGCACACATTCCA
CATCCACCGGTAGGCGCCAACCGGCTCCGTTCTTTGGTGGCCCCTTCGCG
CCACCTTCTACTCCTCCCCTAGTCAGGAAGTTCCCCCCCGCCCCGCAGCT
CGCGTCGTGCAGGACGTGACAAATGGAAGTAGCACGTCTCACTAGTCTCG
TGCAGATGGACAGCACCGCTGAGCAATGGAAGCGGGTAGGCCTTTGGGGC
AGCGGCCAATAGCAGCTTTGGCTCCTTCGCTTTCTGGGCTCAGAGGCTGG
GAAGGGGTGGGTCCGGGGCGGGCTCAGGGGCGGGCTCAGGGGCGGGGCG
GGCGCCCGAAGGTCCTCCGGAAGCCCGGCATTCTGCACGCTTCAAAAGCG
CACGTCTGCCGCGCTGTTCTCCTCTTCCTCATCTCCGGGCCTTTCGACCT
GCAGCCAATATGGGATCGGCCATTGAACAAGATGGATTGCACGCAGGTTC
TCCGGCCGCTTGGGTGGAGAGGCTATTCGGCTATGACTGGGCACAACAGA
CAATCGGCTGCTCTGATGCCGCCGTGTTCCGGCTGTCAGCGCAGGGGCGC
CCGGTTCTTTTTGTCAAGACCGACCTGTCCGGTGCCCTGAATGAACTGCA
GGACGAGGCAGCGCGGCTATCGTGGCTGGCCACGACGGGCGTTCCTTGCG
CAGCTGTGCTCGACGTTGTCACTGAAGCGGGAAGGGACTGGCTGCTATTG
GGCGAAGTGCCGGGGCAGGATCTCCTGTCATCTCACCTTGCTCCTGCCGA
GAAAGTATCCATCATGGCTGATGCAATGCGGCGGCTGCATACGCTTGATC
CGGCTACCTGCCCATTCGACCACCAAGCGAAACATCGCATCGAGCGAGCA
CGTACTCGGATGGAAGCCGGTCTTGTCAATCAGGATGATCTGGACGAAGA
GCATCAGGGGCTCGCGCCAGCCGAACTGTTCGCCAGGCTCAAGGCGCGCA
TGCCCGACGGCGAGGATCTCGTCGTGACCCATGGCGATGCCTGCTTGCCG
AATATCATGGTGGAAAATGGCCGCTTTTCTGGATTCATCGACTGTGGCCG
GCTGGGTGTGGCGGATCGCTATCAGGACATAGCGTTGGCTACCCGTGATA
TTGCTGAAGAGCTTGGCGGCGAATGGGCTGACCGCTTCCTCGTGCTTTAC
GGTATCGCCGCTCCCGATTCGCAGCGCATCGCCTTCTATCGCCTTCTTGA
CGAGTTCTTCTGAGGGGATCAATTCTCTAGAGCTCGCTGATCAGCCTCGA
CTGTGCCTTCTAGTTGCCAGCCATCTGTTGTTTGCCCCTCCCCCGTGCCT
TCCTTGACCCTGGAAGGTGCCACTCCCACTGTCCTTTCCTAATAAAATGA
GGAAATTGCATCGCATTGTCTGAGTAGGTGTCATTCTATTCTGGGGGGTG
GGGTGGGGCAGGACAGCAAGGGGGAGGATTGGGAAGACAATAGCAGGCAT
GCTGGGGATGCGGTGGGCTCTATGGCTTCTGAGGCGGAAAGAACCAGCTG
GGGGCGCGCCCctcgagcggccgccagtgtgatggatatctgcagaattc
gcccttggatcaaacacgcatcctcatggacaatatgttgggttcttagc
ctgctgagacacaacaggaactcccctggcaccactttagaggccagaga
aacagcacagataaaattccctgccctcatgaagcttatagtctagctgg
ggagatatcataggcaagataaacacatacaaatacatcatcttaggtaa
taatatatactaaggagaaaattacaggggagaaagaggacaggaattgc
```

-continued
tagggtaggattataagttcagatagttcatcaggaacactgttgctgag aagataacatttaggtaaagaccgaagtagtaaggaaatggaccgtgtgc ctaagtgggtaagaccattctaggcagcaggaacagcgatgaaagcactg aggtgggtgttcactgcacagagttgttcactgcacagagttgtgtgggg aggggtaggtcttgcaggctcttatggtcacaggaagaattgttttactc ccaccgagatgaaggttggtggattttgagcagaagaataattctgcctg gtttatatataacaggatttccctgggtgctctgatgagaataatctgtc aggggtgggataggagagatatggcaataggagccttggctaggagccc acgacaataattccaagtgagaggtggtgctgcattgaaagcaggactaa caagacctgctgacagtgtggatgtagaaaaagatagaggagacgaaggt gcatctagggttttctgcctgaggaattagaaagataaagctaaagctta tagaagatgcagcgctctgggagaaagaccagcagctcagttttgatcc atctggaattaattttggcataaagtatgaggtatgtgggttaacattat ttgttttttttttttccatgtagctatccaactgtcccagcatcatttat tttaaaagacttttcctttcccctattggattgttttggccacttcactga agatcaactgagcataaaattgggtctatttctaagctcttgattccatt ccatgacctatttgttcatctttaccccagtagacactgccttgatgatt aaagcccctgttaccatgtctgttttggacatggtaaatctgagatgcct attagccaaccaagcaagcacggccctagagagctagatatgagagcct ggaattcagacgagaaaggtcagtcctagagacatacatgtagtgccatc accatgcggatggtgttaaaagccatcagactgcaacagactgtgagagg gtaccaagctagagagcatggatagagaaacccaagcactgagctgggag gtgctcctacattaagagattagtgagatgaaggactgagaagattgatc agagaagaaggaaaatcaggaaaatggtgctgtcctgaaaatccaaggga agagatgttccaaagaggagaaaactgatcagttgtcagctagcgtcaat tgggatgaaaatggaccattggacagagggatgtagtgggtcatgggtga atagataagagcagcttctatagaatggcaggggcaaaattctcatctga tcggcatgggttctaaagaaaacgggaagaaaaaattgagtgcatgacca gtcccttcaagtagagaggtggaaaagggaaggaggaaaatgaggccacg acaacatgagagaaatgacagcattttttaaaaatttttttattttatttta tttatttattttttgcttttttagggctgccctgcaacatatggaggttcc caggttagggtctaatcagagctatagctgccagcctacaccacagcca tagcaatgccagatctacatgacctacaccacagctcacagcaacgccgg atccttaacccactgagtgaggccagagatcaaacccatatccttatgga tactagtcaggttcattaccactgagccaaaatgggaaatcctgagtaat gacagcatttttaatgtgccaggaagcaaaacttgccaccccgaaatgt ctctcaggcatgtggattattttgagctgaaaacgattaaggcccaaaaa acacaagaagaaatgtggaccttccccaacagcctaaaaaatttagatt gagggcctgttcccagaatagagctattgccagacttgtctacagaggct aagggctaggtgtggtgggaaaccctcagagatcagagggacgtttatg taccaagcattgacatttccatctccatgcgaatggccttcttccctct -continued
gtagccccaaaccaccacccccaaaatcttcttctgtctttagctgaaga tggtgttgaaggtgatagtttcagccactttggcgagttcctcagttgtt ctgggtctttcctccTgatccacattattcgactgtgtttgattttctcc tgtttatctgtctcattggcacccatttcattcttagaccagcccaaga acctagaagagtgaaggaaaattcttccaccctgacaaatgctaaatga gaatcaccgcagtagaggaaatgatctggtgctgcgggagatagaagag aaaatcgctggagagatgtcactgagtaggtgagatgggaaggggtgac acaggtggaggtgttgccctcagctaggaagacagacagttcacagaaga gaagcgggtgtccgtggacatcttgcctcatggatgaggaaaccgaggct aagaaagactgcaaaagaaaggtaaggattgcagagaggtcgatccatga ctaaaatcacagtaaccaaccccaaaccaccatgttttctcctagtctgg cacgtggcaggtactgtgtaggttttcaatattattggtttgtaacagta cctattaggcctccatccctcctctaatactaacaaaagtgtgagactg gtcagtgaaaaatggtcttctttctctatgaatcttctcaagaagatac ataacttttattttatcataggcttgaagagcaaatgagaaacagcctc caacctatgacaccgtaacaaaatgtttatgatcagtgaagggcaagaaa caaaacatacacagtaaagaccctccataatattgtgggtggcccaacac aggccaggttgtaaaagcttttattctttgatagaggaatggatagtaa tgtttcaacctggacagagatcatgttcactgaatccttccaaaaattca tgggtagtttgaattataaggaaaataagacttaggataaatactttgtc caagatcccagagttaatgccaaaatcagttttcagactccaggcagcct gatcaagagcctaaactttaaagacacagtcccttaataactactattca cagttgcactttcagggcgcaaagactcattgaatcctacaatagaatga gtttagatatcaaatctctcagtaatagatgaggagactaaatagcggc atgacctggtcacttaaagacagaattgagattcaaggctagtgttcttt ctacctgttttgtttctacaagatgtagcaatgcgctaattacagacctc tcagggaaggaa Porcine Lambda Chain Targeting In particular embodiments of the present invention, targeting vectors are provided to target the porcine lambda chain locus. In one embodiment, lambda can be targeted by designing a targeting construct that contains a 5' arm containing sequence located 5' to the first JC unit and a 3' arm containing sequence 3' to the last JC unit of the J/C cluster region, thus preventing functional expression of the lambda locus (see, FIGS. 3-4). In one embodiment, the targeting vector can contain any contiguous sequence (such as about 17, 20, 30, 40, 50, 75, 100, 200, 300 or 5000 nucleotides of contiguous sequence) or fragment thereof Seq ID No 28. In one embodiment, the 5' targeting arm can contain Seq ID No. 32, which includes 5' flanking sequence to the first lambda J/C region of the porcine lambda light chain genomic sequence or any contiguous sequence (such as about 17, 20, 30, 40, 50, 75, 100, 200, 300 or 5000 nucleotides of contiguous sequence) or fragment thereof (see also, for example FIG. 5). In another embodiment, the 3' targeting arm can contain, but is not limited to one or more of the following: Seq ID No. 33, which includes 3' flanking sequence to the J/C cluster region of the porcine lambda light chain genomic sequence, from approximately 200 base pairs downstream of lambda J/C; Seq ID No. 34, which includes 3' flanking sequence to the J/C cluster region of the porcine lambda light chain genomic sequence, approximately 11.8 Kb downstream of the J/C cluster, near the enhancer; Seq ID No. 35, which includes approximately 12 Kb downstream of lambda, including the enhancer region; Seq ID No. 36, which includes approximately 17.6 Kb downstream of lambda; Seq ID No. 37, which includes approximately 19.1 Kb downstream of lambda; Seq ID No. 38, which includes approximately 21.3 Kb downstream of lambda; and Seq ID No. 39, which includes approximately 27 Kb downstream of lambda, or any contiguous sequence (such as about 17, 20, 30, 40, 50, 75, 100, 200, 300 or 5000 nucleotides of contiguous sequence) or fragment thereof of Seq ID Nos 32-39 (see also, for example FIG. 6). It is understood that in general when designing a targeting construct one targeting arm will be 5' of the other targeting arm.

Seq ID No. 48 (as shown in Example 4) provides a representative, non-limiting example of a targeting construct that contains a 5' arm containing sequence located 5' to the first JC unit and a 3' arm containing sequence 3' to the last JC unit of the J/C cluster region. Representative 5' and 3' arms are shown in Seq ID No. 49 and 50 (also in Example 4).

In another embodiment, lambda is targeted using two targeting vectors. The two lambda targeting vectors, i.e., a vector pair, are utilized in a two step strategy to delete the entire J/C region of porcine lambda. In the first step, a first targeting vector is inserted upstream of the J/C region (or alternatively downstream of the J/C region). If the first targeting vector is inserted upstream of the J/C region, the 5' and 3' recombination arms of the first targeted vector contain homologous sequence to the 5' flanking sequence of the first J/C unit of the J/C cluster region. See FIG. 5, which shows 7 JC units in the J/C cluster region. If the first targeting vector is inserted downstream of the J/C cluster region, the 5' and 3' recombination arms of the first targeting vector contain homologous sequence to the 3' region of the last J/C unit in the JC region.

The first-step vectors are designed with lox sites that flank a fusion gene which can provide both positive and negative selection. Selection of the targeting event utilizes the Tn5 APHII gene commonly described as Neo resistance. Once targeting events are isolated, Cre is provided transiently to facilitate deletion of the selectable marker located between two lox sites. Negative selection is then provided by the Herpes simplex thymidine kinase coding region. This step selects for targeted cells that have deleted the selectable marker and retains a single lox site upstream (alternatively downstream) of the J/C region.

Figure 6:
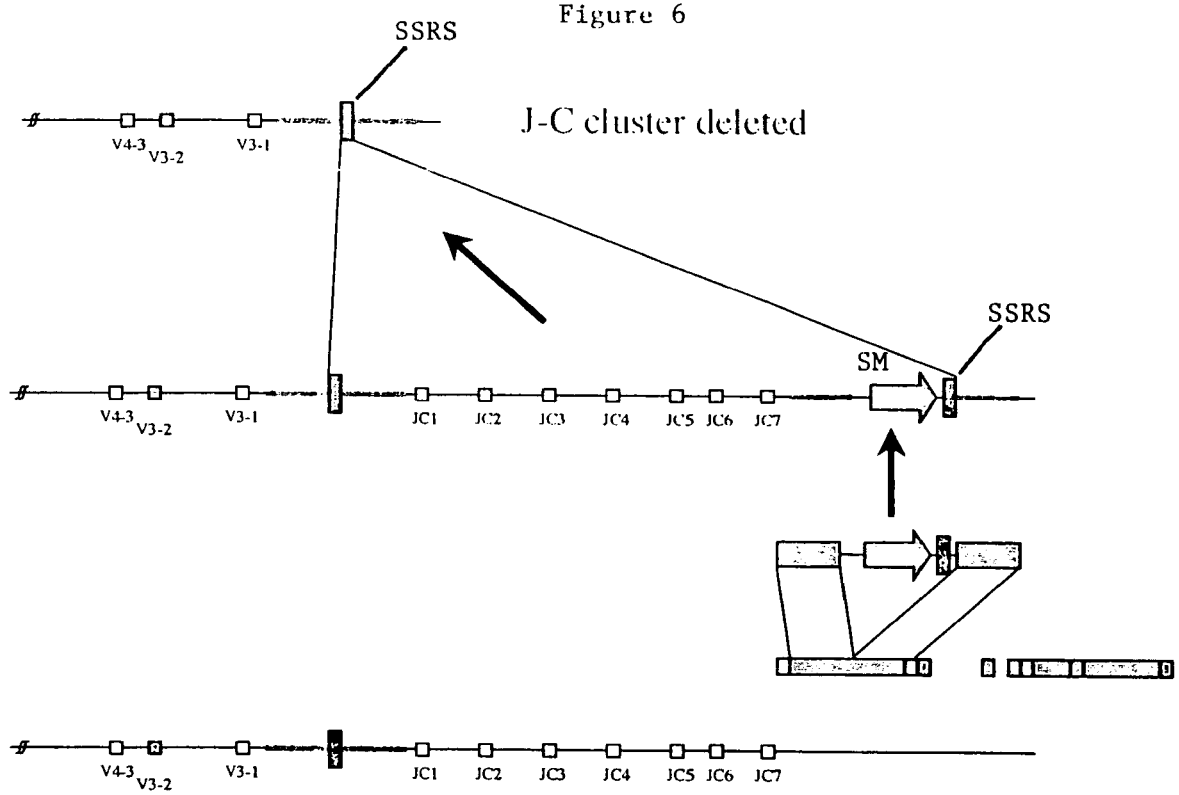
FIG. 6 illustrates a targeting strategy to insert a site specific recombinase target or recognition site into the region 3' of the JC cluster region of the porcine lambda immunoglobulin locus. "SM" stands for a selectable marker gene, which can be used in the targeting vector. "SSRRS" stands for a specific recombinase target or recognition site.

The second step is performed in the same lineage as the first step. The second targeting step also inserts a marker that provides both positive and negative selection. However, the second step inserts the marker on the opposite site of the J/C region in comparison to the first step. That is, if the first vector was inserted upstream of the J/C region, the second targeting vector is inserted downstream, and vice versa. FIG. 6 shows a second targeting vector inserted downstream of the J/C region. In addition, the second targeting vector has a single lox site that is located distally compared to the first vector. In other words, for the first strategy, the second vector has a single lox site located downstream of the marker gene (the alternative vector has the lox site upstream of the marker). After Cre mediated deletion, the region between the first targeting event (which left a lox remnant) and the second targeting event (which has a lox site outside of the marker) is deleted. Cells that have deleted the entire J/C cluster region are thus obtained.

In a representative, non-limiting example, the vector pair is Seq. ID No. 44 (step 1) and Seq. ID No. 45 (step 2).

In a further, non-limiting example, the vector pair is Seq. ID No. 46 (step 1) and Seq. ID No. 47 (step 2).

SEQ. ID 44

```
taaacaaataggggttccgcgcacatttccccgaaaagtgccacctgacgtcgctgagcaggccctggcctccctggcc gagggcggtttgcgtattagaggcctaaatggccgaattcagcggataacaatttcacacaggaaacagctatgaccatg attatctagtaactataacggtcctaaggtagcgagcgatcgcttaattaacctgcagggatatcccatggggccgccag tgtgatggatatctgcagaattcgcccttgatattaagagaagggcaagtcagcttaagtttgggggtagaggggaacag ggagtgaggagatctggcctgagagataggagccctggtggccacaggaggactctttgggtcctgtcggatggacac agggcggccggggggcatgttggagcccggctggttcttaccagaggcaggggcaccctctgacacgggagcagg gcatgttccatacatgacacaccctctgctccagggcaggtgggtggcggcacagaggagccagggactctgagcaa ggggtccaccagtggggcagttggatccagacttctctgggccagcgagagtctagccctcagccgttctctgtccagg agggggtggggcaggcctgggcggccagagctcatccctcaagggttcccagggtcctgccagacccagatttccg accgcagccaccacaagaggatgtggtctgctgtggcagctgccaagaccttgcagcaggtgcagggtgggggggtg ggggcacctgggggcagctgggtcactgagttcagggaaaaccccttttttcccctaaacctggggccatccctaggg gaaaccacaacttctgagccctgggcagtggctgctgggagggaagagcttcatcctggaccctgggggggaaccca gctccaaaggtgcaagggcccaggtccaaggctagagtgggccaagcaccgcaatggccagggagtgggggagg tggagctggactggatcagggcctccttgggactccctacaccctgtgtgacatgttagggtacccacaccccatcacca gtcagggcctggcccatctccagggccagggatgtgcatgtaagtgtgtgtgagtgtgtgtgtggtgtagtacaccct tggcatccggttccgaggccttgggttcctccaaagttgctctctgaattaggtcaaactgtgaggtcctgatcgccatcatc aacttcgttctccccacctcccatcattatcaagagctggggagggtctgggatttcttcccacccacaagccaaagata
```

-continued

```
agcctgctggtgatggcagaagacacaggatcctgggtcagagacaaaggccagtgtgtcacagcgagagaggcag ccggactatcagctgtcacagagaggccttagtccgctgaactcaggcccagtgactcctgttccactgggcactggcc cccctccacagcgccccaggccccagggagaggcgtcacagcttagagatggccctgctgaacagggaacaagaa caggtgtgccccatccagcgcccaggggtgggacaggtgggctggatttggtgtgaagcccttgagccctggaaccc aaccacagcagggcagttggtagatgccatttggggagaggccccaggagtaagggccatgggcccttgaggggc caggagctgaggacagggacagagacggcccaggcagaggacagggccatgaggggtgcactgagatggccact gccagcaggggcagctgccaacccgtccagggaacttattcagcagtcagctggaggtgccattgaccctgagggca gatgaagcccaggccaggctaggtgggctgtgaagacccaggggacagagctctgtccctgggcagcactggcctc tcattctgcagggcttgacgggatcccaaggcctgctgcccctgatggtagtggcagtaccgcccagagcaggacccc agcatggaaccccaacgggacgcagcctgcggagcccacaaaaccagtaaggagccgaagcagtcatggcacgg ggagtgtggacttccctttgatggggcccaggcatgaaggacagaatgggacagcggccatgagcagaaaatcagcc ggaggggatgggcctaggcagacgctggctttatttgaagtgttggcattttgtctggtgtgtattgttggtattgatttttatttt agtatgtcagtgacatactgacatattatgtaacgacatattattatgtgttttaagaagcactccaagggaacaggctgtctg taatgtgtccagagaagagagcaagagcttggctcagtctccccaaggaggtcagttcctcaacagggtcctaaatgt ttcctggagccaggcctgaatcaaggggtcatatctacacgtggggcagacccatggaccattttcggagcaataagat ggcagggaggataccaagctggtcttacagatccagggctttgacctgtgacgcgggcgctcctccaggcaaagggag aagccagcaggaagctttcagaactggggagaacagggtgcagacctccagggtcttgtacaacgcaccctttatcctg gggtccaggaggggtcactgagggattaagtgggggaccatcagaaccaggtttgtgttttggaaaaatggctccaaa gcagagaccagtgtgaggccagattagatgatgaagaagaggcagtggaaagtcgatgggtggccaggtagcaaga gggcctatggagttggcaagtgaatttaaagtggtggcaccagagggcagatggggaggagcaggcactgtcatgga ctgtctatagaaatctaaaatgtataccttttagcaatatgcagtgagtcataaaagaacacatatatatttcctttggccgg ccggcgcgccacgcgtataacttcgtatagcatacattatacgaagttatcttaagggctatggcagggcctgccgcccc gacgttggctgcgagccctgggccttcacccgaacttgggggtgggtgggaaaaggaagaaacgcgggcgtatt ggccccaatggggtctcggtgggtatcgacagagtgccagccctgggaccgaaccccgcgtttatgaacaaacgacc caacaccgtgcgttttattctgtcttttattgccgtcatagcgcgggttccttccggtattgtctccttccgtgtttcactcgagt tagaagaactcgtcaagaaggcgatagaaggcgatgcgctgcgaatcgggagcggcgataccgtaaagcacgagga agcggtcagcccattcgccgccaagctcttcagcaatatcacgggtagccaacgctatgtcctgatagcggtccgccac acccagccggccacagtcgatgaatccagaaaagcggccattttccaccatgatattcggcaagcaggcatcgccatgg gtcacgacgagatcctcgccgtcgggcatgcgcgccttgagcctggcgaacagttcggctggcgcgagccctgatgc tcttcgtccagatcatcctgatcgacaagaccggcttccatccgagtacgtgctcgctcgatgcgatgtttcgcttggtggtc gaatgggcaggtagccggatcaagcgtatgcagccgccgcattgcatcagccatgatggatactttctcggcaggagca aggtgagatgacaggagatcctgccccggcacttcgcccaatagcagccagtcccttcccgcttcagtgacaacgtcga gcacagctgcgcaaggaacgcccgtcgtggccagccacgatagccgcgctgcctcgtcctgcagttcattcagggcac cggacaggtcggtcttgacaaaaagaaccgggcgcccctgcgctgacagccggaacacggcggcatcagagcagcc gattgtctgttgtgcccagtcatagccgaatagcctctccacccaagcggccggagaacctgcgtgcaatccatcttgttc aatggccgatcccattccagatctgttagcctcccccatctcccgtgcaaacgtgcgcgccaggtcgcagatcgtcggtat ggagcctggggtggtgacgtgggtctggatcatcccggaggtaagttgcagcagggcgtcccggcagccggcgggc gattggtcgtaatccaggataaagacgtgcatgggacggaggcgtttggtcaagacgtccaaggcccaggcaaacacg ttgtacaggtcgccgttgggggccagcaactcggggcccgaaacagggtaaataacgtgtcccgatatgggtcgt gggcccgcgttgctctggggctcggcaccctggggcggcacggccgtccccgaaagctgtccccaatcctcccgcca
```

-continued

```
cgacccgccgccctgcagataccgcaccgtattggcaagcagcccgtaaacgcggcgaatcgcggccagcatagcca ggtcaagccgctcgccggggcgctggcgtttggccaggcggtcgatgtgtctgtcctccggaagggcccccaacacg atgtttgtgccgggcaaggtcggcgggatgagggccacgaacgccagcacggcctgggggtcatgctgcccataag gtatcgcgcggccgggtagcacaggagggcggcgatgggatggcggtcgaagatgagggtgagggccgggggcg gggcatgtgagctcccagcctccccccgatatgaggagccagaacggcgtcggtcacggcataaggcatgcccattg ttatctgggcgcttgtcattaccaccgccgcgtccccggccgatatctcaccctggtcaaggcggtgttgtgtggtgtagat gttcgcgattgtctcggaagccccagcacccgccagtaagtcatcggctcgggtacgtagacgatatcgtcgcgcgaa cccagggccaccagcagttgcgtggtggtggttttccccatcccgtggggaccgtctatataaaccgcagtagcgtgg gcattttctgctccgggcggacttccgtggcttcttgctgccggcgagggcgcaacgccgtacgtcggttgctatggccg cgagaacgcgcagcctggtcgaacgcagacgcgtgctgatggccggggtacgaagccatggtggctctagaggtcga aaggcccggagatgaggaagaggagaacagcgcggcagacgtgcgcttttgaagcgtgcagaatgccgggcttccg gaggaccttcgggcgcccgccccgcccctgagcccgcccctgagcccgccccggacccacccctccccagcctctg agcccagaaagcgaaggagccaaagctgctattggccgctgccccaaaggcctacccgcttccattgctcagcggtgc tgtccatctgcacgagactagtgagacgtgctacttccatttgtcacgtcctgcacgacgcgagctgcggggcggggg gaacttcctgactagggggaggagtagaaggtggcgcgaagggggcaccaaagaacgggagccggttggcgcctaccg gtggatgtggaatgtgtgcgaggccagaggccacttgtgtagcgccaagtgcccagcggggctgctaaagcgcatgct ccagactgccttgggaaaagcgcctccctacccggtagggatccgcgttacataacttacggtaaatgcccgcctgg ctgaccgccaacgaccccgcccattgacgtcaataatgacgtatgttcccatagtaacgccaatagggactttccattg acgtcaatgggtggagtatttacggtaaactgcccacttggcagtacatcaagtgtatcatatgccaagtacgccccctatt gacgtcaatgacggtaaatggcccgcctggcattatgcccagtacatgaccttatgggactttcctacttggcagtacatct acgtattagtcatcgctattaccatggtgatgcggttttggcagtacatcaatgggcgtggatagcggtttgactcacgggg atttccaagtctccaccccattgacgtcaatgggagtttgttttggcaccaaaatcaacgggtaacaagcttataacttcgtat agcatacattatacgaagttattacgtagcggccgcgtcgacgataaaattgtgtaattccacttctaaggattcatcccaagg ggggaaaataatcaaagatgtaaccaaaggtttacaaacaagaactcatcattaatcttccttgttgtatttcaacgatattat tattattactattattattattattttgtcttttgcattttctagggccactcccacggcatagagaggttcccaggctagggg tcaaatcggagctacagctgccggcctacgccagagccacagcaacgcaggatctgagccacagcaatgcaggatct acaccacagctcatggtaacgctggatccttaacccaatgagtgaggccagggatcgaacctgtaacttcatggttcctag tcggattcattaaccactgagccacgacaggaactccaacattattaatgatgggagaaaactggaagtaacctaaatatc cagcagaaagggtgtggccaaatacagcatggagtagccatcataaggaatcttacacaagcctccaaaattgtgtttctg aaattgggtttaaagtacgtttgcattttaaaaagcctgccagaaaatacagaaaaatgtctgtgatatgtctctggctgatag gattttgcttagttttaattttggctttataattttctatagttatgaaaatgttcacaagaagatatatttcattttagcttctaaaata attataacacagaagtaatttgtgctttaaaaaaatattcaacacagaagtatataaagtaaaaattgaggagttcccatcgtg gctcagtgattaacaaacccaactagtatccatgaggatatggatttgatccctggccttgctcagtgggttgaggatccag tgttgctgtgagctgtggtgtaggttgcagacacagcactctggcgttgctgtgactctggcgtaggccggcagctacag ctccatttggacccttagcctgggaacctccatatgcctgagatacggccctaaaaagtcaaaagccaaaaaaatagtaa aaattgagtgtttctacttaccacccctgcccacatcttatgctaaaacccgttctccagagacaaacatcgtcaggtgggtc tatatatttccagccctcctcctgtgtgtgtatgtccgtaaaacacacacacacacacacgcacacacacacacacg tatctaattagcattggtattagttttcaaaagggaggtcatgctctacctttaggcggcaaatagattatttaaacaaatctg ttgacattttctatatcaacccataagatctcccatgttcttggaaaggctttgtaagacatcaacatctgggtaaaccagcat ggttttagggggttgtgtggatttttttcatattttttagggcacacctgcagcatatggaggttcccaggctaggggttgaat cagagctgtagctgccggcctacaccacagccacagcaacgccagatccttaacccactgagaaaggccagggattga
```

-continued

```
acctgcatcctcatggatgctggtcagatttattctgctgagccacaacaggaactccctgaaccagaatgcttttaaccat tccactttgcatggacatttagattgtttccatttaaaaatacaaattacaaggagttcccgtcgtggctcagtggtaacgaatt ggactaggaaccatgaggtttcgggttcgatccctggccttgctcggtgggttaaggatccagcattgatgtgagatatgg tgtaggtcgcagacgtggctcggatcccacgttgctgtggctctggcgtaggccggcaacaacagctccgattcgaccc ctagcctgggaacctccatgtgccacaggagcagccctagaaaaggcaaaaagacaaaaaaataaaaaattaaaatga aaaaataaaataaaaatacaaattacaagagacggctacaaggaaatccccaagtgtgtgcaaatgccatatatgtataaa atgtactagtgtctcctcgcgggaaagttgcctaaaagtgggttggctggacagagaggacaggctttgacattctcatag gtagtagcaatgggcttctcaaaatgctgttccagtttacactcaccatagcaaatgacagtgcctcttcctctccaccttg ccaataatgtgacaggtggatctttttctattttgtgtatctgacaagcaaaaaatgagaacaggagttcctgtcgtggtgca gtggagacaaatctgactaggaaccatgaaatttcgggttcaatccctggcctcactcagtaggtaaaggatccagggttg cagtgagctgtggggtaggtcgcagacacagtgcaaatttggccctgttgtggctgtggtgtaggccggcagctatagct ccaattggaccctagcctgggaacctccttatgccgtgggtgaggccctaaaaaaaagagtgcaaaaaaaaaaataa gaacaaaatgatcatcgtttaattctttatttgatcattggtgaaacttattttcctttatatttttattgactgattttatttctcctat gaatttaccggtcatagttttgctgggtgttttactccggttttagttttggttggttgtattttcttagagagctatagaaactct tcatctatttggaatagtaattcctcattaagtatttgtgctgcaaaaaattttccctgatctgttttatgcttttgtttgtgggtctt tcacgagaaagccttttagttttacacctcagcttggttgttttcttgattgtgtctgtaatctgcggccaacataggaaaca cattttactttagtgtttttttcctattttcttcaagtacgtccattgttttggtgtctgattttactttgcctgggtttgttttgtgtg gcaggaatataaacttatgtattttccaaatggagagccaatggttgtatatttgttgaattcaaatgcaactttatcaaacacc aaatcatcgatttatcacaactcttctctggtttattgatctaatgatcaattcctgttccacgctgttttaattattttagctttgtgg attttggtgcctggtagagaacaaagcctccattattttcattcaaaatagtcccgtctattatctgccattgttgtagtattaga ctttaaaatcaatttactgattttcaaaagttattcctttggtgatgtggaatactttatacttcataaggtacatggattcatttgtg gggaattgatgtctttgctattgtggccatttgtcaagttgtgtaatattttacccatgccaactttgcatattgtatgtgagtttat tcccagggttttaataggatgtttattgaagttgtcagtgtttccacaatttcatcgcctcagtgcttactgtttgcataaaagg aaacctactcacttttgcctattgctcttgtattcaatcattttagttaactcttgtgttaattttgagagtttttcagctgactgtctg gggttttctttaatagactagccctttgtctgtaaagaataattttatcgaattttcttaacactcacactctcccacccccacc cccgctcatctcctttcattgggtcaaatctgtagaatacaataaaagtaagagtgggaaccttagcctttaagtcgattttgc ctttaaatgtgaatgttgctatgtttcgggacattctctttatcaagttgcggatgtttccttagataattaacttaataaaagact ggatgtttgctttcttcaaatcagaattgtgttgaatttatattgctattctgtttaattttgtttcaaaaaatttacatgcacaccta aagataaccatgaccaaatagtcctcctgctgagagaaaatgttggcccaatgccacaggttacctcccgactcagata aactacaatgggagataaaatcagatttggcaaagcctgtggattcttgccataactctcagagcatgacttgggtgttttttc ctttttctaagtatttaatggtattttgtgttacaataggaaatctaggacacagagagtgattcaatgaggggaacgcattct gggatgactctaggcctctggtttggggagagctctattgaagtaaagacaatgagaggaagcaagtttgcagggaact gtgaggaatttagatgggaatgttgggtttgaggtttctatagggcacgcaagcagagatgcactcaggaggaagaag gagcataaatctagtggcgctgccggcaagcttgctggaggaggccaattgggagctgctggaatgcatggaggcggc gctctcgaggctggaggaggccagctgatttaaatcggtccgcgtacgatgcatattaccctgttatccctaccgcggtta ctggccgtcgttttacaacgtcgtgactgggaaaaccctggcgatgctcttctcccggtgaaaacctctgacacatggctct tctaaatccggagtttaaacgcttccttcatgtgagcaaaaggccagcaaaaggccaggaaccgtaaaaaggccgcgtt gctggcgttttccataggctccgcccccctgacgagcatcacaaaaatcgacgctcaagtcagaggtggcgaaacccg acaggactataaagataccaggcgtttccccctggaagctccctcgtgcgctctcctgttccgaccctgccgcttaccgga tacctgtccgcctttctcccttcgggaagcgtggcgctttctcatagctcacgctgtaggtatctcagttcggtgtaggtcgtt
```

-continued cgctccaagctgggctgtgtgcacgaaccccccgttcagcccgaccgctgcgccttatccggtaactatcgtcttgagtc caacccggtaagacacgacttatcgccactggcagcagccactggtaacaggattagcagagcgaggtatgtaggcgg tgctacagagttcttgaagtggtggcctaactacggctacactagaaggacagtatttggtatctgcgctctgctgaagcca gttaccttcggaaaaagagttggtagctcttgatccggcaaacaaaccaccgctggtagcggtggttttttttgtttgcaagc agcagattacgcgcagaaaaaaaggatctcaagaagatcctttgatcttttctacggggtctgacgctcagtggaacgaa aactcacgttaagggattttggtcatgcctaggtggcaaacagctattatgggtattatgggtctaccggtgcatgagattat caaaaggatcttcacctagatcctttaaattaaaaatgaagttttaaatcaatctaaagtatatatgagtaaacttggtctga cagttaccaatgcttaatcagtgaggcacctatctcagcgatctgtctatttcgttcatccatagttgcctgactccccgtcgt gtagataactacgatacgggagggcttaccatctggccccagtgctgcaatgataccgcgagacccacgctcaccggct ccagatttatcagcaataaaccagccagccggaagggccgagcgcagaagtggtcctgcaactttatccgcctccatcc agtctattaattgttgccgggaagctagagtaagtagttcgccagttaatagtttgcgcaacgttgttgccattgctacaggc atcgtggtgtcacgctcgtcgtttggtatggcttcattcagctccggttcccaacgatcaaggcgagttacatgatcccccat gttgtgcaaaaaagcggttagctccttcggtcctccgatcgttgtcagaagtaagttggccgcagtgttatcactcatggtta tggcagcactgcataattctcttactgtcatgccatccgtaagatgcttttctgtgactggtgagtactcaaccaagtcattctg agaatagtgtatgcggcgaccgagttgctcttgcccggcgtcaatacgggataataccgcgccacatagcagaactttaa aagtgctcatcattggaaaacgttcttcggggcgaaaactctcaaggatcttaccgctgttgagatccagttcgatgtaacc cactcgtgcacccaactgatcttcagcatcttttactttcaccagcgtttctgggtgagcaaaaacaggaaggcaaaatgcc gcaaaaagggaataagggcgacacggaaatgttgaatactcatactcttcctttttcaatattattgaagcatttatcaggg ttattgtctcgggagcggatacatatttgaatgtatttagaaaaa

SEQ ID 45 taaacaaataggggttccgcgcacatttccccgaaaagtgccacctgacgtcgctgagcaggccctggcctccctggcc gagggcggtttgcgtattagaggcctaaatggccgaattcagcggataacaatttcacacaggaaacagctatgaccatg attatctagtaactataacggtcctaaggtagcgagcgatcgcttaattaacctgcaggataaccactgacccatgacgg gaactcccagggctcagctcttgactccaggttcgcagctgccctcaaagcaatgcaaccctggctggccccgcctcat gcatccggcctcctccccaaagagctctgagcccacctgggcctaggtcctcctccctgggactcatggcctaagggta cagagttactggggctgatgaagggaccaatggggacaggggcctcaaatcaaagtggctgtctctctcatgtcccttcc tctcctcagggtccaaaatcagggtcagggccccagggcaggggctgagagggcctcttcctgaaggccctgtctcagt gcaggttatgggggtctggggagggtcaatgcagggctcacccttcagtgccccaaagcctagagagtgagtgcctg ccagtggcttcccaggcccaatcccttgactgcctgggaatgctcaaatgcaggaactgtcacaacaccttcagtcaggg gctgctctgggaggaaaaacactcagaattgggggttcagggaaggcccagtgccaagcatagcaggagctcaggtg gctgcagatggtgtgaaccccaggagcaggatggccggcactcccccagaccctccagagcccaggttggctgcc ctcttcactgccgacacccctgggtccacttctgcccttccccacctaaaacctttagggctcccactttctcccaaatgtga gacatcaccacggctcccagggagtgtccagaagggcatctggctgagaggtcctgacatctgggagcctcaggcccc acaatggacagacgccctgccaggatgctgctgcagggctgttagctaggcggggtggagatggggtactttgcctctc agaggccccggccccaccatgaaacctcagtgacaccccatttccctgagttcacatacctgtatcctactccagtcacct tccccacgaaccccctgggagcccaggatgatgctggggctggagccacgaccagcccacgagtgatccagctctgcc aatcagcagtcatttcccaagtgttccagccctgccaggtcccactacagcagtaatggaggccccagacaccagtcca gcagttagagggctggactagcaccagcttcaagcctcagcatctcaaggtgaatggccagtgcccctcccccgtggcc atcacaggatcgcagatatgaccctaggggaagaaatatcctgggagtaaggaagtgcccatactcaaggatggcccct ctgtgacctaacctgtccctgaggattgtacttcaggcgttaaaacagtagaacgcctgcctgtgaaccccgccaagg gactgcttggggaggcccctaaaccagaacacaggcactccagcaggacctctgaactctgaccaccctcagcaagt

```
gggcacccccgcagcttccaaggcacccagggctcaccacagcggcccctcctggcagcccctcacccaggccc agaccctctaagatggcacatctaagccaatccacctccttgtcattcctcctgtcccacccaggacccttctcagatgaa accttcgctccagccgctgggccctctctcctgcccctctggcagttctccagggactccgcctcccactctctgtctctcc ctgcactcctaggaacaagcgacctccaggaagcccagtccaattatccctctgtgtcctcccaatctctgcctctggg tggatttgagcaccacatcctgttctcttcgacctgaaactccttggccccggtgtccgctctcctgggccctcttttctctcct cccctcttccgtgcccgtttgtttggtgttacaggcaggccccggggagccgtccctccagctgctcttccttgtctgtctc aggagccagaaactggcagcatctaaaaagggctcctgtttcttcatctgcccagcctcctagcccaaccagggctctgg cctcactccagagggtgggctccagagggcaggggttgcaccctcttagtgcctcagaggctcagctgggtgcaggat gggggggccctcagggagcccctcagtgactgctgatcacttactgcaggactgttcccagctcttcccaatcattggaat gacaatacctagttctgctccatcatagtgatgcaggaaaaatgttactgaaatcctggttcttgtttagcaatcgaagaatg aattccgcgaacacacaggcagcaagcaagcgaagcctttattaaaggaaagcagatagctcccagggctgcaggga gcggggagaagagctccccactctctattgtcctatagggcttttaccccttaaagttggggggatacaaaaaaaataga agaaaaagggagttcccgtcagggcacagcagaaacaaatccaactaggaaccatgaggttgggggttcgattcctgg cctctctcagtgggttaaggatgcagcgttgccgtgagctatgatacaggtcacagatgcagctcagatctactagtcaatt gacaggcgccggagcaggagctaggcctttggccggccggcgcgccagatctcttaagggctatggcagggcctgcc gccccgacgttggctgcgagccctgggccttcacccgaacttggggggtggggtggggaaaaggaagaaacgcggg cgtattggccccaatggggtctcggtggggtatcgacagagtgccagccctgggaccgaaccccgcgtttatgaacaaa cgacccaacaccgtgcgttttattctgtcttttattgccgtcatagcgcgggttccttccggtattgtctccttccgtgtttcact cgagttagaagaactcgtcaagaaggcgatagaaggcgatgcgctgcgaatcgggagcggcgataccgtaaagcacg aggaagcggtcagcccattcgccgccaagctcttcagcaatatcacgggtagccaacgctatgtcctgatagcggtccg ccacacccagccggccacagtcgatgaatccagaaaagcggccattttccaccatgatattcggcaagcaggcatcgcc atgggtcacgacgagatcctcgccgtcgggcatgcgcgccttgagcctggcgaacagttcggctggcgcgagcccctg atgctcttcgtccagatcatcctgatcgacaagaccggcttccatccgagtacgtgctcgctcgatgcgatgtttcgcttggt ggtcgaatgggcaggtagccggatcaagcgtatgcagccgccgcattgcatcagccatgatggatactttctcggcagg agcaaggtgagatgacaggagatcctgccccggcacttcgcccaatagcagccagtcccttcccgcttcagtgacaacg tcgagcacagctgcgcaaggaacgcccgtcgtggccagccacgatagccgcgctgcctcgtcctgcagttcattcagg gcaccggacaggtcggtcttgacaaaaagaaccgggcgcccctgcgctgacagccggaacacggcggcatcagagc agccgattgtctgttgtgcccagtcatagccgaatagcctctccacccaagcggccggagaacctgcgtgcaatccatctt gttcaatggccgatcccattccagatctgttagcctcccccatctcccgtgcaaacgtgcgcgccaggtcgcagatcgtcg gtatggagcctggggtggtgacgtgggtctggatcatcccggaggtaagttgcagcagggcgtcccggcagccggcg ggcgattggtcgtaatccaggataaagacgtgcatgggacggaggcgtttggtcaagacgtccaaggcccaggcaaac acgttgtacaggtcgccgttgggggccagcaactcggggccccgaaacagggtaaataacgtgtccccgatatgggt cgtgggcccgcgttgctctggggctcggcaccctggggcggcacggccgtccccgaaagctgtcccaatcctcccg ccacgacccgccgccctgcagataccgcaccgtattggcaagcagccgtaaacgcggcgaatcgcggccagcatag ccaggtcaagccgctcgccggggcgctggcgtttggccaggcggtcgatgtgtctgtcctccggaagggcccccaaca cgatgtttgtgccgggcaaggtcggcgggatgaggggcacgaacgccagcacggcctgggggtcatgctgcccata aggtatcgcgcggccgggtagcacaggagggcggcgatgggatggcggtcgaagatgagggtgagggccggggg cggggcatgtgagctcccagcctccccccgatatgaggagccagaacgcgtcggtcacggcataaggcatgccca ttgttatctgggcgcttgtcattaccaccgccgcgtccccggccgatatctcaccctggtcaaggcggtgttgtgtggtgta gatgttcgcgattgtctcggaagccccagcacccgccagtaagtcatcggctcgggtacgtagacgatatcgtcgcgc gaacccagggccaccagcagttgcgtggtggtggttttcccatcccgtggggaccgtctatataaacccgcagtagcgt
```

-continued gggcattttctgctccgggcggacttccgtggcttcttgctgccggcgagggcgcaacgccgtacgtcggttgctatggc cgcgagaacgcgcagcctggtcgaacgcagacgcgtgctgatggccggggtacgaagccatggtggctctagaggtc gaaaggcccggagatgaggaagaggagaacagcgcggcagacgtgcgcttttgaagcgtgcagaatgccgggcttc cggaggaccttcgggcgcccgccccgccccctgagcccgcccctgagcccgccccggacccacccctcccagcct ctgagcccagaaagcgaaggagccaaagctgctattggccgctgccccaaaggcctacccgcttccattgctcagcgg tgctgtccatctgcacgagactagtgagacgtgctacttccatttgtcacgtcctgcacgacgcgagctgcggggcgggg gggaacttcctgactaggggaggagtagaaggtggcgcgaaggggccaccaaagaacggagccggttggcgcctac cggtggatgtgtgaatgtgtgcgaggccagaggccacttgtgtagcgccaagtgcccagcggggctgctaaagcgcatg ctccagactgccttgggaaaagcgcctcccctacccggtagggatccgcgttacataacttacggtaaatggcccgcctg gctgaccgcccaacgaccccgcccattgacgtcaataatgacgtatgttcccatagtaacgccaatagggactttccatt gacgtcaatgggtggagtatttacggtaaactgcccacttggcagtacatcaagtgtatcatatgccaagtacgccccctat tgacgtcaatgacggtaaatggcccgcctggcattatgcccagtacatgaccttatgggactttcctacttggcagtacatc tacgtattagtcatcgctattaccatggtgatgcggttttggcagtacatcaatgggcgtggatagcggtttgactcacggg gatttccaagtctccaccccattgacgtcaatgggagtttgttttggcaccaaaatcaacgggtaacaagcttataacttcgta tagcatacattatacgaagttattacgtagcggccgcgtcgacgatatcgctgccggagccccgggccgctgccgga agatctggcattgctgtgactgtggtgtaggccggcagctggagctctgattagacccctcacctgggaatctccatatgc tgcacgtgcggccctaaaaagacaaaagacaaaaaaaaaaaaaaaaaaaaaatcaaaaaaaaacataggggggtta ccaacgtggggtccagaaagatgtggttttctcccattggccttgcccagttacctatatcagtccttgtccaacaggggttt tagggggtggaaatgcccccataaattttacggtttcttttgcccttctcttcctttagactgagtcaccattgctctcattccttttcta tcagttgaggagtgggttagagattaaggtccatgtggtggaggtacacttcttatagtaaacaaggcctatggggaattac tctctggagcccttaaaccacaaatgataatccatgccacatcaaagatgcatcgaagcccatgctcctacactgactacct gagttagcattctgcctcaacaggactgaccatccccagctctggggcagatatcctctctctgccacaagggcagtgac ccccatgctgtctgagggtcacgctttaccccccccccacccctgccgtgaccccccagaccaccccaggaggtgggc actaatatccctcattaccccatagatgaggaaacagaggttccccggggtcccacaggtgctcagggtcacatgcacc gtgggcacccaggccccatcccaaggccaccctccctcctcaggaagctgtgctgcgctgggccagaaggtactgcac acgactcctcagcctccggtggtgggaggcagcctcaagcctctgagtggggggcacccgggctcctcaatctatact gactcctggggtgggagaaggggaggggagctgtggcctctgagtccactaagcaaatcagggtgggcaatgcg ggcccatttcaaggaggagagaaccgaggctctgacagcaggccgggggtccaggacctgcccagggtcataggc tgaactgctggctgacctgccttgggttctttccttggctcctcagccctgtgtgatgtgacaggtcattcattcactcactcg ctcattcattcagcaaaccctcagtgagccctgctgggagcaggtgctaggggcaaggagacaggacctcttgccctgg aacagctgaagcactggggacaggcagtggcagggaggtgcgtgatcaccgctgacccattccatcctccagccc ccaggtcagtttccacccaccattgaccccaccatgtcctccatccccaaggtcagtttccgcccaaggagcatctcctt acacactagggacaaaatttcacggctgtcactgggcatctctccacgctcatcacagccctctagcagccttgaagtcct gtagagcccttcccatttcacagaagggacaagactatgagggccacaccgtgagccatgagccttaggctgtgagccg ggacagcccctgcaggactggtggcctcagggcactgggtggggaggtgcacagtgggtgggccccttgtggaata gagaggagtgtcaggtcaggggagggggcttggcctggccctggcctgcctggtgtgcaaccctaggcagcccctcct tcccaggcctcctacttcctggaggccaagcctcaggaggtaattgagtcaggtggggggagggggggttgtggctttc ttcacagcagaaaaacagagcccacaatagtgtccactgagacagaggggtcctgggggaggggaggggtgggagg tgactgctgagccctgtgggagggaggggagcaactactgagctgagctgggtgactctcccatctgcccgcccccctgt ggggccagcagagtcaccgagagaacatgacccagccaggcctggacaggggacacccatgtcctttaccccaca

```
gggttcactgagcctatctgccccaagcctgtgtctccctgggacggagaccctcactcccaaccacaaaggtctaaact caagttcccaacagccttgaaaatacagcttccggggcctccaaggagcagtcagccgtccactgccaggctcgctg gctcagtgacacaggacacatcctgatgacggtccacctgtctccaagcaggttctcctctgccgatggggcaacgagct cctcctgtggctccctggctggatgcgtggaggcggggtgggggggcaggcggtgttcctggccgcacacaaggag cacccccaccagcatccgaagacgggggcccggtctttccccaaaacactgcttgcgggagactttgtgacgtttccag gggccatgctcccttcgggcagcttggggacttctgctcctatgtggtcacctgcaggactcccccaggccttgggg acaaacaaagtgatgagagggagggttagtgggtcggggcagggccagtctttggaccggtttatctgaaaagccagtt ggtcaccgggaaccacagcaaacctaaacccatttggccaggcatctcccagggacagtctcccccaggatgcgggg cccagggggctccaggggtgacctgcgtcctggatttccctgatgctcccagttcgtgcctctgtccaagcatgattttta atagtgccccttccactcccagaaatgtccaagtgtgggcaataaattctggtcacctgagctcagtgtaactgtttgctgaa tgacacttactgtaacaggttaaaatggaggcccaaggccacgcagagccatcgaaggctctgtgtgtcccagccctg atagaagcatcaggatggggactgtggcctcaccaggggccacatccaggcggtcaccatgggggttcctggtctccgt gggccttgactggaccctggtgtgagctcaccccatcccagcctgtgagaggcctggatgtgggcctgacatcatttc ccacccagtgacagcactgcatgtgatggggcctctgggcagccttttcccggggggaaactggcaggaatcaggacc accaggacagggtcagggagaggcgatgctgggcaccagagcctggaccaccctcgggttctcagcgatgggca acccctgccacccagggccccgccttcctggggagacatcggggtttccaggccatcctgggaggagggtgggagcc tcagctagaccccagctggcttgccccccccatgcccggccaagagagggtcttggagggaaggggaccccagac cagcctggcgagcccatcctcagggtctctggtcagacaggggctcagctgagctccagggtagaccaaggccctgc gtggatgaggccagtgtggtcactgcccagagcaaagccacctctcagcagcccttcctgagcaccttctgtgtgcggg gacatcagcagtggcaacacagccatgctggggactcagggctagagacaggggaccagcctatggagagtgggta gtgtcctgcagggcaggcttgtgccctggagaaaacaaaccaggtgaggccagggacgctggccgggttcacagg gtgatggctgagcacagagtgccagggctggactgtcctgactctgggttggtggctgagggcctgtgtccctctatgc ctctgggttggtgataatgaaacttgctccctggagagacaggacgaatggttgatgggaaatgaatgtttgcttgtcact tggttgactgttgttgccgttagcatgggcttcttgggccaggcagcctcaggccagcactgctgggctccccacaggc ccgacaccctcagccctgtgcagctggcctggcgaaaccaagaggccctgatgcccaaaatagccgggaaaccccaa ccagcccagccctggcagcaggtgcctcccatttgcctgggctgggggagggtggctctggttctggaagtttctgcc agtccagctggagaagggacctgtatcccagcacccaggccgcccaagcccctgcaccagggcctgggccaggcag agttgacatcaatcaattgggagctgctggaatgcatggaggcggcgctctcgaggctggaggaggccagctgatttaa atcggtccgcgtacgatgcatattaccctgttatccctaccgcggttactggccgtcgttttacaacgtcgtgactgggaaa accctggcgatgctcttctcccggtgaaaacctctgacacatggctcttctaaatccggagtttaaacgcttccttcatgtga gcaaaaggccagcaaaaggccaggaaccgtaaaaaggccgcgttgctggcgtttttccataggctccgcccccctgac gagcatcacaaaaatcgacgctcaagtcagaggtggcgaaacccgacaggactataaagataccaggcgtttccccct ggaagctccctcgtgcgctctcctgttccgaccctgccgcttaccggatacctgtccgcctttctcccttcgggaagcgtg gcgctttctcatagctcacgctgtaggtatctcagttcggtgtaggtcgttcgctccaagctgggctgtgtgcacgaacccc ccgttcagcccgaccgctgcgccttatccggtaactatcgtcttgagtccaacccggtaagacacgacttatcgccactgg cagcagccactggtaacaggattagcagagcgaggtatgtaggcggtgctacagagttcttgaagtggtggcctaacta cggctacactagaaggacagtatttggtatctgcgctctgctgaagccagttaccttcggaaaaagagttggtagctcttga tccggcaaacaaaccaccgctggtagcggtggtttttttgtttgcaagcagcagattacgcgcagaaaaaaaggatctca agaagatcctttgatcttttctacggggtctgacgctcagtggaacgaaaactcacgttaagggattttggtcatgctaggt ggcaaacagctattatgggtattatgggtctaccggtgcatgagattatcaaaaaggatcttcacctagatccttttaaattaa aaatgaagttttaaatcaatctaaagtatatatgagtaaacttggtctgacagttaccaatgcttaatcagtgaggcacctatct
```

-continued cagcgatctgtctatttcgttcatccatagttgcctgactcccgtcgtgtagataactacgatacgggagggcttaccatct ggccccagtgctgcaatgataccgcgagacccacgctcaccggctccagatttatcagcaataaaccagccagccgga agggccgagcgcagaagtggtcctgcaactttatccgcctccatccagtctattaattgttgccgggaagctagagtaagt agttcgccagttaatagtttgcgcaacgttgttgccattgctacaggcatcgtggtgtcacgctcgtcgtttggtatggcttca ttcagctccggttcccaacgatcaaggcgagttacatgatcccccatgttgtgcaaaaaagcggttagctccttcggtcctc cgatcgttgtcagaagtaagttggccgcagtgttatcactcatggttatggcagcactgcataattctcttactgtcatgccat ccgtaagatgctttctgtgactggtgagtactcaaccaagtcattctgagaatagtgtatgcggcgaccgagttgctcttgc ccggcgtcaatacgggataataccgcgccacatagcagaactttaaaagtgctcatcattggaaaacgttcttcggggcg aaaactctcaaggatcttaccgctgttgagatccagttcgatgtaacccactcgtgcacccaactgatcttcagcatcttttac tttcaccagcgtttctgggtgagcaaaaacaggaaggcaaaatgccgcaaaaaagggaataaggggcgacacggaaat gttgaatactcatactcttcctttttcaatattattgaagcatttatcagggttattgtctcgggagcggatacatatttgaatgtat ttagaaaaa

SEQ ID 46 taaacaaatagggggttccgcgcacatttccccgaaaagtgccacctgacgtcgctgagcaggccctggcctccctggcc gagggcggtttgcgtattagaggcctaaatggccgaattcagcggataacaatttcacacaggaaacagctatgaccatg attatctagtaactataacggtcctaaggtagcgagcgatcgcttaattaacctgcagggatatcccatgggggccgccag tgtgatggatatctgcagaattcgcccttgatattaagaagggcaagtcagcttaagtttgggggtagagggggaacag ggagtgaggagatctggcctgagagataggagccctggtggccacaggaggactctttgggtcctgtcggatggacac agggcggcccggggcatgttggagcccggctggttcttaccagaggcaggggcaccctctgacacgggagcagg gcatgttccatacatgacacacccctctgctccagggcaggtgggtggcggcacagaggagccagggactctgagcaa ggggtccaccagtggggcagttggatccagacttctctgggccagcgagagtctagccctcagccgttctctgtccagg agggggggtggggcaggcctgggcggccagagctcatccctcaagggttcccagggtcctgccagacccagatttccg accgcagccaccacaagaggatgtggtctgctgtggcagctgccaagaccttgcagcaggtgcagggtgggggggtg ggggcacctgggggcagctggggtcactgagttcagggaaaaccccttttttcccctaaacctggggccatccctaggg gaaaccacaacttctgagccctgggcagtggctgctgggagggaagagcttcatcctggaccctggggggaaccca gctccaaaggtgcaaggggcccaggtccaaggctagagtgggccaagcaccgcaatggccagggagtgggggagg tggagctggactggatcagggcctccttgggactccctacaccctgtgtgacatgttagggtacccacaccccatcacca gtcagggcctggcccatctccagggccagggatgtgcatgtaagtgtgtgtgagtgtgtgtgtgtggtgtagtacacccct tggcatccggttccgaggccttgggttcctccaaagttgctctctgaattaggtcaaactgtgaggtcctgatcgccatcatc aacttcgttctccccacctcccatcattatcaagagctggggagggtctgggattttcttcccacccacaagccaaaagata agcctgctggtgatggcagaagacacaggatcctgggtcagagacaaaggccagtgtgtcacagcgagagaggcag ccggactatcagctgtcacagagaggccttagtccgctgaactcaggccccagtgactcctgttccactgggcactggcc cccctccacagcgcccccaggcccagggagaggcgtcacagcttagagatggccctgctgaacagggaacaagaa caggtgtgccccatccagcgccccaggggtgggacaggtgggctggatttggtgtgaagcccttgagccctggaaccc aaccacagcagggcagttggtagatgccatttggggagaggcccaggagtaagggccatgggcccttgagggggc caggagctgaggacagggacagagacggcccaggcagaggacagggccatgagggtgcactgagatggccact gccagcaggggcagctgccaacccgtccagggaacttattcagcagtcagctggaggtgccattgaccctgagggca gatgaagcccaggccaggctaggtgggctgtgaagaccccaggggacagagctctgtccctgggcagcactggcctc tcattctgcagggcttgacgggatcccaaggcctgctgcccctgatggtagtggcagtaccgcccagagcaggacccc agcatggaaaccccaacgggacgcagcctgcggagcccacaaaaccagtaaggagccgaagcagtcatggcacgg ggagtgtggacttccctttgatggggcccaggcatgaaggacagaatgggacagcggccatgagcagaaaatcagcc -continued ggagggatgggcctaggcagacgctggctttatttgaagtgttggcattttgtctggtgtgtattgttggtattgattttatttt agtatgtcagtgacatactgacatattatgtaacgacatattattatgtgttttaagaagcactccaagggaacaggctgtctg taatgtgtccagagaagagagcaagagcttggctcagtctcccccaaggaggtcagttcctcaacaggggtcctaaatgt ttcctggagccaggcctgaatcaagggggtcatatctacacgtggggcagacccatggaccattttcggagcaataagat ggcagggaggataccaagctggtcttacagatccagggctttgacctgtgacgcgggcgctcctccaggcaaagggag aagccagcaggaagctttcagaactggggagaacaggtgcagacctccagggtcttgtacaacgcacccttatcctg gggtccaggaggggtcactgagggatttaagtgggggaccatcagaaccaggtttgtgttttggaaaaatggctccaaa gcagagaccagtgtgaggccagattagatgatgaagaagaggcagtggaaagtcgatgggtggccaggtagcaaga gggcctatggagttggcaagtgaatttaaagtggtggcaccagagggcagatggggaggagcaggcactgtcatgga ctgtctatagaaatctaaaatgtataccctttttagcaatatgcagtgagtcataaaagaacacatatatatttcctttggccgg ccggcgcgccacgcgtataacttcgtatagcatacattatacgaagttatcttaagggctatggcagggcctgccgcccc gacgttggctgcgagccctgggccttcacccgaacttgggggtggggtggggaaaaggaagaaacgcgggcgtatt ggccccaatggggtctcggtggggtatcgacagagtgccagccctgggaccgaaccccgcgtttatgaacaaacgacc caacaccgtgcgttttattctgtcttttattgccgtcatagcgcgggttccttccggtattgtctccttccgtgtttcactcgagt tagaagaactcgtcaagaaggcgatagaaggcgatgcgctgcgaatcgggagcggcgataccgtaaagcacgagga agcggtcagcccattcgccgccaagctcttcagcaatatcacgggtagccaacgctatgtcctgatagcggtccgccac acccagccggccacagtcgatgaatccagaaaagcggccattttccaccatgatattcggcaagcaggcatcgccatgg gtcacgacgagatcctcgccgtcgggcatgcgcgccttgagcctggcgaacagttcggctggcgcgagcccctgatgc tcttcgtccagatcatcctgatcgacaagaccggcttccatccgagtacgtgctcgctcgatgcgatgtttcgcttggtggtc gaatgggcaggtagccggatcaagcgtatgcagccgccgcattgcatcagccatgatggatactttctcggcaggagca aggtgagatgacaggagatcctgccccggcacttcgcccaatagcagccagtcccttcccgcttcagtgacaacgtcga gcacagctgcgcaaggaacgcccgtcgtggccagccacgatagccgcgctgcctcgtcctgcagttcattcagggcac cggacaggtcggtcttgacaaaaagaaccgggcgcccctgcgctgacagccggaacacggcggcatcagagcagcc gattgtctgttgtgcccagtcatagccgaatagcctctccacccaagcggccggagaacctgcgtgcaatccatcttgttc aatgccgatcccattccagatctgttagcctcccccatctcccgtgcaaacgtgcgcgccaggtcgcagatcgtcggtat ggagcctggggtggtgacgtgggtctggatcatcccggaggtaagttgcagcagggcgtcccggcagccggcgggc gattggtcgtaatccaggataaagacgtgcatgggacggaggcgtttggtcaagacgtccaaggcccaggcaaacacg ttgtacaggtcgccgttgggggccagcaactcgggggcccgaaacagggtaaataacgtgtccccgatatgggtcgt gggcccgcgttgctctgggctcggcaccctgggcggcacggccgtccccgaaagctgtccccaatcctcccgcca cgacccgccgccctgcagataccgcaccgtattggcaagcagcccgtaaacgcggcgaatcgcggccagcatagcca ggtcaagccgctcgccggggcgctggcgtttggccaggcggtcgatgtgtctgtcctccggaagggcccccaacacg atgtttgtgccgggcaaggtcggcgggatgagggccacgaacgccagcacggcctgggggtcatgctgcccataag gtatcgcgcggccgggtagcacaggagggcggcgatgggatggcggtcgaagatgagggtgagggccgggggcg gggcatgtgagctcccagcctccccccgatatgaggagccagaacggcgtcggtcacggcataaggcatgcccattg ttatctgggcgcttgtcattaccaccgccgcgtcccggccgatatctcaccctggtcaaggcggtgttgtgtggtgtagat gttcgcgattgtctcggaagcccccagcacccgccagtaagtcatcggctcgggtacgtagacgatatcgtcgcgcgaa cccagggccaccagcagttgcgtggtggtggttttccccatcccgtggggaccgtctatataaaccgcagtagcgtgg gcattttctgctccgggcggacttccgtggcttcttgctgccggcgagggcgcaacgccgtacgtcggttgctatggccg cgagaacgcgcagcctggtcgaacgcagacgcgtgctgatgccggggtacgaagccatggtggctctagaggtcga aaggcccggagatgaggaagaggagaacagcgcggcagacgtgcgcttttgaagcgtgcagaatgccgggcttccg -continued

```
gaggaccttcgggcgcccgccccgcccctgagcccgcccctgagcccgccccggacccacccttcccagcctctg agcccagaaagcgaaggagccaaagctgctattggccgctgccccaaaggcctaccgcttccattgctcagcggtgc tgtccatctgcacgagactagtgagacgtgctacttccatttgtcacgtcctgcacgacgcgagctgcggggcgggggg gaacttcctgactaggggaggagtagaaggtggcgcgaaggggccaccaaagaacggagccggttggcgcctaccg gtggatgtggaatgtgtgcgaggccagaggccacttgtgtagcgccaagtgcccagcggggctgctaaagcgcatgct ccagactgccttgggaaaagcgcctcccctacccggtagggatccgcgttacataacttacggtaaatggcccgcctgg ctgaccgcccaacgaccccgcccattgacgtcaataatgacgtatgttcccatagtaacgccaatagggactttccattg acgtcaatgggtggagtatttacggtaaactgcccacttggcagtacatcaagtgtatcatatgccaagtacgccccctatt gacgtcaatgacggtaaatggcccgcctggcattatgcccagtacatgaccttatgggactttcctacttggcagtacatct acgtattagtcatcgctattaccatggtgatgcggttttggcagtacatcaatgggcgtggatagcggtttgactcacgggg atttccaagtctccaccccattgacgtcaatgggagtttgttttggcaccaaaatcaacggttaacaagcttagatctgcggc cgcgtcgacgataaattgtgtaattccacttctaaggattcatcccaagggggggaaaataatcaaagatgtaaccaaaggt ttacaaacaagaactcatcattaatcttccttgttgtttatttcaacgatattattattattactattattattattatttttgtcttttttg catttctagggccactcccacggcatagagaggttcccaggctagggggtcaaatcggagctacagctgccggcctacg ccagagccacagcaacgcaggatctgagccacagcaatgcaggatctacaccacagctcatggtaacgctggatccctt aacccaatgagtgaggccagggatcgaacctgtaacttcatggttcctagtcggattcattaaccactgagccacgacag gaactccaacattattaatgatgggagaaaactggaagtaacctaaatatccagcagaaagggtgtggccaaatacagca tggagtagccatcataaggaatcttacacaagcctccaaaattgtgtttctgaaattgggtttaaagtacgtttgcatttttaaaa agcctgccagaaaatacagaaaaatgtctgtgatatgtctctggctgataggattttgcttagttttaattttggctttataattttt ctatagttatgaaaatgttcacaagaagatatatttcattttagcttctaaaataattataacacagaagtaatttgtgctttaaaa aaatattcaacacagaagtatataaagtaaaaattgaggagttcccatcgtggctcagtgattaacaaacccaactagtatc catgaggatatggatttgatccctggccttgctcagtgggttgaggatccagtgttgctgtgagctgtggtgtaggttgcag acacagcactctggcgttgctgtgactctggcgtaggccggcagctacagctccatttgacccttagcctgggaacctc catatgcctgagatacggcccctaaaaagtcaaaagccaaaaaaatagtaaaaattgagtgtttctacttaccaccctgcc cacatcttatgctaaaacccgttctccagagacaaacatcgtcaggtgggtctatatatttccagccctcctcctgtgtgtgta tgtccgtaaaacacacacacacacacacacacgcacacacacacacgtatctaattagcattggtattagttttttcaaaa gggaggtcatgctctaccttttaggcggcaaatagattatttaaacaaatctgttgacattttctatatcaacccataagatctc ccatgttcttggaaaggctttgtaagacatcaacatctgggtaaaccagcatggttttaggggggttgtgtggattttttttcata ttttttagggcacacctgcagcatatggaggttcccaggctaggggttgaatcagagctgtagctgccggcctacaccac agccacagcaacgccagatccttaacccactgagaaaggccagggattgaacctgcatcctcatggatgctggtcagat ttatttctgctgagccacaacaggaactccctgaaccagaatgcttttaaccattccactttgcatggacatttagattgtttcc atttaaaaatacaaattacaaggagttcccgtcgtggctcagtggtaacgaattggactaggaaccatgaggtttcgggttc gatccctggccttgctcggtgggttaaggatccagcattgatgtgagatatggtgtaggtcgcagacgtggctcggatccc acgttgctgtggctctggcgtaggccggcaacaacagctccgattcgaccctagcctgggaacctccatgtgccacag gagcagcccagaaaaggcaaaagacaaaaaataaaaaattaaaatgaaaaataaaataaaaatacaaattacaag agacggctacaaggaaatccccaagtgtgtgcaaatgccatatatgtataaaatgtactagtgtctcctcgcgggaaagtt gcctaaaagtgggttggctggacagagaggacaggctttgacattctcataggtagtagcaatgggcttctcaaaatgctg ttccagtttacactcaccatagcaaatgacagtgcctcttcctctccacccttgccaataatgtgacaggtggatctttttctatt ttgtgtatctgacaagcaaaaaatgagaacaggagttcctgtcgtggtgcagtggagacaaatctgactaggaaccatga aatttcgggttcaatccctggcctcactcagtaggtaaaggatccagggttgcagtgagctgtggggtaggtcgcagaca cagtgcaaatttggccctgttgtggctgtggtgtaggccggcagctatagctccaattggaccccctagcctgggaacctcc
```

-continued

```
ttatgccgtgggtgaggccctaaaaaaaagagtgcaaaaaaaaaaaataagaacaaaaatgatcatcgtttaattctttattt
gatcattggtgaaacttattttcctttatattttattgactgattttatttctcctatgaatttaccggtcatagttttgcctgggtgtt
tttactccggttttagttttggttggttgtattttcttagagagctatagaaactcttcatctatttggaatagtaattcctcattaagt
atttgtgctgcaaaaaattttccctgatctgttttatgcttttgtttgtggggtctttcacgagaaagccttttttagttttttacacctc
agcttggttgttttcttgattgtgtctgtaatctgcggccaacataggaaacacattttttactttagtgttttttttcctattttcttca
agtacgtccattgttttggtgtctgattttactttttgcctgggggtttgtttttgtgtggcaggaatataaacttatgtattttccaaatg
gagagccaatggttgtatatttgttgaattcaaatgcaactttatcaaacaccaaatcatcgatttatcacaactcttctctggtt
tattgatctaatgatcaattcctgttccacgctgttttaattattttagctttgtggattttggtgcctggtagagaacaaagcctc
cattattttcattcaaaatagtcccgtctattatctgccattgttgtagtattagactttaaaatcaatttactgattttcaaaagttat
tcctttggtgatgtggaatactttatacttcataaggtacatggattcatttgtggggaattgatgtctttgctattgtggccatttt
gtcaagttgtgtaatattttacccatgccaactttgcatattgtatgtgagtttattcccagggttttaataggatgtttattgaag
ttgtcagtgtttccacaatttcatcgcctcagtgcttactgtttgcataaaaggaaacctactcacttttgcctattgctcttgtatt
caatcattttagttaactcttgtgttaattttgagagttttcagctgactgtctggggttttctttaatagactagccctttgtctgt
aaagaataattttatcgaattttcttaacactcacactctcccaccccaccccgctcatctccttttcattgggtcaaatct
gtagaatacaataaaagtaagagtgggaaccttagcctttaagtcgattttgcctttaaatgtgaatgttgctatgtttcggga
cattctctttatcaagttgcggatgtttccttagataattaacttaataaaagactggatgtttgctttcttcaaatcagaattgtgt
tgaatttatattgctattctgtttaattttgtttcaaaaaatttacatgcacaccttaaagataaccatgaccaaatagtcctcctg
ctgagagaaaatgttggccccaatgccacaggttacctcccgactcagataaactacaatgggagataaaatcagatttg
gcaaagcctgtggattcttgccataactctcagagcatgacttgggtgttttttccttttctaagtattttaatggtattttttgtgtta
caataggaaatctaggacacagagagtgattcaatgaggggaacgcattctgggatgactctaggcctctggtttgggga
gagctctattgaagtaaagacaatgagaggaagcaagtttgcagggaactgtgaggaatttagatggggaatgttgggttt
gaggtttctatagggcacgcaagcagagatgcactcaggaggaagaaggagcataaatctagtggcgctgccggcaa
gcttgctggaggaggccaattgggagctgctggaatgcatggaggcggcgctctcgaggctggaggaggccagctga
tttaaatcggtccgcgtacgatgcatattaccctgttatccctaccgcggttactggccgtcgttttacaacgtcgtgactgg
gaaaaccctggcgatgctcttctcccggtgaaaacctctgacacatggctcttctaaatccggagtttaaacgcttccttcat
gtgagcaaaaggccagcaaaaggccaggaaccgtaaaaaggccgcgttgctggcgtttttccataggctccgcccccc
tgacgagcatcacaaaaatcgacgctcaagtcagaggtggcgaaacccgacaggactataaagataccaggcgtttcc
ccctggaagctccctcgtgcgctctcctgttccgaccctgccgcttaccggatacctgtccgcctttctcccttcgggaagc
gtggcgctttctcatagctcacgctgtaggtatctcagttcggtgtaggtcgttcgctccaagctgggctgtgtgcacgaac
cccccgttcagcccgaccgctgcgccttatccggtaactatcgtcttgagtccaacccggtaagacacgacttatcgccac
tggcagcagccactggtaacaggattagcagagcgaggtatgtaggcggtgctacagagttcttgaagtggtggcctaa
ctacggctacactagaaggacagtatttggtatctgcgctctgctgaagccagttaccttcggaaaaagagttggtagctct
tgatccggcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcatgcctag
gtggcaaacagctattatgggtattatgggtctaccggtgcatgagattatcaaaaaggatcttcacctagatccttttaaatt
aaaaatgaagttttaaatcaatctaaagtatatatgagtaaacttggtctgacagttaccaatgcttaatcagtgaggcaccta
tctcagcgatctgtctatttcgttcatccatagttgcctgactccccgtcgtgtagataactacgatacgggagggcttaccat
ctggccccagtgctgcaatgataccgcgagacccacgctcaccggctccagatttatcagcaataaaccagccagccg
gaagggccgagcgcagaagtggtcctgcaactttatccgcctccatccagtctattaattgttgccgggaagctagagtaa
gtagttcgccagttaatagtttgcgcaacgttgttgccattgctacaggcatcgtggtgtcacgctcgtcgtttggtatggctt
```

-continued

```
cattcagctccggttcccaacgatcaaggcgagttacatgatcccccatgttgtgcaaaaaagcggttagctccttcggtc ctccgatcgttgtcagaagtaagttggccgcagtgttatcactcatggttatggcagcactgcataattctcttactgtcatgc catccgtaagatgcttttctgtgactggtgagtactcaaccaagtcattctgagaatagtgtatgcggcgaccgagttgctct tgcccggcgtcaatacgggataataccgcgccacatagcagaactttaaaagtgctcatcattggaaaacgttcttcggg gcgaaaactctcaaggatcttaccgctgttgagatccagttcgatgtaacccactcgtgcacccaactgatcttcagcatctt ttactttcaccagcgtttctgggtgagcaaaaacaggaaggcaaaatgccgcaaaaaagggaataagggcgacacgga aatgttgaatactcatactcttcctttttcaatattattgaagcatttatcagggttattgtctcgggagcggatacatatttgaat gtatttagaaaaa
```

SEQ ID 47

```
taaacaaatagggggttccgcgcacatttccccgaaaagtgccacctgacgtcgctgagcaggccctggcctccctggcc gagggcggtttgcgtattagaggcctaaatggccgaattcagcggataacaatttcacacaggaaacagctatgaccatg attatctagtaactataacggtcctaaggtagcgagcgatcgcttaattaacctgcagggataaccactgacccatgacgg gaactcccagggctcagctcttgactccaggttcgcagctgccccaaagcaatgcaaccctggctggccccgcctcat gcatccggcctcctccccaaagagctctgagcccacctgggcctaggtcctcctccctgggactcatggcctaagggta cagagttactggggctgatgaagggaccaatggggacaggggcctcaaatcaaagtggctgtctctctcatgtcccttcc tctcctcagggtccaaaatcagggtcagggccccagggcaggggctgagagggcctctttctgaaggccctgtctcagt gcaggttatgggggtctggggagggtcaatgcagggctcacccttcagtgccccaaagcctagagagtgagtgcctg ccagtggcttcccaggcccaatcccttgactgcctgggaatgctcaaatgcaggaactgtcacaacaccttcagtcaggg gctgctctgggaggaaaaacactcagaattgggggttcagggaaggcccagtgccaagcatagcaggagctcaggtg gctgcagatggtgtgaaccccaggagcaggatggccggcactcccccagaccctccagagcccaggttggctgcc ctcttcactgccgacacccctgggtccacttctgcccttcccacctaaaacctttagggctcccactttctcccaaatgtga gacatcaccacggctcccagggagtgtccagaagggcatctggctgagaggtcctgacatctgggagcctcaggcccc acaatggacagacgccctgccaggatgctgctgcagggctgttagctaggcggggtggagatggggtactttgcctctc agaggccccggccccaccatgaaacctcagtgacacccccatttccctgagttcacatacctgtatcctactccagtcacct tccccacgaaccccctgggagcccaggatgatgctggggctggagccacgaccagcccacgagtgatccagctctgcc aatcagcagtcatttcccaagtgttccagccctgccaggtcccactacagcagtaatggaggccccagacaccagtcca gcagttagagggctggactagcaccagcttttcaagcctcagcatctcaaggtgaatggccagtgccctccccgtggcc atcacaggatcgcagatatgaccctaggggaagaaatatcctgggagtaaggaagtgcccatactcaaggatggcccct ctgtgacctaacctgtccctgaggattgtacttccaggcgttaaaacagtagaacgcctgcctgtgaaccccgccaagg gactgcttggggaggcccctaaaccagaacacaggcactccagcaggacctctgaactctgaccaccctcagcaagt gggcaccccccgcagcttccaaggcaccccagggctcaccacagcggcccctcctggcagcccctcacccaggccc agaccctctaagatggcacatctaagccaatccacctccttgtcattcctcctgtccccacccaggacccttctcagatgaa accttcgctccagccgctgggccctctctcctgcccctctggcagttctccagggactccgcctcccactctctgtctctcc ctgcactcctaggaacaagcgacctccaggaagcccagtccaattatcccctctgtgtcctcccaatctctgcctctggg tggatttgagcaccacatcctgttctcttcgacctgaaactccttggccccggtgtccgctctcctgggccctcttttctctcct cccctcttccgtgcccgtttgtttggtgttacaggcaggccccggggagccgtccctccagctgctcttccttgtctgtctc aggagccagaaactggcagcatctaaaaagggctcctgtttcttcatctgcccagcctcctagcccaaccagggctctgg cctcactccagagggtgggctccagagggcaggggttgcaccctcttagtgcctcagaggctcagctgggtgcaggat gggggggccctcagggagcccctcagtgactgctgatcacttactgcaggactgttcccagctcttcccaatcattggaat gacaatacctagttctgctccatcatagtgatgcaggaaaaatgttactgaaatcctggttcttgtttagcaatcgaagaatg aattccgcgaacacacaggcagcaagcaagcgaagcctttattaaaggaaagcagatagctcccagggctgcaggga
```

-continued

```
gcggggagaagagctccccactctctattgtcctataggggcttttaccccttaaagttggggggatacaaaaaaataga agaaaaagggagttcccgtcagggcacagcagaaacaaatccaactaggaaccatgaggttgggggttcgattcctgg cctctctcagtgggttaaggatgcagcgttgccgtgagctatgatacaggtcacagatgcagctcagatctactagtcaatt gacaggcgccggagcaggagctaggcctttggccggccggcgcgccacgcgtataacttcgtatagcatacattatac gaagttatcttaagggctatggcagggcctgccgccccgacgttggctgcgagccctgggccttcacccgaacttgggg ggtggggtgggggaaaaggaagaaacgcgggcgtattggccccaatgggggtctcggtggggtatcgacagagtgcca gccctgggaccgaaccccgcgtttatgaacaaacgacccaacaccgtgcgttttattctgtcttttttattgccgtcatagcgc gggttccttccggtattgtctccttccgtgtttcactcgagttagaagaactcgtcaagaaggcgatagaaggcgatgcgct gcgaatcgggagcggcgataccgtaaagcacgaggaagcggtcagcccattcgccgccaagctcttcagcaatatcac gggtagccaacgctatgtcctgatagcggtccgccacacccagccggccacagtcgatgaatccagaaaagcggccat tttccaccatgatattcggcaagcaggcatcgccatgggtcacgacgagatcctcgccgtcgggcatgcgcgccttgag cctggcgaacagttcggctggcgcgagcccctgatgctcttcgtccagatcatcctgatcgacaagaccggcttccatcc gagtacgtgctcgctcgatgcgatgtttcgcttggtggtcgaatgggcaggtagccggatcaagcgtatgcagccgccg cattgcatcagccatgatggatactttctcggcaggagcaaggtgagatgacaggagatcctgccccggcacttcgccc aatagcagccagtcccttcccgcttcagtgacaacgtcgagcacagctgcgcaaggaacgcccgtcgtggccagccac gatagccgcgctgcctcgtcctgcagttcattcagggcaccggacaggtcggtcttgacaaaaagaaccgggcgcccct gcgctgacagccggaacacggcggcatcagagcagccgattgtctgttgtgcccagtcatagccgaatagcctctccac ccaagcggccggagaacctgcgtgcaatccatcttgttcaatggccgatcccattccagatctgttagcctccccatctc ccgtgcaaacgtgcgcgccaggtcgcagatcgtcggtatggagcctggggtggtgacgtgggtctggatcatcccgga ggtaagttgcagcagggcgtcccggcagccggcgggcgattggtcgtaatccaggataaagacgtgcatgggacgga ggcgtttggtcaagacgtccaaggcccaggcaaacacgttgtacaggtcgcccgttgggggccagcaactcggggccc cgaaacagggtaaataacgtgtccccgatatgggggtcgtgggcccgcgttgctctggggctcggcaccctggggcggc acggccgtccccgaaagctgtccccaatcctcccgccacgacccgccgcctgcagataccgcaccgtattggcaagc agcccgtaaacgcggcgaatcgcggccagcatagccaggtcaagccgctcgccggggcgctggcgtttggccaggc ggtcgatgtgtctgtcctccggaagggcccccaacacgatgtttgtgccgggcaaggtcggcgggatgagggccacga acgccagcacggcctgggggggtcatgctgcccataaggtatcgcgcggccgggtagcacaggagggcggcgatgg gatggcggtcgaagatgagggtgagggccgggggcggggcatgtgagctcccagcctccccccgatatgaggagc cagaacggcgtcggtcacggcataaggcatgcccattgttatctgggcgcttgtcattaccaccgccgcgtccccggcc gatatctcaccctggtcaaggcggtgttgtgtggtgtagatgttcgcgattgtctcggaagcccccagcacccgccagtaa gtcatcggctcgggtacgtagacgatatcgtcgcgcgaacccagggccaccagcagttgcgtggtggtggttttccccat cccgtggggaccgtctatataaaccccgcagtagcgtgggcattttctgctccgggcggacttccgtggcttcttgctgccg gcgagggcgcaacgccgtacgtcggttgctatggccgcgagaacgcgcagcctggtcgaacgcagacgcgtgctgat ggccggggtacgaagccatggtggctctagaggtcgaaaggcccggagatgaggaagaggagaacagcgcggcag acgtgcgcttttgaagcgtgcagaatgccgggcttccggaggaccttcgggcgcccgccccgcccctgagcccgcccc tgagcccgccccggacccacccctttcccagcctctgagcccagaaagcgaaggagccaaagctgctattggccgct gccccaaaggcctacccgcttccattgctcagcggtgctgtccatctgcacgagactagtgagacgtgctacttccatttgt cacgtcctgcacgacgcgagctgcggggcggggggaacttcctgactaggggaggagtagaaggtggcgcgaag gggccaccaaagaacggagccggttggcgcctaccggtggatgtggaatgtgtgcgaggccagaggccacttgtgta gcgccaagtgcccagcggggctgctaaagcgcatgctccagactgccttgggaaaagcgcctcccctacccggtagg gatccgcgttacataacttacggtaaatggccgcctggctgaccgcccaacgaccccgcccattgacgtcaataatga cgtatgttcccatagtaacgccaatagggactttccattgacgtcaatgggtggagtatttacggtaaactgcccacttggc
```

-continued

```
agtacatcaagtgtatcatatgccaagtacgcccctattgacgtcaatgacggtaaatggcccgcctggcattatgccca gtacatgaccttatgggactttcctacttggcagtacatctacgtattagtcatcgctattaccatggtgatgcggttttggcag tacatcaatgggcgtggatagcggtttgactcacggggatttccaagtctccaccccattgacgtcaatgggagtttgttttg gcaccaaaatcaacggtttaacaagcttataacttcgtatagcatacattatacgaagttattacgtagcggccgcgtcgacg atatcgctgccggagcccccggggccgctgccggaagatctggcattgctgtgactgtggtgtaggccggcagctgga gctctgattagacccctcacctgggaatctccatatgctgcacgtgcggccctaaaaagacaaaagacaaaaaaaaaa aaaaaaaaaaaatcaaaaaaaaacatagggggttaccaacgtggggtccagaaagatgtggttttctcccattggcctt gcccagttacctatatcagtccttgtccaacaggggttttaggggtggaaatgccccataaattttacggtttctttgcccttct cttcctttagactgagtcaccattgctctcattccttttctatcagttgaggagtgggttagagattaaggtccatgtggtggag gtacacttcttatagtaaacaaggcctatggggaattactctctggagcccttaaaccacaaatgataatccatgccacatc aaagatgcatcgaagcccatgctcctacactgactacctgagttagcattctgcctcaacaggactgaccatccccagctc tggggcagatatcctctctctgccacaagggcagtgaccccatgctgtctgagggtcacgctttacccccccccaccc ctgccgtgaccccagaccaccccaggaggtgggcactaatatccctcattaccccatagatgaggaaacagaggttc ccccggggtcccacaggtgctcagggtcacatgcaccgtgggcacccaggccccatcccaaggccaccctccctcctc aggaagctgtgctgcgctgggccagaaggtactgcacacgactcctcagcctccggtggtgggaggcagcctcaagc ctctgagtggggggcaccggggctcctcaatctatactgactcctgggggtgggagaagggagggggagctgtgg cctctgagtccactaagcaaatcagggtgggcaatgcgggcccatttcaaggaggagagaaccgaggctctgacagca ggccggggccagggacctgcccaggtcataggctgaactgctggctgacctgccttgggttctttccttggctcctc agccctgtgtgatgtgacaggtcattcattcactcactcgctcattcattcagcaaaccctcagtgagccctgctgggagca ggtgctaggggcaaggagacaggacctcttgccctggaacagctgaagcactgggggacaggcagtggcagggag gtgcgtgatcaccgctgacccccattccatcctccagcccccaggtcagtttccacccaccattgaccccaccatgtcctcc atccccaaggtcagtttcccgcccaaggagcatctccttacacactaggggacaaaatttcacggctgtcactgggcatctc tccacgctcatcacagccctctagcagccttgaagtcctgtagagccccttcccatttcacagaagggacaagactatgag ggccacaccgtgagccatgagccttaggctgtgagccgggacagcccctgcaggactggtggcctcagggcactggg tggggagggtgcacagtgggtgggcccttgtggaatagagaggagtgtcaggtcaggggaggggggcttggcctggc cctggcctgcctggtgtgcaaccctaggcagcccctccttcccaggcctcctacttcctggaggccaagcctcagggag gtaattgagtcaggtggggagggggggttgtggctttcttcacagcagaaaaacagagcccacaatagtgtccactga gacagaggggtcctgggggaggggaggggtgggaggtgactgctgagccctgtgggagggagggagcaactactg agctgagctgggtgactctcccatctgccccgccccctgtggggccagcagagtcaccgagagaacatgacccagcca ggcctggacagggggacacccatgtcctttaccccacagggttcactgagcctatctgccccaagcctgtgtctccctgg gacgagacccctcactcccaaccacaaaggtctaaactcaagttcccaacagccttgaaaatacagcttccgggggcct ccaaggagcagtcagccgtccactgccaggctcgctggctcagtgacacaggacacatcctgatgacggtccacctgt ctccaagcaggttctcctctgccgatggggcaacgagctcctcctgtggctccctggctggatgcgtgggaggcggggt gggggggcaggcggtgttcctggccgcacacaaggagcaccccaccagcatccgaagacgggggcccggtctttc cccaaaacactgcttgcgggagactttgtgacgtttccagggccatgctcccttcgggcagcttggggggacttctgctcc tatgtggtcacctgcagggactcccccaggccttgggacaaacaaagtgatgagagggagggttagtgggtcgggg cagggccagtctttggaccggtttatctgaaaagccagttggtcaccgggaaccacagcaaacctaaacccatttggcca ggcatctcccagggacagtctcccccaggatgcggggcccagggggggctccaggggtgacctgcgtcctggatttccc tgatgctcccagttcgtgcctctgtccaagcatgattttaatagtgccccttccactcccagaaatgtccaagtgtgggcaa taaattctggtcacctgagctcagtgtaactgtttgctgaatgacacttactgtaacaggttaaaatgggaggcccaaggcc
```

-continued

```
acgcagagccatcgaaggctctgtgtgtcccagccctgatagaagcatcaggatggggactgtggcctcaccaggggc
cacatccaggcggtcaccatggggttcctggtctccgtgggccttgactggagccctggtgtgagctcacccatccca
gcctgtgagaggcctggatgtgggcctgacatcatttcccacccagtgacagcactgcatgtgatggggcctctgggca
gccttttccccgggggaaactggcaggaatcaggaccaccaggacagggtcaggggagaggcgatgctgggcacc
agagcctggaccaccctcgggttctcagcgatgggcaaccctgccacccagggcccgccttcctggggagacatc
ggggtttccaggccatcctgggaggagggtgggagcctcagctagacccagctggcttgccccccatgccccggc
caagagagggtcttggagggaagggggaccccagaccagcctggcgagcccatcctcagggtctctggtcagacag
gggctcagctgagctccagggtagaccaaggccctgcgtggatgaggccagtgtggtcactgcccagagcaaagcca
cctctcagcagcccttcctgagcaccttctgtgtgcggggacatcagcagtggcaacacagccatgctggggactcag
ggctagagacaggggaccagcctatggagagtgggtagtgtcctgcagggcaggcttgtgccctggagaaaacaaac
cagggtgaggccagggacgctggccgggttcacagggtgatggctgagcacagagtgccaggggctggactgtcct
gactctgggttggtggctgagggcctgtgtccctctatgcctctgggttggtgataatggaaacttgctccctggagagac
aggacgaatggttgatgggaaatgaatgtttgcttgtcacttggttgactgttgttgccgttagcattgggcttcttgggccag
gcagcctcaggccagcactgctgggctccccacaggcccgacaccctcagccctgtgcagctggcctggcgaaacca
agaggccctgatgcccaaaatagccgggaaaccccaaccagcccagccctggcagcaggtgcctcccatttgcctgg
gctggggaggggtggctctggttctggaagtttctgccagtccagctggagaagggacctgtatcccagcacccagg
ccgcccaagcccctgcaccagggcctgggccaggcagagttgacatcaatcaattgggagctgctggaatgcatggag
gcggcgctctcgaggctggaggaggccagctgatttaaatcggtccgcgtacgatgcatattaccctgttatccctaccg
cggttactggccgtcgttttacaacgtcgtgactgggaaaaccctggcgatgctcttctcccggtgaaaacctctgacacat
ggctcttctaaatccggagtttaaacgcttccttcatgtgagcaaaaggccagcaaaaggccaggaaccgtaaaaaggc
cgcgttgctggcgttttccataggctccgcccccctgacgagcatcacaaaaatcgacgctcaagtcagaggtggcgaa
acccgacaggactataaagataccaggcgtttccccctggaagctccctcgtgcgctctcctgttccgaccctgccgctta
ccggatacctgtccgcctttctcccttcgggaagcgtggcgctttctcatagctcacgctgtaggtatctcagttcggtgtag
gtcgttcgctccaagctgggctgtgtgcacgaaccccccgttcagcccgaccgctgcgccttatccggtaactatcgtctt
gagtccaacccggtaagacacgacttatcgccactggcagcagccactggtaacaggattagcagagcgaggtatgta
ggcggtgctacagagttcttgaagtggtggcctaactacggctacactagaaggacagtatttggtatctgcgctctgctg
aagccagttaccttcggaaaaagagttggtagctcttgatccggcaaacaaaccaccgctggtagcggtggtttttttgttt
gcaagcagcagattacgcgcagaaaaaaaggatctcaagaagatcctttgatcttttctacggggtctgacgctcagtgg
aacgaaaactcacgttaagggattttggtcatgcctaggtggcaaacagctattatgggtattatgggtctaccggtgcatg
agattatcaaaaaggatcttcacctagatccttttaaattaaaaatgaagttttaaatcaatctaaagtatatatgagtaaacttg
gtctgacagttaccaatgcttaatcagtgaggcacctatctcagcgatctgtctatttcgttcatccatagttgcctgactccc
cgtcgtgtagataactacgatacgggagggcttaccatctggccccagtgctgcaatgataccgcgagacccacgctca
ccggctccagatttatcagcaataaaccagccagccggaagggccgagcgcagaagtggtcctgcaactttatccgcct
ccatccagtctattaattgttgccgggaagctagagtaagtagttcgccagttaatagtttgcgcaacgttgttgccattgcta
caggcatcgtggtgtcacgctcgtcgtttggtatggcttcattcagctccggttcccaacgatcaaggcgagttacatgatc
ccccatgttgtgcaaaaaagcggttagctccttcggtcctccgatcgttgtcagaagtaagttggccgcagtgttatcactc
atggttatggcagcactgcataattctcttactgtcatgccatccgtaagatgcttttctgtgactggtgagtactcaaccaag
tcattctgagaatagtgtatgcggcgaccgagttgctcttgcccggcgtcaatacgggataataccgcgccacatagcag
aactttaaaagtgctcatcattggaaaacgttcttcggggcgaaaactctcaaggatcttaccgctgttgagatccagttcga
```

-continued

```
tgtaacccactcgtgcacccaactgatcttcagcatcttttactttcaccagcgtttctgggtgagcaaaaacaggaaggca aaatgccgcaaaaagggaataagggcgacacggaaatgttgaatactcatactcttcctttttcaatattattgaagcattt atcagggttattgtctcgggagcggatacatatttgaatgtatttagaaaaa
```

The two-step strategy outline above, utilizing a vector pair, can be used to delete the entire J/C cluster region (i.e., all J/C units), multiple J/C units or an individual J/C unit.

Selectable Marker Genes

The DNA constructs can be designed to modify the endogenous, target immunoglobulin gene. The homologous sequence for targeting the construct can have one or more deletions, insertions, substitutions or combinations thereof. The alteration can be the insertion of a selectable marker gene fused in reading frame with the upstream sequence of the target gene.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See, for example, Song, K-Y., et al. Proc. Nat'l Acad. Sci. U.S.A. 84:6820-6824 (1987); Sambrook, J., et al., Molecular Cloning—A Laboratory Manual, Cold Spring Harbor Laboratory, Cold Spring Harbor, N.Y. (1989), Chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, J. Mol. Appl. Genet. 1:327-341 (1982)); and the hygromycin resistance gene (hyg) (Nucleic Acids Research 11:6895-6911 (1983), and Te Riele, H., et al., Nature 348:649-651 (1990)). Other selectable marker genes include: acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline.

Methods for the incorporation of antibiotic resistance genes and negative selection factors will be familiar to those of ordinary skill in the art (see, e.g., WO 99/15650; U.S. Pat. Nos. 6,080,576; 6,136,566; Niwa et al., J. Biochem. 113: 343-349 (1993); and Yoshida et al., Transgenic Research 4:277-287 (1995)).

Combinations of selectable markers can also be used. For example, to target an immunoglobulin gene, a neo gene (with or without its own promoter, as discussed above) can be cloned into a DNA sequence which is homologous to the immunoglobulin gene. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. In this particular example, those cells which are resistant to G418 and gancyclovir are most likely to have arisen by homologous recombination in which the neo gene has been recombined into the immunoglobulin gene but the tk gene has been lost because it was located outside the region of the double crossover.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5'-non-coding region (transcriptional regulatory region). Thus, the homologous region can extend beyond the coding region into the 5'-non-coding region or alternatively into the 3'-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. The mutation can be a subtle change, not exceeding about 5% of the homologous flanking sequences. Where mutation of a gene is desired, the marker gene can be inserted into an intron or an exon.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by E. coli, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

The present invention further includes recombinant constructs containing sequences of immunoglobulin genes. The constructs comprise a vector, such as a plasmid or viral vector, into which a sequence of the invention has been inserted, in a forward or reverse orientation. The construct can also include regulatory sequences, including, for example, a promoter, operably linked to the sequence. Large numbers of suitable vectors and promoters are known to those of skill in the art, and are commercially available. The following vectors are provided by way of example. Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmiacia), viral origin vectors (M13 vectors, bacterial phage 1 vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8). Other vectors include prokaryotic expression vectors such as pcDNA II, pSL301, pSE280, pSE380, pSE420, pTrcHisA, B, and C, pRSET A, B, and C (Invitrogen, Corp.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Invitrogen, Corp.) and variants and derivatives thereof. Other vectors include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof. Additional vectors that can be used include: pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSVSPORT1 (Invitrogen), pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZ☐, pGAPZ, pGAPZ☐, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; ☐ ExCell, ☐ gt11, pTrc99A, pKK223-3, pGEX-1 ☐T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2cp LIC, pBACgus-2cp LIC, pT7Blue-2 LIC, pT7Blue-2, ☐SCREEN-1, ☐BlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBAC-gus-1, pBAC4x-1, pBACgus4x-1, pBAC-3cp, pBACgus-2cp, pBACsurf-1, pig, Signal pig, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, p☐gal-Basic, p☐gal-Control, p☐gal-Promoter, p☐gal-Enhancer, pCMV☐, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, ☐gt10, ☐gt11, pWE15, and ☐TriplEx from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRT☐GAL, pNEO☐GAL, pRS403, pRS404, pRS405, pRS406, pRS413, pRS414, pRS415, and pRS416 from Stratagene and variants or derivatives thereof. Two-hybrid and reverse two-hybrid vectors can also be used, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof. Any other plasmids and vectors may be used as long as they are replicable and viable in the host.

Techniques which can be used to allow the DNA construct entry into the host cell include, for example, calcium phosphate/DNA co precipitation, microinjection of DNA into the nucleus, electroporation, bacterial protoplast fusion with intact cells, transfection, or any other technique known by one skilled in the art. The DNA can be single or double stranded, linear or circular, relaxed or supercoiled DNA. For various techniques for transfecting mammalian cells, see, for example, Keown et al., Methods in Enzymology Vol. 185, pp. 527-537 (1990).

In one specific embodiment, heterozygous or homozygous knockout cells can be produced by transfection of primary fetal fibroblasts with a knockout vector containing immunoglobulin gene sequence isolated from isogenic DNA. In another embodiment, the vector can incorporate a promoter trap strategy, using, for example, IRES (internal ribosome entry site) to initiate translation of the Neor gene.

Site Specific Recombinases

In additional embodiments, the targeting constructs can contain site specific recombinase sites, such as, for example, lox. In one embodiment, the targeting arms can insert the site specific recombinase target sites into the targeted region such that one site specific recombinase target site is located 5' to the second site specific recombinase target site. Then, the site specific recombinase can be activated and/or applied to the cell such that the intervening nucleotide sequence between the two site specific recombinase sites is excised.

Site-specific recombinases include enzymes or recombinases that recognize and bind to a short nucleic acid site or sequence-specific recombinase target site, i.e., a recombinase recognition site, and catalyze the recombination of nucleic acid in relation to these sites. These enzymes include recombinases, transposases and integrases. Examples of sequence-specific recombinase target sites include, but are not limited to, lox sites, att sites, dif sites and frt sites. Non-limiting examples of site-specific recombinases include, but are not limited to, bacteriophage P1 Cre recombinase, yeast FLP recombinase, Inti integrase, bacteriophage λ, phi 80, P22, P2, 186, and P4 recombinase, Tn3 resolvase, the Hin recombinase, and the Cin recombinase, E. coli xerC and xerD recombinases, Bacillus thuringiensis recombinase, TpnI and the β-lactamase transposons, and the immunoglobulin recombinases.

In one embodiment, the recombination site can be a lox site that is recognized by the Cre recombinase of bacteriophage P1. Lox sites refer to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as loxP511, loxP514, lox.DELTA.86, lox.DELTA.117, loxC2, loxP2, loxP3 and lox P23. Additional example of lox sites include, but are not limited to, loxB, loxL, loxR, loxP, loxP3, loxP23, loxΔ86, loxΔ117, loxP511, and loxC2.

In another embodiment, the recombination site is a recombination site that is recognized by a recombinases other than Cre. In one embodiment, the recombinase site can be the FRT sites recognized by FLP recombinase of the 2 pi plasmid of Saccharomyces cerevisiae. FRT sites refer to a nucleotide sequence at which the product of the FLP gene of the yeast 2 micron plasmid, FLP recombinase, can catalyze site-specific recombination. Additional examples of the non-Cre recombinases include, but are not limited to, site-specific recombinases include: att sites recognized by the Int recombinase of bacteriophage λ (e.g. att1, att2, att3, attP, attB, attL, and attR), the recombination sites recognized by the resolvase family, and the recombination site recognized by transposase of Bacillus thruingiensis.

In particular embodiments of the present invention, the targeting constructs can contain: sequence homologous to a porcine immunoglobulin gene as described herein, a selectable marker gene and/or a site specific recombinase target site.

Selection of Homologously Recombined Cells

The cells can then be grown in appropriately-selected medium to identify cells providing the appropriate integration. The presence of the selectable marker gene inserted into the immunoglobulin gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the immunoglobulin gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab, Cold Spring Harbor, N.Y. (pp. 469-497); and Linney and Donerly, Cell 35:693-699, 1983.

The cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics. In some situations, it can be desirable to have two different modified alleles. This can be achieved by successive rounds of gene targeting or by breeding heterozygotes, each of which carries one of the desired modified alleles.

Identification of Cells that have Undergone Homologous Recombination

In one embodiment, the selection method can detect the depletion of the immunoglobulin gene directly, whether due to targeted knockout of the immunoglobulin gene by homologous recombination, or a mutation in the gene that results in a nonfunctioning or nonexpressed immunoglobulin. Selection via antibiotic resistance has been used most commonly for screening (see above). This method can detect the presence of the resistance gene on the targeting vector, but does not directly indicate whether integration was a targeted recombination event or a random integration. Certain technology, such as Poly A and promoter trap technology, increase the probability of targeted events, but again, do not give direct evidence that the desired phenotype, a cell deficient in immunoglobulin gene expression, has been achieved. In addition, negative forms of selection can be used to select for targeted integration; in these cases, the gene for a factor lethal to the cells is inserted in such a way that only targeted events allow the cell to avoid death. Cells selected by these methods can then be assayed for gene disruption, vector integration and, finally, immunoglobulin gene depletion. In these cases, since the selection is based on detection of targeting vector integration and not at the altered phenotype, only targeted knockouts, not point mutations, gene rearrangements or truncations or other such modifications can be detected.

Animal cells believed to lacking expression of functional immunoglobulin genes can be further characterized. Such characterization can be accomplished by the following techniques, including, but not limited to: PCR analysis, Southern blot analysis, Northern blot analysis, specific lectin binding assays, and/or sequencing analysis.

PCR analysis as described in the art can be used to determine the integration of targeting vectors. In one embodiment, amplimers can originate in the antibiotic resistance gene and extend into a region outside the vector sequence. Southern analysis can also be used to characterize gross modifications in the locus, such as the integration of a targeting vector into the immunoglobulin locus. Whereas, Northern analysis can be used to characterize the transcript produced from each of the alleles.

Further, sequencing analysis of the cDNA produced from the RNA transcript can also be used to determine the precise location of any mutations in the immunoglobulin allele.

In another aspect of the present invention, ungulate cells lacking at least one allele of a functional region of an ungulate heavy chain, kappa light chain and/or lambda light chain locus produced according to the process, sequences and/or constructs described herein are provided. These cells can be obtained as a result of homologous recombination. Particularly, by inactivating at least one allele of an ungulate heavy chain, kappa light chain or lambda light chain gene, cells can be produced which have reduced capability for expression of porcine antibodies. In other embodiments, mammalian cells lacking both alleles of an ungulate heavy chain, kappa light chain and/or lambda light chain gene can be produced according to the process, sequences and/or constructs described herein. In a further embodiment, porcine animals are provided in which at least one allele of an ungulate heavy chain, kappa light chain and/or lambda light chain gene is inactivated via a genetic targeting event produced according to the process, sequences and/or constructs described herein. In another aspect of the present invention, porcine animals are provided in which both alleles of an ungulate heavy chain, kappa light chain and/or lambda light chain gene are inactivated via a genetic targeting event. The gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques. Additional genes for a desired protein or regulatory sequence that modulate transcription of an existing sequence can be inserted.

In embodiments of the present invention, alleles of ungulate heavy chain, kappa light chain or lambda light chain gene are rendered inactive according to the process, sequences and/or constructs described herein, such that functional ungulate immunoglobulins can no longer be produced. In one embodiment, the targeted immunoglobulin gene can be transcribed into RNA, but not translated into protein. In another embodiment, the targeted immunoglobulin gene can be transcribed in an inactive truncated form. Such a truncated RNA may either not be translated or can be translated into a nonfunctional protein. In an alternative embodiment, the targeted immunoglobulin gene can be inactivated in such a way that no transcription of the gene occurs. In a further embodiment, the targeted immunoglobulin gene can be transcribed and then translated into a nonfunctional protein.

III. Insertion of Artificial Chromosomes Containing Human Immunoglobulin Genes Artificial Chromosomes One aspect of the present invention provides ungulates and ungulate cells that lack at least one allele of a functional region of an ungulate heavy chain, kappa light chain and/or lambda light chain locus produced according to the processes, sequences and/or constructs described herein, which are further modified to express at least part of a human antibody (i.e. immunoglobulin (Ig)) locus. This human locus can undergo rearrangement and express a diverse population of human antibody molecules in the ungulate. These cloned, transgenic ungulates provide a replenishable, theoretically infinite supply of human antibodies (such as polyclonal antibodies), which can be used for therapeutic, diagnostic, purification, and other clinically relevant purposes.

In one particular embodiment, artificial chromosome (ACs) can be used to accomplish the transfer of human immunoglobulin genes into ungulate cells and animals. ACs permit targeted integration of megabase size DNA fragments that contain single or multiple genes. The ACs, therefore, can introduce heterologous DNA into selected cells for production of the gene product encoded by the heterologous DNA. In a one embodiment, one or more ACs with integrated human immunoglobulin DNA can be used as a vector for introduction of human Ig genes into ungulates (such as pigs).

First constructed in yeast in 1983, ACs are man-made linear DNA molecules constructed from essential cis-acting DNA sequence elements that are responsible for the proper replication and partitioning of natural chromosomes (Murray et al. (1983), Nature 301:189-193). A chromosome requires at least three elements to function. Specifically, the elements of an artificial chromosome include at least: (1) autonomous replication sequences (ARS) (having properties of replication origins—which are the sites for initiation of DNA replication), (2) centromeres (site of kinetochore assembly that is responsible for proper distribution of replicated chromosomes at mitosis and meiosis), and (3) telomeres (specialized structures at the ends of linear chromosomes that function to both stabilize the ends and facilitate the complete replication of the extreme termini of the DNA molecule).

In one embodiment, the human Ig can be maintained as an independent unit (an episome) apart from the ungulate chromosomal DNA. For example, episomal vectors contain the necessary DNA sequence elements required for DNA replication and maintenance of the vector within the cell. Episomal vectors are available commercially (see, for example, Maniatis, T. et al., Molecular Cloning, A Laboratory Manual (1982) pp. 368-369). The AC can stably replicate and segregate along side endogenous chromosomes. In an alternative embodiment, the human IgG DNA sequences can be integrated into the ungulate cell's chromosomes thereby permitting the new information to be replicated and partitioned to the cell's progeny as a part of the natural chromosomes (see, for example, Wigler et al. (1977), Cell 11:223). The AC can be translocated to, or inserted into, the endogenous chromosome of the ungulate cell. Two or more ACs can be introduced to the host cell simultaneously or sequentially.

ACs, furthermore, can provide an extra-genomic locus for targeted integration of megabase size DNA fragments that contain single or multiple genes, including multiple copies of a single gene operatively linked to one promoter or each copy or several copies linked to separate promoters. ACs can permit the targeted integration of megabase size DNA fragments that contain single or multiple human immunoglobulin genes. The ACs can be generated by culturing the cells with dicentric chromosomes (i.e., chromosomes with two centromeres) under such conditions known to one skilled in the art whereby the chromosome breaks to form a minichromosome and formerly dicentric chromosome.

ACs can be constructed from humans (human artificial chromosomes: "HACs"), yeast (yeast artificial chromosomes: "YACs"), bacteria (bacterial artificial chromosomes: "BACs"), bacteriophage P1-derived artificial chromosomes: "PACs") and other mammals (mammalian artificial chromosomes: "MACs"). The ACs derive their name (e.g., YAC, BAC, PAC, MAC, HAC) based on the origin of the centromere. A YAC, for example, can derive its centromere from S. cerevisiae. MACs, on the other hand, include an active mammalian centromere while HACs refer to chromosomes that include human centromeres. Furthermore, plant artificial chromosomes ("PLACs") and insect artificial chromosomes can also be constructed. The ACs can include elements derived from chromosomes that are responsible for both replication and maintenance. ACs, therefore, are capable of stably maintaining large genomic DNA fragments such as human Ig DNA.

In one embodiment, ungulates containing YACs are provided. YACs are genetically engineered circular chromosomes that contain elements from yeast chromosomes, such as S. cerevisiae, and segments of foreign DNAs that can be much larger than those accepted by conventional cloning vectors (e.g., plasmids, cosmids). YACs allow the propagation of very large segments of exogenous DNA (Schlessinger, D. (1990), Trends in Genetics 6:248-253) into mammalian cells and animals (Choi et al. (1993), Nature Gen 4:117-123). YAC transgenic approaches are very powerful and are greatly enhanced by the ability to efficiently manipulate the cloned DNA. A major technical advantage of yeast is the ease with which specific genome modifications can be made via DNA-mediated transformation and homologous recombination (Ramsay, M. (1994), Mol Biotech 1:181-201). In one embodiment, one or more YACs with integrated human Ig DNA can be used as a vector for introduction of human Ig genes into ungulates (such as pigs).

The YAC vectors contain specific structural components for replication in yeast, including: a centromere, telomeres, autonomous replication sequence (ARS), yeast selectable markers (e.g., TRP1, URA3, and SUP4), and a cloning site for insertion of large segments of greater than 50 kb of exogenous DNA. The marker genes can allow selection of the cells carrying the YAC and serve as sites for the synthesis of specific restriction endonucleases. For example, the TRP1 and URA3 genes can be used as dual selectable markers to ensure that only complete artificial chromosomes are maintained. Yeast selectable markers can be carried on both sides of the centromere, and two sequences that seed telomere formation in vivo are separated. Only a fraction of one percent of a yeast cell's total DNA is necessary for replication, however, including the center of the chromosome (the centromere, which serves as the site of attachment between sister chromatids and the sites of spindle fiber attachment during mitosis), the ends of the chromosome (telomeres, which serve as necessary sequences to maintain the ends of eukaryotic chromosomes), and another short stretch of DNA called the ARS which serves as DNA segments where the double helix can unwind and begin to copy itself.

In one embodiment, YACs can be used to clone up to about 1, 2, or 3 Mb of immunoglobulin DNA. In another embodiment, at least 25, 30, 40, 50, 60, 70, 75, 80, 85, 90, or 95 kilobases.

Yeast integrating plasmids, replicating vectors (which are fragments of YACs), can also be used to express human Ig. The yeast integrating plasmid can contain bacterial plasmid sequences that provide a replication origin and a drug-resistance gene for growth in bacteria (e.g., E. coli), a yeast marker gene for selection of transformants in yeast, and restriction sites for inserting Ig sequences. Host cells can stably acquire this plasmid by integrating it directly into a chromosome. Yeast replicating vectors can also be used to express human Ig as free plasmid circles in yeast. Yeast or ARS-containing vectors can be stabilized by the addition of a centromere sequence. YACs have both centromeric and telomeric regions, and can be used for cloning very large pieces of DNA because the recombinant is maintained essentially as a yeast chromosome.

YACs are provided, for example, as disclosed in U.S. Pat. Nos. 6,692,954, 6,495,318, 6,391,642, 6,287,853, 6,221,588, 6,166,288, 6,096,878, 6,015,708, 5,981,175, 5,939,255, 5,843,671, 5,783,385, 5,776,745, 5,578,461, and 4,889,806; European Patent Nos. 1 356 062 and 0 648 265; PCT Publication Nos. WO 03/025222, WO 02/057437, WO 02/101044, WO 02/057437, WO 98/36082, WO 98/12335, WO 98/01573, WO 96/01276, WO 95/14769, WO 95/05847, WO 94/23049, and WO 94/00569.

In another embodiment, ungulates containing BACs are provided. BACs are F-based plasmids found in bacteria, such as E. Coli, that can transfer approximately 300 kb of foreign DNA into a host cell. Once the Ig DNA has been cloned into the host cell, the newly inserted segment can be replicated along with the rest of the plasmid. As a result, billions of copies of the foreign DNA can be made in a very short time. In a particular embodiment, one or more BACs with integrated human Ig DNA are used as a vector for introduction of human Ig genes into ungulates (such as pigs).

The BAC cloning system is based on the E. coli F-factor, whose replication is strictly controlled and thus ensures stable maintenance of large constructs (Willets, N., and R. Skurray (1987), Structure and function of the F-factor and mechanism of conjugation. In Escherichia coli and Salmonella Typhimurium: Cellular and Molecular Biology (F. C. Neidhardt, Ed) Vol. 2 pp 1110-1133, Am. Soc. Microbiol., Washington, D.C.). BACs have been widely used for cloning of DNA from various eukaryotic species (Cai et al. (1995), Genomics 29:413-425; Kim et al. (1996), Genomics 34:213-218; Misumi et al. (1997), Genomics 40:147-150; Woo et al. (1994), Nucleic Acids Res 22:4922-4931; Zimmer, R. and Gibbins, A. M. V. (1997), Genomics 42:217-226). The low occurrence of the F-plasmid can reduce the potential for recombination between DNA fragments and can avoid the lethal overexpression of cloned bacterial genes. BACs can stably maintain the human immunoglobulin genes in a single copy vector in the host cells, even after 100 or more generations of serial growth.

BAC (or pBAC) vectors can accommodate inserts in the range of approximately 30 to 300 kb pairs. One specific type of BAC vector, pBeloBac11, uses a complementation of the lacZ gene to distinguish insert-containing recombinant molecules from colonies carrying the BAC vector, by color. When a DNA fragment is cloned into the lacZ gene of pBeloBac11, insertional activation results in a white colony on X-Gal/IPTG plates after transformation (Kim et al. (1996), Genomics 34:213-218) to easily identify positive clones.

For example, BACs can be provided such as disclosed in U.S. Pat. Nos. 6,713,281, 6,703,198, 6,649,347, 6,638,722, 6,586,184, 6,573,090, 6,548,256, 6,534,262, 6,492,577, 6,492,506, 6,485,912, 6,472,177, 6,455,254, 6,383,756, 6,277,621, 6,183,957, 6,156,574, 6,127,171, 5,874,259, 5,707,811, and 5,597,694; European Patent Nos. 0 805 851; PCT Publication Nos. WO 03/087330, WO 02/00916, WO 01/39797, WO 01/04302, WO 00/79001, WO 99/54487, WO 99/27118, and WO 96/21725.

In another embodiment, ungulates containing bacteriophage PACs are provided. In a particular embodiment, one or more bacteriophage PACs with integrated human Ig DNA are used as a vector for introduction of human Ig genes into ungulates (such as pigs). For example, PACs can be provided such as disclosed in U.S. Pat. Nos. 6,743,906, 6,730,500, 6,689,606, 6,673,909, 6,642,207, 6,632,934, 6,573,090, 6,544,768, 6,489,458, 6,485,912, 6,469,144, 6,462,176, 6,413,776, 6,399,312, 6,340,595, 6,287,854, 6,284,882, 6,277,621, 6,271,008, 6,187,533, 6,156,574, 6,153,740, 6,143,949, 6,017,755, and 5,973,133; European Patent Nos. 0 814 156; PCT Publication Nos. WO 03/091426, WO 03/076573, WO 03/020898, WO 02/101022, WO 02/070696, WO 02/061073, WO 02/31202, WO 01/44486, WO 01/07478, WO 01/05962, and WO 99/63103.

In a further embodiment, ungulates containing MACs are provided. MACs possess high mitotic stability, consistent and regulated gene expression, high cloning capacity, and non-immunogenicity. Mammalian chromosomes can be comprised of a continuous linear strand of DNA ranging in size from approximately 50 to 250 Mb. The DNA construct can further contain one or more sequences necessary for the DNA construct to multiply in yeast cells. The DNA construct can also contain a sequence encoding a selectable marker gene. The DNA construct can be capable of being maintained as a chromosome in a transformed cell with the DNA construct. MACs provide extra-genomic specific integration sites for introduction of genes encoding proteins of interest and permit megabase size DNA integration so that, for example, genes encoding an entire metabolic pathway, a very large gene [e.g., such as the cystic fibrosis (CF) gene (~600 kb)], or several genes [e.g., a series of antigens for preparation of a multivalent vaccine] can be stably introduced into a cell.

Mammalian artificial chromosomes [MACs] are provided. Also provided are artificial chromosomes for other higher eukaryotic species, such as insects and fish, produced using the MACS are provided herein. Methods for generating and isolating such chromosomes. Methods using the MACs to construct artificial chromosomes from other species, such as insect and fish species are also provided. The artificial chromosomes are fully functional stable chromosomes. Two types of artificial chromosomes are provided. One type, herein referred to as SATACs [satellite artificial chromosomes] are stable heterochromatic chromosomes, and the another type are minichromosomes based on amplification of euchromatin. As used herein, a formerly dicentric chromosome is a chromosome that is produced when a dicentric chromosome fragments and acquires new telomeres so that two chromosomes, each having one of the centromeres, are produced. Each of the fragments can be replicable chromosomes.

Also provided are artificial chromosomes for other higher eukaryotic species, such as insects and fish, produced using the MACS are provided herein. In one embodiment, SATACs [satellite artificial chromosomes] are provided. SATACs are stable heterochromatic chromosomes. In another embodiment, minichromosomes are provided wherein the minichromosomes are based on amplification of euchromatin.

In one embodiment, artificial chromosomes can be generated by culturing the cells with the dicentric chromosomes under conditions whereby the chromosome breaks to form a minichromosome and formerly dicentric chromosome. In one embodiment, the SATACs can be generated from the minichromosome fragment, see, for example, in U.S. Pat. No. 5,288,625. In another embodiment, the SATACs can be generated from the fragment of the formerly dicentric chromosome. The SATACs can be made up of repeating units of short satellite DNA and can be fully heterochromatic. In one embodiment, absent insertion of heterologous or foreign DNA, the SATACs do not contain genetic information. In other embodiments, SATACs of various sizes are provided that are formed by repeated culturing under selective conditions and subcloning of cells that contain chromosomes produced from the formerly dicentric chromosomes. These chromosomes can be based on repeating units 7.5 to 10 Mb in size, or megareplicons. These megareplicaonscan be tandem blocks of satellite DNA flanked by heterologous non-satellite DNA. Amplification can produce a tandem array of identical chromosome segments [each called an amplicon] that contain two inverted megareplicons bordered by heterologous ["foreign"] DNA. Repeated cell fusion, growth on selective medium and/or BrdU [5-bromodeoxyuridine] treatment or other genome destabilizing reagent or agent, such as ionizing radiation, including X-rays, and subcloning can result in cell lines that carry stable heterochromatic or partially heterochromatic chromosomes, including a 150-200 Mb "sausage" chromosome, a 500-1000 Mb gigachromosome, a stable 250-400 Mb megachromosome and various smaller stable chromosomes derived therefrom. These chromosomes are based on these repeating units and can include human immunoglobulin DNA that is expressed. (See also U.S. Pat. No. 6,743,967

In other embodiments, MACs can be provided, for example, as disclosed in U.S. Pat. Nos. 6,743,967, 6,682,729, 6,569,643, 6,558,902, 6,548,287, 6,410,722, 6,348,353, 6,297,029, 6,265,211, 6,207,648, 6,150,170, 6,150,160, 6,133,503, 6,077,697, 6,025,155, 5,997,881, 5,985,846, 5,981,225, 5,877,159, 5,851,760, and 5,721,118; PCT Publication Nos. WO 04/066945, WO 04/044129, WO 04/035729, WO 04/033668, WO 04/027075, WO 04/016791, WO 04/009788, WO 04/007750, WO 03/083054, WO 03/068910, WO 03/068909, WO 03/064613, WO 03/052050, WO 03/027315, WO 03/023029, WO 03/012126, WO 03/006610, WO 03/000921, WO 02/103032, WO 02/097059, WO 02/096923, WO 02/095003, WO 02/092615, WO 02/081710, WO 02/059330, WO 02/059296, WO 00/18941, WO 97/16533, and WO 96/40965.

In another aspect of the present invention, ungulates and ungulate cells containing HACs are provided. In a particular embodiment, one or more HACs with integrated human Ig DNA are used as a vector for introduction of human Ig genes into ungulates (such as pigs). In a particular embodiment, one or more HACs with integrated human Ig DNA are used to generate ungulates (for example, pigs) by nuclear transfer which express human Igs in response to immunization and which undergo affinity maturation.

Various approaches may be used to produce ungulates that express human antibodies ("human Ig"). These approaches include, for example, the insertion of a HAC containing both heavy and light chain Ig genes into an ungulate or the insertion of human B-cells or B-cell precursors into an ungulate during its fetal stage or after it is born (e.g., an immune deficient or immune suppressed ungulate) (see, for example, WO 01/35735, filed Nov. 17, 2000, US Ser. No. 02/08,645, filed Mar. 20, 2002). In either case, both human antibody producing cells and ungulate antibody-producing B-cells may be present in the ungulate. In an ungulate containing a HAC, a single B-cell may produce an antibody that contains a combination of ungulate and human heavy and light chain proteins. In still other embodiments, the total size of the HAC is at least to approximately 1, 2, 3, 4, 5, 6, 7, 8, 9 or 10 Mb.

For example, HACs can be provided such as disclosed in U.S. Pat. Nos. 6,642,207, 6,590,089, 6,566,066, 6,524,799, 6,500,642, 6,485,910, 6,475,752, 6,458,561, 6,455,026, 6,448,041, 6,410,722, 6,358,523, 6,277,621, 6,265,211, 6,146,827, 6,143,566, 6,077,697, 6,025,155, 6,020,142, and 5,972,649; U.S. Pat. Application No. 2003/0037347; PCT Publication Nos. WO 04/050704, WO 04/044156, WO 04/031385, WO 04/016791, WO 03/101396, WO 03/097812, WO 03/093469, WO 03/091426, WO 03/057923, WO 03/057849, WO 03/027638, WO 03/020898, WO 02/092812, and WO 98/27200.

Additional examples of ACs into which human immunoglobulin sequences can be inserted for use in the invention include, for example, BACs (e.g., pBeloBAC11 or pBAC108L; see, e.g., Shizuya et al. (1992), Proc Natl Acad Sci USA 89(18):8794-8797; Wang et al. (1997), Biotechniques 23(6):992-994), bacteriophage PACs, YACs (see, e.g., Burke (1990), Genet Anal Tech Appl 7(5):94-99), and MACs (see, e.g., Vos (1997), Nat. Biotechnol. 15(12):1257-1259; Ascenzioni et al. (1997), Cancer Lett 118(2):135-142), such as HACs, see also, U.S. Pat. Nos. 6,743,967, 6,716,608, 6,692,954, 6,670,154, 6,642,207, 6,638,722, 6,573,090, 6,492,506, 6,348,353, 6,287,853, 6,277,621, 6,183,957, 6,156,953, 6,133,503, 6,090,584, 6,077,697, 6,025,155, 6,015,708, 5,981,175, 5,874,259, 5,721,118, and 5,270,201; European Patent Nos. 1 437 400, 1 234 024, 1 356 062, 0 959 134, 1 056 878, 0 986 648, 0 648 265, and 0 338 266; PCT Publication Nos. WO 04/013299, WO 01/07478, WO 00/06715, WO 99/43842, WO 99/27118, WO 98/55637, WO 94/00569, and WO 89/09219. Additional examples include those AC provided in, for example, PCT Publication No. WO 02/076508, WO 03/093469, WO 02/097059; WO 02/096923; US Publication Nos US 2003/0113917 and US 2003/003435; and U.S. Pat. No. 6,025,155.

In other embodiments of the present invention, ACs transmitted through male gametogenesis in each generation. The AC can be integrating or non-integrating. In one embodiment, the AC can be transmitted through mitosis in substantially all dividing cells. In another embodiment, the AC can provide for position independent expression of a human immunogloulin nucleic acid sequence. In a particular embodiment, the AC can have a transmittal efficiency of at least 10% through each male and female gametogenesis. In one particular embodiment, the AC can be circular. In another particular embodiment, the non-integrating AC can be that deposited with the Belgian Coordinated Collections of Microorganisms—BCCM on Mar. 27, 2000 under accession number LMBP 5473 CB. In additional embodiments, methods for producing an AC are provided wherein a mitotically stable unit containing an exogenous nucleic acid transmitted through male gametogenesis is identified; and an entry site in the mitotically stable unit allows for the integration of human immunoglobulin genes into the unit.

In other embodiments, ACs are provided that include: a functional centromere, a selectable marker and/or a unique cloning site. Tin other embodiments, the AC can exhibit one or more of the following properties: it can segregate stably as an independent chromosome, immunoglobulin sequences can be inserted in a controlled way and can expressed from the AC, it can be efficiently transmitted through the male and female germline and/or the transgenic animals can bear the chromosome in greater than about 30, 40, 50, 60, 70, 80 or 90% of its cells.

In particular embodiments, the AC can be isolated from fibroblasts (such as any mammalian or human fibroblast) in which it was mitotically stable. After transfer of the AC into hamster cells, a lox (such as loxP) site and a selectable marker site can be inserted. In other embodiments, the AC can maintain mitotic stability, for example, showing a loss of less than about 5, 2, 1, 0.5 or 0.25 percent per mitosis in the absence of selection. See also, US 2003/0064509 and WO 01/77357.

Xenogenous Immunoglobulin Genes

In another aspect of the present invention, transgenic ungulates are provided that expresses a xenogenous immunoglobulin loci or fragment thereof, wherein the immunoglobulin can be expressed from an immunoglobulin locus that is integrated within an endogenous ungulate chromosome. In one embodiment, ungulate cells derived from the transgenic animals are provided. In one embodiment, the xenogenous immunoglobulin locus can be inherited by offspring. In another embodiment, the xenogenous immunoglobulin locus can be inherited through the male germ line by offspring. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In other embodiments, the transgenic ungulate that lacks any expression of functional endogenous immunoglobulins can be further genetically modified to express an xenogenous immunoglobulin loci. In an alternative embodiment, porcine animals are provided that contain an xenogenous immunoglobulin locus. In one embodiment, the xenogenous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In other embodiments, the transgenic ungulate that lacks any expression of functional endogenous immunoglobulins can be further genetically modified to express an xenogenous immunoglobulin loci. In an alternative embodiment, porcine animals are provided that contain an xenogenous immunoglobulin locus. In one embodiment, the xenogenous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In another embodiment, porcine animals are provided that contain an xenogenous immunoglobulin locus. In one embodiment, the xenogenous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

Human immunoglobulin genes, such as the Ig heavy chain gene (human chromosome 414), Ig kappa chain gene (human chromosome #2) and/or the Ig lambda chain gene (chromosome #22) can be inserted into Acs, as described above. In a particular embodiment, any portion of the human heavy, kappa and/or lambda Ig genes can be inserted into ACs. In one embodiment, the nucleic acid can be at least 70, 80, 90, 95, or 99% identical to the corresponding region of a naturally-occurring nucleic acid from a human. In other embodiments, more than one class of human antibody is produced by the ungulate. In various embodiments, more than one different human Ig or antibody is produced by the ungulate. In one embodiment, an AC containing both a human Ig heavy chain gene and Ig light chain gene, such as an automatic human artificial chromosome ("AHAC," a circular recombinant nucleic acid molecule that is converted to a linear human chromosome in vivo by an endogenously expressed restriction endonuclease) can be introduced. In one embodiment, the human heavy chain loci and the light chain loci are on different chromosome arms (i.e., on different side of the centromere). In one embodiments, the heavy chain can include the mu heavy chain, and the light chain can be a lambda or kappa light chain. The Ig genes can be introduced simultaneously or sequentially in one or more than one ACs.

In particular embodiments, the ungulate or ungulate cell expresses one or more nucleic acids encoding all or part of a human Ig gene which undergoes rearrangement and expresses more than one human Ig molecule, such as a human antibody protein. Thus, the nucleic acid encoding the human Ig chain or antibody is in its unrearranged form (that is, the nucleic acid has not undergone V(D)J recombination). In particular embodiments, all of the nucleic acid segments encoding a V gene segment of an antibody light chain can be separated from all of the nucleic acid segments encoding a J gene segment by one or more nucleotides. In a particular embodiment, all of the nucleic acid segments encoding a V gene segment of an antibody heavy chain can be separated from all of the nucleic acid segments encoding a D gene segment by one or more nucleotides, and/or all of the nucleic acid segments encoding a D gene segment of an antibody heavy chain are separated from all of the nucleic acid segments encoding a J gene segment by one or more nucleotides. Administration of an antigen to a transgenic ungulate containing an unrearranged human Ig gene is followed by the rearrangement of the nucleic acid segments in the human Ig gene locus and the production of human antibodies reactive with the antigen.

In one embodiment, the AC can express a portion or fragment of a human chromosome that contains an immunoglobulin gene. In one embodiment, the AC can express at least 300 or 1300 kb of the human light chain locus, such as described in Davies et al. 1993 Biotechnology 11: 911-914.

In another embodiment, the AC can express a portion of human chromosome 22 that contains at least the λ light-chain locus, including $V_\lambda$ gene segments, $J_\lambda$ gene segments, and the single $C_\lambda$ gene. In another embodiment, the AC can express at least one $V_\lambda$ gene segment, at least one $J_\lambda$ gene segment, and the $C_\lambda$ gene. In other embodiment, ACs can contain portions of the lambda locus, such as described in Popov et al. J Exp Med. 1999 May 17; 189(10):1611-20.

In another embodiment, the AC can express a portion of human chromosome 2 that contains at least the κ light-chain locus, including $V_\kappa$ gene segments, $J_\kappa$ gene segments and the single $C_\kappa$ gene. In another embodiment, the AC can express at least one $V_\kappa$ gene segment, at least one $J_\kappa$ gene segment and the $C_\kappa$ gene. In other embodiments, AC containing portions of the kappa light chain locus can be those describe, for example, in Li et al. 2000 J Immunol 164: 812-824 and Li S Proc Natl Acad Sci USA. 1987 June; 84(12):4229-33. In another embodiment, AC containing approximately 1.3 Mb of human kappa locus are provided, such as described in Zou et al FASEB J. 1996 August; 10(10):1227-32.

In further embodiments, the AC can express a portion of human chromosome 14 that contains at least the human heavy-chain locus, including $V_H$, $D_H$, $J_H$ and $C_H$ gene segments. In another embodiment, the AC can express at least one $V_H$ gene segment, at least one $D_H$ gene segment, at least one $J_H$ gene segment and at least one at least one $C_H$ gene segment. In other embodiments, the AC can express at least 85 kb of the human heavy chain locus, such as described in Choi et al. 1993 Nat Gen 4:117-123 and/or Zou et al. 1996 PNAS 96: 14100-14105.

In other embodiments, the AC can express portions of both heavy and light chain loci, such as, at least 220, 170, 800 or 1020 kb, for example, as disclosed in Green et al. 1994 Nat Gen 7:13-22; Mendez et al 1995 Genomics 26: 294-307; Mendez et al. 1997 Nat Gen 15: 146-156; Green et al. 1998 J Exp Med 188: 483-495 and/or Fishwild et al. 1996 Nat Biotech 14: 845-851. In another embodiment, the AC can express megabase amounts of human immunoglobulin, such as described in Nicholson J Immunol. 1999 Dec. 15; 163(12):6898-906 and Popov Gene. 1996 Oct. 24; 177(1-2):195-201. In addition, in one particular embodiment, MACs derived from human chromosome #14 (comprising the Ig heavy chain gene), human chromosome #2 comprising the Ig kappa chain gene) and human chromosome #22 (comprising the Ig lambda chain gene) can be introduced simultaneously or successively, such as described in US Patent Publication No. 2004/0068760 to Robl et al. In another embodiments, the total size of the MAC is less than or equal to approximately 10, 9, 8, or 7 megabases.

In a particular embodiment, human Vh, human Dh, human Jh segments and human mu segments of human immunoglobulins in germline configuration can be inserted into an AC, such as a YAC, such that the Vh, Dh, Jh and mu DNA segments form a repertoire of immunoglobulins containing portions which correspond to the human DNA segments, for example, as described in U.S. Pat. No. 5,545,807 to the Babraham Institute. Such ACs, after insertion into ungulate cells and generation of ungulates can produce heavy chain immunoglobulins. In one embodiment, these immunoglobulins can form functional heavy chain-light chain immunoglobulins. In another embodiment, these immunoglobulins can be expressed in an amount allowing for recovery from suitable cells or body fluids of the ungulate. Such immunoglobulins can be inserted into yeast artificial chromosome vectors, such as described by Burke, D T, Carle, G F and Olson, M V (1987) "Cloning of large segments of exogenous DNA into yeast by means of artificial chromosome vectors" Science, 236, 806-812, or by introduction of chromosome fragments (such as described by Richer, J and Lo, C W (1989) "Introduction of human DNA into mouse eggs by injection of dissected human chromosome fragments" Science 245, 175-177).

Additional information on specific ACs containing human immunoglobulin genes can be found in, for example, recent reviews by Giraldo & Montoliu (2001) Transgenic Research 10: 83-103 and Peterson (2003) Expert Reviews in Molecular Medicine 5: 1-25.

AC Transfer Methods

The human immunoglobulin genes can be first inserted into ACs and then the human-immunoglobulin-containing ACs can be inserted into the ungulate cells. Alternatively, the ACs can be transferred to an intermediary mammalian cell, such as a CHO cell, prior to insertion into the ungulate call. In one embodiment, the intermediary mammalian cell can also contain and AC and the first AC can be inserted into the AC of the mammalian cell. In particular, a YAC containing human immunoglobulin genes or fragments thereof in a yeast cell can be transferred to a mammalian cell that harbors an MAC. The YAC can be inserted into the MAC. The MAC can then be transferred to an ungulate cell. The human Ig genes can be inserted into ACs by homologous recombination. The resulting AC containing human Ig genes, can then be introduced into ungulate cells. One or more ungulate cells can be selected by techniques described herein or those known in the art, which contain an AC containing a human Ig.

Suitable hosts for introduction of the ACs are provided herein, which include but are not limited to any animal or plant, cell or tissue thereof, including, but not limited to: mammals, birds, reptiles, amphibians, insects, fish, arachnids, tobacco, tomato, wheat, monocots, dicots and algae. In one embodiment, the ACs can be condensed (Marschall et al Gene Ther. 1999 September; 6(9):1634-7) by any reagent known in the art, including, but not limited to, spermine, spermidine, polyethylenimine, and/or polylysine prior to introduction into cells. The ACs can be introduced by cell fusion or microcell fusion or subsequent to isolation by any method known to those of skill in this art, including but not limited to: direct DNA transfer, electroporation, nuclear transfer, microcell fusion, cell fusion, spheroplast fusion, lipid-mediated transfer, lipofection, liposomes, microprojectile bombardment, microinjection, calcium phosphate precipitation and/or any other suitable method. Other methods for introducing DNA into cells, include nuclear microinjection, electroporation, bacterial protoplast fusion with intact cells. Polycations, such as polybrene and polyornithine, may also be used. For various techniques for transforming mammalian cells, see e.g., Keown et al. Methods in Enzymology (1990) Vol. 185, pp. 527-537; and Mansour et al. (1988) Nature 336:348-352.

The ACs can be introduced by direct DNA transformation; microinjection in cells or embryos, protoplast regeneration for plants, electroporation, microprojectile gun and other such methods known to one skilled in the art (see, e.g., Weissbach et al. (1988) Methods for Plant Molecular Biology, Academic Press, N.Y., Section VIII, pp. 421-463; Grierson et al. (1988) Plant Molecular Biology, 2d Ed., Blackie, London, Ch. 7-9; see, also U.S. Pat. Nos. 5,491,075; 5,482,928; and 5,424,409; see, also, e.g., U.S. Pat. No. 5,470,708).

In particular embodiments, one or more isolated YACs can be used that harbor human Ig genes. The isolated YACs can be condensed (Marschall et al Gene Ther. 1999 September; 6(9):1634-7) by any reagent known in the art, including, but not limited to spermine, spermidine, polyethylenimine, and/or polylysine. The condensed YACs can then be transferred to porcine cells by any method known in the art (for example, microinjection, electroporation, lipid mediated transfection, etc). Alternatively, the condensed YAC can be transferred to oocytes via sperm-mediated gene transfer or intracytoplasmic sperm injection (ICSI) mediated gene transfer. In one embodiment, spheroplast fusion can be used to transfer YACs that harbor human Ig genes to porcine cells.

In other embodiments of the invention, the AC containing the human Ig can be inserted into an adult, fetal, or embryonic ungulate cell. Additional examples of ungulate cells include undifferentiated cells, such as embryonic cells (e.g., embryonic stem cells), differentiated or somatic cells, such as epithelial cells, neural cells epidermal cells, keratinocytes, hematopoietic cells, melanocytes, chondrocytes, B-lymphocytes, T-lymphocytes, erythrocytes, macrophages, monocytes, fibroblasts, muscle cells, cells from the female reproductive system, such as a mammary gland, ovarian cumulus, granulosa, or oviductal cell, germ cells, placental cell, or cells derived from any organ, such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, and uterus or any other cell type described herein.

Site Specific Recombinase Mediated Transfer

In particular embodiments of the present invention, the transfer of ACs containing human immunoglobulin genes to porcine cells, such as those described herein or known in the art, can be accomplished via site specific recombinase mediated transfer. In one particular embodiment, the ACs can be transferred into porcine fibroblast cells. In another particular embodiment, the ACs can be YACs.

In other embodiments of the present invention, the circularized DNA, such as an AC, that contain the site specific recombinase target site can be transferred into a cell line that has a site specific resombinase target site within its genome. In one embodiment, the cell's site specific recombinase target site can be located within an exogenous chromosome. The exogenous chromosome can be an artificial chromosome that does not integrate into the host's endogenous genome. In one embodiment, the AC can be transferred via germ line transmission to offspring. In one particular embodiment, a YAC containing a human immunoglobulin gene or fragment thereof can be circularized via a site specific recombinase and then transferred into a host cell that contains a MAC, wherein the MAC contains a site specific recombinase site. This MAC that now contains human immunoglobulin loci or fragments thereof can then be fused with a porcine cell, such as, but not limited to, a fibroblast. The porcine cell can then be used for nuclear transfer.

In certain embodiments of the present invention, the ACs that contain human immunoglobulin genes or fragments thereof can be transferred to a mammalian cell, such as a CHO cell, prior to insertion into the ungulate call. In one embodiment, the intermediary mammalian cell can also contain and AC and the first AC can be inserted into the AC of the mammalian cell. In particular, a YAC containing human immunoglobulin genes or fragments thereof in a yeast cell can be transferred to a mammalian cell that harbors a MAC. The YAC can be inserted in the MAC. The MAC can then be transferred to an ungulate cell. In particular embodiments, the YAC harboring the human Ig genes or fragments thereof can contain site specific recombinase target sites. The YAC can first be circularized via application of the appropriate site specific recombinase and then inserted into a mammalian cell that contains its own site specific recombinase target site. Then, the site specific recombinase can be applied to integrate the YAC into the MAC in the intermediary mammalian cell. The site specific recombinase can be applied in cis or trans. In particular, the site specific recombinase can be applied in trans. In one embodiment, the site specific recombinase can be expressed via transfection of a site specific recombinase expression plasmid, such as a Cre expression plasmid. In addition, one telomere region of the YAC can also be retrofitted with a selectable marker, such as a selectable marker described herein or known in the art. The human Ig genes or fragments thereof within the MAC of the intermediary mammalian cell can then be transferred to an ungulate cell, such as a fibroblast.

Alternatively, the AC, such as a YAC, harboring the human Ig genes or fragments thereof can contain site specific recombinase target sites optionally located near each telomere. The YAC can first be circularized via application of the appropriate site specific recombinase and then inserted into an ungulate cell directly that contains its own site specific recombinase target site within it genome. Alternatively, the ungulate cell can harbor its own MAC, which contains a site specific recombinase target site. In this embodiment, the YAC can be inserted directly into the endogenous genome of the ungulate cell. In particular embodiments, the ungulate cell can be a fibroblast cell or any other suitable cell that can be used for nuclear transfer. See, for example, FIG. 7; Call et al., Hum Mol Genet. 2000 Jul. 22; 9(12):1745-51.

In other embodiments, methods to circularize at least 100 kb of DNA are provided wherein the DNA can then be integrated into a host genome via a site specific recombinase. In one embodiment, at least 100, 200, 300, 400, 500, 1000, 2000, 5000, 10,000 kb of DNA can be circularized. In another embodiment, at least 1000, 2000, 5000, 10,000, or 20,000 megabases of DNA can be circularized. In one embodiment, the circularization of the DNA can be accomplished by attaching site specific recombinase target sites at each end of the DNA sequence and then applying the site specific recombinase to result in circularization of the DNA. In one embodiment, the site specific recombinase target site can be lox. In another embodiment, the site specific recombinase target site can be Fit. In certain embodiments, the DNA can be an artificial chromosome, such as a YAC or any AC described herein or known in the art. In another embodiment, the AC can contain human immunoglobulin loci or fragments thereof.

In another preferred embodiment, the YAC can be converted to, or integrated within, an artificial mammalian chromosome. The mammalian artificial chromosome is either transferred to or harbored within a porcine cell. The artificial chromosome can be introduced within the porcine genome through any method known in the art including but not limited to direct injection of metaphase chromosomes, lipid mediated gene transfer, or microcell fusion.

Site-specific recombinases include enzymes or recombinases that recognize and bind to a short nucleic acid site or sequence-specific recombinase target site, i.e., a recombinase recognition site, and catalyze the recombination of nucleic acid in relation to these sites. These enzymes include recombinases, transposases and integrases. Examples of sequence-specific recombinase target sites include, but are not limited to, lox sites, att sites, dif sites and frt sites. Non-limiting examples of site-specific recombinases include, but are not limited to, bacteriophage P1 Cre recombinase, yeast FLP recombinase, Inti integrase, bacteriophage λ, phi 80, P22, P2, 186, and P4 recombinase, Tn3 resolvase, the Hin recombinase, and the Cin recombinase, *E. coli* xerC and xerD recombinases, *Bacillus thuringiensis* recombinase, TpnI and the β-lactamase transposons, and the immunoglobulin recombinases.

In one embodiment, the recombination site can be a lox site that is recognized by the Cre recombinase of bacteriophage P1. Lox sites refer to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as loxP511, loxP514, lox.DELTA.86, lox.DELTA.117, loxC2, loxP2, loxP3 and lox P23. Additional example of lox sites include, but are not limited to, loxB, loxL, loxR, loxP, loxP3, loxP23, loxΔ86, loxΔ117, loxP511, and loxC2.

In another embodiment, the recombination site is a recombination site that is recognized by a recombinases other than Cre. In one embodiment, the recombinase site can be the FRT sites recognized by FLP recombinase of the 2 pi plasmid of *Saccharomyces cerevisiae*. FRT sites refer to a nucleotide sequence at which the product of the FLP gene of the yeast 2 micron plasmid, FLP recombinase, can catalyze site-specific recombination. Additional examples of the non-Cre recombinases include, but are not limited to, site-specific recombinases include: att sites recognized by the Int recombinase of bacteriophage λ.(e.g. att1, att2, att3, attP, attB, attL, and attR), the recombination sites recognized by the resolvase family, and the recombination site recognized by transposase of *Bacillus thruingiensis*.

IV. Production of Genetically Modified Animals

In additional aspects of the present invention, ungulates that contain the genetic modifications described herein can be produced by any method known to one skilled in the art. Such methods include, but are not limited to: nuclear transfer, intracytoplasmic sperm injection, modification of zygotes directly and sperm mediated gene transfer.

In another embodiment, a method to clone such animals, for example, pigs, includes: enucleating an oocyte, fusing the oocyte with a donor nucleus from a cell in which at least one allele of at least one immunoglobulin gene has been inactivated, and implanting the nuclear transfer-derived embryo into a surrogate mother.

Alternatively, a method is provided for producing viable animals that lack any expression of functional immunoglobulin by inactivating both alleles of the immunoglobulin gene in embryonic stem cells, which can then be used to produce offspring.

In another aspect, the present invention provides a method for producing viable animals, such as pigs, in which both alleles of the immunoglobulin gene have been rendered inactive. In one embodiment, the animals are produced by cloning using a donor nucleus from a cell in which both alleles of the immunoglobulin gene have been inactivated. In one embodiment, both alleles of the immunoglobulin gene are inactivated via a genetic targeting event.

Genetically altered animals that can be created by modifying zygotes directly. For mammals, the modified zygotes can be then introduced into the uterus of a pseudopregnant female capable of carrying the animal to term. For example, if whole animals lacking an immunoglobulin gene are desired, then embryonic stem cells derived from that animal can be targeted and later introduced into blastocysts for growing the modified cells into chimeric animals. For embryonic stem cells, either an embryonic stem cell line or freshly obtained stem cells can be used.

In a suitable embodiment of the invention, the totipotent cells are embryonic stem (ES) cells. The isolation of ES cells from blastocysts, the establishing of ES cell lines and their subsequent cultivation are carried out by conventional methods as described, for example, by Doetchmann et al., J. Embryol. Exp. Morph. 87:27-45 (1985); Li et al., Cell 69:915-926 (1992); Robertson, E. J. "Tetracarcinomas and Embryonic Stem Cells: A Practical Approach," ed. E. J. Robertson, IRL Press, Oxford, England (1987); Wurst and Joyner, "Gene Targeting: A Practical Approach," ed. A. L. Joyner, IRL Press, Oxford, England (1993); Hogen et al., "Manipulating the Mouse Embryo: A Laboratory Manual," eds. Hogan, Beddington, Costantini and Lacy, Cold Spring Harbor Laboratory Press, New York (1994); and Wang et al., Nature 336:741-744 (1992). In another suitable embodiment of the invention, the totipotent cells are embryonic germ (EG) cells. Embryonic Germ cells are undifferentiated cells functionally equivalent to ES cells, that is they can be cultured and transfected in vitro, then contribute to somatic and germ cell lineages of a chimera (Stewart et al., Dev. Biol. 161:626-628 (1994)). EG cells are derived by culture of primordial germ cells, the progenitors of the gametes, with a combination of growth factors: leukemia inhibitory factor, steel factor and basic fibroblast growth factor (Matsui et al., Cell 70:841-847 (1992); Resnick et al., Nature 359:550-551 (1992)). The cultivation of EG cells can be carried out using methods described in the article by Donovan et al., "Transgenic Animals, Generation and Use," Ed. L. M. Houdebine, Harwood Academic Publishers (1997), and in the original literature cited therein.

Tetraploid blastocysts for use in the invention may be obtained by natural zygote production and development, or by known methods by electrofusion of two-cell embryos and subsequently cultured as described, for example, by James et al., Genet. Res. Camb. 60:185-194 (1992); Nagy and Rossant, "Gene Targeting: A Practical Approach," ed. A. L. Joyner, IRL Press, Oxford, England (1993); or by Kubiak and Tarkowski, Exp. Cell Res. 157:561-566 (1985).

The introduction of the ES cells or EG cells into the blastocysts can be carried out by any method known in the art. A suitable method for the purposes of the present invention is the microinjection method as described by Wang et al., EMBO J. 10:2437-2450 (1991).

Alternatively, by modified embryonic stem cells transgenic animals can be produced. The genetically modified embryonic stem cells can be injected into a blastocyst and then brought to term in a female host mammal in accordance with conventional techniques. Heterozygous progeny can then be screened for the presence of the alteration at the site of the target locus, using techniques such as PCR or Southern blotting. After mating with a wild-type host of the same species, the resulting chimeric progeny can then be crossmated to achieve homozygous hosts.

After transforming embryonic stem cells with the targeting vector to alter the immunoglobulin gene, the cells can be plated onto a feeder layer in an appropriate medium, e.g., fetal bovine serum enhanced DMEM. Cells containing the construct can be detected by employing a selective medium, and after sufficient time for colonies to grow, colonies can be picked and analyzed for the occurrence of homologous recombination. Polymerase chain reaction can be used, with primers within and without the construct sequence but at the target locus. Those colonies which show homologous recombination can then be used for embryo manipulating and blastocyst injection. Blastocysts can be obtained from superovulated females. The embryonic stem cells can then be trypsinized and the modified cells added to a droplet containing the blastocysts. At least one of the modified embryonic stem cells can be injected into the blastocoel of the blastocyst. After injection, at least one of the blastocysts can be returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected, and then genotyping can be conducted to probe for the presence of the modified immunoglobulin gene.

In other embodiments, sperm mediated gene transfer can be used to produce the genetically modified ungulates described herein. The methods and compositions described herein to either eliminate expression of endogenous immunoglobulin genes or insert xenogenous immunoglobulin genes can be used to genetically modify the sperm cells via any technique described herein or known in the art. The genetically modified sperm can then be used to impregnate a female recipient via artificial insemination, intracytoplasmic sperm injection or any other known technique. In one embodiment, the sperm and/or sperm head can be incubated with the exogenous nucleic acid for a sufficient time period. Sufficient time periods include, for example, about 30 seconds to about 5 minutes, typically about 45 seconds to about 3 minutes, more typically about 1 minute to about 2 minutes. In particular embodiments, the expression of xenogenous, such as human, immunoglobulin genes in ungulates as described herein, can be accomplished via intracytoplasmic sperm injection.

The potential use of sperm cells as vectors for gene transfer was first suggested by Brackett et al., Proc., Natl. Acad. Sci. USA 68:353-357 (1971). This was followed by reports of the production of transgenic mice and pigs after in vitro fertilization of oocytes with sperm that had been incubated by naked DNA (see, for example, Lavitrano et al., Cell 57:717-723 (1989) and Gandolfi et al. Journal of Reproduction and Fertility Abstract Series 4, 10 (1989)), although other laboratories were not able to repeat these experiments (see, for example, Brinster et al. Cell 59:239-241 (1989) and Gavora et al., Canadian Journal of Animal Science 71:287-291 (1991)). Since then, there have been several reports of successful sperm mediated gene transfer in chicken (see, for example, Nakanishi and Iritani, Mol. Reprod. Dev. 36:258-261 (1993)); mice (see, for example, Maione, Mol. Reprod. Dev. 59:406 (1998)); and pigs (see, for example, Lavitrano et al. Transplant. Proc. 29:3508-3509 (1997); Lavitrano et al., Proc. Natl. Acad. Sci. USA 99:14230-5 (2002); Lavitrano et al., Mol. Reprod. Dev. 64-284-91 (2003)). Similar techniques are also described in U.S. Pat. No. 6,376,743; issued Apr. 23, 2002; U.S. Patent Publication Nos. 20010044937, published Nov. 22, 2001, and 20020108132, published Aug. 8, 2002.

In other embodiments, intracytoplasmic sperm injection can be used to produce the genetically modified ungulates described herein. This can be accomplished by co-inserting an exogenous nucleic acid and a sperm into the cytoplasm of an unfertilized oocyte to form a transgenic fertilized oocyte, and allowing the transgenic fertilized oocyte to develop into a transgenic embryo and, if desired, into a live offspring. The sperm can be a membrane-disrupted sperm head or a demembranated sperm head. The co-insertion step can include the substep of preincubating the sperm with the exogenous nucleic acid for a sufficient time period, for example, about 30 seconds to about 5 minutes, typically about 45 seconds to about 3 minutes, more typically about 1 minute to about 2 minutes. The co-insertion of the sperm and exogenous nucleic acid into the oocyte can be via microinjection. The exogenous nucleic acid mixed with the sperm can contain more than one transgene, to produce an embryo that is transgenic for more than one transgene as described herein. The intracytoplasmic sperm injection can be accomplished by any technique known in the art, see, for example, U.S. Pat. No. 6,376,743. In particular embodiments, the expression of xenogenous, such as human, immunoglobulin genes in ungulates as described herein, can be accomplished via intracytoplasmic sperm injection.

Any additional technique known in the art may be used to introduce the transgene into animals. Such techniques include, but are not limited to pronuclear microinjection (see, for example, Hoppe, P. C. and Wagner, T. E., 1989, U.S. Pat. No. 4,873,191); retrovirus mediated gene transfer into germ lines (see, for example, Van der Putten et al., 1985, Proc. Natl. Acad. Sci., USA 82:6148-6152); gene targeting in embryonic stem cells (see, for example, Thompson et al., 1989, Cell 56:313-321; Wheeler, M. B., 1994, WO 94/26884); electroporation of embryos (see, for example, Lo, 1983, Mol Cell. Biol. 3:1803-1814); cell gun; transfection; transduction; retroviral infection; adenoviral infection; adenoviral-associated infection; liposome-mediated gene transfer; naked DNA transfer; and sperm-mediated gene transfer (see, for example, Lavitrano et al., 1989, Cell 57:717-723); etc. For a review of such techniques, see, for example, Gordon, 1989, Transgenic Animals, Intl. Rev. Cytol. 115:171-229. In particular embodiments, the expression of xenogenous, such as human, immunoglobulin genes in ungulates as described herein, can be accomplished via these techniques.

Somatic Cell Nuclear Transfer to Produce Cloned, Transgenic Offspring

In a further aspect of the present invention, ungulate, such as porcine or bovine, cells lacking one allele, optionally both alleles of an ungulate heavy chain, kappa light chain and/or lambda light chain gene can be used as donor cells for nuclear transfer into recipient cells to produce cloned, transgenic animals. Alternatively, ungulate heavy chain, kappa light chain and/or lambda light chain gene knockouts can be created in embryonic stem cells, which are then used to produce offspring. Offspring lacking a single allele of a functional ungulate heavy chain, kappa light chain and/or lambda light chain gene produced according to the process, sequences and/or constructs described herein can be breed to further produce offspring lacking functionality in both alleles through mendelian type inheritance.

In another embodiment, the present invention provides a method for producing viable pigs that lack any expression of functional alpha-1,3-GT by breeding a male pig heterozygous for the alpha-1,3-GT gene with a female pig heterozygous for the alpha-1,3-GT gene. In one embodiment, the pigs are heterozygous due to the genetic modification of one allele of the alpha-1,3-GT gene to prevent expression of that allele. In another embodiment, the pigs are heterozygous due to the presence of a point mutation in one allele of the alpha-1,3-GT gene. In another embodiment, the point mutation can be a T-to-G point mutation at the second base of exon 9 of the alpha-1,3-GT gene. In one specific embodiment, a method to produce a porcine animal that lacks any expression of functional alpha-1,3-GT is provided wherein a male pig that contains a T-to-G point mutation at the second base of exon 9 of the alpha-1,3-GT gene is bred with a female pig that contains a T-to-G point mutation at the second base of exon 9 of the alpha-1,3-GT gene, or vise versa.

The present invention provides a method for cloning an animal, such as a pig, lacking a functional immunoglobulin gene via somatic cell nuclear transfer. In general, the animal can be produced by a nuclear transfer process comprising the following steps: obtaining desired differentiated cells to be used as a source of donor nuclei; obtaining oocytes from the animal; enucleating said oocytes; transferring the desired differentiated cell or cell nucleus into the enucleated oocyte, e.g., by fusion or injection, to form NT units; activating the resultant NT unit; and transferring said cultured NT unit to a host animal such that the NT unit develops into a fetus.

Nuclear transfer techniques or nuclear transplantation techniques are known in the art (Dai et al. Nature Biotechnology 20:251-255; Polejaeva et al Nature 407:86-90 (2000); Campbell et al, Theriogenology, 43:181 (1995); Collas et al, Mol. Report Dev., 38:264-267 (1994); Keefer et al, Biol. Reprod., 50:935-939 (1994); Sims et al, Proc. Natl. Acad. Sci., USA, 90:6143-6147 (1993); WO 94/26884; WO 94/24274, and WO 90/03432, U.S. Pat. Nos. 4,944,384 and 5,057,420).

A donor cell nucleus, which has been modified to alter the immunoglobulin gene, is transferred to a recipient oocyte. The use of this method is not restricted to a particular donor cell type. The donor cell can be as described herein, see also, for example, Wilmut et al Nature 385 810 (1997); Campbell et al Nature 380 64-66 (1996); Dai et al., Nature Biotechnology 20:251-255, 2002 or Cibelli et al Science 280 1256-1258 (1998). All cells of normal karyotype, including embryonic, fetal and adult somatic cells which can be used successfully in nuclear transfer can be employed. Fetal fibroblasts are a particularly useful class of donor cells. Generally suitable methods of nuclear transfer are described in Campbell et al Theriogenology 43 181 (1995), Dai et al. Nature Biotechnology 20:251-255, Polejaeva et al Nature 407:86-90 (2000), Collas et al Mol. Reprod. Dev. 38 264-267 (1994), Keefer et al Biol. Reprod. 50 935-939 (1994), Sims et al Proc. Nat'l. Acad. Sci. USA 90 6143-6147 (1993), WO-A-9426884, WO-A-9424274, WO-A-9807841, WO-A-9003432, U.S. Pat. Nos. 4,994,384 and 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (Campbell et al (Nature, 380:64-68, 1996) and Stice et al (Biol. Reprod., 20 54:100-110, 1996).

Somatic nuclear donor cells may be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In a suitable embodiment of the invention, nuclear donor cells are selected from the group consisting of epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, extended cells, cumulus cells, epidermal cells or endothelial cells. In another embodiment, the nuclear donor cell is an embryonic stem cell. In a particular embodiment, fibroblast cells can be used as donor cells.

In another embodiment of the invention, the nuclear donor cells of the invention are germ cells of an animal. Any germ cell of an animal species in the embryonic, fetal, or adult stage may be used as a nuclear donor cell. In a suitable embodiment, the nuclear donor cell is an embryonic germ cell.

Nuclear donor cells may be arrested in any phase of the cell cycle (G0, G1, G2, S, M) so as to ensure coordination with the acceptor cell. Any method known in the art may be used to manipulate the cell cycle phase. Methods to control the cell cycle phase include, but are not limited to, G0 quiescence induced by contact inhibition of cultured cells, G0 quiescence induced by removal of serum or other essential nutrient, G0 quiescence induced by senescence, G0 quiescence induced by addition of a specific growth factor; G0 or G1 quiescence induced by physical or chemical means such as heat shock, hyperbaric pressure or other treatment with a chemical, hormone, growth factor or other substance; S-phase control via treatment with a chemical agent which interferes with any point of the replication procedure; M-phase control via selection using fluorescence activated cell sorting, mitotic shake off, treatment with microtubule disrupting agents or any chemical which disrupts progression in mitosis (see also Freshney, R. I. "Culture of Animal Cells: A Manual of Basic Technique," Alan R. Liss, Inc, New York (1983).

Methods for isolation of oocytes are well known in the art. Essentially, this can comprise isolating oocytes from the ovaries or reproductive tract of an animal. A readily available source of oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. This period of time is known as the "maturation period". In certain embodiments, the oocyte is obtained from a gilt. A "gilt" is a female pig that has never had offspring. In other embodiments, the oocyte is obtained from a sow. A "sow" is a female pig that has previously produced offspring.

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated animal 35 to 48, or 39-41, hours past the onset of estrus or past the injection of human chorionic gonadotropin (hCG) or similar hormone. The oocyte can be placed in an appropriate medium, such as a hyaluronidase solution.

After a fixed time maturation period, which ranges from about 10 to 40 hours, about 16-18 hours, about 40-42 hours or about 39-41 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, such as not more than 24 hours later, or not more than 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, Mol. Reprod. Dev., 38:264-267 (1994). After fusion, the resultant fused NT units are then placed in a suitable medium until activation, for example, CR1aa medium. Typically activation can be effected shortly thereafter, for example less than 24 hours later, or about 4-9 hours later, or optimally 1-2 hours after fusion. In a particular embodiment, activation occurs at least one hour post fusion and at 40-41 hours post maturation.

The NT unit can be activated by known methods. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720, to Susko-Parrish et al. Fusion and activation can be induced by application of an AC pulse of 5 V for 5 s followed by two DC pulses of 1.5 kV/cm for 60 s each using an ECM2001 Electrocell Manipulator (BTX Inc., San Diego, Calif.). Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units, or "fused embryos", can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+ 10% fetal calf serum, Tyrodes-Albumin-Lactate-Pyruvate (TALP), Dulbecco's Phosphate Buffered Saline (PBS), Eagle's and Whitten's media, and, in one specific example, the activated NT units can be cultured in NCSU-23 medium for about 1-4 h at approximately 38.6° C. in a humidified atmosphere of 5% CO2.

Afterward, the cultured NT unit or units can be washed and then placed in a suitable media contained in well plates which can contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. These NT units can be cultured until at least about 2 to 400 cells, about 4 to 128 cells, or at least about 50 cells.

Activated NT units can then be transferred (embryo transfers), zero(0)-144 hours post activation, to the oviduct of an female pigs. In one embodiment, the female pigs can be an estrus-synchronized recipient gilt. Crossbred gilts (large white/Duroc/Landrace) (280-400 lbs) can be used. The gilts can be synchronized as recipient animals by oral administration of 18-20 mg Regu-Mate (Altrenogest, Hoechst, Warren, N.J.) mixed into the feed. Regu-Mate can be fed for 14 consecutive days. One thousand units of Human Chorionic Gonadotropin (hCG, Intervet America, Millsboro, Del.) can then be administered i.m. about 105 h after the last Regu-Mate treatment. Embryo transfers can then be performed about 22-26 h after the hCG injection. In one embodiment, the pregnancy can be brought to term and result in the birth of live offspring. In another embodiment, the pregnancy can be terminated early and embryonic cells can be harvested.

Breeding for Desired Homozygous Knockout Animals

In another aspect, the present invention provides a method for producing viable animals that lack any expression of a functional immunoglobulin gene is provided by breeding a male heterozygous for the immunoglobulin gene with a female heterozygous for the immunoglobulin gene. In one embodiment, the animals are heterozygous due to the genetic modification of one allele of the immunoglobulin gene to prevent expression of that allele. In another embodiment, the animals are heterozygous due to the presence of a point mutation in one allele of the alpha-immunoglobulin gene. In further embodiments, such heterozygous knockouts can be bred with an ungulate that expresses xenogenous immunoglobulin, such as human. In one embodiment, a animal can be obtained by breeding a transgenic ungulate that lacks expression of at least one allele of an endogenous immunoglobulin wherein the immunoglobulin is selected from the group consisting of heavy chain, kappa light chain and lambda light chain or any combination thereof with an ungulate that expresses an xenogenous immunoglobulin. In another embodiment, a animal can be obtained by breeding a transgenic ungulate that lacks expression of one allele of heavy chain, kappa light chain and lambda light chain with an ungulate that expresses an xenogenous, such as human, immunoglobulin. In a further embodiment, an animal can be obtained by breeding a transgenic ungulate that lacks expression of one allele of heavy chain, kappa light chain and lambda light chain and expresses an xenogenous, such as human, immunoglobulin with another transgenic ungulate that lacks expression of one allele of heavy chain, kappa light chain and lambda light chain with an ungulate and expresses an xenogenous, such as human, immunoglobulin to produce a homozygous transgenic ungulate that lacks expression of both alleles of heavy chain, kappa light chain and lambda light chain and expresses an xenogenous, such as human, immunoglobulin. Methods to produce such animals are also provided.

In one embodiment, sexually mature animals produced from nuclear transfer from donor cells that carrying a homozygous knockout in the immunoglobulin gene, can be bred and their offspring tested for the homozygous knockout. These homozygous knockout animals can then be bred to produce more animals.

In another embodiment, oocytes from a sexually mature homozygous knockout animal can be in vitro fertilized using wild type sperm from two genetically diverse pig lines and the embryos implanted into suitable surrogates. Offspring from these matings can be tested for the presence of the knockout, for example, they can be tested by cDNA sequencing, and/or PCR. Then, at sexual maturity, animals from each of these litters can be mated. In certain methods according to this aspect of the invention, pregnancies can be terminated early so that fetal fibroblasts can be isolated and further characterized phenotypically and/or genotypically. Fibroblasts that lack expression of the immunoglobulin gene can then be used for nuclear transfer according to the methods described herein to produce multiple pregnancies and offspring carrying the desired homozygous knockout.

Additional Genetic Modifications

In other embodiments, animals or cells lacking expression of functional immunoglobulin, produced according to the process, sequences and/or constructs described herein, can contain additional genetic modifications to eliminate the expression of xenoantigens. The additional genetic modifications can be made by further genetically modifying cells obtained from the transgenic cells and animals described herein or by breeding the animals described herein with animals that have been further genetically modified. Such animals can be modified to eliminate the expression of at least one allele of the alpha-1,3-galactosyltransferase gene, the CMP-Neu5Ac hydroxylase gene (see, for example, U.S. Ser. No. 10/863,116), the iGb3 synthase gene (see, for example, U.S. Patent Application 60/517,524), and/or the Forssman synthase gene (see, for example, U.S. Patent Application 60/568,922). In additional embodiments, the animals discloses herein can also contain genetic modifications to express fucosyltransferase, sialyltransferase and/or any member of the family of glucosyltransferases. To achieve these additional genetic modifications, in one embodiment, cells can be modified to contain multiple genetic modifications. In other embodiments, animals can be bred together to achieve multiple genetic modifications. In one specific embodiment, animals, such as pigs, lacking expression of functional immunoglobulin, produced according to the process, sequences and/or constructs described herein, can be bred with animals, such as pigs, lacking expression of alpha-1,3-galactosyl transferase (for example, as described in WO 04/028243).

In another embodiment, the expression of additional genes responsible for xenograft rejection can be eliminated or reduced. Such genes include, but are not limited to the CMP-NEUAc Hydroxylase Gene, the isoGloboside 3 Synthase gene, and the Forssman synthase gene. In addition, genes or cDNA encoding complement related proteins, which are responsible for the suppression of complement mediated lysis can also be expressed in the animals and tissues of the present invention. Such genes include, but are not limited to CD59, DAF, MCP and CD46 (see, for example, WO 99/53042; Chen et al. Xenotransplantation, Volume 6 Issue 3 Page 194—August 1999, which describes pigs that express CD59/DAF transgenes; Costa C et al, Xenotransplantation. 2002 January; 9(1):45-57, which describes transgenic pigs that express human CD59 and H-transferase; Zhao L et al.; Diamond L E et al. Transplantation. 2001 Jan. 15; 71(1):132-42, which describes a human CD46 transgenic pigs.

Additional modifications can include expression of tissue factor pathway inhibitor (TFPI), heparin, antithrombin, hirudin, TFPI, tick anticoagulant peptide, or a snake venom factor, such as described in WO 98/42850 and U.S. Pat. No. 6,423,316, entitled "Anticoagulant fusion protein anchored to cell membrane"; or compounds, such as antibodies, which down-regulate the expression of a cell adhesion molecule by the cells, such as described in WO 00/31126, entitled "Suppression of xenograft rejection by down regulation of a cell adhesion molecules" and compounds in which co-stimulation by signal 2 is prevented, such as by administration to the organ recipient of a soluble form of CTLA-4 from the xenogeneic donor organism, for example as described in WO 99/57266, entitled "Immunosuppression by blocking T cell co-stimulation signal 2 (B7/CD28 interaction)".

In one embodiment, the animals or cells lacking expression of functional immunoglobulin, produced according to the present invention, can be further modified to transgenically express a cytoxic T-lymphocyte associated protein 4-immunoglobin (CTLA4). The animals or cells can be modified to express CTLA4 peptide or a biologically active fragment (e.g., extracellular domain, truncated form of the peptide in which at least the transmembrane domain has been removed) or derivative thereof. The peptide may be, e.g., human or porcine. The CTLA4 peptide can be mutated. Mutated peptides may have higher affinity than wildtype for porcine and/or human B7 molecules. In one specific embodiment, the mutated CTLA4 can be CTLA4 (Glu104, Tyr29). The CTLA4 peptide can be modified such that it is expressed intracellularly. Other modifications of the CTLA4 peptide include addition of a golgi retention signal to the N or C terminus. The golgi retention signal may be, e.g., the sequence KDEL. The CTLA4 peptide can be fused to a peptide dimerization domain or an immunoglobulin (Ig) molecule. The CTLA4 fusion peptides can include a linker sequence that can join the two peptides.

Certain aspects of the invention are described in greater detail in the non-limiting Examples that follow.

EXAMPLES

Example 1: Porcine Heavy Chain Targeting and Generation of Porcine Animals that Lack Expression of Heavy Chain A portion of the porcine Ig heavy-chain locus was isolated from a 3X redundant porcine BAC library. In general, BAC libraries can be generated by fragmenting pig total genomic DNA, which can then be used to derive a BAC library representing at least three times the genome of the whole animal. BACs that contain porcine heavy chain immunoglobulin can then be selected through hybridization of probes selective for porcine heavy chain immunoglobulin as described herein.

Sequence from a clone (Seq ID 1) was used to generate a primer complementary to a portion of the J-region (the primer is represented by Seq ID No. 2). Separately, a primer was designed that was complementary to a portion of Ig heavy-chain mu constant region (the primer is represented by Seq ID No. 3). These primers were used to amplify a fragment of porcine Ig heavy-chain (represented by Seq ID No. 4) that led the functional joining region (J-region) and sufficient flanking region to design and build a targeting vector. To maintain this fragment and subclones of this fragment in a native state, the E. coli (Stable 2, Invitrogen cat #1026-019) that harbored these fragments was maintained at 30° C. Regions of Seq. ID No. 4 were subcloned and used to assemble a targeting vector as shown in Seq. ID No. 5. This vector was transfected into porcine fetal fibroblasts that were subsequently subjected to selection with G418. Resulting colonies were screened by PCR to detect potential targeting events (Seq ID No. 6 and Seq ID No. 7, 5' screen primers; and Seq ID No. 8 and Seq ID No. 9, 3' screen primers). See FIG. 1 for a schematic illustrating the targeting. Targeting was confirmed by southern blotting. Piglets were generated by nuclear transfer using the targeted fetal fibroblasts as nuclear donors.

Nuclear Transfer.

The targeted fetal fibroblasts were used as nuclear donor cells. Nuclear transfer was performed by methods that are well known in the art (see, e.g., Dai et al., Nature Biotechnology 20: 251-255, 2002; and Polejaeva et al., Nature 407:86-90, 2000).

Enucleation of in vitro-matured oocytes (BoMed, Madison, Wis.; TransOva Genetics, Sioux City, Iowa) was begun between 40 and 42 hours post-maturation as described in Polejaeva, I. A., et al. (*Nature* 407, 86-90 (2000)). For enucleation, we incubated the oocytes in calcium-free phosphate-buffered NCSU-23 medium containing 5 μg ml$^{-1}$ cytochalasin B (Sigma) and 7.5 μg ml$^{-1}$ Hoechst 33342 (Sigma) at 38° C. for 20 min. A small amount of cytoplasm from directly beneath the first polar body was then aspirated using an 18 μM glass pipette (Humagen, Charlottesville, Va.). We exposed the aspirated karyoplast to ultraviolet light to confirm the presence of a metaphase plate.

For nuclear transfer, a single fibroblast cell was placed under the zona pellucida in contact with each enucleated oocyte. Fusion and activation were induced by application of an AC pulse of 5 V for 5 s followed by two DC pulses of 1.5 kV/cm for 60 its each using an ECM2001 Electrocell Manipulator (BTX Inc., San Diego, Calif.). Fused embryos were cultured in NCSU-23 medium for 1-4 h at 38.6° C. in a humidified atmosphere of 5% CO$_2$, and then transferred to the oviduct of an estrus-synchronized recipient gilt. Crossbred gilts (large white/Duroc/landrace) (280-400 lbs) were synchronized as recipients by oral administration of 18-20 mg Regu-Mate (Altrenogest, Hoechst, Warren, N.J.) mixed into their feed. Regu-Mate was fed for 14 consecutive days. Human chorionic gonadotropin (hCG, 1,000 units; Intervet America, Millsboro, Del.) was administered intra-muscularly 105 h after the last Regu-Mate treatment. Embryo transfers were done 22-26 h after the hCG injection.

Nuclear transfer produced 18 healthy piglets from four litters. These animals have one functional wild-type Ig heavy-chain locus and one disrupted Ig heavy chain locus.

```
Seq ID 2: primer from
Butler subclone to
amplify J to C heavychain
(637Xba5')
ggccagacttcctcggaacagctca Seq ID 3: primer for C
to amplify J to C heavychain
(JM1L)
ttccaggagaaggtgacggagct Seq ID 6: heavychain 5'
primer for 5' screen
(HCKOXba5'2)
tctagaagacgctggagagaggccag Seq ID 7: heavychain 3'
primer for 5' screen
(5'arm5')
taaagcgcatgctccagactgcctt
```

```
Seq ID 8: heavychain 5'
primer for 3' screen
(NEO4425)
catcgccttctatcgccttctt Seq ID 9: heavychain 3'
primer for 3' screen
(650 + CA)
Aagtacttgccgcctctcagga
```

Southern Blot Analysis of Cell and Pig Tissue Samples.

Cells or tissue samples were lysed overnight at 60° C. in lysis buffer (10 mM Tris, pH 7.5, 10 mM EDTA, 10 mM NaCl, 0.5% (w/v) Sarcosyl, 1 mg/ml proteinase K) and the DNA precipitated with ethanol. The DNA was then digested with NcoI or XbaI, depending on the probe to be used, and separated on a 1% agarose gel. After electrophoresis, the DNA was transferred to a nylon membrane and probed with digoxigenin-labeled probe (SEQ ID No 41 for NcoI digest, SEQ ID No 40 for XbaI digest). Bands were detected using a chemiluminescent substrate system (Roche Molecular Biochemicals).

Probes for Heavy Chain Southern:

```
HC J Probe (used with Xba I digest)
                                    (Seq ID No 40)
CTCTGCACTCACTACCGCCGGACGCGCACTGCCGTGCTGCCCATGGACCA

CGCTGGGGAGGGGTGAGCGGACAGCACGTTAGGAAGTGTGTGTGTGCGCG

TGGGTGCAAGTCGAGCCAAGGCCAAGATCCAGGGGCTGGGCCCTGTGCCC

AGAGGAGAATGGCAGGTGGAGTGTAGCTGGATTGAAAGGTGGCCTGAAGG

GTGGGGCATCCTGTTTGGAGGCTCACTCTCAGCCCCAGGGTCTCTGGTTC

CTGCCGGGGTGGGGGCGCAAGGTGCCTACCACACCCTGCTAGCCCCTCG

TCCAGTCCCGGGCCTGCCTCTTCACCACGGAAGAGGATAAGCCAGGCTGC

AGGCTTCATGTGCGCCGTGGAGAACCCAGTTCGGCCCTTGGAGG

HC Mu Probe (used with NcoI digest)
                                    (Seq ID No 41)
GGCTGAAGTCTGAGGCCTGGCAGATGAGCTTGGACGTGCGCTGGGGAGTA

CTGGAGAAGGACTCCCGGGTGGGGACGAAGATGTTCAAGACGGGGGGCTG

CTCCTCTACGACTGCAGGCAGGAACGGGGCGTCACTGTGCCGGCGGCACC

CGGCCCCGCCCCCGCCACAGCCACAGGGGGAGCCCAGCTCACCTGGCCCA

GAGATGGACACGGACTTGGTGCCACTGGGGTGCTGGACCTCGCACACCAG

GAAGGCCTCTGGGTCCTGGGGGATGCTCACAGAGGGTAGGAGCACCCGGG

AGGAGGCCAAGTACTTGCCGCCTCTCAGGACGG
```

Example 2: Porcine Kappa Light Chain Targeting and Generation of Porcine Lacking Expression of Kappa Light Chain A portion of the porcine Ig kappa-chain locus was isolated from a 3X redundant porcine BAC library. In general, BAC libraries can be generated by fragmenting pig total genomic DNA, which can then be used to derive a BAC library representing at least three times the genome of the whole animal. BACs that contain porcine kappa chain immunoglobulin can then be selected through hybridization of probes selective for porcine kappa chain immunoglobulin as described herein.

A fragment of porcine Ig light-chain kappa was amplified using a primer complementary to a portion of the J-region (the primer is represented by Seq ID No. 10) and a primer complementary to a region of kappa C-region (represented by Seq ID No. 11). The resulting amplimer was cloned into a plasmid vector and maintained in Stable2 cells at 30° C. (Seq ID No. 12). See FIG. 2 for a schematic illustration.

Separately, a fragment of porcine Ig light-chain kappa was amplified using a primer complementary to a portion of the C-region (Seq ID No. 13) and a primer complementary to a region of the kappa enhancer region (Seq ID No. 14). The resulting amplimer was fragmented by restriction enzymes and DNA fragments that were produced were cloned, maintained in Stable2 cells at 30 degrees C. and sequenced. As a result of this sequencing, two non-overlapping contigs were assembled (Seq ID No. 15, 5' portion of amplimer; and Seq ID No. 16, 3' portion of amplimer). Sequence from the downstream contig (Seq ID No. 16) was used to design a set of primers (Seq ID No. 17 and Seq ID No. 18) that were used to amplify a contiguous fragment near the enhancer (Seq ID No. 19). A subclone of each Seq ID No. 12 and Seq ID No. 19 were used to build a targeting vector (Seq ID No. 20). This vector was transfected into porcine fetal fibroblasts that were subsequently subjected to selection with G418. Resulting colonies were screened by PCR to detect potential targeting events (Seq ID No. 21 and Seq ID No. 22, 5' screen primers; and Seq ID No. 23 and Seq Id No 43, 3' screen primers, and Seq ID No. 24 and Seq Id No 24, endogenous screen primers). Targeting was confirmed by southern blotting. Southern blot strategy design was facilitated by cloning additional kappa sequence, it corresponds to the template for germline kappa transcript (Seq ID No. 25). Fetal pigs were generated by nuclear transfer.

Nuclear Transfer.

The targeted fetal fibroblasts were used as nuclear donor cells. Nuclear transfer was performed by methods that are well known in the art (see, e.g., Dai et al., Nature Biotechnology 20: 251-255, 2002; and Polejaeva et al., Nature 407:86-90, 2000).

Oocytes were collected 46-54 h after the hCG injection by reverse flush of the oviducts using pre-warmed Dulbecco's phosphate buffered saline (PBS) containing bovine serum albumin (BSA; 4 gl$^{-1}$) (as described in Polejaeva, I. A., et al. (Nature 407, 86-90 (2000)). Enucleation of in vitro-matured oocytes (BoMed, Madison, Wis.) was begun between 40 and 42 hours post-maturation as described in Polejaeva, I. A., et al. (Nature 407, 86-90 (2000)). Recovered oocytes were washed in PBS containing 4 gl$^{-1}$ BSA at 38° C., and transferred to calcium-free phosphate-buffered NCSU-23 medium at 38° C. for transport to the laboratory. For enucleation, we incubated the oocytes in calcium-free phosphate-buffered NCSU-23 medium containing 5 μg ml$^{-1}$ cytochalasin B (Sigma) and 7.5 μg ml$^{-1}$ Hoechst 33342 (Sigma) at 38° C. for 20 min. A small amount of cytoplasm from directly beneath the first polar body was then aspirated using an 18 μM glass pipette (Humagen, Charlottesville, Va.). We exposed the aspirated karyoplast to ultraviolet light to confirm the presence of a metaphase plate.

For nuclear transfer, a single fibroblast cell was placed under the zona pellucida in contact with each enucleated oocyte. Fusion and activation were induced by application of an AC pulse of 5 V for 5 s followed by two DC pulses of 1.5 kV/cm for 60 μs each using an ECM2001 Electrocell Manipulator (BTX Inc., San Diego, Calif.). Fused embryos were cultured in NCSU-23 medium for 1-4 h at 38.6° C. in a humidified atmosphere of 5% CO$_2$, and then transferred to the oviduct of an estrus-synchronized recipient gilt. Crossbred gilts (large white/Duroc/landrace) (280-400 lbs) were synchronized as recipients by oral administration of 18-20 mg Regu-Mate (Altrenogest, Hoechst, Warren, N.J.) mixed into their feed. Regu-Mate was fed for 14 consecutive days. Human chorionic gonadotropin (hCG, 1,000 units; Intervet America, Millsboro, Del.) was administered intra-muscularly 105 h after the last Regu-Mate treatment. Embryo transfers were done 22-26 h after the hCG injection.

Nuclear transfer using kappa targeted cells produced 33 healthy pigs from 5 litters. These pigs have one functional wild-type allele of porcine Ig light-chain kappa and one disrupted Ig light-chain kappa allele.

```
Seq ID 10: kappa J to C
5' primer (kjc5'1)
caaggaqaccaagctggaactc

Seq ID 11: kappa J to C
3' primer (kjc3'2)
tgatcaagcacaccacagagacag

Seq ID 13: 5' primer for
Kappa C to E (porKCS1)
gatgccaagccatccgtcttcatc

Seq ID 14: 3' primer for
Kappa C to E (porKCA1)
tgaccaaagcagtgtgacggttgc

Seq ID 17: kappa 5'
primer for amplification
of enhancer region
(K3'arm1S)
ggatcaaacacgcatcctcatggac Seq ID 18: kappa 3'
primer for amplification
of enhancer region
(K3'arm1A)
ggtgattggggcatggttgagg Seq ID 21: kappa screen,
5' primer, 5'
(kappa5armS)
cgaaccctgtgtatatagtt Seq ID 22: kappa screen,
3' primer, 5'
(kappaNeoA)
gagatgaggaagaggagaaca Seq ID 23: kappa screen,
5' primer, 3'
(kappaNeoS)
gcattgtctgagtaggtgtcatt Seq ID 24: kappa screen,
3' primer, 5'
(kappa5armProbe3')
cgcttcttgcagggaacacgat Seq ID No 43, Kappa
screen, 3' primer
(kappa3armA2)
GTCTTTGGTTTTTGCTGAGGGTT
```

Southern Blot Analysis of Cell and Pig Tissue Samples.

Cells or tissue samples were lysed overnight at 60° C. in lysis buffer (10 mM Tris, pH 7.5, 10 mM EDTA, 10 mM NaCl, 0.5% (w/v) Sarcosyl, 1 mg/ml proteinase K) and the DNA precipitated with ethanol. The DNA was then digested with SacI and separated on a 1% agarose gel. After electrophoresis, the DNA was transferred to a nylon membrane and probed with digoxigenin-labeled probe (SEQ ID No 42). Bands were detected using a chemiluminescent substrate system (Roche Molecular Biochemicals).

Probe for Kappa Southern:

```
Kappa5ArmProbe 5'/3'
                                      (SEQ ID No 42)
gaagtgaagccagccagttcctcctgggcaggtggccaaaattacagttg acccctcctggtctggctgaaccttgccccatatggtgacagccatctgg ccagggcccaggtctccctctgaagcctttgggaggagagggagagtggc tggcccgatcacagatgcggaaggggctgactcctcaaccggggtgcaga ctctgcagggtgggtctgggcccaacacacccaaagcacgcccaggaagg aaaggcagcttggtatcactgcccagagctaggagaggcaccgggaaaat gatctgtccaagacccgttcttgcttctaaactccgagggggtcagatga agtggttttgtttcttggcctgaagcatcgtgttccctgcaagaagcgg
```

Example 3 Characterization of the Porcine Lambda Gene Locus

To disrupt or disable porcine lambda, a targeting strategy has been devised that allows for the removal or disruption of the region of the lambda locus that includes a concatamer of J to C expression cassettes. BAC clones that contain portions of the porcine genome can be generated. A portion of the porcine Ig lambda-chain locus was isolated from a 3X redundant porcine BAC library. In general, BAC libraries can be generated by fragmenting pig total genomic DNA, which can then be used to derive a BAC library representing at least three times the genome of the whole animal. BACs that contain porcine lambda chain immunoglobulin can then be selected through hybridization of probes selective for porcine lambda chain immunoglobulin as described herein.

BAC clones containing a lambda J-C flanking region (see FIG. 3), can be independently fragmented and subcloned into a plasmid vector. Individual subclones have been screened by PCR for the presence of a portion of the J to C intron. We have cloned several of these cassettes by amplifying from one C region to the next C region. This amplification was accomplished by using primers that are oriented to allow divergent extension within any one C region (Seq ID 26 and Seq ID 27). To obtain successful amplification, the extended products converge with extended products originated from adjacent C regions (as opposed to the same C region). This strategy produces primarily amplimers that extend from one C to the adjacent C. However, some amplimers are the result of amplification across the adjacent C and into the next C which lies beyond the adjacent C. These multi-gene amplimers contain a portion of a C, both the J and C region of the next J-C unit, the J region of the third J-C unit, and a portion of the C region of the third J-C unit. Seq ID 28 is one such amplimer and represents sequence that must be removed or disrupted.

Other porcine lambda sequences that have been cloned include: Seq ID No. 32, which includes 5' flanking sequence to the first lambda J/C unit of the porcine lambda light chain genomic sequence; Seq ID No. 33, which includes 3' flanking sequence to the J/C cluster region of the porcine lambda light chain genomic sequence, from approximately 200 base pairs downstream of lambda J/C; Seq ID No. 34, which includes 3' flanking sequence to the J/C cluster region of the porcine lambda light chain genomic sequence, approximately 11.8 Kb downstream of the J/C cluster region, near the enhancer; Seq ID No. 35, which includes approximately 12 Kb downstream of lambda, including the enhancer region; Seq ID No. 36, which includes approximately 17.6 Kb downstream of lambda; Seq ID No. 37, which includes approximately 19.1 Kb downstream of lambda; Seq ID No. 38, which includes approximately 21.3 Kb downstream of lambda; and Seq ID No. 39, which includes approximately 27 Kb downstream of lambda.

```
Seq ID 26: 5'primer for
lambda C to C amplimer
(lamC5')
ccttcctcctgcacctgtcaac Seq ID 27: 3' primer for
lambda C to C amplimer
(lamC3')
tagacacaccagggtggccttg
```

Example 4 Production of Targeting Vectors for the Lambda Gene

Following a first targeting strategy, shown in FIG. 4, a vector is designed and built with one targeting arm that is homologous to a region upstream of J1 (i.e., the first J/C unit or sequence) and the other arm homologous to a region that is downstream of the last C (i.e., the last J/C unit or sequence) This targeting vector utilizes a selectable marker (SM).

Seq ID No. 48 represents one example of a vector used in the first targeting strategy. Seq ID No. 48 is a lambda light chain knockout vector which includes both 5' and 3' homology arms and Neo resistance factor.

```
                                         Seq ID No. 48
GCAAAAGGCCAGGAACCGTAAAAAGGCCGCGTTGCTGGCGTTTTTCCATA

GGCTCCGCCCCCCTGACGAGCATCACAAAAATCGACGCTCAAGTCAGAGG

TGGCGAAACCCGACAGGACTATAAAGATACCAGGCGTTTCCCCCTGGAAG

CTCCCTCGTGCGCTCTCCTGTTCCGACCCTGCCGCTTACCGGATACCTGT

CCGCCTTTCTCCCTTCGGGAAGCGTGGCGCTTTCTCAATGCTCACGCTGT

AGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTC

TTGAGTCCAACCCGGTAAGACACGACTTATCGCCACTGGCAGCAGCCACT

GGTAACAGGATTAGCAGAGCGAGGTATGTAGGCGGTGCTACAGAGTTCTT

GAAGTGGTGGCCTAACTACGGCTACACTAGAAGGACAGTATTTGGTATCT

GCGCTCTGCTGAAGCCAGTTACCTTCGGAAAAAGAGTTGGTAGCTCTTGA

TCCGGCAAACAAACCACCGCTGGTAGCGGTGGTTTTTTTGTTTGCAAGCA

GCAGATTACGCGCAGAAAAAAAGGATCTCAAGAAGATCCTTTGATCTTTT

CTACGGGGTCTGACGCTCAGTGGAACGAAAACTCACGTTAAGGGATTTTG

GTCATGAGATTATCAAAAAGGATCTTCACCTAGATCCTTTTAAATTAAAA

ATGAAGTTTTAAATCAATCTAAAGTATATATGAGTAAACTTGGTCTGACA

GTTACCAATGCTTAATCAGTGAGGCACCTATCTCAGCGATCTGTCTATTT

CGTTCATCCATAGTTGCCTGACTCCCCGTCGTGTAGATAACTACGATACG

GGAGGGCTTACCATCTGGCCCCAGTGCTGCAATGATACCGCGAGACCCAC

GCTCACCGGCTCCAGATTTATCAGCAATAAACCAGCCAGCCGGAAGGGCC
```

```
GAGCGCAGAAGTGGTCCTGCAACTTTATCCGCCTCCATCCAGTCTATTAA
TTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGT
ATGGCTTCATTCAGCTCCGGTTCCCAACGATCAAGGCGAGTTACATGATC
CCCCATGTTGTGCAAAAAGCGGTTAGCTCCTTCGGTCCTCCGATCGTTG
TCAGAAGTAAGTTGGCCGCAGTGTTATCACTCATGGTTATGGCAGCACTG
CATAATTCTCTTACTGTCATGCCATCCGTAAGATGCTTTTCTGTGACTGG
TGAGTACTCAACCAAGTCATTCTGAGAATAGTGTATGCGGCGACCGAGTT
GCTCTTGCCCGGCGTCAATACGGGATAATACCGCGCCACATAGCAGAACT
TTAAAAGTGCTCATCATTGGAAAACGTTCTTCGGGGCGAAAACTCTCAAG
GATCTTACCGCTGTTGAGATCCAGTTCGATGTAACCCACTCGTGCACCCA
ACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATG
TTGAATACTCATACTCTTCCTTTTTCAATATTATTGAAGCATTTATCAGG
GTTATTGTCTCATGAGCGGATACATATTTGAATGTATTTAGAAAAATAAA
CAAATAGGGGTTCCGCGCACATTTCCCCGAAAAGTGCCACCTGACGTCAA
ACAGCTATGACCATGGCGGCCGCgtcgacAGGGTGTGGCCAAATACAGCA
TGGAGTAGCCATCATAAGGAATCTTACACAAGCCTCCAAAATTGTGTTTC
TGAAATTGGGTTTAAAGTACGTTTGCATTTTAAAAAGCCTGCCAGAAAAT
ACAGAAAAATGTCTGTGATATGTCTCTGGCTGATAGGATTTTGCTTAGTT
TTAATTTTGGCTTTATAATTTTCTATAGTTATGAAAATGTTCACAAGAAG
ATATATTTCATTTTAGCTTCTAAAATAATTATAACACAGAAGTAATTTGT
GCTTTAAAAAAATATTCAACACAGAAGTATATAAAGTAAAAATTGAGGAG
TTCCCATCGTGGCTCAGTGATTAACAAACCCAACTAGTATCCATGAGGAT
ATGGATTTGATCCCTGGCCTTGCTCAGTGGGTTGAGGATCCAGTGTTGCT
GTGAGCTGTGGTGTAGGTTGCAGACACAGCACTCTGGCGTTGCTGTGACT
CTGGCGTAGGCCGGCAGCTACAGCTCCATTTGGACCCTTAGCCTGGGAAC
CTCCATATGCCTGAGATACGGCCCTAAAAAGTCAAAAGCCAAAAAAATAG
TAAAAATTGAGTGTTTCTACTTACCACCCCTGCCCACATCTTATGCTAAA
ACCCGTTCTCCAGAGACAAACATCGTCAGGTGGGTCTATATATTTCCAGC
CCTCCTCCTGTGTGTGTATGTCCGTAAAACACACACACACACACACACAC
GCACACACACACACGTATCTAATTAGCATTGGTATTAGTTTTTCAAAA
GGGAGGTCATGCTCTACCTTTTAGGCGGCAAATAGATTATTTAAACAAAT
CTGTTGACATTTTCTATATCAACCCATAAGATCTCCCATGTTCTTGGAAA
GGCTTTGTAAGACATCAACATCTGGGTAAACCAGCATGGTTTTTAGGGGG
TTGTGTGGATTTTTTTCATATTTTTTAGGGCACACCTGCAGCATATGGAG
GTTCCCAGGCTAGGGGTTGAATCAGAGCTGTAGCTGCCGGCCTACACCAC
AGCCACAGCAACGCCAGATCCTTAACCCACTGAGAAAGGCCAGGGATTGA
ACCTGCATCCTCATGGATGCTGGTCAGATTTATTTCTGCTGAGCCACAAC
AGGAACTCCCTGAACCAGAATGCTTTTAACCATTCCACTTTGCATGGACA
TTTAGATTGTTTCCATTTAAAAATACAAATTACAAGGAGTTCCCGTCGTG
GCTCAGTGGTAACGAATTGGACTAGGAACCATGAGGTTTCGGGTTCGATC
CCTGGCCTTGCTCGGTGGGTTAAGGATCCAGCATTGATGTGAGATATGGT
GTAGGTCGCAGACGTGGCTCGGATCCCACGTTGCTGTGGCTCTGGCGTAG
GCCGGCAACAACAGCTCCGATTCGACCCCTAGCCTGGGAACCTCCATGTG
CCACAGGAGCAGCCCTAGAAAAGGCAAAAAGACAAAAAAATAAAAAATTA
AAATGAAAAATAAAATAAAAATACAAATTACAAGAGACGGCTACAAGGA
AATCCCCAAGTGTGTGCAAATGCCATATATGTATAAAATGTACTAGTGTC
TCCTCGCGGGAAAGTTGCCTAAAAGTGGGTTGGCTGGACAGAGAGGACAG
GCTTTGACATTCTCATAGGTAGTAGCAATGGGCTTCTCAAAATGCTGTTC
CAGTTTACACTCACCATAGCAAATGACAGTGCCTCTTCCTCTCCACCCTT
GCCAATAATGTGACAGGTGGATCTTTTTCTATTTTGTGTATCTGACAAGC
AAAAAATGAGAACAGGAGTTCCTGTCGTGGTGCAGTGGAGACAAATCTGA
CTAGGAACCATGAAATTTCGGGTTCAATCCCTGGCCTCACTCAGTAGGTA
AAGGATCCAGGGTTGCAGTGAGCTGTGGGGTAGGTCGCAGACACAGTGCA
AATTTGGCCCTGTTGTGGCTGTGGTGTAGGCCGGCAGCTATAGCTCCAAT
TGGACCCCTAGCCTGGGAACCTCCTTATGCCGTGGGTGAGGCCCTAAAAA
AAAGAGTGCAAAAAAAAAAATAAGAACAAAAATGATCATCGTTTAATTC
TTTATTTGATCATTGGTGAAACTTATTTTCCTTTTATATTTTATTGACT
GATTTTATTTCTCCTATGAATTTACCGGTCATAGTTTTGCCTGGGTGTTT
TTACTCCGGTTTTAGTTTTGGTTGGTTGTATTTTCTTAGAGAGCTATAGA
AACTCTTCATCTATTTGGAATAGTAATTCCTCATTAAGTATTTGTGCTGC
AAAAAATTTTCCCTGATCTGTTTTATGCTTTTGTTTGTGGGGTCTTTCAC
GAGAAAGCCTTTTTAGTTTTTACACCTCAGCTTGGTTGTTTTTCTTGATT
GTGTCTGTAATCTGCGGCCAACATAGGAAACACATTTTTACTTTAGTGTT
TTTTTCCTATTTTCTTCAAGTACGTCCATTGTTTTGGTGTCTGATTTTAC
TTTGCCTGGGGTTTGTTTTTGTGTGGCAGGAATATAAACTTATGTATTTT
CCAAATGGAGAGCCAATGGTTGTATATTTGTTGAATTCAAATGCAACTTT
ATCAAACACCAAATCATCGATTTATCACAACTCTTCTCTGGTTTATTGAT
CTAATGATCAATTCCTGTTCCACGCTGTTTTAATTATTTTAGCTTTGTGG
ATTTTGGTGCCTGGTAGAGAACAAAGCCTCCATTATTTTCATTCAAAATA
GTCCCGTCTATTATCTGCCATTGTTGTAGTATTAGACTTTAAAATCAATT
TACTGATTTTCAAAAGTTATTCCTTTGGTGATGTGGAATACTTTATACTT
CATAAGGTACATGGATTCATTTGTGGGGAATTGATGTCTTTGCTATTGTG
GCCATTTGTCAAGTTGTGTAATATTTTACCCATGCCAACTTTGCATATTG
TATGTGAGTTTATTCCCAGGGTTTTTAATAGGATGTTTATTGAAGTTGTC
AGTGTTTCCACAATTTCATCGCCTCAGTGCTTACTGTTTGCATAAAAGGA
AACCTACTCACTTTTGCCTATTGCTCTTGTATTCAATCATTTTAGTTAAC
TCTTGTGTTAATTTTGAGAGTTTTTCAGCTGACTGTCTGGGGTTTTCTTT
AATAGACTAGCCCTTTGTCTGTAAAGAATAATTTTATCGAATTTTTCTTA
ACACTCACACTCTCCCCACCCCCACCCCCGCTCATCTCCTTTCATTGGGT
```

-continued

```
CAAATCTGTAGAATACAATAAAAGTAAGAGTGGGAACCTTAGCCTTTAAG
TCGATTTTGCCTTTAAATGTGAATGTTGCTATGTTTCGGGACATTCTCTT
TATCAAGTTGCGGATGTTTCCTTAGATAATTAACTTAATAAAAGACTGGA
TGTTTGCTTTCTTCAAATCAGAATTGTGTTGAATTTATATTGCTATTCTG
TTTAATTTTGTTTCAAAAAATTTACATGCACACCTTAAAGATAACCATGA
CCAAATAGTCCTCCTGCTGAGAGAAAATGTTGGCCCCAATGCCACAGGTT
ACCTCCCGACTCAGATAAACTACAATGGGAGATAAAATCAGATTTGGCAA
AGCCTGTGGATTCTTGCCATAACTCTCAGAGCATGACTTGGGTGTTTTTT
CCTTTTCTAAGTATTTTAATGGTATTTTTGTGTTACAATAGGAAATCTAG
GACACAGAGAGTGATTCAATGAGGGGAACGCATTCTGGGATGACTCTAGG
CCTCTGGTTTGGGGAGAGCTCTATTGAAGTAAAGACAATGAGAGGAAGCA
AGTTTGCAGGGAACTGTGAGGAATTTAGATGGGGAATGTTGGGTTTGAGG
TTTCTATAGGGCACGCAAGCAGAGATGCACTCAGGAGGAAGAAGGAGCAT
AAATCTAGAGGCAAAAAGAGAGGTCAGGACTGGAAATAGAGATGCGAGAC
ACCAGGGTGGCAGTCAGAGAGCACAGTGTGGGTCAGAAGACAGTGGAAGA
ACACAAGGGACAGAGAGGGATCTCCAACTTCACTGGGATGAGGGCCTTGT
TGGCCTTGACCTGAGAGATTTCCAGGAGTTGAGGGTGGGAAGGAGccgcg
gTCTAGGAAGCTTTCTAGGGTACCTCTAGGGATCCGAACAATGGAAGTCC
GAGCTCATCGCTAATAACTTCGTATAGCATACATTATACGAAGTTATATT
CGATGCGGCCGCAAGGGGTTCGCGTCAGCGGGTGTTGGCGGGTGTCGGGG
CTGGCTTAACTATGCGGCATCAGAGCAGagatccGGCGCGCCCTACCGG
GTAGGGGAGGCGCTTTTCCCAAGGCAGTCTGGAGCATGCGCTTTAGCAGC
CCCGCTGGGCACTTGGCGCTACACAAGTGGCCTCTGGCCTCGCACACATT
CCACATCCACCGGTAGGCGCCAACCGGCTCCGTTCTTTGGTGGCCCCTTC
GCGCCACCTTCTACTCCTCCCCTAGTCAGGAAGTTCCCCCCCGCCCCGCA
GCTCGCGTCGTGCAGGACGTGACAAATGGAAGTAGCACGTCTCACTAGTC
TCGTGCAGATGGACAGCACCGCTGAGCAATGGAAGCGGGTAGGCCTTTGG
GGCAGCGGCCAATAGCAGCTTTGGCTCCTTCGCTTTCTGGGCTCAGAGGC
TGGGAAGGGTGGGTCCGGGGCGGGCTCAGGGGCGGGCTCAGGGGCGGG
GCGGGCGCCCGAAGGTCCTCCGGAAGCCCGGCATTCTGCACGCTTCAAAA
GCGCACGTCTGCCGCGCTGTTCTCCTCTTCCTCATCTCCGGGCCTTTCGA
CCTGCAGCCAATATGGGATCGGCCATTGAACAAGATGGATTGCACGCAGG
TTCTCCGGCCGCTTGGGTGGAGAGGCTATTCGGCTATGACTGGGCACAAC
AGACAATCGGCTGCTCTGATGCCGCCGTGTTCCGGCTGTCAGCGCAGGGG
CGCCCGGTTCTTTTTGTCAAGACCGACCTGTCCGGTGCCCTGAATGAACT
GCAGGACGAGGCAGCGCGGCTATCGTGGCTGGCCACGACGGGCGTTCCTT
GCGCAGCTGTGCTCGACGTTGTCACTGAAGCGGGAAGGGACTGGCTGCTA
TTGGGCGAAGTGCCGGGGCAGGATCTCCTGTCATCTCACCTTGCTCCTGC
CGAGAAAGTATCCATCATGGCTGATGCAATGCGGCGGCTGCATACGCTTG
ATCCGGCTACCTGCCCATTCGACCACCAAGCGAAACATCGCATCGAGCGA
GCACGTACTCGGATGGAAGCCGGTCTTGTCAATCAGGATGATCTGGACGA
```

-continued

```
AGAGCATCAGGGGCTCGCGCCAGCCGAACTGTTCGCCAGGCTCAAGGCGC
GCATGCCCGACGGCGAGGATCTCGTCGTGACCCATGGCGATGCCTGCTTG
CCGAATATCATGGTGGAAAATGGCCGCTTTTCTGGATTCATCGACTGTGG
CCGGCTGGGTGTGGCGGATCGCTATCAGGACATAGCGTTGGCTACCCGTG
ATATTGCTGAAGAGCTTGGCGGCGAATGGGCTGACCGCTTCCTCGTGCTT
TACGGTATCGCCGCTCCCGATTCGCAGCGCATCGCCTTCTATCGCCTTCT
TGACGAGTTCTTCTGAGGGGATCAATTCtctagtGAACAATGGAAGTCCG
AGCTCATCGCTAATAACTTCGTATAGCATACATTATACGAAGTTATATTC
GATGCGGCCGCAAGGGGTTCGCGTCAGCGGGTGTTGGCGGGTGTCGGGC
TGGCTTAACTATGCGGCATCAGAGCAGtctagaGCTCGCTGATCAGCCTC
GACTGTGCCTTCTAGTTGCCAGCCATCTGTTGTTTGCCCCTCCCCCGTGC
CTTCCTTGACCCTGGAAGGTGCCACTCCCACTGTCCTTTCCTAATAAAAT
GAGGAAATTGCATCGCATTGTCTGAGTAGGTGTCATTCTATTCTGGGGGG
TGGGGTGGGGCAGGACAGCAAGGGGGAGGATTGGGAAGACAATAGCAGGC
ATGCTGGGGATGCGGTGGGCTCTATGGCTTCTGAGGCGGAAAGAACCAGC
TGGGGGCGCGCCCctcgagGGGAAGGTATCTCCCAGGAAACTGGCCAGGA
CACATTGGTCCTCCGCCCTCCCCTTCCTCCCACTCCTCCTCCAGACAGGA
CTGTGCCCACCCCCTGCCACCTTTCTGGCCAGAACTGTCCATGGCAGGTG
ACCTTCACATGAGCCCTTCCTCCCTGCCTGCCCTAGTGGGACCCTCCATA
CCTCCCCCTGGACCCCGTTGTCCTTTCTTTCCAGTGTGGCCCTGAGCATA
ACTGATGCCATCATGGGCTGCTGACCCACCCGGGACTGTGTTGTGCAGTG
AGTCACTTCTCTGTCATCAGGGCTTTGTAATTGATAGATAGTGTTTCATC
ATCATTAGGACCGGGTGGCCTCTATGCTCTGTTAGTCTCCAAACACTGAT
GAAAACCTTCGTTGGCATAGTCCCAGCTTCCTGTTGCCCATCCATAAATC
TTGACTTAGGGATGCACATCCTGTCTCCAAGCAACCACCCCTCCCCTAGG
CTAACTATAAAACTGTCCCAATGGCCCTTGTGTGGTGCAGAGTTCATGCT
TCCAGATCATTTCTCTGCTAGATCCATATCTCACCTTGTAAGTCATCCTA
TAATAAACTGATCCATTGATTATTTGCTTCTGTTTTTTCCATCTCAAAAC
AGCTTCTCAGTTCAGTTCGAATTTTTTATTCCCTCCATCCACCCATACTT
TCCTCAGCCTGGGGAACCCTTGCCCCCAGTCCCATGCCCTTCCTCCCTCT
CTGCCCAGCTCAGCACCTGCCCACCCTCACCCTTCCTGTCACTCCCTAGG
ACTGGACCATCCACTGGGGCCAGGACACTCCAGCAGCCTTGGCTTCATGG
GCTCTGAAATCCATGCCCATCTCTATTCCTCACTGGATGGCAGGTTCAG
AGATGTGAAAGGTCTAGGAGGAAGCCAGGAAGGAAACTGTTGCATGAAAG
GCCGGCCTGATGGTTCAGTACTTAAATAATATGAGCTCTGAGCTCCCCAG
GAACCAAAGCATGGAGGGAGTATGTGCCTCAGAATCTCTCTGAGATTCAG
CAAAGCCTTTGCTAGAGGGAAAATAGTGGCTCAACCTTGAGGGCCAGCAT
CTTGCACCACAGTTAAAAGTGGGTATTTGTTTTACCTGAGGCCTCAGCAT
TATGGGAACCGGGCTCTGACACAAACACAGGTGCAGCCCGGCAGCCTCAG
AACACAGCAACGACCACAAGCTGGGACAGCTGCCCCTGAACGGGAGTCC
```

```
ACCATGCTTCTGTCTCGGGTACCACCAGGTCACCATCCCTGGGGGAGGTA
GTTCCATAGCAGTAGTCCCCTGATTTCGCCCCTCGGGCGTGTAGCCAGGC
AAGCTCCTGCCTCTGGACCCAGGGTGGACCCTTGCTCCCCACTACCCTGC
ACATGCCAGACAGTCAAGACCACTCCCACCTCTGTCTGAGGCCCCCTTGG
GTGTCCCAGGGCCCCCGAGCTGTCCTCTACTCATGGTTCTTCCACCTGGG
TACAAAAGAGGCGAGGGACACTTTTCTCAGGTTTGCGGCTCAGAAAGGTA
CCTTCCTAGGGTTTGTCCACTGGGAGTCACCTCCCTTGCATCTCAATGTC
AGTGGGGAAAACTGGGTCCCATGGGGGATTAGTGCCACTGTGAGGCCCC
TGAAGTCTGGGGCCTCTAGACACTATGATGATGAGGGATGTGGTGAAAAA
CCCCACCCCAGCCCTTCTTGCCGGGACCCTGGGCTGTGGCTCCCCCATTG
CACTTGGGGTCAGAGGGGTGGATGGTGGCTATGGTCAGGCATGTTTCCCA
TGAGCTGGGGGCACCCTGGGTGACTTTCTCCTGTGAATCCTGAATTAGCA
GCTATAACAAATTGCCCAAACTCTTAGGCTTAAAACAACACACATTTATT
CCTCTGGGTCCCAGGGTCAGAAGTCCAAAATGAGTCCTATAGGCTAAATT
TGAGGTGTCTCTGGGTTGAGCTCCTCCTGGAAGCCTTTTCCAGCCTCTAG
AGTCCCAAGTCCTTGGCTCTGGGCCCCTCCCTCAAGCTTCAAAGCCACAG
AAGCTTCTAATCTCTCCCTTCCCCTCTGACCTCTGCTCCCATCCTCAT
ACCCTGTCCCCTCACTCTGACCCTCCTGCCTCCCTCTTTCCCTTATAAAG
ACCCTGCATGGGCCACGGAGATAATCCAGGGTAATCGCCCCTCTTCCAG
CCCTTAACTCCATCCCATCTGCAAAATCCCTGTCACCCCATAATGGACCT
ACagatctCCTAGAGTTAACACTGGCCGTCGTTTTACCGGTCCGTAGTCA
GGTTTAGTTCGTCCGGCGGCGCCAGAAATCCGCGCGGTGGTTTTTGGGGG
TCGGGGGTGTTTGGCAGCCACAGACGCCCGGTGTTCGTGTCGCGCCAGTA
CATGCGGTCCATGCCCAGGCCATCCAAAAACCATGGGTCTGTCTGCTCAG
TCCAGTCGTGGACTGACCCCACGCAACGCCCAAAATAATAACCCCCACGA
ACCATAAACCATTCCCCATGGGGACCCCGTCCCTAACCCACGGGGCCCG
TGGCTATGGCAGGCCTGCCGCCCGACGTTGGCTGCGAGCCCTGGGCCTTC
ACCCGAACTTGGGGGGTGGGGTGGGGAAAAGGAAGAAACGCGGGCGTATT
GGCCCCAATGGGGTCTCGGTGGGGTATCGACAGAGTGCCAGCCCTGGGAC
CGAACCCCGCGTTTATGAACAAACGACCCAACACCCGTGCGTTTTATTCT
GTCTTTTTATTGCCGACATAGCGCGGGTTCCTTCCGGTATTGTCTCCTTC
CGTGTTTCAGTTAGCCTCCCCCATCTCCCGTGCAAACGTGCGCGCCAGGT
CGCAGATCGTCGGTATGGAGCCTGGGGTGGTGACGTGGGTCTGGATCATC
CCGGAGGTAAGTTGCAGCAGGGCGTCCCGGCAGCCGGCGGGCGATTGGTC
GTAATCCAGGATAAAGACGTGCATGGGACGGAGGCGTTTGGCCAAGACGT
CCAAGGCCCAGGCAAACACGTTGTACAGGTCGCCGTTGGGGGCCAGCAAC
TCGGGGCCCGAAACAGGGTAAATAACGTGTCCCGATATGGGGTCGTGG
GCCCGCGTTGCTCTGGGGCTCGGCACCCTGGGGCGGCACGGCCGTCCCCG
AAAGCTGTCCCCAATCCTCCCGCCACGACCCGCCGCCCTGCAGATACCGC
ACCGTATTGGCAAGCAGCCCGTAAACGCGGCGAATCGCGGTCAGCATAGC
CAGGTCAAGCCGCTCGCCGGGGCGCTGGCGTTTGGCCAGGCGGTCGATGT
GTCTGTCCTCCGGAAGGGCCCCCAACACGATGTTTGTGCCGGGCAAGGTC
GGCGGGATGAGGGCCACGAACGCCAGCACGGCCTGGGGGGTCATGCTGCC
CATAAGGTATCGCGCGGCCGGGTAGCACAGGAGGGCGGCGATGGGATGGC
GGTCGAAGATGAGGGTGAGGGCCGGGGCGGGGCATGTGAGCTCCCAGCC
TCCCCCCCGATATGAGGAGCCAGAACGGCGTCGGTCACGGTATAAGGCAT
GCCCATTGTTATCTGGGCGCTTGTCATTACCACCGCCGCGTCCCCGGCCG
ATATCTCACCCTGGTCAAGGCGGTGTTGTGTGGTGTAGATGTTCGCGATT
GTCTCGGAAGCCCCCAGCACCCGCCAGTAAGTCATCGGCTCGGGTACGTA
GACGATATCGTCGCGCGAACCCAGGGCCACCAGCAGTTGCGTGGTGGTGG
TTTTCCCCATCCCGTGGGACCGTCTATATAAACCCGCAGTAGCGTGGGC
ATTTTCTGCTCCGGGCGGACTTCCGTGGCTTCTTGCTGCCGGCGAGGGCG
CAACGCCGTACGTCGGTTGCTATGGCCGCGAGAACGCGCAGCCTGGTCGA
ACGCAGACGCGTGCTGATGGCCGGGGTACGAAGCCATACGCGCTTCTACA
AGGCGCTGGCCGAAGAGGTGCGGGAGTTTCACGCCACCAAGATGTGCGGC
ACGCTGTTGACGCTGTTAAGCGGGTCGCTGCAGGGTCGCTCGGTGTTCGA
GGCCACACGCGTCACCTTAATATGCGAAGTGGACCTGGGACCGCGCCGCC
CCGACTGCATCTGCGTGTTCCAATTCGCCAATGACAAGACGCTGGGCGGG
GTTTGCTCGACATTGGGTGGAAACATTCCAGGCCTGGGTGGAGAGGCTTT
TTGCTTCCTCTTGCAAAACCACACTGCTCGACATTGGGTGGAAACATTCC
AGGCCTGGGTGGAGAGGCTTTTTGCTTCCTCTTGAAAACCACACTGCTCG
ACTCTACGGTCCG
```

Seq ID No. 49 is a lambda light chain 5' arm sequence

Seq ID No. 49
```
AGGGTGTGGCCAAATACAGCATGGAGTAGCCATCATAAGGAATCTTACAC
AAGCCTCCAAAATTGTGTTTCTGAAATTGGGTTTAAAGTACGTTTGCATT
TTAAAAAGCCTGCCAGAAAATACAGAAAAATGTCTGTGATATGTCTCTGG
CTGATAGGATTTTGCTTAGTTTTAATTTTGGCTTTATAATTTTCTATAGT
TATGAAAATGTTCACAAGAAGATATATTTCATTTTAGCTTCTAAAATAAT
TATAACACAGAAGTAATTTGTGCTTTAAAAAAATATTCAACACAGAAGTA
TATAAAGTAAAAATTGAGGAGTTCCCATCGTGGCTCAGTGATTAACAAAC
CCAACTAGTATCCATGAGGATATGGATTTGATCCCTGGCCTTGCTCAGTG
GGTTGAGGATCCAGTGTTGCTGTGAGCTGTGGTGTAGGTTGCAGACACAG
CACTCTGGCGTTGCTGTGACTCTGGCGTAGGCCGGCAGCTACAGCTCCAT
TTGGACCCTTAGCCTGGGAACCTCCATATGCCTGAGATACGGCCCTAAAA
AGTCAAAAGCCAAAAAAATAGTAAAAATTGAGTGTTTCTACTTACCACCC
CTGCCCACATCTTATGCTAAAACCCGTTCTCCAGAGACAAACATCGTCAG
GTGGGTCTATATATTTCCAGCCCTCCTCCTGTGTGTATGTCCGTAAAA
CACACACACACACACACACGCACACACACACACACGTATCTAATTAGC
ATTGGTATTAGTTTTTCAAAAGGGAGGTCATGCTCTACCTTTTAGGCGGC
AAATAGATTATTTAAACAAATCTGTTGACATTTTCTATATCAACCCATAA
```

```
GATCTCCCATGTTCTTGGAAAGGCTTTGTAAGACATCAACATCTGGGTAA
ACCAGCATGGTTTTTAGGGGGTTGTGTGGATTTTTTTCATATTTTTTAGG
GCACACCTGCAGCATATGGAGGTTCCCAGGCTAGGGGTTGAATCAGAGCT
GTAGCTGCCGGCCTACACCACAGCCACAGCAACGCCAGATCCTTAACCCA
CTGAGAAAGGCCAGGGATTGAACCTGCATCCTCATGGATGCTGGTCAGAT
TTATTTCTGCTGAGCCACAACAGGAACTCCCTGAACCAGAATGCTTTTAA
CCATTCCACTTTGCATGGACATTTAGATTGTTTCCATTTAAAAATACAAA
TTACAAGGAGTTCCCGTCGTGGCTCAGTGGTAACGAATTGGACTAGGAAC
CATGAGGTTTCGGGTTCGATCCCTGGCCTTGCTCGGTGGGTTAAGGATCC
AGCATTGATGTGAGATATGGTGTAGGTCGCAGACGTGGCTCGGATCCCAC
GTTGCTGTGGCTCTGGCGTAGGCCGGCAACAACAGCTCCGATTCGACCCC
TAGCCTGGGAACCTCCATGTGCCACAGGAGCAGCCCTAGAAAAGGCAAAA
AGACAAAAAATAAAAAATTAAAATGAAAAATAAAATAAAAATACAAAT
TACAAGAGACGGCTACAAGGAAATCCCCAAGTGTGTGCAAATGCCATATA
TGTATAAAATGTACTAGTGTCTCCTCGCGGGAAAGTTGCCTAAAAGTGGG
TTGGCTGGACAGAGAGGACAGGCTTTGACATTCTCATAGGTAGTAGCAAT
GGGCTTCTCAAAATGCTGTTCCAGTTTACACTCACCATAGCAAATGACAG
TGCCTCTTCCTCTCCACCCTTGCCAATAATGTGACAGGTGGATCTTTTTC
TATTTTGTGTATCTGACAAGCAAAAATGAGAACAGGAGTTCCTGTCGTG
GTGCAGTGGAGACAAATCTGACTAGGAACCATGAAATTTCGGGTTCAATC
CCTGGCCTCACTCAGTAGGTAAAGGATCCAGGGTTGCAGTGAGCTGTGGG
GTAGGTCGCAGACACAGTGCAAATTTGGCCCTGTTGTGGCTGTGGTGTAG
GCCGGCAGCTATAGCTCCAATTGGACCCCTAGCCTGGGAACCTCCTTATG
CCGTGGGTGAGGCCCTAAAAAAAAGAGTGCAAAAAAAAAAAATAAGAACA
AAAATGATCATCGTTTAATTCTTTATTTGATCATTGGTGAAACTTATTT
CCTTTTATATTTTTATTGACTGATTTTATTTCTCCTATGAATTTACCGGT
CATAGTTTTGCCTGGGTGTTTTTACTCCGGTTTTAGTTTTGGTTGGTTGT
ATTTTCTTAGAGAGCTATAGAAACTCTTCATCTATTTGGAATAGTAATTC
CTCATTAAGTATTTGTGCTGCAAAAAATTTTCCCTGATCTGTTTTATGCT
TTTGTTTGTGGGGTCTTTCACGAGAAAGCCTTTTTAGTTTTTACACCTCA
GCTTGGTTGTTTTCTTGATTGTGTCTGTAATCTGCGGCCAACATAGGAA
ACACATTTTTACTTTAGTGTTTTTTTCCTATTTTCTTCAAGTACGTCCAT
TGTTTTGGTGTCTGATTTTACTTTGCCTGGGGTTTGTTTTTGTGTGGCAG
GAATATAAACTTATGTATTTTCCAAATGGAGAGCCAATGGTTGTATATTT
GTTGAATTCAAATGCAACTTTATCAAACACCAAATCATCGATTTATCACA
ACTCTTCTCTGGTTTATTGATCTAATGATCAATTCCTGTTCCACGCTGTT
TTAATTATTTTAGCTTTGTGGATTTTGGTGCCTGGTAGAGAACAAAGCCT
CCATTATTTTCATTCAAAATAGTCCCGTCTATTATCTGCCATTGTTGTAG
TATTAGACTTTAAAATCAATTTACTGATTTTCAAAAGTTATTCCTTTGGT
GATGTGGAATACTTTATACTTCATAAGGTACATGGATTCATTTGTGGGGA
ATTGATGTCTTTGCTATTGTGGCCATTTGTCAAGTTGTGTAATATTTTAC
CCATGCCAACTTTGCATATTGTATGTGAGTTTATTCCCAGGGTTTTTAAT
AGGATGTTTATTGAAGTTGTCAGTGTTTCCACAATTTCATCGCCTCAGTG
CTTACTGTTTGCATAAAAGGAAACCTACTCACTTTTGCCTATTGCTCTTG
TATTCAATCATTTTAGTTAACTCTTGTGTTAATTTTGAGAGTTTTTCAGC
TGACTGTCTGGGGTTTTCTTTAATAGACTAGCCCTTTGTCTGTAAAGAAT
AATTTTATCGAATTTTTCTTAACACTCACACTCTCCCCACCCCCACCCCC
GCTCATCTCCTTTCATTGGGTCAAATCTGTAGAATACAATAAAAGTAAGA
GTGGGAACCTTAGCCTTTAAGTCGATTTTGCCTTTAAATGTGAATGTTGC
TATGTTTCGGGACATTCTCTTTATCAAGTTGCGGATGTTTCCTTAGATAA
TTAACTTAATAAAAGACTGGATGTTTGCTTTCTTCAAATCAGAATTGTGT
TGAATTTATATTGCTATTCTGTTTAATTTTGTTTCAAAAAATTTACATGC
ACACCTTAAAGATAACCATGACCAAATAGTCCTCCTGCTGAGAGAAAATG
TTGGCCCCAATGCCACAGGTTACCTCCCGACTCAGATAAACTACAATGGG
AGATAAAATCAGATTTGGCAAAGCCTGTGGATTCTTGCCATAACTCTCAG
AGCATGACTTGGGTGTTTTTTCCTTTTCTAAGTATTTTAATGGTATTTTT
GTGTTACAATAGGAAATCTAGGACACAGAGAGTGATTCAATGAGGGGAAC
GCATTCTGGGATGACTCTAGGCCTCTGGTTTGGGGAGAGCTCTATTGAAG
TAAAGACAATGAGAGGAAGCAAGTTTGCAGGGAACTGTGAGGAATTTAGA
TGGGGAATGTTGGGTTTGAGGTTTCTATAGGGCACGCAAGCAGAGATGCA
CTCAGGAGGAAGAAGGAGCATAAATCTAGAGGCAAAAAGAGAGGTCAGGA
CTGGAAATAGAGATGCGAGACACCAGGGTGGCAGTCAGAGAGCACAGTGT
GGGTCAGAAGACAGTGGAAGAACACAAGGGACAGAGAGGGATCTCCAACT
TCACTGGGATGAGGGCCTTGTTGGCCTTGACCTGAGAGATTTCCAGGAGT
TGAGGGTGGGAAGGAG
```

Seq. ID No. 50 is a lambda 3' arm sequence

Seq. ID No. 50
```
GGGAAGGTATCTCCCAGGAAACTGGCCAGGACACATTGGTCCTCCGCCCT
CCCCTTCCTCCCACTCCTCCTCCAGACAGGACTGTGCCCACCCCCTGCCA
CCTTTCTGGCCAGAACTGTCCATGGCAGGTGACCTTCACATGAGCCCTTC
CTCCCTGCCTGCCCTAGTGGGACCCTCCATACCTCCCCCTGGACCCCGTT
GTCCTTTCTTTCCAGTGTGGCCCTGAGCATAACTGATGCCATCATGGGCT
GCTGACCCACCCGGGACTGTGTTGTGCAGTGAGTCACTTCTCTGTCATCA
GGGCTTTGTAATTGATAGATAGTGTTTCATCATCATTAGGACCGGGTGGC
CTCTATGCTCTGTTAGTCTCCAAACACTGATGAAAACCTTCGTTGGCATA
GTCCCAGCTTCCTGTTGCCCATCCATAAATCTTGACTTAGGGATGCACAT
CCTGTCTCCAAGCAACCACCCCCTCCCCTAGGCTAACTATAAAACTGTCCC
AATGGCCCTTGTGTGGTGCAGAGTTCATGCTTCCAGATCATTTCTCTGCT
AGATCCATATCTCACCTTGTAAGTCATCCTATAATAAACTGATCCATTGA
TTATTTGCTTCTGTTTTTTCCATCTCAAAACAGCTTCTCAGTTCAGTTCG
```

```
-continued
AATTTTTTATTCCCTCCATCCACCCATACTTTCCTCAGCCTGGGGAACCC

TTGCCCCCAGTCCCATGCCCTTCCTCCCTCTCTGCCCAGCTCAGCACCTG

CCCACCCTCACCCTTCCTGTCACTCCCTAGGACTGGACCATCCACTGGGG

CCAGGACACTCCAGCAGCCTTGGCTTCATGGGCTCTGAAATCCATGGCCC

ATCTCTATTCCTCACTGGATGGCAGGTTCAGAGATGTGAAAGGTCTAGGA

GGAAGCCAGGAAGGAAACTGTTGCATGAAAGGCCGGCCTGATGGTTCAGT

ACTTAAATAATATGAGCTCTGAGCTCCCCAGGAACCAAAGCATGGAGGGA

GTATGTGCCTCAGAATCTCTCTGAGATTCAGCAAAGCCTTTGCTAGAGGG

AAAATAGTGGCTCAACCTTGAGGGCCAGCATCTTGCACCACAGTTAAAAG

TGGGTATTTGTTTTACCTGAGGCCTCAGCATTATGGGAACCGGGCTCTGA

CACAAACACAGGTGCAGCCCGGCAGCCTCAGAACACAGCAACGACCACAA

GCTGGGACAGCTGCCCCTGAACGGGGAGTCCACCATGCTTCTGTCTCGGG

TACCACCAGGTCACCATCCCTGGGGGAGGTAGTTCCATAGCAGTAGTCCC

CTGATTTCGCCCCTCGGGCGTGTAGCCAGGCAAGCTCCTGCCTCTGGACC

CAGGGTGGACCCTTGCTCCCCACTACCCTGCACATGCCAGACAGTCAAGA

CCACTCCCACCTCTGTCTGAGGCCCCCTTGGGTGTCCCAGGGCCCCGAG

CTGTCCTCTACTCATGGTTCTTCCACCTGGGTACAAAAGAGGCGAGGGAC

ACTTTTCTCAGGTTTGCGGCTCAGAAAGGTACCTTCCTAGGGTTTGTCCA

CTGGGAGTCACCTCCCTTGCATCTCAATGTCAGTGGGGAAAACTGGGTCC

CATGGGGGATTAGTGCCACTGTGAGGCCCCTGAAGTCTGGGGCCTCTAG

ACACTATGATGATGAGGGATGTGGTGAAAAACCCCACCCCAGCCCTTCTT

GCCGGGACCCTGGGCTGTGGCTCCCCATTGCACTTGGGGTCAGAGGGGT

GGATGGTGGCTATGGTCAGGCATGTTTCCCATGAGCTGGGGGCACCCTGG

GTGACTTTCTCCTGTGAATCCTGAATTAGCAGCTATAACAAATTGCCCAA

ACTCTTAGGCTTAAAACAACACACATTTATTCCTCTGGGTCCCAGGGTCA

GAAGTCCAAAATGAGTCCTATAGGCTAAATTTGAGGTGTCTCTGGGTTGA

GCTCCTCCTGGAAGCCTTTTCCAGCCTCTAGAGTCCCAAGTCCTTGGCTC

TGGGCCCCTCCCTCAAGCTTCAAAGCCACAGAAGCTTCTAATCTCTCTCC

CTTCCCCTCTGACCTCTGCTCCCATCCTCATACCCTGTCCCCTCACTCTG

ACCCTCCTGCCTCCCTCTTTCCCTTATAAAGACCCTGCATGGGGCCACGG

AGATAATCCAGGGTAATCGCCCCTCTTCCAGCCCTTAACTCCATCCCATC

TGCAAAATCCCTGTCACCCCATAATGGACCTAC
```

In a second strategy, the targeting strategy utilizes a vector pair. One targeting vector is designed to target upstream of J1. See FIG. 5. This targeting vector utilizes a selectable marker that can be selected for or against. Any combination of positive and negative selectable markers described herein or known in the art can be used. A fusion gene composed of the coding region of Herpes simplex thymidine kinase (TK) and the Tn5 aminoglycoside phosphotransferase (Neo resistance) genes is used. This fusion gene is flanked by recognition sites for any site specific recombinase (SSRRS) described herein or known in the art, such as lox sites. Upon isolation of targeted cells through the use of G418 selection, Cre is supplied in trans to delete the marker gene (See FIG. 5). Cells that have deleted the marker gene are selected by addition of any drug known in the art that can be metabolized by TK into a toxic product, such as ganciclovir. The resulting genotype is then targeted with a second vector. The second targeting vector (FIG. 6) is designed to target downstream of last C and uses a positive/negative selection system that is flanked on only one side by a specific recombination site (lox). The recombination site is placed distally in relation to the first targeting event. Upon isolation of the targeted genotype, Cre is again supplied in trans to mediate deletion from recombination site provided in the first targeting event to the recombination site delivered in the second targeting event. The entire J to C cluster region will be removed. The appropriate genotype is again selected by administration of ganciclovir.

Two vector pairs, i.e., lambda targeting constructs, were designed and built to target the first and last J/C regions and to include site-specific recombination sites. The first vector pair was composed of Seq ID No. 44 (step 1 vector) and Seq ID No. 45 (step 2 vector). The second vector pair was composed of Seq ID No. 46 (step 2 vector) and Seq ID No. 47 (step 1 vector).

Overview of Seq ID No. 44 (upstream vector, step 1, double lox):
Feature Map
    CDS (3 total)
    NEO (+STOP) CDS
        Start: 3311 End: 4114 (Complementary)
    TK CDS (from VEC1198)
        Start: 4118 End: 5251 (Complementary)
    AP(R)
        Start: 11732 End: 12589 (Complementary)
        bla gene— Ap(r) determinant
    Enhancer (1 total)
    CMV Enhancer
        Start: 5779 End: 6199 (Complementary)
    Misc. Binding Site (2 total)
    Left Homology Arm
        Start: 238 End: 2978
    Right Homology Arm
        Start: 6269 End: 10600
    Misc. Feature (5 total)
    loxP-1
        Start: 3006 End: 3039
    HSVTK-polyA
        Start: 3046 End: 3304 (Complementary)
    loxP-2
        Start: 6212 End: 6245
    Promoter Eukaryotic (1 total)
    Mus-PGK Promoter (correct)
        Start: 5264 End: 5772 (Complementary)
    Replication Origin (2 total)
    Replication Origin
        Start: 10921 End: 11509 (Complementary)
Overview of Seq ID No. 45 (Downstream vector, step 2, single lox
Feature Map
    CDS (3 total)
    NEO (+STOP) CDS
        Start: 3115 End: 3918 (Complementary)
    TK CDS (from VEC1198)
        Start: 3922 End: 5055 (Complementary)
    AP(R)
        Start: 11322 End: 12179 (Complementary)
        bla gene— Ap(r) determinant
    Enhancer (1 total)
    CMV Enhancer
        Start: 5583 End: 6003 (Complementary)

Misc. Binding Site (2 total)
  Left Homology Arm
    Start: 222 End: 2774
  Right Homology Arm
    Start: 6112 End: 10226
Misc. Feature (4 total)
  HSVTK-polyA
    Start: 2850 End: 3108 (Complementary)
  loxP-2
    Start: 6016 End: 6049
Promoter Eukaryotic (1 total)
  Mus-PGK Promoter (correct)
    Start: 5068 End: 5576 (Complementary)
Replication Origin (2 total)
  ORI
    Start: 10511 End: 10511
    RNaseH cleavage point
  Replication Origin
    Start: 10511 End: 11099 (Complementary)
Overview of Seq ID No. 46 (upstream vector alternative, step 2, single lox)
Feature Map
  CDS (3 total)
    NEO (+STOP) CDS
      Start: 3311 End: 4114 (Complementary)
    TK CDS (from VEC1198)
      Start: 4118 End: 5251 (Complementary)
    AP(R)
      Start: 11698 End: 12555 (Complementary)
      bla gene— Ap(r) determinant
  Enhancer (1 total)
    CMV Enhancer
      Start: 5779 End: 6199 (Complementary)
  Misc. Binding Site (2 total)
    Left Homology Arm
      Start: 238 End: 2978
    Right Homology Arm
      Start: 6235 End: 10566
  Misc. Feature (4 total)
    loxP-1
      Start: 3006 End: 3039
    HSVTK-polyA
      Start: 3046 End: 3304 (Complementary)
  Promoter Eukaryotic (1 total)
    Mus-PGK Promoter (correct)
      Start: 5264 End: 5772 (Complementary)
  Replication Origin (2 total)
    ORI
      Start: 10887 End: 10887
      RNaseH cleavage point
    Replication Origin
      Start: 10887 End: 11475 (Complementary)
Overview of Seq ID No. 47 (Downstream vector alternative, step 1, double lox)
Feature Map
  CDS (3 total)
    NEO (+STOP) CDS
      Start: 3149 End: 3952 (Complementary)
    TK CDS (from VEC1198)
      Start: 3956 End: 5089 (Complementary)
    AP(R)
      Start: 11356 End: 12213 (Complementary)
      bla gene— Ap(r) determinant
  Enhancer (1 total)
    CMV Enhancer
      Start: 5617 End: 6037 (Complementary)
  Misc. Binding Site (2 total)
    Left Homology Arm
      Start: 222 End: 2774
    Right Homology Arm
      Start: 6146 End: 10260
  Misc. Feature (5 total)
    loxP-1
      Start: 2844 End: 2877
    HSVTK-polyA
      Start: 2884 End: 3142 (Complementary)
    loxP-2
      Start: 6050 End: 6083
  Promoter Eukaryotic (1 total)
    Mus-PGK Promoter (correct)
      Start: 5102 End: 5610 (Complementary)
  Replication Origin (2 total)
    Replication Origin
      Start: 10545 End: 11133 (Complementary)

The first vector pair is used to produce cells in which the entire J/cluster region is deleted.

The second vector pair is used to produce cells in which the entire J/C cluster region is deleted.

Example 5: Crossbreeding of Heavy Chain Single Knockout with Kappa Single Knockout Pigs To produce pigs that have both one disrupted Ig heavy chain locus and one disrupted Ig light-chain kappa allele, single knockout animals were crossbred. The first pregnancy yielded four fetuses, two of which screened positive by both PCR and Southern for both heavy-chain and kappa targeting events (see examples 1 and 2 for primers). Fetal fibroblasts were isolated, expanded and frozen. A second pregnancy resulting from the mating of a kappa single knockout with a heavy chain single knockout produced four healthy piglets.

Fetal fibroblast cells that contain a heavy chain single knockout and a kappa chain single knockout will be used for further targeting. Such cells will be used to target the lambda locus via the methods and compositions described herein. The resulting offspring will be heterozygous knockouts for heavy chain, kappa chain and lambda chain. These animals will be further crossed with animals containing the human Ig genes as described herein and then crossbred with other single Ig knockout animals to produce porcine Ig double knockout animals with human Ig replacement genes.

This invention has been described with reference to its preferred embodiments. Variations and modifications of the invention, will be obvious to those skilled in the art from the foregoing detailed description of the invention.

The invention claimed is:

1. A targeting vector that inactivates a porcine lambda light chain genetic locus, wherein the target vector comprises:
   (a) a first nucleotide sequence comprising at least 30 contiguous nucleic acids of a nucleotide sequence that flanks the 5' end of the first joining/constant (J/C) region of the porcine lambda light chain genetic locus;
   (b) a selectable marker gene; and
   (c) a second-nucleotide sequence comprising at least 30 contiguous nucleic acids of a nucleotide sequence that flanks the 3' end of the J/C cluster region of the porcine lambda light chain genetic locus.

2. The targeting vector of claim 1, wherein the nucleotide sequence that flanks the 5' end of the first J/C region comprises the nucleotide sequence of SEQ ID NO. 32.

3. The targeting vector of claim 1, wherein the nucleotide sequence that flanks the 5' end of the first J/C region comprises a nucleotide sequence that is at least 85% homologous to the nucleotide sequence of SEQ ID NO. 32.

4. The targeting vector of claim 1, wherein the first nucleotide sequence comprises at least 100 contiguous nucleic acids of the nucleotide sequence that flanks the 5' end of the first J/C region.

5. The targeting vector of claim 1, wherein the first nucleotide sequence comprises at least 500 contiguous nucleic acids of the nucleotide sequence that flanks the 5' end of the first J/C region.

6. The targeting vector of claim 1, wherein the first nucleotide sequence comprises at least 1000 contiguous nucleic acids of the nucleotide sequence that flanks the 5' end of the first J/C region.

7. The targeting vector of claim 1, wherein the nucleotide sequence that flanks the 3' end of the J/C cluster region comprises the nucleotide sequence of any one of SEQ ID NOs. 33-39.

8. The targeting vector of claim 1, wherein the nucleotide sequence that flanks the 3' end of the J/C cluster region comprises a nucleotide sequence that is at least 85% homologous to the nucleotide sequence of any one of SEQ ID NOs. 33-39.

9. The targeting vector of claim 1, wherein the nucleotide sequence that flanks the 3' end of the J/C cluster region comprises the nucleotide sequence of SEQ ID NO. 33.

10. The targeting vector of claim 1, wherein the nucleotide sequence that flanks the 3' end of the J/C cluster region is approximately 200 base pairs downstream of the J/C region of a porcine lambda light chain.

11. The targeting vector of claim 1, wherein the first nucleotide sequence comprises at least 100 contiguous nucleic acids of the nucleotide sequence that flanks the 3' end of the J/C cluster region.

12. The targeting vector of claim 1, wherein the first nucleotide sequence comprises at least 500 contiguous nucleic acids of the nucleotide sequence that flanks the 3' end of the J/C cluster region.

13. The targeting vector of claim 1, wherein the first nucleotide sequence comprises at least 1000 contiguous nucleic acids of the nucleotide sequence that flanks the 3' end of the J/C cluster region.

14. The targeting vector of claim 1, wherein the porcine lambda light chain genetic locus comprises the nucleotide sequence of SEQ ID NO: 28.

15. The targeting vector of claim 1, wherein the porcine lambda light chain genetic locus comprises a nucleotide sequence that is at least 85% homologous to the nucleotide sequence of SEQ ID NO: 28.

* * * * *